United States Patent
Brown et al.

(10) Patent No.: US 9,506,061 B2
(45) Date of Patent: *Nov. 29, 2016

(54) METHODS AND COMPOSITIONS INVOLVING MIRNA AND MIRNA INHIBITOR MOLECULES

(71) Applicant: Asuragen, Inc., Austin, TX (US)

(72) Inventors: David Brown, Austin, TX (US); Lance Ford, Austin, TX (US); Angie Cheng, Austin, TX (US); Rich Jarvis, Austin, TX (US); Mike Byrom, Austin, TX (US); Dmitriy Ovcharenko, Austin, TX (US); Eric Devroe, Pflugerville, TX (US); Kevin Kelnar, Kyle, TX (US)

(73) Assignee: ASURAGEN, INC., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/712,591

(22) Filed: May 14, 2015

(65) Prior Publication Data

US 2015/0344881 A1    Dec. 3, 2015

Related U.S. Application Data

(60) Continuation of application No. 13/887,008, filed on May 3, 2013, now abandoned, which is a continuation of application No. 13/299,255, filed on Nov. 17, 2011, now Pat. No. 8,946,177, which is a division of application No. 11/273,640, filed on Nov. 14, 2005, now Pat. No. 8,173,611.

(60) Provisional application No. 60/683,736, filed on May 23, 2005, provisional application No. 60/649,634, filed on Feb. 3, 2005, provisional application No. 60/627,171, filed on Nov. 12, 2004.

(51) Int. Cl.
| | |
|---|---|
| C12N 15/11 | (2006.01) |
| C12N 15/113 | (2010.01) |
| A61K 31/7105 | (2006.01) |
| A61K 45/06 | (2006.01) |
| A61N 5/10 | (2006.01) |
| C12Q 1/68 | (2006.01) |
| A61K 9/127 | (2006.01) |
| A61K 31/7088 | (2006.01) |
| A61K 31/713 | (2006.01) |

(52) U.S. Cl.
CPC ............ *C12N 15/113* (2013.01); *A61K 9/127* (2013.01); *A61K 31/7088* (2013.01); *A61K 31/713* (2013.01); *A61K 31/7105* (2013.01); *A61K 45/06* (2013.01); *A61N 5/10* (2013.01); *C12N 15/111* (2013.01); *C12N 15/1136* (2013.01); *C12Q 1/68* (2013.01); *C12N 2310/14* (2013.01); *C12N 2310/141* (2013.01); *C12N 2310/321* (2013.01); *C12N 2310/322* (2013.01); *C12N 2310/33* (2013.01); *C12N 2310/344* (2013.01); *C12N 2310/35* (2013.01); *C12N 2310/351* (2013.01); *C12N 2310/3527* (2013.01); *C12N 2310/3535* (2013.01); *C12N 2310/533* (2013.01); *C12N 2320/12* (2013.01); *C12N 2320/30* (2013.01); *C12N 2320/50* (2013.01); *C12N 2330/10* (2013.01)

(58) Field of Classification Search
CPC ....................... C12N 15/113; C12N 2310/141
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,876,187 A | 10/1989 | Duck et al. |
| 4,999,290 A | 3/1991 | Lee |
| 5,011,769 A | 4/1991 | Duck et al. |
| 5,188,934 A | 2/1993 | Menchen et al. |
| 5,256,555 A | 10/1993 | Milburn et al. |
| 5,260,191 A | 11/1993 | Yang |
| 5,262,311 A | 11/1993 | Pardee et al. |
| 5,264,566 A | 11/1993 | Froehler et al. |
| 5,366,860 A | 11/1994 | Bergot et al. |
| 5,432,272 A | 7/1995 | Benner |
| 5,446,137 A | 8/1995 | Maag et al. |
| 5,466,786 A | 11/1995 | Buhr et al. |
| 5,486,603 A | 1/1996 | Buhr |
| 5,538,848 A | 7/1996 | Livak et al. |
| 5,543,296 A | 8/1996 | Sobol et al. |
| 5,545,522 A | 8/1996 | Van Gelder et al. |
| 5,567,811 A | 10/1996 | Misiura et al. |

(Continued)

FOREIGN PATENT DOCUMENTS

| | | |
|---|---|---|
| EP | 0416817 A2 | 3/1991 |
| EP | 870842 A2 | 10/1998 |

(Continued)

OTHER PUBLICATIONS

Chiu et al. Mol. Cell 2002 10:549-61.*

(Continued)

*Primary Examiner* — Brian Whiteman

(74) *Attorney, Agent, or Firm* — Wilson Sonsini Goodrich & Rosati

(57) ABSTRACT

The present invention concerns methods and compositions for introducing miRNA activity or function into cells using synthetic nucleic acid molecules. Moreover, the present invention concerns methods and compositions for identifying miRNAs with specific cellular functions that are relevant to therapeutic, diagnostic, and prognostic applications wherein synthetic miRNAs and/or miRNA inhibitors are used in library screening assays.

7 Claims, 26 Drawing Sheets

(56) References Cited

U.S. PATENT DOCUMENTS

| | | |
|---|---|---|
| 5,602,244 A | 2/1997 | Caruthers et al. |
| 5,660,988 A | 8/1997 | Duck et al. |
| 5,670,633 A | 9/1997 | Cook et al. |
| 5,705,629 A | 1/1998 | Bhongle |
| 5,723,591 A | 3/1998 | Livak et al. |
| 5,739,169 A | 4/1998 | Ocain et al. |
| 5,766,888 A | 6/1998 | Sobol et al. |
| 5,800,996 A | 9/1998 | Lee et al. |
| 5,801,005 A | 9/1998 | Cheever et al. |
| 5,801,155 A | 9/1998 | Kutyavin et al. |
| 5,824,311 A | 10/1998 | Greene et al. |
| 5,830,880 A | 11/1998 | Sedlacek et al. |
| 5,847,162 A | 12/1998 | Lee et al. |
| 5,859,221 A | 1/1999 | Cook et al. |
| 5,861,245 A | 1/1999 | McClelland et al. |
| 5,863,727 A | 1/1999 | Lee et al. |
| 5,871,697 A | 2/1999 | Rothberg et al. |
| 5,898,031 A | 4/1999 | Crooke |
| 5,925,517 A | 7/1999 | Tyagi et al. |
| 5,936,087 A | 8/1999 | Benson et al. |
| 5,942,398 A | 8/1999 | Tartaglia et al. |
| 5,945,526 A | 8/1999 | Lee et al. |
| 5,965,364 A | 10/1999 | Benner |
| 5,976,567 A | 11/1999 | Wheeler et al. |
| 5,998,203 A | 12/1999 | Matulic-Adamic et al. |
| 6,001,983 A | 12/1999 | Benner |
| 6,004,755 A | 12/1999 | Wang |
| 6,008,379 A | 12/1999 | Benson et al. |
| 6,020,481 A | 2/2000 | Benson et al. |
| 6,037,129 A | 3/2000 | Cole et al. |
| 6,040,138 A | 3/2000 | Lockhart et al. |
| 6,051,719 A | 4/2000 | Benson et al. |
| 6,057,105 A | 5/2000 | Hoon et al. |
| 6,084,102 A | 7/2000 | Kutyavin et al. |
| 6,096,314 A | 8/2000 | Cohen et al. |
| 6,103,476 A | 8/2000 | Tyagi et al. |
| 6,107,094 A | 8/2000 | Crooke |
| 6,111,095 A | 8/2000 | Benseler et al. |
| 6,132,997 A | 10/2000 | Shannon |
| 6,140,054 A | 10/2000 | Wittwer et al. |
| 6,140,500 A | 10/2000 | Yan et al. |
| 6,150,097 A | 11/2000 | Tyagi et al. |
| 6,153,737 A | 11/2000 | Manoharan et al. |
| 6,174,670 B1 | 1/2001 | Wittwer et al. |
| 6,184,037 B1 | 2/2001 | Rolland et al. |
| 6,191,278 B1 | 2/2001 | Lee et al. |
| 6,232,066 B1 | 5/2001 | Felder et al. |
| 6,238,869 B1 | 5/2001 | Kris et al. |
| 6,287,792 B1 | 9/2001 | Pardridge et al. |
| 6,344,316 B1 | 2/2002 | Lockhart et al. |
| 6,355,421 B1 | 3/2002 | Coull et al. |
| 6,383,752 B1 | 5/2002 | Agrawal et al. |
| 6,418,382 B2 | 7/2002 | Rothberg et al. |
| 6,435,245 B1 | 8/2002 | Sette et al. |
| 6,458,533 B1 | 10/2002 | Felder et al. |
| 6,476,205 B1 | 11/2002 | Buhr et al. |
| 6,485,901 B1 | 11/2002 | Gildea et al. |
| 6,506,559 B1 | 1/2003 | Fire et al. |
| 6,511,832 B1 | 1/2003 | Guarino et al. |
| 6,548,250 B1 | 4/2003 | Sorge |
| 6,573,048 B1 | 6/2003 | VanAtta et al. |
| 6,573,099 B2 | 6/2003 | Graham |
| 6,586,218 B2 | 7/2003 | Milburn et al. |
| 6,586,219 B2 | 7/2003 | Milburn et al. |
| 6,589,743 B2 | 7/2003 | Sorge |
| 6,593,091 B2 | 7/2003 | Keys et al. |
| 6,596,490 B2 | 7/2003 | Dattagupta |
| 6,706,480 B1 | 3/2004 | Armour |
| 6,720,138 B2 | 4/2004 | Sharma et al. |
| 6,723,509 B2 | 4/2004 | Ach |
| 6,730,477 B1 | 5/2004 | Sun et al. |
| 6,737,520 B2 | 5/2004 | Manoharan et al. |
| 6,787,335 B2 | 9/2004 | Salceda et al. |
| 6,797,471 B2 | 9/2004 | Katz et al. |
| 6,815,432 B2 | 11/2004 | Wheeler et al. |
| 6,858,225 B2 | 2/2005 | Semple et al. |
| 6,964,847 B1 | 11/2005 | Englert |
| 6,967,016 B2 | 11/2005 | van Gemen et al. |
| 6,998,268 B2 | 2/2006 | Terada et al. |
| 7,001,724 B1 | 2/2006 | Greenfield |
| 7,005,261 B1 | 2/2006 | Lloyd et al. |
| 7,014,838 B2 | 3/2006 | Mueller et al. |
| 7,015,047 B2 | 3/2006 | Huang et al. |
| 7,056,704 B2 | 6/2006 | Tuschl et al. |
| 7,078,180 B2 | 7/2006 | Genetta |
| 7,078,196 B2 | 7/2006 | Tuschl et al. |
| 7,109,167 B2 | 9/2006 | Von Wronski et al. |
| 7,141,372 B2 | 11/2006 | Spivack et al. |
| 7,171,311 B2 | 1/2007 | Dai et al. |
| 7,192,586 B2 | 3/2007 | Bander |
| 7,205,105 B2 | 4/2007 | Afonina et al. |
| 7,232,806 B2 | 6/2007 | Tuschl et al. |
| 7,282,564 B2 | 10/2007 | Mello et al. |
| 7,297,480 B2 | 11/2007 | Vogt |
| 7,306,906 B2 | 12/2007 | Maruyama et al. |
| 7,307,067 B2 | 12/2007 | Sarnow et al. |
| 7,354,725 B2 | 4/2008 | Muraca |
| 7,365,058 B2 | 4/2008 | Stoffel et al. |
| 7,368,098 B2 | 5/2008 | Mueller et al. |
| 7,390,792 B2 | 6/2008 | Srivastava et al. |
| 7,402,389 B2 | 7/2008 | Mousses et al. |
| 7,452,987 B2 | 11/2008 | Giese et al. |
| 7,459,547 B2 | 12/2008 | Zamore et al. |
| 7,473,525 B2 | 1/2009 | Kreutzer et al. |
| 7,495,073 B2 | 2/2009 | Hsu et al. |
| 7,582,744 B2 | 9/2009 | Manoharan et al. |
| 7,592,441 B2 | 9/2009 | Bentwich et al. |
| 7,642,348 B2 | 1/2010 | Bentwich et al. |
| 7,655,785 B1 | 2/2010 | Bentwich |
| 7,683,036 B2 | 3/2010 | Esau et al. |
| 7,723,030 B2 | 5/2010 | Croce et al. |
| 7,723,035 B2 | 5/2010 | Croce et al. |
| 7,723,510 B1 | 5/2010 | Tuschl et al. |
| 7,772,389 B2 | 8/2010 | Tuschl et al. |
| 7,825,229 B2 | 11/2010 | Itzhak et al. |
| 7,888,010 B2 | 2/2011 | Brown et al. |
| 7,893,034 B2 | 2/2011 | Slack et al. |
| 7,919,245 B2 | 4/2011 | Brown et al. |
| 7,960,359 B2 | 6/2011 | Brown et al. |
| 7,993,831 B2 | 8/2011 | Latham et al. |
| 8,058,250 B2 | 11/2011 | Brown et al. |
| 8,071,562 B2 | 12/2011 | Bader et al. |
| 8,084,199 B2 | 12/2011 | Croce et al. |
| 8,110,558 B2 | 2/2012 | Bennett et al. |
| 8,129,515 B2 | 3/2012 | Esau et al. |
| 8,137,910 B2 | 3/2012 | Cullen et al. |
| 8,173,611 B2 | 5/2012 | Brown et al. |
| 8,202,979 B2 | 6/2012 | McSwiggen et al. |
| 8,211,867 B2 | 7/2012 | Bennett et al. |
| 8,236,777 B2 | 8/2012 | Thum et al. |
| 8,258,111 B2 | 9/2012 | Shen et al. |
| 8,361,714 B2 | 1/2013 | Huibregtse et al. |
| 8,361,980 B2 | 1/2013 | Kauppinen et al. |
| 8,465,914 B2 | 6/2013 | Brown et al. |
| 8,563,708 B2 | 10/2013 | Brown et al. |
| 8,568,971 B2 | 10/2013 | Brown et al. |
| 8,586,727 B2 | 11/2013 | Kelnar et al. |
| 8,592,389 B2 | 11/2013 | Thurn et al. |
| 8,680,067 B2 | 3/2014 | Bennett et al. |
| 8,729,036 B2 | 5/2014 | Zamore et al. |
| 8,785,709 B2 | 7/2014 | Ratnasamy et al. |
| 8,846,631 B2 | 9/2014 | Marcusson et al. |
| 8,916,533 B2 | 12/2014 | Croce |
| 9,068,219 B2 | 6/2015 | Brown et al. |
| 2002/0006630 A1 | 1/2002 | Sirbasku |
| 2002/0037540 A1 | 3/2002 | Ali et al. |
| 2002/0065396 A1 | 5/2002 | Yang et al. |
| 2002/0065406 A1 | 5/2002 | Meyers |
| 2002/0068307 A1 | 6/2002 | Pluta et al. |
| 2002/0086356 A1 | 7/2002 | Tuschl et al. |
| 2002/0094546 A1 | 7/2002 | Shimkets et al. |
| 2002/0119156 A1 | 8/2002 | Chen et al. |
| 2002/0165189 A1 | 11/2002 | Crooke |
| 2003/0009295 A1 | 1/2003 | Markowitz et al. |

(56) References Cited

U.S. PATENT DOCUMENTS

| | | |
|---|---|---|
| 2003/0027783 A1 | 2/2003 | Zernicka-Goetz et al. |
| 2003/0031678 A1 | 2/2003 | Ali et al. |
| 2003/0033614 A1 | 2/2003 | French et al. |
| 2003/0084471 A1 | 5/2003 | Beach et al. |
| 2003/0099976 A1 | 5/2003 | Chang |
| 2003/0108923 A1 | 6/2003 | Tuschl et al. |
| 2003/0124114 A1 | 7/2003 | McIntire et al. |
| 2003/0143732 A1 | 7/2003 | Fosnaugh et al. |
| 2003/0157030 A1 | 8/2003 | Davis et al. |
| 2003/0170623 A1 | 9/2003 | Chen et al. |
| 2003/0175768 A1 | 9/2003 | Carson et al. |
| 2003/0180298 A1 | 9/2003 | Old et al. |
| 2003/0204322 A1 | 10/2003 | Loehrlein et al. |
| 2003/0215842 A1 | 11/2003 | Sledziewski et al. |
| 2004/0001841 A1 | 1/2004 | Nagavarapu et al. |
| 2004/0010001 A1 | 1/2004 | Au et al. |
| 2004/0029121 A1 | 2/2004 | Cottrell et al. |
| 2004/0029128 A1 | 2/2004 | Cottrell et al. |
| 2004/0053411 A1 | 3/2004 | Cullen et al. |
| 2004/0058373 A1 | 3/2004 | Winkler et al. |
| 2004/0063197 A1 | 4/2004 | Tilles et al. |
| 2004/0063654 A1 | 4/2004 | Davis et al. |
| 2004/0072164 A1 | 4/2004 | Maruyama et al. |
| 2004/0086504 A1 | 5/2004 | Sampath et al. |
| 2004/0110191 A1 | 6/2004 | Winkler et al. |
| 2004/0114800 A1 | 6/2004 | Ponomarev et al. |
| 2004/0115630 A1 | 6/2004 | Olek et al. |
| 2004/0115671 A1 | 6/2004 | Zlokovic et al. |
| 2004/0142895 A1 | 7/2004 | Lockridge et al. |
| 2004/0147027 A1 | 7/2004 | Troy et al. |
| 2004/0152112 A1 | 8/2004 | Croce et al. |
| 2004/0166511 A1 | 8/2004 | Clasina Timmermans et al. |
| 2004/0175732 A1 | 9/2004 | Rana |
| 2004/0198640 A1 | 10/2004 | Leake et al. |
| 2004/0203145 A1 | 10/2004 | Zamore et al. |
| 2004/0209832 A1 | 10/2004 | McSwiggen et al. |
| 2004/0214198 A1 | 10/2004 | Rana |
| 2004/0215651 A1 | 10/2004 | Markowitz et al. |
| 2004/0224337 A1 | 11/2004 | Foehr et al. |
| 2004/0229211 A1 | 11/2004 | Yeung |
| 2004/0236516 A1 | 11/2004 | Brandon |
| 2004/0243362 A1 | 12/2004 | Liebman |
| 2004/0259247 A1 | 12/2004 | Tuschl et al. |
| 2005/0020521 A1 | 1/2005 | Rana |
| 2005/0026278 A1 | 2/2005 | Tuschl et al. |
| 2005/0033030 A1 | 2/2005 | Lo et al. |
| 2005/0037362 A1 | 2/2005 | Remacle et al. |
| 2005/0059024 A1 | 3/2005 | Conrad |
| 2005/0065333 A1 | 3/2005 | Seth |
| 2005/0074788 A1 | 4/2005 | Dahlberg et al. |
| 2005/0075492 A1 | 4/2005 | Chen et al. |
| 2005/0095646 A1 | 5/2005 | Sherman |
| 2005/0112604 A1 | 5/2005 | Fujimoto et al. |
| 2005/0125161 A1 | 6/2005 | Cairney et al. |
| 2005/0130170 A1 | 6/2005 | Harvey et al. |
| 2005/0130172 A1 | 6/2005 | Beard et al. |
| 2005/0142556 A1 | 6/2005 | Hoon et al. |
| 2005/0153337 A1 | 7/2005 | Manoharan |
| 2005/0176018 A1 | 8/2005 | Thompson et al. |
| 2005/0181382 A1 | 8/2005 | Zamore et al. |
| 2005/0182005 A1 | 8/2005 | Tuschl et al. |
| 2005/0186018 A1 | 8/2005 | Byun |
| 2005/0186586 A1 | 8/2005 | Zamore et al. |
| 2005/0208493 A1 | 9/2005 | Alon |
| 2005/0234006 A1 | 10/2005 | Tuschl et al. |
| 2005/0234007 A1 | 10/2005 | Tuschl et al. |
| 2005/0261218 A1 | 11/2005 | Essau et al. |
| 2005/0266418 A1 | 12/2005 | Chen et al. |
| 2005/0287539 A1 | 12/2005 | Labourier et al. |
| 2006/0051768 A1 | 3/2006 | Hoon et al. |
| 2006/0078894 A1 | 4/2006 | Winkler et al. |
| 2006/0088521 A1 | 4/2006 | Mahadevan |
| 2006/0095980 A1 | 5/2006 | Petitte et al. |
| 2006/0105350 A1 | 5/2006 | Qiao et al. |
| 2006/0105360 A1 | 5/2006 | Croce et al. |
| 2006/0134639 A1 | 6/2006 | Huffel et al. |
| 2006/0134661 A1 | 6/2006 | Essner |
| 2006/0154275 A1 | 7/2006 | Sgarlato et al. |
| 2006/0165659 A1 | 7/2006 | Croce et al. |
| 2006/0183128 A1 | 8/2006 | Berlin et al. |
| 2006/0185026 A1 | 8/2006 | Sacktor et al. |
| 2006/0185027 A1 | 8/2006 | Bartel et al. |
| 2006/0189557 A1 | 8/2006 | Slack et al. |
| 2006/0195269 A1 | 8/2006 | Yeatman et al. |
| 2006/0210979 A1 | 9/2006 | Yang et al. |
| 2006/0247193 A1 | 11/2006 | Taira et al. |
| 2006/0252057 A1 | 11/2006 | Raponi et al. |
| 2006/0258566 A1 | 11/2006 | Von Wronski et al. |
| 2006/0265771 A1 | 11/2006 | Lewis et al. |
| 2006/0271309 A1 | 11/2006 | Showe et al. |
| 2006/0292616 A1 | 12/2006 | Neely et al. |
| 2007/0003960 A1 | 1/2007 | Tuschl et al. |
| 2007/0003961 A1 | 1/2007 | Tuschl et al. |
| 2007/0003962 A1 | 1/2007 | Tuschl et al. |
| 2007/0003963 A1 | 1/2007 | Tuschl et al. |
| 2007/0009484 A1 | 1/2007 | Hunt et al. |
| 2007/0025997 A1 | 2/2007 | Nagavarapu et al. |
| 2007/0031840 A1 | 2/2007 | Klussmann et al. |
| 2007/0031873 A1 | 2/2007 | Wang et al. |
| 2007/0041934 A1 | 2/2007 | William et al. |
| 2007/0048758 A1 | 3/2007 | Lokhov et al. |
| 2007/0050146 A1 | 3/2007 | Bentwich et al. |
| 2007/0054287 A1 | 3/2007 | Bloch |
| 2007/0065844 A1 | 3/2007 | Golub et al. |
| 2007/0072204 A1 | 3/2007 | Hannon et al. |
| 2007/0093445 A1 | 4/2007 | Tuschl et al. |
| 2007/0099196 A1 | 5/2007 | Kauppinen et al. |
| 2007/0142313 A1 | 6/2007 | Srivastava et al. |
| 2007/0161004 A1 | 7/2007 | Brown et al. |
| 2007/0213292 A1 | 9/2007 | Stoffel et al. |
| 2007/0259827 A1 | 11/2007 | Aronin et al. |
| 2007/0287179 A1 | 12/2007 | Tuschl et al. |
| 2007/0299030 A1 | 12/2007 | Dmitrovsky et al. |
| 2008/0026951 A1 | 1/2008 | Brown et al. |
| 2008/0050744 A1 | 2/2008 | Brown et al. |
| 2008/0076674 A1 | 3/2008 | Litman et al. |
| 2008/0131878 A1 | 6/2008 | Latham et al. |
| 2008/0132461 A1 | 6/2008 | Tuschi et al. |
| 2008/0171667 A1 | 7/2008 | Brown et al. |
| 2008/0171715 A1 | 7/2008 | Brown et al. |
| 2008/0176766 A1 | 7/2008 | Brown et al. |
| 2008/0182237 A1 | 7/2008 | Bentwich et al. |
| 2008/0182245 A1 | 7/2008 | Brown et al. |
| 2008/0261908 A1 | 10/2008 | Croce et al. |
| 2008/0269147 A1 | 10/2008 | Tuschl et al. |
| 2008/0306006 A1 | 12/2008 | Croce et al. |
| 2008/0306017 A1 | 12/2008 | Croce et al. |
| 2008/0306018 A1 | 12/2008 | Croce et al. |
| 2009/0029932 A1 | 1/2009 | Voinnet et al. |
| 2009/0075258 A1 | 3/2009 | Latham et al. |
| 2009/0092974 A1 | 4/2009 | Davison et al. |
| 2009/0131348 A1 | 5/2009 | Labourier et al. |
| 2009/0131354 A1 | 5/2009 | Bader et al. |
| 2009/0131356 A1 | 5/2009 | Bader et al. |
| 2009/0163430 A1 | 6/2009 | Johnson et al. |
| 2009/0163434 A1 | 6/2009 | Bader et al. |
| 2009/0163435 A1 | 6/2009 | Bader et al. |
| 2009/0175827 A1 | 7/2009 | Byrom et al. |
| 2009/0176723 A1 | 7/2009 | Brown et al. |
| 2009/0186015 A1 | 7/2009 | Latham et al. |
| 2009/0186348 A1 | 7/2009 | Huibregtse et al. |
| 2009/0186353 A1 | 7/2009 | Aharonov et al. |
| 2009/0186843 A1 | 7/2009 | Tuschl et al. |
| 2009/0192102 A1 | 7/2009 | Bader et al. |
| 2009/0192111 A1 | 7/2009 | Bader et al. |
| 2009/0192114 A1 | 7/2009 | Ovcharenko et al. |
| 2009/0227533 A1 | 9/2009 | Bader et al. |
| 2009/0232893 A1 | 9/2009 | Bader et al. |
| 2009/0233297 A1 | 9/2009 | Mambo et al. |
| 2009/0247549 A1 | 10/2009 | Frankel et al. |
| 2009/0253780 A1 | 10/2009 | Takeshita et al. |
| 2009/0258928 A1 | 10/2009 | Beaudenon-Huibregtse et al. |
| 2009/0263803 A1 | 10/2009 | Beaudenon et al. |
| 2009/0281167 A1 | 11/2009 | Shen et al. |

(56) References Cited

U.S. PATENT DOCUMENTS

| | | |
|---|---|---|
| 2009/0281298 A1 | 11/2009 | Manoharan et al. |
| 2009/0298916 A1 | 12/2009 | Kauppinen et al. |
| 2010/0087507 A1 | 4/2010 | Ochiya et al. |
| 2010/0144850 A1 | 6/2010 | Croce |
| 2010/0203544 A1 | 8/2010 | Croce et al. |
| 2010/0234241 A1 | 9/2010 | Croce et al. |
| 2010/0257618 A1 | 10/2010 | Croce et al. |
| 2010/0286232 A1 | 11/2010 | Schmittgen et al. |
| 2011/0009469 A1 | 1/2011 | Mendell et al. |
| 2011/0071211 A1 | 3/2011 | Thum et al. |
| 2011/0105583 A1 | 5/2011 | Cleary et al. |
| 2011/0251150 A2 | 10/2011 | Bennett et al. |
| 2011/0313025 A1 | 12/2011 | Brown et al. |
| 2012/0065248 A1 | 3/2012 | Brown et al. |
| 2012/0295962 A1 | 11/2012 | Bennett et al. |
| 2013/0018088 A1 | 1/2013 | Adam et al. |
| 2013/0116299 A1 | 5/2013 | Leedman et al. |
| 2013/0143945 A1 | 6/2013 | Brown et al. |
| 2013/0195858 A1 | 8/2013 | Craig et al. |
| 2013/0310446 A1 | 11/2013 | Rosin-Arbesfeld et al. |
| 2014/0348908 A1 | 11/2014 | Brown et al. |
| 2014/0351963 A1 | 11/2014 | Croce et al. |
| 2014/0378528 A1 | 12/2014 | Bader et al. |
| 2015/0004221 A1 | 1/2015 | Brown et al. |

FOREIGN PATENT DOCUMENTS

| | | |
|---|---|---|
| EP | 921195 A1 | 6/1999 |
| EP | 1352061 A2 | 10/2003 |
| EP | 1627925 A1 | 2/2006 |
| FR | 2877350 A1 | 5/2006 |
| JP | 2005-296014 A | 10/2005 |
| JP | 2008519606 A | 6/2008 |
| JP | 2010524968 A | 7/2010 |
| WO | WO-93/21329 A1 | 10/1993 |
| WO | WO-97/27317 A1 | 7/1997 |
| WO | WO-97/43450 A1 | 11/1997 |
| WO | WO-97/45539 A1 | 12/1997 |
| WO | WO-98/08973 A1 | 3/1998 |
| WO | WO-99/21881 A1 | 5/1999 |
| WO | WO-99/23256 A1 | 5/1999 |
| WO | WO-99/36760 A1 | 7/1999 |
| WO | WO-00/05409 A1 | 2/2000 |
| WO | WO-00/24939 A1 | 5/2000 |
| WO | WO-00/44895 A1 | 8/2000 |
| WO | WO-00/56748 A1 | 9/2000 |
| WO | WO-00/66604 A2 | 11/2000 |
| WO | WO-00/75356 A1 | 12/2000 |
| WO | WO-01/68255 A2 | 9/2001 |
| WO | WO-01/75164 A2 | 10/2001 |
| WO | WO-02/00169 | 1/2002 |
| WO | WO-02/44321 | 6/2002 |
| WO | WO-02/064835 A2 | 8/2002 |
| WO | WO-03/020898 A2 | 3/2003 |
| WO | WO-03/020931 A2 | 3/2003 |
| WO | WO-03/022421 A2 | 3/2003 |
| WO | WO-03/023058 A2 | 3/2003 |
| WO | WO-03/029459 A2 | 4/2003 |
| WO | WO-03/029485 A2 | 4/2003 |
| WO | WO-03/040410 A1 | 5/2003 |
| WO | WO-03/053586 A1 | 7/2003 |
| WO | WO-03/066906 A2 | 8/2003 |
| WO | WO-03/067217 A2 | 8/2003 |
| WO | WO-03/076928 A1 | 9/2003 |
| WO | WO-03/087297 A2 | 10/2003 |
| WO | WO-03/091426 A1 | 11/2003 |
| WO | WO-03/093810 A1 | 11/2003 |
| WO | WO-03/100012 A2 | 12/2003 |
| WO | WO-03/100448 A1 | 12/2003 |
| WO | WO-2004/020085 A1 | 3/2004 |
| WO | WO-2004/027093 A1 | 4/2004 |
| WO | WO-2004/029212 A2 | 4/2004 |
| WO | WO-2004/043387 A2 | 5/2004 |
| WO | WO-2004/046324 A2 | 6/2004 |
| WO | WO-2004/050125 A1 | 6/2004 |
| WO | WO-2004/057017 A2 | 7/2004 |
| WO | WO-2004/066183 A2 | 8/2004 |
| WO | WO-2004066183 A2 | 8/2004 |
| WO | WO-2004/074509 A2 | 9/2004 |
| WO | WO-2004/076622 A2 | 9/2004 |
| WO | WO-2004074509 A2 | 9/2004 |
| WO | WO-2005/013901 A2 | 2/2005 |
| WO | WO-2005/017145 A1 | 2/2005 |
| WO | WO-2005/078139 A2 | 8/2005 |
| WO | WO-2005/079397 A2 | 9/2005 |
| WO | WO2005103298 A2 | 11/2005 |
| WO | WO-2005/116261 A2 | 12/2005 |
| WO | WO-2005/118806 A2 | 12/2005 |
| WO | WO-2006/028967 A2 | 3/2006 |
| WO | WO-2006/033928 A2 | 3/2006 |
| WO | WO-2006/101173 A1 | 9/2006 |
| WO | WO-2006/113679 A2 | 10/2006 |
| WO | WO-2006108718 A1 | 10/2006 |
| WO | WO-2006/119365 A2 | 11/2006 |
| WO | WO-2006/128245 A1 | 12/2006 |
| WO | WO-2006/135765 A1 | 12/2006 |
| WO | WO-2006/137941 A2 | 12/2006 |
| WO | WO-2007/016548 A2 | 2/2007 |
| WO | WO-2007/033023 A2 | 3/2007 |
| WO | WO-2007/073737 A1 | 7/2007 |
| WO | WO-2007/081720 A2 | 7/2007 |
| WO | WO-2007/081740 A2 | 7/2007 |
| WO | WO-2007/087113 A2 | 8/2007 |
| WO | WO-2008/014008 A2 | 1/2008 |
| WO | WO-2008/088858 A2 | 7/2008 |
| WO | WO-2008/092099 A2 | 7/2008 |
| WO | WO-2008/095096 A2 | 8/2008 |
| WO | WO-2008/136971 A1 | 11/2008 |
| WO | WO-2008/137867 A2 | 11/2008 |
| WO | WO-2008/154333 A2 | 12/2008 |
| WO | WO-2009/058907 A2 | 5/2009 |
| WO | WO-2009/108856 A2 | 9/2009 |
| WO | WO-2010056737 A2 | 5/2010 |
| WO | WO-2011088309 A1 | 7/2011 |
| WO | WO-2012041959 A1 | 4/2012 |
| WO | WO2012106591 A1 | 5/2012 |
| WO | WO2014143855 A2 | 9/2014 |
| WO | WO2014143855 A3 | 12/2014 |
| WO | WO-2015153757 A1 | 10/2015 |

OTHER PUBLICATIONS

Czauderna et al. Nucleic Acid Res. 31 2705-2716 2003.*
Co-pending U.S. Appl. No. 14/735,046, filed Jun. 9, 2015, Mirna Therapeautics, Inc.
Co-pending U.S. Appl. No. 14/738,646, filed Jun. 12, 2015, Mirna Therapeautics, Inc.
Co-pending U.S. Appl. No. 14/738,706, filed Jun. 12, 2015, Mirna Therapeautics, Inc.
Co-pending U.S. Appl. No. 14/738,716, filed Jun. 12, 2015, Mirna Therapeautics, Inc.
Co-pending U.S. Appl. No. 14/738,728, filed Jun. 12, 2015, Mirna Therapeautics, Inc.
Co-pending U.S. Appl. No. 14/738,734, filed Jun. 12, 2015, Mirna Therapeautics, Inc.
Co-pending U.S. Appl. No. 14/741,064, filed Jun. 12, 2015, Mirna Therapeautics, Inc.
Canadian Office Action for Application No. 2,826,043 mailed Jan. 31, 2015.
Canadian Office Action for Application No. 2,825,981 mailed Jan. 28, 2015.
Chui et al. siRNA function in RNAi: A chemical modification analysis. RNA 9: 1034-1048 (2003).
European Office Action for Application No. 12703943.6 mailed Mar. 12, 2015.
International Search Report, issued in International Application No. PCT/US2014/028006, mailed Dec. 4, 2014.
Japanese Office Action for Application No. 2013-552671 mailed Dec. 24, 2014.
Kalinowski et al. Regulation of epidermal growth factor receptor signaling and erlotinib sensitivity in head and neck cancer cells by miR-7. Plos One 7(10):1-16 (2012).

(56) References Cited

OTHER PUBLICATIONS

Kasinski et al. MicroRNAs en route to the clinic: progress in validating the targeting microRNAs for cancer therapy. Nature Reviews Cancer 11(12):849-864 (2011).
US Office Action for U.S. Appl. No. 13/440,743 mailed May 23, 2014.
US Office Action for U.S. Appl. No. 13/887,008 mailed Jun. 24, 2014.
US Final Office Action for U.S. Appl. No. 13/190,232, mailed Aug. 7, 2014.
US Office Action for U.S. Appl. No. 14/254,532 mailed Oct. 16, 2014.
US Office Action for U.S. Appl. No. 14/459,192 mailed Dec. 5, 2014.
US Office Action for U.S. Appl. No. 14/212,105 mailed Dec. 10, 2014.
US Final Office Action for U.S. Appl. No. 13/440,743 mailed Jan. 9, 2015.
US Office Action for U.S. Appl. No. 13/365,646 mailed Feb. 4, 2015.
US Final Office Action for U.S. Appl. No. 14/459,119 mailed Feb. 5, 2015.
US Office Action for U.S. Appl. No. 14/459,158 mailed Feb. 23, 2015.
US Final Office Action for U.S. Appl. No. 14/459,192 mailed Mar. 10, 2015.
US Office Action for U.S. Appl. No. 13/761,284 mailed Mar. 18, 2015.
US Office Action for U.S. Appl. No. 14/215,669 mailed Apr. 1, 2015.
Wiggens et al. Development of a Lung Cancer Therapeutic Based on the Tumor Suppressor MicroRNA-34. Cancer Research 70(14):5923-5930 (2010).
Zhao et al. In-depth analysis shows synergy between erlotinib and miR-34a. Plos One 9(2):e89105 (2014).
Zhong et al. MicroRNAs reduce tumor growth and contribute to enhance cytotoxicity induced by gefitinib in non-small cell lung cancer. Chemico-Biological Interations. 184(3):431-438 (2010).
Aagaard et al., An inflammatory role for the mammalian carboxypeptidase inhibitor latexin: relationship to cystatins and the tumor suppressor TIG1, Structure (Camb), 13: 309-317 , 2005.
Abuharbeid et al., the fibroblast growth factor-binding protein FGF-BP, Int. J. Biochem. Cell Biol., 38(9):1463-1468 , 2006.
Adams et al., Infrequent mutation of Trail receptor 2 (TRAIL-R2/DR5) in transitional cell carcinoma of the bladder with 8p21loss of heterozygosity, Cancer Lett. 220 (2): 137-144, 2005.
Afanasyeva et al., New miRNAs cloned from neuroblastoma, BMC Genomics, 9(1):52, 2008.
Agrawal and Kandimalla, Antisense therapeutics: is it as simple as complementary base recognition, Molecular Medicine Today, 6:72-81, 2000.
Agrawal and Syngal, Colon cancer screening strategies, Curr Opin Gastroenterol, 21(1):59-63 , 2005.
Aiello et al., Suppression of retinal neovascularization in vivo by inhibition of vascular endothelial growth factor(VEGF) using soluble VEGF-receptor chimeric proteins, Proc. Natl. Acad. Sci. USA. 92(23):10457-10461, 1995.
Aievizos et al., Oral cancer in vivo gene expression profiling assisted by laser capture microdissection and microarray analysis, Oncogene, 20(43):6196-6204, 2001.
Ai-Hajj et al., Prospective identification of tumorigenic breast cancer cells, Proc. Natl. Acad. Sci. US A, 100 (7):3983-8, 2003.
Aitucci and Gronomeyer, Retinoids and Trail: two cooperating actors to fight against cancer, Vitam. Harm., 67:319-345, 2004.
Akao et al., MicroRNAs 143 and 145 are possible common onco-microRNAs in human cancers, Oncology Reports, 16:845-850, 2006.
Akao et al., Bioi Pharm Bull, 29:903-6, 2006.
Akiba et al., Expression and function of interleukin-8 in human hepatocellular carcinoma, Int. J. Oneal., 18 (2):257-264, 2001.
Allawi et al., Quantitation of MicroRNAs using a modified Invader assay, RNA, 10:1153-1161 , 2004.
Altucci and Gronomeyer, The promise ofretinoids to fight against cancer, Nat. Rev. Cancer, 1:181-193 , 2001.
Ambros et al., A uniform system for microRNA annotation, RNA, 9(3):277-279, 2003.
Ambros, microRNAs: tiny regulators with great potential, Cell, 107(7):823-826, 2001.
Anathararnan and Aravind, Evolutionary history, structural features and biochemical diversity of the N1pC/P60 superfamily of enzymes, Genome Biol., 4: R11, 2003.
Ando et al., Polo-like kinase 1 (Plk1) inhibits p53 function by physical interaction and phosphorylation, J. Biol. Chem., 279 (24): 25549-25561, 2004.
Aoki et al., Proteasomal degradation of the Fox01 transcriptional regulator in cells transformed by the P3k and Akt oncoproteins, Proc Natl Aced Sci US A, 101(37):13613-13617, 2004.
Armour et al., Measurement of locus copy number by hybridisation with amplifiable probes, Nucleic Acids Research, 28(2):605-609, 2000.
Association of Directors of Anatomic and Surgical Pathology, Recommendations for the reporting of resected large intestinal carcinomas. Association of directors of anatomic and surgical pathology, Am. J. Clin. Pathol., 106 (1): 12-15,1996.
Astler and Coller, The prognostic significance of direct extension of carcinoma of the colon and rectum, Ann. Surg.,139: 846-852, 1954.
Asuragen, Inc. website, Asuragen's DiscovArray miRNA Expression Profiling Service, located at http://www.asuragen.com/Services/solutions/discovarray.aspx, printed Mar. 6, 2009.
Austin and Cook, Increased expression of Mcl-1 is required for protection against serum starvation in phosphatase and tensin homologue on chromosome 10 null mouse embryonic fibroblasts, but repression of Bim is favored in human glioblastomas, J Biol Chem, 280(39):33280-33288, 2005.
Australian Office Action for Application No. 2005250432, mailed Jun. 10, 2011.
Australian Office Action for Application No. 2005250432, mailed Mar. 29, 2011.
Australian Office Action for Application No. 2005333165, mailed Feb. 7, 2011.
Baba et al., Involvement of deregulated epiregulin expression in tumorigenesis in vivo through activated Ki-Ras signaling pathway in human colon cancer cells, Cancer Res, 60(24):6886-6889 , 2000.
Bader and Vogt, An essential role for protein synthesis in oncogenic cellular transformation, Oncogene, 23 (18):3145-3150, 2004.
Bader et al.. Oncogenic PI3K deregulates transcription and translation, Nat Rev Cancer, 5(12):921-929, 2005.
Bae et al., MCL-1S, a splicing variant of the antiapoptotic BCL-2 family member MCL-1, encodes a proapoptotic protein possessing only the BH3 domain, J. Biol. Chem., 275(33):25255-61, 2000.
Baffa et al., MicroRNA expression profiling of human metastatic cancers identifies cancer gene targets, J. Pathol., Epub Ahead of Print, 2009.
Bagga et al., Cell, 122(4):553-563, 2005.
Bai et al., Downregulation of selective microRNAs in trigeminal ganglion neurons following inflammatory muscle pain, Mol Pain, 3:15 , 2007.
Bandreset al., Identification by Real-time PCR of 13 mature microRNAs differentially expressed in colorectal cancer and non-tumoral tissues, Mol. Cancer, 5:29, 2006.
Bangoura et al., Expression ofHIF-2alpha/EPAS1 in hepatocellular carcinoma, World J. Gastroenterol., 10 (4):525-530, 2004.
Bao et al., Glioma stem cells promote radioresistance by preferential activation of the DNA damage response, Nature, 444(7120):756-60, 2006.
Barnetson et al., Genetic analysis of multiple sporadic colon carcinomas from a single patient, Int J Colorectal Dis, 15:83-86, 2000.
Bartel et al., Alternative and aberrant splicing ofMDM2 mRNA in human cancer, Cancer Cell, 2(1):9-15, 2002.
Bartel, Cell, 116:281-97, 2004.
Bartlett and Davis. Effect of siRNA nuclease stability on the in vitro and in vivo kinetics of siRNA-mediated gene silencing, Biotechnol. Bioeng., 97(4): 909-921, 2007.

(56) References Cited

OTHER PUBLICATIONS

Bartlett et al., Impact of tumor-specific targeting on the biodistribution and efficacy of siRNA nanoparticles measured by multimodality in vivo imaging, 104(39):15549-15554, 2007.
Bartlett et al., Insights into the kinetics of siRNA-mediated gene silencing from live-cell and live-animal bioluminescent imaging, Nucleic Acids Research, 34(1):322-333, 2006.
Barton et al., Angiogenic protein expression in advanced epithelial ovarian cancer, Clin. Cancer Res., 3 (9):1579-1586, 1997.
Basturk et al., MicroRNA expression in androgen independent and metastatic prostate cancer, Modern Pathology, Abstract No. 669, 21 (Suppl. 1): 148A, 2008.
Bedell et al., Amplification of human papillomavirus genomes in vitro is dependent on epithelial differentiation, JViral. 65(5):2254-60, 1991.
Beeram et al., Raf: a strategic target for therapeutic development against cancer, J Clin Oneal, 23(27):6771-6790 , 2005.
Beier et al., CD133(+) and CD133(-) glioblastoma-derived cancer stem cells show differential growth characteristics and molecular profiles, Cancer Res., 67(9):4010-5, 2007.
Bellovin et al., Reciprocal regulation of RhoA and RhoC characterizes the EMT and identifies RhoC as a prognostic marker of colon carcinoma, Oncogene, 25 (52): 6959-6967, 2006.
Bell and Dutta, DNA replication in eukaryotic cells, Annu Rev Biochem, 71:333-374, 2002.
Bello et al., Androgen responsive adult human prostatic epithelial cell lines immortalized by humanpapillomavirus18, Carcinogenesis, 18(6):1215-1223, 1997.
Bendtsen et al., Feature-based prediction of non-classical and leaderless protein secretion, Protein Eng. Des. Sel.,17: 349-356, 2004.
Benlloch et al., Role of CEA, PLUNC and CK19 mRNA expression in lymph nodes from resected stage I non-small cell lung cancer (NSCLC) patients as markers of occult micrometastasis: A pilot study, Lung Cancer, Abstract No. P-649, 49(1):S289, 2005.
Ben-Porath et al., An embryonic stem cell-like gene expression signature in poorly differentiated aggressive human tumors, Nat. Genet., 40(5):499-507, 2008.
Bentwich et al., Identification of hundreds of conserved and nonconserved human microRNAs, Nat Genet., 37 (7):766-770, 2005.
Berezikov et al, Cell, Phylogenetic shadowing and computational identification of human microRNA genes, 120 (1):21-24, 2005.
Berman et al., Medulloblastoma growth inhibition by hedgehog pathway blockade, Science, 297(5586):1559-61 , 2002.
Bertagnolli et al., Sentinel node staging of resectable colon cancer: results of a multicenter study, Ann. Surg., 240 (4):624-630, 2004.
Billottet et al., A selective inhibitor of the p110delta isoform of PI 3-kinase inhibits AML cell proliferation and survival and increases the cytotoxic effects oNP16, Oncogene, 25 (50): 6648-6659, 2006.
Blobe et al., Functional roles for the cytoplasmic domain of the type III transforming growth factor beta receptor in regulating transforming growth factor beta signaling, J Biol Chem, 276(27):24627-24634, 2001.
Birchmeier et al., Met, metastasis, motility and more, Nat Rev Mol Cell Biol, 4(12):915-925, 2003.
Birnie et al., Gene expression profiling of human prostate cancer stem cells reveals a proinflammatory phenotype and the importance of extracellular matrix interactions, Genome Biol., 9(5):R83. [Epub ahead of print], 2008.
Biswas et al., Transforming growth factor beta receptor type II inactivation promotes the establishment and progression of colon cancer, Cancer Res., 64 (14): 4687-4692, 2004.
Bitomsky et al., Transformation suppressor protein Pdcd4 interferes with JNK-mediated phosphorylation of c-Jun and recruitment of the coactivator p300 by c-Jun, Oncogene, 23( 45):7484-93, 2004.
Black et al., Expression of cyclin 01, cyclin E, EGFR, UBE1Land K167 in paired benign and malignant lung tissues, Lung Cancer, 49:S289, Abstract P-650, 2005.
Blanc et al., Wnt-5a gene expression in malignant human neuroblasts, Cancer Lett., 228 (1-2): 117-123 , 2005.
Blower et al., MicroRNAs modualte the chemosensitivity of tumor cells, Mol Cancer Ther, 7(1 ): 1-9, 2008.
Boccaccio and Comoglio, Invasive growth: a MET-driven genetic programme for cancer and stem cells, Nat Rev Cancer, 6(8):637-645, 2006.
Bodner-Adler et al., Serum levels of angiogenin (ANG) in invasive cervical cancer and in cervical intraepithelial neoplasia (GIN), Anticancer Res., 21 (IB): 809-812, 2001.
Bommer et al., p53-mediated activation ofmiRNA34 candidate tumor-suppressor genes, Current Biology,17:1298-1307, mailed 2007.
Bonci et al., The miR-15AimiR-16-1 cluster controls prostate cancer progression by targeting multiple oncogenic activities, European Urology Supplements, Abstract No. 802, 7(3):271, 2008.
Bonci et al., The miR-15a-miR-16-I cluster controls prostate cancer by targeting multiple oncogenic activities, Nature Medicine, 14(11):1271-1277, 2008.
Bosch and de Sanjose. The epidemiology of human papillomavirus infection and cervical cancer. Dis Markers . . . 23 (4):213-27, 2007.
Bostwick et al., Amphiregulin expression in prostatic intraepithelial neoplasia and adenocarcinoma: a study of93 cases, Prostate, 58(2):164-168, 2004.
Bottoni et al., miR-15a and miR-16-1 Down-Regulation in Pituitary Adenomas, J. Cell. Physiol., 204:280-285 , 2005.
Boultwood et al., Low expression of the putative tumour suppressor gene gravin in chronic myeloid leukaemia, myelodysplastic syndromes and acute myeloid leukaemia, Br J Haematol, 126(4):508-511, 2004.
Bourguignon et al., Hyaluronan-CD44 interaction activates stem cell marker Nanog, Stat-3-mediated MDR1 gene expression, and ankyrin-regulated multidrug efflux in breast and ovarian tumor cells, J Biol. Chem., 283(25):17635-51, 2008.
Braasch et al., RNA interference in mammalian cells by chemically-modified RNA, Biochemistry, 42:7967-7975 , 2003.
Brazma and Vilo, Gene expression data analysis, FEES Letters, 480:17-24 , 2000.
Brennecke et al., Bantam encodes a developmentally regulated microRNA that controls cell; proliferation and regulates the proapoptotic gene hid in *Drosophila*, Cell, 113:25-36, 2003.
Brioschi et al., Down-regulation of microRNAs 222/221 in acute myelogenous leukemia with deranged core-binding factor subunits, Neoplasia, 12(11):866-876, 2010.
Brothman et al., Metastatic properties of the human prostatic cell line, PPC-1, in athymic nude mice, JUral., 145 (5):1088-1091, 1991.
Brown and Regillo, Anti-VEGF agents in the treatment of neovascular age-related macular degeneration: applying clinical trial results to the treatment of everyday patients, Am. J Ophthalmol., 144(4):627-637, 2007.
Bullinger et al.. Gene expression profiling in acute myeloid leukemia, Journal of Clinical Oncology, 23 (26):6296-6305, 2005.
Burdy et al., Identifying patients with T3-T4 node-negative colon cancer at high risk of recurrence, Dis Colon Rectum, 44:1682-1688 , 2001.
Bussing et al., let-7 microRNAs in development, stem cells and cancer, Trends in Molecular Medicine, 14 (9):400-409, 2008.
Bustin et al., Real-time reverse transcription PCR (qRT-PCR) and its potential use in clinical diagnosis, Clinical Science, 109:365-379, 2005.
Byrd et al., Pretreatment cytogenetic abnormalities are predictive of induction success, cumulative incidence of relapse, and overall survival in adult patients with de novo acute myeloid leukemia: results from Cancer and Leukemia Group B (CALGB 8461) Blood, 100:4325-4336, 2002.
Cai et al., Human papilloma virus genotype 31 does not express detectable micro RNA levels during latent or productive virus replication, J Viral., 80(21 ): 10890-3, 2006.
Calin and Croce, Genomics of chronic lymphocytic leukemia microRNAs as new players with clinical significance, Seminars in Oncology, 33(2):167-173, 2006.
Calin and Croce, MicroRNA-cancer connection: the beginning of a new tale, Cancer Res., 66 (15):7390-7394, 2006.

(56) References Cited

OTHER PUBLICATIONS

Calin and Croce, MicroRNAs and chromosomal abnormalities in cancer cells, Oncogene, 25 (46):6202-6210, 2006.
Calin and Croce, Nat Rev Cancer, 6(11):857-866, 2006.
Calin et al., A MicroRNA signature associated with prognosis and progression in chronic lymphocytic leukemia, New England Journal of Medicine, 353(17):1793-1801, 2005.
Calin et al., Frequent deletions and down-regulation of micro-RNA genes miR15 and miRI6 at 13q14 in chronic lymphocytic leukemia, Proc Natl A cad Sci; 99: 15524-15529; 2002.
Calin et al., MicroRNA profiling reveals distinct signatures in B cell chronic lymphocytic leukemias, Proc Natl A cad Sci USA, 101(32): 11755-11760, 2004.
Calin et al., Proc Natl Acad Sci USA, 101(9):2999-3004, 2004.
Campochiaro and Hackett, Ocular neovascularization: a valuable model system, Oncogene, 22(42):6537-6548, 2003.
Cao et al., A functional study ofmiR-124 in the developing neural tube, Genes & Development, 21(5):531-536, 2007.
Carrano et al., SKP2 is required for ubiquitin-mediated degradation of the CDK inhibitor p27, Nat. Cell. Biol, 1 (4):193-199, 1999.
Carreiras et al., Expression and localization of alpha v integrins and their ligand vitronectin in normal ovarian epithelium and in ovarian carcinoma, Gynecol. Oncol., 62 (2): 260-267, 1996.
Carreiras et al., Human ovarian adenocarcinoma cells synthesize vitronectin and use it to organize their adhesion, Gynecol. Oncol., 72 (3): 312-322, 1999.
Carrington et al., Science, 301:336-8, 2003.
Carter and Brunet, FOXO transcription factors, Curr Biol, 17(4):R113-114, 2007.
Casanova et al., The class II tumor-suppressor gene RARRES3 is expressed in B cell lymphocytic leukemias and down-regulated with disease progression, Leukemia, 15 (10): 1521-1526, 2001.
Caselitz et al., Malignant melanomas contain only the vimentin type of intermediate filaments, Virchows Arch A Pathol Anat Histopathol, 400(1):43-51, 1983.
Castillo et al., Amphiregulin contributes to the transformed phenotype of human; hepatocellular carcinoma cells, Cancer Res., 66(12):6129-6138, 2006.
Caudy et al., Fragile X-related protein and VIG associate with the RNA interference; machinery, Genes & Development. 16:2491-2496; 2002.
Chan et al., Downregulation of ID4 by promoter hypermethylation in gastric; adenocarcinoma, Oncogene, 22 (44):6946-6953, 2003.
Chan et al., MicroRNA-21 is an antiapoptotic factor in human glioblastoma cells, Cancer Res., 65(14):6029-6033, 2005.
Chandler et al., Prevalent expression of fibroblast growth factor (FGF) receptors and FGF2 in human tumor cell lines, Int. J. Cancer, 81(3):451-458, 1999.
Chang et al. Mol. Cell, 26: 745-752, 2007.
Chang et al., Elevated circulating level of osteopontin is associated with advanced disease state of non-small cell lung cancer, Lung Cancer, 57(3):373-380, 2007.
Chang et al., MicroRNAs act sequentially and asymmetrically to control chemosensory; laterality in the nematode, Nature, 430(7001):785-789, 2004.
Chen et al., Identification of trophinin as an enhancer for cell invasion and a prognostic factor for early stage lung cancer, European Journal of Cancer, 43(4):782-790, 2007.
Chen et al., Loss ofPDCD4 expression in human lung cancer correlates with tumour progression and prognosis, J. Pathol., 200(5):640-646, 2003.
Chen et al., MicroRNAs modulate hematopoietic lineage differentiation, Science,; 303(5654):83-86, 2004.
Chen et al., Real-time quanitfication of microRNAs by stem-loop RT-PCR, Nucleic Acids Research, 33(20): e179 (13 printed pages), 2005.
Chendrimada et al.. MicroRNA silencing through RISC recruitment of eiF6. Nature. 447(7146):823-828, 2007.

Cheng et al., Antisense inhibition of human miRNAs and indications for an involvement of miRNA in cell growth and apoptosis, Nucleic Acids Res., 33(4):1290-1297, 2005.
Chiarelli et al., Gene expression profiling identifies a subset of adult T-cell acute lymphoblastic leukemia with myeloid-like gene features and over-expression ofmiR-223, Haematologica, 95(7):1114-1121, 2010.
Chieffi et al., Aurora B expression directly correlates with prostate cancer malignancy and influence prostate cell proliferation, Prostate, 66(3):326-333, 2006.
Chirila et al., The use of synthetic polymers for delivery of therapeutic antisense oligodeoxynucleotides, Biomaterials, 23:321-342, 2002.
Chmielarz et al., Prognostic factors for the time of occurrence and dynamics of distant metastases and local recurrences after radical treatment in patients with rectal cancer, Med Sci Manit., 7(6):1263-1269, 2001.
Choi et al., AKAP12/Gravin is inactivated by epigenetic mechanism in human gastric carcinoma and shows growth suppressor activity, Oncogene, 23(42):7095-7103, 2004.
Churg, Immunohistochemical staining for vimentin and keratin in malignant mesothelioma, Am J Surg Pathol, 9 (5):360-365, 1985.
Ciafre et al., Extensive modulation of a set of microRNAs in primary glioblastoma, Biochem. Biophys. Res. Commun., 334(4):1351-1358, 2005.
Cimmino et al., miR-15 and miR-16 induce apoptosis by targeting BCL2, Proceedings of the National Academy of Sciences of the USA, 102(39):13944-13949, 2005.
Ciocca et al., Heat shock portein hsp70 in patients with axillary lymph node-negative breast cancer: Prognostic implications, Journal of the National Cancer Institute, 85(7):570-574, 1993.
Cipriano and Chen, Insensitivity to growth inhibition by TGF-betal correlates with a lack of inhibition of the CD K2 activity in prostate carcinoma cells, Oncogene, 17 (12): 1549-15 56, 1998.
Claudio et al., Expression of cell-cycle-regulated proteins pRb2/p130, p107, p27 (kip1), p53, mdm-2, andKi-67 (MIB-1) in prostatic gland adenocarcinoma, Clin Cancer Res, 8(6):1808-1815, 2002.
Clement et al., Hedgehog-GLil signaling regulates human glioma growth, cancer stem cell self-renewal, and tumorigenicity, Curr. Biol., 17(2): 165-72, 2007.
Clifford et al., Human papilloma virus types in invasive cervical cancer worldwide: a metaanalysis, Br. J Cancer, 88 (1):63-73, 2003.
Coello et al., Prognostic significance of micrometastasis in non-small-cell lung cancer, Clin. Lung Cancer,5:214-225, 2004.
Cogliano et al., Carcinogenicity of human papillomaviruses, Lancet Oneal., 6(4):204, 2005.
Cohen et al., Expression of a down-regulated target, SSeCKS, reverses v-Jun-induced transformation of 10TI/2 murine fibroblasts, Oncogene, 20(2):141-146, 2001.
Cohen et al., Prognosis of node-positive colon cancer, Cancer, 67(7):1859-1861, 1991.
Coleman et al., Superior 5' homogeneity of RNA from ATP-initiated transcription under T7 phi 2.5 promoter, Nucleic Acids Research, 32(1):e14, 2004.
Coli et al., Molecular cloning of the avian acute transforming retrovirus MH2 reveals a novel cell-derived sequence(v-mil) in addition to the myc oncogene, Embo J, 2(12):2189-2194, 1983.
Collins et al., Prospective identification of tumorigenic prostate cancer stem cells. Cancer Res. 65(23):10946-51, 2005.
Conaco et al., Reciprocal actions of Rest and a microRNA promote neuronal identity, PNAS, 1 03(7):2422-2427, 2006.
Cooper et al., Molecular cloning of a new transforming gene from a chemically transformed human cell line, Nature,311(5981):29-33, 1984.
Costello et al., Cyclin-dependent kinase 6 (CDK6) amplification in human gliomas identified using two-dimensional separation of genomic DNA, Cancer Res, 57(7):1250-1254, 1997.
Costinean et al., Pre-B cell proliferation and lymphoblastic leukemia/high-grade lymphoma in Ej..L-miR155 transgenic mice, Proc. Natl. Acad. Sci. USA, 103(18):7024-7029, 2006.
Cox et al., Significance of sentinel lymph node micrometastases in human breast cancer, J. Am. Coli. Surg., 206 (2):261-268, 2008.

(56) References Cited

OTHER PUBLICATIONS

Cox, Epidemiology and natural history of HPV, J. Fam. Pract., Suppl:3-9, 2006.
Craig et al., Myc-mediated repression of microRNA-34a promotes high-grade transformation of B-celllymphoma by dysregulation of FoxP1. Blood, 117(23):6227-36, 2011.
Crnogorac-Jurcevic et al., Proteomic analysis of chronic pancreatitis and pancreatic adenocarcinoma, Gastroenterology, 129:1454-1463, 2005.
Croci et al., Inhibition of connective tissue growth factor (CTGF/CCN2) expressiop. Decreases the survival and myogenic differentiation of human rhabdomyosarcoma cells, Cancer Res., 64(5): 1730-1736, 2004.
Crooke, Progress in antisense technology, Annu. Rev. Med., 55:61-95, 95427772.1, 2004.
Cross et al., 25-Hydroxyvitamin D (3)-1alpha-hydroxylase and vitamin D receptor gene expression in human colonic mucosa is elevated during early cancerogenesis, Steroids, 66: 287-292, 2001.
Cully et al., Transforming acidic coiled coil1 promotes transformation and mannnary tumorigenesis, Cancer Res.,65(22):10363-10370, 2005.
Cummins and Velculescu, Implications of micro-RNA profiling for cancer diagnosis, Oncogene, 25(46):6220-6227, 2006.
Cummins et al., The colorectal microRNAome, Proc. Natl. Acad. Sci. USA, 103(10):3687-3692, 2006.
Dahl et al., Identification of sentinel nodes in patients with colon cancer, Eur. J. Surg. Oneal., 31(4):381-385, 2005.
Dai et al., Prostate cancer induces bone metastasis through Wnt-induced bone morphogenetic protein-dependent and independent mechanisms, Cancer Res., 68(14): 5785-94, 2008.
Danilkovitch-Miagkova and Zbar, Dysregulation of Met receptor tyrosine kinase activity in invasive tumors, J Clin Invest, 109(7):863-867, 2002.
D'Antonio et al., Transforming growth factor alpha, amphiregulin and cripto-1 are frequently expressed in advanced human ovarian carcinomas, Int. J Oncol., 21(5):941-948, 2002.
Database EMBL, Human DNA related to regulating mammalian cells using miRNAs Seq 471, EBI Database Accession No. ADR83569, Dec. 2, 2004.
Davalos et al., High EPHB2 mutation rate in gastric but not endometrial tumors with microsatellite instability, Oncogene, 26 (2): 308-311, 2006.
Davis et al., Modeling of repeated-batch transcription for production of RNA, Journal of Biotechnology, 71:25-37, 1999.
Davison et al., Analyzing micro-RNA expression using microarrays, Meth. Enzymol., 411:14-34, 2006.
D'Cunha et al., Poor correspondence between clinical and pathologic staging in stage 1 nonsmall cell lung cancer: results from CALGB 9761, a prospective trial, Lung Cancer, 48:241-246, 2005.
De Boer et al., Micrometastases and isolated tumor cells: relevant and robust or rubbish? (MIRROR): preliminary results of the MIRROR study from the Dutch breast cancer trialists' group (BOOG), San Antonio Breast Cancer Symposium, Abstract 23, 2008.
De Candia et al., Id4 messenger RNA and estrogen receptor expression: inverse correlation in human normal breast epithelium and carcinoma, Hum. Pathol., 37 (8): 1032-1041, 2006.
Dean et al., The human met oncogene is related to the tyrosine kinase oncogenes, Nature, 318(6044):385-388, 1985.
Decision on Appeal, Appeal2008-002253, issued in U.S. Appl. No. 10/880,350, decided May 29, 2009.
Declaration of Dr. David P. Bartel under37 C.F.R. 1.132, submitted in U.S. Appl. No. 10/913,288, 2009.
DeNigris et al., Induction of ETS-1 and ETS-2 transcription factors is required for thyroid cell transformation, Cancer Res., 61 (5): 2267-2275, 2001.
Denli and Hannon., RNAi: an ever-growing puzzle, Trends Biochem. Sci., 28:196, 2003.
Devine et al., Serum markers CASA, CEA, CYFRA, TPS, and NSE in lung cancer, Lung Cancer, Abstract, 11:37,1994.

Dews et al., Augmentation of tumor angiogenesis by a Myc-activated microRNA cluster, Nat. Genet., 38 (9):1060-1065, 2006.
Diederichs and Haber, Sequence variations of microRNAs in human cancer: Alterations in predicted secondary structure do not affect processing, Cancer Res., 66(12):6097-6104, 2006.
Dillon et al., An April to remember: novel TNF; ligands as therapeutic targets. Nat. Rev Drug Discov., 5 (3):235-46, 2006.
DiSepio et al., Identification and characterization of a retinoid-induced class II tumor suppressor/growth regulatory gene, Proc. Natl. Acad. Sci. USA, 95: 14811-14815, 1998.
Dittmer, The biology of the Ets1 proto-oncogene, Mol Cancer, 2:29, 2003.
Doench and Sharp Specificity ofmicroRNA target selection in translational repression, Genes Dev, 18(5):504-11, 2004.
Doench et al.. siRNAs can function as miRNAs. Genes & Dev. 17:438-442, 2003.
Dong et al., Telomerase: regulation, function and transformation, Grit Rev Oneal Hematol. 54(2):85-93, 2005.
Donnellan and Chetty, Cyclin DI and human neoplasia, Mol Pathol, 51(1):1-7, 1998.
Dontu et al., In vitro propagation and transcriptional profiling of human mammary stem/progenitor cells, Genes Dev., 17:1253-70, 2003.
Dostie et al., RNA 2003;9(2):180-6.
Doyle and Ross, Multidrug resistance mediated by the breast cancer resistance protein BCRP (ABCG2), Oncogene, 22(47):7340-58, 2003.
Droge and Davey, Do cells let-7 determine sternness? Cell Stem Cell, 2(1):8-9, 2008.
D'Souza et al., Case-control study of human papillomavirus and oropharyngeal cancer, New Engl. J. Med., 356:1944-1956, 2007.
Duvic et al., Expression of a retinoid-inducible tumor suppressor, tazarotene-inducible gene-3 is decreased in psoriasis and skin cancer, Clin. Cancer Res., 6 (8): 3249-3259, 2000.
Duvic et al., Tazarotene-induced gene 3 is suppressed in basal cell carcinomas and reversed in vivo by tazarotene application, J Invest. Dermatol., 121:902-909, 2003.
Dyer and Bremner, The search for the retinoblastoma cell of origin, Nat Rev Cancer, 5(2):91-101, 2005.
Dylla et al., Colorectal cancer stem cells are enriched in xenogeneic tumors following chemotherapy, PLoS One, 3 (6):e2428, 13 pages, 2008.
Ebert et al., Induction and expression of amphiregulin in human pancreatic cancer, Cancer Res., 54(15):3959-3962, 1994.
Eferl et al., Liver tumor development. c-Jun antagonizes the proapoptotic activity ofp53, Cell, 112 (2):181-192, 2003.
Egle et al., Bim is a suppressor of Myc-induced mouse B cell leukemia, Proc Natl Acad Sci US A, 101 (16):6164-6169, 2004.
Egloff et al., Cyclin B 1 and other cyclins as tumor antigens in immunosurveillance and immunotherapy of cancer, Cancer Res, 66(1):6-9, 2006.
Einama et al., High-level Skp2 expression in pancreatic ductal adenocarcinoma: correlation with the extent of lymph node metastasis, higher histological grade, and poorer patient outcome, Pancreas, 32(4):376-381, 2006.
Engelmann et al., MCF7 side population cells with characteristics of cancer stem/progenitor cells express the tumor antigen MUC1, Cancer Res., 68(7):2419-26, 2008.
Esau et al., Micro RNA-143 regulates adipocyte differentiation, Journal of Biological Chemistry, 279 (50):52361-52365, 2004.
Esquela-Kerscher et al., Cell Cycle, 7:759-64, 2008.
Esser et al., The role of sentinel lymph node mapping in staging of colon and rectal cancer, Dis Colon Rectum, 44 (6):850-856, 2001.
European Office Action for Application No. 07814937, issued Apr. 8, 2011.
European Office Action for Application No. 09154092, issued Mar. 30, 2011.
European Office Communication for Application No. 05858321.2, issued Oct. 18, 2013. (5 pages).
European Office Communication for Application No. 10183577.5, issued Jul. 27, 2012. (7 pages).

(56) References Cited

OTHER PUBLICATIONS

European Search Report and Search Opinion issued in European Application No. 09154092.2, mailed Aug. 12, 2009. (ASUR:007EPD1).
European Search Report for Application No. 10183525.4, issued Feb. 7, 2011. (6 pages).
European Search Report for Application No. 10183543.7, issued Feb. 4, 2011. (6 pages).
European Search Report for Application No. 10183560.1 issued Jan. 7, 2011. (6 pages).
European Search Report for Application No. 10183567.6 issued Jan. 7, 2011. (7 pages).
European Search Report for Application No. 10183577.5, issued Feb. 14, 2011. (7 pages).
Extended European Search Report issued in European Application No. 10181713.8, mailed Jun. 24, 2011.
Extended European Search Report issued in European Application No. 10181728.6, mailed Jul. 8, 2011.
Extended European Search Report issued in European Application No. 10181821.9, mailed Jul. 29, 2011.
Extended European Search Report issued in European Application No. 10183451.3, mailed Jan. 12, 2011.
Extended European Search Report issued in European Application No. 10183456.2, mailed Jan. 12, 2011.
Extended European Search Report issued in European Application No. 10183462.0, mailed Feb. 4, 2011.
Extended European Search Report issued in European Application No. 10183470.3, mailed Feb. 3, 2011.
Extended European Search Report issued in European Application No. 10183481.0, mailed Jan. 7, 2011.
Extended European Search Report issued in European Application No. 10183490.1, mailed Feb. 4, 2011.
Extended European Search Report issued in European Application No. 10183515.5, mailed Feb. 7, 2011.
Extended European Search Report issued in European Application No. 10183534.5, mailed Feb. 15, 2011.
Extended European Search Report issued in European Application No. 10183538.7, mailed Jan. 12, 2011.
Extended European Search Report issued in European Application No. 10183589.0, mailed Jan. 7, 2011.
Extended European Search Report issued in European Application No. 10183596.5, mailed Feb. 14, 2011.
Extended European Search Report issued in European Application No. 10183611.2, mailed Jan. 7, 2011.
Extended European Search Report issued in European Application No. 10183639.3, mailed Mar. 2, 2011.
Ezzat et al., Dual inhibition of RET and FGFR4 restrains medullary thyroid cancer cell growth, Clin. Cancer Res., 11 (3): 1336-1341, 2005.
Fakharzadeh et al., Tumorigenic potential associated with enhanced expression of a gene that is amplified in a mouse tumor cell line, EmboJ, 10(6):1565-1569, 1991.
Fan et al., Hedgehog signaling promotes prostate xenograft tumor growth, Endocrinology, 145:3961-3970, 2004.
Fan et al., Notch pathway inhibition depletes stem-like cells and blocks engraftment in embryonal brain tumors, Cancer Res., 66(15): 7445-52, 2006.
Faried et al., RhoA and RhoC proteins promote both cell proliferation and cell invasion of human oesophageal squamous cell carcinoma cell lines in vitro and in vivo, Eur. J. Cancer, 42 (10): 1455-1465, 2006.
Fay et al., Analysis ofCUL-5 expression in breast epithelial cells, breast cancer cell lines, normal tissues and tumor tissues, Mol. Cancer, 2:40, 2003.
Fazi et al., A minicircuitry comprised ofmicroRNA-223 and transcription factors NFI-A and C/EBPa regulates human granulopoiesis, Cell, 123:819-831, 2005.
Feldman and Feldman, The development of androgen-independent prostate cancer, Nat. Rev. Cancer, 1(1):34-45, 2001.

Fernandez et al., The matrix metalloproteinase-9/neutrophil gelatinase-associated lipocalin complex plays a role in breast tumor growth and is present in the urine of breast cancer patients, Clin. Cancer Res., 11(15):5390-5395, 2005.
Ferris et al., Molecular staging of cervical lymph nodes in squamous cell carcinoma of the head and neck, Cancer Res., 65:2147-2156, 2005.
Fesik, Promoting apoptosis as a strategy for cancer drug discovery, Nat Rev Cancer, 5(11):876-885, 2005.
Firth and Baxter, Cellular actions of the insulin-like growth factor binding proteins, Endocrin. Rev., 23 (6): 824-854, 2002.
Folkman, Successful treatment of an angiogenic disease, N Engl J Med 320:1211-1212, 1989.
Fontana et al, MicroRNA's 17-5p-20a-106a control monocytopeiesis through AMLI targeting and M-CSF receptor upregulation, Nature Cell Biology, 9(7):775-787, 2007.
Francipane et al., Crucial role of interleukin-4 in the survival of colon cancer stem cells, Cancer Res., 68 (11):4022-4025, 2008.
Freelove and Walling, Pancreatic cancer: diagnosis and management, Am. Fam. Physician, 73(3):485-492, 2006.
Fujiwara et al., Isolation of a candidate tumor suppressor gene on chromosome 8p21.3-p22 that is homologous to an extracellular domain of the PDGF receptor beta gene, Oncogene, 10(5):891-895, 1995.
Galardi et al., rniR-221 and rniR-222 expression affects the proliferation potential of human prostate carcinoma cell lines by targeting p27Kip1, J. Biol. Chem, 282(32):23716-23724, 2007.
Gao et al., Frequent loss ofPDCD4 expression in human glioma: possible role in the tumorigenesis of glioma, Oneal. Rep., 17(1):123-128, 2007.
Garzon et al., MicroRNA fingerprints during human megakaryocytopoiesis, Proc. Natl. Acad. Sci. USA, 103 (13):5078-5083, 2006.
Garzon et al., MicroRNA signatures associated with cytogenetics and outcome in acute myeloid leukemia. Session Type: Oral Session, Blood, 108(11): 49A, Abstract #151, 2006.
Geary et al., The Journal of Pharmacology and Experimental Techniques 294, pp. 890-897, 2001.
Gerald and Haber, The EWS-WTI gene fusion in desmoplastic small round cell tumor, Semin Cancer Biol, 15 (3):197-205, 2005.
Giannakakis et al., miRNA genetic alterations in human cancers, Expert opinion on biological therapy, 7 (9):1375-1386, 2007.
Gillanders et al., Molecular detection of micrometastatic breast cancer in histopathologynegative axillary lymph nodes correlates with traditional predictors of prognosis: an interim analysis of a prospective multi-institutional cohort study, Ann. Surg., 239:828-840, 2004.
Gilles et al., Vimentin expression in cervical carcinomas: association with invasive and migratory potential, J Pathol, 180(2):175-180, 1996.
Ginestier et al., ALDH1 is a marker of normal and malignant human mammary stem cells and a predictor of poor clinical outcome, Cell Stem Cell, 1(5):555-567, 2007.
Gipponi et al., Sentinel lymph node as a new marker for therapeutic planning in breast cancer patients, J. Surg. Oneal., 85(3):102-111, 2004.
Goke et al., Programmed cell death protein 4 suppresses CDK1/cdc2 via induction of p21(Wafi/Cip1),Am. J. Physiol. Cell Physiol., 287(6):C1541-6, 2004.
Gomez-Bougie et al., The imbalance between Bim and Mcl-1 expression controls the survival of human myeloma cells, EurJ Immunol, 34(11):3156-3164, 2004.
Gonzalez et al., Oncogenic activity ofCdc6 through repression of the INK.4/ARF locus, Nature, 440(7084):702-706, 2006.
Goodell et al., Isolation and functional properties of murine hematopoietic stem cells that are replicating in vivo, J Exp. Med., 183(4):1797-806, 1996.
Goyns et al., The c-ets-1 proto-oncogene is rearranged in some cases of acute lymphoblastic leukaemia, Br J Cancer, 56(5):611-613, 1987.
Grandori et al., The Myc/Max/Mad network and the transcriptional control of cell behavior, Annu. Rev. Cell. Dev. Biol., 16: 653-699, 2000.

(56) References Cited

OTHER PUBLICATIONS

Grenier et al., Cyfra 21-1, a new marker for lung cancer, Nucl. Med. Bioi., 21(3):471-476, 1994.
Griffiths-Janes et al., Nucleic Acids Res., 34:D140-D144, 2006.
Griffiths-Jones et al., miRBase: tools for microRNA genomics, Nucl. Acids Res., 36 (Database Issue):D154-D158, 2008.
Grimwade, The clinical significance of cytogenetic abnormalities in acute myeloid leukaemia, Best. Pract. Res. Clin. Haematol., 14:497-529, 2001.
Grishok et al., Genes and mechanisms related to RNA interference regulate expression of the; small temporal RNAs that control C. elegans developmental timing, Cell, 106:23-34, 2001.
Grosshans et al., The temporal patterning microRNA let-7 regulates several transcription factors at the larval to adul transition in C. elegans, Dev. Cell, 8(3):321-330, 2005.
Gstaiger et al., Skp2 is oncogenic and overexpressed in human cancers, Proc. Natl. Acad. Sci. USA, 98 (9):5043-5048, 2001.
Gu et al., Prostate cancer cells with stem cell characteristics reconstitute the original human tumor in vivo, Cancer Res., 67(10):4807-15, 2007.
Guda and Subramaniam, Target: a new method for predicting protein subcellular localization in eukaryotes, Bioinformatics, 21: 3963-3969, 2005.
Guo et al.. Reduced expression of EphB2 that parallels invasion and metastasis in colorectal tumours. Carcinogenesis. 27(3):454-464, 2006.
Gurevich, Preparative in vitro mRNA synthesis using SP6 and T7 RNA polymerases, Anal Biochem., 195 (2):207-213, 1991.
Ha et al., A bulged lin-4/lin-14 RNA duplex is sufficient for Caenorhabditis elegans lin-14 temporal gradient formation, Genes Dev., 10,3041-3050, 1996.
Hajnal et al., Subtaction cloning ofH-rev107, a gene specifically expressed in H-ras resistant fibroblasts, Oncogene,9: 479-490, 1994.
Hamamura et al., Ganglioside GD3 promotes cell growth and invasion through p 130Cas and paxillin in malignant melanoma cells, Proc Natl Acad Sci US A, 102(31):11041-11046, 2005.
Hambardzumyan et al., PI3K pathway regulates survival of cancer stem cells residing in the perivascular niche following radiation in medulloblastoma in vivo, Genes Dev., 22(4):436-48, 2008.
Han et al., Cyclin D I expression in human prostate carcinoma cell lines and primary tumors, The Prostate,35:95-101, 1998.
Hanahan and Weinberg, The hallmarks of cancer, Cell, 100(1):57-70, 2000.
Hannigan et al., Integrin-linked kinase: a cancer therapeutic target unique among its ILK, Nat Rev Cancer, 5 (1):51-63, 2005.
Hardenbol et al., Multiplexed genotyping with sequence-tagged molecular inversion probes, Nat Biotechnol, 21 (6):673-678, 2003.
Harfe, MicroRNAs in vertebrate development, Curr. Opin. Genet. Dev., 15(4):410-5, 2005.
Hartmann et al., Hypoxia-induced up-regulation of angiogenin in human malignant melanoma, Cancer Res., 59 (7):1578-1583, 1999.
Hayashita et al., A polycistronic micro RNA cluster, miR-17-9 2, is overexpressed in human lung cancers and enhances cell proliferation, Cancer Res., 65(21):9628-9632, 2005.
Hayette et al., In B-cell chronic lymphocytic leukemias, 7q21 translocations lead to overexpression ofthe CDK6 gene, Blood, 102(4):1549-1550, 2003.
He et al., A microRNA component of the p53 tumour suppressor network, Nature, 447(7148):1130-1134, 2007.
He et al., A microRNA polycistron as a potential human oncogene, Nature, 435(7043):828-833, 2005.
He et al., The role of microRNA genes in papillary thyroid carcinoma, Proc. Natl. Acad. Sci. USA, 102 (52):19075-19080, 2005.
Hermann et al., Distinct populations of cancer stem cells determine tumor growth and metastatic activity in human pancreatic cancer, Cell Stem Cell, 1(3):313-23, 2007.
Hermeking, p53 enters the microRNA world, Cancer Cell, 12(5):414-418, 2007.

Hirschmann-Jax et al., A distinct side population of cells with high drug efflux capacity in human tumor cells, Proc. Natl. Acad. Sci. USA, 101:14228-33, 2004.
Hishikawa et al., Connective tissue growth factor induces apoptosis in human breast cancer cell line MCF-7, J. Biol. Chem., 274(52):37461-37466, 1999.
Ho et al., MDR1 and BCRP1 expression in leukemic progenitors correlates with; chemotherapy response in acute myeloid leukemia, Exp. Hematol., 36(4): 433-42, 2008.
Ho et al., Quantification of colorectal cancer micrometastases in lymph nodes by nested and real-time reverse transcriptase-PCR analysis for carcinoembryonic antigen, Clin. Cancer Res., 10(17):5777-5784, 2004.
Hodge et al., The role of IL-6 and STAT3 in inflammation and cancer, Eur J Cancer, 41(16):2502-2512, 2005.
Hoeflich et al., Insulin-like growth factor-binding protein 2 in tumorigenesis: protector or promoter? Cancer Res, 61 (24):8601-8610, 2001.
Hofer et al., The role of metastasis-associated protein 1 in prostate cancer progression, Cancer Res, 64 (3):825-829, 2004.
Holmquist-Mengelbier et al., Recruitment ofHIF-1alpha and HIF-2alpha to common target genes is differentially regulated in neuroblastoma: HIF-2alpha promotes an aggressive phenotype, Cancer Cell, 10(5):413-423, 2006.
Honma et al., The role of atelocollagen-based cell transfection array in high-throughput screening of gene functions and in drug discovery, Current Drug Discovery Technologies, 1(4):287-294, 2004.
Hornstein et al., The microRNA mir-196 acts upstream ofHoxb8 and Shh in limb; development, Nature, 438:671-674, 2005.
Horoszewicz et al., The LNCaP cell line—a new model for studies on human prostatic carcinoma, Prog Clin Biol Res., 37:115-32, 1980.
Houbaviy et al., Embryonic stem cell-specific micro-RNAs, Developmental Cell, 5:351-358, 2003.
Houston and O'Connell, The Fas signalling pathway and its role in the pathogenesis of cancer, Curr Opin Pharmacal, 4(4):321-326, 2004.
Houvenaeghel et al., Micrometastases in sentinel lymph node in a multicentric study: predictive factors of nonsentinellymph node involvement—Groupe des Chirurgiens de la Federation des Centres de Lotte Contre le Cancer, J. Clin. Oncol., 24:1814-1822 , 2006.
Hsu et al., BOD (Bcl-2-related ovarian death gene) is an ovarian BH3 domain-containing proapoptotic Bcl-2 protein capable of dimerization with diverse antiapoptotic Bcl-2 members, Mol Endocrinol, 12(9):1432-1440, 1998.
Huang et al., Cloning and characterization of a novel retinoid-inducible gene 1 (RIG 1) deriving from human gastric cancer cells, Mol. Cell. Endocrinol., 159: 15-24 , 2000.
Huang et al., Skp2 inhibits FOX01 in tumor suppression through ubiquitin-mediated degradation, Proc. Natl. Acad. Sci. USA, 102(5):1649-1654, 2005.
Huang et al., Skp2 overexpression is highly representative of intrinsic biological; aggressiveness and independently associated with poor prognosis in primary localized myxofibrosarcomas, Clin. Cancer Res., 12 (2): 487-498, 2006.
Huang et al., The retinoid-inducible gene 1: effect on apoptosis and mitogen-activated kinase signal pathways, Anticancer Res., 22: 799-804, 2002.
Huang et al., Wnt5a expression is associated with the tumor proliferation and the stromal vascular endothelial growth factor—an expression in non-small-cell lung cancer, J. Clin. Oncol., 23 (34): 8765-8773, 2005.
Huber et al., Variance stabilization applied to microarray data calibration and to the quantification of differential expression, Bioinformatics, 18:Suppl1:S96-104, 2002.
Hughes et al., A rapid, fully automated, molecular-based assay accurately analyzes sentinel lymph nodes for the presence of metastatic breast cancer, Ann. Surg., 243:389-398, 2006.
Human miRNA targets, for mmu-miR-126-3p Apr. 2005 version, accessed and retrieved from miRanda webserver at www.microRNA.org and http://cbio.mskcc.org/cgi-bin/mimaviewer, p. 1 of the 23 print-out pages included, 2009.

(56) References Cited

OTHER PUBLICATIONS

Hummel et al., Differentiation-induced and constitutive transcription of human papillomavirus type 31 bin cell lines containing viral episomes, J Viral., 66(10):6070-80, 1992.
Hurt et al., CD44+ CD24(-) prostate cells are early cancer progenitor/stem cells that provide a model for patients with poor prognosis, Br. J Cancer, 98(4):756-65, 2008.
Hutvagner and Zamore, A microRNA in a multiple-turnover RNAi enzyme complex, Science, 297(5589):2056-2060, 2002.
Hutvagner et al., Sequence-specific inhibition of small RNA function, PLoS Biol. 2(4):E98, 2004.
Huusko et al, Nonsense-mediated decay microarray analysis identifies mutations ofEPHB2 in human prostate cancer, Nat. Genet., 36 (9): 979-983, 2004.
Hynes and Lane, ERBB receptors and cancer: the complexity of targeted inhibitors, Nat Rev Cancer, 5(5):341-354, 2005.
Ibarra et al., A role for microRNAs in maintenance of mouse mammary epithelial progenitor cells, Genes Dev., 21 (24):3238-3243, 2007.
International Preliminary Report on Patentability and Written Opinion issued in; International Application No. PCT/US2008/080318, mailed Apr. 29, 2010.
International Preliminary Report on Patentability and Written Opinion, issued in; International Application No. PCT/US2007/086396, mailed Jun. 18, 2009.
International Preliminary Report on Patentability and Written Opinion, issued in; International Application No. PCT/US2007/087021, mailed Jun. 18, 2009.
International Preliminary Report on Patentability and Written Opinion, issued in; International Application No. PCT/US2007/087037, mailed Jun. 18, 2009.
International Preliminary Report on Patentability and Written Opinion, issued in; International Application No. PCT/US2007/087038, mailed Jun. 18, 2009.
International Preliminary Report on Patentability and Written Opinion, issued in; International Application No. PCT/US2007/089206, mailed Jun. 18, 2009.
International Preliminary Report on Patentability issued in International Application No. PCT/US2007/078952, mailed Feb. 11, 2010.
International Preliminary Report on Patentability issued in International Application No. PCT/US2008/066025, mailed Dec. 23, 2009.
International Preliminary Report on Patentability issued in International Application No. PCT/US2008/076246, mailed Mar. 16, 2010.
International Preliminary Report on Patentability issued in International Application No. PCT/US2009/033556, mailed Aug. 19, 2010.
International Preliminary Report on Patentability issued in International Application No. PCT/US2009/036195, mailed Sep. 16, 2010.
International Preliminary Report on Patentability issued in International Application No. PCT/US2009/038399, mailed Oct. 7, 2010.
International Preliminary Report on Patentability issued in International Application No. PCT/US2009/039935, mailed Oct. 21, 2010.
International Preliminary Report on Patentability issued in International Application No. PCT/US2009/043361, mailed Nov. 18, 2010.
International Search Report and Written Opinion issued in International Application No. PCT/US2009/036195, mailed Sep. 4, 2009.
International Search Report and Written Opinion issued in International Application No. PCT/US2009/038399, mailed Mar. 3, 2010.
International Search Report and Written Opinion issued in International Application No. PCT/US2009/039935, mailed Sep. 17, 2009.
International Search Report and Written Opinion issued in International Application No. PCT/US2009/043361, mailed Nov. 4, 2009.
International Search Report and Written Opinion issued in International Application No. PCT/US2009/064015, mailed Jul. 26, 2010.
International Search Report and Written Opinion, issued in International Application No. PCT/US2005/022710, mailed Oct. 7, 2005.
International Search Report and Written Opinion, issued in International Application No. PCT/US2005/036799, mailed Jun. 22, 2006.
International Search Report and Written Opinion, issued in International Application No. PCT/US2005/041162, dated Nov. 16, 2007.
International Search Report and Written Opinion, issued in International Application No. PCT/US2007 /078894, mailed Apr. 14, 2008.
International Search Report and Written Opinion, issued in International Application No. PCT/US2007 /089206, mailed Aug. 26, 2008.
International Search Report and Written Opinion, issued in International Application No. PCT/US2007/078859, mailed Mar. 25, 2008.
International Search Report and Written Opinion, issued in International Application No. PCT/US2007/086396, mailed May 30, 2008.
International Search Report and Written Opinion, issued in International Application No. PCT/US2007/087021, mailed Sep. 3, 2008.
International Search Report and Written Opinion, issued in International Application No. PCT/US2007/087029, mailed Jan. 13, 2009.
International Search Report and Written Opinion, issued in International Application No. PCT/US2007/087031, mailed Jan. 13, 2009.
International Search Report and Written Opinion, issued in International Application No. PCT/US2007/087033, mailed Jan. 13, 2009.
International Search Report and Written Opinion, issued in International Application No. PCT/US2007/087037, mailed Jan. 12, 2009.
International Search Report and Written Opinion, issued in International Application No. PCT/US2007/087038, mailed Oct. 17, 2008.
International Search Report and Written Opinion, issued in International Application No. PCT/US2008/076246, mailed Feb. 27, 2009.
International Search Report and Written Opinion, issued in International Application No. PCT/US2008/080318, mailed Feb. 9, 2009.
International Search Report and Written Opinion, issued in International Application No. PCT/US2008/085178, mailed Aug. 21, 2009.
International Search Report and Written Opinion, issued in International Application No. PCT/US2007/078936. mailed Apr. 14, 2008.
International Search Report and Written Opinion, issued in International Application No. PCT/US2009/033556. mailed Aug. 4, 2009.
International Search Report, issued in International Application No. PCT/US2002/003169, mailed Feb. 17, 2003.
International Preliminary Report on Patentability and Written Opinion issued in; International Application No. PCT/ US2008/085178, mailed Jun. 10, 2010.
International Preliminary Report on Patentability and Written Opinion issued in; International Application No. PCT/ US2008/087762, mailed Jul. 1, 2010.
International Preliminary Report on Patentability and Written Opinion, issued in; International Application No. PCT/ US2005/018826, mailed Dec. 7, 2006.
International Preliminary Report on Patentability and Written Opinion, issued in; International Application No. PCT/ US2005/022710, mailed Jan. 18, 2007.
International Preliminary Report on Patentability and Written Opinion, issued in; International Application No. PCT/ US2005/036799, mailed Apr. 26, 2007.
International Preliminary Report on Patentability and Written Opinion, issued in; International Application No. PCT/ US2005/041162, mailed Dec. 6, 2007.
International Preliminary Report on Patentability and Written Opinion, issued in; International Application No. PCT/ US2007/087029, mailed Jun. 18, 2009.

(56) References Cited

OTHER PUBLICATIONS

International Preliminary Report on Patentability and Written Opinion, issued in; International Application No. PCT/ US2007/087031, mailed Jun. 18, 2009.
International Preliminary Report on Patentability and Written Opinion, issued in; International Application No. PCT/ US2007/087033, mailed Jun. 18, 2009.
International Preliminary Report on Patentability, issued in International Application No. PCT/US2007/078859, mailed Apr. 2, 2009.
International Preliminary Report on Patentability, issued in International Application No. PCT/US2007/078894, mailed Apr. 2, 2009.
International Preliminary Report on Patentability, issued in International Application No. PCT/US2007/078936, mailed Apr. 2, 2009.
International Search Report and Written Opinion issued in International Application No. PCT/US2007/078952, mailed Jan. 26, 2010.
International Search Report and Written Opinion issued in International Application No. PCT/US2008/066025, mailed Sep. 16, 2009.
International Search Report and Written Opinion issued in International Application No. PCT/US2008/087762, mailed Mar. 16, 2010.
Invitation to Pay Additional Fees and Partial International Search, issued in International Application No. PCT/ US2005/018826, mailed Mar. 20, 2006.
Invitation to Pay Additional Fees and Partial International Search, issued in International Application No. PCT/ US2005/041162, mailed Aug. 31, 2007.
Invitation to Pay Additional Fees and Partial International Search, issued in International Application No. PCT/ US2007 /087038, mailed Jul. 16, 2008.
Invitation to Pay Additional Fees and Partial International Search, issued in International Application No. PCT/ US2007/078859, mailed Jan. 28, 2008.
Invitation to Pay Additional Fees and Partial International Search, issued in International Application No. PCT/ US2007/078894, mailed Feb. 11, 2008.
Invitation to Pay Additional Fees and Partial International Search, issued in International Application No. PCT/ US2007/078936, mailed Feb. 5, 2008.
Invitation to Pay Additional Fees and Partial International Search, issued in International Application No. PCT/ US2007/087021, mailed Jul. 10, 2008.
Invitation to Pay Additional Fees and Partial International Search, issued in International Application No. PCT/ US2007/087029, mailed Sep. 10, 2008.
Invitation to Pay Additional Fees and Partial International Search, issued in International Application No. PCT/ US2007/087031, mailed Sep. 10, 2008.
Invitation to Pay Additional Fees and Partial International Search, issued in International Application No. PCT/ US2007/087037, mailed Aug. 25, 2008.
Invitation to Pay Additional Fees and Partial International Search, issued in International Application No. PCT/ US2007/089206, mailed Jul. 7, 2008.
Invitation to Pay Additional Fees and Partial International Search, issued in International Application No. PCT/ US2008/076246, mailed Dec. 30, 2008.
Invitation to Pay Additional Fees and Partial International Search, issued in International Application No. PCT/ US2008/085178, mailed May 8, 2009.
Invitation to Pay Additional Fees and Partial International Search, issued in International Application No. PCT/ US2009/033556, mailed Jun. 5, 2009.
Invitation to Pay Additional Fees and Partial International Search, issued in International Application No. PCT/ US2009/036195, mailed Jul. 2, 2009.
Invitation to Pay Additional Fees and Partial International Search, issued in International Application No. PCT/ US2009/043361, mailed Jul. 22, 2009.
Invitation to Pay Additional Fees and Partial International Search, issued in International Application No. PCT/ US2007/087033, mailed Sep. 5, 2008.
Iorio et al., MicroRNA gene expression deregulation in human breast cancer, Cancer Res, 65(16):7065-7070, 2005.
Ishikawa et al., Increases of amphiregulin and transforming growth factor-alpha in serum as predictors of poor response to gefitinib among patients with advanced non-small cell lung cancers, Cancer Res., 65(20):9176-9184, 2005.
Islam et al., Vimentin expression in human squamous carcinoma cells: relationship with phenotypic changes and cadherin-based cell adhesion, J Cell Biochem, 78(1): 141-150, 2000.
Ito et al., Decreased expression of cyclin G2 is significantly linked to the malignant transformation of papillary carcinoma of the thyroid, Anticancer Res., 23(3B):2335-2338, 2003.
Ito et al., Decreased expression of p 107 is correlated with anaplastic transformation in papillary carcinoma of the thyroid, Anticancer Res., 23(5A):3819-3824, 2003.
Ito et al., Expression of ets-1 and ets-2 in colonic neoplasms, Anticancer Res., 22 (3): 1581-1584, 2002.
Ito et al., Expression ofp8 protein in medullary thyroid carcinoma, Anticancer Res., 25 (5):3419-3423, 2005.
Jaakkola et al., Amplification offgfr4 gene in human breast and gynecological cancers, Int. J. Cancer, 54 (3):378-382, 1993.
Jaattela, Over-expression of hsp70 confers tumorigenicity to mouse fibrosarcoma cells, Int. J. Cancer, 60 (5):689-693, 1995.
Jackson and Foster, The enigmatic protein kinase Cdelta: complex roles in cell proliferation and survival, Faseb J, 18(6):627-636, 2004.
Jamieson et al., Granulocyte-macrophage progenitors as candidate leukemic stem cells in blast-crisis CML, N Engl. J Med., 351(7):657-67, 2004.
Jang et al., Gene delivery from polymer scaffolds for tissue engineering, Expert Rev. Medical Devices, 1 (1):127-138, 2004.
Jang et al., MTA1 overexpression correlates significantly with tumor grade and angiogenesis in human breast cancers, Cancer Sci, 97(5):374-379, 2006.
Janknecht, EWS-ETS oncoproteins: the linchpins of Ewing tumors, Gene, 363:1-14, 2005.
Jansen et al., Characterization of programmed cell death 4 in multiple human cancers reveals a novel enhancer of drug sensitivity, Mol. Cancer Ther., 3(2):103-110, 2004.
Jansen et al., Epidermal expression of the translation inhibitor programmed cell death 4 suppresses tumorigenesis, Cancer Res., 65(14):6034-41, 2005.
Jansen et al., Two unrelated cell-derived sequences in the genome of avian leukemia and carcinoma inducing retrovirus MH2, Embo J, 2(11): 1969-1975, 1983.
Japanese Office Action, issued May 29, 2013, in Japanese Application No. 2012-150997. (6 pages).
Japanese Office Action for application No. 2007-541398 issued Mar. 28, 2011.
Japanese Office Action issued in Japanese Application No. 2007-515415, mailed Jan. 26, 2011.
Japanese Office Action for Application No. 2010-036925 issued Mar. 11, 2013.
Japanese Office Communication issued in Japanese Patent Application No. 2007-541398, dated Jun. 4, 2012. (English translation).
Jemal et al., Cancer statistics, 2007, CA Cancer J. Clin., 57:43-66, 2007.
Jemiality et al., Novel 'anti-reverse' cap analogs with superior translational properties, RNA, 9(9):1108-1122, 2003.
Ji et al. BMC Cancer, vol. 8. p. 266-277, 2008.
Jiang et al., Decreased expression of type II tumor suppressor gene RARRES3 in tissues of hepatocellular carcinoma and cholangiocarcinoma, World J. Gastroenterol., 11: 948-953, 2005.
Jiang et al., Real-time expression profiling of microRNA precursors in human cancer cell lines, Nucleic Acids Research, 33(17):5394-5403, 2005.
Jiang et al., RNA silencing of S-phase kinase-interacting protein 2 inhibits proliferation and centrosome amplification in lung cancer cells, Oncogene, 24(21):3409-3418, 2005.

(56) References Cited

OTHER PUBLICATIONS

Jin et al., Tumorigenic transformation by CPI-17 through inhibition of a merlin phosphatase, Nature, 442 (7102):576-579, 2006.
Jing et al., Tazarotene-induced gene 1 (TIG1) expression in prostate carcinomas and its relationship to tumorigenicity, J. Nat/. Cancer Inst., 94: 482-490, 2002.
John et al., Human microRNA targets, PLOS Biology, 2(11):1862-1879, 2004.
Johnson et al., Cancer Res., 67:7713-22, 2007.
Johnson et al., RAS is regulated by the let-7 microRNA family, Cell, 120:635-647, 2005.
Jonsson et al., Loss of Wnt-5a protein is associated with early relapse in invasive ductal breast carcinomas, Cancer Res., 62 (2): 409-416, 2002.
Jopling et al., Modulation of hepatitis C virus RNA abundance by a liver-specific; MicroRNA, Science, 309 (5740):1577-81, 2005.
Jubb et al., EphB2 is a prognostic factor in colorectal cancer, Clin. Cancer Res., 11 (14): 5181-5187, 2005.
Kabbarah et al., Expression Profiling of Mouse Endometrial Cancers Microdissected from Ethanol-Fixed, Paraffin-Embedded Tissues, Am. J. Pathology, 162:755-762, 2003.
Kalin et al., Increased levels of the FoxM1 transcription factor accelerate development and progression of prostate carcinomas in both Tramp and Lady transgenic mice, Cancer Res, 66(3):1712-1720, 2006.
Kalinichenko et al., Foxm1b transcription factor is essential for development ofhepatocellular carcinomas and is negatively regulated by the p19ARF tumor suppressor, Genes Dev, 18(7):830-850, 2004.
Kelley et al., Vitamin D receptor activity and prevention of colonic hyperproliferation and oxidative stress, Food Chem. Toxicol., 40: 1191-1196, 2002.
Kamala et al., High expression of skp2 correlates with poor prognosis in endometrial endometrioid adenocarcinoma, J. Cancer Res. Clin. Oneal., 131(9):591-596, 2005.
Kammula et al., Serial follow-up and the prognostic significance of reverse transcriptasepolymerase chain reaction—staged sentinel lymph nodes from melanoma patients. J Clin. Oneal., 22:3989-3996, 2004.
Kapsimali et al., MicroRNAs show a wide diversity of expression profiles in the developing and mature central nervous system, Genome Biol, 8(8):R173, 2007.
Karakaidos et al., Overexpression of the replication licensing regulators hCdt1 and hCdc6 characterizes a subset of non-small-cell lung carcinomas: synergistic effect with mutant p53 on tumor growth and chromosomal instability—evidence of E2F-1 transcriptional control over hCdt1, Am J Pathol, 165(4):1351-1365, 2004.
Karginov et al., A biochemical approach to identifying microRNA targets, PNAS, 104(49):19291-19296, 2007.
Karhadkar et al., Hedgehog signalling in prostate regeneration, neoplasia and metastasis, Nature, 431 (7009):707-12, 2004.
Karin et al., NF-kappaB in cancer: from innocent bystander to major culprit, Nat Rev Cancer, 2(4):301-310, 2002.
Kasashima et al., Altered expression profiles of microRNAs during TPA-induced; differentiation of HL-60 cells, Biochemical and Biophysical Research Communications, 322(2):403-410, 2004.
Kastan and Lim, The many substrates and functions of ATM, Nat Rev Mol Cell Biol, 1(3):179-186, 2000.
Kato, Adaptor-tagged competitive PCR: a novel method for measuring relative gene expression, Nucleic Acids Research, Oxford University Press, Surrey, GB, 25(22):4694-4696, 1997.
Kaufmann et al., Elevated expression of the apoptotic regulator Mcl-1 at the time of leukemic relapse, Blood, 91 (3):991-1000, 1998.
Kayed et al., Hedgehog signaling in the normal and diseased pancreas, Pancreas, 32(2):119-129, 2006.
Keen and Taylor. Aurora-kinase inhibitors as anticancer agents, Nat. Rev. Cancer, 4(12):927-936, 2004.
Kern et al., Application of a fed-batch system to produce RNA by in vitro transcription, Biotechnol. Prog., 15:174-184, 1999.

Kern et al., Application of solution equilibrium analysis to in vitro RNA transcription, Biotechnol. Prog., 13:747-756,1997.
Keshet et al., MDR1 expression identifies human melanoma stem cells, Biochem. Biophys. Res. Commun., 368 (4):930-6, 2008.
Kim et al. PNAS 2004;101:360-5.
Kim et al., Genomics of microRNA, Trends in Genetics, 22:165-173, 2006.
Kim et al., The Forkhead Box m1 transcription factor stimulates the proliferation of tumor cells during development of lung cancer, Cancer Res, 66(4):2153-2161, 2006.
Kiriakidou et al., A combined computational-experimental approach predicts humanmicroRNA targets, Genes Dev. 18(10):1165-78, 2004.
Kiriakidou et al., An mRNA m7G cap binding-like motif within human Ago2 represses translation, Cell, 129 (6):1141-1151, 2007.
Kirikoshi et al., Up-regulation ofFrizzled-7 (FZD7) in human gastric cancer, Int. J. Oneal., 19 (1): 111-115, 2001.
Kita et al., Modulation ofpolygulutamine-induced cell death by genes identified by expression profiling, Human Molecular Genetics, 11(19):2279-2287, 2002.
Kitadai et al., Expression of amphiregulin, a novel gene of the epidermal growth factor family, in human gastric carcinomas, Jpn. J. Cancer Res., 84(8):879-884, 1993.
Kleer et al., RhoC GTPase expression as a potential marker of lymph node metastasis in squamous cell carcinomas of the head and neck, Clin. Cancer Res., 12 (15): 4485-4490, 2006.
Kohno and Pouyssegur, Pharmacological inhibitors of the ERK signaling pathway: application as anticancer drugs, Progress in Cell Cycle Research., (Meijer, L., Jezequel, A., and Roberge, M., Eds), Chapter 22, vol. 5:219-224, 2003.
Koivunen et al., Protein kinase C (PKC) family in cancer progression, Cancer Lett, 235(1):1-10, 2006.
Koivunen et al., Protein kinase C alpha/beta inhibitor Go6976 promotes formation of cell junctions and inhibits invasion of urinary bladder carcinoma cells, Cancer Res, 64(16):5693-5701, 2004.
Kokko et al., EPHB2 germline variants in patients with colorectal cancer or hyperplastic polyposis, BMC Cancer, 6:145, 2006.
Komatsu et al., Increased expression ofS100A6 (Calcyclin), a calcium-binding protein of the S 100 family, in human colorectal adenocarcinomas, Clin. Cancer Res., 6: 172-177, 2000.
Komiya et al., PRLTS gene alterations in human prostate cancer, Jpn. J. Cancer Res., 88(4):389-393, 1997.
Konopleva et al., Mechanisms of apoptosis sensitivity and resistance to the BH3 mimetic ABT-737 in acute myeloid leukemia, Cancer Cell, 10(5):375-88, 2006.
Kops et al., On the road to cancer: aneuploidy and the mitotic checkpoint, Nat Rev Cancer, 5(10):773-785. 2005.
Krek et al., Combinatorial microRNA target predictions, Nature Genet., 37:495-500, 2005.
Krichevsky et al., A microRNA array reveals extensive regulation of microRNAs during brain development, RNA, 9 (10):1274-1281, 2003.
Kristjansdottir and Rudolph, Cdc25 phosphatases and cancer, Chem Biol, 11(8): 1043-1051, 2004.
Kubista et al., Light-up probe based real-time Q-PCR, SPIE, 4264:53-58, 2001.
Kuehbacher et al., Targeting microRNA expression to regulate angiogenesis, Trends Pharmacal Sci., 29(1):12-15, 2008.
Kuhajda, Fatty acid synthase and cancer: new application of an old pathway, Cancer Res, 66(12):5977-5980, 2006.
Kumar et al., Suppression of non-small cell lung tumor development by the let-7 micro RNA family, PNAS, 105 (10):3903-3908, 2008.
Kwak et al., VEGF is major stimulator in model of choroidal neovascularization. Invest. Ophthalmol. Vis. Sci., 41 (10):3158-3164, 2000.
Kwong et al., Silencing of the retinoid response gene TIG 1 by promoter hypermethylation in nasopharyngeal carcinoma, Int. J. Cancer, 113 (3): 386-392, 2005.
Labourier et al., Improving in vitro transcription for large scale synthesis of human quality capped RNA, Ambion Diagnostics,

(56) References Cited

OTHER PUBLICATIONS

RNA Healthcare Solutions, Eukaryotic mRNA Processing meeting, Cold Spring Harbor Laboratory, Cold Spring Harbor, NY, Aug. 2003.
Lagos-Quintana et al., Curr Biol., 12:735-9, 2002.
Lagos-Quintana et al., RNA 9(2): 175-179, 2003.
Lagos-Quintana et al., Science, 294:853-8, 2001.
Lam et al., Expression ofp19 1NK4d, CDK4, CDK6 in glioblastoma multiforme, BrJ Neurosurg, 14(1):28-32, 2000.
Lanza et al., mRNA/microRNA gene expression profile in microsatellite unstable colorectal cancer, Male Cancer, 6:54, 2007.
Lao et al., Multiplexing RT-PCR for the detection of multiple miRNA species in small samples, Biochemical and Biophysical Research Communications, 343:85-89, 2006.
Lau et al., Science, 294(5543):858-862, 2001.
Lecellier et al., A cellular microRNA mediates antiviral defense in human cells, Science, 308(5721):557-60, 2005.
Lechner et al., Nestin-positive progenitor cells derived from adult human pancreatic islets of Langerhans contain side population (SP) cells defined by expression ofthe ABCG2 (BCRP1) ATP-binding cassette transporter, Biochem. Biophys. Res. Commun., 293(2):670-674, 2002.
Lee and Ambros, Science, 294(5543):862-864, 2001.
Lee et al., A protein reacted with anti-vitronectin antibody accumulates in tumors derived from B16F10 melanoma cells, Cell Struct. Funct., 23 (4): 193-199, 1998.
Lee et al., Altered microRNA expression in cervical carcinomas, Clin Cancer Res, 14(9):2535-2542, 2008.
Lee et al., Ectopic expression of neutrophil gelatinase-associated lipocalin suppresses the invasion and liver metastasis of colon cancer cells, Int. J. Cancer, 118(10):2490-2497, 2006.
Lee et al., Expression profiling identifies stroma- and tumor-related microRNAs in pancreatic cancer, 97th Annual AACR, Washington D.C., Abstract No. 5725, 2006.
Lee et al., The C. elegans heterochronic gene lin-4 encodes small RNAs with antisense complementarity to lin-14, Cell, 75(5):843-854, 1993.
Lee et al., the nuclear RNase III Drosha initiates microRNA processing, Nature, 425(6956):415-419, 2003.
Lee, EMBO J., 21(17):4663-4670, 2002.
Leong and Gao, The Notch pathway in prostate development and cancer, Differentiation, 76(6): 699-716, 2008.
Leprince et al., A putative second cell-derived oncogene of the avian leukaemia retrovirus E26, Nature, 306 (5941):395-397, 1983.
Leris et al., WNT5A expression in human breast cancer, Anticancer Res., 25 (2a): 731-734, 2005.
Lessard and Sauvageau, Bmi-1 determines the proliferative capacity of normal and leukaemic stem cells, Nature, 423(6937):255-60, 2003.
Lewis et al., Conserved seed pairing, often flanked by adenosines, indicates that thousands of human genes are microRNA targets, Cell, 120:15-20 , 2005.
Lewis et al., Prediction of mammalian microRNA targets, Cell, 115(7):787-798, 2003.
L'hote and Knowles, Cell responses to FGFR3 signalling: growth, differentiation and apoptosis, Exp. Cell. Res., 304 (2): 417-431, 2005.
Li et al., Apoptosis of non-small-celllung cancer cell lines after paclitaxel treatment involves the BH3-only proapoptotic protein Bim, Cell Death Differ, 12(3):292-303, 2005.
Li et al., Intrinsic resistance of tumorigenic breast cancer cells to chemotherapy, J Natl. Cancer Inst., 100(9):672-9, 2008.
Li et al., Mutant TNFalpha negatively regulates human breast cancer stem cells from MCF7 in vitro, Cancer Biol. Ther., 6(9):1480-9, 2007.
Li et al., Overexpression ofETS2 in human esophageal squamous cell carcinoma, World J. Gastroenterol., 9 (2):205-208, 2003.
Li et al., PDGF-D is a potent transforming and angiogenic growth factor, Oncogene, 22(10):1501-1510, 2003.
Li et al., Evidence that transgenes encoding components of the Wnt signaling pathway preferentially induce mammary cancers from progenitor cells. Proc Natl Aced Sci USA, 100(26):15853-8, 2003.
Liang et al., Chacterization of micro RNA expression profiles in normal human tissues, BMC Genomics, 8:166, 2007.
Lilja et al., Prostate-specific antigen and prostate cancer: prediction, detection and monitoring, Nat. Rev. Cancer, 8 (4):268-278, 2008.
Lim et al., The microRNAs of Caenorhabditis elegans, Genes and Development, 17:991-1008, 2003.
Lim et al., Nature, 433(7027):769-773, 2005.
Lima e Silva et al., The SDF-I/CXCR4ligand/receptor pair is an important contributor to several types of ocular neovascularization, FASEB J, 21(12):3219-3230, 2007.
Lin and Gelman, Reexpression of the major protein kinase C substrate, SSeCKS, suppresses vsrc-induced morphological transformation and tumorigenesis, Cancer Res, 57(11):2304-2312, 1997.
Lin et al., The C. elegans hunchback homolog, hbl-1, controls temporal patterning and is a probable microRNA target, Dev. Cell, 4(5):639-650, 2003.
Lin et al., Connective tissue growth factor inhibits metastasis and acts as an independent prognostic marker in colorectal cancer. Gastroenterology, 128(1):9-23, 2005.
Linsley et al., Transcripts targeted by the microRNA-16 family cooperatively regulate cell cycle progression, Molecular and Cellular Biology, 27(6):2240-2252, 2007.
Liu and Erikson, Polo-like kinase (Plk)1 depletion induces apoptosis in cancer cells, Proc Natl Acad Sci US A, 100 (10):5789-5794, 2003.
Liu and Matsuura, Inhibition of Smad antiproliferative function by CDK phosphorylation, Cell Cycle, 4(1):63-66, 2005.
Liu et al., An oligonucleotide microchip for genome-wide micronRNA profiling in human and mouse tissue, Proc. Nat. Acad. Sci. USA, 101:9740-9744, 2004.
Liu et al., CpG island methylation and expression of the secreted frizzled-related protein gene family in chronic lymphocytic leukemia, Cancer Res., 66 (2): 653-658, 2006.
Liu et al., FoxM1B is overexpressed in human glioblastomas and critically regulates the tumorigenicity of glioma cells, Cancer Res., 66 (7): 3593-3602, 2006.
Liu et al., Functional studies of BCL11A: characterization of the conserved BCL11A-XL splice variant and its interaction with BCL6 in nuclear paraspeckles of germinal center B cells, Mol. Cancer, 5:18, 2006.
Liu et al., Hedgehog signaling and Bmi-1 regulate self-renewal of normal and malignant human mammary stem cells, Cancer Res., 66(12):6063-71, 2006.
Liu et al., Sex-determining region Y box 4 is a transforming oncogene in human prostate cancer cells, Cancer Res., 66(8):4011-9, 2006.
Liu et al., The prognostic role of a gene signature from tumorigenic breast-cancer cells. N Engl. J Med., 356 (3):217-26, 2007.
Illmer et al., MiRNA expression signatures in acute myeloid leukemia are predictors for patient outcome. Session Type: Oral Session, Blood, 108(11): 49A, Abstract #152, 2006.
Lo et al., High resolution allelotype ofmicrodissected primary nasopharyngeal carcinoma, Cancer Res., 60:3348-3353, 2000.
Lo Vasco et al., Inositide-specific phospholipase c betel gene deletion in the progression of myelodysplastic syndrome to acute myeloid leukemia, Leukemia, 18 (6): 1122-1126, 2004.
Logsdon et al., Molecular profiling of pancreatic adenocarcinoma and chronic pancreatitis identifies multiple genes differentially regulated in pancreatic cancer, Cancer Research, 63:2649-2657, 2003.
Isbarn et al., Association of numerous micro-RNAs (J-LRNAs) with prostate cancer initiation and progression, European Urology Supplements, Abstract No. 429, 6(2):130, 2007.
Lu et al., Defined culture conditions of human embryonic stem cells,Proc. Natl. Acad. Sci. USA, 103(15): 5688-93, 2006.
Lu et al., MicroRNA expression profiles classify human cancers, Nature, 435(7043):834-838, 2005.
Lucke et al., Inhibiting mutations in the transforming growth factor beta type 2 receptor in recurrent human breast cancer, Cancer Res, 61(2):482-485, 2001.

(56) References Cited

OTHER PUBLICATIONS

Lui et al., Patterns of known and novel small RNAs in human cervical cancer, Cancer Res., 67(13):6031-6043, 2007.
Lujambio et al., Genetic unmasking of an epigenetically silenced micro RNA in human cancer cells, Cancer Research, 67(4):1424-1429, 2007.
Lukiw, Micro-RNA speciation in fetal, adult and Alzheimer's disease hippocampus, Neuroreport, 18(3):297-300, 2007.
Ma et al., Tumour invasion and metastasis initiated by microRNA-IOb in breast cancer, Nature, 449(7163):682-688, 2007.
Mahato et al. Modulation of gene expression by antisense and antigene oligodeoxynucleotides and small interfering RNA, Expert Opinion on Drug Delivery, 2(1):3-28, 2005.
Maitland & Collins, Prostate cancer stem cells: a new target for therapy, J Clin Oneal., 26(17):2862-70, 2008. (Abstract).
Makeyev et al., The microRNA miR-124 promotes neuronal differentiation by triggering brain-specific alternative pre-mRNA splicing, Molecular Cell, 27(3):435-448, 2007.
Maki et al., Avian sarcoma virus 17 carries the jun oncogene, Proc. Natl. A cad. Sci. USA, 84 (9): 2848-2852, 1987.
Malanchi et al., Cutaneous cancer stem cell maintenance is dependent on beta-catenin signalling, Nature, 452 (7187):650-3, 2008.
Malumbres and Barbacid, to cycle or not to cycle: a critical decision in cancer, Nat Rev Cancer, 1(3):222-231, 2001.
Mammalian Gene Collection (MGC) Program Team, Generation and initial analysis of more than 15,000 full-length human and mouse eDNA sequences, PNAS, 99(26):16899-16903, 2002.
Manion and Hockenbery, Targeting Bcl-2-related proteins in cancer therapy, Cancer Biol Ther, 2(4 Suppl1): S105-114, 2003.
Manoharan, Antisense & Nucleic Acids Drug Development 12:103-128, 2002.
Mansfield et al, MicroRNA-responsive 'sensor' transgenes uncover Hox-like and other developmentally regulated patterns of vertebrate microRNA expression, Nature Genetics, 36 (10):1079-1083, 2004.
Marcucci et al., Prognostic factors and outcome of core binding factor acute myeloid leukemia patients with t(8;21)differ from those of patients with inv(16): a Cancer and Leukemia Group B study, J.Ciin.Oncol., 23:5705-5717, 2005.
Markowitz et al., Inactivation of the type II TGF-beta receptor in colon cancer cells with microsatellite instability, Science, 268(5215):1336-1338, 1995.
Markowitz, TGF-beta receptors and DNA repair genes, coupled targets in a pathway of human colon carcinogenesis, Biochim. Biophys. Acta., 1470 (1): M13-20, 2000.
Marks, Thioredoxin in cancer—role of histone deacetylase inhibitors, Semin. Cancer Biol., 16(6):436-443, 2006.
Marone et al., Analysis of cyclin E and CDK2 in ovarian cancer: gene amplification and RNA overexpression, Int J Cancer, 75(1):34-39, 1998.
Martello et al., MicroRNA control of nodal signaling, Nature, 449(7159):183-188, 2007.
Martin and Keller, Tailing and 3'-end labeling of RNA with yeast poly(A) polymerase and various nucleotides, RNA,4(2):226-230, 1998.
Martinet al., Molecular profiling of cervical neoplasia, Expert Review of Molecular Diagnostics, 6(2):217-229, 2006.
Martinez et al., Human papilloma virus type 16 reduces the expression of micro RNA-218 in cervical carcinoma cells, Oncogene, 27:2575-2582, 2008.
Martinez, Identification of differentially expressed genes in HPV associated cancers using gene expression, tissue, and microRNA microarrays, Dissertation Abstract, University of Pittsburg, 2007.
Massague et al., TGFbeta signaling in growth control, cancer, and heritable disorders, Cell, 103 (2): 295-309, 2000.
Matoba et al., Gene expression in mouse cerebellum during its development, Gene, 241:125-131, 2000.
Matoba et al., Gene expression profiling of mouse postnatal cerebellar development, Physioi. Genomics, 4:155-164, 2000.

Mattie et al., Optimized high-throughput microRNA expression profiling provides novel biomarker assessment of clinical prostate and breast cancer biopsies, Mol. Cancer, 5:24, 2006.
Mcinroy and Maatta, Down-regulation ofvimentin expression inhibits carcinoma cell migration and adhesion, Biochem Biophys Res Commun, 360(1):109-114, 2007.
McManus, MicroRNAs and cancer, Seminars in Cancer Biology, 13:253-258, 2003.
Meister et al., Sequence-specific inhibition ofmicroRNA- and siRNA-induced RNA silencing, RNA, 10(3):544-50, 2004.
Meister et al., Human Argonaute2 mediates RNA cleavage targeted by miRNAs and siRNAs. Mol Cell. 15(2):185-97, 2004.
Mendrzyk et al., Genomic and protein expression profiling identifies CDK6 as novel independent prognostic marker in medulloblastoma, J Clin Oneal, 23(34):8853-8862, 2005.
Meng et al., Involvement of human micro-ma in growth and response to chemotherapy in human cholangiocarcinoma cell lines, Gastroenterology, 130(7):2113-2129, 2006.
Merle et al., Functional consequences offrizzled-7 receptor overexpression in human hepatocellular carcinoma, Gastroenterology, 127 (4): 110-1122, 2004.
Metzer et al., High Expression of Precursor MicroRNA-155/B/C RNA in Children with Burkitt Lymphoma, Genes, Chromosomes, & Cancer 39:167-169; 2004.
Mi et al., MicroRNA expression signatures accurately discriminate acute lymphoblastic leukemia from acute myeloid leukemia, PNAS, 104(50):19971-19976, 2007.
Michael et al., The p53-Mdm2 module and the ubiquitin system, Semin. Cancer Biol. 13:49-58, 2003.
Michael et al., Reduced Accumulation of Specific MicroRNAs in colorectal Neoplasia, Molecular Cancer Research, 1:882-891, 2003.
Miki et al., Prostate cell cultures as in vitro models for the study of normal stem cells and cancer stem cells, Prost. Can. Prost. Dis., 11:32-39, 2008.
Miki et al., Identification of putative stem cell markers, CD133 and CXCR4, in hTERT-immortalized primary nonmalignant and malignant tumor-derived human prostate epithelial cell lines and in prostate cancer specimens, Cancer Res., 67(7):3153-61, 2007.
Miller et al., Vascular endothelial growth factor/vascular permeability factor is temporally and spatially correlated with ocular angiogenesis in a primate mode, Am. J Pathol., 145(3):574-584, 1994.
Minakuchi et al., Atelocollagen-mediated synthetic small interfering RNA delivery for effective gene silencing in vitro and in vivo, Nucleic Acids Research, 32(13):e109, 2004.
miRBase::SequencesStem loop sequence MI0000268. Sep. 2008, [online], The Wellcome Trust Sanger Institute,; [retrieved on Dec. 23, 2008], <URL: http://microRNA.sangerac.uk>.
Mishima et al., RT-PCR-based analysis of microRNA (miR-1 and -124) expression in mouse CNS, Brain Res, 1131 (1):37-43, 2007.
Miyake et al., Increased angiogenin expression in the tumor tissue and serum of urothelial carcinoma patients is related to disease progression and recurrence, Cancer, 86 (2): 316-324, 1999.
Mizunuma et al., The LIM-only protein, LM04, and the LIM domain-binding protein, LDB1, expression in squamous cell carcinomas of the oral cavity, Br J Cancer, 88(1 0): 1543-1548, 2003.
Moller et al., Expression of AP0-1 (CD95), a member of the NGF/TNF receptor superfamily, in normal and neoplastic colon epithelium, Int J Cancer, 57(3):371-377, 1994.
Momand et al., The MDM2 gene amplification database, Nucleic Acids Res, 26(15):3453-3459, 1998.
Monhanty and Kushner, Polynucleotide phosphorylase functions both as a 3'-5' exonuclease and a poly(A)polymerase in *Escherichia coli*, PNAS, 97:11966-11971; 2000.
Montero et al., Angiogenin expression and prognosis in primary breast carcinoma, Clin. Cancer Res., 4 (9):2161-2168, 1998.
Mori et al., A genome-wide search identifies epigenetic silencing of somatostatin, tachykinin-1, and 5 other genes in colon cancer, Gastroenterology, 131(3):797-808, 2006.
Morse et al., Clinical relevance of mutations and gene-expression changes in adult acute myeloid leukemia with normal cytogenetics: are we ready for a prognostically prioritized molecular classification?, Blood, 109:431-448, 2007.

(56) References Cited

OTHER PUBLICATIONS

Morton et al., Sentinel-node biopsy or nodal observation in melanoma, N Engl. J Med., 355(13):1307-1317, 2006.
Morton et al., Technical details of intraoperative lymphatic mapping for early stage melanoma, Arch Surg, 127 (4):392-399, 1992.
Mourelatos et al., miRNPs: a novel class of ribonucleoproteins containing numerous microRNAs, Genes & Development, 16:720-728, 2002.
Mundt et al., on the regulation and function of human polo-like kinase 1 (PLK1): effects of overexpression on cell cycle progression, Biochem Biophys Res Commun, 239(2):377-385, 1997.
Muralidhar et al., Global microRNA profiles in cervical squamous cell carcinoma depend on Drosha expression levels, J. Pathol., 212:368-377, 2007.
Murphy et al., p16INK4A, CDC6, and MCM5: predictive biomarkers in cervical preinvasive neoplasia and cervical cancer, J Clin Pathol, 58(5):525-534, 2005.
Nagpal et al., Tazaratone-induced gen 1 (TIG 1), a novel retinoic acid receptor-responsive gene in skin, J. Invest. Dermatol., 106 (2): 269-274, 1996.
Nakada et al., The phosphorylation ofEphB2 receptor regulates migration and invasion of human glioma cells, Cancer Res., 64 (9): 3179-3185, 2004.
Nakamura et al., MARCH-II is a syntaxin-6-binding protein involved in endosomal trafficking, Molecular Biology of the Cell, 16(4): 1696-1710, 2005.
Nauert et al., Gravin, an auto antigen recognized by serum from myasthenia gravis patients, is a kinase scaffold protein, Curr Biol, 7(1):52-62, 1997.
Nelson et al., Microarray-based, high-throughput gene expression profiling of microRNAs, Nature Methods, 1(2):1-7, 2004.
Nerlov, C/EBP? mutations in acute myeloid leukaemias, Nat Rev Cancer, 4(5):394-400, 2004.
Nesbit et al., MYC oncogenes and human neoplastic disease, Oncogene, 18 (19): 3004-3016, 1999.
Ngan et al., Quantitative evaluation of vimentin expression in tumour stroma of colorectal cancer, Br J Cancer, 96 (6):986-992, 2007.
Nikiforova et al., MicroRNA expression profiling of thyroid tumors: biological significance and diagnostic utility, 93 (5):1600-1608, 2008.
Nordgard et al., Quantitative RT-PCR detection of tumor cells in sentinel lymph nodes isolated from colon cancer patients with an ex vivo approach, Annals of Surgery, 249(4):602-607, 2009.
Notice of Allowance issued in U.S. Appl. No. 11/141,707, mailed Oct. 4, 2010.
Notice of Allowance issued in U.S. Appl. No. 11/837,490, mailed Apr. 1, 2011.
Notice of Allowance issued in U.S. Appl. No. 11/837,495, mailed Dec. 2, 2010.
Nykanen et al., ATP requirements and small interfering RNA structure in the RNA interference pathway, Cell, 107:309-321, 2001.
Oberg et al., Detection of occult tumour cells in lymph nodes of colorectal cancer patients using real-time quantitative RT-PCR for CEA and CK20 mRNAS, Int. J. Cancer, 111(1):101-110, 2004.
O'Connor et al., Bim: a novel member of the Bcl-2 family that promotes apoptosis, Embo J, 17(2):384-395, 1998.
O'Donnel et al., c-Myc-regulated microRNA's modulcate E2F1 expression, Nature, 435(7043):839-43, 2005.
Office Action issued in Australian Application No. 2005250432, mailed Aug. 25, 2010.
Office Action issued in Australian Application No. 2005250432, mailed Dec. 1, 2009.
Office Action issued in European Application No. 02720894.1, mailed Jul. 11, 2007.
Office Action issued in European Application No. 05804851.3, mailed Dec. 21, 2007.
Office Action issued in European Application No. 05804851.3, mailed Jul. 30, 2008.
Office Action issued in European Application No. 05815286.9, mailed Apr. 3, 2008.
Office Action issued in European Application No. 05858321.2, mailed Apr. 11, 2008.
Office Action issued in European Application No. 05858321.2, mailed Apr. 16, 2010.
Office Action issued in European Application No. 07 871 691.7, mailed Oct. 28, 2010.
Office Action issued in European Application No. 07 871 693.3, mailed Oct. 18, 2010.
Office Action issued in European Application No. 07871689.1, mailed Dec. 15, 2009.
Office Action issued in European Application No. 07871690.9, mailed Dec. 14, 2009.
Office Action issued in European Application No. 07871691.7, mailed Dec. 14, 2009.
Office Action issued in European Application No. 07871693.3, mailed Dec. 9, 2009.
Office Action issued in European Application No. 07871694.1, mailed Dec. 10, 2009.
Office Action issued in European Application No. 07871756.8, mailed Jun. 30, 2010.
Office Action issued in European Application No. 07871756.8, mailed Oct. 20, 2009.
Office Action issued in European Application No. 08 831 073.5, mailed Aug. 16, 2010.
Office Action issued in European Application No. 08770269.2, mailed Jul. 30, 2010.
Office Action issued in European Application No. 08831073.5, mailed Feb. 25, 2011.
Office Action issued in European Application No. 09 154 092.2, mailed Mar. 30, 2011.
Office Action issued in European Application No. 09 154 092.2, mailed Nov. 10, 2010.
Office Action issued in European Application No. 09154092.2, mailed Apr. 1, 2010.
Office Action issued in European Application No. 09717913.9, mailed Mar. 7, 2011.
Office Action issued in European Application No. 10 183 451.3, mailed Oct. 24, 2011.
Office Action issued in European Application No. 10 183 456.2, mailed Oct. 24, 2011.
Office Action issued in European Application No. 10 183 462.0, mailed Oct. 26, 2011.
Office Action issued in European Application No. 10 183 470.3, mailed Oct. 26, 2011.
Office Action issued in European Application No. 10 183 481.0, mailed Oct. 24, 2011.
Office Action issued in European Application No. 10 183 490.1, mailed Oct. 26, 2011.
Office Action issued in European Application No. 10 183 525.4, mailed Oct. 24, 2011.
Office Action issued in European Application No. 10 183 534.6, mailed Oct. 25, 2011.
Office Action issued in European Application No. 10 183 538.7, mailed Oct. 17, 2011.
Office Action issued in European Application No. 10 183 543.7, mailed Nov. 25, 2011.
Office Action issued in European Application No. 10 183 560.1, mailed Oct. 26, 2011.
Office Action issued in European Application No. 10 183 567.6, mailed Oct. 26, 2011.
Office Action issued in European Application No. 10 183 589.0, mailed Oct. 17, 2011.
Office Action issued in European Application No. 10 183 596.5, mailed Oct. 25, 2011.
Office Action issued in European Application No. 10 183 611.2, mailed Oct. 24, 2011.
Office Action issued in European Application No. 10 183 577.5, mailed Oct. 25, 2011.
Office Action issued in U.S. Appl. No. 10/632,534, mailed Jul. 11, 2006.

(56) References Cited

OTHER PUBLICATIONS

Office Action issued in U.S. Appl. No. 10/632,534, mailed Mar. 24, 2006.
Office Action issued in U.S. Appl. No. 10/632,534, mailed Mar. 29, 2007.
Office Action issued in U.S. Appl. No. 10/632,539, mailed Jul. 27, 2006.
Office Action issued in U.S. Appl. No. 10/632,539, mailed Mar. 27, 2006.
Office Action issued in U.S. Appl. No. 10/632,539, mailed Apr. 17, 2007.
Office Action issued in U.S. Appl. No. 10/880,350, mailed Feb. 21, 2006.
Office Action issued in U.S. Appl. No. 10/880,350, mailed Oct. 4, 2006.
Office Action issued in U.S. Appl. No. 10/880,350, mailed Sep. 10, 2007.
Office Action issued in U.S. Appl. No. 10/963,415, mailed Apr. 13, 2007.
Office Action issued in U.S. Appl. No. 10/963,415, mailed Aug. 2, 2007.
Office Action issued in U.S. Appl. No. 10/963,415, mailed Mar. 17, 2008.
Office Action issued in U.S. Appl. No. 10/963,415, mailed Mar. 9, 2009.
Office Action issued in U.S. Appl. No. 11/141,707, mailed Feb. 9, 2009.
Office Action issued in U.S. Appl. No. 11/141,707, mailed Jul. 17, 2008.
Office Action issued in U.S. Appl. No. 11/141,707, mailed Jun. 19, 2009.
Office Action issued in U.S. Appl. No. 11/141,707, mailed Mar. 11, 2010.
Office Action issued in U.S. Appl. No. 11/141,707, mailed May 15, 2007.
Office Action issued in U.S. Appl. No. 11/141,707, mailed Oct. 17, 2007.
Office Action issued in U.S. Appl. No. 11/141,707, mailed Sep. 2, 2010.
Office Action issued in U.S. Appl. No. 11/141,707, mailed Jan. 6, 2010.
Office Action issued in U.S. Appl. No. 11/273,640, mailed Jul. 26, 2011.
Office Action issued in U.S. Appl. No. 11/273,640, mailed Jun. 26, 2009.
Office Action issued in U.S. Appl. No. 11/273,640, mailed May 5, 2010.
Office Action issued in U.S. Appl. No. 11/273,640, mailed Nov. 20, 2009.
Office Action issued in U.S. Appl. No. 11/567,082, mailed Jul. 21, 2008.
Office Action issued in U.S. Appl. No. 11/567,082, mailed Jul. 3, 2007.
Office Action issued in U.S. Appl. No. 11/567,082, mailed Nov. 13, 2007.
Office Action issued in U.S. Appl. No. 11/567,082, mailed Sep. 30, 2009.
Office Action issued in U.S. Appl. No. 11/567,082, mailed Jan. 27, 2009.
Office Action issued in U.S. Appl. No. 11/837,490, mailed Aug. 18, 2009.
Office Action issued in U.S. Appl. No. 11/837,487, mailed Mar. 25, 2009.
Office Action issued in U.S. Appl. No. 11/837,487, mailed May 28, 2010.
Office Action issued in U.S. Appl. No. 11/837,487, mailed Nov. 22, 2010.
Office Action issued in U.S. Appl. No. 11/837,487, mailed Sep. 15, 2009.
Office Action issued in U.S. Appl. No. 11/837,488, mailed Feb. 15, 2011.
Office Action issued in U.S. Appl. No. 11/837,490, mailed Apr. 9, 2010.
Office Action issued in U.S. Appl. No. 11/837,490, mailed Aug. 6, 2008.
Office Action issued in U.S. Appl. No. 11/837,490, mailed Jan. 13, 2009.
Office Action issued in U.S. Appl. No. 11/837,494, mailed Dec. 9, 2010.
Office Action issued in U.S. Appl. No. 11/837,494, mailed Jan. 15, 2009.
Office Action issued in U.S. Appl. No. 11/837,494, mailed Jan. 5, 2010.
Office Action issued in U.S. Appl. No. 11/837,494, mailed Mar. 5, 2009.
Office Action issued in U.S. Appl. No. 11/837,494, mailed Oct. 30, 2008.
Office Action issued in U.S. Appl. No. 11/837,495, mailed Jan. 5, 2010.
Office Action issued in U.S. Appl. No. 11/837,495, mailed Mar. 5, 2009.
Office Action issued in U.S. Appl. No. 11/837,495, mailed Sep. 2, 2010.
Office Action issued in U.S. Appl. No. 11/837,498, mailed Apr. 30, 2009.
Office Action issued in U.S. Appl. No. 11/837,498, mailed Jan. 15, 2009.
Office Action issued in U.S. Appl. No. 11/837,498, mailed May 7, 2010.
Office Action issued in U.S. Appl. No. 11/837,498, mailed Nov. 20, 2009.
Office Action issued in U.S. Appl. No. 11/837,488, mailed Feb. 19, 2010.
Office Action issued in U.S. Appl. No. 11/837,495, mailed Oct. 30, 2008.
Office Action issued in U.S. Appl. No. 11/837,498, mailed Oct. 29, 2008.
Office Action issued in U.S. Appl. No. 11/857,948, mailed Aug. 24, 2010.
Office Action issued in U.S. Appl. No. 11/857,948, mailed Jan. 26, 2011.
Office Action issued in U.S. Appl. No. 11/857,948, mailed Jun. 4, 2009.
Office Action issued in U.S. Appl. No. 11/857,948, mailed May 25, 2010.
Office Action issued in U.S. Appl. No. 11/857,948, mailed Nov. 3, 2009.
Office Action issued in U.S. Appl. No. 11/953,606, mailed Aug. 10, 2009.
Office Action issued in U.S. Appl. No. 11/953,606, mailed Jan. 8, 2010.
Office Action issued in U.S. Appl. No. 11/953,606, mailed Jul. 1, 2010.
Office Action issued in U.S. Appl. No. 11/953,606, mailed Oct. 1, 2010.
Office Action issued in U.S. Appl. No. 11/967,639, mailed Mar. 13, 2009.
Office Action issued in U.S. Appl. No. 11/967,639, mailed May 14, 2009.
Office Action issued in U.S. Appl. No. 11/967,663, mailed Feb. 12, 2010.
Office Action issued in U.S. Appl. No. 11/967,663, mailed Oct. 1, 2009.
Office Action issued in U.S. Appl. No. 11/967,639, mailed Mar. 24, 2010.
Office Action issued in U.S. Appl. No. 12/112,291, mailed Mar. 1, 2010.
Office Action issued in U.S. Appl. No. 12/112,291, mailed Nov. 16, 2009.
Office Action issued in U.S. Appl. No. 12/120,388, mailed Feb. 19, 2010.

(56) References Cited

OTHER PUBLICATIONS

Office Action issued in U.S. Appl. No. 12/120,388, mailed Jul. 21, 2010.
Office Action issued in U.S. Appl. No. 12/124,394, mailed Feb. 5, 2010.
Office Action issued in U.S. Appl. No. 12/124,394, mailed Nov. 6, 2009.
Office Action issued in U.S. Appl. No. 12/125,412, mailed Feb. 16, 2010.
Office Action issued in U.S. Appl. No. 12/125,675, mailed Apr. 22, 2010.
Office Action issued in U.S. Appl. No. 12/125,675, mailed Jan. 28, 2011.
Office Action issued in U.S. Appl. No. 12/125,675, mailed Oct. 14, 2010.
Office Action issued in U.S. Appl. No. 12/125,675, mailed Sep. 10, 2009.
Office Action issued in U.S. Appl. No. 12/125,412, mailed Nov. 12, 2009.
Office Action issued in U.S. Appl. No. 12/134,932, mailed Feb. 24, 2011.
Office Action issued in U.S. Appl. No. 12/134,932, mailed Mar. 24, 2010.
Office Action issued in U.S. Appl. No. 12/134,932, mailed Nov. 12, 2009.
Office Action issued in U.S. Appl. No. 12/134,932, mailed Nov. 4, 2010.
Office Action issued in U.S. Appl. No. 12/167,492, mailed Aug. 12, 2010.
Office Action issued in U.S. Appl. No. 12/167,492, mailed Feb. 12, 2010.
Office Action issued in U.S. Appl. No. 12/167,492, mailed Feb. 25, 2011.
Office Action issued in U.S. Appl. No. 12/209,822, mailed Mar. 15, 2011.
Office Action issued in U.S. Appl. No. 12/253,718, mailed Jun. 11, 2010.
Office Action issued in U.S. Appl. No. 12/253,718, mailed Nov. 1, 2010.
Office Action issued in U.S. Appl. No. 12/325,917, mailed Feb. 14, 2011.
Office Action issued in U.S. Appl. No. 12/325,917, mailed Jul. 28, 2010.
Office Action issued in U.S. Appl. No. 12/325,917, mailed May 3, 2010.
Office Action issued in U.S. Appl. No. 12/340,329, mailed Sep. 28, 2010.
Office Action issued in U.S. Appl. No. 12/368,053, mailed Aug. 19, 2010.
Office Action issued in U.S. Appl. No. 12/368,053, mailed Dec. 21, 2010.
Office Action issued in U.S. Appl. No. 12/398,852, mailed Aug. 11, 2011.
Office Action issued in U.S. Appl. No. 12/398,852, mailed Mar. 7, 2011.
Office Action issued in U.S. Appl. No. 12/412,087, mailed Aug. 18, 2011.
Office Action issued in U.S. Appl. No. 12/420,634, mailed Aug. 30, 2010.
Office Action issued in U.S. Appl. No. 12/420,634, mailed May 26, 2010.
Office Action issued in U.S. Appl. No. 12/437,899, mailed Jun. 29, 2011.
Office Action issued in U.S. Appl. No. 12/437,899, mailed Mar. 7, 2011.
Office Action issued in U.S. Appl. No. 12/616,616, mailed Aug. 13, 2010.
Office Action issued in U.S. Appl. No. 13/887,008, mailed Sep. 18, 2013.
Office Action issued in U.S. Appl. No. 14/012,302, mailed Nov. 26, 2013.
Ohlsson et al., Biomarker selection for detection of occult tumour cells in lymph nodes of colorectal cancer patients using real-time quantitative RT-PCR, Br. J Cancer, 95(2):218-225, 2006.
Ohsaki et al., Antitumor activity of magainin analogues against human lung cancer cell lines, Cancer Res, 52 (13):3534-3538, 1992.
Ollila et al., Metastatic melanoma cells in the sentinel node cannot be ignored, JAm. Call. Surg., 208(5):924-929, 2009.
Olsen and Ambros, The lin-4 regulatory RNA controls developmental timing in; Caenorhabditis elegans by blockingLIN-14 protein synthesis after the initiation of translation, Dev. Biol., 216:671, 1999.
Opalinska and Gewirtz, Nucleic-acid therapeutics: basic principles and recent applications, Nature Reviews, 1:503-514, 2002.
Ovcharenko et al., High-throughput RNAi screening in vitro: from cell lines to primary cells, RNA, 11(6):985-93, 2005.
Ozaki et al., Blockade of vascular endothelial cell growth factor receptor signaling is sufficient to completely prevent retinal neovascularization. Am J Pathol., 156(2):697-707, 2000.
Pallares et al., Structure of human arboxypeptidase A4 with its endogenous protein inhibitor, latexin. Proc Natl Acad Sci USA, 102(11):3978-83, 2005.
Palleres et al., Structure of human carboxypeptidase A4: with its endogenous protein inhibitor, latexin, Proc. Natl. Acad. Sci. USA, 102: 3978-3983, 2005.
Paramo et al., Validation of sentinel node mapping in patients with colon cancer, Ann Surg Oneal, 9(6):550-554, 2002.
Parkin et al., Global cancer statistics, 2002, CA Cancer J. Clin., 55(2):74-108, 2005.
Partial European Search Report for Application No. 09154092.2, mailed May 7, 2009.
Pasquinelli and Ruvkun, Control of developmental timing by micrornas and their targets, Ann. Rev. Cell Dev. Biol., 18:495-513, 2002.
Pasquinelli et al., Reverse 5' caps in RNAs made in vitro by phage RNA polymerases, RNA, 1:957-967, 1995.
Patrawala et al., Hierarchical organization of prostate cancer cells in xenograft tumors: the CD44+alpha2beta1 +cell population is enriched in tumor-initiating cells, Cancer Res., 67(14):6796-805, 2007.
Patrawala et al., Highly purified CD44+ prostate cancer cells from xenograft human tumors are enriched in tumorigenic and metastatic progenitor cells, Oncogene, 25(12): 1696-708, 2006.
Patrawala et al., MicroRNAs in prostate cancer stem cells, AACR Cancer Stem Cell Special Conference—Los Angeles, Feb. 12-15 2008.
Patrawala et al., Side population is enriched in tumorigenic, stem-like cancer cells, whereas ABCG2+and ABCG2- cancer cells are similarly tumorigenic, Cancer Res., 65(14):6207-19, 2005.
Payton and Coats, Cyclin E2, the cycle continues, Int J Biochem Cell Biol, 34(4):315-320, 2002.
Payton et al., Deregulation of cyclin E2 expression and associated kinase activity in primary breast tumors, Oncogene, 21(55):8529-8534, 2002.
PCT Invitation to Pay Additional Fees issued in International Application No. PCT/US2007/078952, mailed Sep. 22, 2009.
PCT Invitation to Pay Additional Fees issued in International Application No. PCT/US2008/087762, mailed Nov. 9, 2009.
Peacock et al., Hedgehog signaling maintains a tumor stem cell compartment in multiple myeloma, Proc. Natl. Acad. Sci. USA, 104(10):4048-53, 2007.
Pendas et al., Worldwide experience with lymphatic mapping for invasive breast cancer, Semin. Oneal., 31 (3):318-323, 2004.
Peng et al., Overexpression of microRNA let-7c in prostate cancer, Modern Pathology, Abstract No. 768, 20 (Suppl.2):169A, 2007.
Peracchi, Prospects for antiviral ribozymes and deoxyribozymes, Rev. Med. Viral., 14:47-64, 2004.
Petit et al., LHFP, a novel translocation partner gene of HMGIC in a lipoma, is a member of a new family of LHFP-like genes, Genomics, 57 (3): 438-441, 1999.
Phan et al., Sentinel lymph node biopsy for melanoma: indications and rationale, Cancer Control, 16(3):234-239, 2009.

(56) References Cited

OTHER PUBLICATIONS

Phillips et al., Antisense RNA amplification: A linear amplification method for analyzing the mRNA Population, Methods, a Companion to Methods in Enzymology, 10(3):283-288, 1996.
Pietras et al., PDGF receptors as cancer drug targets, Cancer Cell, 3(5):439-443, 2003.
Poliseno et al., MicroRNAs modulate the angiogenic properties of HUVECs, Blood; 108(9):3068-3071, 2006.
Porkka et al., MicroRNA expression profiling in prostate cancer, Cancer Res., 67(13):6130-6135, 2007.
Poster Abstracts. Annals of Surgical Oncology, 15(Suppl1):33-64, 2008.
Poy et al., Nature, 432(7014):226-30, 2004.
Pretlow et al., K-ras mutations in putative preneoplastic lesions in human colon, J. Natl Cancer Inst., 85 (24):2004-2007, 1993.
Qian et al., Expression profiling ofCD34+ hematopoietic sternl progenitor cells reveals distinct subtypes of therapy-related acute myeloid leukemia, Proc Natl Acad Sci USA, 99(23):14925-14930, 2002.
Quan et al., The evolution of lymph node assessment in breast cancer, Journal of Surgical Oncology, 2008.
Rader et al., In vitro differentiation of epithelial cells from cervical neoplasias resembles in vivo lesions, Oncogene, 5(4):571-6, 1990.
Rapp et al., Structure and biological activity ofv-raf, a unique oncogene transduced by a retrovirus, Proc Natl Acad Sci US A, 80(14):4218-4222, 1983.
Redston et al., Analysis of micrometastatic disease in sentinel lymph nodes from resectable colon cancer: results of Cancer and Leukemia Group B Trial80001, J. Clin. Oncol., 24(6):878-883, 2006.
Ree et al., Expression of a novel factor in human breast cancer cells with metastatic potential, Cancer Res., 59 (18): 4675-4680, 1999.
Reimer et al., Altered regulation of cyclinG in human breast cancer and its specific localization at replication foci in response to DNA damage in p53+/+ cells, J. Biol. Chem., 274 (16): 11022-11029, 1999.
Reinhart et al. The 21-nucleotide let-7 RNA regulates developmental timing in Caenorhabditis elegans, Nature, 403:901-906, 2000.
Reintgen et al., Sentinel Node Biopsy in Breast Cancer: An Overview. Breast J., 6(5):299-305, 2000.
Reiter and Sawyers, Xenograft models and the molecular biology of human prostate cancer, In :Prostate Cancer: Biology, Genetics, and the New Therapeutics; Totowa, NJ, 163-173 , 2001.
Reshmi and Pillai, Beyond HPV: oncomirs as new players in cervical cancer, FEES Letters, 582:4113-4116, 2008.
Richardson et al., CD133, a novel marker for human prostatic epithelial stem cells, J Cell Sci., 117(Pt 16):3539-45, 2004.
Rickert et al., Multiplexed Real-Time PCR Using Universal Reporters, Clin. Chem., 50(9): 1680-1683, 2004.
Roberts et al., Interpretive disparity among pathologists in breast sentinel lymph node evaluation, Am. J. Surg., 186:324-329, 2003.
Rosenfeld et al., Ranibizumab: Phase III clinical trial results, Ophthalmol. Clin. North Am. 19(3):361-372, 2006.
Rosenkilde and Schwartz, The chemokine system—a major regulator of angiogenesis in health and disease, Aprnis, 112(7-8):481-495, 2004.
Rossi et al., Identification of inactivating mutations in the JAK1, SYNJ2, and CLPTM1 genes in prostate cancer cells using inhibition of nonsense-mediated decay and microarray analysis, Cancer Genet. Cytogenet., 161 (2): 97-103 , 2005.
Rous, A sarcoma of the fowl transmissible by an agent separable from the tumor cells, J Exp Med, 13:397-411, 1911.
Rubin and Gutmann, Neurofibromatosis type 1—a model for nervous system tumour formation?, Nat Rev Cancer, 5 (7):557-564, 2005.
Ruth et al., RhoC promotes human melanoma invasion in a PI3K/Akt-dependent pathway, J. Invest. Derrnatol., 126 (4): 862-868, 2006.
Ryan et al., MicroRNAs of the mammalian eye display distinct and overlapping tissue specificity, Molecular Vision, 12:1175-1184, 2006.
Sacchi et al., Hu-ets-1 and Hu-ets-2 genes are transposed in acute leukemias with (4;11) and (8;21) translocations, Science, 231 (4736): 379-382, 1986.
Saha et al., Historical review of tymphatic mapping in gastrointestinal malignancies, Ann Surge Oncol, 11(3Suppi):245S-249S, 2004.
Saha et al., Ultrastaging of colorectal cancer by sentinel lymph node mapping technique—a multicenter trial, Ann. Surg. Oncol., 8(9 Suppl):94S-98S, 2001.
Saigusa et al., Overexpressed Skp2 within 5p amplification detected by array-based comparative genomic hybridization is associated with poor prognosis of glioblastomas, Cancer Sci, 96(10):676-683, 2005.
Saitoh et al., Frequent up-regulation ofWNT5A mRNA in primary gastric cancer, Int. J. Mol. Med., 9 (5):515-519, 2002.
Saiz et al., MicroRNA expression profiling in acute myelogenous leukemia, Blood, ASH Annual Meeting Abstracts, 104:320a, Abstract No. 1131, Poster board No. session 285-I, 2004.
Sakai et al., Microarray hybridization with fractionated eDNA: enhanced identification of differentially expressed genes, Analytical Biochemistry, 287(1):32-37, 2000.
Sampson and Uhlenbeck, Bichemical and physical characterization of an unmodified yeast phenylalanine transfer RNA transcribed in vitro, Proc. Natl. Acad. Sci., USA, 85(4):1033-1037, 1988.
Sanger Institute, miRBase miRBase Sequence Database, located at; http:l/microrna.sanger.ac.ukl, printed Jan. 21, 2009.
Sasaki et al., Expression of the MTA1 mRNA in advanced lung cancer, Lung Cancer, 35(2):149-154, 2002.
Scaria et al., Host-virus genome interactions: macro roles for microRNAs, Cell Microbial., (12):2784-94 2007.
Scaria et al., Host-virus interaction: a new role for microRNAs, Retrovirology, 3:68, 2006.
Schenborn and Stecha, Ribo m7G cap analog: A reagent for preparing in vitro capped transcripts, Promega Notes, 74:18-20, 2000.
Schepeler et al., Diagnostic and prognostic microRNAs in stage II colon cancer, Cancer Research, 68 (15):6416-6424, 2008.
Scherer and Rossi, Approaches for the sequence-specific knockdown of mRNA, Nat. Biotechnol., 21 (12):1457-1465, 2003.
Scherr et al., Lentrivirus-mediated antagomir expression for specific inhibition of miRNA function, Nucleic Acids Research, 35(22):e149, 2007.
Scherr et al., Modulation of gene expression by lentiviral-mediated delivery of small interfering RNA, Cell Cycle, 2 (3):251-257, 2003.
Schetter et al., MicroRNA expression profiles associated with prognosis and therapeutic outcome in colon adenocarcinoma, JAMA, 299(4):425-436, 2008.
Schouten et al., Relative quantification of 40 nucleic acid sequences by multiplex ligationdependent probe amplification, Nucleic Acids Research, 30(12):e57, 2002.
Schulze-Bergkamen et al., Suppression of Mcl-1 via RNA interference sensitizes human hepatocellular carcinoma cells towards apoptosis induction, BMC Cancer, 6:232, 2006.
Schurr et al., Lymphatic spread and microinvolvement in adenocarcinoma of the esophagogastric junction, J Surg. Oneal., 94:307-315 , 2006.
Schuster and Porse, C/EBPalpha: a tumour suppressor in multiple tissues? Biochim Biophys Acta, 1766(1):88-103, 2006.
Schwarz et al., Asymmetry in the assembly of the RNAi enzyme complex, Cell, 115:199-208, 2003.
Scoggins et al., Prospective multi-institutional study of reverse transcriptase polymerase chain reaction for molecular staging of melanoma, J Clin. Oneal., 24:2849-2857, 2006.
Scott et al., BCL2 antisense reduces prostate cancer cell survival following irradiation, Cancer Biotherapy & Radiopharmaceuticals, 17(6):647-656, 2002.
Segal et al., A module map showing conditional activity of expression modules in cancer, Nature Genetics, 36(10):1090-1098, 2004.
Seggerson et al., Dev. Biol., 243:215, 2002.
Sellner et al., Reverse transcriptase inhibits Taq polymerase activity, Nucleic Acids Research, 20(7):1487-1490,1992.

(56) References Cited

OTHER PUBLICATIONS

Sementchenko et al, ETS2 function is required to maintain the transformed state of human prostate cancer cells, Oncogene, 17 (22): 2883-2888, 1998.
Semple and Duncker, ORC-associated replication factors as biomarkers for cancer, Biotechnol Adv, 22(8):621-631, 2004.
Sevignani et al., Mammalian microRNAs: a small world for fine-tuning gene expression, Mamm. Genome, 17(3):189-202, 2006.
Shah et al., FGFR4 overexpression in pancreatic cancer is mediated by an intronic enhancer activated by HNF1alpha, Oncogene, 21 (54): 8251-8261, 2002.
Shelly et al., Epiregulin is a potent pan-ErbB ligand that preferentially activates heterodimeric receptor complexes, J. Biol. Chem., 273 (17): 10496-10505, 1998.
Shelton et al., MicroRNAs and Human Cancer, Abstract submitted for a Cold Spring Symposium in early Jun. 2006—71 st Symposium: Regulatory RNAs.
Shen et al., MicroRNAs regulate ocular neovascularization, Molecular Therapy, 16(7):1208-1216, 2008.
Shen et al., Oxidative damage in age-related macular degeneration, Histol. Histopathol. 22(12):1301-1308, 2007.
Shen et al., Suppression of ocular neovascularization with siRNA targeting VEGF receptor 1,Gene Therapy,13:225-234 , 2006.
Shepherd et al., Expression profiling of CD133+ and CD133- epithelial cells from human prostate. Prostate, 68 (9):1007-1024, 2008.
Sherr and McCormick, The RB and p53 pathways in cancer, Cancer Cell, 2(2):103-112, 2002.
Sherr and Roberts, CDK inhibitors: positive and negative regulators of G 1-phase progression, Genes Dev, 13 (12):1501-1512, 1999.
Shi et al., Facile means for quantifying microRNA expression by real-time PCR, BioTechniques, 39(4):519-524, 2005.
Shibahara et al., Down-regulation of Skp2 is correlated with p27-associated cell cycle arrest induced by phenylacetate in human prostate cancer cells, Anticancer Res., 25 (3b): 1881-1888, 2005.
Shigemasa et al., Increased MCL-1 expression is associated with poor prognosis in ovarian carcinomas, Jpn. J. Cancer Res., 93(5):542-550, 2002.
Shimo et al., Connective tissue growth factor as a major angiogenic agent that is induced by hypoxia in a human breast cancer cell line, Cancer Lett., 174(1):57-64, 2001.
Shimoyama et al., Increased serum angiogenin concentration in colorectal cancer is correlated with cancer progression, Clin. Cancer Res., 5 (5): 1125-1130, 1999.
Shingara et al., An optimized isolation and labeling platform for accurate microRNA expression profiling, RNA, 11:1461-1470, 2005.
Shipitsin et al., Molecular definition of breast tumor heterogeneity, Cancer Cell, 11(3):259-73, 2007.
Shuldiner et al., RNA template-specific polymerase chain reaction RS-PCR a novel strategy to reduce dramatically false positives, Gene, 91(1):139-142, 1990.
Shyu et al., RARRES3 expression positively correlated to tumour differentiation in tissues of colorectal adenocarcinoma, Br. J. Cancer, 89 (1): 146-151, 2003.
Si et al., miR-21-mediated tumor growth, Oncogene, 26(19):2799-2803, 2007.
Simpson et al., Altered expression of Erg and Ets-2 transcription factors is associated with genetic changes at 21q22.2-22.3 in immortal and cervical carcinoma cell lines, Oncogene, 14 (18): 2149-2157, 1997.
Singh et al., Overexpression of vimentin: role in the invasive phenotype in an androgenindependent model of prostate cancer, Cancer Res, 63(9):2306-2311, 2003.
Singh et al., 1dentification of a cancer stem cell in human brain tumors, Cancer Res., 63(18):5821-8, 2003.
Sinner et al., Sox17 and Sox4 differentially regulate beta-catenin/ T-cell factor activity and proliferation of colon carcinoma cells, Mol. Cell Biol., 27(22):7802-15, 2007.
Sirera et al., The analysis of serum DNA concentration by means of hTERT quantification: A useful prognostic factor in advanced non-small cell lung cancer (NSCLC). Lung Cancer. 49:S74, Abstract PD-026, 2005.
Skotzko et al., Retroviral vector-mediated gene transfer of antisense cyclin G1 (CYCG1) inhibits proliferation of human osteogenic sarcoma cells, Cancer Res., 55 (23): 5493-5498, 1995.
Slaby et al., Altered expression of miR-21, miR-31, miR-143 and miR-145 is related to clinicopathologic features of colorectal cancer, Oncology, 72(5-6):397-402, 2007.
Slack Control of Develonment by microRNAs believed at the time of the filing of this form to have been presented by Frank Slack at IIT Bombay on Jan. 28, 2004.
Slack et al., The lin-41 RBCC gene acts in the C. elegans heterochronic pathway between the let-7 regulatory RNA and the LIN-29 transcription factor, MoZee. Cell, 5(4):659-669, 2000.
Slack MicroRNA control of oncogene expression, believed at the time of the filing of this form to have been presented by Frank Slack at Slack GTBIO on Nov. 8, 2004.
Slack, Control of Development by microRNAs. believed at the time of the filing of this form to have been presented by Frank Slack at Keystone miRNAs on Apr. 15, 2005.
Slack, Control of Development by microRNAs. believed at the time of the filing of this form to have been presented by Frank Slack at UCT on Feb. 17, 2004.
Slack, Control of Development by microRNAs. believed at the time of the filing of this form to have been presented by Frank Slack at UNMC on Mar. 26, 2004.
Slack, Control of Developmental timing by microRNAs. believed at the time of the filing of this form to have been presented by Frank Slack at Santa Cruz in Aug. 2004.
Slack, MicroRNAs and cancer, believed at the time of the filing of this form to have been presented by Frank Slack at University of Puerto Rico Bayamon on Sep. 22, 2004.
Slack, Multiple, dynamic microRNA ribonucleoprotein complexes with select microRNA cargos in C. elegans, believed at the time of the filing of this form to have been presented by Frank Slack at Gordon on Jun. 8, 2004.
Slack, Small RNA genese as potential causes and treatments of cancer, believed at the time of the filing of this form to have been presented by Frank Slack at Jaslok on Feb. 1, 2004.
Slack, Temperal patterning and biological timing, believed at the time of the filing of this form to have been presented by Frank Slack at Dartmouth on Mar. 19, 2004.
Smirnova et al., Regulation of miRNA expression during neural cell specification, Eur J Neurosci, 21(6):1469-1477, 2005.
Smith et al., Exclusive amplification of eDNA template (Exact) RT-PCR to avoid amplifying contaminating genomic pseudogenes, Bio Techniques, 31 (4): 776-778, 780, 782, 2001.
Smith et al., Human papilloma virus type distribution in invasive cervical cancer and highgrade cervical lesions: a meta-analysis update, Int. J Cancer, 121(3):621-32, 2007.
Smith et al., Malignant transformation of mammalian cells initiated by constitutive expression of the polo-like kinase, Biochem Biophys Res Commun, 234(2):397-405, 1997.
Smith et al., Overexpression of aurora B kinase (A URKB) in primary non-small cell lung carcinoma is frequent, generally driven from one allele, and correlates with the level of genetic instability, Br J Cancer, 93( 6):719-729, 2005.
Smith et al., Oxygen-induced retinopathy in the mouse, Invest. Ophthalmol. Vis. Sci. 35(1):101-111, 1994.
Sommers et al., Loss of epithelial markers and acquisition ofvimentin expression in adriamycin- and vinblastine-resistant human breast cancer cell lines, Cancer Res, 52(19):5190-5197, 1992.
Sparmann and Bar-Sagi, Ras-induced interleukin-8 expression plays a critical role in tumor growth and angiogenesis, Cancer Cell, 6(5):447-458, 2004.
Stehelin et al., DNA related to the transforming gene(s) of avian sarcoma viruses is present in normal avian DNA, Nature, 260(5547):170-173, 1976.

(56) References Cited

OTHER PUBLICATIONS

Stepinski et al., Synthesis and properties ofmRNAs containing the novel 'anti-reverse' cap analogs 7-methyl(3'0-methyi)GpppG and 7-methyl(e'-deoxy)GpppG, RNA, 7:1486-1495 , 2001.
Stone et al., Isolation of a human prostate carcinoma cell line (DU 145), Int. J Cancer, 21 (3):274-281, 1978.
Strebhardt and Ullrich, Targeting polo-like kinase 1 for cancer therapy, Nat. Rev. Cancer, 6 (4): 321-330, 2006.
Sturniolo et al., A novel tumor suppressor protein promotes keratinocyte terminal differentiation via activation of typel transglutaminase, J Bial. Chem., 278 (48): 48066-48073, 2003.
Su et al., Overexpression of p8 is inversely correlated with apoptosis in pancreatic cancer, Clin. Cancer Res., 7 (5):1320-1324, 2001.
Sueoka et al., Detection of plasma hnRNP B 1 mRNA, a new cancer biomarker, in lung cancer patients by quantitative real-time polymerase chain reaction, Lung Cancer, 48(1):77-83, 2005.
Suh et al., Devel Biol., 270:488-98, 2004.
Sui et al., Clinical significance of Skp2 expression, alone and combined with Jab 1 and p27 in epithelial ovarian tumors, Oneal. Rep., 15 (4): 765-771, 2006.
Sum et al., Overexpression of LM04 induces mammary hyperplasia, promotes cell invasion, and is a predictor of poor outcome in breast cancer, Prac Natl Acad Sci US A, 102(21):7659-7664, 2005.
Sum et al., The LIM domain protein LM04 interacts with the cofactor CliP and the tumor suppressor BRCA1 and inhibits BRCA1 activity, J Bial Chem, 277(10):7849-7856, 2002.
Sun et al., Downregulation ofCCND1 and CDK6 by miR-34a induces cell cycle arrest, FEES Letters, 582:1564-1568, 2008.
Sun et al., Development of a micro-array to detect human and mouse microRNAs and characterization of expression in human organs. Nucleic Acids Research, 32(22):e188, 2004.
Sunpaweravong et al., Epidermal growth factor receptor and cyclin D1 are independently amplified and overexpressed in esophageal squamous cell carcinoma, J Cancer Res Clin Oneal, 131(2):111-119, 2005.
Swanson et al., The prognosis of T3NO colon cancer is dependent on the number oftymph nodes examined, Ann. Surg. Oneal., 10(1):65-71, 2003.
Szafranska et al., A unique microRNA molecular signature for pancreatic carcinoma, AACR Pancreatic Cancer: Early Detection and Novel Therapeutics, Chapel Hill, NC, Jun. 26-27, 2006.
Szafranska et al., MicroRNA expression alterations are linked to tumorigenesis and nonneoplastic processes in pancreatic ductal adenocarcinoma, Oncogene, 26:4442-4452, 2007.
Tagawa et al., Genome-wide array-based CGH for mantle cell lymphoma: identification of homozygous deletions of the proapoptotic gene BIM. Oncogene. 24(8):1348-1358, 2005.
Takamizawa et al., Reduced expression of the let-7 microRNAs in human lung cancers in association with shortened postoperative survival, Cancer Research, 64:3753-3756, 2004.
Takanami, The prognostic value of overexpression of Skp2 mRNA in non-small cell lung cancer. Oneal. Rep., 13 (4): 727-731, 2005.
Takei et al., A small interfering RNA targeting vascular endothelial growth factor as cancer therapeutics, CancerResearch, 64:3365-3370, 2004.
Takeshita et al., Efficient delivery of small interfering RNA to bone-metastatic tumors by using atelocollagen in vivo, PNAS, 102(34):12177-12182, 2005.
Takeshita et al., Systemic delivery of synthetic microRNA-16 inhibits the growth of metastatic prostate tumors via downregulation of multiple cell-cycle genes, Molecular Therapy, 18(1):181-187, 2010.
Takeuchi et al., Prognostic significance of molecular upstaging of paraffin-embedded sentinel lymph nodes in melanoma patients, J. Clin. Oncol., 22:2671-2680, 2004.
Takimoto et al., Genetic alterations in the retinoblastoma protein-related p107 gene in human hematologic malignancies, Biochem Biophys Res Commun, 251(1):264-268, 1998.
Tanaka et al., A novel frizzled gene identified in human esophageal carcinoma mediates APC/beta-catenin signals, Proc. Natl. Acad. Sci. USA, 95 (17): 10164-10169, 1998.
Tang et al., Prostate cancer stem/progenitor cells: identification, characterization, and implications, Mol. Carcinog.,46(1):1-14, 2007.
Tang et al., PS 7-2 microna expression profile in cervical cancer and its derived cell lines, 23rd InternationalPapillomavirus Conference and Clinical Workshop, Prague, Czech Republic, Sep. 1-7, 2006.
Tang et al., Transforming growth factor-beta can suppress tumorigenesis through effects on the putative cancer stem or early progenitor cell and committed progeny in a breast cancer xenograft model, Cancer Res., 67 (18):8643-52, 2007.
Taniwaki et al., Gene expression profiles of small-celllung cancers: molecular signatures of lung cancer, Int J Oneal, 29(3):567-575, 2006.
Tassi et al., Enhancement of fibroblast growth factor (FGF) activity by an FGF-binding protein, J. Biol. Chem., 276 (43):40247-40253, 2001.
Tazawa et al. PNAS 104: 15472-15477 , 2007.
Thiyagarajan et al., Role of GLI2 transcription factor in growth and tumorigenicity of prostate cells, Cancer Res., 67 (22):10642-6, 2007.
Thogersen et al., A subclass of HER1 ligands are prognostic markers for survival in bladder cancer patients, CancerRes., 61 (16): 6227-6233 , 2001.
Tijsterman and Plasterk, Dicers at Risc: the mechanism of RNAi, Cell, 117:1-4, 2004.
Tockman et al., Considerations in bringing a cancer biomarker to clinical application, Cancer Research, 52:2711s-2718s, 1992.
Toh et al., A novel candidate metastasis-associated gene, mta1, differentially expressed in highly metastatic mammary adenocarcinoma cell lines. eDNA cloning, expression, and protein analyses, J Biol Chem, 269 (37):22958-22963, 1994.
Toh et al., Overexpression of metastasis-associated MTA1 mRNA in invasive oesophageal carcinomas, BrJCancer, 79(11-12):1723-1726, 1999.
Toh et al., Overexpression of the MTA1 gene in gastrointestinal carcinomas: correlation with invasion and metastasis, Int J Cancer, 74(4):459-463, 1997.
Tomasini-Johansson et al.. Vitronectin in colorectal adenocarcinoma—synthesis by stromal cells in culture. Exp. Cell. Res., 214 (1): 303-312, 1994.
Torring et al., Increased expression of heparin binding EGF (HB-EGF), amphiregulin, TGF alpha and epiregulin in androgen-independent prostate cancer cell lines, Anticancer Res., 20 (1a): 91-95, 2000.
Toyoda et al., Distribution of mRNA for human epiregulin, a differentially expressed member of the epidermal growth factor family, Biochem J, 326 (Pt 1):69-75, 1997.
Trang et al., Regression of murine lung tumors by the let-7 microRNA, Oncogene, 29(11):1580-1587, Epub 2009.
Traub et al., Prognostic impact of Skp2 and p27 in human breast cancer, Breast Cancer Res. Treat., 99 (2):185-191, 2006.
Tricoli et al., MicroRNA: potential for cancer detection, diagnosis, and prognosis, Cancer Res., 67(10):4553-4555, 2007.
Tsai et al., Correlation of intrinsic chemoresistance of non-small-celllung cancer cell lines with HER-2/neu gene expression but not with ras gene mutations, J Natl Cancer Inst, 85(11):897-901, 1993.
Tsai et al., RIG 1 inhibits the Ras/mitogen-activated protein kinase pathway suppressing the activation of Ras., Cell Signal, 18 (3): 349-358, 2006.
Turner et al., Hallmarks of 'BRCAness' in sporadic cancers, Nat Rev Cancer, 4(10):814-819, 2004.
Tuveson et al., BRAF as a potential therapeutic target in melanoma and other malignancies, Cancer Cell, 4 (2):95-98, 2003.
U.S. Appl. No. 10/778,908, entitled Anti-microRNA oligonucleotide molecules, by Thomas Tuschl et al., filed Feb. 13, 2004.
U.S. Appl. No. 11/273,640, entitled Methods and compositions involving miRNA and miRNA inhibitors molecules, by David Brown et al., filed Nov. 14, 2005.

(56) References Cited

OTHER PUBLICATIONS

U.S. Appl. No. 11/855,792, entitled Methods of normalization in microRNA detection assays, by GaryLatham et al., filed Sep. 14, 2007.
U.S. Appl. No. 11/967,639, entitled Functions and targets of LET-7 micro RNAs, by Charles Johnson et al., filed Dec. 31, 2007.
U.S. Appl. No. 11/967,663, entitled miR-16 regulated genes and pathways as targets for therapeutic intervention, by Mike Byrom et al., filed Dec. 31, 2007.
U.S. Appl. No. 12/112,291, entitled miR-20 Regulated Genes and Pathways as Targets for Therapeutic Intervention, by Andreas Bader et al., filed Apr. 30, 2008.
U.S. Appl. No. 12/120,388, entitled miR-21 regulated genes and pathways as targets for therapeutic intervention, by Andreas Bader eta/., filed May 14, 2008.
U.S. Appl. No. 12/124,394, entitled miR-200 Regulated Genes and Pathways as Targets for Therapeutic Intervention, by Andreas Bader eta/., filed May 21, 2008.
U.S. Appl. No. 12/125,412, entitled miR-143 regulated genes and pathways as targets for therapeutic intervention, by Andreas Bader et al., filed May 22, 2008.
U.S. Appl. No. 12/134,932, entitled miR-134 Regulated Genes and Pathways as Targets for Therapeutic Intervention, by Andreas Bader eta/., filed Jun. 6, 2008.
U.S. Appl. No. 12/209,822, entitled MicroRNAs idfferentially expressed in cervical cancer and uses thereof, by Sylvie Beaudenon eta/., filed Sep. 12, 2008.
U.S. Appl. No. 12/325,917, entitled miR-124 Regulated Genes and Pathways as Targets for Therapeutic Intervention, by Andreas Bader eta/., filed Dec. 1, 2008.
U.S. Appl. No. 12/616,616, entitled Methods and compositions involving miRNAs in cancer stem cells, by Lubna Patrawala et al., filed Nov. 11, 2009.
U.S. Appl. No. 12/340,329, entitled miR-10 Regulated Genes and Pathways as Targets for Therapeutic Intervention, by Ovcharenko et al., filed Dec. 19, 2008.
U.S. Appl. No. 12/368,053, entitled miRNAs Differentially Expressed in Lymph Nodes from Cancer Patients, by Sylvie Beaudenon eta/., filed Feb. 9, 2009.
U.S. Appl. No. 12/398,852, entitled MicroRNA markers for recurrence of colorectal cancer, by Elizabeth Mambo et al., filed Mar. 5, 2009.
U.S. Appl. No. 12/412,087, entitled Compositions and methods related to miR-16 and therapy of prostate cancer, by Fumitaka Takeshita et al., filed Mar. 26, 2009.
U.S. Appl. No. 12/420,634, entitled Methods and compositions for diagnosing and modulating human papillomavirus (HPV), by Sylvie Beaudenon-Huibregtse, filed Apr. 8 2009.
U.S. Appl. No. 12/437,899, entitled Compositions and methods related to miRNA modulation of neovascularization or angiogenesis, by Jikui Shen et al., filed May 8, 2009.
U.S. Appl. No. 12/253,718, mailed Apr. 22, 2011.
U.S. Appl. No. 60/650,807, entitled Compositions and methods involving MDA-7 and COX-2 inhibitors for the treatment of cancer, by Sunil Chada et al., filed Feb. 8, 2005.
U.S. Appl. No. 60/906,028, entitled Prostate cancer specific rniRNAs, by David Brown, filed Mar. 9, 2007.
U.S. Appl. No. 60/869,295 entitled MicroRNAs Differentially Expressed in Leukemia and Uses Thereof by Tim Davison, et al., submitted Dec. 8, 2006.
Uhm et al., Vitronectin, a glioma-derived extracellular matrix protein, protects tumor cells from apoptotic death, Clin. Cancer Res., 5 (6): 1587-1594, 1999.
Ulisse et al., Expression of Aurora kinases in human thyroid carcinoma cell lines and tissues, Int. J. Cancer, 119 (2): 275-282, 2006.
Upton et al., Expression of vimentin in surgically resected adenocarcinomas and large cell carcinomas of lung, Am J Surg Pathol, 10(8):560-567, 1986.
US Office Action for U.S. Appl. No. 12/167,492, issued Jun. 7, 2011.
US Office Action for U.S. Appl. No. 12/325,917, mailed Apr. 22, 2011.
US Office Action for U.S. Appl. No. 12/368,053, mailed Jun. 22, 2011.
US Office Action for U.S. Appl. No. 12/412,087, mailed Apr. 22, 2011.
US Office Action for U.S. Appl. No. 12/420,634, mailed Apr. 29, 2011.
Vanhaesebroeck et al., Phosphoinositide 3-kinases: a conserved family of signal transducers, Trends Biochem Sci, 22(7):267-272, 1997.
Vargas-Roig et al., Heat shock protein expression and drug resistance in breast cancer patients treated with induction chemotherapy, Cancer Detection and Prevention, 21(5):441-451, 1997.
Vella et al., Architecture of a validated microRNA::target interaction, Chem. Biol., 11(12): 1619-1623, 2004.
Vella et al., The C. elegans microRNA let-7 binds to imperfect let-7 complementary sites from the lin-41 3'UTR, Genes Dev., 18(2):132-7, 2004.
Vermeulen et al., Single-cell cloning of colon cancer stem cells reveals a multi-lineage differentiation capacity, PNAS, 105(360):13427-13432, 2008.
Vezina & Bushman, Hedgehog signaling in prostate growth and benign prostate hyperplasia, Curr. Ural. Rep., 8(4):275-80, 2007.
Visvader et al., The LIM domain gene LM04 inhibits differentiation of mammary epithelial cells in vitro and is overexpressed in breast cancer, Proc Natl Acad Sci USA, 98(25):14452-14457, 2001.
Visvanathan etal., The microRNA miR-124 antagonizes the anti-neural REST/SCPI pathway during embryonic CNS development, Genes & Development, 21 (7):744-749, 2007.
Vogt et al., Triple layer control: phosphorylation, acetylation and ubiquitination of FOXO proteins, Cell Cycle, 4 (7):908-913, 2005.
Volinia et al., A microRNA expression signature of human solid tumors defines cancer gene targets, Proc. Natl. Acad. Sci. USA, 103(7):2257-2261, 2006.
Volloch and Sherman, Oncogenic potential ofHsp72, Oncogene, 18(24):3648-3651, 1999.
Voorhoeve et al., A genetic screen implicates miRNA-372 and miRNA-373 as oncogenes in testicular germ cell tumors, Cell, 124(6): 1169-1181, 2006.
Vos et al., RASSF2 is a novel K-Ras-specific effector and potential tumor suppressor, J Bioi Chem, 278 (30):28045-28051, 2003.
Wade, Transcriptional control at regulatory checkpoints by histone deacetylases: molecular connections between cancer and chromatin, Hum. Mol. Genet., 10(7):693-698, 2001.
Wagner and Sondak, The sentinel lymph node: more than just another blue lymph node, Cancer, 97(8):1821-1823, 2003.
Walboomers et al., Human papillomavirus is a necessary cause of invasive cervical cancer worldwide, J Pathol., 189(1):12-9, 1999.
Wang & Dick, Cancer stem cells: lessons from leukemia, Trends Cell Biol., 15(9):494-501, 2005.
Wang and Wang, Systematic identification of micro RNA functions by combining target prediction and expression profiling, Nucleic Acids Research, 34(5): 1646-1652, 2006.
Wang et al., Aberrant expression of oncogenic and tumor-suppressive microRNAs in cervical cancer is required for cancer cell growth, PLoS One, 3(7):e2557, 2008.
Wang et al., Identification of rat lung-specific microRNAs by rnicoRNA rnicroarray: valuable discoveries for the facilitation of lung research, BMC Genomics, 8:29-42, 2007.
Wang et al., Increased levels of forkhead box M1B transcription factor in transgenic mouse hepatocytes prevent age-related proliferation defects in regenerating liver, Proc Natl Acad Sci US A, 98(20):11468-11473, 2001.
Wang et al., Oncogenic HPV infection interrupts the expression of tumor-suppressive miR-34a through viral oncoprotein E6, RNA, 15(4):637-647, 2009.
Wang et al., Pten deletion leads to the expansion of a prostatic stem/progenitor cell subpopulation and tumor initiation, Proc. Natl. Acad. Sci. USA, 103(5):1480-1485, 2006.

(56) References Cited

OTHER PUBLICATIONS

Watabe et al., Growth, regeneration, and tumorigenesis of the prostate activates the PSCA promoter, Proc Natl Acad Sci USA, 99(1):401-6, 2002.
Weeraratna et al., Wnt5a signaling directly affects cell motility and invasion of metastatic melanoma, Cancer Cell, 1 (3): 279-288, 2002.
Weidhaas et al., MicroRNAs as potential agents to alter resistance to cytotoxic anticancer therapy, Cancer Res, 67 (23):11111-11116, 2007.
Weil et al., Targeting the kinesin Eg5 to monitor siRNA transfection in mammalian cells, Biotechniques, 33 (6):1244-1248, 2002.
Weinstein, Disorders in cell circuitry during multistage carcinogenesis, the role of homeostasis, Carcinogenesis, 21 (5): 857-864, 2000.
Weiss and Bohmann, Deregulated repression of c-Jun provides a potential link to its role in tumorigenesis, CellCycle, 3 (2): 111-113, 2004.
Welsh et al., Fingerprinting genomes using PCR with arbitrary primers, Nucleic Acids Research, Oxford University Press, Surrey, GB, 18(24):7213-7218, 1990.
Welsh et al., Nucleic acid fingerprinting by PCR-based methods: applications to problems in aging and mutagenesis, Mutation Research, 338(1-6):215-229, 1995.
Wheeler and Ridley, Why three Rho proteins? RhoA, RhoB, RhoC, and cell motility, Exp. Cell. Res., 301 (1): 43-49, 2004.
Whitcombe et al., A homogeneous fluorescence assay for PCR amplicons: its application to realtime, single-tube genotyping, Clin. Chem., 44(5):918-923, 1998.
Whitcombe et al., Advances in approaches to DNA-based diagnostics, Curr. Opin. Biotechnol., 9(6):602-608, 1998.
White et al., Treatment of pulmonary hemangiomatosis with recombinant interferon alfa-2a, N Engl J Med320:1197-1200, 1989.
Wiemer, EurJ Cancer, 43(10):1529-1544, 2007.
Wikman et al., Identification of differentially expressed genes in pulmonary adenocarcinoma by using eDNA array, Oncogene, 21(37):5804-5813, 2002.
Willert et al., Wnt proteins are lipid-modified and can act as stem cell growth factors, Nature, 423(6938):448-52, 2003.
Wilson and Laimins, Differentiation of HPV-containing cells using organotypic raft culture or methylcellulose, Methods Mol. Med., 119:157-69, 2005.
Wong et al., Number of nodes examined and staging accuracy in colorectal carcinoma, J. Clin. Oncol., 17 (9):2896-2900, 1999.
Wood et al., DNA rnicroarray analysis of vitamin D-induced gene expression in a human colon carcinoma cell line, Physiol. Genomics, 17 (2): 122-129, 2004.
Wood et al., One hundred consecutive cases of sentinel lymph node mapping in early colorectal carcinoma: detection of missed micrometastases, J Gastrointest Surg., 6(3):322-330, 2002.
Wooster and Weber, Breast and ovarian cancer, N. Engl. J. Med., 348(23):2339-2347, 2003.
Wu et al., Expression of Ephb2 and Ephb4 in breast carcinoma, Pathol. Oncol. Res., 10 (1):26-33, 2004.
Wu et al., MicroRNA and cancer: current status and prospective, International Journal of Cancer, 120:953-960, 2006.
Wu et al., p107 Expression in colorectal tumours rises during carcinogenesis and falls during invasion, EurJCancer, 38(14):1838-1848, 2002.
Wu et al., Rarres 1 expression is significantly related to tumour differentiation and staging in colorectal adenocarcinoma, Eur. J. Cancer, 42(4):557-565, 2006.
Wu et al., RhoC induces differential expression of genes involved in invasion and metastasis in MCF10A breast cells, Breast Cancer Res., Treat., 84 (1); 3-12 , 2004.
Wu et al., The prognostic impact ofEphB2/B4 expression on patients with advanced ovarian carcinoma. Gynecol. Oneal., 102 (1): 15-21, 2006.
Wyatt et al., Synthesis and purification oftarge amounts of RNA oligonucleotides. Biotechniques. 11(6):764-769, 1991.

Wyttenbach et al., Polyglutarnine expansions cause decreased CRE-mediated transcription and early gene expression changes prior to cell death in an inducible cell model of Huntington's disease, Human Molecular Genetics,10(17):1829-1845, 2001.
Xi et al., A combination of molecular markers accurately detects lymph node metastasis in non-small cell lung cancer patients, Clin. Cancer Res., 12:2484-2491, 2006.
Xi et al., Differentially regulated micro-RNAs and actively translated messenger RNA transcripts by tumor suppressor p53 in colon cancer, Clin Cancer Res., 12:2014-2024, 2006.
Xi et al., Identification of mRNA markers for molecular staging of lymph nodes in colorectal cancer, Clin. Chem., 52 (3):520-523, 2006.
Xi et al., Molecular staging of lymph nodes from patients with esophageal adenocarcinoma, Clin. Cancer Res., 11:1099-1109, 2005.
Xi et al., Prognostic Values of microRNAs in Colorectal Cancer, Biomark Insights, 2:113-121, 2006.
Xia et al., Positive expression ofHIF-2alpha/EPAS1 in invasive bladder cancer, Urology, 59(5):774-778, 2002.
Xia et al., Regulation of vascular endothelial growth factor transcription by endothelial PAS domain protein 1 (EPAS1) and possible involvement ofEPAS1 in the angiogenesis of renal cell carcinoma, Cancer, 91(8):1429-1436, 2001.
Xia et al., The Src-suppressed C kinase substrate, SSeCKS, is a potential metastasis inhibitor in prostate cancer, Cancer Res, 61(14):5644-5651, 2001.
Xie et al., Negative feedback regulation of Dicer-Like1 in Arabidopsis by microRNA-guided mRNA degradation. Current Biology, 13:784-789, 2003.
Xie, et al., Systematic discovery of regulatory motifs in human promoters and 3' UTRs by comparison of several mammals, Nature, 434(7031):338-345, 2005.
Xu et al., The *Drosophila* microRNA Mir-14 suppresses cell death and is required for normal fat metabolism, Curr. Biol., 13:790-795, 2003.
Yamamoto et al., Cdk2/cdc2 expression in colon carcinogenesis and effects of cdk2/cdc2 inhibitor in colon cancer cells, Int J Oncol, 13(2):233-239, 1998.
Yamato et al., New highly potent and specific E6 and E7 siRNAs for treatment of HPV16 positive cervical cancer, Cancer Gene Therapy, 15:140-153, 2008.
Yanaihara et al., Unique microRNA molecular profiles in lung cancer diagnosis and prognosis, Cancer Cell, 9:189-198, 2006.
Yang et al., Dicer is required for embryonic angiogenesis during mouse development, J Biol. Chem. 280 (10):9330-9335, 2005.
Yang et al., Differential expression of CCAAT/enhancer-binding protein-delta (c/EBPdelta) in rat androgen-dependent tissues and human prostate cancer, J. Androl., 22 (3): 471-480, 2001.
Yang et al., Significance of CD90+ cancer stem cells in human liver cancer, Cancer Cell, 13(2):153-66, 2008.
Yang et al., Smad3 reduces susceptibility to hepatocarcinoma by sensitizing hepatocytes to apoptosis through downregulation of Bcl-2, Cancer Cell, 9(6):445-457, 2006.
Yang et al., Stromal expression of connective tissue growth factor promotes angiogenesis and prostate cancer tumorigenesis, Cancer Res., 65(19):8887-8895, 2005.
Yang et al., Tumorigenesis suppressor Pdcd4 down-regulates mitogen-activated protein kinase kinase kinase 1 expression to suppress colon carcinoma cell invasion, Mol Cell Biol, 26(4):1297-1306, 2006.
Yang et al., The transformation suppressor Pdcd4 is a novel eukaryotic translation initiation factor 4A binding protein that inhibits translation, Mol. Cell Biol., 23(1):26-37, 2003.
Yao et al., RhoC GTPase is required for PC-3 prostate cancer cell invasion but not motility, Oncogene, 25 (16):2285-2296, 2006.
Yeatman, A renaissance for SRC, Nat Rev Cancer, 4(6):470-480, 2004.
Yi et al., The association of the expression of MTA1, nm23H1 with the invasion, metastasis of ovarian carcinoma, Chin Med Sci J, 18(2):87-92, 2003.
Yi et al., Genes Dev. 17(24):3011-6, 2003.

(56) References Cited

OTHER PUBLICATIONS

Yoon and De Micheli, Prediction of regulatory modules comprising microRNAs and target genes, Bioinformatics, 21 (Suppl.2):ii93-ii100, 2005.
Yoshida et al., the clinical significance of Cyclin B 1 and Wee 1 expression in non-small-cell lung cancer, Ann Oneal, 15(2):252-256, 2004.
Yoshimura et al., Prognostic impact of hypoxia-inducible factors 1alpha and 2alpha in colorectal cancer patients:correlation with tumor angiogenesis and cyclooxygenase-2 expression, Clin. Cancer Res., 10(24):8554-8560, 2004.
Yoshioka et al., A role for LIM kinase in cancer invasion, Proc. Natl. Acad. Sci. USA, 100 (12): 7247-7252, 2003.
Youssef et al., Hypermethylation and silencing of the putative tumor suppressor, Tazaroteneinduced gene 1 in human cancers, Cancer Res., 64 (7): 2411-2417, 2004.
Yu et al,. Global assessment of promoter methylation in a mouse model of cancer identifies 104 as a putative tumor-suppressor gene in human leukemia, Nat. Genet., 37 (3): 265-274, 2005.
Yu et al., Crosstalk between cancer and immune cells: role of STAT3 in the tumour microenvironment, Nat Rev Immunol, 7(1):41-51, 2007.
Yu et al., Cell. 2007;131:1109-23.
Zangemeister-Wittke and Huwiler, Antisense targeting of Mcl-1 has therapeutic potential in gastric cancer, Cancer Biol. Ther., 5(10):1355-1356, 2006.
Zeng et al., Both natural and designed micro RNAs can inhibit the expression of cognate mRNAs when expressed in human cells, Mol Cell. 9, 1327-33 , 2002.
Zeng et al., MicroRNAs and small interfering RNAs can inhibit mRNA expression by similar mechanisms, Proc. Natl. Acad. Sci. 100: 9779-9784, 2003.
Zhang et al., Enhancement of hematopoietic stem cell repopulating capacity and self-renewal in the absence of the transcription factor C/EBP alpha, Immunity, 21(6):853-863, 2004.
Zhang et al., Identification and characterization of ovarian cancer-initiating cells from primary human tumors, Cancer Res., 68(11):4311-20, 2008.
Zhang et al., Involvement of programmed cell death 4 in transforming growth factor-beta1-induced apoptosis in human hepatocellular carcinoma, Oncogene, 25(45):6101-6112, 2006.
Zhang et al., Methylation of the retinoid response gene TIG 1 in prostate cancer correlates with methylation of the retinoic acid receptor beta gene, Oncogene, 23 (12): 2241-2249, 2004.
Zhang et al., microRNAs as oncogenes and tumor suppressors, Dev. Biol., 302(1):1-12, 2007.
Zhang et al., NANOGP8 is a retrogene expressed in cancers, FEES J, 273(8):1723-30, 2006.
Zhao et al., Cyclin G1 has growth inhibitory activity linked to the ARF-Mdm2-p53 and pRb tumor suppressor pathways, Mol Cancer Res, 1(3): 195-206, 2003.
Zhou et al., Activation of the PTEN/mTOR/STAT3 pathway in breast cancer stem-like cells is required for viability and maintenance, Proc. Natl. Acad. Sci. USA, 104(41):16158-63, 2007.
Zhou et al., The ABC transporter Bcrp1/ ABCG2 is expressed in a wide variety of stem cells and is a molecular determinant of the side-population phenotype, Nat. Med., 7(9):1028-1034, 2001.
Zhu et al., Epiregulin is Up-regulated in pancreatic cancer and stimulates pancreatic cancer cell growth, Biochem. Biophys. Res. Commun., 273 (3): 1019-1024, 2000.
Zhu et al., MicroRNA-21 targets the tumor suppressor gene tropomyosin 1 (TIPM1)The Journal of BiologicalChemistry, 282(19):14328-14336, 2007.
Zimmerman et al. Technical aspects of quantitative competitive PCR, Biotechniques, 21(2):268-270, 1996.
Bader A. G. et al. The promise of microRNA replacement therapy. Cancer Res. vol. 70, pp. 7027-7030 (2010).
Blower et al. MicroRNAs modulate the chemosensitivity of tumor cells, Mol. Cancer Therapy. 7(1):1-9, 2008.
Co-pending U.S. Appl. No. 14/676,308, filed Apr. 1, 2015.
Croce C., MicroRNAs in leukemia. Clinical Advances in Hematology & Oncology, vol. 4, pp. 577-578 (2006).
Czauderna et al. Structural variations and stabilising modifications of synthetic siRNAs in mammalian cells. Nucleic Acids Research. vol. 31, No. 11, pp. 2705-2716 (2003).
Dorsett, et al. siRNAs: Applications in functional genomics and potential as therapeutics. Nature 3:318-329 (2004).
Esquela-Kerscher et al., Oncomirs—microRNAs with a role in cancer. Nat Rev Cancer 6(4):259-69 (2006).
Garzon, et al., MicroRNA expression and function in cancer. Trends Mol Med, vol. 12, No. 12, pp. 580-587, Dec. 2006.
Hammond et al., RNAi, microRNAs, and human disease. Cancer Chemother Pharmacol. Nov. 2006; 58 Suppl. 1:s63-8.
International Application No. PCT/US2015/023878 International Search Report and Written Opinion Mailed Jul. 10, 2015.
Iorio et al. MicroRNA involvement in human cancer. Carcinogenesis 33; 1126-1133 (2012).
Kasinski et al. MicroRNAs en route to the clinic: Progress in validating and targeting microRNAs for cancer therapy, Nature Reviews Cancer, 11(12) Nov. 24, 2011.
Liu et al. Uncovering growth-suppressive MicroRNAs in lung cancer. Clinical Cancer Research 15(4); 1177-1183 (2009).
Lui et al. Patterns of known and novel small RNAs in human cervical cancer. Cancer Res., 67(13):6031-6043, 2007.
Martin et al. Ein neuer Zugang zu 2'-O-Alkylribonucleosiden und Eigenschaften deren Oligonucleotide. Helv. Chim. Acta, 78:486-504, 1995.
Nikitina et al. MicroRNAs and human cancer. Experimental Oncology, 34(1);2-8 (2012).
Prakash et al. Positional effect of chemical modifications on short interference RNA activity in mammalian cells. J. Med. Chem. Jun. 30, 2005;48(13):4247-53.
Schoof et al. MicroRNAs in cancer treatment and prognosis, American Journal of Cancer Research, vol. 2, No. 4, pp. 414-433 (2012).
Tong, AW et al. Modulation of miRNA activity in human cancer: a new paradigm for cancer gene therapy? Cancer Gene Therapy, vol. 15, No. 6, pp. 341-355 (2008).
U.S. Appl. No. 13/365,646 Office Action Mailed Feb. 4, 2015.
U.S. Appl. No. 13/365,676 Office Action Mailed Mar. 19, 2013.
U.S. Appl. No. 14/081,295 Office Action Mailed Nov. 6, 2014.
U.S. Appl. No. 14/459,182 Office Action Mailed Oct. 26, 2015.
U.S. Appl. No. 14/459,192 Office Action Mailed Sep. 16, 2015.
U.S. Appl. No. 14/565,049 Office Action Mailed Mar. 29, 2016.
U.S. Appl. No. 14/738,734 Final Office Action Mailed Mar. 17, 2016.
Wiggins et al., Development of a lung cancer therapeutic based on the tumor suppressor microRNA-34, Cancer Res 70(14):5923-5930 (2010).
Zhang, C. et al. Co-Suppression of miR-221/222 cluster suppresses human glioma cell growth by targeting p27kip1 in vitro and in vivo. International Journal of Oncology 34: 1653-1660.
Khvorava, et al. Functional siRNAs and miRNAs exhibit strand bias. Cell, 2003, vol. 115, p. 209-216.

\* cited by examiner

Fig. 2
| Vector Expression | siRNA Design | miRNA Design |
|---|---|---|
| 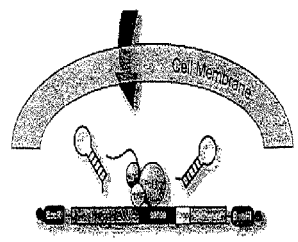 | 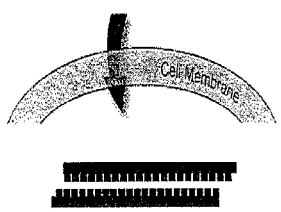 | 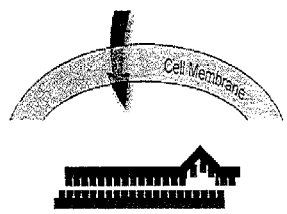 |
| Correct strand uptake<br>Low transfection efficiency | High transfection efficiency<br>Off-strand uptake | High transfection efficiency<br>Correct strand uptake |
| X | X | ✓ |

Fig. 3
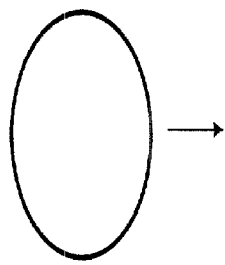
Active strand reporter
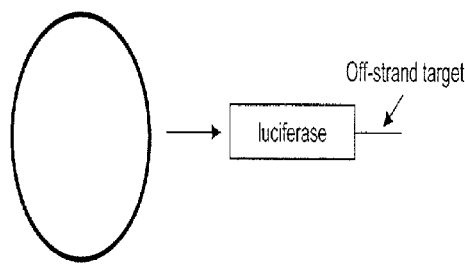
Complementary-strand reporter
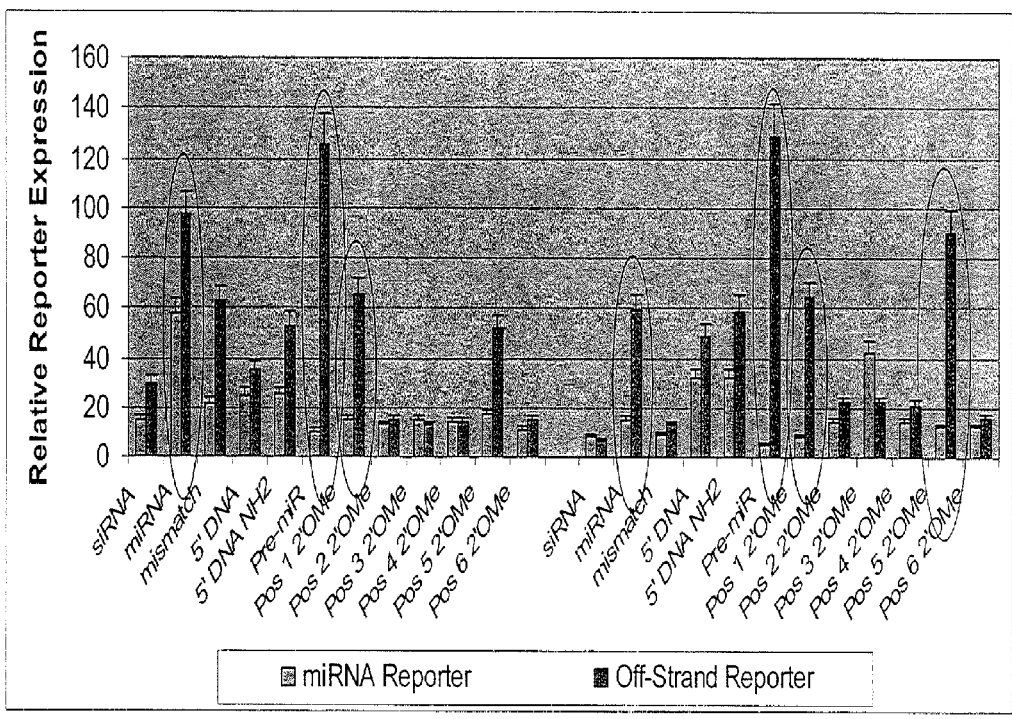

Fig. 5
Synthetic miRNAs in multiple cell types
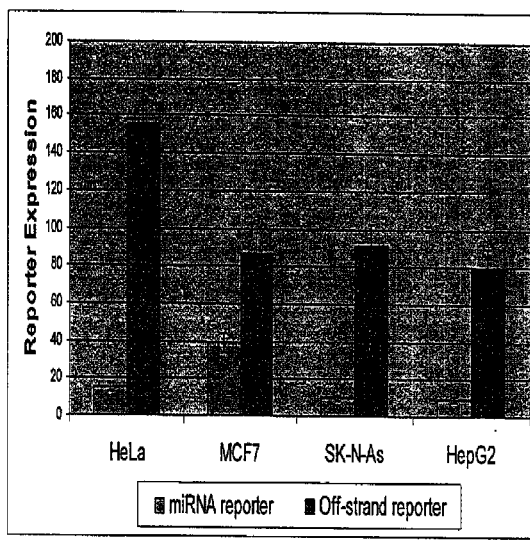
Effect of Synthetic miRNAs on endogenous targets
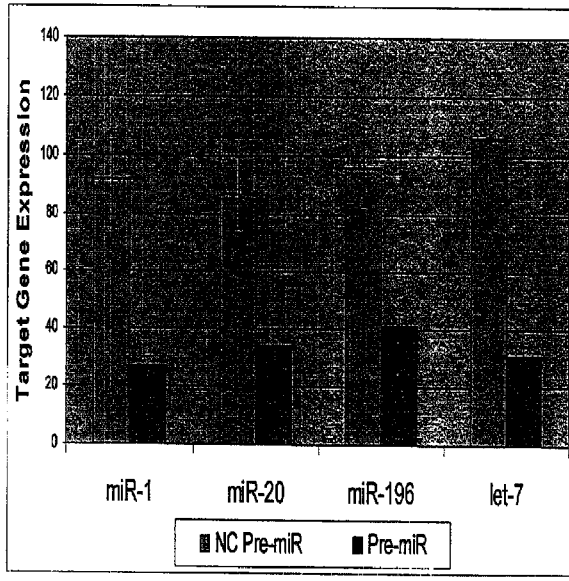

FIG. 15A

Breast BT549

| miRNA | % of neg cont | St Dev |
|---|---|---|
| mir-101 | 87 | 3 |
| mir-105 | 88 | 2 |
| mir-124 | 88 | 5 |
| mir-126 | 82 | 2 |
| mir-129 | 85 | 1 |
| mir-132 | 87 | 4 |
| mir-142 | 87 | 4 |
| mir-192 | 81 | 3 |
| mir-201 | 79 | 14 |
| mir-215 | 82 | 1 |
| mir-27a | 87 | 4 |
| mir-346 | 88 | 1 |
| mir-92 | 85 | 11 |
| mir-96 | 87 | 9 |
| mir-98 | 87 | 1 |
| mir-99a | 88 | 1 |

Breast MCF12A

| miRNA | % of neg cont | St Dev |
|---|---|---|
| mir-126 | 88 | 32 |
| mir-142 | 87 | 27 |
| mir-147 | 87 | 33 |
| mir-206 | 86 | 12 |
| mir-208 | 87 | 12 |
| mir-210 | 86 | 11 |
| mir-211 | 83 | 7 |
| mir-214 | 85 | 19 |
| mir-215 | 70 | 10 |
| mir-219 | 88 | 10 |
| mir-220 | 85 | 7 |
| mir-221 | 88 | 7 |
| mir-223 | 87 | 10 |
| mir-331 | 88 | 12 |
| mir-345 | 88 | 10 |
| mir-346 | 82 | 12 |
| mir-297 | 78 | 15 |
| mir-329 | 82 | 17 |
| mir-409 | 86 | 11 |
| mir-411 | 86 | 7 |

Cervical HeLa

| miRNA | % of neg cont | St Dev |
|---|---|---|
| mir-1 | 20 | 2 |
| mir-101 | 12 | 2 |
| mir-124 | 16 | 4 |
| mir-192 | 13 | 3 |
| mir-193 | 5 | 2 |
| mir-195 | 21 | 7 |
| mir-201 | 26 | 7 |
| mir-206 | 12 | 6 |
| mir-208 | 21 | 12 |
| mir-210 | 23 | 4 |
| mir-215 | 33 | 21 |
| mir-299 | 20 | 18 |
| mir-337 | 18 | 3 |
| mir-339 | 31 | 2 |
| mir-340 | 31 | 7 |
| mir-345 | 31 | 21 |
| mir-34a | 35 | 7 |
| mir-367 | 31 | 12 |
| mir-292-3p | 29 | 21 |
| mir-293 | 26 | 30 |
| mir-297 | 19 | 16 |
| mir-344 | 32 | 1 |
| mir-409 | 30 | 16 |

Prostate 22 Rv1

| miRNA | % of neg cont | St Dev |
|---|---|---|
| mir-126 | 63 | 3 |
| mir-101 | 77 | 9 |
| mir-103 | 75 | 10 |
| mir-105 | 75 | 12 |
| mir-107 | 84 | 22 |
| mir-124 | 77 | 6 |
| mir-128 | 81 | 4 |
| mir-129 | 81 | 4 |
| mir-132 | 84 | 10 |
| mir-135 | 79 | 4 |
| mir-137 | 81 | 4 |
| mir-141 | 85 | 2 |
| mir-142 | 69 | 4 |
| mir-147 | 66 | 4 |
| mir-15a | 85 | 9 |
| mir-16 | 74 | 6 |
| mir-27a | 83 | 7 |
| mir-28 | 82 | 9 |
| mir-30a-3p | 80 | 8 |
| mir-34a | 72 | 8 |
| mir-297 | 84 | 5 |

FIG. 15B

| Skin TE354T | | | Skin TE353SK | | | BJ cells | | | Lung A549 | | |
|---|---|---|---|---|---|---|---|---|---|---|---|
| miRNA | % of neg cont | St Dev | miRNA | % of neg cont | St Dev | miRNA | % of neg cont | St Dev | miRNA | % of neg cont | St Dev |
| mir-1 | 53 | 7 | mir-101 | 63 | 11 | miR-206 | 19 | 7 | mir-124 | 44 | 0 |
| mir-101 | 49 | 6 | mir-105 | 42 | 40 | let7a | 69 | 10 | Let-7b | 70 | 0 |
| mir-124 | 64 | 10 | mir-124 | 70 | 8 | mir1 | 38 | 2.65 | Let-7d | 71 | 0 |
| mir-136 | 59 | 4 | mir-126 | 56 | 8 | miR-105 | 65 | 5 | Let-7g | 62 | 1 |
| mir-154 | 51 | 5 | mir-128 | 53 | 46 | miR-147 | 35 | 7 | mir-126 | 68 | 0 |
| mir-15a | 63 | 4 | mir-132 | 66 | 8 | miR-15a | 43 | 8 | mir-129 | 67 | 1 |
| mir-16 | 58 | 5 | mir-133A | 56 | 49 | miR-16 | 51 | 4 | mir-137 | 64 | 0 |
| mir-192 | 62 | 7 | mir-136 | 27 | 24 | miR-195 | 48 | 10 | mir-147 | 65 | 0 |
| mir-193 | 69 | 4 | mir-137 | 55 | 13 | miR-297 | 46 | 6.85 | mir-15a | 61 | 0 |
| mir-195 | 58 | 3 | mir-141 | 62 | 23 | miR-324-3p | 68 | 8.84 | mir-16 | 53 | 1 |
| mir-201 | 67 | 8 | mir-142 | 60 | 19 | miR-337 | 27 | 7.26 | mir-192 | 70 | 2 |
| mir-206 | 51 | 4 | mir-144 | 65 | 22 | miR-376b | 63 | 6.53 | mir-193 | 64 | 3 |
| mir-215 | 59 | 6 | mir-15a | 57 | 20 | | | | mir-195 | 59 | 0 |
| mir-221 | 62 | 8 | mir-16 | 59 | 9 | | | | mir-22 | 68 | 1 |
| mir-26a | 69 | 12 | mir-181a | 65 | 23 | | | | mir-28 | 61 | 0 |
| mir-28 | 60 | 18 | mir-20 | 47 | 41 | | | | mir-292-3p | 62 | 0 |
| mir-346 | 67 | 6 | mir-206 | 67 | 15 | | | | mir-29a | 67 | 1 |
| mir-34a | 65 | 5 | mir-215 | 68 | 11 | | | | mir-337 | 55 | 0 |
| mir-7 | 63 | 1 | mir-223 | 56 | 49 | | | | mir-344 | 63 | 0 |
| mir-96 | 60 | 8 | mir-302 | 63 | 1 | | | | mir-345 | 69 | 1 |
| mir-329 | 60 | 4 | mir-330 | 66 | 59 | | | | mir-34a | 61 | 0 |
| mir-376b | 65 | 3 | mir-346 | 59 | 52 | | | | mir-7 | 63 | 1 |
| | | | mir-373 | 66 | 7 | | | | | | |
| | | | mir-96 | 65 | 16 | | | | | | |
| | | | mir-291 | 48 | 17 | | | | | | |
| | | | mir-329 | 68 | 62 | | | | | | |
| | | | mir-380-3p | 64 | 55 | | | | | | |
| | | | mir-411 | 54 | 47 | | | | | | |

FIG. 15C

| Lung CRL5826 | | | Lung HTB-57 | | | Jurkats | | | Primary T-cells | | |
|---|---|---|---|---|---|---|---|---|---|---|---|
| miRNA | % of NC | STDEV | miRNA | % of NC | STDEV | miRNA | % of neg cont | St Dev | miRNA | % of neg cont | St Dev |
| ambi-mir7100 | 63 | 21 | mir-108 | 79 | | let-7a | 21 | 1 | miR-107 | 89 | 15 |
| mir-101 | 70 | 20 | mir-122 | 79 | | let-7b | 50 | 5 | miR-134 | 75 | 23 |
| mir-105 | 74 | 11 | mir-124 | 79 | | miR-101 | 69 | 30 | miR-135 | 88 | 13 |
| mir-124 | 63 | 8 | mir-125a | 77 | 11 | miR-10b | 37 | 3 | miR-139 | 87 | 0 |
| mir-125b | 74 | 11 | mir-126 | 78 | 2 | miR-122 | 67 | 18 | miR-141 | 89 | 1 |
| mir-126 | 61 | 3 | mir-132 | 59 | 7 | miR-133a | 73 | 18 | miR-145 | 86 | 12 |
| mir-128 | 71 | 13 | mir-133A | 77 | 7 | miR-17-3p | 63 | 16 | | | |
| mir-132 | 73 | 18 | mir-136 | 78 | 13 | miR-29a | 68 | 7 | | | |
| mir-141 | 74 | 5 | mir-147 | 72 | 4 | miR-30a-3p | 66 | 27 | | | |
| mir-142 | 67 | 5 | mir-151 | 67 | 10 | miR-34a | 67 | 21 | | | |
| mir-147 | 75 | 7 | mir-152 | 73 | 13 | | | | | | |
| mir-149 | 71 | 9 | mir-16 | 79 | 6 | | | | | | |
| mir-188 | 67 | 11 | mir-182 | 63 | 9 | | | | | | |
| mir-223 | 68 | 14 | mir-183 | 72 | 9 | | | | | | |
| mir-28 | 74 | 19 | mir-186 | 69 | 17 | | | | | | |
| mir-29a | 74 | 14 | mir-188 | 67 | 20 | | | | | | |
| mir-337 | 74 | 17 | mir-28 | 79 | 16 | | | | | | |
| mir-346 | 72 | 13 | mir-377 | 79 | 3 | | | | | | |
| mir-96 | 74 | 6 | mir-526b* | 79 | 0 | | | | | | |
| | | | mir-96 | 76 | 10 | | | | | | |

FIG. 16

Cervical HeLa

| miRNA | % of neg cont | St Dev |
|---|---|---|
| Let-7a | 119 | 15 |
| Let-7b | 124 | 12 |
| Let-7c | 114 | 21 |
| Let-7d | 113 | 29 |
| Let-7g | 114 | 27 |
| mir-145 | 111 | 29 |
| mir-155 | 114 | 17 |
| mir-181a | 113 | 21 |
| mir-186 | 111 | 29 |
| mir-190 | 114 | 21 |
| mir-191 | 116 | 22 |
| mir-199 | 118 | 14 |
| mir-9 | 112 | 27 |

Prostate 22 Rv1

| miRNA | % of neg cont | St Dev |
|---|---|---|
| Let-7a | 124 | 6 |
| Let-7b | 127 | 27 |
| mir-127 | 127 | 11 |
| mir-154 | 123 | 10 |
| mir-181a | 124 | 11 |
| mir-194 | 132 | 16 |
| mir-198 | 126 | 10 |
| mir-199 | 146 | 18 |
| mir-201 | 125 | 24 |
| mir-369 | 130 | 9 |
| mir-93 | 129 | 16 |

Skin TE354T

| miRNA | % of neg cont | St Dev |
|---|---|---|
| mir-139 | 117 | 20 |
| mir-141 | 120 | 52 |
| mir-143 | 122 | 35 |
| mir-145 | 156 | 71 |
| mir-146 | 143 | 85 |
| mir-188 | 117 | 37 |
| mir-190 | 131 | 55 |
| mir-198 | 119 | 3 |
| mir-204 | 125 | 8 |
| mir-410 | 133 | 3 |
| mir-412 | 125 | 11 |

Skin TE353SK

| miRNA | % of neg cont | St Dev |
|---|---|---|
| mir-138 | 126 | 7 |
| mir-196 | 134 | 7 |
| mir-197 | 135 | 8 |
| mir-198 | 144 | 4 |
| mir-199 | 135 | 9 |
| mir-204 | 125 | 6 |
| mir-216 | 136 | 13 |
| mir-410 | 134 | 7 |

BJ cells

| miRNA | % of neg cont | St Dev |
|---|---|---|
| miR-26a | 130 | 17 |
| miR-128 | 131 | 24 |
| miR-223 | 134 | 14 |
| miR-188 | 139 | 19 |
| miR-125a | 140 | 10 |
| miR-201 | 153 | 18 |
| miR-291-3p | 155 | 30 |
| miR-145 | 161 | 2 |
| miR-294 | 165 | 21 |
| miR-150 | 171 | 7 |
| miR-322 | 212 | 19.93 |
| miR-295 | 215 | 40.78 |
| miR-187 | 246 | 19 |
| miR-373 | 268 | 41.39 |

Lung Cancer A549

| miRNA | % of neg cont | St Dev |
|---|---|---|
| mir-25 | 112 | 0 |
| mir-294 | 112 | 1 |
| mir-32 | 121 | 0 |
| mir-92 | 122 | 0 |

Jurkats

| miRNA | % of neg cont | St Dev |
|---|---|---|
| miR-100 | 134 | 15 |
| miR-125b | 132 | 4 |
| miR-126 | 134 | 19 |
| miR-129 | 150 | 10 |
| miR-140 | 139 | 4 |
| miR-143 | 162 | 2 |
| miR-155 | 146 | 23 |
| miR-15a | 146 | 12 |
| miR-23b | 135 | 4 |
| miR-25 | 154 | 18 |
| miR-26a | 170 | 14 |

Primary T-cells

| miRNA | % of neg cont | St Dev |
|---|---|---|
| let-7a | 151 | 17 |
| let-7b | 150 | 14 |
| let-7c | 159 | 4 |
| let-7d | 142 | 10 |
| let-7g | 141 | 7 |
| miR-10a | 130 | 10 |
| miR-10b | 127 | 20 |
| miR-125a | 131 | 5 |
| miR-126 | 126 | 42 |
| miR-15a | 135 | 11 |
| miR-17-3p | 128 | 4 |
| miR-18 | 138 | 2 |
| miR-182 | 126 | 18 |
| miR-19a | 126 | 5 |
| miR-20 | 130 | 14 |
| miR-7 | 126 | 1 |

CRL5826

| miRNA | % of NC | STDEV |
|---|---|---|
| mir-130a | 126 | 27 |
| mir-145 | 112 | 8 |
| mir-30e-5p | 122 | 11 |
| mir-333 | 112 | 35 |
| mir-335 | 114 | 33 |
| mir-369 | 111 | 8 |
| mir-350 | 111 | 5 |
| mir-412 | 123 | 14 |

HTB-57

| miRNA | % of NC | STDEV |
|---|---|---|
| mir-135 | 121 | 8 |
| mir-216 | 126 | 7 |
| mir-293 | 121 | 4 |
| mir-338 | 122 | 14 |
| mir-341 | 118 | 22 |

FIG. 17

| Prostate 22Rv1 | | | Skin TE354T | | | Breast MCF12a | | | Lung A549 | | |
| --- | --- | --- | --- | --- | --- | --- | --- | --- | --- | --- | --- |
| miRNA | % NC | St Dev | miRNA | % NC | St Dev | miRNA | % NC | St Dev | miRNA | % NC | St Dev |
| mir-100 | 59 | 26 | mir-210 | 67 | 13 | mir-216 | 92 | 9 | mir-129 | 90 | 5 |
| mir-130a | 58 | 16 | mir-216 | 53 | 1 | mir-217 | 95 | 14 | mir-326 | 88 | 2 |
| mir-211 | 54 | 7 | | | | mir-294 | 93 | 23 | mir-331 | 92 | 2 |
| mir-212 | 58 | 1 | | | | | | | mir-338 | 91 | 2 |
| mir-213 | 57 | 11 | | | | | | | mir-341 | 89 | 5 |
| mir-215 | 59 | 8 | | | | | | | mir-370 | 91 | 0 |
| mir-224 | 49 | 30 | | | | | | | mir-92 | 88 | 0 |
| mir-292 | 59 | 4 | | | | | | | | | |
| mir-320 | 58 | 6 | | | | | | | | | |
| mir-324 | 55 | 6 | | | | | | | | | |
| mir-325 | 59 | 10 | | | | | | | | | |
| mir-330 | 58 | 28 | | | | | | | | | |
| mir-338 | 55 | 10 | | | | | | | | | |
| mir-369 | 57 | 6 | | | | | | | | | |
| mir-370 | 54 | 16 | | | | | | | | | |
| mir-99a | 58 | 15 | | | | | | | | | |

FIG. 18

| Prostate 22Rv1 | | | Skin TE354T | | | Breast MCF12a | | | Lung A549 | | |
| --- | --- | --- | --- | --- | --- | --- | --- | --- | --- | --- | --- |
| miRNA | % NC | St Dev | miRNA | % NC | St Dev | miRNA | % NC | St Dev | miRNA | % NC | St Dev |
| mir-10b | 104 | 27 | Let-7a | 139 | 9 | let7a | 180 | 35 | let7a-1 | 116 | 5 |
| mir-152 | 111 | 20 | Let-7b | 148 | 8 | let7b-1 | 176 | 36 | mir-133a-2 | 126 | 2 |
| | | | Let-7g | 133 | 8 | let7c | 177 | 21 | mir-142 | 112 | 4 |
| | | | mir-10a | 135 | 10 | let7d | 172 | 37 | mir-187 | 110 | 6 |
| | | | mir-10b | 140 | 10 | mir-10a | 178 | 22 | mir-199a-1 | 111 | 4 |
| | | | mir-133B | 135 | 8 | mir-10b | 190 | 18 | mir-206 | 110 | 4 |
| | | | mir-155 | 138 | 3 | mir-133a | 182 | 33 | mir-211 | 110 | 6 |
| | | | mir-15a | 142 | 12 | mir-152 | 175 | 33 | mir-222 | 111 | 2 |
| | | | mir-16 | 134 | 8 | mir-153 | 178 | 27 | mir-223 | 112 | 2 |
| | | | mir-181a | 138 | 6 | mir-155 | 186 | 24 | mir-23b | 118 | 6 |
| | | | mir-182 | 133 | 9 | mir-16 | 174 | 30 | mir-298 | 111 | 1 |
| | | | mir-193 | 134 | 12 | mir-181a | 172 | 26 | mir-328 | 115 | 1 |
| | | | mir-194 | 137 | 28 | mir-183 | 184 | 15 | mir-342 | 118 | 0 |
| | | | mir-196 | 133 | 6 | mir-184 | 177 | 14 | mir-371 | 122 | 2 |
| | | | mir-204 | 135 | 9 | mir-186 | 176 | 16 | | | |
| | | | mir-23a | 133 | 16 | mir-191 | 174 | 11 | | | |
| | | | mir-24 | 132 | 11 | mir-200b | 179 | 8 | | | |
| | | | mir-25 | 142 | 13 | mir-412 | 174 | 24 | | | |
| | | | mir-92 | 132 | 11 | mir-9 | 178 | 24 | | | |
| | | | mir-95 | 137 | 5 | | | | | | |

FIG. 19 miRNAs that Decrease Cell Viability

| Jurkat Cell Viability | | | Primary T-cell Cell Viability | | | HeLa Cell Viability | | | A549 Cell Viability | | |
|---|---|---|---|---|---|---|---|---|---|---|---|
| miRNA | % NC | %SD | miRNA | % NC | %SD | miRNA | % NC | %STDEV | miRNA | %NC | %SD |
| let-7a | 21 | 1 | miR-107 | 89 | 15 | mir-1 | 20 | 2 | mir-193 | 80 | 15 |
| let-7b | 50 | 5 | miR-134 | 75 | 23 | mir-101 | 12 | 2 | mir-206 | 80 | 7 |
| miR-101 | 69 | 30 | miR-135 | 88 | 13 | mir-124 | 16 | 4 | mir-210 | 86 | 5 |
| miR-108 | 75 | 18 | miR-139 | 87 | 0 | mir-192 | 13 | 3 | mir-292-3p | 86 | 3 |
| miR-10b | 37 | 3 | miR-141 | 89 | 1 | mir-193 | 5 | 2 | mir-293 | 83 | 2 |
| miR-122 | 67 | 18 | miR-145 | 86 | 12 | mir-195 | 21 | 7 | mir-299 | 84 | 4 |
| miR-133a | 73 | 18 | | | | mir-206 | 12 | 6 | mir-329 | 85 | 5 |
| miR-17-3p | 63 | 16 | | | | mir-208 | 21 | 12 | mir-337 | 81 | 3 |
| miR-19a | 73 | 24 | | | | mir-210 | 23 | 4 | mir-345 | 75 | 6 |
| miR-29a | 68 | 7 | | | | mir-297 | 19 | 16 | mir-346 | 78 | 8 |
| miR-30a-3p | 66 | 27 | | | | mir-299 | 20 | 18 | mir-409 | 86 | 3 |
| miR-34a | 67 | 21 | | | | mir-337 | 18 | 3 | | | | miRNAs that Increase Cell Viability

| Jurkat | | | Primary T-cell | | | HeLa | | | A549 | | |
|---|---|---|---|---|---|---|---|---|---|---|---|
| miR-129 | 150 | 10 | let-7a | 151 | 17 | mir-128 | 128 | 18 | | | |
| miR-143 | 162 | 2 | let-7b | 150 | 14 | mir-139 | 133 | 12 | | | |
| miR-155 | 146 | 23 | let-7c | 159 | 4 | mir-23a | 159 | 13 | | | |
| miR-15a | 146 | 12 | let-7d | 142 | 10 | mir-23b | 155 | 12 | | | |
| miR-25 | 154 | 18 | let-7g | 141 | 7 | mir-24 | 132 | 20 | | | |
| miR-26a | 170 | 14 | miR-10a | 130 | 10 | mir-32 | 133 | 20 | | | |
| | | | miR-10b | 127 | 20 | mir-331 | 128 | 13 | | | |
| | | | miR-125a | 131 | 5 | | | | | | |
| | | | miR-126 | 126 | 42 | | | | | | |
| | | | miR-15a | 135 | 11 | | | | | | |
| | | | miR-17-3p | 128 | 4 | | | | | | |
| | | | miR-18 | 138 | 2 | | | | | | |
| | | | miR-182 | 126 | 18 | | | | | | |
| | | | miR-19a | 126 | 5 | | | | | | |
| | | | miR-20 | 130 | 14 | | | | | | |

FIG. 20

Synthetic miRNAs that Increase Apoptosis

| Prostate 22Rv1 | | | Skin TE354T | | | Jurkat | | | HeLa | | |
|---|---|---|---|---|---|---|---|---|---|---|---|
| miRNA | %NC | St Dev | miRNA | %NC | St Dev | miRNA | %NC | St Dev | miRNA | %NC | St Dev |
| Let-7g | 164 | 17 | mir-149 | 179 | 22 | let-7b | 201 | 41 | let-7b | 369 | 89 |
| mir-1 | 192 | 20 | mir-154 | 252 | 15 | let-7g | 152 | 19 | let-7g | 594 | 260 |
| mir-10a | 205 | 15 | mir-195 | 174 | 16 | miR-1 | 170 | 11 | miR-1 | 410 | 65 |
| mir-149 | 169 | 14 | mir-208 | 189 | 18 | miR-10b | 198 | 24 | miR-10b | 378 | 28 |
| mir-184 | 166 | 19 | mir-214 | 187 | 14 | miR-122 | 154 | 29 | miR-122 | 303 | 44 |
| mir-186 | 166 | 23 | mir-217 | 177 | 21 | miR-17-3p | 171 | 12 | miR-17-3p | 346 | 68 |
| mir-188 | 197 | 12 | mir-293 | 234 | 19 | miR-19a | 153 | 6 | miR-19a | 312 | 7 |
| mir-192 | 182 | 26 | mir-299 | 193 | 12 | miR-28 | 154 | 20 | miR-28 | 347 | 56 |
| | | | mir-328 | 198 | 17 | miR-29a | 155 | 15 | miR-29a | 439 | 63 |
| | | | mir-344 | 204 | 8 | miR-32 | 156 | 30 | miR-32 | 473 | 209 |
| | | | | | | miR-34a | 181 | 39 | miR-34a | 361 | 82 |
| | | | | | | | | | let-7b | 317 | 63 |
| | | | | | | | | | let-7g | 607 | 150 |
| | | | | | | | | | miR-1 | 355 | 47 |
| | | | | | | | | | miR-10b | 404 | 53 |
| | | | | | | | | | miR-122 | 374 | 61 |
| | | | | | | | | | miR-17-3p | 443 | 101 |
| | | | | | | | | | miR-19a | 773 | 70 |
| | | | | | | | | | miR-28 | 402 | 42 |

Synthetic miRNAs that Decrease Apoptosis

| Prostate 22Rv1 | | | Skin TE354T | | | Jurkat | | | HeLa | | |
|---|---|---|---|---|---|---|---|---|---|---|---|
| mir-128 | 54 | 27 | Let-7b | 56 | 10 | miR-125b | 75 | 2 | miR-32 | 8 | 7 |
| mir-21 | 47 | 23 | mir-100 | 55 | 11 | miR-126 | 66 | 11 | mir-105 | 40 | 9 |
| mir-216 | 48 | 37 | mir-101 | 44 | 9 | miR-143 | 68 | 3 | mir-108 | 39 | 12 |
| mir-223 | 54 | 36 | mir-126 | 38 | 11 | miR-155 | 67 | 22 | mir-126 | 29 | 4 |
| mir-23b | 46 | 44 | mir-207 | 59 | 8 | miR-23b | 70 | 14 | mir-137 | 13 | 12 |
| mir-328 | 22 | 29 | mir-25 | 59 | 9 | miR-26a | 68 | 11 | mir-292-3p | 31 | 4 |
| mir-335 | 40 | 26 | mir-28 | 41 | 7 | miR-98 | 74 | 27 | mir-34a | 38 | 8 |
| mir-340 | 51 | 11 | mir-29a | 39 | 8 | | | | mir-96 | 32 | 13 |
| mir-367 | 37 | 34 | mir-30a-3p | 30 | 6 | | | | | | |
| mir-368 | 53 | 36 | | | | | | | | | |
| mir-380-3p | 30 | 42 | | | | | | | | | |
| mir-410 | 50 | 47 | | | | | | | | | |
| mir-341 | 53 | 0 | | | | | | | | | |

FIG. 21 miRNAs that reduce cell viability in the presence of a therapeutic

| A549 +/- TRAIL | | A549 +/- etoposide | | HTB-57 +/- etoposide | | CRL-5826 +/- etoposide | | HeLa +/- etoposide | |
|---|---|---|---|---|---|---|---|---|---|
| miRNA | %NC | miRNA | % NC | miRNA | % NC | miRNA | % NC | miRNA | % NC |
| mir-101 | 135 | mir-28 | 319 | mir-126 | 171 | mir-132 | 142 | mir-124 | 162 |
| mir-124 | 158 | mir-124 | 139 | mir-132 | 201 | mir-182 | 134 | mir-126 | 161 |
| mir-125a | 134 | mir-126 | 141 | mir-28 | 176 | mir-28 | 154 | mir-132 | 170 |
| mir-132 | 147 | mir-147 | 120 | mir-337 | 217 | mir-292-3p | 212 | mir-147 | 171 |
| mir-136 | 178 | mir-216 | 108 | mir-292-3p | 268 | | | mir-216 | 199 |
| mir-155 | 181 | mir-292-3p | 489 | miR-7100 | 227 | | | mir-28 | 169 |
| mir-182 | 153 | mir-337 | 251 | | | | | mir-292-3p | 208 |
| mir-186 | 176 | | | | | | | mir-337 | 285 |
| mir-202 | 152 | | | | | | | | |
| mir-206 | 138 | | | | | | | | |
| mir-221 | 143 | | | | | | | | |
| mir-224 | 129 | | | | | | | | |
| mir-28 | 136 | | | | | | | | |
| mir-291 | 145 | | | | | | | | |
| mir-292-3p | 169 | | | | | | | | |
| mir-297 | 140 | | | | | | | | |
| mir-302 | 134 | | | | | | | | |
| mir-372 | 125 | | | | | | | | |
| mir-373 | 169 | | | | | | | | |
| mir-376b | 145 | | | | | | | | | miRNAs that increase cell viability in the presence of a therapeutic

| miRNA | %NC |
|---|---|
| mir-125b | 83 |
| mir-152 | 73 |
| mir-16 | 90 |
| mir-194 | 78 |
| mir-197 | 82 |
| mir-214 | 82 |
| mir-24 | 87 |
| mir-30a-3p | 63 |
| mir-331 | 73 |

FIG. 22

Figure 22. miRNAs that Affect Cell Cycle

BJ Cells

| G1 | | S | | G2/M | | >2N | |
|---|---|---|---|---|---|---|---|
| miRNA | %NC %SD | miRNA | %NC %SD | miRNA | %NC %SD | miRNA | %NC %SD |
| let7a | 90  22 | mir128 | 46  7 | mir128 | 69  4 | mir125a | 50  22 |
| mir1 | 87  12 | mir142 | 49  41 | mir146 | 61  9 | mir128 | 31  29 |
| mir20 | 67  15 | mir146 | 53  27 | mir147 | 54  12 | mir142 | 59  36 |
| mir206 | 70  13 | mir186 | 60  8 | mir15a | 71  20 | mir146 | 40  45 |
| mir21 | 57  8 | mir187 | 60  15 | mir195 | 62  7 | mir16 | 49  21 |
| mir26a | 62  5 | mir195 | 54  0 | mir371 | 56  5 | mir191 | 56  40 |
| mir290 | 85  2 | mir297 | 54  22 | | | mir201 | 59  27 |
| mir294 | 84  17 | mir324-3p | 60  13 | | | mir224 | 53  17 |
| mir373 | 76  8 | mir337 | 54  17 | | | mir324-3p | 46  33 |
| | | mir376b | 57  17 | | | mir92 | 41  20 |
| mir125a | 120  3 | let7a | 117  14 | mir145 | 145  10 | mir1 | 171  9 |
| mir128 | 150  2 | mir15a | 112  10 | mir187 | 140  3 | mir21 | 205  22 |
| mir142 | 133  10 | mir16 | 124  17 | mir20 | 151  7 | mir337 | 191  27 |
| mir146 | 148  5 | mir191 | 113  21 | mir21 | 169  4 | mir345 | 172  10 |
| mir147 | 126  6 | mir20 | 116  13 | mir223 | 131  11 | mir373 | 174  18 |
| mir195 | 131  2 | mir224 | 125  6 | mir26a | 139  4 | | |
| mir201 | 122  6 | mir26a | 113  6 | mir294 | 135  13 | | |
| mir297 | 125  8 | mir290 | 117  8 | mir373 | 146  4 | | |
| mir320 | 124  2 | mir345 | 119  32 | | | | |
| mir324-3p | 130  4 | | | | | | |
| mir325 | 128  4 | | | | | | |
| mir371 | 135  2 | | | | | | |
| mir376b | 133  2 | | | | | | |
| mir409 | 129  11 | | | | | | |

HeLa Pre-miR

| G1 | | S | | G2/M | |
|---|---|---|---|---|---|
| miRNA | %NC %SD | miRNA | %NC %SD | miRNA | %NC %SD |
| mir-1 | 43.5  3.3 | mir-108 | 76.6  1.1 | mir-122 | 38.6  7.2 |
| mir-192 | 44.1  1.4 | mir-122 | 66.3  1.7 | mir-124 | 58.4  10.4 |
| mir-193 | 32.1  1.4 | mir-129 | 75.3  0.6 | mir-126 | 55.7  13.5 |
| mir-206 | 27.4  2.6 | mir-137 | 62.8  1.7 | mir-129 | 66.0  4.9 |
| mir-220 | 29.3  1.9 | mir-147 | 76.8  3.3 | mir-137 | 46.1  13.1 |
| mir-329 | 38.0  0.5 | mir-324-3p | 71.7  0.4 | mir-147 | 60.0  4.0 |
| mir-371 | 47.0  3.6 | mir-337 | 64.3  3.9 | mir-18 | 62.5  12.2 |
| mir-409 | 38.9  3.6 | | | mir-219 | 64.2  1.9 |
| mir-7d | 57.0  0.5 | | | mir-337 | 66.7  1.0 |
| mir-108 | 143.9  0.7 | mir-197 | 163.8  1.7 | mir-1 | 161.2  1.9 |
| mir-122 | 171.7  0.3 | mir-205 | 183.7  0.9 | mir-192 | 171.9  4.5 |
| mir-124 | 150.0  0.2 | mir-220 | 170.9  0.7 | mir-193 | 185.3  5.9 |
| mir-126 | 153.6  0.3 | mir-290 | 167.2  1.4 | mir-206 | 187.9  7.1 |
| mir-129 | 145.1  0.3 | mir-291 | 200.5  0.9 | mir-215 | 147.5  2.7 |
| mir-137 | 165.9  0.2 | mir-294 | 164.6  1.1 | mir-220 | 170.1  3.9 |
| mir-147 | 150.1  0.4 | mir-295 | 188.2  0.9 | mir-329 | 171.5  1.2 |
| mir-337 | 147.2  0.4 | mir-302 | 214.6  1.7 | mir-371 | 171.6  3.0 |
| | | mir-372 | 203.3  0.8 | mir-409 | 169.7  7.6 |
| | | mir-411 | 168.8  0.9 | mir-7a | 154.6  4.7 |
| | | | | mir-7d | 159.1  2.8 |
| | | | | mir-7g | 160.8  3.0 |

FIG. 23

| miRNA | sequence | A549 Proliferation (% NC) | Jurkats Proliferation (% NC) |
|---|---|---|---|
| let-7a | ugagguaguagguuguauaguu | 119 | 21 |
| let-7b | ugagguaguagguugugugguu | 124 | 50 |
| let-7c | ugagguaguagguuguaugguu | 114 | 85 |
| let-7d | agagguaguagguugcauagu | 113 | 97 |
| let-7g | ugagguaguaguuuguacagu | 114 | 105 |

SEQUENCE LISTING

```
<160> NUMBER OF SEQ ID NOS: 807

<210> SEQ ID NO 1
<211> LENGTH: 85
<212> TYPE: RNA
<213> ORGANISM: Homo sapiens

<400> SEQUENCE: 1
accuacucag aguacauacu ucuuuaugua cccauaugaa cauacaaugc uauggaaugu      60
aaagaaguau guauuuuugg uaggc                                           85

<210> SEQ ID NO 2
<211> LENGTH: 71
<212> TYPE: RNA
<213> ORGANISM: Homo sapiens
```

<400> SEQUENCE: 2
ugggaaacau acuucuuuau augcccauau ggaccugcua agcuauggaa uguaaagaag    60
uauguaucuc a    71

<210> SEQ ID NO 3
<211> LENGTH: 80
<212> TYPE: RNA
<213> ORGANISM: Homo sapiens

<400> SEQUENCE: 3
ugggaugagg uaguagguug uauaguuuua gggucacacc caccacuggg agauaacuau    60
acaaucuacu gucuuuccua    80

<210> SEQ ID NO 4
<211> LENGTH: 72
<212> TYPE: RNA
<213> ORGANISM: Homo sapiens

<400> SEQUENCE: 4
agguugaggu aguagguugu auaguuuaga auuacaucaa gggagauaac uguacagccu    60
ccuagcuuuc cu    72

<210> SEQ ID NO 5
<211> LENGTH: 74
<212> TYPE: RNA
<213> ORGANISM: Homo sapiens

<400> SEQUENCE: 5
gggugaggua guagguugua uaguuugggg cucugcccug cuaugggaua acuauacaau    60
cuacugucuu uccu    74

<210> SEQ ID NO 6
<211> LENGTH: 83
<212> TYPE: RNA
<213> ORGANISM: Homo sapiens

<400> SEQUENCE: 6
cggggugagg uaguagguug ugugguuuca gggcagugau guugcccuc ggaagauaac    60 uauacaaccu acugccuucc cug    83

<210> SEQ ID NO 7
<211> LENGTH: 84
<212> TYPE: RNA
<213> ORGANISM: Homo sapiens

<400> SEQUENCE: 7
gcauccgggu ugagguagua gguuguaugg uuuagaguua cacccuggga guuaacugua    60
caaccuucua gcuuuccuug gagc    84

<210> SEQ ID NO 8
<211> LENGTH: 87
<212> TYPE: RNA
<213> ORGANISM: Homo sapiens

<400> SEQUENCE: 8
ccuaggaaga gguaguaggu ugcauaguuu uagggcaggg auuuugccca caaggaggua    60
acuauacgac cugcugccuu ucuuagg    87

```
<210> SEQ ID NO 9
<211> LENGTH: 79
<212> TYPE: RNA
<213> ORGANISM: Homo sapiens

<400> SEQUENCE: 9
cccgggcuga gguaggaggu uguauaguug aggaggacac ccaaggagau cacuauacgg      60
ccuccuagcu uuccccagg                                                  79

<210> SEQ ID NO 10
<211> LENGTH: 87
<212> TYPE: RNA
<213> ORGANISM: Homo sapiens

<400> SEQUENCE: 10
ucagagugag guaguagauu guauaguugu ggguaguga uuuuacccug uucaggagau       60
aacuauacaa ucuauugccu uccuga                                          87

<210> SEQ ID NO 11
<211> LENGTH: 83
<212> TYPE: RNA
<213> ORGANISM: Homo sapiens

<400> SEQUENCE: 11
ugugggauga gguaguagau uguauaguuu uagggucaua ccccaucuug gagauaacua      60 uacagcuac ugucuuuccc acg                                              83

<210> SEQ ID NO 12
<211> LENGTH: 110
<212> TYPE: RNA
<213> ORGANISM: Homo sapiens

<400> SEQUENCE: 12
uuggauguug gccuaguucu guguggaaga cuagugauuu uguuguuuuu agauaacuaa      60
aucgacaaca aaucacaguc ugccauaugg cacaggccau gccucuacag                110

<210> SEQ ID NO 13
<211> LENGTH: 110
<212> TYPE: RNA
<213> ORGANISM: Homo sapiens

<400> SEQUENCE: 13
cuggauacag aguggaccgg cuggccccau cuggaagacu agugauuuug uuguugucuu      60
acugcgcuca acaacaaauc ccagucuacc uaauggugcc agccaucgca                110

<210> SEQ ID NO 14
<211> LENGTH: 110
<212> TYPE: RNA
<213> ORGANISM: Homo sapiens

<400> SEQUENCE: 14
agauuagagu ggcugugguc uagugcugug uggaagacua gugauuuugu uguucugaug      60
uacuacgaca acaagucaca gccggccuca uagcgcagac ucccuucgac                110

<210> SEQ ID NO 15
<211> LENGTH: 84
<212> TYPE: RNA
<213> ORGANISM: Homo sapiens

<400> SEQUENCE: 15
```

```
aggcugaggu aguaguuugu acaguuugag ggucuaugau accacccggu acaggagaua      60
acuguacagg ccacugccuu gcca                                            84

<210> SEQ ID NO 16
<211> LENGTH: 84
<212> TYPE: RNA
<213> ORGANISM: Homo sapiens

<400> SEQUENCE: 16
cuggcugagg uaguaguuug ugcuguuggu cggguuguga cauugcccgc uguggagaua      60
acugcgcaag cuacugccuu gcua                                            84

<210> SEQ ID NO 17
<211> LENGTH: 89
<212> TYPE: RNA
<213> ORGANISM: Homo sapiens

<400> SEQUENCE: 17
cgggguuggu uguuaucuuu gguuaucuag cuguaugagu ggugguggagu cuucauaaag     60 cuagauaacc gaaaguaaaa auaacccca                                       89

<210> SEQ ID NO 18
<211> LENGTH: 87
<212> TYPE: RNA
<213> ORGANISM: Homo sapiens

<400> SEQUENCE: 18
ggaagcgagu uguuaucuuu gguuaucuag cuguaugagu guauuggucu ucauaaagcu     60
agauaaccga aaguaaaaac uccuuca                                         87

<210> SEQ ID NO 19
<211> LENGTH: 90
<212> TYPE: RNA
<213> ORGANISM: Homo sapiens

<400> SEQUENCE: 19
ggaggcccgu uucucucuuu gguuaucuag cuguaugagu gccacagagc cgucauaaag      60
cuagauaacc gaaaguagaa augauucuca                                      90

<210> SEQ ID NO 20
<211> LENGTH: 110
<212> TYPE: RNA
<213> ORGANISM: Homo sapiens

<400> SEQUENCE: 20
gaucugucug ucuucuguau auacccugua gauccgaauu uguguaagga auuuuguggu      60
cacaaauucg uaucuagggg aauauguagu ugacauaaac acuccgcucu                110

<210> SEQ ID NO 21
<211> LENGTH: 110
<212> TYPE: RNA
<213> ORGANISM: Homo sapiens

<400> SEQUENCE: 21
ccagagguug uaacguuguc uauauauacc cuguagaacc gaauugugu gguauccgua      60 uagucacaga uucgauucua ggggaauaua uggucgaugc aaaaacuuca               110

<210> SEQ ID NO 22
<211> LENGTH: 83
```

<212> TYPE: RNA
<213> ORGANISM: Homo sapiens

<400> SEQUENCE: 22
ccuuggagua aaguagcagc acauaauggu uuguggauuu ugaaaaggug caggccauau    60
ugugcugccu caaaaauaca agg                                           83

<210> SEQ ID NO 23
<211> LENGTH: 98
<212> TYPE: RNA
<213> ORGANISM: Homo sapiens

<400> SEQUENCE: 23
uugaggccuu aaaguacugu agcagcacau caugguuuac augcuacagu caagaugcga    60
aucauuauuu gcugcucuag aaauuuaagg aaauucau                           98

<210> SEQ ID NO 24
<211> LENGTH: 89
<212> TYPE: RNA
<213> ORGANISM: Homo sapiens

<400> SEQUENCE: 24
gucagcagug ccuuagcagc acguaaauau uggcguuaag auucuaaaau uaucuccagu    60
auuaacugug cugcugaagu aagguugac                                     89

<210> SEQ ID NO 25
<211> LENGTH: 81
<212> TYPE: RNA
<213> ORGANISM: Homo sapiens

<400> SEQUENCE: 25
guuccacucu agcagcacgu aaauauuggc guagugaaau auauauuaaa caccauauau    60
acugugcugc uuuaguguga c                                             81

<210> SEQ ID NO 26
<211> LENGTH: 84
<212> TYPE: RNA
<213> ORGANISM: Homo sapiens

<400> SEQUENCE: 26
gucagaauaa ugucaaagug cuuacagugc agguagugau augugcaucu acugcaguga    60
aggcacuugu agcauuaugg ugac                                          84

<210> SEQ ID NO 27
<211> LENGTH: 71
<212> TYPE: RNA
<213> ORGANISM: Homo sapiens

<400> SEQUENCE: 27
uguucuaagg ugcaucuagu gcagauagug aaguagauua gcaucuacug cccuaagugc    60
uccuucuggc a                                                        71

<210> SEQ ID NO 28
<211> LENGTH: 82
<212> TYPE: RNA
<213> ORGANISM: Homo sapiens

<400> SEQUENCE: 28
gcaguccucu guuaguuuug cauaguugca cuacaagaag aauguaguug ugcaaaucua    60

```
ugcaaaacug augguggccu gc                                      82

<210> SEQ ID NO 29
<211> LENGTH: 87
<212> TYPE: RNA
<213> ORGANISM: Homo sapiens

<400> SEQUENCE: 29
cacuguucua gguuaguuu ugcagguuug cauccagcug ugugauauuc ugcugugcaa   60
auccaugcaa aacugacugu gguagug                                     87

<210> SEQ ID NO 30
<211> LENGTH: 96
<212> TYPE: RNA
<213> ORGANISM: Homo sapiens

<400> SEQUENCE: 30
acauugcuac uuacaauuag uuuugcaggu uugcauuuca gcguauauau guauaugugg   60
cugugcaaau ccaugcaaaa cugauguga uaaugu                              96

<210> SEQ ID NO 31
<211> LENGTH: 71
<212> TYPE: RNA
<213> ORGANISM: Homo sapiens

<400> SEQUENCE: 31
guagcacuaa agugcuuaua gugcagguag uguuuaguua ucuacugcau uaugagcacu   60
uaaaguacug c                                                        71

<210> SEQ ID NO 32
<211> LENGTH: 72
<212> TYPE: RNA
<213> ORGANISM: Homo sapiens

<400> SEQUENCE: 32 ugucgguag cuuaucagac ugauguugac uguugaaucu cauggcaaca ccagucgaug   60
ggcugucuga ca                                                       72

<210> SEQ ID NO 33
<211> LENGTH: 85
<212> TYPE: RNA
<213> ORGANISM: Homo sapiens

<400> SEQUENCE: 33
ggcugagccg caguaguucu ucaguggcaa gcuuuauguc cugacccagc uaaagcugcc   60
aguugaagaa cuguugcccu cugcc                                         85

<210> SEQ ID NO 34
<211> LENGTH: 73
<212> TYPE: RNA
<213> ORGANISM: Homo sapiens

<400> SEQUENCE: 34
ggccggcugg gguuccuggg gaugggauuu gcuuccuguc acaaaucaca uugccaggga   60
uuuccaaccg acc                                                      73

<210> SEQ ID NO 35
<211> LENGTH: 97
<212> TYPE: RNA
<213> ORGANISM: Homo sapiens
```

```
<400> SEQUENCE: 35
cucaggugcu cuggcugcuu ggguuccugg caugcugauu ugugacuuaa gauuaaaauc    60
acauugccag ggauuaccac gcaaccacga ccuuggc                             97

<210> SEQ ID NO 36
<211> LENGTH: 68
<212> TYPE: RNA
<213> ORGANISM: Homo sapiens

<400> SEQUENCE: 36
cuccggugcc uacugagcug auaucaguuc ucauuuuaca cacuggcuca guucagcagg    60
aacaggag                                                             68

<210> SEQ ID NO 37
<211> LENGTH: 73
<212> TYPE: RNA
<213> ORGANISM: Homo sapiens

<400> SEQUENCE: 37
cucugccucc cgugccuacu gagcugaaac acaguugguu uguguacacu ggcucaguuc    60
agcaggaaca ggg                                                       73

<210> SEQ ID NO 38
<211> LENGTH: 84
<212> TYPE: RNA
<213> ORGANISM: Homo sapiens

<400> SEQUENCE: 38
ggccaguguu gagaggcgga gacuugggca auugcuggac gcugcccugg cauugcacu     60 ugucucgguc ugacagugcc ggcc                                           84

<210> SEQ ID NO 39
<211> LENGTH: 77
<212> TYPE: RNA
<213> ORGANISM: Homo sapiens

<400> SEQUENCE: 39
guggccucgu ucaaguaauc caggauaggc ugugcagguc ccaaugggcc uauucuuggu    60
uacuugcacg gggacgc                                                   77

<210> SEQ ID NO 40
<211> LENGTH: 77
<212> TYPE: RNA
<213> ORGANISM: Homo sapiens

<400> SEQUENCE: 40
ccgggaccca guucaaguaa uucaggauag guugugugcu guccagccug uucuccauua    60
cuuggcucgg ggaccgg                                                   77

<210> SEQ ID NO 41
<211> LENGTH: 84
<212> TYPE: RNA
<213> ORGANISM: Homo sapiens

<400> SEQUENCE: 41
ggcuguggcu ggauucaagu aauccaggau aggcuguuuc caucugugag gccuauucuu    60
gauuacuugu uucggaggc agcu                                            84
```

```
<210> SEQ ID NO 42
<211> LENGTH: 78
<212> TYPE: RNA
<213> ORGANISM: Homo sapiens

<400> SEQUENCE: 42
cugaggagca gggcuuagcu gcuugugagc aggguccaca ccaagucgug uucacagugg      60
cuaaguuccg cccccag                                                    78

<210> SEQ ID NO 43
<211> LENGTH: 97
<212> TYPE: RNA
<213> ORGANISM: Homo sapiens

<400> SEQUENCE: 43
accucucuaa caaggugcag agcuuagcug auuggugaac agugauuggu uccgcuuug       60 uucacagugg cuaaguucug caccugaaga gaaggug                              97

<210> SEQ ID NO 44
<211> LENGTH: 86
<212> TYPE: RNA
<213> ORGANISM: Homo sapiens

<400> SEQUENCE: 44
gguccuugcc cucaaggagc ucacagucua uugaguuacc uuucugacuu ucccacuaga     60
uugugagcuc cuggagggca ggcacu                                         86

<210> SEQ ID NO 45
<211> LENGTH: 64
<212> TYPE: RNA
<213> ORGANISM: Homo sapiens

<400> SEQUENCE: 45
augacugauu ucuuuuggug uucagaguca auauaauuuu cuagcaccau cugaaaucgg     60
uuau                                                                 64

<210> SEQ ID NO 46
<211> LENGTH: 81
<212> TYPE: RNA
<213> ORGANISM: Homo sapiens

<400> SEQUENCE: 46
cuucaggaag cugguuucau auggugguuu agauuuaaau agugauuguc uagcaccauu     60
ugaaaucagu guucuugggg g                                              81

<210> SEQ ID NO 47
<211> LENGTH: 81
<212> TYPE: RNA
<213> ORGANISM: Homo sapiens

<400> SEQUENCE: 47
cuucuggaag cugguuucac auggugggcuu agauuuuucc aucuuuguau cuagcaccau    60
uugaaaucag uguuuuagga g                                              81

<210> SEQ ID NO 48
<211> LENGTH: 88
<212> TYPE: RNA
<213> ORGANISM: Homo sapiens

<400> SEQUENCE: 48
```
aucucuuaca caggcugacc gauuucuccu ggguguucaga gucuguuuuu gucuagcacc    60
auuugaaauc gguuaugaug uaggggga                                       88

<210> SEQ ID NO 49
<211> LENGTH: 71
<212> TYPE: RNA
<213> ORGANISM: Homo sapiens

<400> SEQUENCE: 49
gcgacuguaa acauccucga cuggaagcug ugaagccaca gaugggcuuu cagucggaug    60
uuugcagcug c                                                         71

<210> SEQ ID NO 50
<211> LENGTH: 72
<212> TYPE: RNA
<213> ORGANISM: Homo sapiens

<400> SEQUENCE: 50
agauacugua aacauccuac acucucagcu guggaaagua agaaagcugg gagaaggcug    60
uuuacucuuu cu                                                        72

<210> SEQ ID NO 51
<211> LENGTH: 70
<212> TYPE: RNA
<213> ORGANISM: Homo sapiens

<400> SEQUENCE: 51
guuguuguaa acaucccccga cuggaagcug uaagacacag cuaagcuuuc agucagaugu    60
uugcugcuac                                                           70

<210> SEQ ID NO 52
<211> LENGTH: 88
<212> TYPE: RNA
<213> ORGANISM: Homo sapiens

<400> SEQUENCE: 52
accaaguuuc aguucaugua aacauccuac acucagcugu aauacaugga uuggcuggga    60
gguggauguu uacuucagcu gacuugga                                       88

<210> SEQ ID NO 53
<211> LENGTH: 89
<212> TYPE: RNA
<213> ORGANISM: Homo sapiens

<400> SEQUENCE: 53
accaugcugu agugugugua aacauccuac acucucagcu gugagcucaa ggguggcuggg    60 agagggguugu uuacuccuuc ugccaugga                                     89

<210> SEQ ID NO 54
<211> LENGTH: 64
<212> TYPE: RNA
<213> ORGANISM: Homo sapiens

<400> SEQUENCE: 54
cuguaaacau ccuugacugg aagcuguaag guguucagag gagcuuucag ucggauguuu    60
acag                                                                 64

<210> SEQ ID NO 55

```
<211> LENGTH: 71
<212> TYPE: RNA
<213> ORGANISM: Homo sapiens

<400> SEQUENCE: 55
ggagaggagg caagaugcug gcauagcugu ugaacuggga accugcuaug ccaacauauu    60
gccaucuuuc c                                                         71

<210> SEQ ID NO 56
<211> LENGTH: 70
<212> TYPE: RNA
<213> ORGANISM: Homo sapiens

<400> SEQUENCE: 56
ggagauauug cacauuacua aguugcaugu ugucacggcc ucaaugcaau uuagugugug    60
ugauauuuuc                                                           70

<210> SEQ ID NO 57
<211> LENGTH: 69
<212> TYPE: RNA
<213> ORGANISM: Homo sapiens

<400> SEQUENCE: 57
cuguggugca uuguaguugc auugcauguu cuggugguac ccaugcaaug uuuccacagu    60
gcaucacag                                                            69

<210> SEQ ID NO 58
<211> LENGTH: 110
<212> TYPE: RNA
<213> ORGANISM: Homo sapiens

<400> SEQUENCE: 58
ggccagcugu gaguguuucu uuggcagugu cuuagcuggu uguugagagc aauaguaagg    60
aagcaaucag caaguauacu gcccuagaag ugcugcacgu ugugggggccc              110

<210> SEQ ID NO 59
<211> LENGTH: 84
<212> TYPE: RNA
<213> ORGANISM: Homo sapiens

<400> SEQUENCE: 59
gugcucgguu uguaggcagu gucauuagcu gauuguacug uggugguuac aaucacuaac    60
uccacugcca ucaaaacaag gcac                                           84

<210> SEQ ID NO 60
<211> LENGTH: 77
<212> TYPE: RNA
<213> ORGANISM: Homo sapiens

<400> SEQUENCE: 60
agucuaguua cuaggcagug uaguuagcug auugcuaaua guaccaauca cuaaccacac    60
ggccagguaa aaagauu                                                   77

<210> SEQ ID NO 61
<211> LENGTH: 78
<212> TYPE: RNA
<213> ORGANISM: Homo sapiens

<400> SEQUENCE: 61
cuuucuacac agguugggau cgguugcaau gcuguguuuc uguauggauu ugcacuugguc    60
```

```
ccggccuguu gaguuugg                                                       78

<210> SEQ ID NO 62
<211> LENGTH: 75
<212> TYPE: RNA
<213> ORGANISM: Homo sapiens

<400> SEQUENCE: 62
ucaucccugg gugggauuu guugcauuac uuguguucua auaaaguau ugcacuuguc           60 ccggccugug aaga                                                           75

<210> SEQ ID NO 63
<211> LENGTH: 80
<212> TYPE: RNA
<213> ORGANISM: Homo sapiens

<400> SEQUENCE: 63 cuggggcuc caaagugcug uucgugcagg uagugugauu acccaaccua cugcugagcu         60
agcacuuccc gagccccgg                                                      80

<210> SEQ ID NO 64
<211> LENGTH: 81
<212> TYPE: RNA
<213> ORGANISM: Homo sapiens

<400> SEQUENCE: 64
aacacagugg gcacucaaua aaugucuguu gaauugaaau gcguuacauu caacgggau         60 uuauugagca cccacucugu g                                                   81

<210> SEQ ID NO 65
<211> LENGTH: 78
<212> TYPE: RNA
<213> ORGANISM: Homo sapiens

<400> SEQUENCE: 65
uggccgauuu uggcacuagc acauuuuugc uugugucucu ccgcucugag caaucaugug         60
cagugccaau augggaaa                                                       78

<210> SEQ ID NO 66
<211> LENGTH: 80
<212> TYPE: RNA
<213> ORGANISM: Homo sapiens

<400> SEQUENCE: 66
gugagguagu aaguuguauu guugugggu agggauauua ggccccaauu agaagauaac         60
uauacaacuu acuacuuucc                                                     80

<210> SEQ ID NO 67
<211> LENGTH: 81
<212> TYPE: RNA
<213> ORGANISM: Homo sapiens

<400> SEQUENCE: 67
cccauuggca uaaacccgua gauccgaucu uguggugaag uggaccgcac aagcucgcuu         60
cuaugggucu gugucagugu g                                                   81

<210> SEQ ID NO 68
<211> LENGTH: 70
<212> TYPE: RNA
```

```
<213> ORGANISM: Homo sapiens

<400> SEQUENCE: 68
ggcacccacc cguagaaccg accuugcggg gccuucgccg cacacaagcu cgugucugug    60
gguccguguc                                                          70

<210> SEQ ID NO 69
<211> LENGTH: 80
<212> TYPE: RNA
<213> ORGANISM: Homo sapiens

<400> SEQUENCE: 69
ccuguugcca caaacccgua gauccgaacu ugugguauua guccgcacaa gcuuguaucu    60
auagguaugu gucuguuagg                                               80

<210> SEQ ID NO 70
<211> LENGTH: 75
<212> TYPE: RNA
<213> ORGANISM: Homo sapiens

<400> SEQUENCE: 70
ugcccuggcu caguuaucac agugcugaug cugucuauuc uaaagguaca guacugugau    60
aacugaagga uggca                                                    75

<210> SEQ ID NO 71
<211> LENGTH: 79
<212> TYPE: RNA
<213> ORGANISM: Homo sapiens

<400> SEQUENCE: 71
acuguccuuu uucgguuauc augguaccga ugcuguauau cugaaaggua caguacugug    60
auaacugaag aaugguggu                                                79

<210> SEQ ID NO 72
<211> LENGTH: 78
<212> TYPE: RNA
<213> ORGANISM: Homo sapiens

<400> SEQUENCE: 72
uugugcuuuc agcuucuuua cagugcugcc uuguagcauu caggucaagc agcauuguac    60
agggcuauga aagaacca                                                 78

<210> SEQ ID NO 73
<211> LENGTH: 78
<212> TYPE: RNA
<213> ORGANISM: Homo sapiens

<400> SEQUENCE: 73
uacugcccuc ggcuucuuua cagugcugcc uuguugcaua uggaucaagc agcauuguac    60
agggcuauga aggcauug                                                 78

<210> SEQ ID NO 74
<211> LENGTH: 81
<212> TYPE: RNA
<213> ORGANISM: Homo sapiens

<400> SEQUENCE: 74
ugugcaucgu ggucaaaugc ucagacuccu gugguggcug cucaugcacc acggauguuu    60
gagcaugugc uacggugucu a                                             81
```

```
<210> SEQ ID NO 75
<211> LENGTH: 81
<212> TYPE: RNA
<213> ORGANISM: Homo sapiens

<400> SEQUENCE: 75
ugugcaucgu ggucaaaugc ucagacuccu gugguggcug cuuaugcacc acggauguuu    60
gagcaugugc uaugguqucu a                                             81

<210> SEQ ID NO 76
<211> LENGTH: 81
<212> TYPE: RNA
<213> ORGANISM: Homo sapiens

<400> SEQUENCE: 76
ccuuggccau guaaaagugc uuacagugca gguagcuuuu ugagaucuac ugcaauguaa    60
gcacuucuua cauuaccaug g                                             81

<210> SEQ ID NO 77
<211> LENGTH: 82
<212> TYPE: RNA
<213> ORGANISM: Homo sapiens

<400> SEQUENCE: 77
ccugccgggg cuaaagugcu gacagugcag auaguggucc ucuccgugcu accgcacugu    60
ggguacuugc ugcuccagca gg                                            82

<210> SEQ ID NO 78
<211> LENGTH: 81
<212> TYPE: RNA
<213> ORGANISM: Homo sapiens

<400> SEQUENCE: 78
cucucugcuu ucagcuucuu uacagguuug ccuuguggca uggaguucaa gcagcauugu    60
acagggcuau caaagcacag a                                             81

<210> SEQ ID NO 79
<211> LENGTH: 85
<212> TYPE: RNA
<213> ORGANISM: Homo sapiens

<400> SEQUENCE: 79
ccuuagcaga gcugggagu gugacaaugg uguuuguguc uaaacuauca aacgccauua    60
ucacacuaaa uagcuacugc uaggc                                         85

<210> SEQ ID NO 80
<211> LENGTH: 85
<212> TYPE: RNA
<213> ORGANISM: Homo sapiens

<400> SEQUENCE: 80
aggccucucu cuccguguuc acagcggacc uugauuuaaa uguccauaca auuaaggcac    60
gcggugaaug ccaagaaugg ggcug                                         85

<210> SEQ ID NO 81
<211> LENGTH: 109
<212> TYPE: RNA
<213> ORGANISM: Homo sapiens
```

```
<400> SEQUENCE: 81
aucaagauua gaggcucugc ucuccguguu cacagcggac cuugauuuaa ugucauacaa    60
uuaaggcacg cggugaaugc caagagcgga gccuacggcu gcacuugaa               109

<210> SEQ ID NO 82
<211> LENGTH: 87
<212> TYPE: RNA
<213> ORGANISM: Homo sapiens

<400> SEQUENCE: 82
ugagggcccc ucugcguguu cacagcggac cuugauuuaa ugucuauaca auuaaggcac    60
gcggugaaug ccaagagagg cgccucc                                       87

<210> SEQ ID NO 83
<211> LENGTH: 88
<212> TYPE: RNA
<213> ORGANISM: Homo sapiens

<400> SEQUENCE: 83
ugcgcuccuc ucagucccug agacccuaac uugugauguu uaccguuuaa auccacgggu    60
uaggcucuug ggagcugcga gucgugcu                                      88

<210> SEQ ID NO 84
<211> LENGTH: 86
<212> TYPE: RNA
<213> ORGANISM: Homo sapiens

<400> SEQUENCE: 84
ugccagucuc uagucccug agaccuuua accugugagg acauccaggg ucacagguga     60
gguucuuggg agccuggcgu cuggcc                                        86

<210> SEQ ID NO 85
<211> LENGTH: 89
<212> TYPE: RNA
<213> ORGANISM: Homo sapiens

<400> SEQUENCE: 85
accagacuuu uccuagcccu ugagacccua acuugugagg uauuuuagua acaucacaag    60
ucaggcucuu gggaccuagg cggagggga                                     89

<210> SEQ ID NO 86
<211> LENGTH: 85
<212> TYPE: RNA
<213> ORGANISM: Homo sapiens

<400> SEQUENCE: 86
cgcuggcgac gggacauuau uacuuuuggu acgcgcugug acacuucaaa cucguaccgu    60
gaguaauaau gcgccgucca cggca                                         85

<210> SEQ ID NO 87
<211> LENGTH: 97
<212> TYPE: RNA
<213> ORGANISM: Homo sapiens

<400> SEQUENCE: 87
ugugaucacu gucuccagcc ugcugaagcu cagagggcuc ugauucagaa agaucaucgg    60
auccgucuga gcuuggcugg ucggaagucu caucauc                            97
```

```
<210> SEQ ID NO 88
<211> LENGTH: 82
<212> TYPE: RNA
<213> ORGANISM: Homo sapiens

<400> SEQUENCE: 88
ugagcuguug gauucggggc cguagcacug ucugagaggu uuacauuucu cacagugaac    60
cggucucuuu uucagcugcu uc                                            82

<210> SEQ ID NO 89
<211> LENGTH: 84
<212> TYPE: RNA
<213> ORGANISM: Homo sapiens

<400> SEQUENCE: 89
ugugcagugg aaggggggc cgauacacug uacgagagug aguagcaggu cucacaguga    60
accggucucu uucccuacug uguc                                          84

<210> SEQ ID NO 90
<211> LENGTH: 90
<212> TYPE: RNA
<213> ORGANISM: Homo sapiens

<400> SEQUENCE: 90
ugcccuucgc gaaucuuuuu gcggucuggg cuugcuguac auaacucaau agccggaagc    60
ccuuacccca aaaagcauuu gcggagggcg                                    90

<210> SEQ ID NO 91
<211> LENGTH: 89
<212> TYPE: RNA
<213> ORGANISM: Homo sapiens

<400> SEQUENCE: 91
ugcugcuggc cagagcucuu uucacauugu gcuacugucu gcaccuguca cuagcagugc    60
aauguuaaaa gggcauuggc cguguagug                                     89

<210> SEQ ID NO 92
<211> LENGTH: 82
<212> TYPE: RNA
<213> ORGANISM: Homo sapiens

<400> SEQUENCE: 92
ggccugcccg acacucuuuc ccuguugcac uacuauaggc cgcugggaag cagugcaaug    60
augaaagggc aucggucagg uc                                            82

<210> SEQ ID NO 93
<211> LENGTH: 101
<212> TYPE: RNA
<213> ORGANISM: Homo sapiens

<400> SEQUENCE: 93
ccgcccccgc gucuccaggg caaccguggc uuucgauugu acuguggga acuggaggua    60 acagucuaca gccauggucg ccccgcagca cgcccacgcg c                       101

<210> SEQ ID NO 94
<211> LENGTH: 88
<212> TYPE: RNA
<213> ORGANISM: Homo sapiens

<400> SEQUENCE: 94
```

```
acaaugcuuu gcuagagcug guaaaaugga accaaaucgc cucuucaaug gauuuggucc    60
ccuucaacca gcuguagcua ugcauuga                                      88

<210> SEQ ID NO 95
<211> LENGTH: 102
<212> TYPE: RNA
<213> ORGANISM: Homo sapiens

<400> SEQUENCE: 95
gggagccaaa ugcuuugcua gagcugguaa aauggaacca aaucgacugu ccaauggauu    60
ugguccccuu caaccagcug uagcugugca uugauggcgc cg                     102

<210> SEQ ID NO 96
<211> LENGTH: 119
<212> TYPE: RNA
<213> ORGANISM: Homo sapiens

<400> SEQUENCE: 96
ccucagaaga aagaugcccc cugcucuggc uggucaaacg gaaccaaguc cgucuuccug    60
agagguuugg uccccuucaa ccagcuacag cagggcuggc aaugcccagu ccuuggaga   119

<210> SEQ ID NO 97
<211> LENGTH: 73
<212> TYPE: RNA
<213> ORGANISM: Homo sapiens

<400> SEQUENCE: 97
cagggugugu gacugguuga ccagaggggc augcacugug uucacccugu gggccaccua    60
gucaccaacc cuc                                                      73

<210> SEQ ID NO 98
<211> LENGTH: 90
<212> TYPE: RNA
<213> ORGANISM: Homo sapiens

<400> SEQUENCE: 98
aggccucgcu guucucuaug gcuuuuuauu ccuaugugau ucuacugcuc acucauauag    60
ggauuggagc cguggcgcac ggcggggaca                                    90

<210> SEQ ID NO 99
<211> LENGTH: 100
<212> TYPE: RNA
<213> ORGANISM: Homo sapiens

<400> SEQUENCE: 99
agauaaauuc acucuagugc uuuauggcuu uuuauuccua ugugauagua auaaagcuc     60 auguagggau ggaagccaug aaauacauug ugaaaaauca                        100

<210> SEQ ID NO 100
<211> LENGTH: 97
<212> TYPE: RNA
<213> ORGANISM: Homo sapiens

<400> SEQUENCE: 100
cacucugcug uggccuaugg cuuuucauuc cuaugugauu gcugucccaa acucauguag    60
ggcuaaaagc caugggcuac agugaggggc gagcucc                            97

<210> SEQ ID NO 101
<211> LENGTH: 82
```

```
<212> TYPE: RNA
<213> ORGANISM: Homo sapiens

<400> SEQUENCE: 101
ugagcccucg gaggacucca uuuguuuuga ugauggauuc uuaugcucca ucaucgucuc    60
aaaugagucu ucagaggguu cu                                             82

<210> SEQ ID NO 102
<211> LENGTH: 102
<212> TYPE: RNA
<213> ORGANISM: Homo sapiens

<400> SEQUENCE: 102
gguccucuga cucucuucgg ugacggguau ucuuggguag auaauacgga uuacguuguu    60
auugcuuaag aauacgcgua gucgaggaga guaccagcgg ca                      102

<210> SEQ ID NO 103
<211> LENGTH: 84
<212> TYPE: RNA
<213> ORGANISM: Homo sapiens

<400> SEQUENCE: 103
cguugcugca gcuguguug ugaaucaggc cgacgagcag cgcauccucu uacccggcua     60
uuucacgaca ccaggguugc auca                                           84

<210> SEQ ID NO 104
<211> LENGTH: 99
<212> TYPE: RNA
<213> ORGANISM: Homo sapiens

<400> SEQUENCE: 104
cccuggcaug gugugguggg gcagcuggug uugugaauca ggccguugcc aaucagagaa    60
cggcuacuuc acaacaccag ggccacacca cacuacagg                           99

<210> SEQ ID NO 105
<211> LENGTH: 68
<212> TYPE: RNA
<213> ORGANISM: Homo sapiens

<400> SEQUENCE: 105
guguauucua cagugcacgu gucccagug uggcucggag gcuggagacg cggcccuguu     60
ggaguaac                                                             68

<210> SEQ ID NO 106
<211> LENGTH: 100
<212> TYPE: RNA
<213> ORGANISM: Homo sapiens

<400> SEQUENCE: 106 uguguucuc ucuguguccu gccaguggu uuacccuaug guagguuacg ucaugcuguu      60
cuaccacagg guagaaccac ggacaggaua ccggggcacc                         100

<210> SEQ ID NO 107
<211> LENGTH: 95
<212> TYPE: RNA
<213> ORGANISM: Homo sapiens

<400> SEQUENCE: 107
cggccggccc uggguccauc uuccaguaca guguuggaug gucuaauugu gaagcuccua    60
```

```
acacugucug guaaagaugg cucccgggug gguuc                                 95

<210> SEQ ID NO 108
<211> LENGTH: 87
<212> TYPE: RNA
<213> ORGANISM: Homo sapiens

<400> SEQUENCE: 108
gacagugcag ucacccauaa aguagaaagc acuacuaaca gcacuggagg guguagguguu     60 uccuacuuua uggaugagug uacugug                                         87

<210> SEQ ID NO 109
<211> LENGTH: 106
<212> TYPE: RNA
<213> ORGANISM: Homo sapiens

<400> SEQUENCE: 109
gcgcagcgcc cugucuccca gccugaggug cagugcugca ucucggguca guugggaguc     60
ugagaugaag cacuguagcu caggaagaga gaaguuguuc ugcagc                   106

<210> SEQ ID NO 110
<211> LENGTH: 86
<212> TYPE: RNA
<213> ORGANISM: Homo sapiens

<400> SEQUENCE: 110
uggggcccug gcugggauau caucauauac uguaaguuug cgaugagaca cuacaguaua     60
gaugauguac uaguccgggc accccc                                         86

<210> SEQ ID NO 111
<211> LENGTH: 88
<212> TYPE: RNA
<213> ORGANISM: Homo sapiens

<400> SEQUENCE: 111
caccuugucc ucacggucca guuuucccag gaaucccuua gaugcuaaga ugggggauucc    60 uggaaauacu guucuugagg ucaugguu                                       88

<210> SEQ ID NO 112
<211> LENGTH: 99
<212> TYPE: RNA
<213> ORGANISM: Homo sapiens

<400> SEQUENCE: 112
ccgaugugua uccucagcuu ugagaacuga auuccauggg uugugucagu gucagaccuc     60
ugaaauucag uucuucagcu gggauaucuc ugucaucgu                           99

<210> SEQ ID NO 113
<211> LENGTH: 72
<212> TYPE: RNA
<213> ORGANISM: Homo sapiens

<400> SEQUENCE: 113
aaucuaaaga caacauuucu gcacacacac cagacuaugg aagccagugu guggaaaugc     60
uucugcuaga uu                                                        72

<210> SEQ ID NO 114
<211> LENGTH: 68
<212> TYPE: RNA
<213> ORGANISM: Homo sapiens
```

```
<400> SEQUENCE: 114
gaggcaaagu ucugagacac uccgacucug aguaugauag aagucagugc acuacagaac    60
uuugucuc                                                            68

<210> SEQ ID NO 115
<211> LENGTH: 99
<212> TYPE: RNA
<213> ORGANISM: Homo sapiens

<400> SEQUENCE: 115
caagcacgau uagcauuuga ggugaaguuc uguuauacac ucaggcugug gcucucugaa    60
agucagugca ucacagaacu uugucucgaa agcuuucua                          99

<210> SEQ ID NO 116
<211> LENGTH: 89
<212> TYPE: RNA
<213> ORGANISM: Homo sapiens

<400> SEQUENCE: 116
gccggcgccc gagcucuggc uccgugucuu cacucccgug cuuguccgag gagggaggga    60
gggacggggg cugugcuggg gcagcugga                                     89

<210> SEQ ID NO 117
<211> LENGTH: 84
<212> TYPE: RNA
<213> ORGANISM: Homo sapiens

<400> SEQUENCE: 117
cuccccaugg cccugucucc caacccuugu accagugcug ggcucagacc cugguacagg    60 ccuggggac agggaccugg ggac                                           84

<210> SEQ ID NO 118
<211> LENGTH: 90
<212> TYPE: RNA
<213> ORGANISM: Homo sapiens

<400> SEQUENCE: 118
uuuccugccc ucgaggagcu cacagucuag uaugucucau ccccuacuag acugaagcuc    60
cuugaggaca gggaugguca uacucaccuc                                    90

<210> SEQ ID NO 119
<211> LENGTH: 87
<212> TYPE: RNA
<213> ORGANISM: Homo sapiens

<400> SEQUENCE: 119 ugucccccc ggcccagguu cugugauaca cuccgacucg ggcucuggag cagucagugc     60
augacagaac uugggcccgg aaggacc                                       87

<210> SEQ ID NO 120
<211> LENGTH: 90
<212> TYPE: RNA
<213> ORGANISM: Homo sapiens

<400> SEQUENCE: 120
cucacagcug ccagugucau uuuugugauc ugcagcuagu auucucacuc caguugcaua    60
gucacaaaag ugaucauugg caggugaggc                                    90
```

```
<210> SEQ ID NO 121
<211> LENGTH: 87
<212> TYPE: RNA
<213> ORGANISM: Homo sapiens

<400> SEQUENCE: 121
agcgguggcc agugucauuu uugugauguu gcagcuagua auaugagccc aguugcauag      60
ucacaaaagu gaucauugga aacugug                                         87

<210> SEQ ID NO 122
<211> LENGTH: 84
<212> TYPE: RNA
<213> ORGANISM: Homo sapiens

<400> SEQUENCE: 122
gugguacuug aagauagguu auccgguguug ccuucgcuuu auuugugacg aaucauacac    60
gguugaccua uuuuucagua ccaa                                            84

<210> SEQ ID NO 123
<211> LENGTH: 65
<212> TYPE: RNA
<213> ORGANISM: Homo sapiens

<400> SEQUENCE: 123
cuguuaaugc uaaucgugau agggguuuuu gccuccaacu gacuccuaca uauuagcauu     60
aacag                                                                 65

<210> SEQ ID NO 124
<211> LENGTH: 110
<212> TYPE: RNA
<213> ORGANISM: Homo sapiens

<400> SEQUENCE: 124
agaagggcua ucaggccagc cuucagagga cuccaaggaa cauucaacgc ugucggugag     60
uuugggauuu gaaaaaacca cugaccguug acuguaccuu ggggguccuua              110

<210> SEQ ID NO 125
<211> LENGTH: 110
<212> TYPE: RNA
<213> ORGANISM: Homo sapiens

<400> SEQUENCE: 125
ccugugcaga gauuauuuuu uaaaagguca caaucaacau ucauugcugu cggugggguug    60 aacugugugg acaagcucac ugaacaauga augcaacugu ggccccgcuu               110

<210> SEQ ID NO 126
<211> LENGTH: 110
<212> TYPE: RNA
<213> ORGANISM: Homo sapiens

<400> SEQUENCE: 126
cggaaaauuu gccaaggguu uggggaaca uucaaccugu cggugaguuu gggcagcuca      60
ggcaaaccau cgaccguuga guggacccug aggccuggaa uugccauccu                110

<210> SEQ ID NO 127
<211> LENGTH: 89
<212> TYPE: RNA
<213> ORGANISM: Homo sapiens

<400> SEQUENCE: 127
```

```
cugauggcug cacucaacau ucauugcugu cgguggguuu gagucugaau caacucacug      60
aucaaugaau gcaaacugcg gaccaaaca                                        89

<210> SEQ ID NO 128
<211> LENGTH: 110
<212> TYPE: RNA
<213> ORGANISM: Homo sapiens

<400> SEQUENCE: 128
gagcugcuug ccucccccg uuuuggcaa ugguagaacu cacacuggug agguaacagg        60
auccgguggu ucuagacuug ccaacuaugg ggcgaggacu cagccggcac                 110

<210> SEQ ID NO 129
<211> LENGTH: 110
<212> TYPE: RNA
<213> ORGANISM: Homo sapiens

<400> SEQUENCE: 129
ccgcagagug ugacuccugu ucuguguaug gcacugguag aauucacugu gaacagucuc      60
agucagugaa uuaccgaagg gccauaaaca gagcagagac agauccacga                 110

<210> SEQ ID NO 130
<211> LENGTH: 84
<212> TYPE: RNA
<213> ORGANISM: Homo sapiens

<400> SEQUENCE: 130
ccagucacgu ccccuuauca cuuuccagc ccagcuuugu gacuguaagu guuggacgga       60
gaacugauaa ggguagguga uuga                                             84

<210> SEQ ID NO 131
<211> LENGTH: 82
<212> TYPE: RNA
<213> ORGANISM: Homo sapiens

<400> SEQUENCE: 131 aggggggcgag ggauuggaga gaaaggcagu uccgauggu ccccuccca ggggcuggcu      60 uuccucuggu ccuucccucc ca                                               82

<210> SEQ ID NO 132
<211> LENGTH: 86
<212> TYPE: RNA
<213> ORGANISM: Homo sapiens

<400> SEQUENCE: 132
ugcuuguaac uuccaaaga auucuccuuu ugggcuuucu gguuuauuu uaagcccaaa        60 ggugaauuuu uuggggaaguu ugagcu                                          86

<210> SEQ ID NO 133
<211> LENGTH: 109
<212> TYPE: RNA
<213> ORGANISM: Homo sapiens

<400> SEQUENCE: 133
ggucgggcuc accaugacac agugugagac cucgggcuac aacacaggac ccgggcgcug     60
cucugacccc ucgugucuug uguugcagcc ggagggacgc aggucccgca                 109

<210> SEQ ID NO 134
```

```
<211> LENGTH: 86
<212> TYPE: RNA
<213> ORGANISM: Homo sapiens

<400> SEQUENCE: 134
ugcucccucu cuacaucccu uugcauggug gagggugagc uuucugaaaa ccccucccac    60 augcagggu ugcaggaugg cgagcc                                          86

<210> SEQ ID NO 135
<211> LENGTH: 85
<212> TYPE: RNA
<213> ORGANISM: Homo sapiens

<400> SEQUENCE: 135
ugcaggccuc uguguauau guuugauaua uuagguuguu auuuaaucca acuauauauc     60
aaacauauuc cuacaguguc uugcc                                          85

<210> SEQ ID NO 136
<211> LENGTH: 92
<212> TYPE: RNA
<213> ORGANISM: Homo sapiens

<400> SEQUENCE: 136
cggcuggaca gcgggcaacg gaaucccaaa agcagcuguu gucuccagag cauuccagcu    60
gcgcuuggau uucguccccu gcucuccugc cu                                  92

<210> SEQ ID NO 137
<211> LENGTH: 110
<212> TYPE: RNA
<213> ORGANISM: Homo sapiens

<400> SEQUENCE: 137
gccgagaccg agugcacagg gcucugaccu augaauugac agccagugcu cucgucuccc    60
cucuggcugc caauuccaua ggucacaggu auguucgccu caaugccagc                110

<210> SEQ ID NO 138
<211> LENGTH: 88
<212> TYPE: RNA
<213> ORGANISM: Homo sapiens

<400> SEQUENCE: 138
cgaggauggg agcugagggc ugggucuuug cgggcgagau gagggugucg gaucaacugg    60
ccuacaaagu cccaguucuc ggcccccg                                       88

<210> SEQ ID NO 139
<211> LENGTH: 85
<212> TYPE: RNA
<213> ORGANISM: Homo sapiens

<400> SEQUENCE: 139
augguguuau caaguguaac agcaaccucca ugggacugu guaccaauuu ccaguggaga    60
ugcuguuacu uuugauggu accaa                                           85

<210> SEQ ID NO 140
<211> LENGTH: 85
<212> TYPE: RNA
<213> ORGANISM: Homo sapiens

<400> SEQUENCE: 140
ugguucccgc ccccuguaac agcaaccucca ugggaagug cccacugguu ccaguggggc    60
```
ugcuguuauc uggggcgagg gccag                                              85

<210> SEQ ID NO 141
<211> LENGTH: 87
<212> TYPE: RNA
<213> ORGANISM: Homo sapiens

<400> SEQUENCE: 141
agcuucccug gcucuagcag cacagaaaua uuggcacagg gaagcgaguc ugccaauauu        60
ggcugugcug cuccaggcag gguggug                                           87

<210> SEQ ID NO 142
<211> LENGTH: 70
<212> TYPE: RNA
<213> ORGANISM: Homo sapiens

<400> SEQUENCE: 142
gugaauuagg uaguuucaug uuguugggcc uggguuucug aacacaacaa cauuaaacca        60
cccgauucac                                                              70

<210> SEQ ID NO 143
<211> LENGTH: 110
<212> TYPE: RNA
<213> ORGANISM: Homo sapiens

<400> SEQUENCE: 143
ugcucgcuca gcugaucugu ggcuuaggua guuucauguu guugggauug aguuuugaac        60
ucggcaacaa gaaacugccu gaguuacauc agucgguuuu cgucgagggc                  110

<210> SEQ ID NO 144
<211> LENGTH: 75
<212> TYPE: RNA
<213> ORGANISM: Homo sapiens

<400> SEQUENCE: 144
ggcugugccg gguagagagg gcagugggag guaagagcuc uucacccuuc accaccuucu        60
ccacccagca uggcc                                                        75

<210> SEQ ID NO 145
<211> LENGTH: 62
<212> TYPE: RNA
<213> ORGANISM: Homo sapiens

<400> SEQUENCE: 145
ucauuggucc agaggggaga uagguuccug ugauuuuucc uucuucucua uagaauaaau        60
ga                                                                      62

<210> SEQ ID NO 146
<211> LENGTH: 71
<212> TYPE: RNA
<213> ORGANISM: Homo sapiens

<400> SEQUENCE: 146
gccaacccag uguucagacu accuguucag gaggcucuca auguguacag uagucugcac        60
auugguuagg c                                                            71

<210> SEQ ID NO 147
<211> LENGTH: 110
<212> TYPE: RNA

<213> ORGANISM: Homo sapiens

<400> SEQUENCE: 147
aggaagcuuc uggagauccu gcuccgucgc cccaguguuc agacuaccug uucaggacaa    60
ugccguugua caguagucug cacauugguu agacgggca agggagagca    110

<210> SEQ ID NO 148
<211> LENGTH: 110
<212> TYPE: RNA
<213> ORGANISM: Homo sapiens

<400> SEQUENCE: 148
ccagaggaca ccuccacucc gucuacccag uguuuagacu aucuguucag gacucccaaa    60
uuguacagua gucugcacau ugguuaggcu gggcuggguu agacccucgg    110

<210> SEQ ID NO 149
<211> LENGTH: 95
<212> TYPE: RNA
<213> ORGANISM: Homo sapiens

<400> SEQUENCE: 149
ccagcucggg cagccguggc caucuuacug ggcagcauug gauggaguca ggucucuaau    60
acugccuggu aaugaugacg gcggagcccu gcacg    95

<210> SEQ ID NO 150
<211> LENGTH: 68
<212> TYPE: RNA
<213> ORGANISM: Homo sapiens

<400> SEQUENCE: 150
cccucgucuu acccagcagu guuggggugc gguuggagu cucuaauacu gccggguaau    60
gauggagg    68

<210> SEQ ID NO 151
<211> LENGTH: 90
<212> TYPE: RNA
<213> ORGANISM: Homo sapiens

<400> SEQUENCE: 151 ccgggcccu gugagcaucu uaccggacag ugcuggauuu cccagcuuga cucuaacacu    60
gucugguaac gauguucaaa ggugacccgc    90

<210> SEQ ID NO 152
<211> LENGTH: 110
<212> TYPE: RNA
<213> ORGANISM: Homo sapiens

<400> SEQUENCE: 152 guguuggga cucgcgcgcu ggguccagug guucuuaaca guucaacagu ucuguagcgc    60
aauugugaaa uguuuaggac cacuagaccc ggcgggcgcg gcgacagcga    110

<210> SEQ ID NO 153
<211> LENGTH: 110
<212> TYPE: RNA
<213> ORGANISM: Homo sapiens

<400> SEQUENCE: 153
ggcuacaguc uuucuucaug ugacucgugg acucccuuu gcauccuau gccugagaau    60 auaugaagga ggcugggaag gcaaagggac guucaauugu caucacuggc    110

```
<210> SEQ ID NO 154
<211> LENGTH: 110
<212> TYPE: RNA
<213> ORGANISM: Homo sapiens

<400> SEQUENCE: 154
aaagauccuc agacaaucca ugugcuucuc uguccuuca uuccaccgga gucugucuca    60
uacccaacca gauuucagug gagugaaguu caggaggcau ggagcugaca             110

<210> SEQ ID NO 155
<211> LENGTH: 86
<212> TYPE: RNA
<213> ORGANISM: Homo sapiens

<400> SEQUENCE: 155
ugcuucccga ggccacaugc uucuuuauau ccccauaugg auuacuuugc uauggaaugu    60
aaggaagugu gugguuucgg caagug                                        86

<210> SEQ ID NO 156
<211> LENGTH: 71
<212> TYPE: RNA
<213> ORGANISM: Homo sapiens

<400> SEQUENCE: 156
ugacgggcga gcuuuuggcc cggguuauac cugaugcuca cguauaagac gagcaaaaag    60
cuuguugguc a                                                        71

<210> SEQ ID NO 157
<211> LENGTH: 110
<212> TYPE: RNA
<213> ORGANISM: Homo sapiens

<400> SEQUENCE: 157
acccggcagu gccuccaggc gcagggcagc cccugcccac cgcacacugc gcugcccag     60 acccacugug cgugugacag cggcugaucu gugccugggc agcgcgaccc              110

<210> SEQ ID NO 158
<211> LENGTH: 110
<212> TYPE: RNA
<213> ORGANISM: Homo sapiens

<400> SEQUENCE: 158
ucaccuggcc augugacuug ugggcuuccc uuugucaucc uucgccuagg gcucugagca    60
gggcagggac agcaaagggg ugcucaguug ucacuuccca cagcacggag              110

<210> SEQ ID NO 159
<211> LENGTH: 110
<212> TYPE: RNA
<213> ORGANISM: Homo sapiens

<400> SEQUENCE: 159
cggggcaccc cgcccggaca gcgcgccggc accuuggcuc uagacugcuu acugcccggg    60
ccgcccucag uaacagucuc cagucacggc caccgacgcc uggccccgcc              110

<210> SEQ ID NO 160
<211> LENGTH: 110
<212> TYPE: RNA
<213> ORGANISM: Homo sapiens
```

<400> SEQUENCE: 160
ugaguuuuga gguugcuuca gugaacauuc aacgcugucg gugaguuugg aauuaaaauc    60
aaaaccaucg accguugauu guacccuaug gcuaaccauc aucuacucca              110

<210> SEQ ID NO 161
<211> LENGTH: 110
<212> TYPE: RNA
<213> ORGANISM: Homo sapiens

<400> SEQUENCE: 161
ggccuggcug gacagaguug ucaugugucu gccugucuac acuugcugug cagaacaucc    60
gcucaccugu acagcaggca cagacaggca gucacaugac aacccagccu              110

<210> SEQ ID NO 162
<211> LENGTH: 110
<212> TYPE: RNA
<213> ORGANISM: Homo sapiens

<400> SEQUENCE: 162
aucauucaga aauggauauac aggaaaauga ccaugaauu gacagacaau auagcugagu    60
uugucuguca uuucuuuagg ccaauauucu guaugacugu gcuacuucaa              110

<210> SEQ ID NO 163
<211> LENGTH: 110
<212> TYPE: RNA
<213> ORGANISM: Homo sapiens

<400> SEQUENCE: 163
gauggcugug aguuggcuua aucucagcug gcaacuguga gauguucaua caaucccuca    60
caguggucuc ugggauuaug cuaaacagag caauuuccua gcccucacga              110

<210> SEQ ID NO 164
<211> LENGTH: 110
<212> TYPE: RNA
<213> ORGANISM: Homo sapiens

<400> SEQUENCE: 164
aguauaauua uuacauaguu uuugaugucg cagauacugc aucaggaacu gauuggauaa    60
gaaucaguca ccaucaguuc cuaaugcauu gccuucagca ucuaaacaag              110

<210> SEQ ID NO 165
<211> LENGTH: 110
<212> TYPE: RNA
<213> ORGANISM: Homo sapiens

<400> SEQUENCE: 165
gugauaaugu agcgagauuu ucuguugugc uugaucuaac caugggguug cgagguauga    60
guaaaacaug guuccgucaa gcaccaugga acgucacgca gcuuucuaca              110

<210> SEQ ID NO 166
<211> LENGTH: 110
<212> TYPE: RNA
<213> ORGANISM: Homo sapiens

<400> SEQUENCE: 166
gaccagucgc ugcggggcuu uccuuugugc uugaucuaac caugggguga acgauggaa     60 acggaacaug guucugucaa gcaccgcgga aagcaccgug cucuccugca              110

```
<210> SEQ ID NO 167
<211> LENGTH: 110
<212> TYPE: RNA
<213> ORGANISM: Homo sapiens

<400> SEQUENCE: 167
ccgccccggg ccgcggcucc ugauugucca aacgcaauuc ucgagcuau ggcuccggcc      60 gagaguugag ucuggacguc ccgagccgcc gcccccaaac cucgagcggg              110

<210> SEQ ID NO 168
<211> LENGTH: 97
<212> TYPE: RNA
<213> ORGANISM: Homo sapiens

<400> SEQUENCE: 168
acucaggggc uucgccacug auuguccaaa cgcaauucuu guacgagucu gcggccaacc      60
gagaauugug gcuggacauc uguggcugag cuccggg                             97

<210> SEQ ID NO 169
<211> LENGTH: 110
<212> TYPE: RNA
<213> ORGANISM: Homo sapiens

<400> SEQUENCE: 169
gacagugugg cauuguaggg ucccacaccg uaucugacac uuugggcgag ggcaccaugc      60 ugaaggguguu caugaugcgg ucugggaacu ccucacggau cuuacugaug             110

<210> SEQ ID NO 170
<211> LENGTH: 110
<212> TYPE: RNA
<213> ORGANISM: Homo sapiens

<400> SEQUENCE: 170
ugaacaucca ggucuggggc augaaccugg cauacaaugu agauuucugu guucguuagg      60
caacagcuac auugucugcu ggguuucagg cuaccuggaa acauguucuc              110

<210> SEQ ID NO 171
<211> LENGTH: 110
<212> TYPE: RNA
<213> ORGANISM: Homo sapiens

<400> SEQUENCE: 171
gcugcuggaa gguguaggua cccucaaugg cucaguagcc aguguagauc cugucuuucg      60
uaaucagcag cuacaucugg cuacugggguc ucgauggca ucuucuagcu              110

<210> SEQ ID NO 172
<211> LENGTH: 110
<212> TYPE: RNA
<213> ORGANISM: Homo sapiens

<400> SEQUENCE: 172
ccuggccucc ugcagugcca cgcuccgugu auuugacaag cugaguugga cacuccaugu      60
gguagagugu caguuuguca aauaccccaa gugcggcaca ugcuuaccag              110

<210> SEQ ID NO 173
<211> LENGTH: 81
<212> TYPE: RNA
<213> ORGANISM: Homo sapiens

<400> SEQUENCE: 173
```

```
gggcuuucaa gucacuagug guuccguuua guagaugauu gugcauuguu ucaaaauggu    60
gcccuaguga cuacaaagcc c                                              81

<210> SEQ ID NO 174
<211> LENGTH: 80
<212> TYPE: RNA
<213> ORGANISM: Homo sapiens

<400> SEQUENCE: 174
aggacccuuc cagagggccc ccccucaauc cuguugugcc uaauucagag gguugggugg    60
aggcucuccu gaagggcucu                                                80

<210> SEQ ID NO 175
<211> LENGTH: 63
<212> TYPE: RNA
<213> ORGANISM: Homo sapiens

<400> SEQUENCE: 175
aagaaauggu uuaccguccc acauacauuu ugaauaugua gugggaugg uaaaccgcuu     60 cuu                                                                  63

<210> SEQ ID NO 176
<211> LENGTH: 86
<212> TYPE: RNA
<213> ORGANISM: Homo sapiens

<400> SEQUENCE: 176
acugcuaacg aaugcucuga cuuuauugca cuacuguacu uuacagcuag cagugcaaua    60
guauugucaa agcaucugaa agcagg                                         86

<210> SEQ ID NO 177
<211> LENGTH: 69
<212> TYPE: RNA
<213> ORGANISM: Homo sapiens

<400> SEQUENCE: 177
ccaccacuua aacguggaug uacuugcuuu gaaacuaaag aaguaagugc uuccauguuu    60
uggugaugg                                                            69

<210> SEQ ID NO 178
<211> LENGTH: 82
<212> TYPE: RNA
<213> ORGANISM: Homo sapiens

<400> SEQUENCE: 178
gcuucgcucc ccuccgccuu cucuucccgg uucuucccgg agucgggaaa agcugggusug   60 agagggcgaa aaaggaugag gu                                             82

<210> SEQ ID NO 179
<211> LENGTH: 59
<212> TYPE: RNA
<213> ORGANISM: Homo sapiens

<400> SEQUENCE: 179
uuggccuccu aagccaggga uguggguuc gagucccacc cggggruaaag aaaggccga     59

<210> SEQ ID NO 180
<211> LENGTH: 86
<212> TYPE: RNA
<213> ORGANISM: Homo sapiens
```

```
<400> SEQUENCE: 180
uugguacuug gagagaggug guccguggcg cguucgcuuu auuuauggcg cacauuacac    60
ggucgaccuc uuugcaguau cuaauc                                         86

<210> SEQ ID NO 181
<211> LENGTH: 83
<212> TYPE: RNA
<213> ORGANISM: Homo sapiens

<400> SEQUENCE: 181
cugacuaugc cuccccgcau ccccuagggc auugguguaa agcuggagac ccacugcccc    60
aggugcugcu gggggguugua guc                                           83

<210> SEQ ID NO 182
<211> LENGTH: 95
<212> TYPE: RNA
<213> ORGANISM: Homo sapiens

<400> SEQUENCE: 182
cucaucuguc uguugggcug gaggcagggc cuuugugaag gcggguggug cucagaucgc    60
cucugggccc uuccuccagc cccgaggcgg auuca                               95

<210> SEQ ID NO 183
<211> LENGTH: 75
<212> TYPE: RNA
<213> ORGANISM: Homo sapiens

<400> SEQUENCE: 183 uggaguggggg gggcaggagg ggcucaggga gaaagugcau acagcccug gcccucucug    60 cccuuccguc cccug                                                     75

<210> SEQ ID NO 184
<211> LENGTH: 94
<212> TYPE: RNA
<213> ORGANISM: Homo sapiens

<400> SEQUENCE: 184
cuuuggcgau cacugccucu cugggccugu gucuuaggcu cugcaagauc aaccgagcaa    60
agcacacggc cugcagagag gcagcgcucu gccc                                94

<210> SEQ ID NO 185
<211> LENGTH: 94
<212> TYPE: RNA
<213> ORGANISM: Homo sapiens

<400> SEQUENCE: 185
gaguuugguu uuguuugggu uuguucuagg uauggcccca gggaucccag aucaaaccag    60
gccccugggc cuauccuaga accaaccuaa gcuc                                94

<210> SEQ ID NO 186
<211> LENGTH: 94
<212> TYPE: RNA
<213> ORGANISM: Homo sapiens

<400> SEQUENCE: 186
uguuuugagc ggggggucaag agcaauaacg aaaaauguuu gucauaaacc guuuucauu    60 auugcuccug accucucuc auuugcuaua uuca                                 94
```

```
<210> SEQ ID NO 187
<211> LENGTH: 93
<212> TYPE: RNA
<213> ORGANISM: Homo sapiens

<400> SEQUENCE: 187
guagucagua guuggggggu gggaacggcu ucauacagga guugaugcac aguuauccag    60
cuccuauaug augccuuucu ucaucccuu caa                                  93

<210> SEQ ID NO 188
<211> LENGTH: 67
<212> TYPE: RNA
<213> ORGANISM: Homo sapiens

<400> SEQUENCE: 188
ucuccaacaa uauccuggug cugagugaug acucaggcga cuccagcauc agugauuuug    60
uugaaga                                                              67

<210> SEQ ID NO 189
<211> LENGTH: 94
<212> TYPE: RNA
<213> ORGANISM: Homo sapiens

<400> SEQUENCE: 189
cggggcggcc gcucucccug uccuccagga gcucacgugu gccugccugu gagcgccucg    60
acgacagagc cggcgccugc cccagugucu gcgc                                94

<210> SEQ ID NO 190
<211> LENGTH: 95
<212> TYPE: RNA
<213> ORGANISM: Homo sapiens

<400> SEQUENCE: 190
uuguaccugg ugugauuaua aagcaaugag acugauuguc auaugucguu uguggauuc     60 gucucaguua cuuuauagcc auaccuggua ucuua                               95

<210> SEQ ID NO 191
<211> LENGTH: 99
<212> TYPE: RNA
<213> ORGANISM: Homo sapiens

<400> SEQUENCE: 191
gaaacugggc ucaaggugag gggugcuauc ugugauugag ggacauggu aauggaauug     60 ucucacacag aaaucgcacc cgucaccuug gccuacuua                           99

<210> SEQ ID NO 192
<211> LENGTH: 77
<212> TYPE: RNA
<213> ORGANISM: Homo sapiens

<400> SEQUENCE: 192
gcuugggaca cauacuucuu uauaugccca uaugaaccug cuaagcuaug gaauguaaag    60
aaguauguau uucaggc                                                   77

<210> SEQ ID NO 193
<211> LENGTH: 72
<212> TYPE: RNA
<213> ORGANISM: Homo sapiens

<400> SEQUENCE: 193
```

```
ucagagcaca uacuucuuua uguacccaua ugaacauuca gugcuaugga auguaaagaa    60
guauguauuu ug                                                       72

<210> SEQ ID NO 194
<211> LENGTH: 88
<212> TYPE: RNA
<213> ORGANISM: Homo sapiens

<400> SEQUENCE: 194
ccaggcugag guaguaguuu guacaguuug agggucuaug auaccacccg guacaggaga    60
uaacuguaca ggccacugcc uugccagg                                      88

<210> SEQ ID NO 195
<211> LENGTH: 85
<212> TYPE: RNA
<213> ORGANISM: Homo sapiens

<400> SEQUENCE: 195
cuggcugagg uaguaguuug ugcuguuggu cgguuguga cauugcccgc uguggagaua     60
acugcgcaag cuacugccuu gcuag                                         85

<210> SEQ ID NO 196
<211> LENGTH: 103
<212> TYPE: RNA
<213> ORGANISM: Homo sapiens

<400> SEQUENCE: 196
aaugggUUCC uaggaagagg uaguagguug cauaguuuua gggcagagau uuugcccaca    60
aggaguuaac uauacgaccu gcugccuuuc uuagggccuu auu                     103

<210> SEQ ID NO 197
<211> LENGTH: 94
<212> TYPE: RNA
<213> ORGANISM: Homo sapiens

<400> SEQUENCE: 197
uucacugugg gaugagguag uagguuguau aguuuuaggg ucacacccac cacugggaga    60
uaacuauaca aucuacuguc uuuccuaagg ugau                               94

<210> SEQ ID NO 198
<211> LENGTH: 96
<212> TYPE: RNA
<213> ORGANISM: Homo sapiens

<400> SEQUENCE: 198
cugcauguuc ccagguugag guaguagguu guauaguuua gaguuacauc aagggagaua    60
acuguacagc cuccuagcuu uccuugggac uugcac                             96

<210> SEQ ID NO 199
<211> LENGTH: 85
<212> TYPE: RNA
<213> ORGANISM: Homo sapiens

<400> SEQUENCE: 199
gcagggugag guaguagguu gugugguuuc agggcaguga uguugccccu ccgaagauaa    60
cuauacaacc uacugccuuc ccuga                                         85

<210> SEQ ID NO 200
```

```
<211> LENGTH: 94
<212> TYPE: RNA
<213> ORGANISM: Homo sapiens

<400> SEQUENCE: 200
ugugugcauc cggguugagg uaguagguug uaugguuuag aguuacaccc ugggaguuaa    60 cguacaacc uucuagcuuu ccuuggagca cacu                                94

<210> SEQ ID NO 201
<211> LENGTH: 95
<212> TYPE: RNA
<213> ORGANISM: Homo sapiens

<400> SEQUENCE: 201
acggccuuug ggugagguua guagguugua ugguuuuggg cucugccccg cucugcggua    60
acuauacaau cuacugucuu uccugaagug gccgc                              95

<210> SEQ ID NO 202
<211> LENGTH: 93
<212> TYPE: RNA
<213> ORGANISM: Homo sapiens

<400> SEQUENCE: 202 cgcgccccc gggcugaggu aggagguugu auaguugagg aagacacccg aggagaucac    60
uauacggccu ccuagcuuuc cccaggcugc gcc                                93

<210> SEQ ID NO 203
<211> LENGTH: 89
<212> TYPE: RNA
<213> ORGANISM: Homo sapiens

<400> SEQUENCE: 203
aucagaguga gguaguagau uguauaguug uggggguagug auuuuacccu guuuaggaga    60
uaacuauaca aucuauugcc uucccugag                                      89

<210> SEQ ID NO 204
<211> LENGTH: 83
<212> TYPE: RNA
<213> ORGANISM: Homo sapiens

<400> SEQUENCE: 204
ugugggauga gguaguagau uguauaguuu uagggucaua ccccaucuug gagauaacua    60
uacagucuac ugucuuuccc acg                                            83

<210> SEQ ID NO 205
<211> LENGTH: 108
<212> TYPE: RNA
<213> ORGANISM: Homo sapiens

<400> SEQUENCE: 205
uuggauguug gccaguucu guguggaaga cuagugauuu uguuguuuuu agauaacuaa     60
aacgacaaca aaucacaguc ugccauaugg cacaggccac cucuacag               108

<210> SEQ ID NO 206
<211> LENGTH: 97
<212> TYPE: RNA
<213> ORGANISM: Homo sapiens

<400> SEQUENCE: 206
ggucgggcca gccccguuug gaagacuagu gauuuuguug uugugucucu guauccaaca    60
```

```
acaaguccca gucugccaca uggugcuggu cauuuca                              97
```

<210> SEQ ID NO 207
<211> LENGTH: 111
<212> TYPE: RNA
<213> ORGANISM: Homo sapiens

<400> SEQUENCE: 207

```
aggagcggag uacgugagcc agugcuaugu ggaagacuug ugauuuuguu guucugauau    60
gauaugacaa caagucacag ccagcccau agcguggacu ccaucaccu u              111
```

<210> SEQ ID NO 208
<211> LENGTH: 72
<212> TYPE: RNA
<213> ORGANISM: Homo sapiens

<400> SEQUENCE: 208

```
guuguuaucu uugguuaucu agcuguauga guguauuggu cuucauaaag cuagauaacc    60
gaaaguaaaa ac                                                        72
```

<210> SEQ ID NO 209
<211> LENGTH: 89
<212> TYPE: RNA
<213> ORGANISM: Homo sapiens

<400> SEQUENCE: 209

```
cggggguuggu uguuaucuuu gguuaucuag cuguaugagu ggugaggagu cuucauaaag   60
cuagauaacc gaaaguaaaa auaacccca                                      89
```

<210> SEQ ID NO 210
<211> LENGTH: 90
<212> TYPE: RNA
<213> ORGANISM: Homo sapiens

<400> SEQUENCE: 210

```
ggaggcccgu uucucucuuu gguuaucuag cuguaugagu gccacagagc cgucauaaag    60
cuagauaacc gaaaguagaa augacucuca                                     90
```

<210> SEQ ID NO 211
<211> LENGTH: 68
<212> TYPE: RNA
<213> ORGANISM: Homo sapiens

<400> SEQUENCE: 211

```
uauauacccu guagaaccga auuugugugg uacccacaua gucacagauu cgauucuagg    60
ggaauaua                                                             68
```

<210> SEQ ID NO 212
<211> LENGTH: 110
<212> TYPE: RNA
<213> ORGANISM: Homo sapiens

<400> SEQUENCE: 212

```
gaucugucug ucuucuguau auacccugua gauccgaauu uguuaagga auuuguggu      60 cacaaauucg uaucuagggg aauauguagu ugacauaaac acuccgcuca              110
```

<210> SEQ ID NO 213
<211> LENGTH: 110
<212> TYPE: RNA

<213> ORGANISM: Homo sapiens

<400> SEQUENCE: 213
gaccugucug ucuucuguau auacccugua gauccgaauu uguguaagga auuuuguggu    60
cacaaauucg uaucuagggg aauauguagu ugacauaaac acuccgcuca    110

<210> SEQ ID NO 214
<211> LENGTH: 64
<212> TYPE: RNA
<213> ORGANISM: Homo sapiens

<400> SEQUENCE: 214
cuguagcagc acaucauggu uuacauacua cagucaagau gcgaaucauu auuugcugcu    60
cuag    64

<210> SEQ ID NO 215
<211> LENGTH: 84
<212> TYPE: RNA
<213> ORGANISM: Homo sapiens

<400> SEQUENCE: 215
cccuuggagu aaaguagcag cacauaaugg uuuguggaug uugaaaaggu gcaggccaua    60
cugugcugcc ucaaaauaca agga    84

<210> SEQ ID NO 216
<211> LENGTH: 93
<212> TYPE: RNA
<213> ORGANISM: Homo sapiens

<400> SEQUENCE: 216
augucagcgg ugccuuagca gcacguaaau auuggcguua agauucugaa auuaccucca    60
guauugacug ugcugcugaa guaagguugg caa    93

<210> SEQ ID NO 217
<211> LENGTH: 95
<212> TYPE: RNA
<213> ORGANISM: Homo sapiens

<400> SEQUENCE: 217
caugcuuguu ccacucuagc agcacguaaa uauuggcgua gugaaauaaa uauuaaacac    60
caauauuauu gugcugcuuu agugugacag ggaua    95

<210> SEQ ID NO 218
<211> LENGTH: 84
<212> TYPE: RNA
<213> ORGANISM: Homo sapiens

<400> SEQUENCE: 218
gucagaauaa ugucaaagug cuuacagugc agguagugau gugugcaucu acugcaguga    60
gggcacuugu agcauuaugc ugac    84

<210> SEQ ID NO 219
<211> LENGTH: 96
<212> TYPE: RNA
<213> ORGANISM: Homo sapiens

<400> SEQUENCE: 219
ugcgugcuuu uuguucuaag gugcaucuag ugcagauagu gaaguagacu agcaucuacu    60
gcccuaagug cuccuucugg cauaagaagu uauguc    96

<210> SEQ ID NO 220
<211> LENGTH: 84
<212> TYPE: RNA
<213> ORGANISM: Homo sapiens

<400> SEQUENCE: 220
acuuacgauu aguuugcag auuugcaguu cagcguauau gugaauauau ggcugugcaa    60
auccaugcaa aacugauugu ggga                                        84

<210> SEQ ID NO 221
<211> LENGTH: 82
<212> TYPE: RNA
<213> ORGANISM: Homo sapiens

<400> SEQUENCE: 221
gcagcccucu guuaguuug cauaguugca cuacaagaag aauguaguug ugcaaaucua    60
ugcaaaacug augguggccu gc                                           82

<210> SEQ ID NO 222
<211> LENGTH: 87
<212> TYPE: RNA
<213> ORGANISM: Homo sapiens

<400> SEQUENCE: 222
cacuggucua ugguuaguuu ugcagguuug cauccagcug uauaauauuc ugcugugcaa    60
auccaugcaa aacugacugu gguggug                                       87

<210> SEQ ID NO 223
<211> LENGTH: 107
<212> TYPE: RNA
<213> ORGANISM: Homo sapiens

<400> SEQUENCE: 223
gugugaugug acagcuucug uagcacuaaa gugcuuauag ugcagguagu guguagccau    60
cuacugcauu acgagcacuu aaaguacugc cagcuguaga acuccag                107

<210> SEQ ID NO 224
<211> LENGTH: 92
<212> TYPE: RNA
<213> ORGANISM: Homo sapiens

<400> SEQUENCE: 224
uguaccaccu ugucggauag cuuaucagac ugauguugac uguugaaucu cauggcaaca    60
gcagucgaug ggcugucuga cauuuuggua uc                                92

<210> SEQ ID NO 225
<211> LENGTH: 95
<212> TYPE: RNA
<213> ORGANISM: Homo sapiens

<400> SEQUENCE: 225
accuggcuga gccgcaguag uucuucagug gcaagcuuua uguccugacc cagcuaaagc    60
ugccaguuga agaacuguug cccucugccc cuggc                              95

<210> SEQ ID NO 226
<211> LENGTH: 74
<212> TYPE: RNA
<213> ORGANISM: Homo sapiens

<400> SEQUENCE: 226
ggcugcuugg guuccuggca ugcugauuug ugacuugaga uuaaaaucac auugccaggg    60
auuaccacgc aacc                                                      74

<210> SEQ ID NO 227
<211> LENGTH: 75
<212> TYPE: RNA
<213> ORGANISM: Homo sapiens

<400> SEQUENCE: 227
cggacggcug ggguuccugg ggaugggauu ugaugccagu cacaaaucac auugccaggg    60
auuuccaacu gaccc                                                     75

<210> SEQ ID NO 228
<211> LENGTH: 68
<212> TYPE: RNA
<213> ORGANISM: Homo sapiens

<400> SEQUENCE: 228
cuccggugcc uacugagcug auaucaguuc ucauuucaca cacuggcuca guucagcagg    60
aacaggag                                                             68

<210> SEQ ID NO 229
<211> LENGTH: 107
<212> TYPE: RNA
<213> ORGANISM: Homo sapiens

<400> SEQUENCE: 229
gccucucucc gggcuccgcc ucccgugccu acugagcuga aacaguugau uccagugcac    60
uggcucaguu cagcaggaac aggaguccag cccccuagga gcuggca                 107

<210> SEQ ID NO 230
<211> LENGTH: 84
<212> TYPE: RNA
<213> ORGANISM: Homo sapiens

<400> SEQUENCE: 230
ggccaguguu gagaggcgga gacuugggca auugcuggac gcugcccugg gcauugcacu    60
ugucucgguc ugacagugcc ggcc                                           84

<210> SEQ ID NO 231
<211> LENGTH: 90
<212> TYPE: RNA
<213> ORGANISM: Homo sapiens

<400> SEQUENCE: 231
aaggccgugg ccucguucaa guaauccagg auaggcugug cagguccaa ggggccuauu    60 cuugguuacu ugcacgggga cgcgggccug                                     90

<210> SEQ ID NO 232
<211> LENGTH: 85
<212> TYPE: RNA
<213> ORGANISM: Homo sapiens

<400> SEQUENCE: 232
ugcccgggac ccaguucaag uaauucagga uagguugugg ugcugaccag ccuguucucc    60
auuacuuggc ucgggggccg gugcc                                          85

```
<210> SEQ ID NO 233
<211> LENGTH: 84
<212> TYPE: RNA
<213> ORGANISM: Homo sapiens

<400> SEQUENCE: 233
ggcugcggcu ggauucaagu aauccaggau aggcuguguc cguccaugag gccuguucuu      60
gauuacuugu uucuggaggc agcg                                            84

<210> SEQ ID NO 234
<211> LENGTH: 73
<212> TYPE: RNA
<213> ORGANISM: Homo sapiens

<400> SEQUENCE: 234
aggugcagag cuuagcugau uggugaacag ugauugguuu ccgcuuuguu cacaguggcu      60
aaguucugca ccu                                                        73

<210> SEQ ID NO 235
<211> LENGTH: 87
<212> TYPE: RNA
<213> ORGANISM: Homo sapiens

<400> SEQUENCE: 235
uggccugagg agcagggcuu agcugcuugu gagcaagguc cacagcaaag ucguguucac      60
aguggcuaag uuccgccccc uggaccc                                         87

<210> SEQ ID NO 236
<211> LENGTH: 86
<212> TYPE: RNA
<213> ORGANISM: Homo sapiens

<400> SEQUENCE: 236
ggucccuacc uucaaggagc ucacagucua uugaguugcc uuucugauuc ucccacuaga      60
uugugagcug cuggagggca ggcacu                                          86

<210> SEQ ID NO 237
<211> LENGTH: 71
<212> TYPE: RNA
<213> ORGANISM: Homo sapiens

<400> SEQUENCE: 237
aggaagcugg uuucauaugg ugguuuagau uuaaauagug auugcuagc accauuugaa       60 aucaguguuc u                                                          71

<210> SEQ ID NO 238
<211> LENGTH: 88
<212> TYPE: RNA
<213> ORGANISM: Homo sapiens

<400> SEQUENCE: 238
accccuuaga ggaugacuga uuucuuuugg uguucagagu caauagaauu uucuagcacc      60
aucugaaauc gguuauaaug auuggga                                         88

<210> SEQ ID NO 239
<211> LENGTH: 88
<212> TYPE: RNA
<213> ORGANISM: Homo sapiens

<400> SEQUENCE: 239
```

```
aucucuuaca caggcugacc gauuucuccu gguguucaga gucuguuuuu gucuagcacc    60
auuugaaauc gguaugaug uagggga                                        88
```

<210> SEQ ID NO 240
<211> LENGTH: 81
<212> TYPE: RNA
<213> ORGANISM: Homo sapiens

<400> SEQUENCE: 240

```
cuucuggaag cugguuucac augguggcuu agauuuuucc aucuuuguau cuagcaccau    60
uugaaaucag uguuuuagga g                                             81
```

<210> SEQ ID NO 241
<211> LENGTH: 71
<212> TYPE: RNA
<213> ORGANISM: Homo sapiens

<400> SEQUENCE: 241

```
gcgacuguaa acauccucga cuggaagcug ugaagccaca aaugggcuuu cagucggaug    60
uuugcagcug c                                                        71
```

<210> SEQ ID NO 242
<211> LENGTH: 60
<212> TYPE: RNA
<213> ORGANISM: Homo sapiens

<400> SEQUENCE: 242

```
auguaaacau ccuacacuca gcugucauac augcguuggc ugggaugugg auguuuacgu    60
```

<210> SEQ ID NO 243
<211> LENGTH: 64
<212> TYPE: RNA
<213> ORGANISM: Homo sapiens

<400> SEQUENCE: 243

```
cuguaaacau ccuugacugg aagcuguaag guguugagag gagcuuucag ucggauguuu    60
acag                                                                64
```

<210> SEQ ID NO 244
<211> LENGTH: 89
<212> TYPE: RNA
<213> ORGANISM: Homo sapiens

<400> SEQUENCE: 244

```
accauguugu agugugugua aacauccuac acucucagcu gugagcucaa gguggcuggg    60 agagggguugu uuacuccuuc ugccaugga                                    89
```

<210> SEQ ID NO 245
<211> LENGTH: 84
<212> TYPE: RNA
<213> ORGANISM: Homo sapiens

<400> SEQUENCE: 245

```
gagugacaga uauuguaaac auccuacacu cucagcugug aaaaguaaga aagcugggag    60
aaggcuguuu acucucucug ccuu                                          84
```

<210> SEQ ID NO 246
<211> LENGTH: 82
<212> TYPE: RNA
<213> ORGANISM: Homo sapiens

```
<400> SEQUENCE: 246
aagucugugu cuguaaacau ccccgacugg aagcuguaag ccacagccaa gcuuucaguc    60
agauguuugc ugcuacuggc uc                                            82

<210> SEQ ID NO 247
<211> LENGTH: 106
<212> TYPE: RNA
<213> ORGANISM: Homo sapiens

<400> SEQUENCE: 247
ugcuccugua acucggaacu ggagaggagg caagaugcug gcauagcugu ugaacugaga    60
accugcuaug ccaacauauu gccaucuuuc cugucugaca gcagcu                 106

<210> SEQ ID NO 248
<211> LENGTH: 70
<212> TYPE: RNA
<213> ORGANISM: Homo sapiens

<400> SEQUENCE: 248
ggagauauug cacauuacua aguugcaugu ugucacggcc ucaaugcaau uuagugugug    60
ugauauuuuc                                                          70

<210> SEQ ID NO 249
<211> LENGTH: 69
<212> TYPE: RNA
<213> ORGANISM: Homo sapiens

<400> SEQUENCE: 249
cuguggugca uuguaguugc auugcauguu cuggcaauac cugugcaaug uuuccacagu    60
gcaucacgg                                                           69

<210> SEQ ID NO 250
<211> LENGTH: 77
<212> TYPE: RNA
<213> ORGANISM: Homo sapiens

<400> SEQUENCE: 250
agucuaguua cuaggcagug uaguuagcug auugcuaaua guaccaauca cuaaccacac    60
agccagguaa aaagacu                                                  77

<210> SEQ ID NO 251
<211> LENGTH: 84
<212> TYPE: RNA
<213> ORGANISM: Homo sapiens

<400> SEQUENCE: 251
gugcucgguu uguaggcagu guaauuagcu gauugu agug cggugcugac aaucacuaac    60
uccacugcca ucaaaacaag gcac                                          84

<210> SEQ ID NO 252
<211> LENGTH: 102
<212> TYPE: RNA
<213> ORGANISM: Homo sapiens

<400> SEQUENCE: 252
ccagcuguga guaauucuuu ggcagugucu uagcugguug uugugaguau uagcuaagga    60
agcaaucagc aaguauacug cccuagaagu gcugcacauu gu                     102
```

<210> SEQ ID NO 253
<211> LENGTH: 91
<212> TYPE: RNA
<213> ORGANISM: Homo sapiens

<400> SEQUENCE: 253
ugcccauuca uccacaggug gggauuggug gcauuacuug uguuagauau aaaguauugc     60 acugucccg gccugaggaa gaaagagggu u                                    91

<210> SEQ ID NO 254
<211> LENGTH: 80
<212> TYPE: RNA
<213> ORGANISM: Homo sapiens

<400> SEQUENCE: 254
cuuucuacac agguugggau uugucgcaau gcuguguuuc ucuguauggu auugcacuug     60
ucccggccug uugaguuugg                                                80

<210> SEQ ID NO 255
<211> LENGTH: 88
<212> TYPE: RNA
<213> ORGANISM: Homo sapiens

<400> SEQUENCE: 255 agucauggg gcuccaaagu gcuguucgug cagguagugu aauuaccuga ccuacugcug      60
agcuagcacu ucccgagccc ccaggaca                                       88

<210> SEQ ID NO 256
<211> LENGTH: 106
<212> TYPE: RNA
<213> ORGANISM: Homo sapiens

<400> SEQUENCE: 256
ccaguaccau cugcuuggcc gauuuuggca cuagcacauu uuugcuugug ucucuccgcu     60
gugagcaauc auguguagug ccaauauggg aaaagcgggc ugcugc                  106

<210> SEQ ID NO 257
<211> LENGTH: 80
<212> TYPE: RNA
<213> ORGANISM: Homo sapiens

<400> SEQUENCE: 257
gugagguagu aaguuguauu guugugggu agggauuuua ggcccagua agaagauaac       60 uauacaacuu acuacuuucc                                                80

<210> SEQ ID NO 258
<211> LENGTH: 65
<212> TYPE: RNA
<213> ORGANISM: Homo sapiens

<400> SEQUENCE: 258
cauaaacccg uagauccgau cuugugguga aguggaccgc gcaagcucgu uucuaugggu     60
cugug                                                                65

<210> SEQ ID NO 259
<211> LENGTH: 70
<212> TYPE: RNA
<213> ORGANISM: Homo sapiens

<400> SEQUENCE: 259
ggcacccacc cguagaaccg accuugcggg gccuucgccg cacacaagcu cgugucugug    60
gguccguguc                                                            70

<210> SEQ ID NO 260
<211> LENGTH: 80
<212> TYPE: RNA
<213> ORGANISM: Homo sapiens

<400> SEQUENCE: 260
ccuguugcca caaacccgua gauccgaacu ugugcugauu cugcacacaa gcuugugucu    60
auagguaugu gucuguuagg                                                 80

<210> SEQ ID NO 261
<211> LENGTH: 57
<212> TYPE: RNA
<213> ORGANISM: Homo sapiens

<400> SEQUENCE: 261
ucaguuauca cagugcugau gcuguccauu cuaaagguac aguacuguga uaacuga       57

<210> SEQ ID NO 262
<211> LENGTH: 97
<212> TYPE: RNA
<213> ORGANISM: Homo sapiens

<400> SEQUENCE: 262
aucugagacu gaacugcccu uuuucgguua ucaugguacc gaugcuguag cucugaaagg    60
uacaguacug ugauagcuga agaauggcgg ugccauc                              97

<210> SEQ ID NO 263
<211> LENGTH: 86
<212> TYPE: RNA
<213> ORGANISM: Homo sapiens

<400> SEQUENCE: 263
uucuuacugc ccucggcuuc uuuacagugc ugccuuguug cauauggauc aagcagcauu    60
guacagggcu augaaggcau ugagac                                          86

<210> SEQ ID NO 264
<211> LENGTH: 86
<212> TYPE: RNA
<213> ORGANISM: Homo sapiens

<400> SEQUENCE: 264
gucuucgugc uuucagcuuc uuuacagugc ugccuuguag cauucagguc aagcagcauu    60
guacagggcu augaaagaac caagaa                                          86

<210> SEQ ID NO 265
<211> LENGTH: 65
<212> TYPE: RNA
<213> ORGANISM: Homo sapiens

<400> SEQUENCE: 265
augucaaagu gcuaacagug cagguagcuu uuugaguucu acugcagugc cagcacuucu    60
uacau                                                                 65

<210> SEQ ID NO 266
<211> LENGTH: 82
<212> TYPE: RNA

<213> ORGANISM: Homo sapiens

<400> SEQUENCE: 266
ccugcuggga cuaaagugcu gacagugcag auaguggucc ucucugugcu accgcacugu    60
ggguacuugc ugcuccagca gg    82

<210> SEQ ID NO 267
<211> LENGTH: 87
<212> TYPE: RNA
<213> ORGANISM: Homo sapiens

<400> SEQUENCE: 267
uucucugugc uuucagcuuc uuuacagugu ugccuugugg cauggaguuc aagcagcauu    60
guacagggcu aucaaagcac agagagc    87

<210> SEQ ID NO 268
<211> LENGTH: 66
<212> TYPE: RNA
<213> ORGANISM: Homo sapiens

<400> SEQUENCE: 268
agcuguggag ugugacaaug guguuugugu ccaaaccauc aaacgccauu aucacacuaa    60
auagcu    66

<210> SEQ ID NO 269
<211> LENGTH: 68
<212> TYPE: RNA
<213> ORGANISM: Homo sapiens

<400> SEQUENCE: 269
cucugcgugu ucacagcgga ccuugauuua augucuauac aauuaaggca cgcggugaau    60
gccaagag    68

<210> SEQ ID NO 270
<211> LENGTH: 85
<212> TYPE: RNA
<213> ORGANISM: Homo sapiens

<400> SEQUENCE: 270
aggccucucu cuccguguuc acagcggacc uugauuuaaa uguccauaca auuaaggcac    60
gcggugaaug ccaagaaugg ggcug    85

<210> SEQ ID NO 271
<211> LENGTH: 109
<212> TYPE: RNA
<213> ORGANISM: Homo sapiens

<400> SEQUENCE: 271
aucaagauca gagacucugc ucuccguguu cacagcggac cuugauuuaa ugucauacaa    60
uuaaggcacg cggugaaugc caagagcgga gccuacggcu gcacuugaa    109

<210> SEQ ID NO 272
<211> LENGTH: 68
<212> TYPE: RNA
<213> ORGANISM: Homo sapiens

<400> SEQUENCE: 272 cuggguccccu gagacccuuu aaccugugag gacguccagg gucacaggug agguucuugg    60
gagccugg    68

```
<210> SEQ ID NO 273
<211> LENGTH: 71
<212> TYPE: RNA
<213> ORGANISM: Homo sapiens

<400> SEQUENCE: 273
gccuaguccc ugagacccua acuugugagg uauuuuagua acaucacaag ucagguucuu    60
gggaccuagg c                                                        71

<210> SEQ ID NO 274
<211> LENGTH: 77
<212> TYPE: RNA
<213> ORGANISM: Homo sapiens

<400> SEQUENCE: 274
ugcgcucccc ucagucccug agacccuaac uugugauguu uaccguuuaa auccacgggu    60
uaggcucuug ggagcug                                                  77

<210> SEQ ID NO 275
<211> LENGTH: 73
<212> TYPE: RNA
<213> ORGANISM: Homo sapiens

<400> SEQUENCE: 275
ugacagcaca uuauuacuuu ugguacgcgc ugugacacuu caaacucgua ccgugaguaa    60
uaaugcgcgg uca                                                      73

<210> SEQ ID NO 276
<211> LENGTH: 70
<212> TYPE: RNA
<213> ORGANISM: Homo sapiens

<400> SEQUENCE: 276
ccagccugcu gaagcucaga gggcucugau ucagaaagau caucggaucc gucugagcuu    60
ggcuggucgg                                                          70

<210> SEQ ID NO 277
<211> LENGTH: 70
<212> TYPE: RNA
<213> ORGANISM: Homo sapiens

<400> SEQUENCE: 277
guuggauucg gggccguagc acugucugag agguuuacau uucucacagu gaaccggucu    60
cuuuuucagc                                                          70

<210> SEQ ID NO 278
<211> LENGTH: 76
<212> TYPE: RNA
<213> ORGANISM: Homo sapiens

<400> SEQUENCE: 278
cagugggaag gggggccgau gcacuguaag agagugagua gcaggucuca cagugaaccg    60
gucucuuucc cuacug                                                   76

<210> SEQ ID NO 279
<211> LENGTH: 73
<212> TYPE: RNA
<213> ORGANISM: Homo sapiens
```

<400> SEQUENCE: 279
uggaucuuuu ugcggucugg gcuugcuguu cucucgacag uagucaggaa gcccuuaccc    60
caaaaaguau cua                                                       73

<210> SEQ ID NO 280
<211> LENGTH: 90
<212> TYPE: RNA
<213> ORGANISM: Homo sapiens

<400> SEQUENCE: 280
ugccuuucgc gaaucuuuuu gcggucuggg cuugcuguac auaacucaau agccggaagc    60
ccuuacccca aaaagcauuc gcggagggcg                                     90

<210> SEQ ID NO 281
<211> LENGTH: 64
<212> TYPE: RNA
<213> ORGANISM: Homo sapiens

<400> SEQUENCE: 281
gagcucuuuu cacauugugc uacugucuaa cguguaccga gcagugcaau guuaaaggg     60 cauc                                                                 64

<210> SEQ ID NO 282
<211> LENGTH: 82
<212> TYPE: RNA
<213> ORGANISM: Homo sapiens

<400> SEQUENCE: 282
ggcuuguugg acacucuuuc ccuguugcac uacugugggc cucugggaag cagugcaaug    60
augaaagggc aucugucggg cc                                             82

<210> SEQ ID NO 283
<211> LENGTH: 66
<212> TYPE: RNA
<213> ORGANISM: Homo sapiens

<400> SEQUENCE: 283
gggcaaccgu ggcuuucgau uguuacugug ggaaccggag guaacagucu acagccaugg    60
ucgccc                                                               66

<210> SEQ ID NO 284
<211> LENGTH: 68
<212> TYPE: RNA
<213> ORGANISM: Homo sapiens

<400> SEQUENCE: 284
gcuaaagcug guaaaaugga accaaaucgc cucuucaaug gauuuggucc ccuucaacca    60
gcuguagc                                                             68

<210> SEQ ID NO 285
<211> LENGTH: 104
<212> TYPE: RNA
<213> ORGANISM: Homo sapiens

<400> SEQUENCE: 285
agaagccaaa ugcuuugcug aagcugguaa aauggaacca aaucagcugu uggauggauu    60 uggucccuu caaccagcug uagcugcgca uugaucacgc cgca                     104

<210> SEQ ID NO 286
<211> LENGTH: 119
<212> TYPE: RNA
<213> ORGANISM: Homo sapiens

<400> SEQUENCE: 286
ccuccaaagg gaguggcccc cugcucuggc uggucaaacg gaaccaaguc cgucuuccug    60
agagguuugg uccccuucaa ccagcuacag cagggcuggc aaagcucaau auuggaga    119

<210> SEQ ID NO 287
<211> LENGTH: 71
<212> TYPE: RNA
<213> ORGANISM: Homo sapiens

<400> SEQUENCE: 287
agggugugug acugguugac cagaggggcg ugcacucugu cacccugug ggccaccuag    60 ucaccaaccc u    71

<210> SEQ ID NO 288
<211> LENGTH: 90
<212> TYPE: RNA
<213> ORGANISM: Homo sapiens

<400> SEQUENCE: 288
aggccucacu guucucuaug gcuuuuuauu ccuaugugau ucuauugcuc gcucauauag    60
ggauuggagc cguggcguac ggugaggaua    90

<210> SEQ ID NO 289
<211> LENGTH: 97
<212> TYPE: RNA
<213> ORGANISM: Homo sapiens

<400> SEQUENCE: 289
cgcucugcug uggccuaugg cuuuucauuc cuaugugauu gcugcuccga acucauguag    60
ggcuaaaagc caugggcuac agugaggggc aagcucc    97

<210> SEQ ID NO 290
<211> LENGTH: 100
<212> TYPE: RNA
<213> ORGANISM: Homo sapiens

<400> SEQUENCE: 290
agauaaauuc acucuagugc uuuauggcuu uuuauuccua ugugaucgua auaaagucuc    60
auguagggau ggaagccaug aaauacauug ugaaaauuca    100

<210> SEQ ID NO 291
<211> LENGTH: 62
<212> TYPE: RNA
<213> ORGANISM: Homo sapiens

<400> SEQUENCE: 291
gaggacucca uuuguuuuga ugauggauuc uuaagcucca ucaucgucuc aaaugagucu    60
uc    62

<210> SEQ ID NO 292
<211> LENGTH: 73
<212> TYPE: RNA
<213> ORGANISM: Homo sapiens

<400> SEQUENCE: 292
cuucggugac ggguauucuu gguggauaa uacggauuac guuguuauug cuuaagaaua       60
cgcguagucg agg                                                          73

<210> SEQ ID NO 293
<211> LENGTH: 71
<212> TYPE: RNA
<213> ORGANISM: Homo sapiens

<400> SEQUENCE: 293
cagcuggugu ugugaaucag gccgacgagc agcgcauccu cuuacccggc uauuucacga       60
caccagGGuu g                                                            71

<210> SEQ ID NO 294
<211> LENGTH: 99
<212> TYPE: RNA
<213> ORGANISM: Homo sapiens

<400> SEQUENCE: 294
cucuagcaug guguguggg acagcuggug uugugaauca ggccguugcc aaucagagaa        60
cggcuacuuc acaacaccag ggccacacug cacugcaag                              99

<210> SEQ ID NO 295
<211> LENGTH: 68
<212> TYPE: RNA
<213> ORGANISM: Homo sapiens

<400> SEQUENCE: 295
guguauucua cagugcacgu gucccagug uggcucggag gcuggagacg cggcccuguu        60
ggaguaac                                                                68

<210> SEQ ID NO 296
<211> LENGTH: 70
<212> TYPE: RNA
<213> ORGANISM: Homo sapiens

<400> SEQUENCE: 296
ccugccagug guuuuacccu augguagguu acgucaugcu guucuaccac aggguagaac       60
cacggacagg                                                              70

<210> SEQ ID NO 297
<211> LENGTH: 72
<212> TYPE: RNA
<213> ORGANISM: Homo sapiens

<400> SEQUENCE: 297
ggguccaucu uccagugcag uguuggaugg uugaaguaug aagcuccuaa cacugucugg       60
uaaagauggc cc                                                           72

<210> SEQ ID NO 298
<211> LENGTH: 64
<212> TYPE: RNA
<213> ORGANISM: Homo sapiens

<400> SEQUENCE: 298
acccauaaag uagaaagcac uacuaacagc acuggagggu guaguuuuc cuacuuuaug        60 gaug                                                                    64

<210> SEQ ID NO 299
<211> LENGTH: 63

```
<212> TYPE: RNA
<213> ORGANISM: Homo sapiens

<400> SEQUENCE: 299
ccugaggugc agugcugcau cucuggucag uugggagucu gagaugaagc acuguagcuc    60
agg                                                                 63

<210> SEQ ID NO 300
<211> LENGTH: 66
<212> TYPE: RNA
<213> ORGANISM: Homo sapiens

<400> SEQUENCE: 300
ggcugggaua ucaucauaua cuguaaguuu gugaugagac acuacaguau agaugaugua    60
cuaguc                                                              66

<210> SEQ ID NO 301
<211> LENGTH: 70
<212> TYPE: RNA
<213> ORGANISM: Homo sapiens

<400> SEQUENCE: 301
cucacggucc aguuucccca ggaaucccuu ggaugcuaag auggggauuc cuggaaauac    60
uguucuugag                                                          70

<210> SEQ ID NO 302
<211> LENGTH: 65
<212> TYPE: RNA
<213> ORGANISM: Homo sapiens

<400> SEQUENCE: 302
agcucugaga acugaauucc augguuaua ucaaugucag accugugaaa uucaguucuu     60
cagcu                                                               65

<210> SEQ ID NO 303
<211> LENGTH: 99
<212> TYPE: RNA
<213> ORGANISM: Homo sapiens

<400> SEQUENCE: 303
agccaguuug gucuuuugag acaaaguucu gagacacucc gacucugagu augauagaag    60
ucagugcacu acagaacuuu gucucuagag gcugugguc                          99

<210> SEQ ID NO 304
<211> LENGTH: 66
<212> TYPE: RNA
<213> ORGANISM: Homo sapiens

<400> SEQUENCE: 304
ggcucuggcu ccugucuuc acucccgugu uuguccgagg agggagggag ggacggggc      60 ggugcu                                                              66

<210> SEQ ID NO 305
<211> LENGTH: 65
<212> TYPE: RNA
<213> ORGANISM: Homo sapiens

<400> SEQUENCE: 305
cccugucucc caacccuugu accagugcug ugccucagac ccugguacag gccuggggga    60
``` uaggg                                                                65

<210> SEQ ID NO 306
<211> LENGTH: 68
<212> TYPE: RNA
<213> ORGANISM: Homo sapiens

<400> SEQUENCE: 306
ccugcccucg aggagcucac agucuaguau gucuccuccc uacuagacug aggcuccuug    60
aggacagg                                                             68

<210> SEQ ID NO 307
<211> LENGTH: 73
<212> TYPE: RNA
<213> ORGANISM: Homo sapiens

<400> SEQUENCE: 307
ccgggccuag guucugugau acacuccgac ucgggcucug gagcagucag ugcaugacag    60
aacuugggcc cgg                                                       73

<210> SEQ ID NO 308
<211> LENGTH: 69
<212> TYPE: RNA
<213> ORGANISM: Homo sapiens

<400> SEQUENCE: 308
cggugucauu uuugugacgu ugcagcuagu aauaugagcc caguugcaua gucacaaaag    60
ugaucauug                                                            69

<210> SEQ ID NO 309
<211> LENGTH: 66
<212> TYPE: RNA
<213> ORGANISM: Homo sapiens

<400> SEQUENCE: 309
gaagauaggu uauccguguu gccuucgcuu uauucgugac gaaucauaca cgguugaccu    60
auuuuu                                                               66

<210> SEQ ID NO 310
<211> LENGTH: 65
<212> TYPE: RNA
<213> ORGANISM: Homo sapiens

<400> SEQUENCE: 310
cuguuaaugc uaauugugau agggguuuug gccucugacu gacuccuacc uguuagcauu    60
aacag                                                                65

<210> SEQ ID NO 311
<211> LENGTH: 76
<212> TYPE: RNA
<213> ORGANISM: Homo sapiens

<400> SEQUENCE: 311
ccauggaaca uucaacgcug ucggugaguu ugggauucaa aaacaaaaaa accaccgacc    60
guugacugua ccuugg                                                    76

<210> SEQ ID NO 312
<211> LENGTH: 80
<212> TYPE: RNA
<213> ORGANISM: Homo sapiens

<400> SEQUENCE: 312
aggucacaau caacauucau ugcugucggu ggguugaacu guguagaaaa gcucacugaa    60
caaugaaugc aacugggcc                                                80

<210> SEQ ID NO 313
<211> LENGTH: 89
<212> TYPE: RNA
<213> ORGANISM: Homo sapiens

<400> SEQUENCE: 313
gccaaggguu uggggaaca uucaaccugu cggugaguuu gggcagcuca gacaaaccau    60
cgaccguuga guggaccccg aggccugga                                    89

<210> SEQ ID NO 314
<211> LENGTH: 89
<212> TYPE: RNA
<213> ORGANISM: Homo sapiens

<400> SEQUENCE: 314
uugauggcug cacucaacau ucauugcugu cggugguuu gaaugucaac caacucacug     60
aucaaugaau gcaaacugcg ggccaaaaa                                    89

<210> SEQ ID NO 315
<211> LENGTH: 75
<212> TYPE: RNA
<213> ORGANISM: Homo sapiens

<400> SEQUENCE: 315
accauuuuug gcaaugguag aacucacacc gguaagguaa ugggacccgg ugguucuaga    60
cuugccaacu auggu                                                   75

<210> SEQ ID NO 316
<211> LENGTH: 70
<212> TYPE: RNA
<213> ORGANISM: Homo sapiens

<400> SEQUENCE: 316
cuguguaugg cacugguaga auucacugug aacagucuca gucagugaau uaccgaaggg    60
ccauaaacag                                                         70

<210> SEQ ID NO 317
<211> LENGTH: 69
<212> TYPE: RNA
<213> ORGANISM: Homo sapiens

<400> SEQUENCE: 317 ccuuccuua ucacuuuucc agccagcuuu gugacucuaa guguuggacg gagaacugau    60
aaggguagg                                                          69

<210> SEQ ID NO 318
<211> LENGTH: 65
<212> TYPE: RNA
<213> ORGANISM: Homo sapiens

<400> SEQUENCE: 318
agggauugga gagaaaggca guuccugaug gucccucccc agggcuggc uuccucugg     60 uccuu                                                              65

<210> SEQ ID NO 319
<211> LENGTH: 71
<212> TYPE: RNA
<213> ORGANISM: Homo sapiens

<400> SEQUENCE: 319
acuuuccaaa gaauucuccu uugggcuuu cucauuuuau uuuaagcccu aaggugaauu      60
uuuugggaag u                                                         71

<210> SEQ ID NO 320
<211> LENGTH: 61
<212> TYPE: RNA
<213> ORGANISM: Homo sapiens

<400> SEQUENCE: 320
ucaggcuaca acacaggacc cgggcgcugc ucugaccccu cgucuugu guugcagccg      60 g                                                                    61

<210> SEQ ID NO 321
<211> LENGTH: 68
<212> TYPE: RNA
<213> ORGANISM: Homo sapiens

<400> SEQUENCE: 321
ucucacaucc cuugcauggu ggagggugag cucucugaaa accccuccca caugcagggu    60
uugcagga                                                             68

<210> SEQ ID NO 322
<211> LENGTH: 67
<212> TYPE: RNA
<213> ORGANISM: Homo sapiens

<400> SEQUENCE: 322
cugugugaua uguuugauau auuagguugu uauuuaaucc aacuauauau caagcauauu    60
ccuacag                                                              67

<210> SEQ ID NO 323
<211> LENGTH: 74
<212> TYPE: RNA
<213> ORGANISM: Homo sapiens

<400> SEQUENCE: 323
agcgggcaac ggaaucccaa aagcagcugu ugucccaga gcauuccagc ugcacuugga     60
uuucguuccc ugcu                                                      74

<210> SEQ ID NO 324
<211> LENGTH: 89
<212> TYPE: RNA
<213> ORGANISM: Homo sapiens

<400> SEQUENCE: 324
cgugcacagg gcucugaccu augaauugac agccaguacu cuuuucucuc cucggcugc     60 caauuccaua ggucacaggu auguucacc                                      89

<210> SEQ ID NO 325
<211> LENGTH: 66
<212> TYPE: RNA
<213> ORGANISM: Homo sapiens

<400> SEQUENCE: 325

```
gagagcuggg ucuuugcggg caagaugaga gugucaguuc aacuggccua caaagcccca    60
guccuc                                                              66

<210> SEQ ID NO 326
<211> LENGTH: 67
<212> TYPE: RNA
<213> ORGANISM: Homo sapiens

<400> SEQUENCE: 326
aucgggugua acagcaacuc cauguggacu gugcucggau uccaguggag cugcuguuac    60
uucugau                                                             67

<210> SEQ ID NO 327
<211> LENGTH: 86
<212> TYPE: RNA
<213> ORGANISM: Homo sapiens

<400> SEQUENCE: 327
guggcuccca cccucuguaa cagcaacucc augguggaagu gcccacuggu uccagugggg   60
cugcuguuau cuggguggc ggcuag                                         86

<210> SEQ ID NO 328
<211> LENGTH: 58
<212> TYPE: RNA
<213> ORGANISM: Homo sapiens

<400> SEQUENCE: 328
uagcagcaca gaaauauugg caugggaag ugagucugcc aauauuggcu gugcugcu       58

<210> SEQ ID NO 329
<211> LENGTH: 102
<212> TYPE: RNA
<213> ORGANISM: Homo sapiens

<400> SEQUENCE: 329
ugagccggga cuguugagug aaguagguag uuucauguug uugggccugg cuuucugaac    60
acaacgacau caaaccaccu gauucauggc aguuacugcu uc                     102

<210> SEQ ID NO 330
<211> LENGTH: 85
<212> TYPE: RNA
<213> ORGANISM: Homo sapiens

<400> SEQUENCE: 330
agcugaucug uggcuuaggu aguuucaugu uguggauu gaguuugaa cucggcaaca       60 agaaacugcc ugaguuacau caguc                                         85

<210> SEQ ID NO 331
<211> LENGTH: 70
<212> TYPE: RNA
<213> ORGANISM: Homo sapiens

<400> SEQUENCE: 331
gccaucccag uguucagacu accuguucag gaggcuggga cauguacagu agucugcaca    60
uugguuaggc                                                          70

<210> SEQ ID NO 332
<211> LENGTH: 110
<212> TYPE: RNA
```

<213> ORGANISM: Homo sapiens

<400> SEQUENCE: 332
uggaagcuuc aggagauccu gcuccgucgc cccaguguuc agacuaccug uucaggacaa    60
ugccguugua caguagucug cacauugguu agacugggca agggccagca               110

<210> SEQ ID NO 333
<211> LENGTH: 110
<212> TYPE: RNA
<213> ORGANISM: Homo sapiens

<400> SEQUENCE: 333
ccagaggaua ccuccacucc gucuacccag uguuuagacu accuguucag gacucccaaa    60
uuguacagua gucugcacau ugguuaggcu gggcuggguu agacccucgg               110

<210> SEQ ID NO 334
<211> LENGTH: 70
<212> TYPE: RNA
<213> ORGANISM: Homo sapiens

<400> SEQUENCE: 334
gccguggcca ucuuacuggg cagcauugga uagugucuga ucucuaauac ugccgguaa     60 ugaugacggc                                                            70

<210> SEQ ID NO 335
<211> LENGTH: 90
<212> TYPE: RNA
<213> ORGANISM: Homo sapiens

<400> SEQUENCE: 335
cugggccucu gugggcaucu uaccggacag ugcuggauuu cuuggcuuga cucuaacacu    60
gucugguaac gauguucaaa ggugacccac                                      90

<210> SEQ ID NO 336
<211> LENGTH: 69
<212> TYPE: RNA
<213> ORGANISM: Homo sapiens

<400> SEQUENCE: 336
cccucgucuu acccagcagu guuugggugc ugguugggag ucucuaauac ugccgguaa     60 ugauggagg                                                             69

<210> SEQ ID NO 337
<211> LENGTH: 66
<212> TYPE: RNA
<213> ORGANISM: Homo sapiens

<400> SEQUENCE: 337
uaccuuacuc aguaaggcau uguucuucua uauuaauaaa ugaacagugc cuucugugu     60 agggua                                                                66

<210> SEQ ID NO 338
<211> LENGTH: 72
<212> TYPE: RNA
<213> ORGANISM: Homo sapiens

<400> SEQUENCE: 338
guuccuuuuu ccuaugcaua uacuucuuug uggaucuggu cuaaagaggu auagcgcaug    60
ggaagaugga gc                                                         72

<210> SEQ ID NO 339
<211> LENGTH: 76
<212> TYPE: RNA
<213> ORGANISM: Homo sapiens

<400> SEQUENCE: 339
gccuggucca gugguucuug acaguucaac aguucuguag cacaauugug aaauguuuag    60
gaccacuaga cccggc                                                   76

<210> SEQ ID NO 340
<211> LENGTH: 68
<212> TYPE: RNA
<213> ORGANISM: Homo sapiens

<400> SEQUENCE: 340
uggacuuccc uuugucaucc uaugccugag aauauaugaa ggaggcuggg aaggcaaagg    60
gacguuca                                                            68

<210> SEQ ID NO 341
<211> LENGTH: 68
<212> TYPE: RNA
<213> ORGANISM: Homo sapiens

<400> SEQUENCE: 341
cucuuguccu ucauuccacc ggagucuguc uuaugccaac cagauuucag uggagugaag    60
cucaggag                                                            68

<210> SEQ ID NO 342
<211> LENGTH: 73
<212> TYPE: RNA
<213> ORGANISM: Homo sapiens

<400> SEQUENCE: 342
ccaggccaca ugcuucuuua uauccucaua gauaucucag cacuauggaa uguaaggaag    60 uguguggbuuu ugg                                                     73

<210> SEQ ID NO 343
<211> LENGTH: 79
<212> TYPE: RNA
<213> ORGANISM: Homo sapiens

<400> SEQUENCE: 343
aaggcagggg ugaggggcug cgggaggagc cgggcggagg cugcggcuug cgcuucuccu    60
ggcucuccuc ccucucuuu                                                79

<210> SEQ ID NO 344
<211> LENGTH: 83
<212> TYPE: RNA
<213> ORGANISM: Homo sapiens

<400> SEQUENCE: 344
uuccuuugac gggugagcuu uuggcccggg uuauaccuga cacucacgua uaagacgagc    60
aaaaagcuug uuggucagag gag                                           83

<210> SEQ ID NO 345
<211> LENGTH: 110
<212> TYPE: RNA
<213> ORGANISM: Homo sapiens

<400> SEQUENCE: 345
ccggggcagu cccuccaggc ucaggacagc cacugcccac cgcacacugc guugcuccgg    60
acccacugug cgugugacag cggcugaucu gucccugggc agcgcgaacc             110

<210> SEQ ID NO 346
<211> LENGTH: 106
<212> TYPE: RNA
<213> ORGANISM: Homo sapiens

<400> SEQUENCE: 346
cugcuuggac cugugaccug ugggcuuccc uuugucaucc uuugccuagg ccucugagug    60
aggcaaggac agcaaagggg ggcucagugg ucaccucuac ugcaga                106

<210> SEQ ID NO 347
<211> LENGTH: 91
<212> TYPE: RNA
<213> ORGANISM: Homo sapiens

<400> SEQUENCE: 347
gggcagcgcg ccggcaccuu ggcucuagac ugcuuacugc ccgggccgcc uucaguaaca    60
gucuccaguc acggccaccg acgccuggcc c                                 91

<210> SEQ ID NO 348
<211> LENGTH: 87
<212> TYPE: RNA
<213> ORGANISM: Homo sapiens

<400> SEQUENCE: 348
gguugcuuca gugaacauuc aacgcugucg gugaguuugg aauucaaaua aaaaccaucg    60
accguugauu guacccuaua gcuaacc                                      87

<210> SEQ ID NO 349
<211> LENGTH: 110
<212> TYPE: RNA
<213> ORGANISM: Homo sapiens

<400> SEQUENCE: 349
ggccuggcug gacagaguug ucaugugucu gccugcuac acuugcugug cagaacaucc    60
gcucaccugu acagcaggca cagacaggca gucacaugac aacccagccu             110

<210> SEQ ID NO 350
<211> LENGTH: 112
<212> TYPE: RNA
<213> ORGANISM: Homo sapiens

<400> SEQUENCE: 350
agcucucagc aucaacggug uacaggagaa ugaccuauga uuugacagac cgugcagcug    60
uguaugucug ucauucugua ggccaauauu cuguaugucu cugcuacuua aa           112

<210> SEQ ID NO 351
<211> LENGTH: 72
<212> TYPE: RNA
<213> ORGANISM: Homo sapiens

<400> SEQUENCE: 351
uugguuuaau cucagcuggc aacugugaga ugucccuauc auuccucaca gugguucucug    60 ggauuaugcu aa                                                      72

```
<210> SEQ ID NO 352
<211> LENGTH: 108
<212> TYPE: RNA
<213> ORGANISM: Homo sapiens

<400> SEQUENCE: 352
aaacauaguc auuacaguuu uugauguugc agauacugca ucaggaacug acuggauaag      60
acuuaauccc caucaguucc uaaugcauug ccuucagcau cuaaacaa                  108

<210> SEQ ID NO 353
<211> LENGTH: 110
<212> TYPE: RNA
<213> ORGANISM: Homo sapiens

<400> SEQUENCE: 353
gaccaguugc cgcggggcuu uccuuugugc uugaucuaac caugugguggg aacgauggaa     60 acggaacaug guucugucaa gcaccgcgga aagcaucgcu cuccuugca                110

<210> SEQ ID NO 354
<211> LENGTH: 110
<212> TYPE: RNA
<213> ORGANISM: Homo sapiens

<400> SEQUENCE: 354
ccgucccggg ccgcggcucc ugauugucca aacgcaauuc ucgagucucu ggcuccggcc      60
gagaguugcg ucuggacguc ccgagccgcc gcccccaaac cucgagggggg             110

<210> SEQ ID NO 355
<211> LENGTH: 97
<212> TYPE: RNA
<213> ORGANISM: Homo sapiens

<400> SEQUENCE: 355 acucagggggc uucgccacug auuguccaaa cgcaauucuu guacgagucu gcggccaacc     60
gagaauugug gcuggacauc ugugguugag cuccggg                              97

<210> SEQ ID NO 356
<211> LENGTH: 95
<212> TYPE: RNA
<213> ORGANISM: Homo sapiens

<400> SEQUENCE: 356
auccaggucu ggggcaugaa ccuggcauac aauguagauu ucuguguuug uuaggcaaca     60
gcuacauugu cugcuggguu ucaggcuacc uggaa                                95

<210> SEQ ID NO 357
<211> LENGTH: 79
<212> TYPE: RNA
<213> ORGANISM: Homo sapiens

<400> SEQUENCE: 357
cccucagugg cucaguagcc aguguagauc cugucuuugg uaaucagcag cuacaucugg     60
cuacuggguc ucuggguggc                                                 79

<210> SEQ ID NO 358
<211> LENGTH: 110
<212> TYPE: RNA
<213> ORGANISM: Homo sapiens

<400> SEQUENCE: 358
```

```
ucuggccauc ugcagugnca cgcuccgugu auuugacaag cugaguugga cacucugugu    60
gguagagugu caguuuguca aauacccaa guguggcuca ugccuaucag                110
```

<210> SEQ ID NO 359
<211> LENGTH: 82
<212> TYPE: RNA
<213> ORGANISM: Homo sapiens

<400> SEQUENCE: 359

```
gggcuuuuaa gucacuagug guuccguuua guagauggu ugugcauugu uucaaaaugg     60
ugcccuagug acuacaaagc cc                                             82
```

<210> SEQ ID NO 360
<211> LENGTH: 83
<212> TYPE: RNA
<213> ORGANISM: Homo sapiens

<400> SEQUENCE: 360

```
cucaucuugc gguacucaaa cuauggggc acuuuuuuu uucuuaaaa agugccgccu       60 aguuuuaagc cccgccgguu gag                                            83
```

<210> SEQ ID NO 361
<211> LENGTH: 82
<212> TYPE: RNA
<213> ORGANISM: Homo sapiens

<400> SEQUENCE: 361

```
ccuauguagc ggccaucaaa guggaggccc ucucuugagc cugaaugaga aagugcuucc    60
acuuugugug ccacugcaug gg                                             82
```

<210> SEQ ID NO 362
<211> LENGTH: 82
<212> TYPE: RNA
<213> ORGANISM: Homo sapiens

<400> SEQUENCE: 362

```
cagccuguga uacucaaacu gggggcucuu uuggauuuuc aucggaagaa aagugccgcc    60
agguuuugag ugucaccggu ug                                             82
```

<210> SEQ ID NO 363
<211> LENGTH: 80
<212> TYPE: RNA
<213> ORGANISM: Homo sapiens

<400> SEQUENCE: 363

```
uucaaucugu gguacucaaa cugugugaca uuuuguucuu uguaagaagu gccgcagagu    60
uuguagnguu gccgauugag                                                80
```

<210> SEQ ID NO 364
<211> LENGTH: 84
<212> TYPE: RNA
<213> ORGANISM: Homo sapiens

<400> SEQUENCE: 364

```
uuccauauag ccauacucaa aauggaggcc cuaucuaagc uuuuaagugg aaagugcuuc    60
ccuuuugugu guugccaugu ggag                                           84
```

<210> SEQ ID NO 365
<211> LENGTH: 69

```
<212> TYPE: RNA
<213> ORGANISM: Homo sapiens

<400> SEQUENCE: 365
ggugagacuc aaaugugggg cacacuucug dacuguacau agaaagugcu acuacuuuug    60
agucucucc                                                            69

<210> SEQ ID NO 366
<211> LENGTH: 79
<212> TYPE: RNA
<213> ORGANISM: Homo sapiens

<400> SEQUENCE: 366
gggccuuucu ggagggcccc cccucaaucc uguugugcuc gcuucagagg guugggugga    60
ggcucuccug aaggugucc                                                 79

<210> SEQ ID NO 367
<211> LENGTH: 76
<212> TYPE: RNA
<213> ORGANISM: Homo sapiens

<400> SEQUENCE: 367
auauguaugu auguauguau gugugcaugu gcaugugcau guaugcauau uguauguaua    60
uauuaugcau acaugu                                                    76

<210> SEQ ID NO 368
<211> LENGTH: 64
<212> TYPE: RNA
<213> ORGANISM: Homo sapiens

<400> SEQUENCE: 368
uguaugugca ugcauaugug cucaugugug uguacaugua ugugugcaug ugcauguaua    60
uaug                                                                 64

<210> SEQ ID NO 369
<211> LENGTH: 82
<212> TYPE: RNA
<213> ORGANISM: Homo sapiens

<400> SEQUENCE: 369
ccaggccuuu ggcagaggag ggcuguucuu cccugaguu uuaugacugg gaggaacuag     60
ccuucucuca gcuuaggagu gg                                             82

<210> SEQ ID NO 370
<211> LENGTH: 63
<212> TYPE: RNA
<213> ORGANISM: Homo sapiens

<400> SEQUENCE: 370
aagaaauggu uuaccguccc acauacauuu ugaguaugua ugugggacgg uaaaccgcuu    60
cuu                                                                  63

<210> SEQ ID NO 371
<211> LENGTH: 79
<212> TYPE: RNA
<213> ORGANISM: Homo sapiens

<400> SEQUENCE: 371
gcuacuugaa gagagguuau ccuuugugug uuugcuuuac gcgaaaugaa uaugcaaggg    60
```
caagcucucu ucgaggagc                                                       79

<210> SEQ ID NO 372
<211> LENGTH: 86
<212> TYPE: RNA
<213> ORGANISM: Homo sapiens

<400> SEQUENCE: 372
ccugcuaacg gcugcucuga cuuuauugca cuacuguacu uuacagcgag cagugcaaua         60
guauugucaa agcauccgcg agcagg                                              86

<210> SEQ ID NO 373
<211> LENGTH: 69
<212> TYPE: RNA
<213> ORGANISM: Homo sapiens

<400> SEQUENCE: 373
ccaccacuua aacgugguug uacuugcuuu agaccuaaga aaguaagugc uuccauguuu         60
uggugaugg                                                                 69

<210> SEQ ID NO 374
<211> LENGTH: 82
<212> TYPE: RNA
<213> ORGANISM: Homo sapiens

<400> SEQUENCE: 374
gccucgccgc ccuccgccuu cucuucccgg uucuucccgg agucgggaaa agcuggguug         60
agagggcgaa aaaggaugug gg                                                  82

<210> SEQ ID NO 375
<211> LENGTH: 59
<212> TYPE: RNA
<213> ORGANISM: Homo sapiens

<400> SEQUENCE: 375
uuggccuccu aagccaggga uguggguuc gagucccacc cgggguaaug agguguuuu           59

<210> SEQ ID NO 376
<211> LENGTH: 86
<212> TYPE: RNA
<213> ORGANISM: Homo sapiens

<400> SEQUENCE: 376
uugguacuug gagagaggug guccguggcg cguucgcuuc auuuauggcg cacauuacac         60
ggucgaccuc uuugcgguau cuaauc                                              86

<210> SEQ ID NO 377
<211> LENGTH: 89
<212> TYPE: RNA
<213> ORGANISM: Homo sapiens

<400> SEQUENCE: 377
aacugacuau gccuccucgc auccccuagg gcauuggugu aaagcuggag acccacugcc         60
ccaggugcug cuggggguug uagucugac                                           89

<210> SEQ ID NO 378
<211> LENGTH: 98
<212> TYPE: RNA
<213> ORGANISM: Homo sapiens

<400> SEQUENCE: 378
auauagugcu ugguuccuag uaggugcuca guaaguguuu gugacauaau ucguuuauug     60
agcaccuccu aucaaucaag cacugugcua ggcucugg                            98

<210> SEQ ID NO 379
<211> LENGTH: 95
<212> TYPE: RNA
<213> ORGANISM: Homo sapiens

<400> SEQUENCE: 379
cucaucuguc uguugggcug ggggcagggc cuuugugaag gcgguuuaug cucagaucgc     60
cucugggccc uuccuccagu cccgaggcag auuua                               95

<210> SEQ ID NO 380
<211> LENGTH: 97
<212> TYPE: RNA
<213> ORGANISM: Homo sapiens

<400> SEQUENCE: 380
cugucucgga gccuggggca gggggcagg aggggcucag ggagaaagua ucuacagccc     60
cuggcccucu cugccuucc gucccuguc cccaagu                               97

<210> SEQ ID NO 381
<211> LENGTH: 97
<212> TYPE: RNA
<213> ORGANISM: Homo sapiens

<400> SEQUENCE: 381
uguucgcuuc ugguaccgga agagagguuu ucugggucuc uguuucuuug augagaauga     60
aacacaccca gcuaaccuuu uuuucaguau caaaucc                             97

<210> SEQ ID NO 382
<211> LENGTH: 98
<212> TYPE: RNA
<213> ORGANISM: Homo sapiens

<400> SEQUENCE: 382
gacccuuugg cgaucucugc cucucugggc cugugucuua ggcucuucaa gauccaacga     60
gcaaagcaca gggccugcag agagguagcg cucugcuc                            98

<210> SEQ ID NO 383
<211> LENGTH: 96
<212> TYPE: RNA
<213> ORGANISM: Homo sapiens

<400> SEQUENCE: 383
gagucugguu uuguuugggu uuguucuagg uaugguccca gggaucccag aucaaaccag     60
gccccugggc cuauccuaga accaaccuaa acccgu                              96

<210> SEQ ID NO 384
<211> LENGTH: 97
<212> TYPE: RNA
<213> ORGANISM: Homo sapiens

<400> SEQUENCE: 384
caguguagug agaaguuggg ggguggaac ggcgucaugc aggaguugau ugcacagcca      60
uucagcuccu auaugaugcc uuucuucacc cccuuca                             97

<210> SEQ ID NO 385

```
<211> LENGTH: 98
<212> TYPE: RNA
<213> ORGANISM: Homo sapiens

<400> SEQUENCE: 385
caacgcugca caggccgucc uccccaacaa uauccuggug cugagugggu gcacagugac    60
uccagcauca gugauuuugu ugaagagggc agcugcca                            98

<210> SEQ ID NO 386
<211> LENGTH: 96
<212> TYPE: RNA
<213> ORGANISM: Homo sapiens

<400> SEQUENCE: 386
acggggugga cacuaucccu guccuccagg agcucacgua ugccugccug ugagcgccuc    60
ggcgacagag ccggugucca ccccugcacu guccac                              96

<210> SEQ ID NO 387
<211> LENGTH: 98
<212> TYPE: RNA
<213> ORGANISM: Homo sapiens

<400> SEQUENCE: 387
caauuguacu ggguguggauu auaaagcaau gagacugauu gucauauguc guuuguggga    60
uccgucucag uuacuuuaua gccauaccug guaucuua                            98

<210> SEQ ID NO 388
<211> LENGTH: 96
<212> TYPE: RNA
<213> ORGANISM: Homo sapiens

<400> SEQUENCE: 388
aaaaugauga ugucaguugg ccggucggcc gaucgcucgg ucugucaguc agucggucgg    60
ucgaucgguc ggucggucag ucggcuuccu gucuuc                              96

<210> SEQ ID NO 389
<211> LENGTH: 99
<212> TYPE: RNA
<213> ORGANISM: Homo sapiens

<400> SEQUENCE: 389 gaaaauggge ucaaggugag gggugcuauc ugugauugag ggacaugguc aauggaauug    60
ucucacacag aaaucgcacc cgucaccuug gccugcuga                           99

<210> SEQ ID NO 390
<211> LENGTH: 95
<212> TYPE: RNA
<213> ORGANISM: Homo sapiens

<400> SEQUENCE: 390
cugcagccag gguuuuuacc agucaggcuc cuggcuagau uccagguacc agcugguacc    60
ugaucuagcc aaagccugac uguaagcccu gaaca                               95

<210> SEQ ID NO 391
<211> LENGTH: 96
<212> TYPE: RNA
<213> ORGANISM: Homo sapiens

<400> SEQUENCE: 391
acccaagucc aggccugcug accccuaguc cagugcuugu gguggcuacu gggcccugaa    60
```

```
cuaggggucu ggagaccugg guuugaucuc cacagg                           96
```

<210> SEQ ID NO 392
<211> LENGTH: 98
<212> TYPE: RNA
<213> ORGANISM: Homo sapiens

<400> SEQUENCE: 392

```
ucuguuugg gcgucugucu gcccgagugc cugccucucu guugcucuga aggaggcagg   60
ggcugggccu gcagcugccu gggcagagcu gcuccuuc                         98
```

<210> SEQ ID NO 393
<211> LENGTH: 99
<212> TYPE: RNA
<213> ORGANISM: Homo sapiens

<400> SEQUENCE: 393

```
agaugccuug cuccuacaag aguaaagugc augcgcuuug ggacagugag gaaaauaaug   60
uucacaaagc ccauacacuu ucacccuuua ggagaguug                        99
```

<210> SEQ ID NO 394
<211> LENGTH: 98
<212> TYPE: RNA
<213> ORGANISM: Rattus norvegicus

<400> SEQUENCE: 394

```
ugggcuccua ggaagaggua guagguugca uaguuuuagg gcagagauuu ugcccacaag   60
gaguuaacua uacgaccugc ugccuuucuu agggccuu                         98
```

<210> SEQ ID NO 395
<211> LENGTH: 97
<212> TYPE: RNA
<213> ORGANISM: Rattus norvegicus

<400> SEQUENCE: 395

```
uguuggccua guucugugug gaagacuagu gauuuuguug uuuuuagaua acuaagacga   60
caacaaauca cagucugcca uauggcacag gccaccu                          97
```

<210> SEQ ID NO 396
<211> LENGTH: 94
<212> TYPE: RNA
<213> ORGANISM: Rattus norvegicus

<400> SEQUENCE: 396

```
uucacugugg gaugagguag uagguuguau aguuuuaggg ucacacccac cacugggaga   60
uaacuauaca aucuacuguc uuuccuaagg ugau                             94
```

<210> SEQ ID NO 397
<211> LENGTH: 96
<212> TYPE: RNA
<213> ORGANISM: Rattus norvegicus

<400> SEQUENCE: 397

```
cggcaugcuc ccaggcugag guaguagguu guauaguuua gaguuacaac aagggagaua   60
acuguacagc cuccuagcuu uccuugggac uugcac                           96
```

<210> SEQ ID NO 398
<211> LENGTH: 85
<212> TYPE: RNA

```
<213> ORGANISM: Rattus norvegicus

<400> SEQUENCE: 398
gcggggugag guaguagguu guguggeuuuc agggcaguga ugucgcccccu ccgaagauaa    60 cuauacaacc uacugccuuc ccuga                                           85

<210> SEQ ID NO 399
<211> LENGTH: 94
<212> TYPE: RNA
<213> ORGANISM: Rattus norvegicus

<400> SEQUENCE: 399
ugugugcauc cggguugagg uaguagguug uaugguuuag aguuacaccc ugggaguuaa    60 cguacaacc uucuagcuuu ccuuggagca cacu                                  94

<210> SEQ ID NO 400
<211> LENGTH: 95
<212> TYPE: RNA
<213> ORGANISM: Rattus norvegicus

<400> SEQUENCE: 400
acggccuuug ggugaggua guagguugua ugguuuggg cucugccccg cucugcggua       60
acuauacaau cuacugucuu uccgaagug gccgc                                 95

<210> SEQ ID NO 401
<211> LENGTH: 93
<212> TYPE: RNA
<213> ORGANISM: Rattus norvegicus

<400> SEQUENCE: 401 cgcgccccc gggcugaggu aggagguugu auaguugagg aagacacccg aggagaucac      60
uauacggccu ccuagcuuuc cccaggcugc gcc                                  93

<210> SEQ ID NO 402
<211> LENGTH: 89
<212> TYPE: RNA
<213> ORGANISM: Rattus norvegicus

<400> SEQUENCE: 402
aucagaguga gguaguagau uguauaguug uggguaguag auuuuacccu guuuaggaga     60
uaacuauaca aucuauugcc uucccugag                                       89

<210> SEQ ID NO 403
<211> LENGTH: 83
<212> TYPE: RNA
<213> ORGANISM: Rattus norvegicus

<400> SEQUENCE: 403
ugugggauga gguaguagau uguauaguuu uagggucaua ccccaucuug gagauaacua     60
uacagucuac ugucuuuccc acg                                             83

<210> SEQ ID NO 404
<211> LENGTH: 85
<212> TYPE: RNA
<213> ORGANISM: Rattus norvegicus

<400> SEQUENCE: 404
cuggcugagg uaguaguuug ugcuguuggu cgggguuguga cauugcccgc uggagaaua     60 acugcgcaag cuacugccuu gcuag                                           85
```

```
<210> SEQ ID NO 405
<211> LENGTH: 95
<212> TYPE: RNA
<213> ORGANISM: Rattus norvegicus

<400> SEQUENCE: 405
ggacagacca gcccugucug aagacuagu gauuuguug uugugucugu guccaacaac      60
aagucccagu cugccacaug guguggguca cauca                               95

<210> SEQ ID NO 406
<211> LENGTH: 110
<212> TYPE: RNA
<213> ORGANISM: Rattus norvegicus

<400> SEQUENCE: 406
aggccagaac acaugagcca augcuaugug gaagacuugu gauuuguug uucugauaug     60 auaugacaac aagucacagc cagccucaua gaguggacuc ccaucaccuu              110

<210> SEQ ID NO 407
<211> LENGTH: 89
<212> TYPE: RNA
<213> ORGANISM: Rattus norvegicus

<400> SEQUENCE: 407
cgggguuggu uguuaucuuu gguuaucuag cuguaugagu gguguggagu cuucauaaag    60
cuagauaacc gaaaguaaaa auaacccca                                      89

<210> SEQ ID NO 408
<211> LENGTH: 90
<212> TYPE: RNA
<213> ORGANISM: Rattus norvegicus

<400> SEQUENCE: 408
ggaggcccgu uucucucuuu gguuaucuag cuguaugagu gccacagagc cgucauaaag    60
cuagauaacc gaaaguagaa augacucuaa                                     90

<210> SEQ ID NO 409
<211> LENGTH: 87
<212> TYPE: RNA
<213> ORGANISM: Rattus norvegicus

<400> SEQUENCE: 409
ggaagcgagu uguuaucuuu gguuaucuag cuguaugagu guauggucu ucauaaagcu     60 agauaaccga aaguaaaaac uccuuca                                        87

<210> SEQ ID NO 410
<211> LENGTH: 110
<212> TYPE: RNA
<213> ORGANISM: Rattus norvegicus

<400> SEQUENCE: 410
gaccugucug ucuucuguau uacccugua gauccgaauu uguguaagga auuuguggu      60 cacaaauucg uaucuagggg aauauguagu ugacauaaac acuccgcuca              110

<210> SEQ ID NO 411
<211> LENGTH: 109
<212> TYPE: RNA
<213> ORGANISM: Rattus norvegicus
```

-continued

```
<400> SEQUENCE: 411
ccaaaguugu aacguugucu auauauaccc uguagaaccg aauuugugug guacccacau    60
agucacagau ucgauucuag gggaauauau ggucgaugca aaaacuuca               109

<210> SEQ ID NO 412
<211> LENGTH: 98
<212> TYPE: RNA
<213> ORGANISM: Rattus norvegicus

<400> SEQUENCE: 412
uuggaaccuu aaaguacugu agcagcacau caugguuuac auacuacagu caagaugcga    60
aucauuauuu gcugcucuag aaauuuaagg aaauucau                           98

<210> SEQ ID NO 413
<211> LENGTH: 95
<212> TYPE: RNA
<213> ORGANISM: Rattus norvegicus

<400> SEQUENCE: 413
cauacuuguu ccgcucuagc agcacguaaa uauuggcgua gugaaauaaa auuuaaacac    60
caauauuauu gugcugcuuu agugugacag gaaua                              95

<210> SEQ ID NO 414
<211> LENGTH: 84
<212> TYPE: RNA
<213> ORGANISM: Rattus norvegicus

<400> SEQUENCE: 414
gucaggauaa ugucaaagug cuuacagugc agguaguggu gugugcaucu acugcaguga    60
aggcacuugu ggcauugugc ugac                                          84

<210> SEQ ID NO 415
<211> LENGTH: 96
<212> TYPE: RNA
<213> ORGANISM: Rattus norvegicus

<400> SEQUENCE: 415
ugcgugcuuu uuguucuaag gugcaucuag ugcagauagu gaaguagacu agcaucuacu    60
gcccuaagug cuccuucugg cauaagaagu uauguc                             96

<210> SEQ ID NO 416
<211> LENGTH: 87
<212> TYPE: RNA
<213> ORGANISM: Rattus norvegicus

<400> SEQUENCE: 416
cacuggucua ugguuaguuu ugcagguuug cauccagcug uauaauauuc ugcugugcaa    60
auccaugcaa aacugacugu gguggug                                       87

<210> SEQ ID NO 417
<211> LENGTH: 96
<212> TYPE: RNA
<213> ORGANISM: Rattus norvegicus

<400> SEQUENCE: 417
acauugcuac uuacgguuag uuuugcagau uugcaguuca gcguauaugu ggauauaugg    60
cugugcaaau ccaugcaaaa cugauuguga ugaugu                             96
```

```
<210> SEQ ID NO 418
<211> LENGTH: 82
<212> TYPE: RNA
<213> ORGANISM: Rattus norvegicus

<400> SEQUENCE: 418
gcagcccucu guucguuuug cauaguugca cuacaagaag aauguaguug ugcaaaucua    60
ugcaaaacug augguggccu gc                                            82

<210> SEQ ID NO 419
<211> LENGTH: 85
<212> TYPE: RNA
<213> ORGANISM: Rattus norvegicus

<400> SEQUENCE: 419
cagcuucugu agcacuaaag ugcuuauagu gcagguagug ugucgucauc uacugcauua    60
cgagcacuua caguacugcc agcug                                         85

<210> SEQ ID NO 420
<211> LENGTH: 92
<212> TYPE: RNA
<213> ORGANISM: Rattus norvegicus

<400> SEQUENCE: 420
uguaccaccu ugucggguag cuuaucagac ugauguugac uguugaaucu cauggcaaca    60
gcagucgaug ggcugucuga cauuuuggua uc                                 92

<210> SEQ ID NO 421
<211> LENGTH: 95
<212> TYPE: RNA
<213> ORGANISM: Rattus norvegicus

<400> SEQUENCE: 421
accuggcuga gccgcaguag uucuucagug gcaagcuuua uguccugacc cagcuaaagc    60
ugccaguuga agaacuguug cccucugcca cuggc                              95

<210> SEQ ID NO 422
<211> LENGTH: 75
<212> TYPE: RNA
<213> ORGANISM: Rattus norvegicus

<400> SEQUENCE: 422
cggccggcug ggguuccugg ggaugggauu ugaugccagu cacaaaucac auugccaggg    60
auuuccaacu gaccc                                                    75

<210> SEQ ID NO 423
<211> LENGTH: 97
<212> TYPE: RNA
<213> ORGANISM: Rattus norvegicus

<400> SEQUENCE: 423
cucaccugcu cuggcugcuu ggguuccugg caugcugauu ugugacuuga gauuaaaauc    60
acauugccag ggauuaccac gcaaccauga ccuuggc                            97

<210> SEQ ID NO 424
<211> LENGTH: 68
<212> TYPE: RNA
<213> ORGANISM: Rattus norvegicus

<400> SEQUENCE: 424
```

```
cuccggugcc uacugagcug auaucaguuc ucauuucaca cacuggcuca guucagcagg    60
aacaggag                                                            68

<210> SEQ ID NO 425
<211> LENGTH: 108
<212> TYPE: RNA
<213> ORGANISM: Rattus norvegicus

<400> SEQUENCE: 425 gccucuccccu gggcuccgcc uccugugccu acugagcuga aacaguugau uccagugcac   60
uggcucaguu cagcaggaac aggaguccag cccccauagg agcuggca               108

<210> SEQ ID NO 426
<211> LENGTH: 84
<212> TYPE: RNA
<213> ORGANISM: Rattus norvegicus

<400> SEQUENCE: 426
ggccaguguu gagaggcgga gacacgggca auugcuggac gcugcccugg gcauugcacu    60
ugucucgguc ugacagugcc ggcc                                          84

<210> SEQ ID NO 427
<211> LENGTH: 90
<212> TYPE: RNA
<213> ORGANISM: Rattus norvegicus

<400> SEQUENCE: 427
aaggccgugg ccuuguucaa guaauccagg auaggcugug caggucccaa ggggccuauu    60
cuugguuacu ugcacgggga cgcgggccug                                    90

<210> SEQ ID NO 428
<211> LENGTH: 85
<212> TYPE: RNA
<213> ORGANISM: Rattus norvegicus

<400> SEQUENCE: 428
ugcccgggac ccaguucaag uaauucagga uagguugugg ugcuggccag ccuguucucc    60
auuacuuggc ucgggggccg gugcc                                         85

<210> SEQ ID NO 429
<211> LENGTH: 97
<212> TYPE: RNA
<213> ORGANISM: Rattus norvegicus

<400> SEQUENCE: 429
accucucuaa caaggugcag agcuuagcug auuggugaac agugauuggu uccgcuuug     60 uucacagugg cuaaguucug caccugaaga gaaggug                            97

<210> SEQ ID NO 430
<211> LENGTH: 87
<212> TYPE: RNA
<213> ORGANISM: Rattus norvegicus

<400> SEQUENCE: 430
uggccugugg agcagggcuu agcugcuugu gagcaagguc uacagcaaag ucguguucac    60
aguggcuaag uuccgccccc uggaccc                                       87

<210> SEQ ID NO 431
<211> LENGTH: 86
```

```
<212> TYPE: RNA
<213> ORGANISM: Rattus norvegicus

<400> SEQUENCE: 431
ggucccuacc cgcaaggagc ucacagucua uugaguuccu uuucugauuc ucccacuaga    60
uugugagcuc cuggagggca ggcacu                                        86

<210> SEQ ID NO 432
<211> LENGTH: 81
<212> TYPE: RNA
<213> ORGANISM: Rattus norvegicus

<400> SEQUENCE: 432
cuucuggaag cugguuucac augguggcuu agauuuuucc aucuuuguau cuagcaccau    60
uugaaaucag uguuuuagga g                                             81

<210> SEQ ID NO 433
<211> LENGTH: 88
<212> TYPE: RNA
<213> ORGANISM: Rattus norvegicus

<400> SEQUENCE: 433 acccuuaga ggaugacuga uuucuuuugg uguucagagu caauagaauu uucuagcacc     60
aucugaaauc gguuauaaug auuggga                                       88

<210> SEQ ID NO 434
<211> LENGTH: 81
<212> TYPE: RNA
<213> ORGANISM: Rattus norvegicus

<400> SEQUENCE: 434
cuucaggaag cugguuucau augguggului agauuuaaau agugauugc uagcaccauu    60 ugaaaucagu guucuuggug g                                             81

<210> SEQ ID NO 435
<211> LENGTH: 88
<212> TYPE: RNA
<213> ORGANISM: Rattus norvegicus

<400> SEQUENCE: 435
aucucuuaca caggcugacc gauuucuccu gguguucaga gucuguuuuu gucuagcacc    60
auuugaaauc gguuaugaug uaggggga                                      88

<210> SEQ ID NO 436
<211> LENGTH: 89
<212> TYPE: RNA
<213> ORGANISM: Rattus norvegicus

<400> SEQUENCE: 436
accauguugu agugugugua aacauccuac acucucagcu gugagcucaa gguggcuggg    60 agagguugu uuacuccuuc ugccaugga                                      89

<210> SEQ ID NO 437
<211> LENGTH: 64
<212> TYPE: RNA
<213> ORGANISM: Rattus norvegicus

<400> SEQUENCE: 437
cuguaaacau ccuugacugg aagcuguaag guguugagag gagcuuucag ucggauguuu    60
``` acag                                                              64

<210> SEQ ID NO 438
<211> LENGTH: 87
<212> TYPE: RNA
<213> ORGANISM: Rattus norvegicus

<400> SEQUENCE: 438
ccgaguuuca guucauguaa acauccuaca cucagcuguc auacaugagu uggcugggau    60
guggauguuu acgucagcug ucuugga                                       87

<210> SEQ ID NO 439
<211> LENGTH: 82
<212> TYPE: RNA
<213> ORGANISM: Rattus norvegicus

<400> SEQUENCE: 439
aagucugugu cuguaaacau ccccgacugg aagcuguaag ccacagccaa gcuucaguc     60 agauguuugc ugcuacuggc uc                                            82

<210> SEQ ID NO 440
<211> LENGTH: 71
<212> TYPE: RNA
<213> ORGANISM: Rattus norvegicus

<400> SEQUENCE: 440
gcaacuguaa acauccucga cuggaagcug ugaagccaca aaugggcuuu cagucggaug    60
uuugcagcug c                                                        71

<210> SEQ ID NO 441
<211> LENGTH: 84
<212> TYPE: RNA
<213> ORGANISM: Rattus norvegicus

<400> SEQUENCE: 441
gagugacaga uacuguaaac auccuacacu cucagcugug aaaaguaaga aagcugggag    60
aaggcuguuu acucucucug ccuu                                          84

<210> SEQ ID NO 442
<211> LENGTH: 106
<212> TYPE: RNA
<213> ORGANISM: Rattus norvegicus

<400> SEQUENCE: 442
ugcuccugaa acuuggaacu ggagaggagg caagaugcug gcauagcugu ugaacugaga    60
accugcuaug ccaacauauu gccaucuuuc cugucugaca gcagcu                 106

<210> SEQ ID NO 443
<211> LENGTH: 70
<212> TYPE: RNA
<213> ORGANISM: Rattus norvegicus

<400> SEQUENCE: 443
ggggauauug cacauuacua aguugcaugu ugcacggcc ucaaugcaau uuagugugug     60
ugauauucuc                                                          70

<210> SEQ ID NO 444
<211> LENGTH: 69
<212> TYPE: RNA
<213> ORGANISM: Rattus norvegicus

<400> SEQUENCE: 444
ccguggugca uuguaguugc auugcauguu cuggcaguac cugugcaaug uuuccacagu     60
gcaucacgg                                                             69

<210> SEQ ID NO 445
<211> LENGTH: 84
<212> TYPE: RNA
<213> ORGANISM: Rattus norvegicus

<400> SEQUENCE: 445
gugcucgguu uguaggcagu guaauuagcu gauuguagug cggugcugac aaucacuaac     60
uccacugcca ucaaaacaag gcac                                            84

<210> SEQ ID NO 446
<211> LENGTH: 77
<212> TYPE: RNA
<213> ORGANISM: Rattus norvegicus

<400> SEQUENCE: 446
agucuaguua cuaggcagug uaguuagcug auugcuaaua guaccaauca cuaaccacac     60
agccagguaa aaagacu                                                    77

<210> SEQ ID NO 447
<211> LENGTH: 102
<212> TYPE: RNA
<213> ORGANISM: Rattus norvegicus

<400> SEQUENCE: 447
ccggcuguga guaauucuuu ggcagugucu uagcugguug uugugaguau uagcuaagga     60
agcaaucagc aaguauacug cccuagaagu gcugcacguu gu                        102

<210> SEQ ID NO 448
<211> LENGTH: 78
<212> TYPE: RNA
<213> ORGANISM: Rattus norvegicus

<400> SEQUENCE: 448
cuuucuacac agguugggau uugucgcaau gcuguguuuc uguauaguau ugcacuuguc     60
ccggccuguu gaguuugg                                                   78

<210> SEQ ID NO 449
<211> LENGTH: 92
<212> TYPE: RNA
<213> ORGANISM: Rattus norvegicus

<400> SEQUENCE: 449
ugcccauuca uccacaggug gggauuagug ccauuacuug uguagauaa aaaguauugc      60 acuugucccg gccugaggaa gaaaagaggg uu                                   92

<210> SEQ ID NO 450
<211> LENGTH: 87
<212> TYPE: RNA
<213> ORGANISM: Rattus norvegicus

<400> SEQUENCE: 450
agucaugggg gcuccaaagu gcuguucgug caggaguguc auugccugac cuacugcuga     60
gcuagcacuu cccgagccccc caggaca                                        87

```
<210> SEQ ID NO 451
<211> LENGTH: 106
<212> TYPE: RNA
<213> ORGANISM: Rattus norvegicus

<400> SEQUENCE: 451
ccaguaccau cugcuuggcc gauuuuggca cuagcacauu uuugcuugug ucucuccgcu      60
cugagcaauc augugcagug ccaauauggg aaaagcgggc ugcugc                    106

<210> SEQ ID NO 452
<211> LENGTH: 80
<212> TYPE: RNA
<213> ORGANISM: Rattus norvegicus

<400> SEQUENCE: 452
gugagguagu aaguuguauu guguggggu agggauuuua ggccccaaua agaagauaac       60
uauacaacuu acuacuuucc                                                  80

<210> SEQ ID NO 453
<211> LENGTH: 81
<212> TYPE: RNA
<213> ORGANISM: Rattus norvegicus

<400> SEQUENCE: 453
cccauuggca uaaacccgua gauccgaucu uguggugaag uggaccgcac aagcucguuu      60
cuaugggucu guggcagugu g                                                81

<210> SEQ ID NO 454
<211> LENGTH: 70
<212> TYPE: RNA
<213> ORGANISM: Rattus norvegicus

<400> SEQUENCE: 454 ggcaccccacc cguagaaccg accuugcggg gccuucgccg cacacaagcu cgucucugug    60
gguccguguc                                                             70

<210> SEQ ID NO 455
<211> LENGTH: 80
<212> TYPE: RNA
<213> ORGANISM: Rattus norvegicus

<400> SEQUENCE: 455
ccuguugcca caaacccgua gauccgaacu ugugcugacc augcacacaa gcuugugucu      60
auagguaugu gucuguuagg                                                  80

<210> SEQ ID NO 456
<211> LENGTH: 97
<212> TYPE: RNA
<213> ORGANISM: Rattus norvegicus

<400> SEQUENCE: 456
aucugagacu gaacuguccu uuuucgguua ucaugguacc gaugcuguag aucugaaagg      60
uacaguacug ugauagcuga agaauggugg ugccauc                               97

<210> SEQ ID NO 457
<211> LENGTH: 75
<212> TYPE: RNA
<213> ORGANISM: Rattus norvegicus

<400> SEQUENCE: 457
```
ugcccuggcu caguuaucac agugcugaug cguccauuc uaaagguaca guacugugau    60
aacugaagga uggca    75

<210> SEQ ID NO 458
<211> LENGTH: 86
<212> TYPE: RNA
<213> ORGANISM: Rattus norvegicus

<400> SEQUENCE: 458
gucuucgugc uuucagcuuc uuuacagugc ugccuguag cauucagguc aagcagcauu    60
guacagggcu augaaagaac caagaa    86

<210> SEQ ID NO 459
<211> LENGTH: 86
<212> TYPE: RNA
<213> ORGANISM: Rattus norvegicus

<400> SEQUENCE: 459
uucuuacugc ccucggcuuc uuuacagugc ugccuguug cauuggauc aagcagcauu    60 guacagggcu augaaggcau ugagac    86

<210> SEQ ID NO 460
<211> LENGTH: 82
<212> TYPE: RNA
<213> ORGANISM: Rattus norvegicus

<400> SEQUENCE: 460
ccugcuggga cuaaagugcu gacagugcag auaguggucc ucucugugcu accgcacugu    60
ggguacuugc ugcuccagca gg    82

<210> SEQ ID NO 461
<211> LENGTH: 87
<212> TYPE: RNA
<213> ORGANISM: Rattus norvegicus

<400> SEQUENCE: 461
uucucucugc uuuaagcuuc uuuacagugu gccuugugg cauggaguuc aagcagcauu    60
guacagggcu aucaaagcac agagagc    87

<210> SEQ ID NO 462
<211> LENGTH: 85
<212> TYPE: RNA
<213> ORGANISM: Rattus norvegicus

<400> SEQUENCE: 462
ccuuagcaga gcucuggagu gugacaaugg uguuuguguc caaaacauca aacgccauca    60
ucacacuaaa cagcuacugc uaggc    85

<210> SEQ ID NO 463
<211> LENGTH: 87
<212> TYPE: RNA
<213> ORGANISM: Rattus norvegicus

<400> SEQUENCE: 463
ugagggcccc ucugcguguu cacagcggac cuugauuuaa ugucuauaca auuaaggcac    60
gcggugaaug ccaagagagg cgccucc    87

<210> SEQ ID NO 464

```
<211> LENGTH: 85
<212> TYPE: RNA
<213> ORGANISM: Rattus norvegicus

<400> SEQUENCE: 464
aggccucucu cuccguguuc acagcggacc uugauuuaaa ugccauaca auuaaggcac      60 gcggugaaug ccaagaaugg ggcug                                          85

<210> SEQ ID NO 465
<211> LENGTH: 109
<212> TYPE: RNA
<213> ORGANISM: Rattus norvegicus

<400> SEQUENCE: 465
aucaagauca gagacucugc ucccguguu cacagcggac cuugauuuaa ugcauacaa       60 uuaaggcacg cggugaaugc caagagcgga gccuacggcu gcacuugaa                109

<210> SEQ ID NO 466
<211> LENGTH: 85
<212> TYPE: RNA
<213> ORGANISM: Rattus norvegicus

<400> SEQUENCE: 466
ugccggccuc ugggucccug agacccuuua accgugagg acguccaggg ucacagguga     60
gguucuuggg agccggcgc cuggc                                           85

<210> SEQ ID NO 467
<211> LENGTH: 87
<212> TYPE: RNA
<213> ORGANISM: Rattus norvegicus

<400> SEQUENCE: 467
ugcgcucccc ucagucccug agacccuaac uugugauguu uaccguuuaa auccacgggu    60
uaggcucuug ggagcugcga gucgugc                                        87

<210> SEQ ID NO 468
<211> LENGTH: 88
<212> TYPE: RNA
<213> ORGANISM: Rattus norvegicus

<400> SEQUENCE: 468
accagacuuu uccuagucccc ugagacccua acuugugagg uauuuuagua acaucacaag    60
ucaggcucuu gggaccuagg cggagagg                                        88

<210> SEQ ID NO 469
<211> LENGTH: 73
<212> TYPE: RNA
<213> ORGANISM: Rattus norvegicus

<400> SEQUENCE: 469
ugacagcaca uuauuacuuu ugguacgcgc ugugacacuu caaacucgua ccgugaguaa     60
uaaugcgugg uca                                                        73

<210> SEQ ID NO 470
<211> LENGTH: 97
<212> TYPE: RNA
<213> ORGANISM: Rattus norvegicus

<400> SEQUENCE: 470
uuugaucacu gucuccagcc ugcugaagcu cagagggcuc ugauucagaa agaucaucgg    60
```
auccgucuga gcuuggcugg ucggaagucu caucauc                                    97

<210> SEQ ID NO 471
<211> LENGTH: 82
<212> TYPE: RNA
<213> ORGANISM: Rattus norvegicus

<400> SEQUENCE: 471
ugagcuguug gauucggggc cguagcacug ucugagaggu uuacauuucu cacagugaac           60
cggucucuuu uucagcugcu uc                                                    82

<210> SEQ ID NO 472
<211> LENGTH: 84
<212> TYPE: RNA
<213> ORGANISM: Rattus norvegicus

<400> SEQUENCE: 472
ugugcagugg aaggggggc cgaugcacug uaagagagug aguagcaggu cucacaguga            60
accggucucu uucccuacug uguc                                                  84

<210> SEQ ID NO 473
<211> LENGTH: 97
<212> TYPE: RNA
<213> ORGANISM: Rattus norvegicus

<400> SEQUENCE: 473
agacugcccu ucgcgaaucu uuuugcgguc ugggcuugcu guacauaacu caauagccgg           60
aagcccuuac cccaaaaagc auucgcggag ggcgcgc                                    97

<210> SEQ ID NO 474
<211> LENGTH: 72
<212> TYPE: RNA
<213> ORGANISM: Rattus norvegicus

<400> SEQUENCE: 474
ugggucuuuu ugcggucugg gcuugcuguu cucuccacag uagucaggaa gcccuuaccc           60
caaaaaguau cu                                                               72

<210> SEQ ID NO 475
<211> LENGTH: 88
<212> TYPE: RNA
<213> ORGANISM: Rattus norvegicus

<400> SEQUENCE: 475
ugcugcuggc cggagcucuu uucacauugu gcuacugucu acacguguac cgagcagugc           60
aauguuaaaa gggcaucggc cuuguagu                                              88

<210> SEQ ID NO 476
<211> LENGTH: 82
<212> TYPE: RNA
<213> ORGANISM: Rattus norvegicus

<400> SEQUENCE: 476
ggcuugcugg acacucuuuc ccuguugcac uacugugggc cucugggaag cagugcaaug           60
augaaagggc auccgucagg cc                                                    82

<210> SEQ ID NO 477
<211> LENGTH: 101
<212> TYPE: RNA

<213> ORGANISM: Rattus norvegicus

<400> SEQUENCE: 477
ccgcccccgc gucuccaggg caaccguggc uuucgauugu acugugggg accggaggua    60 acagucuaca gccauggucg ccccgcagca cgcccacgcu c    101

<210> SEQ ID NO 478
<211> LENGTH: 87
<212> TYPE: RNA
<213> ORGANISM: Rattus norvegicus

<400> SEQUENCE: 478
caaugcuuug cuaaagcugg uaaaauggaa ccaaaucgcc ucuucaaugg auuggucc    60 cuucaaccag cuguagcuau gcauuga    87

<210> SEQ ID NO 479
<211> LENGTH: 73
<212> TYPE: RNA
<213> ORGANISM: Rattus norvegicus

<400> SEQUENCE: 479
cagggugugu gacugguuga ccagagggc gugcacuuug uucacccugu gggccaccua    60
gucaccaacc cuc    73

<210> SEQ ID NO 480
<211> LENGTH: 97
<212> TYPE: RNA
<213> ORGANISM: Rattus norvegicus

<400> SEQUENCE: 480
cgcucugcug uggccuaugg cuuuucauuc cuaugugauu gcuguccga acucauguag    60 ggcuaaaagc caugggcuac agugaggggc aagcucc    97

<210> SEQ ID NO 481
<211> LENGTH: 100
<212> TYPE: RNA
<213> ORGANISM: Rattus norvegicus

<400> SEQUENCE: 481
agauaaauuc acucuagugc uuuauggcuu uuuauuccua ugugaucgua auaaagcuc    60 auguagggau ggaagccaug aaauacauug ugaaaauuca    100

<210> SEQ ID NO 482
<211> LENGTH: 82
<212> TYPE: RNA
<213> ORGANISM: Rattus norvegicus

<400> SEQUENCE: 482
ugagcccucg gaggacucca uuuguuuuga ugauggauuc uuaagcucca ucaucgucuc    60
aaaugagucu ucagaggguu cu    82

<210> SEQ ID NO 483
<211> LENGTH: 102
<212> TYPE: RNA
<213> ORGANISM: Rattus norvegicus

<400> SEQUENCE: 483
ggcccucuga cucucuucgg ugacggguau ucuuggugg auaauacgga uuacguuguu    60
auugcuuaag aauacgcgua gucgaggaga guaccagcgg ca    102

<210> SEQ ID NO 484
<211> LENGTH: 82
<212> TYPE: RNA
<213> ORGANISM: Rattus norvegicus

<400> SEQUENCE: 484
guugcugcag cuggguguugu gaaucaggcc gacgagcaac gcauccucuu acccggcuau    60
uucacgacac caggguugca cc    82

<210> SEQ ID NO 485
<211> LENGTH: 99
<212> TYPE: RNA
<213> ORGANISM: Rattus norvegicus

<400> SEQUENCE: 485
cucuggcaug guguuguggg acagcuggug uugugaauca ggccguugcc aaucagagaa    60
cggcuacuuc acaacaccag ggucucacug cacugcagg    99

<210> SEQ ID NO 486
<211> LENGTH: 68
<212> TYPE: RNA
<213> ORGANISM: Rattus norvegicus

<400> SEQUENCE: 486
guguauucua cagugcacgu gucccagug uggcucggag gcuggagacg cggcccuguu    60
ggaguaac    68

<210> SEQ ID NO 487
<211> LENGTH: 99
<212> TYPE: RNA
<213> ORGANISM: Rattus norvegicus

<400> SEQUENCE: 487
gugucucucu cuguguccug ccagugguuu uacccuaugg uagguuacau caugcuguuc    60
uaccacaggg uagaaccacg gacaggauac uggagcacc    99

<210> SEQ ID NO 488
<211> LENGTH: 94
<212> TYPE: RNA
<213> ORGANISM: Rattus norvegicus

<400> SEQUENCE: 488
ggcugacucu gaguccaucu uccagugcag uguuggaugg uugaaguacg aagcuccuaa    60
cacugucugg uaaagauggc ccccgggucA guuc    94

<210> SEQ ID NO 489
<211> LENGTH: 87
<212> TYPE: RNA
<213> ORGANISM: Rattus norvegicus

<400> SEQUENCE: 489
gacagugcag ucacccauaa aguagaaagc acuacuaaca gcacuggagg guguagguguu    60 uccuacuuua uggaugagug uacugug    87

<210> SEQ ID NO 490
<211> LENGTH: 105
<212> TYPE: RNA
<213> ORGANISM: Rattus norvegicus

<400> SEQUENCE: 490
gcggagcgcc ugucucccag ccugaggugc agugcugcau cucuggucag uugggagucu    60
gagaugaagc acuguagcuc aggaagggag aagauguucu gcagc                  105

<210> SEQ ID NO 491
<211> LENGTH: 83
<212> TYPE: RNA
<213> ORGANISM: Rattus norvegicus

<400> SEQUENCE: 491 gggccuugc ugggauauca ucauauacug uaaguuugug augagacacu acaguauaga    60
ugauguacua gucugggac ccc                                            83

<210> SEQ ID NO 492
<211> LENGTH: 88
<212> TYPE: RNA
<213> ORGANISM: Rattus norvegicus

<400> SEQUENCE: 492
caccuugucc ucacggucca guuucccag gaaucccuug gaugcuaaga uggggauucc    60
uggaaauacu guucuugagg ucauggcu                                      88

<210> SEQ ID NO 493
<211> LENGTH: 95
<212> TYPE: RNA
<213> ORGANISM: Rattus norvegicus

<400> SEQUENCE: 493
uguguauccu cagcucugag aacugaauuc caugggu uau agcaauguca gaccugugaa    60
guucaguucu uuagcuggga uagcucuauc gucau                              95

<210> SEQ ID NO 494
<211> LENGTH: 97
<212> TYPE: RNA
<213> ORGANISM: Rattus norvegicus

<400> SEQUENCE: 494
caggcacucu uagcauuuga ggugaaguuc uguuauacac ucaggcugug gcucugaaag    60
ucagugcauc acagaacuuu gucucgaaag cuuucua                            97

<210> SEQ ID NO 495
<211> LENGTH: 85
<212> TYPE: RNA
<213> ORGANISM: Rattus norvegicus

<400> SEQUENCE: 495
cuucucaagg cccugucucc caacccuugu accagugcug ugccucagac ccugguacag    60
gccuggggga cagggacuug gggac                                         85

<210> SEQ ID NO 496
<211> LENGTH: 97
<212> TYPE: RNA
<213> ORGANISM: Rattus norvegicus

<400> SEQUENCE: 496
agcgcuuucc ugcccucgag gagcucacag ucuaguaugu cuccucccua cuagacugag    60
gcuccuugag gacagggauc gucauacuca ccucccg                            97

```
<210> SEQ ID NO 497
<211> LENGTH: 85
<212> TYPE: RNA
<213> ORGANISM: Rattus norvegicus

<400> SEQUENCE: 497 uguucccgg  gcccagguuc  ugugauacac  uccgacucgg  gcucuggagc  agucagugca    60
ugacagaacu  ugggcccggu  aggac                                            85

<210> SEQ ID NO 498
<211> LENGTH: 87
<212> TYPE: RNA
<213> ORGANISM: Rattus norvegicus

<400> SEQUENCE: 498
agcgguggcc  agugucauuu  uugugauguu  gcagcuagua  auaugagccc  aguugcauag    60
ucacaaaagu  gaucauugga  aacugug                                          87

<210> SEQ ID NO 499
<211> LENGTH: 84
<212> TYPE: RNA
<213> ORGANISM: Rattus norvegicus

<400> SEQUENCE: 499
gcggugcuug  aagauagguu  auccguguug  ccuucgcuuu  auucgugacg  aaucauacac    60
gguugaccua  uuuucagua  ccaa                                              84

<210> SEQ ID NO 500
<211> LENGTH: 106
<212> TYPE: RNA
<213> ORGANISM: Rattus norvegicus

<400> SEQUENCE: 500
agaacuugcc  aaggguuugg  gggaacauuc  aaccugucgg  ugaguuuggg  cagcucagac    60
aaaccaucga  ccguugagug  gaccccgagg  ccuggaacug  ccaccc                   106

<210> SEQ ID NO 501
<211> LENGTH: 117
<212> TYPE: RNA
<213> ORGANISM: Rattus norvegicus

<400> SEQUENCE: 501
agaugggcaa  ccaaggcagc  cuuaagagga  cuccauggaa  cauucaacgc  ugucggugag    60
uuugggauuc  aaaaacaaaa  aaaaccacca  accguugacu  guaccuuggg  auucuua     117

<210> SEQ ID NO 502
<211> LENGTH: 110
<212> TYPE: RNA
<213> ORGANISM: Rattus norvegicus

<400> SEQUENCE: 502
ccugugcaga  gaugauguuu  acaaagguca  caaucaacau  ucauugcugu  cgguggguug    60
aacuguguag  aaaagcucac  ugaacaauga  augcaacugu  ggccccgcuu              110

<210> SEQ ID NO 503
<211> LENGTH: 88
<212> TYPE: RNA
<213> ORGANISM: Rattus norvegicus

<400> SEQUENCE: 503
```

```
ugauggcugc acucaacauu cauugcuguc ggugggu uug aaugucaacc aacucacugg    60
ucaaugaaug caaacugcgg gccaaaaa                                       88

<210> SEQ ID NO 504
<211> LENGTH: 110
<212> TYPE: RNA
<213> ORGANISM: Rattus norvegicus

<400> SEQUENCE: 504
ccagagagug ugacuccugu ccuguguaug gcacugguag aauucacugu gaacagucuc    60
ggucagugaa uuaccgaagg gccauaaaca gagcagagac agauccgcga              110

<210> SEQ ID NO 505
<211> LENGTH: 77
<212> TYPE: RNA
<213> ORGANISM: Rattus norvegicus

<400> SEQUENCE: 505
cacuuucccu uaucaguuuu ccagccagcu uugugacugu aaauguugga cggagaacug    60
auaaggguaa gugacug                                                  77

<210> SEQ ID NO 506
<211> LENGTH: 80
<212> TYPE: RNA
<213> ORGANISM: Rattus norvegicus

<400> SEQUENCE: 506
gggggugagg gauuggagag aaaggcaguu ccugaugguc cccucccagg ggcuggcuuu    60 ccucggucc uucucuccca                                                80

<210> SEQ ID NO 507
<211> LENGTH: 86
<212> TYPE: RNA
<213> ORGANISM: Rattus norvegicus

<400> SEQUENCE: 507
ugcuuacaac uuuccaaaga auucuccuuu ugggcuuucu cauuuuauuu uaagcccaaa    60
ggugaauuuu uugggaaguu ugagcu                                        86

<210> SEQ ID NO 508
<211> LENGTH: 104
<212> TYPE: RNA
<213> ORGANISM: Rattus norvegicus

<400> SEQUENCE: 508
gggcucacag gacacaaugc ggauccucag gcuacaacac aggacccggg cgcugcucug    60
accccucgug ucuuguguug cagccggagg gacgcaagguc ugca                   104

<210> SEQ ID NO 509
<211> LENGTH: 85
<212> TYPE: RNA
<213> ORGANISM: Rattus norvegicus

<400> SEQUENCE: 509
ugcaggccuc ugugugauau guuugauaua uuagguuguu auuuaaucca acuauauauc    60
aagcauauuc cuacaguguc uugcc                                         85

<210> SEQ ID NO 510
<211> LENGTH: 91
```

```
<212> TYPE: RNA
<213> ORGANISM: Rattus norvegicus

<400> SEQUENCE: 510
ggcuggacag cgggcaacgg aaucccaaaa gcagcuguug ucuccagagc auuccagcug    60
cacuuggauu ucguucccug cucuccugcc u                                  91

<210> SEQ ID NO 511
<211> LENGTH: 110
<212> TYPE: RNA
<213> ORGANISM: Rattus norvegicus

<400> SEQUENCE: 511
gucaagaugg agugcacagg gcucugaccu augaauugac agccaguacu cugaucucgc    60
cucuggcugc caguuccaua ggucacaggu auguucgccu caaugccagc               110

<210> SEQ ID NO 512
<211> LENGTH: 86
<212> TYPE: RNA
<213> ORGANISM: Rattus norvegicus

<400> SEQUENCE: 512
gcggacggga gcugagagcu gggucuuugc gggcaagaug aggguguncag uucaacuggc    60 cuacaaaguc ccaguccucg gcuccc                                        86

<210> SEQ ID NO 513
<211> LENGTH: 83
<212> TYPE: RNA
<213> ORGANISM: Rattus norvegicus

<400> SEQUENCE: 513
auggagucau cacguguaac agcaaccucca ugggacugu gcacagaucc caguggagcu    60
gcuguuacuu uugauggccu cca                                           83

<210> SEQ ID NO 514
<211> LENGTH: 85
<212> TYPE: RNA
<213> ORGANISM: Rattus norvegicus

<400> SEQUENCE: 514
uggcucccac ccccuguaac agcaaccuca ugggaagug cccacugauu ccagggggc     60 ugcuguuauc uggggugagg gcugg                                         85

<210> SEQ ID NO 515
<211> LENGTH: 87
<212> TYPE: RNA
<213> ORGANISM: Rattus norvegicus

<400> SEQUENCE: 515
aacucuccug gcucuagcag cacagaaaua uuggcacggg uaagugaguc ugccaauauu   60
ggcugugcug cuccaggcag gguggug                                       87

<210> SEQ ID NO 516
<211> LENGTH: 110
<212> TYPE: RNA
<213> ORGANISM: Rattus norvegicus

<400> SEQUENCE: 516
uguuugcuca gcugaucugu ggcuuaggua guuucauguu guugggauug aguuuugaac   60
```
ucggcaacaa gaaacugccu gaguuacauc agucgguuuu cgucgagggc    110

<210> SEQ ID NO 517
<211> LENGTH: 110
<212> TYPE: RNA
<213> ORGANISM: Rattus norvegicus

<400> SEQUENCE: 517
uggaagcuuc uggagauccu gcuccgucgc cccaguguuc agacuaccug uucaggacaa    60
ugccguugua caguagucug cacauugguu agacugggca agggccagca    110

<210> SEQ ID NO 518
<211> LENGTH: 69
<212> TYPE: RNA
<213> ORGANISM: Rattus norvegicus

<400> SEQUENCE: 518
cccucgucuu acccagcagu guuugggugc ugguugggag ucucuaauac ugccggguaa    60
ugauggagg    69

<210> SEQ ID NO 519
<211> LENGTH: 89
<212> TYPE: RNA
<213> ORGANISM: Rattus norvegicus

<400> SEQUENCE: 519
cugggccucu gugggcaucu uaccggacag ugcuggauuu cuuggcuuga cucuaacacu    60
gucugguaac gauguucaaa ggugaccca    89

<210> SEQ ID NO 520
<211> LENGTH: 95
<212> TYPE: RNA
<213> ORGANISM: Rattus norvegicus

<400> SEQUENCE: 520
ccaacuuggg cagccguggc caucuuacug ggcagcauug gauagugucu gaucucuaau    60
acugccuggu aaugaugacg gcggagcccu gcacg    95

<210> SEQ ID NO 521
<211> LENGTH: 97
<212> TYPE: RNA
<213> ORGANISM: Rattus norvegicus

<400> SEQUENCE: 521
gcgcgccugg uccagugguu cuuaacaguu caacaguucu guagcgcaau ugugaaaugu    60
uuaggaccac uagacccggc gcgcacggca gcggcga    97

<210> SEQ ID NO 522
<211> LENGTH: 110
<212> TYPE: RNA
<213> ORGANISM: Rattus norvegicus

<400> SEQUENCE: 522
ggcuacagcc cuucuucaug ugacucgugg acuuccccuuu gucauccuau gccugagaau    60
auaugaagga ggcugggaag gcaaagggac guucaauugu caucacuggc    110

<210> SEQ ID NO 523
<211> LENGTH: 108
<212> TYPE: RNA
<213> ORGANISM: Rattus norvegicus

<400> SEQUENCE: 523
aaacagcccc agacaaucca ugggguccucc uguccuucau uccaccggag ucugucuuau    60
gccaaccaga uuucagugga gugaagcuca ggaggcaugg agcugcca                 108

<210> SEQ ID NO 524
<211> LENGTH: 84
<212> TYPE: RNA
<213> ORGANISM: Rattus norvegicus

<400> SEQUENCE: 524
cuuccccagg ccacaugcuu cuuuauaucc ucauagauau cacugcgcua uggaauguaa    60
ggaagugugu gguuuuggca agug                                           84

<210> SEQ ID NO 525
<211> LENGTH: 83
<212> TYPE: RNA
<213> ORGANISM: Rattus norvegicus

<400> SEQUENCE: 525
uuccuuugac gggugagcuu uuggcccggg uuauaccuga cucucacgua uaagacgagc    60
aaaaagcuug uuggucagag gag                                            83

<210> SEQ ID NO 526
<211> LENGTH: 110
<212> TYPE: RNA
<213> ORGANISM: Rattus norvegicus

<400> SEQUENCE: 526
ccggggcagu ccuccaggc ucaggacagc cacugcccac agcacacugc guugcuccgg     60
acccacugug cgugugacag cggcugaucu gucccugggc agcgcgaacc              110

<210> SEQ ID NO 527
<211> LENGTH: 106
<212> TYPE: RNA
<213> ORGANISM: Rattus norvegicus

<400> SEQUENCE: 527
cagcuuggac cugugaccuc ugggcuuccc uuugucaucc uuugccuagg ccucugagug    60
gggcaaggac agcaaagggg ggcucagugg ucaccucuac ugcaga                  106

<210> SEQ ID NO 528
<211> LENGTH: 111
<212> TYPE: RNA
<213> ORGANISM: Rattus norvegicus

<400> SEQUENCE: 528
cgggauaucc ccgcccgggc agcgcgccgg caccuuggcu cuagacugcu uacugcccgg    60
gccgcccuca guaacagucu ccagucacgg ccaccgacgc cuggccccgc c            111

<210> SEQ ID NO 529
<211> LENGTH: 100
<212> TYPE: RNA
<213> ORGANISM: Rattus norvegicus

<400> SEQUENCE: 529
agguugcuuc agugaacauu caacgcuguc ggugaguuug gaauucaaau aaaaaccauc    60
gaccguugau uguacccuau agcuaaccau uaucuacucc                         100

```
<210> SEQ ID NO 530
<211> LENGTH: 110
<212> TYPE: RNA
<213> ORGANISM: Rattus norvegicus

<400> SEQUENCE: 530
guccuggaug gacagaguug ucaugugucu gccugucuac acuugcugug cagaacaucc       60
gcucaccugu acagcaggca cagacaggca gucacaugac aacccagccu                 110

<210> SEQ ID NO 531
<211> LENGTH: 106
<212> TYPE: RNA
<213> ORGANISM: Rattus norvegicus

<400> SEQUENCE: 531
guuagcuaug aguuaguuua aucucagcug gcaacuguga gauguccua ucauuccuca        60 caguggucuc ugggauuaug cuaaacagag caauuccuu gaccuc                      106

<210> SEQ ID NO 532
<211> LENGTH: 105
<212> TYPE: RNA
<213> ORGANISM: Rattus norvegicus

<400> SEQUENCE: 532
accacaguca uuguaguuuu gaugucgcag auacugcauc aggaacugac uggauaagac       60
ucagucacca ucaguuccua augcauugcc uucagcaucu aaaca                      105

<210> SEQ ID NO 533
<211> LENGTH: 110
<212> TYPE: RNA
<213> ORGANISM: Rattus norvegicus

<400> SEQUENCE: 533
gaccaguugc cgcggggcuu uccuuugugc uugaucuaac caugguggg aacgauggaa        60 acggaacaug guucugucaa gcaccgcgga aagcaucgcu cucuccugca                 110

<210> SEQ ID NO 534
<211> LENGTH: 110
<212> TYPE: RNA
<213> ORGANISM: Rattus norvegicus

<400> SEQUENCE: 534
gugauaacgu agcgagauuu ucuguugugc uugaucuaac caugugcuug cgagguauga      60
guaaaacaug guuccgucaa gcaccaugga acgucacgca gcuuucuaca                 110

<210> SEQ ID NO 535
<211> LENGTH: 110
<212> TYPE: RNA
<213> ORGANISM: Rattus norvegicus

<400> SEQUENCE: 535
cugucccggg ccgcggcucc ugauugucca aacgcaauuc ucgagucucu ggcuccggcc       60
gagaguugcg ucuggacguc ccgagccgcc gcccccaaac cucgagggg                  110

<210> SEQ ID NO 536
<211> LENGTH: 96
<212> TYPE: RNA
<213> ORGANISM: Rattus norvegicus

<400> SEQUENCE: 536
```

```
acucagggc uucaccacug auuguccaaa cgcaauucuu guacgagucu gcggccaacc    60
gagaauugug gcuggacauc uggguugag cuccgg                              96

<210> SEQ ID NO 537
<211> LENGTH: 109
<212> TYPE: RNA
<213> ORGANISM: Rattus norvegicus

<400> SEQUENCE: 537
ugaauaucca ggucuggggc augaaccugg cauacaaugu agauuucugu guuuguuagg    60
caacagcuac auugucugcu ggguucagg cuaccuggaa gcauuucuc                109

<210> SEQ ID NO 538
<211> LENGTH: 103
<212> TYPE: RNA
<213> ORGANISM: Rattus norvegicus

<400> SEQUENCE: 538
aaggauuagg gugcccucag uggcucagua gccaguguag auccugucuu ugguaaucag    60
cagcuacauc uggcuacugg gucucugaug gcaucaucua gcu                    103

<210> SEQ ID NO 539
<211> LENGTH: 110
<212> TYPE: RNA
<213> ORGANISM: Rattus norvegicus

<400> SEQUENCE: 539
ucuggccuuc ugcaguguua cgcuccgugu auuugacaag cugaguugga cacucugugu    60
gguagagugu caguuuguca aauacccaa guguggcuca ugcuuaucag               110

<210> SEQ ID NO 540
<211> LENGTH: 81
<212> TYPE: RNA
<213> ORGANISM: Rattus norvegicus

<400> SEQUENCE: 540
ucaucuugcg guucucaaac auggggca cuuuuuuuu cuuuaaaaag ugccgccagg      60
uuuuagggcc ugccgguuga g                                             81

<210> SEQ ID NO 541
<211> LENGTH: 82
<212> TYPE: RNA
<213> ORGANISM: Rattus norvegicus

<400> SEQUENCE: 541 ccggguagu agccaucaaa guggaggccc ucucuggc ccgagcuaga aagugcuucc      60
acuuugugug ccacugcaug gg                                            82

<210> SEQ ID NO 542
<211> LENGTH: 82
<212> TYPE: RNA
<213> ORGANISM: Rattus norvegicus

<400> SEQUENCE: 542
caaccuguga uacucaaacu gggggcucuu uuggguuuuc uuuggaagaa aagugccgcc    60
agguuuugag uguuaccgau ug                                            82

<210> SEQ ID NO 543
```

```
<211> LENGTH: 78
<212> TYPE: RNA
<213> ORGANISM: Rattus norvegicus

<400> SEQUENCE: 543
ggaccuuucu ggagggcccc cccucaaucc uguugugcuc gcuucagagg guugggugga      60
ggcucuccug aaguguc                                                    78

<210> SEQ ID NO 544
<211> LENGTH: 68
<212> TYPE: RNA
<213> ORGANISM: Rattus norvegicus

<400> SEQUENCE: 544
uauguaugua uguauguaug uaugcaugua ugugcaug uaugcaugca ugcauguaug       60
uauguaug                                                              68

<210> SEQ ID NO 545
<211> LENGTH: 82
<212> TYPE: RNA
<213> ORGANISM: Rattus norvegicus

<400> SEQUENCE: 545
ccaggccuuc ggcagaggag ggcuguucuu cccugggguu uuaugacugg gaggaacuag      60
ccuucucucu gcuuaggagu gg                                              82

<210> SEQ ID NO 546
<211> LENGTH: 63
<212> TYPE: RNA
<213> ORGANISM: Rattus norvegicus

<400> SEQUENCE: 546
aagaaauggu uuaccguccc acauacauuu ugaguaugua ugugggacgg uaaaccgcuu      60
cuu                                                                   63

<210> SEQ ID NO 547
<211> LENGTH: 79
<212> TYPE: RNA
<213> ORGANISM: Rattus norvegicus

<400> SEQUENCE: 547
gcuacuugaa gagagguuau ccuuugugug uuugcuuuac gcgaaaugaa uaugcaaggg      60
caagcucucu ucgaggagc                                                  79

<210> SEQ ID NO 548
<211> LENGTH: 100
<212> TYPE: RNA
<213> ORGANISM: Rattus norvegicus

<400> SEQUENCE: 548
ccugcuggcu acugcugacg acugcucuga cuuuauugca cuacuguacu guacagcuag      60
cagugcaaua guauugucaa agcauccggg agcaggcuac                          100

<210> SEQ ID NO 549
<211> LENGTH: 82
<212> TYPE: RNA
<213> ORGANISM: Rattus norvegicus

<400> SEQUENCE: 549
gccucgcugu ccuccgccuu cucuucccgg uucuucccgg agcgggaaa agcugggung      60
```

```
agagggcgaa aaaggauaug gg                                              82

<210> SEQ ID NO 550
<211> LENGTH: 59
<212> TYPE: RNA
<213> ORGANISM: Rattus norvegicus

<400> SEQUENCE: 550
uuggccuccu aagccaggga uuguggguuc gagucccacc cggggugaaga gguuguguu    59

<210> SEQ ID NO 551
<211> LENGTH: 95
<212> TYPE: RNA
<213> ORGANISM: Rattus norvegicus

<400> SEQUENCE: 551
ccucgcugac uccgaaggga ugcagcagca auucauguuu uggaguauug ccaagguuca    60
aaacaugaag cgcugcaaca ccccuucgug ggaaa                               95

<210> SEQ ID NO 552
<211> LENGTH: 86
<212> TYPE: RNA
<213> ORGANISM: Rattus norvegicus

<400> SEQUENCE: 552
uugguacuug gagagaggug guccguggcg cguucgcuuc auuuauggcg cacauuacac    60
ggucgaccuc uuugcgguau cuaauc                                         86

<210> SEQ ID NO 553
<211> LENGTH: 83
<212> TYPE: RNA
<213> ORGANISM: Rattus norvegicus

<400> SEQUENCE: 553
cugacuaugc cuccucgcau ccccuagggc auugguguaa agcuggagac ccacugcccc    60
aggugcugcu gggggunguga guc                                           83

<210> SEQ ID NO 554
<211> LENGTH: 98
<212> TYPE: RNA
<213> ORGANISM: Rattus norvegicus

<400> SEQUENCE: 554
auauagugcu ugguuccuag uaggugcuca guaaguguuu ugacauaau ucguuuauug     60 agcaccuccu aucaaucaag cacugugcua ggcucugg                            98

<210> SEQ ID NO 555
<211> LENGTH: 95
<212> TYPE: RNA
<213> ORGANISM: Rattus norvegicus

<400> SEQUENCE: 555
cucaucuguc ugugggggcug ggggcagggc cuuugugaag gcggguuaug cucagaucgc   60
cucugggccc uuccuccagu cccgaggcag auuua                               95

<210> SEQ ID NO 556
<211> LENGTH: 84
<212> TYPE: RNA
<213> ORGANISM: Rattus norvegicus
```

```
<400> SEQUENCE: 556 ugggcaggg gggcaggagg ggcucaggga gaaagcaucu acagcccug gcccucucug    60 cccuccguc cccuguccc aaau                                          84

<210> SEQ ID NO 557
<211> LENGTH: 97
<212> TYPE: RNA
<213> ORGANISM: Rattus norvegicus

<400> SEQUENCE: 557
uguucgcuuc ugguaccgga agagagguuu ucgggucuc uguucuuug augagaauga    60 aacacaccca gcuaaccuuu uuuucaguau caaaucc                          97

<210> SEQ ID NO 558
<211> LENGTH: 97
<212> TYPE: RNA
<213> ORGANISM: Rattus norvegicus

<400> SEQUENCE: 558
acccuuuggc gaucucugcc ucucugggcc ugugucuuag gcucuucaag aucuaacgag   60
caaagcacag ggccugcaga gagguagcgc ucugcuc                          97

<210> SEQ ID NO 559
<211> LENGTH: 96
<212> TYPE: RNA
<213> ORGANISM: Rattus norvegicus

<400> SEQUENCE: 559
gagucugguc uuguuugggu uuguucuagg uauggcccca gggaucccag aucaaaccag   60
gccccugggc cuauccuaga accaaccuaa acccau                           96

<210> SEQ ID NO 560
<211> LENGTH: 95
<212> TYPE: RNA
<213> ORGANISM: Rattus norvegicus

<400> SEQUENCE: 560
ccccggugga accacguggu gugcuaguua cuuugggcu ggagagacgg cucagggguu    60
aagagcacag acugcucuuc cagagguccu gaguu                            95

<210> SEQ ID NO 561
<211> LENGTH: 96
<212> TYPE: RNA
<213> ORGANISM: Rattus norvegicus

<400> SEQUENCE: 561
augugaccgu gccucucacc cuuccauauc uagucucuga gaaaaaugaa gacuggauuc    60
caugaaggga ugugaggccu ggaaacugga gcuuua                           96

<210> SEQ ID NO 562
<211> LENGTH: 97
<212> TYPE: RNA
<213> ORGANISM: Rattus norvegicus

<400> SEQUENCE: 562
aguguaguga gaaguugggg ggugggaacg gcgucaugca ggaguugauu gcacagccau    60
ucagcuccua uaugaugccu uucuucaccc ccuucaa                          97
```

```
<210> SEQ ID NO 563
<211> LENGTH: 66
<212> TYPE: RNA
<213> ORGANISM: Rattus norvegicus

<400> SEQUENCE: 563
uccccaacaa uauccuggug cugaguggu gcacagugac uccagcauca gugauuuugu    60
ugaaga                                                              66

<210> SEQ ID NO 564
<211> LENGTH: 96
<212> TYPE: RNA
<213> ORGANISM: Rattus norvegicus

<400> SEQUENCE: 564
acggggugga caccgucccu guccuccagg agcucacgua ugccugccug ugagcgccuc    60
gacgacagag ccagagucca ccccugcacu gcccaa                             96

<210> SEQ ID NO 565
<211> LENGTH: 96
<212> TYPE: RNA
<213> ORGANISM: Rattus norvegicus

<400> SEQUENCE: 565
aaaaugauga ugucaguugg ccggucggcc gaucgcucgg ucugucaguc agucggucgg    60
ucgaucgguc ggucggucag ucggcuuccu gucuuc                             96

<210> SEQ ID NO 566
<211> LENGTH: 99
<212> TYPE: RNA
<213> ORGANISM: Rattus norvegicus

<400> SEQUENCE: 566
gaaaaugggc ucaaggugag gggugcuauc ugugauugag ggacaugguc aauggaauug    60
ucucacacag aaaucgcacc cgucaccuug gccugcuga                          99

<210> SEQ ID NO 567
<211> LENGTH: 98
<212> TYPE: RNA
<213> ORGANISM: Rattus norvegicus

<400> SEQUENCE: 567
cugcagccag aguuuuuacc agucaggcuc cuggcuagau uccagguacc aacugguacc    60
ugaucuagcc aaagccugac cguaagcugc aaaagaaa                           98

<210> SEQ ID NO 568
<211> LENGTH: 96
<212> TYPE: RNA
<213> ORGANISM: Rattus norvegicus

<400> SEQUENCE: 568
acccaagucc aggccugcug accccuaguc cagugcuugu gguggcuacu gggcccugaa    60
cuaggggucu ggagaccugg guuugaucuc cacagg                             96

<210> SEQ ID NO 569
<211> LENGTH: 98
<212> TYPE: RNA
<213> ORGANISM: Rattus norvegicus

<400> SEQUENCE: 569
```

```
ucuguguugg gcaucugucu gccugagugc cugccucucu guugcucuga aggaggcagg      60
ggcugggccu gcagcugccu gggcagagcu gcuccuuc                              98

<210> SEQ ID NO 570
<211> LENGTH: 97
<212> TYPE: RNA
<213> ORGANISM: Rattus norvegicus

<400> SEQUENCE: 570
gaagacucua gcauguaagg uuggggagg gggcuguguc uagcaagucu ucuuccccca       60
cagcccugcu gucuuaaccu cuagguguuc cggcucc                               97

<210> SEQ ID NO 571
<211> LENGTH: 99
<212> TYPE: RNA
<213> ORGANISM: Rattus norvegicus

<400> SEQUENCE: 571
agaugccuug cuccuacaag aguaaagugc acgugcuuug ggacagugag gaaaauaaug      60
uucacaaagc ccauacacuu ucacccuuua ggagaguug                             99

<210> SEQ ID NO 572
<211> LENGTH: 81
<212> TYPE: RNA
<213> ORGANISM: Rattus norvegicus

<400> SEQUENCE: 572
cauggcaccu ccauuucccu gaggagcccu uugagccuga ggugaaaaaa aaacagguca     60
agaggcgccu gggaacugga g                                                81

<210> SEQ ID NO 573
<211> LENGTH: 98
<212> TYPE: RNA
<213> ORGANISM: Homo sapiens

<400> SEQUENCE: 573
acccaaaccc uaggucugcu gacuccuagu ccagggcucg ugauggcugg ugggcccuga      60
acgagggguc uggaggccug gguuugaaua ucgacagc                              98

<210> SEQ ID NO 574
<211> LENGTH: 86
<212> TYPE: RNA
<213> ORGANISM: Homo sapiens

<400> SEQUENCE: 574
gucugucugc ccgcaugccu gcccucucugu ugcucugaag gaggcagggg cugggccugc    60
agcugccugg gcagagcggc uccugc                                           86

<210> SEQ ID NO 575
<211> LENGTH: 68
<212> TYPE: RNA
<213> ORGANISM: Homo sapiens

<400> SEQUENCE: 575
ccauuacugu ugcuaauaug caacucuguu gaauauaaau uggaauugca cuuuagcaau     60
ggugaugg                                                               68

<210> SEQ ID NO 576
<211> LENGTH: 66
```

```
<212> TYPE: RNA
<213> ORGANISM: Homo sapiens

<400> SEQUENCE: 576
aaaaggugga uauuccuucu auguuuaugu uauuuauggu uaaacauaga ggaaauucca    60
cguuuu                                                              66

<210> SEQ ID NO 577
<211> LENGTH: 70
<212> TYPE: RNA
<213> ORGANISM: Homo sapiens

<400> SEQUENCE: 577
uugaagggag aucgaccgug uuauauucgc uuuauugacu ucgaauaaua cagguugau    60 cuuuucucag                                                          70

<210> SEQ ID NO 578
<211> LENGTH: 75
<212> TYPE: RNA
<213> ORGANISM: Homo sapiens

<400> SEQUENCE: 578
agacagagaa gccaggucac gucucugcag uuacacagcu cacgagugcc ugcuggggug    60
gaaccugguc ugucu                                                    75

<210> SEQ ID NO 579
<211> LENGTH: 67
<212> TYPE: RNA
<213> ORGANISM: Homo sapiens

<400> SEQUENCE: 579
guggcacuca aacugugggg gcacuuucug cucucuggug aaagugccgc caucuuuga    60 guguuac                                                             67

<210> SEQ ID NO 580
<211> LENGTH: 67
<212> TYPE: RNA
<213> ORGANISM: Homo sapiens

<400> SEQUENCE: 580
gugggccuca aauguggagc acuauucuga uguccaagug gaaagugcug cgacauuuga    60
gcgucac                                                             67

<210> SEQ ID NO 581
<211> LENGTH: 69
<212> TYPE: RNA
<213> ORGANISM: Homo sapiens

<400> SEQUENCE: 581
gggauacuca aauggggggc gcuuuccuuu uugucuguac ugggaagugc uucgauuuug    60 gggugsccc                                                           69

<210> SEQ ID NO 582
<211> LENGTH: 72
<212> TYPE: RNA
<213> ORGANISM: Homo sapiens

<400> SEQUENCE: 582
uacaucggcc auuauaauac aaccugauaa guguuauagc acuuaucaga uuguauugua    60
```

-continued

```
auugucugug ua                                                72

<210> SEQ ID NO 583
<211> LENGTH: 99
<212> TYPE: RNA
<213> ORGANISM: Mus musculus

<400> SEQUENCE: 583
cauggcaccu ccguuucccu gaggagcccu uugagccugg agugaaaaaa aaaaacaggu    60
caagaggcgc cugggaacug gagaagagug uuaaacuuc                          99

<210> SEQ ID NO 584
<211> LENGTH: 79
<212> TYPE: RNA
<213> ORGANISM: Mus musculus

<400> SEQUENCE: 584
agacggagag accaggucac gucucugcag uuacacagcu caugagugcc ugcuggggug    60
gaaccugguu ugucugucu                                                79

<210> SEQ ID NO 585
<211> LENGTH: 68
<212> TYPE: RNA
<213> ORGANISM: Mus musculus

<400> SEQUENCE: 585
uaaaagguag auucuccuuc uaugaguaca auauuaauga cuaaucguag aggaaaaucc    60
acguuuuc                                                            68

<210> SEQ ID NO 586
<211> LENGTH: 82
<212> TYPE: RNA
<213> ORGANISM: Mus musculus

<400> SEQUENCE: 586
ugguauuuaa aagguggaua uuccuucuau gguuacgugc uuccuggaua aucauagagg    60
aacauccacu uuuucaguau ca                                            82

<210> SEQ ID NO 587
<211> LENGTH: 61
<212> TYPE: RNA
<213> ORGANISM: Mus musculus

<400> SEQUENCE: 587 aagagguug accauagaac augcgcuacu ucugugucgu auguaguaug guccacaucu    60
u                                                                   61

<210> SEQ ID NO 588
<211> LENGTH: 79
<212> TYPE: RNA
<213> ORGANISM: Mus musculus

<400> SEQUENCE: 588
ugguacucgg agagagguua cccgagcaac uuugcaucug gaggacgaau guugcucggu    60
gaaccccuuu ucgguauca                                                79

<210> SEQ ID NO 589
<211> LENGTH: 81
<212> TYPE: RNA
<213> ORGANISM: Mus musculus
```

```
<400> SEQUENCE: 589
ggguacuuga ggagagguug ucugugauga guucgcuuua uuaaugacga auauaacaca    60
gauggccugu uuucaauacc a                                             81

<210> SEQ ID NO 590
<211> LENGTH: 82
<212> TYPE: RNA
<213> ORGANISM: Mus musculus

<400> SEQUENCE: 590
ugguacuugg agagauagua gaccguauag cguacgcuuu aucgugacg uauguaacac     60 ggccacuaa cccucaguau ca                                             82

<210> SEQ ID NO 591
<211> LENGTH: 80
<212> TYPE: RNA
<213> ORGANISM: Mus musculus

<400> SEQUENCE: 591
ggguauggga cggauggucg accagcugga aaguaauugu uucuaaugua cuucaccugg   60
uccacuagcc gucggugccc                                               80

<210> SEQ ID NO 592
<211> LENGTH: 96
<212> TYPE: RNA
<213> ORGANISM: Rattus norvegicus

<400> SEQUENCE: 592
guacauaugu ugaagauuau uaauauauag aguggguguu guggugguag uaugauaugu   60
agaguaguag guugcauagu acgauguagu guauga                             96

<210> SEQ ID NO 593
<211> LENGTH: 79
<212> TYPE: RNA
<213> ORGANISM: Rattus norvegicus

<400> SEQUENCE: 593
cacacuguag gccucauuaa auguuuguug aaugaaaaaa ugaaucauca acagacauua   60
auugggcgcc ugcucugug                                                79

<210> SEQ ID NO 594
<211> LENGTH: 22
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 594
cauacuucuu uauaugccca ua                                            22

<210> SEQ ID NO 595
<211> LENGTH: 21
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 595
```
uggaauguaa agaaguaugu a                                              21

```
<210> SEQ ID NO 596
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: This is combined DNA/RNA sequence
<220> FEATURE:
<223> OTHER INFORMATION: Description of Artificial Sequence: Synthetic
      Primer

<400> SEQUENCE: 596
```
cauacuucuu uacauucugt t                                              21

```
<210> SEQ ID NO 597
<211> LENGTH: 21
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 597
```
uggaauguaa agaaguaugu a                                              21

```
<210> SEQ ID NO 598
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: This is combined DNA/RNA sequence
<220> FEATURE:
<223> OTHER INFORMATION: Description of Artificial Sequence: Synthetic
      Primer

<400> SEQUENCE: 598
```
cauacuucuu uacauuccat t                                              21

```
<210> SEQ ID NO 599
<211> LENGTH: 21
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 599
```
uggaauguaa agaaguaugu a                                              21

```
<210> SEQ ID NO 600
<211> LENGTH: 22
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 600
```
guguucacag cggaccuuga uu                                             22

```
<210> SEQ ID NO 601
<211> LENGTH: 22
<212> TYPE: RNA
```

```
<213> ORGANISM: Artificial Sequence
<220> FEATURE:
<223> OTHER INFORMATION: Description of Artificial Sequence: Synthetic
      Primer

<400> SEQUENCE: 601
uuaaggcacg cggugaaugc ca                                              22

<210> SEQ ID NO 602
<211> LENGTH: 22
<212> TYPE: DNA
<213> ORGANISM: Artificial Sequence
<220> FEATURE:
<221> NAME/KEY: modified_base
<222> LOCATION: (21)..(22)
<223> OTHER INFORMATION: t = t/u
<220> FEATURE:
<223> OTHER INFORMATION: Description of Artificial Sequence: Synthetic
      Primer

<400> SEQUENCE: 602
gcauucaccg cgugccuugg tt                                              22

<210> SEQ ID NO 603
<211> LENGTH: 22
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 603
uuaaggcacg cggugaaugc ca                                              22

<210> SEQ ID NO 604
<211> LENGTH: 22
<212> TYPE: DNA
<213> ORGANISM: Artificial Sequence
<220> FEATURE:
<221> NAME/KEY: modified_base
<222> LOCATION: (21)..(22)
<223> OTHER INFORMATION: t = t/u
<220> FEATURE:
<223> OTHER INFORMATION: Description of Artificial Sequence: Synthetic
      Primer

<400> SEQUENCE: 604
gcauucaccg cgugccuuaa tt                                              22

<210> SEQ ID NO 605
<211> LENGTH: 22
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 605
uuaaggcacg cggugaaugc ca                                              22

<210> SEQ ID NO 606
<211> LENGTH: 19
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 606
```

-continued ucuuuucaca uugugcuac                                                19

<210> SEQ ID NO 607
<211> LENGTH: 20
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 607
cagugcaaug uuaaaagggc                                               20

<210> SEQ ID NO 608
<211> LENGTH: 20
<212> TYPE: DNA
<213> ORGANISM: Artificial Sequence
<220> FEATURE:
<221> NAME/KEY: modified_base
<222> LOCATION: (19)..(20)
<223> OTHER INFORMATION: t = t/u
<220> FEATURE:
<223> OTHER INFORMATION: Description of Artificial Sequence: Synthetic
      Primer

<400> SEQUENCE: 608
uauuuuaaca uugcacugtt                                               20

<210> SEQ ID NO 609
<211> LENGTH: 20
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 609
cagugcaaug uuaaaagggc                                               20

<210> SEQ ID NO 610
<211> LENGTH: 20
<212> TYPE: DNA
<213> ORGANISM: Artificial Sequence
<220> FEATURE:
<221> NAME/KEY: modified_base
<222> LOCATION: (19)..(20)
<223> OTHER INFORMATION: t = t/u
<220> FEATURE:
<223> OTHER INFORMATION: Description of Artificial Sequence: Synthetic
      Primer

<400> SEQUENCE: 610
ccuuuuaaca uugcacugtt                                               20

<210> SEQ ID NO 611
<211> LENGTH: 20
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 611
cagugcaaug uuaaaagggc                                               20

<210> SEQ ID NO 612
<211> LENGTH: 20

-continued

```
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 612
aguuuugcau aguugcacua                                              20

<210> SEQ ID NO 613
<211> LENGTH: 23
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 613
ugugcaaauc uaugcaaaac uga                                          23

<210> SEQ ID NO 614
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: This is combined DNA/RNA sequence
<220> FEATURE:
<223> OTHER INFORMATION: Description of Artificial Sequence: Synthetic
      Primer

<400> SEQUENCE: 614
acauuugcau agauuugcac att                                          23

<210> SEQ ID NO 615
<211> LENGTH: 23
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 615
ugugcaaauc uaugcaaaac uga                                          23

<210> SEQ ID NO 616
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: This is combined DNA/RNA sequence
<220> FEATURE:
<223> OTHER INFORMATION: Description of Artificial Sequence: Synthetic
      Primer

<400> SEQUENCE: 616
aguuuugcau agauuugcac att                                          23

<210> SEQ ID NO 617
<211> LENGTH: 23
<212> TYPE: RNA
<213> ORGANISM: Artificial Sequence
<220> FEATURE:
<223> OTHER INFORMATION: Description of Artificial Sequence: Synthetic
      Primer
```

```
<400> SEQUENCE: 617
ugugcaaauc uaugcaaaac uga                                              23

<210> SEQ ID NO 618
<211> LENGTH: 22
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 618
caaauucgua ucuagggaa ua                                                22

<210> SEQ ID NO 619
<211> LENGTH: 23
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 619
uacccuguag auccgaauuu gug                                              23

<210> SEQ ID NO 620
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: This is combined DNA/RNA sequence
<220> FEATURE:
<223> OTHER INFORMATION: Description of Artificial Sequence: Synthetic
      Primer

<400> SEQUENCE: 620
agaauucgga ucuacagggu att                                              23

<210> SEQ ID NO 621
<211> LENGTH: 23
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 621
uacccuguag auccgaauuu gug                                              23

<210> SEQ ID NO 622
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: This is combined DNA/RNA sequence
<220> FEATURE:
<223> OTHER INFORMATION: Description of Artificial Sequence: Synthetic
      Primer

<400> SEQUENCE: 622
caaauucgga ucuacagggu att                                              23

<210> SEQ ID NO 623
```

```
<211> LENGTH: 23
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 623
uacccuguag auccgaauuu gug                                           23

<210> SEQ ID NO 624
<211> LENGTH: 19
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 624 auguuccac agugcauca                                                 19

<210> SEQ ID NO 625
<211> LENGTH: 19
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 625
gugcauugua guugcauug                                                19

<210> SEQ ID NO 626
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: This is combined DNA/RNA sequence
<220> FEATURE:
<223> OTHER INFORMATION: Description of Artificial Sequence: Synthetic
      Primer

<400> SEQUENCE: 626
guccaacuac aaugcactt                                                19

<210> SEQ ID NO 627
<211> LENGTH: 19
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 627
gugcauugua guugcauug                                                19

<210> SEQ ID NO 628
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: This is combined DNA/RNA sequence
<220> FEATURE:
<223> OTHER INFORMATION: Description of Artificial Sequence: Synthetic
      Primer
```

-continued

<400> SEQUENCE: 628
augcaacuac aaugcactt                                                    19

<210> SEQ ID NO 629
<211> LENGTH: 19
<212> TYPE: RNA
<213> ORGANISM: Artificial Sequence
<220> FEATURE:
<223> OTHER INFORMATION: Description of Artificial Sequence: Synthetic
      Primer <400> SEQUENCE: 629
gugcauugua guugcauug                                                    19

<210> SEQ ID NO 630
<211> LENGTH: 21
<212> TYPE: RNA
<213> ORGANISM: Artificial Sequence
<220> FEATURE:
<223> OTHER INFORMATION: Description of Artificial Sequence: Synthetic
      Primer <400> SEQUENCE: 630
cuauacaacc uacugccuuc c                                                 21

<210> SEQ ID NO 631
<211> LENGTH: 22
<212> TYPE: RNA
<213> ORGANISM: Artificial Sequence
<220> FEATURE:
<223> OTHER INFORMATION: Description of Artificial Sequence: Synthetic
      Primer <400> SEQUENCE: 631
ugagguagua gguugugugg uu                                                22

<210> SEQ ID NO 632
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: This is combined DNA/RNA sequence
<220> FEATURE:
<223> OTHER INFORMATION: Description of Artificial Sequence: Synthetic
      Primer <400> SEQUENCE: 632
ccacacaacc uacuaucuua tt                                                22

<210> SEQ ID NO 633
<211> LENGTH: 22
<212> TYPE: RNA
<213> ORGANISM: Artificial Sequence
<220> FEATURE:
<223> OTHER INFORMATION: Description of Artificial Sequence: Synthetic
      Primer <400> SEQUENCE: 633
ugagguagua gguugugugg uu                                                22

<210> SEQ ID NO 634
<211> LENGTH: 22
<212> TYPE: DNA
<213> ORGANISM: Artificial Sequence

```
<220> FEATURE:
<221> NAME/KEY: misc_feature
<222> LOCATION: (1)..(22)
<223> OTHER INFORMATION: This is combined DNA/RNA sequence
<220> FEATURE:
<223> OTHER INFORMATION: Description of Artificial Sequence: Synthetic
      Primer

<400> SEQUENCE: 634
ccacacaacc uacuaccuca tt                                             22

<210> SEQ ID NO 635
<211> LENGTH: 22
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 635
ugagguagua gguugugugg uu                                             22

<210> SEQ ID NO 636
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: This is combined DNA/RNA sequence
<220> FEATURE:
<223> OTHER INFORMATION: Description of Artificial Sequence: Synthetic
      Primer

<400> SEQUENCE: 636
aacaacauga aacuaccuat t                                              21

<210> SEQ ID NO 637
<211> LENGTH: 21
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 637
uagguaguuu cauguuguug g                                              21

<210> SEQ ID NO 638
<211> LENGTH: 22
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 638
caaauucgua ucuaggggaa ua                                             22

<210> SEQ ID NO 639
<211> LENGTH: 21
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 639
```

-continued uagguaguuu cauguuguug g                                          21

<210> SEQ ID NO 640
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: This is combined DNA/RNA sequence
<220> FEATURE:
<223> OTHER INFORMATION: Description of Artificial Sequence: Synthetic
      Primer

<400> SEQUENCE: 640
aauaacauga aacuaccuat t                                          21

<210> SEQ ID NO 641
<211> LENGTH: 21
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 641
uagguaguuu cauguuguug g                                          21

<210> SEQ ID NO 642
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: This is combined DNA/RNA sequence
<220> FEATURE:
<223> OTHER INFORMATION: Description of Artificial Sequence: Synthetic
      Primer

<400> SEQUENCE: 642
augcaacuac aaugcactt                                             19

<210> SEQ ID NO 643
<211> LENGTH: 19
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 643
gugcauugua guugcauug                                             19

<210> SEQ ID NO 644
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: This is combined DNA/RNA sequence
<220> FEATURE:
<223> OTHER INFORMATION: Description of Artificial Sequence: Synthetic
      Primer

<400> SEQUENCE: 644
augcaacuac aaugcactt                                             19

<210> SEQ ID NO 645
<211> LENGTH: 19
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 645
gugcauugua guugcauug                                                19

<210> SEQ ID NO 646
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: This is combined DNA/RNA sequence
<220> FEATURE:
<223> OTHER INFORMATION: Description of Artificial Sequence: Synthetic
      Primer

<400> SEQUENCE: 646
augcaacuac aaugcactt                                                19

<210> SEQ ID NO 647
<211> LENGTH: 19
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 647
gugcauugua guugcauug                                                19

<210> SEQ ID NO 648
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: This is combined DNA/RNA sequence
<220> FEATURE:
<223> OTHER INFORMATION: Description of Artificial Sequence: Synthetic
      Primer

<400> SEQUENCE: 648
augcaacuac aaugcactt                                                19

<210> SEQ ID NO 649
<211> LENGTH: 19
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 649
gugcauugua guugcauug                                                19

<210> SEQ ID NO 650
<211> LENGTH: 19
<212> TYPE: DNA
<213> ORGANISM: Artificial Sequence
<220> FEATURE:

```
<221> NAME/KEY: misc_feature
<222> LOCATION: (1)..(19)
<223> OTHER INFORMATION: This is combined DNA/RNA sequence
<220> FEATURE:
<223> OTHER INFORMATION: Description of Artificial Sequence: Synthetic
      Primer

<400> SEQUENCE: 650
augcaacuac aaugcactt                                                   19

<210> SEQ ID NO 651
<211> LENGTH: 19
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 651
gugcauugua guugcauug                                                   19

<210> SEQ ID NO 652
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: This is combined DNA/RNA sequence
<220> FEATURE:
<223> OTHER INFORMATION: Description of Artificial Sequence: Synthetic
      Primer

<400> SEQUENCE: 652
ccacacaacc uacuaccuca tt                                               22

<210> SEQ ID NO 653
<211> LENGTH: 22
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 653
ugagguagua gguugugugg uu                                               22

<210> SEQ ID NO 654
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: This is combined DNA/RNA sequence
<220> FEATURE:
<223> OTHER INFORMATION: Description of Artificial Sequence: Synthetic
      Primer

<400> SEQUENCE: 654
ccacacaacc uacuaccuca tt                                               22

<210> SEQ ID NO 655
<211> LENGTH: 22
<212> TYPE: RNA
<213> ORGANISM: Artificial Sequence
<220> FEATURE:
<223> OTHER INFORMATION: Description of Artificial Sequence: Synthetic
      Primer
```

-continued

```
<400> SEQUENCE: 655
ugagguagua gguugugugg uu                                             22

<210> SEQ ID NO 656
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: This is combined DNA/RNA sequence
<220> FEATURE:
<223> OTHER INFORMATION: Description of Artificial Sequence: Synthetic
      Primer

<400> SEQUENCE: 656
ccacacaacc uacuaccuca tt                                             22

<210> SEQ ID NO 657
<211> LENGTH: 22
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 657
ugagguagua gguugugugg uu                                             22

<210> SEQ ID NO 658
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: This is combined DNA/RNA sequence
<220> FEATURE:
<223> OTHER INFORMATION: Description of Artificial Sequence: Synthetic
      Primer

<400> SEQUENCE: 658
ccacacaacc uacuaccuca tt                                             22

<210> SEQ ID NO 659
<211> LENGTH: 22
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 659
ugagguagua gguugugugg uu                                             22

<210> SEQ ID NO 660
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: This is combined DNA/RNA sequence
<220> FEATURE:
<223> OTHER INFORMATION: Description of Artificial Sequence: Synthetic
      Primer

<400> SEQUENCE: 660
```
cauacuucuu uacauuccat t                                              21

<210> SEQ ID NO 661
<211> LENGTH: 21
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 661
uggaauguaa agaaguaugu a                                              21

<210> SEQ ID NO 662
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: This is combined DNA/RNA sequence
<220> FEATURE:
<223> OTHER INFORMATION: Description of Artificial Sequence: Synthetic
      Primer

<400> SEQUENCE: 662
cauacuucuu uacauuccat t                                              21

<210> SEQ ID NO 663
<211> LENGTH: 21
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 663
uggaauguaa agaaguaugu a                                              21

<210> SEQ ID NO 664
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: This is combined DNA/RNA sequence
<220> FEATURE:
<223> OTHER INFORMATION: Description of Artificial Sequence: Synthetic
      Primer

<400> SEQUENCE: 664
gcauucaccg cgugccuuaa tt                                             22

<210> SEQ ID NO 665
<211> LENGTH: 22
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 665
uuaaggcacg cggugaaugc ca                                             22

<210> SEQ ID NO 666
<211> LENGTH: 22

```
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: This is combined DNA/RNA sequence
<220> FEATURE:
<223> OTHER INFORMATION: Description of Artificial Sequence: Synthetic
      Primer

<400> SEQUENCE: 666
gcauucaccg cgugccuuaa tt                                              22

<210> SEQ ID NO 667
<211> LENGTH: 22
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 667
uuaaggcacg cggugaaugc ca                                              22

<210> SEQ ID NO 668
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: This is combined DNA/RNA sequence
<220> FEATURE:
<223> OTHER INFORMATION: Description of Artificial Sequence: Synthetic
      Primer

<400> SEQUENCE: 668
ccuuuuaaca uugcacugtt                                                 20

<210> SEQ ID NO 669
<211> LENGTH: 20
<212> TYPE: RNA
<213> ORGANISM: Artificial Sequence
<220> FEATURE:
<223> OTHER INFORMATION: Description of Artificial Sequence: Synthetic
      Primer

<400> SEQUENCE: 669
cagugcaaug uuaaaagggc                                                 20

<210> SEQ ID NO 670
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: This is combined DNA/RNA sequence
<220> FEATURE:
<223> OTHER INFORMATION: Description of Artificial Sequence: Synthetic
      Primer

<400> SEQUENCE: 670
ccuuuuaaca uugcacugtt                                                 20

<210> SEQ ID NO 671
<211> LENGTH: 20
<212> TYPE: RNA
<213> ORGANISM: Artificial Sequence
```

```
<220> FEATURE:
<223> OTHER INFORMATION: Description of Artificial Sequence:  Synthetic
      Primer

<400> SEQUENCE: 671
cagugcaaug uuaaaagggc                                                   20

<210> SEQ ID NO 672
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: This is combined DNA/RNA sequence
<220> FEATURE:
<223> OTHER INFORMATION: Description of Artificial Sequence:  Synthetic
      Primer

<400> SEQUENCE: 672
caaauucgga ucuacagggu att                                               23

<210> SEQ ID NO 673
<211> LENGTH: 23
<212> TYPE: RNA
<213> ORGANISM: Artificial Sequence
<220> FEATURE:
<223> OTHER INFORMATION: Description of Artificial Sequence:  Synthetic
      Primer

<400> SEQUENCE: 673
uacccuguag auccgaauuu gug                                               23

<210> SEQ ID NO 674
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: This is combined DNA/RNA sequence
<220> FEATURE:
<223> OTHER INFORMATION: Description of Artificial Sequence:  Synthetic
      Primer

<400> SEQUENCE: 674
caaauucgga ucuacagggu att                                               23

<210> SEQ ID NO 675
<211> LENGTH: 23
<212> TYPE: RNA
<213> ORGANISM: Artificial Sequence
<220> FEATURE:
<223> OTHER INFORMATION: Description of Artificial Sequence:  Synthetic
      Primer

<400> SEQUENCE: 675
uacccuguag auccgaauuu gug                                               23

<210> SEQ ID NO 676
<211> LENGTH: 21
<212> TYPE: RNA
<213> ORGANISM: Artificial Sequence
<220> FEATURE:
<223> OTHER INFORMATION: Description of Artificial Sequence:  Synthetic
      Primer

<400> SEQUENCE: 676
```
uauacaagag augaaauccu c						21

<210> SEQ ID NO 677
<211> LENGTH: 64
<212> TYPE: RNA
<213> ORGANISM: Homo sapiens

<400> SEQUENCE: 677
ccccgcgacg agccccucgc acaaaccgga ccugagcguu uuguucguuc ggcucgcgug						60 aggc						64

<210> SEQ ID NO 678
<211> LENGTH: 68
<212> TYPE: RNA
<213> ORGANISM: Homo sapiens

<400> SEQUENCE: 678
uaaaagguag auucuccuuc uaugaguaca uuauuuauga uuaaucauag aggaaaaucc						60 acguuuuc						68

<210> SEQ ID NO 679
<211> LENGTH: 69
<212> TYPE: RNA
<213> ORGANISM: Homo sapiens

<400> SEQUENCE: 679
uugagcagag guugcccuug gugaauucgc uuuauuuaug uugaaucaca caaaggcaac						60 uuuuguuug						69

<210> SEQ ID NO 680
<211> LENGTH: 66
<212> TYPE: RNA
<213> ORGANISM: Homo sapiens

<400> SEQUENCE: 680
agggcuccug acuccagguc cuguguguua ccuagaaaua gcacuggacu uggagucaga						60 aggccu						66

<210> SEQ ID NO 681
<211> LENGTH: 67
<212> TYPE: RNA
<213> ORGANISM: Homo sapiens

<400> SEQUENCE: 681
agagauggua gacuauggaa cguaggcguu augauuucug accuauguaa cauggccac						60 uaacucu						67

<210> SEQ ID NO 682
<211> LENGTH: 61
<212> TYPE: RNA
<213> ORGANISM: Homo sapiens

<400> SEQUENCE: 682
aagaugguug accauagaac augcgcuauc ucugugucgu auguaauaug guccacaucu						60 u						61

<210> SEQ ID NO 683
<211> LENGTH: 75
<212> TYPE: RNA
<213> ORGANISM: Homo sapiens

<400> SEQUENCE: 683
uacuuaaagc gagguugccc uuuguauauu cgguuuauug acauggaaua uacaagggca    60
agcucucugu gagua                                                    75

<210> SEQ ID NO 684
<211> LENGTH: 76
<212> TYPE: RNA
<213> ORGANISM: Homo sapiens

<400> SEQUENCE: 684
uacuugaaga gaaguuguuc gugguggauu cgcuuuacuu augacgaauc auucacggac    60
aacacuuuuu ucagua                                                   76

<210> SEQ ID NO 685
<211> LENGTH: 73
<212> TYPE: RNA
<213> ORGANISM: Homo sapiens

<400> SEQUENCE: 685
cuccucagau cagaagguga uuguggcuuu ggguggauau uaaucagcca cagcacugcc    60
uggucagaaa gag                                                      73

<210> SEQ ID NO 686
<211> LENGTH: 88
<212> TYPE: RNA
<213> ORGANISM: Homo sapiens

<400> SEQUENCE: 686
uguuaaauca ggaauuuuaa acaauuccua gacaauaugu auaauguuca uaagucauuc    60
cuagaaauug uucauaaugc cuguaaca                                      88

<210> SEQ ID NO 687
<211> LENGTH: 90
<212> TYPE: RNA
<213> ORGANISM: Homo sapiens

<400> SEQUENCE: 687
gagagaagca cuggacuuag ggucagaagg ccugagcucu ucugcugcag augggcucuc    60
ugucccugag ccaagcuuug uccucccugg                                    90

<210> SEQ ID NO 688
<211> LENGTH: 94
<212> TYPE: RNA
<213> ORGANISM: Homo sapiens

<400> SEQUENCE: 688
auaaaggaag uuaggcugag gggcagagag cgagacuuuu cuauuuucca aaagcucggu    60
cugaggcccc ucagucuugc uuccuaaccc gcgc                               94

<210> SEQ ID NO 689
<211> LENGTH: 98
<212> TYPE: RNA
<213> ORGANISM: Homo sapiens

<400> SEQUENCE: 689
cgaggggaua cagcagcaau ucauguuuug aaguguucua aaugguucaa aacgugaggc    60
gcugcuauac ccccucgugg ggaagguaga aggugggg                           98

<210> SEQ ID NO 690
<211> LENGTH: 87
<212> TYPE: RNA
<213> ORGANISM: Homo sapiens

<400> SEQUENCE: 690
gaaagcgcuu uggaaugaca cgaucacucc cguugagugg gcacccgaga agccaucggg     60
aaugucgugu ccgcccagug cucuuuc                                        87

<210> SEQ ID NO 691
<211> LENGTH: 111
<212> TYPE: RNA
<213> ORGANISM: Homo sapiens

<400> SEQUENCE: 691
gccgggaggu ugaacauccu gcauagugcu gccaggaaau cccuauuuca uauaagaggg     60
ggcuggcugg uugcauaugu aggauguccc aucucccagc ccacuucguc a             111

<210> SEQ ID NO 692
<211> LENGTH: 83
<212> TYPE: RNA
<213> ORGANISM: Homo sapiens

<400> SEQUENCE: 692
cgccggccga ugggcgucuu accagacaug guuagaccug gcccucuguc uaauacuguc     60
ugguaaaacc guccauccgc ugc                                            83

<210> SEQ ID NO 693
<211> LENGTH: 91
<212> TYPE: RNA
<213> ORGANISM: Homo sapiens

<400> SEQUENCE: 693
cuguguguga ugagcuggca guguauuguu agcugguuga auaugugaau ggcaucggcu     60
aacaugcaac ugcugucuua uugcauauac a                                   91

<210> SEQ ID NO 694
<211> LENGTH: 91
<212> TYPE: RNA
<213> ORGANISM: Homo sapiens

<400> SEQUENCE: 694
aaacgauacu aaacuguuuu ugcgaugugu uccuaauaug cacuauaaau auauugggaa     60
cauuuugcau guauaguuuu guaucaauau a                                   91

<210> SEQ ID NO 695
<211> LENGTH: 85
<212> TYPE: RNA
<213> ORGANISM: Mus musculus

<400> SEQUENCE: 695
aaagugcuuu ggaaugacac gaucacuccc guugagugg cacccaagaa gccaucggga     60
augucguguc cgcccagugc ucuuu                                          85

<210> SEQ ID NO 696
<211> LENGTH: 112
<212> TYPE: RNA
<213> ORGANISM: Mus musculus

<400> SEQUENCE: 696

```
acgaggaggu ugaacauccu gcauagugcu gccaggaaau cccuacuuca uacuaagagg    60
gggcuggcug guugcauaug uaggaugucc caucuccugg cccacuucgu ca          112

<210> SEQ ID NO 697
<211> LENGTH: 83
<212> TYPE: RNA
<213> ORGANISM: Mus musculus

<400> SEQUENCE: 697
ccugcugaug gaugucuuac cagacauggu uagaucugga ugcaucuguc uaauacuguc    60
ugguaaugcc guccauccac ggc                                           83

<210> SEQ ID NO 698
<211> LENGTH: 91
<212> TYPE: RNA
<213> ORGANISM: Mus musculus

<400> SEQUENCE: 698
cuguguguga uggcuuggca guguauuguu agcugguuga guaugugagc ggcaccagcu    60
aacaugcgac ugcucuccua uugcacacac a                                  91

<210> SEQ ID NO 699
<211> LENGTH: 91
<212> TYPE: RNA
<213> ORGANISM: Mus musculus

<400> SEQUENCE: 699
gagagauacu gagcuguuuu ugcgaugugu uccuaauaug ugcauaaauu auauugggaa    60
cauuuugcau aaauagcuuu gugucaauac a                                  91

<210> SEQ ID NO 700
<211> LENGTH: 112
<212> TYPE: RNA
<213> ORGANISM: Rattus norvegicus

<400> SEQUENCE: 700
acggggaggu ugaacauccu gcauagugcu gccaggaaau cccuacuuca uacuaagagg    60
gggcuggcug guugcauaug uaggaugucc caucucccgg cccacuucgu ca          112

<210> SEQ ID NO 701
<211> LENGTH: 85
<212> TYPE: RNA
<213> ORGANISM: Rattus norvegicus

<400> SEQUENCE: 701
ugccugcuga uggaugucuu accagacaug guuagaucug gauguaucug ucuaauacug    60
ucugguaaug ccguccaucc auggc                                         85

<210> SEQ ID NO 702
<211> LENGTH: 91
<212> TYPE: RNA
<213> ORGANISM: Rattus norvegicus

<400> SEQUENCE: 702
cugugugcga ugggguuggca guguauuguu agcugguuga guauguaaaa ggcaccagcu    60
aacaugcaac ugcucuccua uugcacauac a                                  91

<210> SEQ ID NO 703
```

```
<211> LENGTH: 91
<212> TYPE: RNA
<213> ORGANISM: Rattus norvegicus

<400> SEQUENCE: 703
gagagaugcg gagcuguuuu ugcgaugugu uccuaaugug ugcuacaauu auauugggaa    60
cauuuugcau aaauaguuuu acaucgacac a                                  91

<210> SEQ ID NO 704
<211> LENGTH: 100
<212> TYPE: RNA
<213> ORGANISM: Homo sapiens

<400> SEQUENCE: 704
ccaaagaaag augcuaaacu auuuuugcga uguguuccua auauguaaua uaaauguauu    60
ggggacauuu ugcauucaua guuuuguauc aauaauaugg                         100

<210> SEQ ID NO 705
<211> LENGTH: 72
<212> TYPE: RNA
<213> ORGANISM: Homo sapiens

<400> SEQUENCE: 705
cuugggaaug gcaaggaaac cguuaccauu acgaguuua guaaugguaa ugguucucuu    60
gcuauaccca ga                                                      72

<210> SEQ ID NO 706
<211> LENGTH: 85
<212> TYPE: RNA
<213> ORGANISM: Homo sapiens

<400> SEQUENCE: 706
gcuaagcacu uacaacuguu ugcagaggaa acugagacuu uguaacuaug ucucagucuc    60
aucugcaaag aaguaagugc uuugc                                        85

<210> SEQ ID NO 707
<211> LENGTH: 22
<212> TYPE: RNA
<213> ORGANISM: Homo sapiens

<400> SEQUENCE: 707
gagguugucc guggugaguu cg                                           22

<210> SEQ ID NO 708
<211> LENGTH: 96
<212> TYPE: RNA
<213> ORGANISM: Homo sapiens

<400> SEQUENCE: 708
ucccuggcgu gagguaugu gccuuuggac uacaucgugg aagccagcac caugcagucc    60
augggcauau acacuugccu caaggccuau gucauc                            96

<210> SEQ ID NO 709
<211> LENGTH: 76
<212> TYPE: RNA
<213> ORGANISM: Homo sapiens

<400> SEQUENCE: 709 gaggggggaag acgggaggaa agaagggagu gguuccauca cgccuccuca cuccucuccu    60
cccgucuucu ccucuc                                                  76
```

<210> SEQ ID NO 710
<211> LENGTH: 63
<212> TYPE: RNA
<213> ORGANISM: Homo sapiens

<400> SEQUENCE: 710
gucaggcuca guccccuccc gauaaacccc uaaauaggga cuucccgggg gggugacccu    60
ggc    63

<210> SEQ ID NO 711
<211> LENGTH: 73
<212> TYPE: RNA
<213> ORGANISM: Homo sapiens

<400> SEQUENCE: 711
acuuggagag aggcuggccg ugaugaauuc gauucaucaa agcgagucau acacggcucu    60
ccucucuuuu agu    73

<210> SEQ ID NO 712
<211> LENGTH: 68
<212> TYPE: RNA
<213> ORGANISM: Homo sapiens

<400> SEQUENCE: 712
guauccugua cugagcugcc ccgagcuggg cagcaugaag ggccucgggg cagcucagua    60
caggaugc    68

<210> SEQ ID NO 713
<211> LENGTH: 80
<212> TYPE: RNA
<213> ORGANISM: Homo sapiens

<400> SEQUENCE: 713
gguacuugaa gagugguuau cccugcugug uucgcuuaau uuaugacgaa ucauacaggg    60
acauccaguu uuucaguauc    80

<210> SEQ ID NO 714
<211> LENGTH: 83
<212> TYPE: RNA
<213> ORGANISM: Homo sapiens

<400> SEQUENCE: 714
gagaaucauc ucucccagau aauggcacuc ucaaacaagu uccaaauug uuugaaaggc    60 uauuucuugg ucagaugacu cuc    83

<210> SEQ ID NO 715
<211> LENGTH: 84
<212> TYPE: RNA
<213> ORGANISM: Homo sapiens

<400> SEQUENCE: 715
guggcagcuu ggguggucgua ugugugacgc cauuuacuug aaccuuuagg agugacauca    60
cauauacggc agcuaaacug cuac    84

<210> SEQ ID NO 716
<211> LENGTH: 128
<212> TYPE: RNA
<213> ORGANISM: Homo sapiens -continued

```
<400> SEQUENCE: 716
uggaggccuu gcugguuugg aaaguucauu guucgacacc auggaucucc aggugggggca    60 aguuuagaga ugcaccaacc uggaggacuc caugcuguug agcuguucac aagcagcgga   120
cacuucca                                                            128

<210> SEQ ID NO 717
<211> LENGTH: 84
<212> TYPE: RNA
<213> ORGANISM: Homo sapiens

<400> SEQUENCE: 717
uugacuuagc uggguagugg ggaacccuuc caugaggagu agaacacucc uuaugcaaga    60
uucccuucua ccuggcuggg uugg                                           84

<210> SEQ ID NO 718
<211> LENGTH: 116
<212> TYPE: RNA
<213> ORGANISM: Homo sapiens

<400> SEQUENCE: 718
caacuacagc cacuacuaca ggaccaucga ggaccugcgg gacaagauuc uuggugccac    60
cauugagaac gccaggauug uccugcagau caacaaugcu caacuggcug cagaug       116

<210> SEQ ID NO 719
<211> LENGTH: 89
<212> TYPE: RNA
<213> ORGANISM: Homo sapiens

<400> SEQUENCE: 719
cuggccucca gggcuuugua caugguaggc uuucauucau ucguuugcac auucggugaa    60
ggucuacugu gugccaggcc cugugccag                                      89

<210> SEQ ID NO 720
<211> LENGTH: 24
<212> TYPE: RNA
<213> ORGANISM: Homo sapiens

<400> SEQUENCE: 720
ugaaacauac acgggaaacc ucuu                                           24

<210> SEQ ID NO 721
<211> LENGTH: 82
<212> TYPE: RNA
<213> ORGANISM: Homo sapiens

<400> SEQUENCE: 721
ugguaccuga aaagaaguug cccauguuau uuucgcuuua uaugugacga aacaaacaug    60
gugcacuucu uuucgguau ca                                              82

<210> SEQ ID NO 722
<211> LENGTH: 17
<212> TYPE: RNA
<213> ORGANISM: Homo sapiens

<400> SEQUENCE: 722
auuacauggc caaucuc                                                   17

<210> SEQ ID NO 723
<211> LENGTH: 21
```

```
<212> TYPE: RNA
<213> ORGANISM: Homo sapiens

<400> SEQUENCE: 723
cagcagcaca cugugguuug u                                               21

<210> SEQ ID NO 724
<211> LENGTH: 124
<212> TYPE: RNA
<213> ORGANISM: Homo sapiens

<400> SEQUENCE: 724
aacccuccuu gggaagugaa gcucaggcug ugauuucaag ccaggggggcg uuuuucuaua    60 acuggaugaa aagcaccucc agagcuugaa gcucacaguu ugagagcaau cgucuaagga   120
aguu                                                                124

<210> SEQ ID NO 725
<211> LENGTH: 122
<212> TYPE: RNA
<213> ORGANISM: Homo sapiens

<400> SEQUENCE: 725
gcccuguccc cugugccuug ggcgggcggc uguuaagacu ugcagugaug uuuaacuccu    60
cuccacguga acaucacagc aagucugugc ugcuucccgu cccuacgcug ccugggcagg   120
gu                                                                  122

<210> SEQ ID NO 726
<211> LENGTH: 84
<212> TYPE: RNA
<213> ORGANISM: Homo sapiens

<400> SEQUENCE: 726 gcuccccuc ucuaauccuu gcuaccuggg ugagagugcu gucugaaugc aaugcaccug     60
ggcaaggauu cugagagcga gagc                                           84

<210> SEQ ID NO 727
<211> LENGTH: 84
<212> TYPE: RNA
<213> ORGANISM: Homo sapiens

<400> SEQUENCE: 727
gcucuuccuc ucuaauccuu ugcccuggg ugagagugcu uucugaaugc aaugcacccg     60
ggcaaggauu cugagagggu gagc                                           84

<210> SEQ ID NO 728
<211> LENGTH: 55
<212> TYPE: RNA
<213> ORGANISM: Homo sapiens

<400> SEQUENCE: 728
auccuugcua ucugggugcu agugcuggcu caaugcaaug caccugggca aggau          55

<210> SEQ ID NO 729
<211> LENGTH: 71
<212> TYPE: RNA
<213> ORGANISM: Homo sapiens

<400> SEQUENCE: 729
ugcccuagca gcgggaacag uucugcagug agcgaucggu gcucgggggu auuguuccg     60
```

```
cugccagggu a                                                               71

<210> SEQ ID NO 730
<211> LENGTH: 83
<212> TYPE: RNA
<213> ORGANISM: Homo sapiens

<400> SEQUENCE: 730
gcugcuguug ggagacccug gucugcacuc uaucuguauu cuuacugaag ggagugcagg          60
gcaggguuuc ccauacagag ggc                                                  83

<210> SEQ ID NO 731
<211> LENGTH: 84
<212> TYPE: RNA
<213> ORGANISM: Homo sapiens

<400> SEQUENCE: 731
gaugcaccca gugggggagc caggaaguau ugauguuucu gccaguuuag cgucaacacu          60
ugcugguuuc cucucuggag cauc                                                 84

<210> SEQ ID NO 732
<211> LENGTH: 124
<212> TYPE: RNA
<213> ORGANISM: Homo sapiens

<400> SEQUENCE: 732
gccaccacca ucagccauac uauguguagu gccuuauuca ggaaggucuu acuuaauaga          60
uuaauauuug uaaggcaccc uucgaguag aguaaugugc aacauggaca acauuugugg          120
uggc                                                                      124

<210> SEQ ID NO 733
<211> LENGTH: 94
<212> TYPE: RNA
<213> ORGANISM: Homo sapiens

<400> SEQUENCE: 733
gugcugugug uagugcuuca cuucaagaag ugccaugcau gugucuagaa auauguuuug          60
caccuuuugg agugaaauaa ugcacaacag auac                                      94

<210> SEQ ID NO 734
<211> LENGTH: 115
<212> TYPE: RNA
<213> ORGANISM: Homo sapiens

<400> SEQUENCE: 734
ccaccuucag cugaguguag ugcccuacuc cagagggcgu cacucaugua aacuaaaaca          60
ugauuguagc cuuuuggagu agaguaauac acaucacgua acgcauauuu ggugg              115

<210> SEQ ID NO 735
<211> LENGTH: 94
<212> TYPE: RNA
<213> ORGANISM: Homo sapiens

<400> SEQUENCE: 735
caugcugugu gugguacccu acugcagaca gugggcaauca uguauaauua aaaugauug          60 guacgucugu ggguagagua cugcaugaca caug                                      94

<210> SEQ ID NO 736
<211> LENGTH: 74
```

```
<212> TYPE: RNA
<213> ORGANISM: Homo sapiens

<400> SEQUENCE: 736
gugguguccu acucaggaga guggcaauca cauguaauua ggugugauug aaaccucuaa    60
gaguggagua acac                                                     74

<210> SEQ ID NO 737
<211> LENGTH: 87
<212> TYPE: RNA
<213> ORGANISM: Homo sapiens

<400> SEQUENCE: 737
caauagacac ccaucguguc uuuugcucug cagucaguaa auauuuuuuu gugaaugugu    60
agcaaaagac agaauggugg uccauug                                       87

<210> SEQ ID NO 738
<211> LENGTH: 87
<212> TYPE: RNA
<213> ORGANISM: Homo sapiens

<400> SEQUENCE: 738
caauagacac ccaucguguc uuuugcucug cagucaguaa auauuuuuuu gugaaugugu    60
agcaaaagac agaauggugg uccauug                                       87

<210> SEQ ID NO 739
<211> LENGTH: 84
<212> TYPE: RNA
<213> ORGANISM: Homo sapiens

<400> SEQUENCE: 739
ucucagucug uggcacucag ccuugagggc acuuucuggu gccagaauga aagugcuguc    60
auagcugagg uccaaugacu gagg                                          84

<210> SEQ ID NO 740
<211> LENGTH: 98
<212> TYPE: RNA
<213> ORGANISM: Homo sapiens

<400> SEQUENCE: 740
gguacuucuc agucugugge acucagccuu gagggcacuu ucuggugcca gaaugaaagu    60
gcugucauag cugaggucca augacugagg cgagcacc                           98

<210> SEQ ID NO 741
<211> LENGTH: 129
<212> TYPE: RNA
<213> ORGANISM: Homo sapiens

<400> SEQUENCE: 741
gggaugccac auucagccau ucagcguaca gugccuuuca cagggaggug ucauuuaugu    60
gaacuaaaau auaaauuuca ccuuucugag aaggguaaug uacagcaugc acugcauaug   120 uggugucoc                                                          129

<210> SEQ ID NO 742
<211> LENGTH: 127
<212> TYPE: RNA
<213> ORGANISM: Homo sapiens

<400> SEQUENCE: 742
```
ggaugccaca uucagccauu cagugugcag ugccuuucac agggaggugu cauuuaugug    60
aacuaaaaua uaaauuucac cuuucugaga aggguaaugu acagcaugca cugcauaugu   120
ggugucc                                                             127

<210> SEQ ID NO 743
<211> LENGTH: 58
<212> TYPE: RNA
<213> ORGANISM: Homo sapiens

<400> SEQUENCE: 743
cuacucugga gagugacaau cauguauaau uaaauuugau ugacacuucu gugaguag      58

<210> SEQ ID NO 744
<211> LENGTH: 58
<212> TYPE: RNA
<213> ORGANISM: Homo sapiens

<400> SEQUENCE: 744
cuacucugga gagugacaau cauguauaac uaaauuugau ugacacuucu gugaguag      58

<210> SEQ ID NO 745
<211> LENGTH: 58
<212> TYPE: RNA
<213> ORGANISM: Homo sapiens

<400> SEQUENCE: 745
cuacucugga gagugacaau cauguauaac uaaauuugau ugacacuucu gugaguag      58

<210> SEQ ID NO 746
<211> LENGTH: 83
<212> TYPE: RNA
<213> ORGANISM: Homo sapiens

<400> SEQUENCE: 746
ucucaugcag ucauucucca aaagaaagca cuuucuguug ucugaaagca gagugccuuc    60
uuuuggagcg uuacuguuug aga                                            83

<210> SEQ ID NO 747
<211> LENGTH: 83
<212> TYPE: RNA
<213> ORGANISM: Homo sapiens

<400> SEQUENCE: 747
ucucaugcag ucauucucca aaagaaagca cuuucuguug ucugaaagca gagugccuuc    60
uuuuggagcg uuacuguuug aga                                            83

<210> SEQ ID NO 748
<211> LENGTH: 90
<212> TYPE: RNA
<213> ORGANISM: Homo sapiens

<400> SEQUENCE: 748
ucucaggcug ugaccuucuc gaggaaagaa gcacuuucug uugucugaaa gaaaagaaag    60
ugcuuccuuu cagaggguua cgguuugaga                                     90

<210> SEQ ID NO 749
<211> LENGTH: 90
<212> TYPE: RNA
<213> ORGANISM: Homo sapiens

<400> SEQUENCE: 749
ucucagguug ugaccuucuc gaggaaagaa gcacuuucug uugucugaaa gaaaagaaag     60
ugcuuccuuu cagaggguua cgguuugaga                                     90

<210> SEQ ID NO 750
<211> LENGTH: 85
<212> TYPE: RNA
<213> ORGANISM: Homo sapiens

<400> SEQUENCE: 750
ucucaugaug ugaccaucug gagguaagaa gcacuuugug uuuugugaaa gaaagugcuu     60
ccuuucagag gguuacucuu ugaga                                          85

<210> SEQ ID NO 751
<211> LENGTH: 90
<212> TYPE: RNA
<213> ORGANISM: Homo sapiens

<400> SEQUENCE: 751
ucucaggcug ugaccaucug gagguaagaa gcacuuucug uuuugugaaa gaaaagaaag     60
ugcuuccuuu cagaggguua cucuuugaga                                     90

<210> SEQ ID NO 752
<211> LENGTH: 87
<212> TYPE: RNA
<213> ORGANISM: Homo sapiens

<400> SEQUENCE: 752
ucucaggcag ugacccucua dauggaagca cugucuguug uauaaaagaa aagaucgugc     60
aucccuuuag aguguuacug uuugaga                                        87

<210> SEQ ID NO 753
<211> LENGTH: 67
<212> TYPE: RNA
<213> ORGANISM: Homo sapiens

<400> SEQUENCE: 753
gugacccucu agauggaagc acugucuguu gucuaagaaa agaucgugca ucccuuuaga     60
guguuac                                                              67

<210> SEQ ID NO 754
<211> LENGTH: 95
<212> TYPE: RNA
<213> ORGANISM: Homo sapiens

<400> SEQUENCE: 754
gaagaucuca ggcagugacc cucuagaugg aagcacuguc uguugcuaa gaaaagaucg     60 ugcauccuuu uagaguguua cuguuugaga aaauc                               95

<210> SEQ ID NO 755
<211> LENGTH: 85
<212> TYPE: RNA
<213> ORGANISM: Homo sapiens

<400> SEQUENCE: 755
ucucaagcug ugacugcaaa gggaagcccu uucuguuguc ugaaagaaga gaaagcgcuu     60
cccuuugcug gauuacgguu ugaga                                          85

<210> SEQ ID NO 756

```
<211> LENGTH: 87
<212> TYPE: RNA
<213> ORGANISM: Homo sapiens

<400> SEQUENCE: 756
ucucaagcug ugggucugca aagggaagcc cuuucuguug ucuaaaagaa gagaaagcgc    60
uucccuuugc uggauuacgg uuugaga                                       87

<210> SEQ ID NO 757
<211> LENGTH: 83
<212> TYPE: RNA
<213> ORGANISM: Homo sapiens

<400> SEQUENCE: 757
ucaugcugug gcccuccaga gggaagcgcu uucuguuguc ugaaagaaaa caaagcgcuc    60
cccuuuagag guuuacgguu uga                                           83

<210> SEQ ID NO 758
<211> LENGTH: 101
<212> TYPE: RNA
<213> ORGANISM: Homo sapiens

<400> SEQUENCE: 758
gcgagaagau ucaugcugu gacucucugg agggaagcac uuucuguugu cugaaagaaa     60
acaaagcgcu ucucuuuaga guguuacggu uugagaaaag c                      101

<210> SEQ ID NO 759
<211> LENGTH: 87
<212> TYPE: RNA
<213> ORGANISM: Homo sapiens

<400> SEQUENCE: 759
ucccaugcug ugacccucua gagggaagca cuuucuguug ucugaaagaa accaaagcgc    60
uucccuuugg agcguuacgg uuugaga                                       87

<210> SEQ ID NO 760
<211> LENGTH: 88
<212> TYPE: RNA
<213> ORGANISM: Homo sapiens

<400> SEQUENCE: 760
ucucaggcug ugacccucua gagggaagcg cuuucuguug gcuaaaagaa aagaaagcgc    60
uucccuucag aguguuaacg cuuugaga                                      88

<210> SEQ ID NO 761
<211> LENGTH: 87
<212> TYPE: RNA
<213> ORGANISM: Homo sapiens

<400> SEQUENCE: 761
ucucaugcug ugacccucua gagggaagca cuuucucuug ucuaaaagaa aagaaagcgc    60
uucucuuuag aggauuacuc uuugaga                                       87

<210> SEQ ID NO 762
<211> LENGTH: 85
<212> TYPE: RNA
<213> ORGANISM: Homo sapiens

<400> SEQUENCE: 762
cucaggcugu gacacucuag agggaagcgc uuucuguugu cugaaagaaa ggaaagugca    60
```
uccuuuuaga uguuuacugu uugag                                              85

<210> SEQ ID NO 763
<211> LENGTH: 87
<212> TYPE: RNA
<213> ORGANISM: Homo sapiens

<400> SEQUENCE: 763
ucucaggcug ugcccucua cagggaagcg cuuucuguug ucugaaagaa aggaaagugc         60
auccuuuuag aguguuacug uuugaga                                            87

<210> SEQ ID NO 764
<211> LENGTH: 81
<212> TYPE: RNA
<213> ORGANISM: Homo sapiens

<400> SEQUENCE: 764
caugcuguga cccucuagag ggaagcgcuu ucguugucu gaaagaaaag aaagugcauc         60
cuuuuagagg uuuacuguuu g                                                  81

<210> SEQ ID NO 765
<211> LENGTH: 87
<212> TYPE: RNA
<213> ORGANISM: Homo sapiens

<400> SEQUENCE: 765
ucucagccug ugacccucua gagggaagcg cuuucuguug ucugaaagaa aagaaagugc         60
aucuuuuuag aggauuacag uuugaga                                            87

<210> SEQ ID NO 766
<211> LENGTH: 88
<212> TYPE: RNA
<213> ORGANISM: Homo sapiens

<400> SEQUENCE: 766
ucccaugcug ugacccucca aagggaagcg cuuucuguuu guuuucucuu aaacaaagug         60
ccucccuuua gaguguuacc guuuggga                                           88

<210> SEQ ID NO 767
<211> LENGTH: 84
<212> TYPE: RNA
<213> ORGANISM: Homo sapiens

<400> SEQUENCE: 767
ucucaugcag ucauucucca aagggagca cuuucuguuu gaaagaaaac aaagugccuc         60
cuuuuagagu guuacuguuu gaga                                               84

<210> SEQ ID NO 768
<211> LENGTH: 85
<212> TYPE: RNA
<213> ORGANISM: Homo sapiens

<400> SEQUENCE: 768
cucaggcugu gacccuccag agggaaguac uuucuguugu cugagagaaa agaaagugcu         60
ucccuuugga cuguuucggu uugag                                              85

<210> SEQ ID NO 769
<211> LENGTH: 61
<212> TYPE: RNA

<213> ORGANISM: Homo sapiens

<400> SEQUENCE: 769
cccucuacag ggaagcgcuu ucuguugucu gaaagaaaag aaagugcuuc cuuuuagagg    60
g                                                                   61

<210> SEQ ID NO 770
<211> LENGTH: 87
<212> TYPE: RNA
<213> ORGANISM: Homo sapiens

<400> SEQUENCE: 770
ucucaggcug ucguccucua gagggaagca cuuucuguug ucugaaagaa aagaaagugc    60
uuccuuuuag aggguuaccg uuugaga                                       87

<210> SEQ ID NO 771
<211> LENGTH: 87
<212> TYPE: RNA
<213> ORGANISM: Homo sapiens

<400> SEQUENCE: 771
ucucaagcug ugagucuaca aagggaagcc cuuucuguug ucuaaaagaa aagaaagugc    60
uucucuuugg uggguuacgg uuugaga                                       87

<210> SEQ ID NO 772
<211> LENGTH: 87
<212> TYPE: RNA
<213> ORGANISM: Homo sapiens

<400> SEQUENCE: 772
ucuccugcug ugacccucaa gauggaagca guuucuguug ucugaaagga aagaaagugc    60
uuccuuuuug aggguuacug uuugaga                                       87

<210> SEQ ID NO 773
<211> LENGTH: 87
<212> TYPE: RNA
<213> ORGANISM: Homo sapiens

<400> SEQUENCE: 773
ucucaggcug ugacccucua aagggaagcg cuuucugugg ucagaaagaa aagcaagugc    60
uuccuuuuag aggguuaccg uuuggga                                       87

<210> SEQ ID NO 774
<211> LENGTH: 90
<212> TYPE: RNA
<213> ORGANISM: Homo sapiens

<400> SEQUENCE: 774
ucccaugcug ugacccucua gaggaagcac uuucuguuug uugucugaga aaaacaaag    60 ugcuucccuu uagaguguua ccguuuggga                                    90

<210> SEQ ID NO 775
<211> LENGTH: 88
<212> TYPE: RNA
<213> ORGANISM: Homo sapiens

<400> SEQUENCE: 775
ucccaugcug ugacccucua gaggaagcac uuucuguuug uugucugaga aaaacaaag    60 ugcuucccuu uagaguuacu guuuggga                                      88

<210> SEQ ID NO 776
<211> LENGTH: 87
<212> TYPE: RNA
<213> ORGANISM: Homo sapiens

<400> SEQUENCE: 776
ucucaggcug ugacccucca aagggaagaa cuuucuguug ucuaaaagaa aagaacgcac    60
uucccuuuag aguguuaccg ugugaga    87

<210> SEQ ID NO 777
<211> LENGTH: 87
<212> TYPE: RNA
<213> ORGANISM: Homo sapiens

<400> SEQUENCE: 777
ucucgggcug ugacucucca aagggaagaa uuuucucuug ucuaaaagaa aagaacgcac    60
uucccuuuag aguguuaccg ugugaga    87

<210> SEQ ID NO 778
<211> LENGTH: 87
<212> TYPE: RNA
<213> ORGANISM: Homo sapiens

<400> SEQUENCE: 778
ucucaggcug uguccucua gagggaagcg cuuucuguug ucugaaagaa aagaaaaugg    60
uucccuuuag aguguuacgc uuugaga    87

<210> SEQ ID NO 779
<211> LENGTH: 87
<212> TYPE: RNA
<213> ORGANISM: Homo sapiens

<400> SEQUENCE: 779
ucucaugcug ugacccucua gagggaagcg cuuucuguug ucugaaagaa aagaacgcgc    60
uucccuauag aggguuaccc uuugaga    87

<210> SEQ ID NO 780
<211> LENGTH: 87
<212> TYPE: RNA
<213> ORGANISM: Homo sapiens

<400> SEQUENCE: 780
ucucaugcug ugacccuaca aagggaagca cuuucucuug uccaaggaa aagaaggcgc    60 uucccuuugg aguguuacgg uuugaga    87

<210> SEQ ID NO 781
<211> LENGTH: 85
<212> TYPE: RNA
<213> ORGANISM: Homo sapiens

<400> SEQUENCE: 781
cucaagcugu gacucuccag agggaugcac uuucucuuau gugaaaaaaa agaaggcgcu    60
ucccuuuaga gcguuacggu uuggg    85

<210> SEQ ID NO 782
<211> LENGTH: 85
<212> TYPE: RNA
<213> ORGANISM: Homo sapiens

<400> SEQUENCE: 782
cucaggcugu gacccucuag agggaagcac uuucuguugc uugaaagaag agaaagcgcu    60
uccuuuuaga ggauuacucu uugag    85

<210> SEQ ID NO 783
<211> LENGTH: 65
<212> TYPE: RNA
<213> ORGANISM: Homo sapiens

<400> SEQUENCE: 783
gugacccucu agagggaagc acuuucuguu gaaagaaaag aacaugcauc cuuucagagg    60
guuac    65

<210> SEQ ID NO 784
<211> LENGTH: 83
<212> TYPE: RNA
<213> ORGANISM: Homo sapiens

<400> SEQUENCE: 784
ucaggcugug acccucuuga gggaagcacu uucuguuguc ugaaagaaga gaaagugcuu    60
ccuuuuagag gcuuacuguc uga    83

<210> SEQ ID NO 785
<211> LENGTH: 85
<212> TYPE: RNA
<213> ORGANISM: Homo sapiens

<400> SEQUENCE: 785
ucucaagcug ugacugcaaa gggaagcccu uucuguuguc uaaaagaaaa gaaagugcuu    60
cccuuuggug aauuacgguu ugaga    85

<210> SEQ ID NO 786
<211> LENGTH: 72
<212> TYPE: RNA
<213> ORGANISM: Mus musculus

<400> SEQUENCE: 786
cuugggaaug gcgaggaaac cguuaccauu acugaguuua guaaugguaa cgguucucuu    60
gcugcuccca ca    72

<210> SEQ ID NO 787
<211> LENGTH: 85
<212> TYPE: RNA
<213> ORGANISM: Mus musculus

<400> SEQUENCE: 787
gcuaagcagu uacaacuguu ugcagaggaa acugagacuu uauaacuaug ucucagucuc    60
aucugcaaag agguaagugc uuugc    85

<210> SEQ ID NO 788
<211> LENGTH: 75
<212> TYPE: RNA
<213> ORGANISM: Mus musculus

<400> SEQUENCE: 788
cuuuaccuaa uuuguugucc aucauguaaa acauaaauga ugauagacac cauauaaggu    60
agaggaaggu ucacu    75

<210> SEQ ID NO 789
<211> LENGTH: 71
<212> TYPE: RNA
<213> ORGANISM: Mus musculus

<400> SEQUENCE: 789
accuuguuau gggggucugg gguaaggagu ggucaucagg gggacuacc aaguuuauuc    60 ugugagauag a                                                       71

<210> SEQ ID NO 790
<211> LENGTH: 74
<212> TYPE: RNA
<213> ORGANISM: Mus musculus

<400> SEQUENCE: 790
gcccuauuua gaauggcacu gaugugauaa aauaaaaaau ugaucagggc cuuucuaagu    60
agaguaaggc uuac                                                     74

<210> SEQ ID NO 791
<211> LENGTH: 73
<212> TYPE: RNA
<213> ORGANISM: Mus musculus

<400> SEQUENCE: 791
uauaugucuu uaugugugug uacauguaca uaugugaaua ugauauccau auacauacac    60
gcacacauaa gac                                                      73

<210> SEQ ID NO 792
<211> LENGTH: 71
<212> TYPE: RNA
<213> ORGANISM: Mus musculus

<400> SEQUENCE: 792
gugccugugu gcguaagugc cugcauguau augcguguau auuuaugca uauacauaca    60 cacaccuaca c                                                        71

<210> SEQ ID NO 793
<211> LENGTH: 78
<212> TYPE: RNA
<213> ORGANISM: Mus musculus

<400> SEQUENCE: 793
auaagaaacu uggcgugucg ugacugaugu acugauaaga aacucagugu gauaugacug    60
augugcgugu gucugucu                                                 78

<210> SEQ ID NO 794
<211> LENGTH: 74
<212> TYPE: RNA
<213> ORGANISM: Mus musculus

<400> SEQUENCE: 794
cgcggugccu cuuucauuga ucuuggguguc cucaaauuga aagccaagga agaggugggg    60
ggcgugguag ccuu                                                     74

<210> SEQ ID NO 795
<211> LENGTH: 75

```
<212> TYPE: RNA
<213> ORGANISM: Mus musculus

<400> SEQUENCE: 795
cagugcucuu cuuggacugg cacuggugag uuaaacuaaa uacaaccagu accuuucuga    60
gaagaguaaa gcuca                                                    75

<210> SEQ ID NO 796
<211> LENGTH: 67
<212> TYPE: RNA
<213> ORGANISM: Mus musculus

<400> SEQUENCE: 796
gugcuuuacg uaguauagug cuuuucacau uaaacaaaaa gugaaaggug ccauacuaug    60
uauagga                                                             67

<210> SEQ ID NO 797
<211> LENGTH: 73
<212> TYPE: RNA
<213> ORGANISM: Mus musculus

<400> SEQUENCE: 797 gaggggaag acgggagaag agaagggagu gguuuuggg ugccucacuc cuccccuccc     60
gucuuguucu cuc                                                      73

<210> SEQ ID NO 798
<211> LENGTH: 58
<212> TYPE: RNA
<213> ORGANISM: Mus musculus

<400> SEQUENCE: 798
gucaggcuca gucccucccc gauaaaccuc aaaauagggu cuuaccuagg gggcuggc     58

<210> SEQ ID NO 799
<211> LENGTH: 73
<212> TYPE: RNA
<213> ORGANISM: Mus musculus

<400> SEQUENCE: 799
acuuggagag aggcuggccg ugaugaauuc gauucaucua aacgagucau acacggcucu    60
ccucucuucu agu                                                      73

<210> SEQ ID NO 800
<211> LENGTH: 65
<212> TYPE: RNA
<213> ORGANISM: Mus musculus

<400> SEQUENCE: 800
gcauccugua cugagcugcc ccgagcugag cacagugaag gaccucgggg cagcucagua    60
cagga                                                               65

<210> SEQ ID NO 801
<211> LENGTH: 72
<212> TYPE: RNA
<213> ORGANISM: Rattus norvegicus

<400> SEQUENCE: 801
```

```
uuugggaaug gcgaggaaac cguuaccauu acugaguuua guaaugguaa ugguucucuu    60
gcugcuccca ca                                                       72

<210> SEQ ID NO 802
<211> LENGTH: 73
<212> TYPE: RNA
<213> ORGANISM: Rattus norvegicus

<400> SEQUENCE: 802 gaggggaag acgggagaag agaagggagu gguuuuggg ugccucacuc cuccccuccc    60
gucuuguucu cuc                                                      73

<210> SEQ ID NO 803
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 803
tcatcgtctc aaatgagtct                                               20

<210> SEQ ID NO 804
<211> LENGTH: 21
<212> TYPE: RNA
<213> ORGANISM: Homo sapiens

<400> SEQUENCE: 804
aaagugcuuc cuuuuagagg c                                             21

<210> SEQ ID NO 805
<211> LENGTH: 21
<212> TYPE: RNA
<213> ORGANISM: Homo sapiens

<400> SEQUENCE: 805
cuccagaggg aaguacuuuc u                                             21

<210> SEQ ID NO 806
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: This is combined DNA/RNA sequence
<220> FEATURE:
<223> OTHER INFORMATION: Description of Artificial Sequence:  Synthetic
      Primer

<400> SEQUENCE: 806
ggauuucauc ucuuguauau t                                             21

<210> SEQ ID NO 807
<211> LENGTH: 23
<212> TYPE: RNA
<213> ORGANISM: Artificial Sequence
<220> FEATURE:
<223> OTHER INFORMATION: Synthetic primer

<400> SEQUENCE: 807
ccuaguaggu guccaguaag ugu                                           23
```

METHODS AND COMPOSITIONS INVOLVING MIRNA AND MIRNA INHIBITOR MOLECULES

CROSS-REFERENCE TO RELATED APPLICATIONS

This application is a continuation of U.S. application Ser. No. 13/887,008, filed May 3, 2013, which is a continuation of U.S. application Ser. No. 13/299,255, filed Nov. 17, 2011, now issued as U.S. Pat. No. 8,946,177 on Feb. 3, 2015, which is divisional of U.S. application Ser. No. 11/273,640 filed Nov. 14, 2005, now issued as U.S. Pat. No. 8,173,611 on May 8, 2012, which claims the benefit of priority to U.S. Provisional Patent Application No. 60/683,736, filed on May 23, 2005, U.S. Provisional Patent Application No. 60/649,634, filed on Feb. 3, 2005, and U.S. Provisional Patent Application No. 60/627,171, filed on Nov. 12, 2004, all of which are hereby incorporated by reference in their entireties.

INCORPORATION BY REFERENCE OF SEQUENCE LISTING

The present application contains a Sequence Listing which has been submitted in ASCII format via EFS-Web and is hereby incorporated by reference in its entirety. Said ASCII copy, created Jul. 14, 2015, is named "48436701308.txt" and is 179,559 bytes in size.

BACKGROUND OF THE INVENTION

1. Field of the Invention

The present invention relates generally to the field of molecular biology. More particularly, it concerns methods and compositions involving nucleic acid molecules that simulate microRNA (miRNAs) and that inhibit miRNAs. Methods and compositions involving synthetic miRNAs and miRNA inhibitor molecules are described. In addition, methods and compositions for identifying miRNAs that contribute to cellular processes are also described. In addition, the identification of miRNAs that contribute to cellular processes provides targets for therapeutic intervention as well as diagnostic and/or prognostic analysis.

2. Description of the Related Art

In 2001, several groups used a novel cloning method to isolate and identify a large group of "microRNAs" (miRNAs) from *C. elegans, Drosophila*, and humans (Lagos-Quintana et al., 2001; Lau et al., 2001; Lee and Ambros, 2001). Several hundreds of miRNAs have been identified in plants and animals—including humans—which do not appear to have endogenous siRNAs. Thus, while similar to siRNAs, miRNAs are nonetheless distinct.

miRNAs thus far observed have been approximately 21-22 nucleotides in length and they arise from longer precursors, which are transcribed from non-protein-encoding genes. See review of Carrington et al. (2003). The precursors form structures that fold back on each other in self-complementary regions; they are then processed by the nuclease Dicer in animals or DCL1 in plants. miRNA molecules interrupt translation through precise or imprecise base-pairing with their targets.

miRNAs seem to be involved in gene regulation. Some miRNAs, including lin-4 and let-7, inhibit protein synthesis by binding to partially complementary 3' untranslated regions (3' UTRs) of target mRNAs. Others, including the Scarecrow miRNA found in plants, function like siRNA and bind to perfectly complementary mRNA sequences to destroy the target transcript (Grishok et al., 2001).

Research on microRNAs is increasing as scientists are beginning to appreciate the broad role that these molecules play in the regulation of eukaryotic gene expression. The two best understood miRNAs, lin-4 and let-7, regulate developmental timing in *C. elegans* by regulating the translation of a family of key mRNAs (reviewed in Pasquinelli, 2002). Several hundred miRNAs have been identified in *C. elegans, Drosophila*, mouse, and humans. As would be expected for molecules that regulate gene expression, miRNA levels have been shown to vary between tissues and developmental states. In addition, one study shows a strong correlation between reduced expression of two miRNAs and chronic lymphocytic leukemia, providing a possible link between miRNAs and cancer (Calin, 2002). Although the field is still young, there is speculation that miRNAs could be as important as transcription factors in regulating gene expression in higher eukaryotes.

There are a few examples of miRNAs that play critical roles in cell differentiation, early development, and cellular processes like apoptosis and fat metabolism. lin-4 and let-7 both regulate passage from one larval state to another during *C. elegans* development (Ambros, 2003). mir-14 and bantam are *drosophila* miRNAs that regulate cell death, apparently by regulating the expression of genes involved in apoptosis (Brennecke et al., 2003, Xu et al., 2003). MiR14 has also been implicated in fat metabolism (Xu et al., 2003). Lsy-6 and miR-273 are *C. elegans* miRNAs that regulate asymmetry in chemosensory neurons (Chang et al., 2004). Another animal miRNA that regulates cell differentiation is miR-181, which guides hematopoietic cell differentiation (Chen et al., 2004). These molecules represent the full range of animal miRNAs with known functions. Enhanced understanding of the functions of miRNAs will undoubtedly reveal regulatory networks that contribute to normal development, differentiation, inter- and intra-cellular communication, cell cycle, angiogenesis, apoptosis, and many other cellular processes. Given their important roles in many biological functions, it is likely that miRNAs will offer important points for therapeutic intervention or diagnostic analysis.

Characterizing the functions of biomolecules like miRNAs often involves introducing the molecules into cells or removing the molecules from cells and measuring the result. If introducing a miRNA into cells results in apoptosis, then the miRNA undoubtedly participates in an apoptotic pathway. Methods for introducing and removing miRNAs from cells have been described. Two recent publications describe antisense molecules that can be used to inhibit the activity of specific miRNAs (Meister et al., 2004; Hutvagner et al., 2004). Another publication describes the use of plasmids that are transcribed by endogenous RNA polymerases and yield specific miRNAs when transfected into cells (Zeng et al., 2002). These two reagent sets have been used to evaluate single miRNAs.

A limitation of the plasmid-based miRNA expression system is that the transfection efficiencies for plasmids tend to be very low, with only approximately 50% of cells expressing RNA from the plasmid in cells that are easy to transfect. Transfection efficiencies for plasmids in primary cells are much lower, with fewer than 10% of cells typically expressing the desired RNA. Therefore, there is a need for alternative compositions and methods for introducing miRNA molecules into cells so that they can be characterized and studied.

SUMMARY OF THE INVENTION

The present invention is based on the inventors' studies regarding the introduction into cells of one or more nucleic acids that function like miRNA or inhibit the activities of one or more miRNAs in cells to characterize their roles in various biological processes. The invention concerns nucleic acids that perform the activities of endogenous miRNAs when introduced into cells. These nucleic acids are synthetic miRNA in some embodiments. The invention further concerns a library of synthetic miRNAs specific to a variety of known miRNAs that can be used to introduce sequentially or in combination one or more miRNAs into cells in vitro or in vivo for the purpose of identifying miRNAs that participate in cellular processes. The invention further involves a library of sequence-specific miRNA inhibitors that can be used to inhibit sequentially or in combination the activities of one or more miRNAs in cells. The two libraries of miRNA-specific reagents are used to introduce or eliminate specific miRNAs or combinations of miRNAs to define the roles of miRNAs in cells.

The term "miRNA" is used according to its ordinary and plain meaning and refers to a microRNA molecule found in eukaryotes that is involved in RNA-based gene regulation. See, e.g., Carrington et al., 2003, which is hereby incorporated by reference. The term will be used to refer to the single-stranded RNA molecule processed from a precursor. Individual miRNAs have been identified and sequenced in different organisms, and they have been given names. Names of miRNAs and their sequences are provided herein. Additionally, other miRNAs are known to those of skill in the art and can be readily implemented in embodiments of the invention. The methods and compositions should not be limited to miRNAs identified in the application, as they are provided as examples, not necessarily as limitations of the invention.

The present invention concerns, in some embodiments of the invention, short nucleic acid molecules that function as miRNAs or as inhibitors of miRNA in a cell. The term "short" refers to a length of a single polynucleotide that is 150 nucleotides or fewer. The nucleic acid molecules are synthetic. The term "synthetic" means the nucleic acid molecule is isolated and not identical in sequence (the entire sequence) and/or chemical structure to a naturally-occurring nucleic acid molecule, such as an endogenous precursor miRNA molecule. While in some embodiments, nucleic acids of the invention do not have an entire sequence that is identical to a sequence of a naturally-occurring nucleic acid, such molecules may encompass all or part of a naturally-occurring sequence. It is contemplated, however, that a synthetic nucleic acid administered to a cell may subsequently be modified or altered in the cell such that its structure or sequence is the same as non-synthetic or naturally occuring nucleic acid, such as a mature miRNA sequence. For example, a synthetic nucleic acid may have a sequence that differs from the sequence of a precursor miRNA, but that sequence may be altered once in a cell to be the same as an endogenous, processed miRNA. The term "isolated" means that the nucleic acid molecules of the invention are initially separated from different (in terms of sequence or structure) and unwanted nucleic acid molecules such that a population of isolated nucleic acids is at least about 90% homogenous, and may be at least about 95, 96, 97, 98, 99, or 100% homogenous with respect to other polynucleotide molecules. In many embodiments of the invention, a nucleic acid is isolated by virtue of it having been synthesized in vitro separate from endogenous nucleic acids in a cell. It will be understood, however, that isolated nucleic acids may be subsequently mixed or pooled together.

Of course, it is understood that a "synthetic nucleic acid" of the invention means that the nucleic acid does not have a chemical structure or sequence of a naturally occuring nucleic acid. Consequently, it will be understood that the term "synthetic miRNA" refers to a "synthetic nucleic acid" that functions in a cell or under physiological conditions as a naturally occuring miRNA.

While many of the embodiments of the invention involve synthetic miRNAs or synthetic nucleic acids, in some embodiments of the invention, the nucleic acid molecule(s) need not be "synthetic." In certain embodiments, a non-synthetic miRNA employed in methods and compositions of the invention may have the entire sequence and structure of a naturally occurring miRNA precursor or the mature miRNA. For example, non-synthetic miRNAs used in methods and compositions of the invention may not have one or more modified nucleotides or nucleotide analogs. In these embodiments, the non-synthetic miRNA may or may not be recombinantly produced. In particular embodiments, the nucleic acid in methods and/or compositions of the invention is specifically a synthetic miRNA and not a non-synthetic miRNA (that is, not an miRNA that qualifies as "synthetic"); though in other embodiments, the invention specifically involves a non-synthetic miRNA and not a synthetic miRNA. Any embodiments discussed with respect to the use of synthetic miRNAs can be applied with respect to non-synthetic miRNAs, and vice versa.

It will be understood that the term "naturally occurring" refers to something found in an organism without any intervention by a person; it could refer to a naturally-occurring wildtype or mutant molecule. In some embodiments a synthetic miRNA molecule does not have the sequence of a naturally occurring miRNA molecule. In other embodiments, a synthetic miRNA molecule may have the sequence of a naturally occurring miRNA molecule, but the chemical structure of the molecule, particularly in the part unrelated specifically to the precise sequence (non-sequence chemical structure) differs from chemical structure of the naturally occurring miRNA molecule with that sequence. In some cases, the synthetic miRNA has both a sequence and non-sequence chemical structure that are not found in a naturally-occurring miRNA. Moreover, the sequence of the synthetic molecules will identify which miRNA is effectively being provided or inhibited; the endogenous miRNA will be referred to as the "corresponding miRNA." Corresponding miRNA sequences that can be used in the context of the invention include, but are not limited to, those sequences in SEQ ID NOs: 1-593 and those miRNAs listed in the appendix. In addition synthetic nucleic acids of the invention may include SEQ ID NOs:594-703 as well as any other miRNA sequence, miRNA precursor sequence, or any sequence complementary thereof. In some embodiments, the sequence is or is derived from a probe sequence identified in the appendix to target the particular miRNA (or set of miRNAs) that can be used with that probe sequence.

Synthetic miRNA of the invention are RNA or RNA analogs in some embodiments of the invention. MiRNA inhibitors may be DNA or RNA, or analogs thereof. miRNA and miRNA inhibitors of the invention are collectively referred to as "synthetic nucleic acids."

In some embodiments, there is a synthetic miRNA having a length of between 17 and 130 residues. The present invention concerns synthetic miRNA molecules that are, are at least, or are at most 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, or 130 residues in length, or any range derivable therein.

In certain embodiments, synthetic miRNA have a) an "miRNA region" whose sequence from 5' to 3' is identical to a mature miRNA sequence, and b) a "complementary region" whose sequence from 5' to 3' is between 60% and 100% complementary to the miRNA sequence. In certain embodiments, these synthetic miRNA are also isolated, as defined above. The term "miRNA region" refers to a region on the synthetic miRNA that is at least 90% identical to the entire sequence of a mature, naturally occurring miRNA sequence. In certain embodiments, the miRNA region is or is at least 90, 91, 92, 93, 94, 95, 96, 97, 98, 99, 99.1, 99.2, 99.3, 99.4, 99.5, 99.6, 99.7, 99.8, 99.9 or 100% identical to the sequence of a naturally-occurring miRNA.

The term "complementary region" refers to a region of a synthetic miRNA that is or is at least 60% complementary to the mature, naturally occurring miRNA sequence that the miRNA region is identical to. The complementary region is or is at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, 99.9 or 100% complementary, or any range derivable therein. With single polynucleotide sequences, there is a hairpin loop structure as a result of chemical bonding between the miRNA region and the complementary region. In other embodiments, the complementary region is on a different nucleic acid molecule than the miRNA region, in which case the complementary region is on the complementary strand and the miRNA region is on the active strand.

In other embodiments of the invention, there are synthetic nucleic acids that are miRNA inhibitors. An miRNA inhibitor is between about 17 to 25 nucleotides in length and comprises a 5' to 3' sequence that is at least 90% complementary to the 5' to 3' sequence of a mature miRNA. In certain embodiments, an miRNA inhibitor molecule is 17, 18, 19, 20, 21, 22, 23, 24, or 25 nucleotides in length, or any range derivable therein. Moreover, an miRNA inhibitor has a sequence (from 5' to 3') that is or is at least 90, 91, 92, 93, 94, 95, 96, 97, 98, 99, 99.1, 99.2, 99.3, 99.4, 99.5, 99.6, 99.7, 99.8, 99.9 or 100% complementary, or any range derivable therein, to the 5' to 3' sequence of a mature miRNA, particularly a mature, naturally occurring miRNA. Probe sequences for miRNAs are disclosed in the appendix. While they have more sequence than an miRNA inhibitor, one of skill in the art could use that portion of the probe sequence that is complementary to the sequence of a mature miRNA as the sequence for an miRNA inhibitor. Table 1 indicates what the mature sequence of an miRNA is. Moreover, that portion of the probe sequence can be altered so that it is still 90% complementary to the sequence of a mature miRNA.

In some embodiments, of the invention, a synthetic miRNA contains one or more design elements. These design elements include, but are not limited to: i) a replacement group for the phosphate or hydroxyl of the nucleotide at the 5' terminus of the complementary region; ii) one or more sugar modifications in the first or last 1 to 6 residues of the complementary region; or, iii) noncomplementarity between one or more nucleotides in the last 1 to 5 residues at the 3' end of the complementary region and the corresponding nucleotides of the miRNA region.

In certain embodiments, a synthetic miRNA has a nucleotide at its 5' end of the complementary region in which the phosphate and/or hydroxyl group has been replaced with another chemical group (referred to as the "replacement design"). In some cases, the phosphate group is replaced, while in others, the hydroxyl group has been replaced. In particular embodiments, the replacement group is biotin, an amine group, a lower alkylamine group, an acetyl group, 2'-Me (2' oxygen-methyl), DMTO (4,4'-dimethoxytrityl with oxygen), fluoroscein, a thiol, or acridine, though other replacement groups are well known to those of skill in the art and can be used as well. This design element can also be used with an miRNA inhibitor.

Additional embodiments concern a synthetic miRNA having one or more sugar modifications in the first or last 1 to 6 residues of the complementary region (referred to as the "sugar replacement design"). In certain cases, there is one or more sugar modifications in the first 1, 2, 3, 4, 5, 6 or more residues of the complementary region, or any range derivable therein. In additional cases, there is one or more sugar modifications in the last 1, 2, 3, 4, 5, 6 or more residues of the complementary region, or any range derivable therein, have a sugar modification. It will be understood that the terms "first" and "last" are with respect to the order of residues from the 5' end to the 3' end of the region. In particular embodiments, the sugar modification is a 2'O-Me modification. In further embodiments, there is one or more sugar modifications in the first or last 2 to 4 residues of the complementary region or the first or last 4 to 6 residues of the complementary region. This design element can also be used with an miRNA inhibitor. Thus, an miRNA inhibitor can have this design element and/or a replacement group on the nucleotide at the 5' terminus, as discussed above.

In other embodiments of the invention, there is a synthetic miRNA in which one or more nucleotides in the last 1 to 5 residues at the 3' end of the complementary region are not complementary to the corresponding nucleotides of the miRNA region ("noncomplementarity") (referred to as the "noncomplementarity design"). The noncomplementarity may be in the last 1, 2, 3, 4, and/or 5 residues of the complementary miRNA. In certain embodiments, there is noncomplementarity with at least 2 nucleotides in the complementary region.

It is contemplated that synthetic miRNA of the invention have one or more of the replacement, sugar modification, or noncomplementarity designs. In certain cases, synthetic RNA molecules have two of them, while in others these molecules have all three designs in place.

The miRNA region and the complementary region may be on the same or separate polynucleotides. In cases in which they are contained on or in the same polynucleotide, the miRNA molecule will be considered a single polynucleotide. In embodiments in which the different regions are on separate polynucleotides, the synthetic miRNA will be considered to be comprised of two polynucleotides.

When the RNA molecule is a single polynucleotide, there is a linker region between the miRNA region and the complementary region. In some embodiments, the single polynucleotide is capable of forming a hairpin loop structure as a result of bonding between the miRNA region and the complementary region. The linker constitutes the hairpin loop. It is contemplated that in some embodiments, the linker region is, is at least, or is at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 residues in length, or any range derivable therein. In certain embodiments, the linker is between 3 and 30 residues (inclusive) in length.

In addition to having an miRNA region and a complementary region, there may be flanking sequences as well at either the 5' or 3' end of the region. In some embodiments, there is or is at least 1, 2, 3, 4, 5, 6, 7, 8, 9, 10 nucleotides or more, or any range derivable therein, flanking one or both sides of these regions.

The present invention also concerns a collection of synthetic nucleic acid molecules, referred to as a library. A collection may contain, contain at least or contain at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550 or more different types (by structure and/or sequence) of nucleic acids. Libraries may contain synthetic miRNAs and/or miRNA inhibitors.

Embodiments involving libraries and methods of using nucleic acids of the invention may be applied to miRNA and miRNA inhibitors. Thus, any embodiment discussed with respect to nucleic acids of the invention may generally be applicable to miRNA and miRNA inhibitor molecules, and vice versa. Moreover, embodiments discussed with respect to miRNA may be applied to miRNA inhibitors and vice versa.

The present invention also concerns methods of characterizing an miRNA activity or function in a cell. In some embodiments, a method comprises: a) introducing into one or more cells a synthetic miRNA molecule; and b) comparing one or more characteristics of cell(s) having the RNA molecule with cells in which the synthetic miRNA molecule has not been introduced. In certain embodiments, the cells with the synthetic miRNA may be compared to cells in which a different molecule was introduced (such as a negative control that does not include an miRNA region or has an miRNA region for a different miRNA). It is contemplated that the compared cells need not be evaluated at the same time. In fact, the comparison cells need not have been cultured at the same time; one may refer to a report or previous observation.

Other methods include reducing or eliminating activity of one or more miRNAs from a cell comprising: a) introducing into a cell an miRNA inhibitor. In certain embodiment, methods also include comparing one or more characteristics of a cell having the miRNA inhibitor with a cell not having the miRNA inhibitor.

The synthetic nucleic acids discussed above and herein can be used in methods of the invention. Thus, in certain embodiments, the methods involve synthetic nucleic acids with the different designs in them.

Characteristics of cells that may be evaluated are not limited. They include the following characteristics and characteristics associated with the following: cell proliferation, mitotic index, cell cycle, apoptosis, motility, adhesion, signal transduction, protein localization, gene expression, RNA localization, cell division, DNA replication, post-translational modification, differentiation, de-differentiation, transcriptional activation, protein activation, angiogenesis, metabolism (energy production and/or consumption), protein degradation, chromatin condensation, microtubule production, DNA replication, recombination, and DNA repair functions. It is contemplated that these characteristics may be relevant globally to the cell (for example, overall protein production reduced) or to individual species in the cell (for example, induction of a specific protein(s)).

It is contemplated that this method may be applied with respect to a variety of different synthetic and/or nonsynthetic miRNAs in separate or the same cells. In some cases, the following numbers of different synthetic miRNA molecules may be introduced into different cells: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300 or more, or any range derivable therein (or at least or at most these numbers). The invention is not limited by cell type. It is contemplated that any cell expressing miRNA or any cell having a characteristic altered by an miRNA is amenable to the methods and compositions of the invention. Use of two or more miRNAs may be combined in a single pharmaceutical composition as a cocktail or may be used in any therapeutic, diagnostic or prognostic method of the invention. It is contemplated that methods of the invention may involve, involve at least, or involve at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300 or more, or any range derivable therein, nucleic acid molecules corresponding to different miRNAs. Such nucleic acid molecules include synthetic miRNAs molecules, non-synthetic miRNA molecules, and miRNA inhibitors.

In some embodiments, it may be useful to know whether a cell expresses a particular miRNA endogenously or whether such expression is affected under particular conditions or when it is in a particular disease state. Thus, in some embodiments of the invention, methods include assaying the cell for the presence of the miRNA that is effectively being introduced by the synthetic miRNA molecule or inhibited by an miRNA inhibitor. Consequently, in some embodiments, methods include a step of generating an miRNA profile for a sample. The term "miRNA profile" refers to a set of data regarding the expression pattern for a plurality of miRNAs in the sample; it is contemplated that the miRNA profile can be obtained using an miRNA array. In some embodiments of the invention, an miRNA profile is generated by steps that include: a) labeling miRNA in the sample; b) hybridizing the miRNA to an miRNA array; and, c) determining miRNA hybridization to the array, wherein an miRNA profile is generated. See U.S. Provisional Patent Application 60/575, 743 and the U.S. Provisional Patent Application 60/649,584, and U.S. patent application Ser. No. 11/141,707, all of which are hereby incorporated by reference.

Additionally, a cell that is introduced with a synthetic miRNA or an miRNA inhibitor may be subsequently evaluated or assayed for the amount of endogenous or exogenous miRNA or miRNA inhibitor. Any cell type is contemplated for use with the invention. The cell may be from or in a mammal, such as a monkey, horse, cow, pig, sheep, dog, cat, rabbit, mouse, rat, or human.

In other methods of the invention, a step of synthesizing or obtaining the synthetic RNA molecule is included.

In additional embodiments, the synthetic nucleic acid is introduced into the cell by calcium phosphate transfection, lipid transfection, electroporation, microinjection, or injection. In addition, a cell may be in a subject, which may be a patient or an animal model. In this case, synthetic nucleic acids can be administered to the subject or patient using modes of administration that are well known to those of skill in the art, particularly for therapeutic applications. It is particularly contemplated that a patient is human or any other mammal or animal having miRNA.

The present invention also concerns inducing certain cellular characteristics by providing to a cell a particular nucleic acid, such as a specific synthetic miRNA molecule or a synthetic miRNA inhibitor molecule. However, in methods of the invention, the miRNA molecule or miRNA inhibitor need not be synthetic. They may have a sequence that is identical to a naturally occurring miRNA or they may not have any design modifications. In certain embodiments, the miRNA molecule and/or an miRNA inhibitor are synthetic, as discussed above.

The particular nucleic acid molecule provided to the cell is understood to correspond to a particular miRNA in the cell, and thus, the miRNA in the cell is referred to as the "corresponding miRNA." In situations in which a named miRNA molecule is introduced into a cell, the corresponding miRNA will be understood to be the induced miRNA. It is contemplated, however, that the miRNA molecule provided introduced into a cell is not a mature miRNA but is capable of becoming a mature miRNA under the appropriate physiological conditions. In cases in which a particular corresponding miRNA is being inhibited by a miRNA inhibitor, the particular miRNA will be referred to as the targeted miRNA. It is contemplated that multiple corresponding miRNAs may be involved. In particular embodiments, more than one miRNA molecule is introduced into a cell. Moreover, in other embodiments, more than one miRNA inhibitor is introduced into a cell. Furthermore, a combination of miRNA molecule(s) and miRNA inhibitor(s) may be introduced into a cell.

Methods include identifying a cell or patient in need of inducing those cellular characteristics. Also, it will be understood that an amount of a synthetic nucleic acid that is provided to a cell or organism is an "effective amount," which refers to an amount needed to achieve a desired goal, such as inducing a particular cellular characteristic(s).

In certain embodiments of the methods include providing or introducing to a cell a nucleic acid molecule corresponding to a mature miRNA in the cell in an amount effective to achieve a desired physiological result. Such methods are disclosed herein. Moreover, methods of the invention involve diagnosing a patient based on an miRNA expression profile. In certain embodiments, the elevation or reduction in the level of expression of a particular miRNA in a cell is correlated with a disease state compared to the expression level of that miRNA in a normal cell. This correlation allows for diagnostic methods to be carried out when that the expression level of an miRNA is measured in a biological sample being assessed and then compared to the expression level of a normal cell.

In these different methods, the corresponding miRNA involved in the method may be one or more of at least the following: Let 7a, let 7a-1, let 7b, let 7b-1, let-7c, let-7d, let 7g, miR-1, miR-1-d, miR-1-2, miR-9, miR-10a, miR-10b, miR-15a, miR-16, miR-17, miR-17-3p, miR-18, miR-19a, miR-20, miR-21, miR-22, miR-23, miR-23a, miR-23b, miR-24, miR-25, miR-26a, miR-27a, miR-28, miR-29a, miR-29b, miR-30a-3p, miR-30a, miR-30e-5p, miR-31, miR-32, miR-34a, miR-92, miR-93, miR-95, miR-96, miR-98, miR-99a, miR-100, miR-101, miR-105, miR-106, miR-107, miR-108, miR-122, miR-124, miR-125, miR-125b, miR-126, miR-127, miR-128, miR-129, miR-130, miR-130a, miR-133, miR-133a, miR-133a-2, miR-133b, miR-134, miR-135, miR-137, miR-138, miR-139, miR-140, miR-141, miR-142, miR-143, miR-145, miR-147, miR-148, miR-149, miR-150, miR-152, miR-153, miR-154, miR-155, miR-181, miR-182, miR-183, miR-184, miR-186, miR-187, miR-188, miR-190, miR-191, miR-192, miR-193, miR-194, miR-195, miR-196, miR-197, miR-198, miR-199, miR-199a-1, miR-200b, miR-201, miR-203, miR-204, miR-206, miR-207, miR-208, miR-210, miR-211, miR-212, miR-213, miR-214, miR-215, miR-216, miR-217, miR-218, miR-222, miR-223, miR-224, miR-291-3p, miR-292, miR-292-3p, miR-293, miR-294, miR-295, miR-296, miR-297, miR-298, miR-299, miR-320, miR-321, miR-322, miR-324, miR-325, miR-326, miR-328, miR-329, miR-330, miR-331, miR-333, miR-335, miR-337, miR-338, miR-340, miR-341, miR-342, miR-344, miR-345, miR-346, miR-350, miR-367, miR-368, miR-369, miR-370, miR-371, miR-373, miR-380-3p, miR-409, miR-410, or miR-412.

Moreover, methods can involve providing synthetic or nonsynthetic miRNA molecules. It is contemplated that in these embodiments, methods may or may not be limited to providing only one or more synthetic miRNA molecules or only on or more nonsynthetic miRNA molecules. Thus, in certain embodiments, methods may involve providing both synthetic and nonsynthetic miRNA molecules. In this situation, a cell or cells are most likely provided a synthetic miRNA molecule corresponding to a particular miRNA and a nonsynthetic miRNA molecule corresponding to a different miRNA. Furthermore, any method articulated a list of miRNAs using Markush group language may be articulated without the Markush group language and a disjunctive article (i.e., or) instead, and vice versa.

In some embodiments, there is a method for reducing or inhibiting cell proliferation in a cell comprising introducing into or providing to the cell an effective amount of i) an miRNA inhibitor molecule or ii) a synthetic or nonsynthetic miRNA molecule that corresponds to an miRNA sequence. In certain embodiments the methods involves introducing into the cell an effective amount of i) an miRNA inhibitor molecule having a 5' to 3' sequence that is at least 90% complementary to the 5' to 3' sequence of a mature miRNA selected from the group consisting of: mir-31, mir-92, mir-99a, mir-100, mir-125a, mir-129, mir-130a, mir-150, mir-187, miR-190, miR-191, miR-193, miR 204, mir-210, mir-211, mir-212, mir-213, mir-215, mir-216, mir-217, miR 218, mir-224, mir-292, mir-294, mir-320, mir-324, mir-325, mir-326, mir-330, mir-331, mir-338, mir-341, mir-369, and mir-370; or ii) a synthetic or nonsynthetic miRNA molecule that corresponds to an miRNA sequence selected from the group consisting of: miR-15a, miR-16, miR 21, miR 24, miR-96, miR-101, miR-105, miR-124, miR-126, miR-142, miR-147, miR-192, miR-194, miR-206, miR-215, or miR-346.

In addition or alternatively, any of the following may be included in the group from which the miRNA inhibitor molecule (i) may be chosen: Let-7a, Let-7b, Let-7c, Let-7d, Let-7g, miR-7, mir-9, miR-10a, miR-10b, miR-18, miR-19a, miR-17-3p, miR-20, miR-23b, mir-25, miR-26a, miR-26a, mir-30e-5p, mir-31, mir-32, mir-92, mir-93, miR-100, miR-125a, miR-125b, mir-127, miR-128, miR-129, miR-130a, mir-135, mir-138, mir-139, miR-140, mir-141, mir-143, mir-145, mir-146, miR-150, mir-154, mir-155, mir-181a, miR-182, mir-186, miR-187, miR-188, mir-190, mir-191, mir-193, mir-196, mir-197, mir-198, mir-199, mir-201, mir-204, mir-216, mir-218, miR-223, mir-293, miR-291-3p, miR-294, miR-295, miR-322, mir-333, mir-335, mir-338, mir-341, mir-350, mir-369, miR-373, mir-410, and mir-412.

In addition or alternatively, any of the following may be included in the group from which the miRNA molecule that corresponds to an miRNA sequence (ii) may be chosen: let7a-1, Let-7a, Let-7b, let7b-1, let7c, let7d, Let-7g, mir-9, mir-10a, mir-10b, mir-15a, mir-16, mir-21, mir-23a, mir-23b, mir-24, mir-25, mir-92, mir-95, mir-133a, mir-133a-2, mir-133b, mir-142, mir-152, mir-153, mir-155, mir-181a, mir-182, mir-183, mir-184, mir-186, mir-187, mir-191, mir-193, mir-194, mir-196, mir-199a-1, mir-200b, mir-204, mir-206, mir-211, mir-222, mir-223, mir-298, mir-328, mir-342, mir-371, and mir-412.

In other words, methods involve providing a synthetic miRNA inhibitor having a sequence that is at least 90% complementary to the 5' to 3' sequence of a corresponding miRNA that is mir-31, mir-92, mir-99a, mir-100, mir-125a, mir-129, mir-130a, mir-150, mir-187, miR-190, miR-191, miR-193, miR 204, mir-210, mir-211, mir-212, mir-213, mir-215, mir-216, mir-217, miR 218, mir-224, mir-292, mir-294, mir-320, mir-324, mir-325, mir-326, mir-330, mir-331, mir-338, mir-341, mir-369, mir-370, Let-7a, Let-7b, Let-7c, Let-7d, Let-7g, miR-7, mir-9, miR-10a, miR-10b, miR-18, miR-19a, miR-17-3p, miR-20, miR-23b, mir-25, miR-26a, miR-26a, mir-30e-5p, mir-31, mir-32, mir-92, mir-93, miR-100, miR-125a, miR-125b, mir-127, miR-128, miR-129, miR-130a, mir-135, mir-138, mir-139, miR-140, mir-141, mir-143, mir-145, mir-146, miR-150, mir-154, mir-155, mir-181a, miR-182, mir-186, miR-187, miR-188, mir-190, mir-191, mir-193, mir-196, mir-197, mir-198, mir-199, mir-201, mir-204, mir-216, mir-218, miR-223, mir-293, miR-291-3p, miR-294, miR-295, miR-322, mir-333, mir-335, mir-338, mir-341, mir-350, mir-369, miR-373, mir-410, or mir-412. Alternatively or additionally, methods involve providing a synthetic or nonsynthetic miRNA molecule that corresponds to miR-15a, miR-16, miR 21, miR 24, miR-96, miR-101, miR-105, miR-124, miR-126, miR-142, miR-147, miR-192, miR-194, miR-206, miR-215, miR-346, let7a-1, Let-7a, Let-7b, let7b-1, let7c, let7d, Let-7g, mir-9, mir-10a, mir-10b, mir-15a, mir-16, mir-21, mir-23a, mir-23b, mir-24, mir-25, mir-92, mir-95, mir-133a, mir-133a-2, mir-133b, mir-142, mir-152, mir-153, mir-155, mir-181a, mir-182, mir-183, mir-184, mir-186, mir-187, mir-191, mir-193, mir-194, mir-196, mir-199a-1, mir-200b, mir-204, mir-206, mir-211, mir-222, mir-223, mir-298, mir-328, mir-342, mir-371, or mir-412. Methods for reducing or inhibiting cell proliferation can be used as a treatment for diseases and conditions that include, but are not limited to, hyperproliferative diseases, such as cancer.

The present invention also concerns methods for inducing or increasing cell proliferation in a cell comprising introducing into or providing to the cell an effective amount of i) an miRNA inhibitor molecule or ii) a synthetic or nonsynthetic miRNA molecule that corresponds to an miRNA sequence. In certain embodiments the methods involves introducing into or providing the cell an effective amount of i) an miRNA inhibitor corresponding to let7a-1, Let-7a, Let-7b, let7b-1, let7c, let7d, Let-7g, mir-9, mir-10a, mir-10b, mir-15a, mir-16, mir-21, mir-23a, mir-23b, mir-24, mir-25, mir-92, mir-95, mir-133a, mir-133a-2, mir-133b, mir-142, mir-152, mir-153, mir-155, mir-181a, mir-182, mir-183, mir-184, mir-186, mir-187, mir-191, mir-193, mir-194, mir-196, mir-199a-1, mir-200b, mir-204, mir-206, mir-211, mir-222, mir-223, mir-298, mir-328, mir-342, mir-371, and mir-412; or ii) a miRNA molecule corresponding to Let-7a, Let-7b, Let-7c, Let-7d, Let-7g, miR-7, mir-9, miR-10a, miR-10b, miR-15a, miR-18, miR-19a, miR-17-3p, miR-20, miR-23b, mir-25, miR-26a, miR-26a, mir-30e-5p, mir-31, mir-32, mir-92, mir-93, miR-100, miR-125a, miR-125b, miR-126, mir-127, miR-128, miR-129, mir-130a, mir-135, mir-138, mir-139, miR-140, mir-141, mir-143, mir-145, mir-146, miR-150, mir-154, mir-155, mir-181a, miR-182, mir-186, miR-187, miR-188, mir-190, mir-191, mir-193, mir-194, mir-196, mir-197, mir-198, mir-199, mir-201, mir-204, mir-216, mir-218, miR-223, mir-293, miR-291-3p, miR-294, miR-295, miR-322, mir-333, mir-335, mir-338, mir-341, mir-350, mir-369, miR-373, mir-410, and mir-412. Alternatively or additionally, the group of miRNA inhibitors includes miR-15a, miR-16, miR 21, miR 24, miR-96, miR-101, miR-105, miR-124, miR-126, miR-142, miR-147, miR-192, miR-194, miR-206, miR-215, or miR-346 and the group of miRNAs molecules corresponding to miRNAs includes mir-31, mir-92, mir-99a, mir-100, mir-125a, mir-129, mir-130a, mir-150, mir-187, miR-190, miR-191, miR-193, miR 204, mir-210, mir-211, mir-212, mir-213, mir-215, mir-216, mir-217, miR 218, mir-224, mir-292, mir-294, mir-320, mir-324, mir-325, mir-326, mir-330, mir-331, mir-338, mir-341, mir-369, and mir-370.

Such methods can be used for the treatment of wounds, burns, ischemia, or any other condition, disease, or symptom in which cell proliferation is desirable.

It will be understood in methods of the invention that a cell or other biological matter such as an organism (including patients) can be provided an miRNA or miRNA molecule corresponding to a particular miRNA by administering to the cell or organism a nucleic acid molecule that functions as the corresponding miRNA once inside the cell. The form of the molecule provided to the cell may not be the form that acts an an miRNA once inside the cell. Thus, it is contemplated that in some embodiments, biological matter is provided a synthetic miRNA or a nonsynthetic miRNA, such as one that becomes processed into a mature and active miRNA once it has access to the cell's miRNA processing machinery. In certain embodiments, it is specifically contemplated that the miRNA molecule provided to the biological matter is not a mature miRNA molecule but a nucleic acid molecule that can be processed into the mature miRNA once it is accessible to miRNA processing machinery. The term "nonsynthetic" in the context of miRNA means that the miRNA is not "synthetic," as defined herein. Furthermore, it is contemplated that in embodiments of the invention that concern the use of synthetic miRNAs, the use of corresponding nonsynthetic miRNAs is also considered an aspect of the invention, and vice versa.

In other embodiments, the methods involve reducing cell viability comprising introducing into or providing to the cell an effective amount of i) an miRNA inhibitor molecule or ii) a synthetic or nonsynthetic miRNA molecule that corresponds to an miRNA sequence. In certain embodiments the methods involves introducing into one or more cells an effective amount of i) an miRNA inhibitor corresponding to miR-107, miR-133, miR-137, miR-152, miR-155, miR-181a, miR-191, miR-203, or miR-215; or ii) an miRNA molecule corresponding to let-7a, let-7b, mir-1, mir-7, miR-10b, miR-17-3p, miR-19a, mir-23, mir-24, mir-27a, miR-29a, miR-30a-3p, mir-31, mir-32, miR-34a, miR-101, miR-107, miR-108, miR-122, mir-124, miR-133a, miR-134, miR-135, miR-139, mir-140, miR-141, miR-145, mir-150, mir-192, mir-193, mir-195, mir-206, mir-208, mir-210, mir-210, mir-292-3p, mir-293, mir-297, mir-299, mir-329, mir-337, mir-337, mir-345, mir-346, and mir-409. Alternatively or additionally, the group of miRNA inhibitors (group i) includes let-7a, let-7b, let-7c, let-7d, let-7g, miR-10a, miR-10b, miR-15a, miR-17-3p, miR-18, miR-19a, miR-20, mir-23a, mir-23b, mir-24, miR-25, miR-26a, mir-32, miR-107, miR-125a, miR-126, mir-128, miR-129, miR-133, miR-137, mir-139, miR-143, miR-152, miR-155, miR-181a, miR-182, miR-191, miR-203, miR-215, and mir-331

Other aspects of the invention include a method for increasing cell viability comprising introducing into or providing to the cell an effective amount of i) an miRNA inhibitor molecule or ii) a synthetic or nonsynthetic miRNA molecule that corresponds to an miRNA sequence. In certain embodiments the methods involves introducing into one or more cells an effective amount of i) an miRNA inhibitor corresponding to miR-7, miR-19a, miR-23, miR-24, miR-27a, miR-31, miR-32, miR-134, miR-140, miR-150, miR-192, or miR-193; or ii) an miRNA molecule corresponding to let-7a, let-7b, let-7c, let-7d, let-7g, miR-10a, miR-10b, miR-15a, miR-17-3p, miR-18, miR-19a, miR-20, mir-23a, mir-23b, mir-24, miR-25, miR-26a, mir-32, miR-107, miR-125a, miR-126, mir-128, miR-129, miR-133, miR-137, mir-139, miR-143, miR-152, miR-155, miR-181a, miR-182, miR-191, miR-203, miR-215, and mir-331. Alternatively or additionally, the group of miRNA inhibitors (group i) includes let-7a, let-7b, mir-1, mir-7, miR-10b, miR-17-3p, miR-19a, mir-23, mir-24, mir-27a, miR-29a, miR-30a-3p, mir-31, mir-32, miR-34a, miR-101, miR-107, miR-108, miR-122, mir-124, miR-133a, miR-134, miR-135, miR-139, mir-140, miR-141, miR-145, mir-150, mir-192, mir-193, mir-195, mir-206, mir-208, mir-210, mir-210, mir-292-3p, mir-293, mir-297, mir-299, mir-329, mir-337, mir-337, mir-345, mir-346, or mir-409, and the group of miRNAs molecules corresponding to miRNAs (group ii) includes. The present invention also concerns a method for inducing apoptosis in a cell comprising introducing into or providing to the cell an effective amount of i) an miRNA inhibitor molecule or ii) a synthetic or nonsynthetic miRNA molecule that corresponds to an miRNA sequence. In certain embodiments the methods involves introducing into the cell an effective amount of i) an miRNA inhibitor corresponding to miR-31 or miR-214; or ii) an miRNA molecule corresponding to let-7b, let-7g, mir-1, mir-1d, mir-7, mir-10a, miR-10b, miR-17-3p, miR-19a, miR-28, miR-28, miR-28, miR-29a, miR-32, miR-34a, miR-122, mir-148, mir-149, mir-154, mir-184, mir-186, mir-188, mir-192, mir-195, mir-196, mir-199a, mir-204, mir-208, mir-210, mir-211, mir-212, mir-214, mir-215, mir-216, mir-217, mir-218, mir-293, mir-296, mir-299, mir-321, mir-328, or mir-344. Alternatively or additionally, the group of miRNA inhibitors (group i) includes Let-7b, mir-21, mir-23b, mir-25, miR-26a, mir-28, mir-29a, mir-31, miR-32, miR-30a-3p, mir-34a, mir-96, miR-98, mir-100, mir-101, mir-105, mir-108, miR-125b, miR-126, mir-126, mir-128, mir-137, miR-143, miR-155, mir-207, mir-214, mir-216, mir-223, mir-292-3p, mir-328, mir-335, mir-340, mir-341, mir-367, mir-368, mir-380-3p, and mir-410.

Methods for inducing apoptosis have a number of therapeutic applications including, but not limited to, the treatment of cancer.

Other embodiments of the invention involve a method for inhibiting apoptosis in a cell comprising introducing into or providing to the cell an effective amount of i) an miRNA inhibitor molecule or ii) a synthetic or nonsynthetic miRNA molecule that corresponds to an miRNA sequence. In certain embodiments the methods involves introducing into the cell an effective amount of i) an miRNA inhibitor corresponding to miR-7, miR-1-2, miR-148, miR-195, miR-196, miR-199a, miR-204, miR-210, miR-211, miR-212, miR-215, miR-216, miR-218, miR-296, or miR-321; or ii) an miRNA molecule corresponding to Let-7b, mir-21, mir-23b, mir-25, miR-26a, mir-28, mir-29a, mir-31, miR-32, mir-30a-3p, mir-34a, mir-96, miR-98, mir-100, mir-101, mir-105, mir-108, miR-125b, miR-126, mir-126, mir-128, mir-137, miR-143, miR-155, mir-207, mir-214, mir-216, mir-223, mir-292-3p, mir-328, mir-335, mir-340, mir-341, mir-367, mir-368, mir-380-3p, or mir-410. Alternatively or additionally, the group of miRNA inhibitors (group i) includes let-7b, let-7g, mir-1, mir-1d, mir-7, mir-10a, miR-10b, miR-17-3p, miR-19a, miR-28, miR-28, miR-28, miR-29a, miR-32, miR-34a, miR-122, mir-148, mir-149, mir-154, mir-184, mir-186, mir-188, mir-192, mir-195, mir-196, mir-199a, mir-204, mir-208, mir-210, mir-211, mir-212, mir-214, mir-215, mir-216, mir-217, mir-218, mir-293, mir-296, mir-299, mir-321, mir-328, or mir-344.

The present invention also concerns using miRNA compositions to treat diseases or conditions or to prepare therapeutics for the treatment of diseases or conditions. In some embodiments, the invention involves one or more human miRNA selected from the group consisting of let-7, miR-10a, miR-15a, miR-16, miR-17, miR-21, miR-22, miR-23, miR-24, miR-26a, miR-29b, miR-30a, miR-96, miR-101, miR-105, miR-106, miR-124, miR-125a, miR-126, miR-130, miR130a, miR-133, miR-142, miR-143, miR-144, miR-145, miR-147, miR-181a, miR-182, miR-183, miR-188, miR-189, miR-192, miR-194, miR-195, miR-199a, miR-200b, miR-201, miR-205, miR-219, 206, miR-215, miR-219, miR-223, miR-224, miR-321, miR-328, miR-331, miR-342. and miR-219,346. It is contemplated that 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 more miRNA (or any range derivable therein) may be used for these embodiments. In certain embodiments, methods involve one or more miRNA inhibitors and/or an miRNA molecules corresponding to any of these miRNAs, particularly for the treatment or prevention of cancer. Cancer includes, but is not limited to, malignant cancers, tumors, metastatic cancers, unresectable cancers, chemo- and/or radiation-resistant cancers, and terminal cancers.

In some embodiments of the invention, methods involve one or more miRNA inhibitors and/or an miRNA molecules corresponding to miR-17, miR-21, miR-126, miR-143, miR-145, miR-188, miR-200b, miR-219, or miR-331. In certain embodiments, methods involve one or more of 1) an inhibitor of miR-17, miR-21, miR-182, miR-183, miR-200b, miR-205, miR-223, and/or miR-224; and/or 2) an miRNA corresponding to let-7, miR-10a, miR-16, miR-22, miR-23, miR-24, miR-26a, miR-29b, miR-30a, miR-106, miR-125a, miR-126, miR-130, miR-133, miR-143, miR-144, miR-145, miR-181a, miR-188, miR-219, miR-192, miR-194, miR-195, miR-199a, mmu-miR-201, miR-215, miR-321, miR-328, miR-331, and/or miR-342. Such methods can be used, in some embodiments to treat cancer, including specific cancers. Additionally, an miRNA corresponding to one or more of miR-15a, miR-16, miR-96, miR-101, miR-105, miR-124, miR-126, miR-142, miR-147, miR-192, miR-194, miR-206, miR-215, or miR-346 may be used to treat cancer or inhibit cell proliferation. It is contemplated that these miRNAs may be used regardless of the source of the cell in which proliferation is undesirable.

It will be understood that shorthand notations are employed such that a generic description of an miRNA refers to any of its gene family members (distinguished by a number), unless otherwise indicated. It is understood by those of skill in the art that a "gene family" refers to a group of genes having the same miRNA coding sequence. Typically, members of a gene family are identified by a number following the initial designation. For example, miR-16-1 and miR-16-2 are members of the miR-16 gene family and "mir-7" refers to miR-7-1, miR-7-2 and miR-7-3. Moreover, unless otherwise indicated, a shorthand notation refers to related miRNAs (distinguished by a letter). Thus, "let-7," for example, refers to let-7a-1, let7-a-2, let-7b, let-7c, let-7d, let-7e, let-7f-1, and let-7f-2." Exceptions to this shorthand notations will be otherwise identified.

The present invention concerns treating breast cancer or decreasing cell proliferation of breast cancer cells by introducing into or providing to the cell an effective amount of i) an miRNA inhibitor molecule or ii) a synthetic or nonsynthetic miRNA molecule that corresponds to an miRNA sequence. In certain embodiments the methods involves providing an effective amount of at least 1) one or more miRNA inhibitors corresponding to miR-21, miR-15a, miR-16, miR-24, and/or miR-25, and/or 2) one or more miRNAs corresponding to miR-99, miR-100, miR-205, miR-197, miR-126, miR-143, miR-145 and/or miR-321. Alternatively or additionally, the miRNAs molecules corresponding to miRNAs (group ii) can include mir-27a, mir-92, mir-96, mir-98, mir-99a, mir-101, mir-105, mir-124, mir-126, mir-129, mir-132, mir-142, mir-147, mir-192, mir-201, mir-206, mir-208, mir-210, mir-211, mir-214, mir-215, mir-219, mir-220, mir-221, mir-223, mir-297, mir-329, mir-331, mir-345, mir-346, mir-409, or mir-411.

It will be understand that the term "providing" an agent is used to include "administering" the agent to a patient.

The present invention also relates to treating colon cancer by introducing into or providing to a colon cancer cell an effective amount of i) an miRNA inhibitor molecule or ii) a synthetic or nonsynthetic miRNA molecule that corresponds to an miRNA sequence. In certain embodiments the methods involves providing 1) one or more miRNA inhibitors corresponding to miR-21, miR-106, miR-200b, miR-223, miR-224, miR-31, and/or miR-17; and/or 2) one or more miRNAs corresponding to miR-145, miR-143, miR-133, miR-342, miR-125a, miR-195, miR-30a, miR-10a, miR-130, miR-192, miR-194, miR-215, miR-144, miR-23, miR-26a, miR-126, miR-199a, miR-188, miR-331, and/or miR-21.

Moreover, methods for treating thyroid cancer involve introducing into or providing to a thyroid cancer cell an effective amount of i) an miRNA inhibitor molecule or ii) a synthetic or nonsynthetic miRNA molecule that corresponds to an miRNA sequence. In certain embodiments the methods involves providing to the patient 1) one or more miRNA inhibitors corresponding to miR-21 miR-125, miR-24, miR-200b, miR-29b, miR-221, miR-222, miR-224, miR-10a, and/or miR-183; and/or 2) one or more miRNAs corresponding to miR-145, miR-22, miR-331, miR-126, miR-30a, miR-199a, miR-223, and/or miR-321.

The treatment of lung cancer is also contemplated as part of the invention. Methods involve introducing into or providing to a lung cancer cell an effective amount of i) an miRNA inhibitor molecule or ii) a synthetic or nonsynthetic miRNA molecule that corresponds to an miRNA sequence. In certain embodiments the methods involves providing to the patient 1) one or more miRNA inhibitors corresponding to miR-223, miR-106, miR-21, miR-200b, miR-321, miR-182, miR-183, miR-17, and/or miR-205; and/or 2) one or more miRNAs corresponding to miR-130a, miR-145, miR-126, miR-331, miR-342, miR-143, Let-7, miR-30a, miR-16, miR-26a, miR-125a, miR-29b, miR-24, miR-328, miR-195, miR-22, miR-181a, miR-331, and/or miR-321. Alternatively or additionally, the group of miRNA inhibitors (group 1)

includes mir-30e-5p, mir-25, mir-32, mir-92, mir-130a, mir-135, mir-145, mir-216, mir-293, mir-294, mir-333, mir-335, mir-338, mir-341, mir-350, mir-369, or mir-412, and the group of miRNAs molecules corresponding to miRNAs (group 2) includes ambi-mir7100, Let-7b, Let-7d, Let-7g, mir-7, mir-15a, mir-16, mir-22, mir-28, mir-29a, mir-34a, mir-96, mir-101, mir-105, mir-108, mir-122, mir-124, mir-125a, mir-125b, mir-126, mir-128, mir-129, mir-132, mir-133A, mir-136, mir-137, mir-141, mir-142, mir-147, mir-149, mir-151, mir-152, mir-182, mir-183, mir-186, mir-188, mir-192, mir-193, mir-195, mir-223, mir-292-3p, mir-337, mir-337, mir-344, mir-345, mir-346, mir-377, or mir-526b*.

The present invention concerns treating cervical cancer or decreasing cell proliferation of cervical cancer cells by providing an effective amount of at least 1) one or more miRNA inhibitors corresponding to Let-7a, Let-7b, Let-7c, Let-7d, Let-7g, mir-9, mir-145, mir-155, mir-181a, mir-186, mir-190, mir-191, or mir-199, and/or 2) one or more miRNAs corresponding to mir-1, mir-34a, mir-101, mir-124, mir-192, mir-193, mir-195, mir-201, mir-206, mir-208, mir-210, mir-215, mir-292-3p, mir-293, mir-297, mir-299, mir-337, mir-339, mir-340, mir-344, mir-345, mir-367, or mir-409.

The present invention concerns treating prostate cancer or decreasing cell proliferation of prostate cancer cells by introducing into or providing to the cell an effective amount of i) an miRNA inhibitor molecule or ii) a synthetic or nonsynthetic miRNA molecule that corresponds to an miRNA sequence. In certain embodiments the methods involves providing an effective amount of at least 1) one or more miRNA inhibitors corresponding to Let-7a, Let-7b, mir-93, mir-127, mir-154, mir-181a, mir-194, mir-198, mir-199, mir-201, or mir-369, and/or 2) one or more miRNAs corresponding to mir-15a, mir-16, mir-27a, mir-28, mir-30a-3p, mir-34a, mir-101, mir-103, mir-105, mir-107, mir-124, mir-126, mir-128, mir-129, mir-132, mir-135, mir-137, mir-141, mir-142, mir-147, or mir-297.

The present invention concerns treating skin cancer or decreasing cell proliferation of skin cancer cells by introducing into or providing to the cell an effective amount of i) an miRNA inhibitor molecule or ii) a synthetic or nonsynthetic miRNA molecule that corresponds to an miRNA sequence. In certain embodiments the methods involves providing an effective amount of at least 1) one or more miRNA inhibitors corresponding to miR-26a, miR-125a, miR-128, mir-138, mir-139, mir-141, mir-143, miR-145, mir-146, miR-150, miR-187, miR-188, mir-190, mir-196, mir-197, mir-198, mir-199, miR-201, mir-204, mir-216, miR-223, miR-291-3p, miR-294, miR-295, miR-322, miR-373, mir-410, or mir-412, and/or 2) one or more miRNAs corresponding to let 7a, mir-1, mir-7, mir-15a, mir-16, mir-20, mir-26a, mir-28, mir-34a, mir-96, mir-101, mir-105, miR-105, mir-124, mir-126, mir-128, mir-132, mir-133A, mir-136, mir-137, mir-141, mir-142, mir-144, miR-147, mir-154, mir-181a, mir-192, mir-193, miR-195, mir-201, mir-206, mir-206, mir-215, mir-221, mir-223, mir-291, miR-297, mir-302, miR-324-3p, mir-329, mir-330, miR-337, mir-346, mir-346, mir-373, mu-mir-376b, mir-380-3p, or mir-411. The present invention concerns treating leukemia or decreasing cell proliferation of cancerous T cells by introducing into or providing to the cell an effective amount of i) an miRNA inhibitor molecule or ii) a synthetic or nonsynthetic miRNA molecule that corresponds to an miRNA sequence. In certain embodiments the methods involves providing an effective amount of at least 1) one or more miRNA inhibitors corresponding to miR-15a, miR-23b, miR-25, miR-26a, miR-100, miR-125b, miR-126, miR-129, miR-140, miR-143, or miR-155, and/or 2) one or more miRNAs corresponding to let-7a, let-7b, miR-10b, miR-17-3p, miR-29a, miR-30a-3p, miR-34a, miR-101, miR-122, or miR-133a. Alternatively or additionally, the group of miRNA inhibitors (group 1) includes let-7a, let-7b, let-7c, let-7d, let-7g, miR-7, miR-10a, miR-10b, miR-15a, miR-17-3p, miR-18, miR-19a, miR-20, miR-125a, miR-126, or miR-182, and the group of miRNAs molecules corresponding to miRNAs (group 2) includes miR-107, miR-134, miR-135, miR-139, miR-141, or miR-145. Moreover, such methods can extend to T-cells generally.

In addition to any miRNAs disclosed herein in the context of decreasing cell proliferation, embodiments of the invention include methods for decreasing cell proliferation comprising introducing into or providing to the cell an effective amount of i) an miRNA inhibitor molecule or ii) a synthetic or nonsynthetic miRNA molecule that corresponds to an miRNA sequence. In certain embodiments the methods involves providing or introducing an effective amount of at least 1) one or more miRNA inhibitors corresponding to Let-7a, Let-7b, Let-7c, Let-7d, Let-7g, miR-7, mir-9, miR-10a, miR-10b, miR-15a, miR-18, miR-19a, miR-17-3p, miR-20, miR-23b, mir-25, miR-25, miR-26a, miR-26a, mir-30e-5p, mir-32, mir-92, mir-93, mir-100, miR-125a, miR-125b, miR-126, mir-127, miR-128, miR-129, miR-130a, mir-135, mir-138, mir-139, miR-140, mir-141, mir-143, mir-145, mir-146, miR-150, mir-154, mir-155, mir-181a, miR-182, mir-186, miR-187, miR-188, mir-190, mir-191, mir-194, mir-196, mir-197, mir-198, mir-199, mir-201, mir-204, mir-216, miR-223, mir-293, miR-291-3p, miR-294, miR-295, miR-322, mir-333, mir-335, mir-338, mir-341, mir-350, mir-369, miR-373, mir-410, or mir-412, and/or 2) one or more miRNAs corresponding to ambi-mir7100, let 7a, let-7b, let-7d, let-7g, mir-1, mir-7, miR-10b, miR-15a, mir-16, miR-17-3p, mir-20, mir-22, mir-26a, mir-27a, mir-28, mir-28, miR-29a, mir-30a-3p, mir-34a, mir-92, mir-96, mir-98, mir-99a, mir-101, mir-103, mir-105, mir-107, mir-108, mir-122, mir-124, mir-125a, mir-125b, mir-126, mir-128, mir-129, mir-132, miR-133a, miR-134, mir-135, mir-136, mir-137, miR-139, mir-141, mir-142, mir-144, miR-145, mir-147, mir-149, mir-151, mir-152, mir-154, mir-181a, mir-182, mir-183, mir-186, mir-188, mir-192, mir-193, mir-195, mir-195, mir-201, mir-206, mir-208, mir-210, mir-211, mir-214, mir-215, mir-219, mir-220, mir-221, mir-223, mir-291, mir-292-3p, mir-293, mir-297, mir-299, mir-302, miR-324-3p, mir-329, mir-330, mir-331, mir-337, mir-339, mir-340, mir-344, mir-345, mir-346, mir-367, mir-373, miR-376b, mir-377, mir-380-3p, mir-409, mir-411, or mir-526b*. It is particularly contemplated that such methods may be employed in the context of treating cancer or another disease or condition in which cell proliferation plays a role, such as hyperproliferative diseases and conditions.

The present invention also concerns embodiments methods for increasing cell proliferation comprising introducing into or providing to the cell an effective amount of i) an miRNA inhibitor molecule or ii) a synthetic or nonsynthetic miRNA molecule that corresponds to an miRNA sequence. In certain embodiments the methods involves providing or introducing an effective amount of at least 1) one or more miRNA inhibitors corresponding to ambi-mir7100, let 7a, let-7b, let-7d, let-7g, mir-1, mir-7, miR-10b, miR-15a, mir-16, miR-17-3p, mir-20, mir-22, mir-26a, mir-27a, mir-28, mir-28, miR-29a, mir-30a-3p, mir-34a, mir-92, mir-96, mir-98, mir-99a, mir-101, mir-103, mir-105, mir-107, mir-108, mir-122, mir-124, mir-125a, mir-125b, mir-126, mir-128, mir-129, mir-132, miR-133a, miR-134, mir-135, mir-136, mir-137, miR-139, mir-141, mir-142, mir-144, miR-145, mir-147, mir-149, mir-151, mir-152, mir-154, mir-181a, mir-182, mir-183, mir-186, mir-188, mir-192, mir-193, mir-195, mir-195, mir-201, mir-206, mir-208, mir-210, mir-211, mir-214, mir-215, mir-219, mir-220, mir-221, mir-223, mir-291, mir-292-3p, mir-293, mir-297, mir-299, mir-302, miR-324-3p, mir-329, mir-330, mir-331, mir-337, mir-339, mir-340, mir-344, mir-345, mir-346, mir-367, mir-373, miR-376b, mir-377, mir-380-3p, mir-409, mir-411, or mir-526b*, and/or 2) one or more miRNAs corresponding to Let-7a, Let-7b, Let-7c, Let-7d, Let-7g, miR-7, mir-9, miR-10a, miR-10b, miR-15a, miR-18, miR-19a, miR-17-3p, miR-20, miR-23b, mir-25, miR-25, miR-26a, miR-26a, mir-30e-5p, mir-32, mir-92, mir-93, miR-100, miR-125a, miR-125b, miR-126, mir-127, miR-128, miR-129, mir-130a, mir-135, mir-138, mir-139, miR-140, mir-141, mir-143, mir-145, mir-146, miR-150, mir-154, mir-155, mir-181a, miR-182, mir-186, miR-187, miR-188, mir-190, mir-191, mir-194, mir-196, mir-197, mir-198, mir-199, mir-201, mir-204, mir-216, miR-223, mir-293, miR-291-3p, miR-294, miR-295, miR-322, mir-333, mir-335, mir-338, mir-341, mir-350, mir-369, miR-373, mir-410, or mir-412. While not limited to such an embodiment, one use for such a method is to increase or induce proliferation of normal cells or other desirable cells in the context of pretreatment or therapy.

Other aspects of the invention include the treatment of systemic lupus erythrematosus (SLE). In certain embodiments, methods concern introducing into or providing to a patient an effective amount of i) an miRNA inhibitor molecule or ii) a synthetic or nonsynthetic miRNA molecule that corresponds to an miRNA sequence. In certain embodiments the methods involves providing to a patient with SLE or suspect of having SLE 1) one or more miRNA inhibitors corresponding to miR-21, miR-223, and/or mir-342 expression; and/or 2) one or more miRNAs corresponding to miR-95, miR-105, miR-137, miR-186, miR-188, miR-199, miR-211, miR-215, mu-miR-290, miR-301, and/or miR-331.

Treatment or prevention of prion diseases is included in methods of the invention. In some cases, method include introducing into or providing to a patient with a prion disease an effective amount of i) an miRNA inhibitor molecule or ii) a synthetic or nonsynthetic miRNA molecule that corresponds to an miRNA sequence. In certain embodiments the methods involves providing to a patient 1) one or more miRNA inhibitors corresponding miR-7, miR-9, miR-16, miR-24, miR-26A, miR-27A, and/or miR-130A; and/or 2) one or more miRNAs corresponding to miR-95 and/or miR-135A. The patient may be one diagnosed with a prion disease, one at risk for a prion disease, or one suspected of having a prion disease. It is specifically contemplated that in some embodiments of the invention, a nucleic acid molecule corresponding to an miRNA is double stranded, wherein both strands have the sequence of the mature miRNA it corresponds to. Such a molecule may be designated with an "as" suffix in embodiments of the invention. For example, a nucleic acid molecule called miR-9-as was used in some experiments described herein. It is contemplated that in some embodiments, a nucleic acid molecule is an miRNA-as molecule.

The present invention also concerns patients diagnosed as having ischemia, those at risk for ischemia, those suspected of having ischemia, or patients with symptoms of ischemia. Methods involve introducing into or providing to a patient an effective amount of i) an miRNA inhibitor molecule or ii) a synthetic or nonsynthetic miRNA molecule that corresponds to an miRNA sequence. In certain embodiments the methods involves providing to a patient 1) one or more miRNA inhibitors corresponding to miR-28, miR-30A, miR-31, miR-138, miR-139, miR-140, miR-291 and/or mmu-miR-298; and/or 2) one or more miRNAs corresponding to Let-7f-2 and/or miR-16.

In certain experiments, a synthetic miRNA in which both the sense and antisense strand are derived from a single precursor miRNA is used in methods and compositions of the invention. These are frequently designated with a "P" suffix in which "5P" indicates that the mature miRNA derives from the 5' end of the precursor and a corresponding "3P" indicates that it dferives from the 3' end of the precursor, as described on the world wide web at sanger-.ac.uk/cgi-bin/rfam/mirna. Moreover, in some embodiments, an miRNA that does not correspond to a known human miRNA was evaluated. It is contemplated that these non-human miRNAs may be used in embodiments of the invention or that there may exist a human miRNA that is homologous to the non-human miRNA.

The present invention in some embodiments concerns methods for reducing cell viability comprising introducing into or providing to the cell an effective amount of i) an miRNA inhibitor molecule or ii) a synthetic or nonsynthetic miRNA molecule that corresponds to an miRNA sequence. In certain embodiments the methods involves providing to or introducing into cells an effective amount of 1) at least one nucleic acid molecule capable of being processed into a mature miRNA when it is inside the cell, wherein the mature miRNA is let-7a, let-7b, miR-1, miR-10b, miR-17, miR-19a, miR-20, miR-28, miR-29a, miR-30a, miR-32, miR-34a, miR-96, miR-101, miR-122, miR-124, miR-132, miR-133a, miR-134, miR-139, miR-140, miR-144, miR-145, miR-147, miR-155, miR-182, miR-183, miR-184, miR-186, miR-190, miR-193, miR-197, miR-206, miR-208, miR-210, miR-216, miR-217, miR-224, mu-miR-292, mu-miR-293, mu-miR-298, miR-299, miR-301, mu-miR-329, miR-337, mu-miR-344, miR-345, miR-346, miR-369, mu-miR-380, or mu-miR-409; or 2) at least one miRNA inhibitor corresponding to let-7a, let-7b, let-7c, miR-9, miR-10a, miR-10b, miR-15a, miR-17, miR-18, miR-20, mir-23b, miR-25, miR-26a, miR-98, miR-100, miR-125a, miR-125b, miR-126, miR-129, miR-140, miR-141, miR-143, miR-155, or miR-181-a. The term "reducing cell viability" means reducing the number of live cells.

Methods concerning cell viability and cell proliferation may generally be used for therapeutics, diagnostics, creating cell lines with interesting research properties, and inducing differentiation. miRNAs that selectively reduce the proliferation of cancer cells may be employed as therapeutics since they can be delivered to cancer and non-cancer cells alike but will only affect the growth of the cancerous cells. In addition, methods may be used to halt or prevent metastasis or reduce the number of metastases.

It is contemplated in some embodiments that the cell in which the effect is desired (referred to as a "targeted cell"), such as a reduction in cell viability, may be a cell that is diseased or involved in maintaining, promoting, or causing a disease or condition. In certain embodiments, the cell is a cancer cell, while in other embodiments, it is contemplated to be a healthy (non-diseased) cell. In certain embodiments, a targeted cell is in an organism.

Moreover, it is particularly contemplated that a nucleic acid molecule capable of being processed into a mature miRNA when it is inside the cell is a synthetic miRNA in some embodiments of the invention.

In other embodiments, the present invention involves methods for increasing cell viability comprising introducing into or providing to the cell an effective amount of i) an miRNA inhibitor molecule or ii) a synthetic or nonsynthetic miRNA molecule that corresponds to an miRNA sequence. In certain embodiments the methods involves providing to or introducing into cells an effective amount of 1) at least one nucleic acid molecule capable of being processed into a mature miRNA when it is inside the cell, wherein the mature miRNA is let-7a, let-7b, let-7c, miR-9, miR-10a, miR-10b, miR-15a, miR-17, miR-18, miR-20, mir-23b, miR-25, miR-26a, miR-98, miR-100, miR-125a, miR-125b, miR-126, miR-129, miR-140, miR-141, miR-143, miR-155, or miR-181-a; or 2) at least one miRNA inhibitor corresponding to let-7a, let-7b, miR-1, miR-10b, miR-17, miR-19a, miR-20, miR-28, miR-29a, miR-30a, miR-32, miR-34a, miR-96, miR-101, miR-122, miR-124, miR-132, miR-133a, miR-134, miR-139, miR-140, miR-144, miR-145, miR-147, miR-155, miR-182, miR-183, miR-184, miR-186, miR-190, miR-193, miR-197, miR-206, miR-208, miR-210, miR-216, miR-217, miR-224, mu-miR-292, mu-miR-293, mu-miR-298, miR-299, miR-301, mu-miR-329, miR-337, mu-miR-344, miR-345, miR-346, miR-369, mu-miR-380, or mu-miR-409. The term "increasing cell viability" means that cell death is inhibited. In particular embodiments, a cancer cell, such as a leukemia cell, is provided with an effective amount of a nucleic acid capable of being processed into a mature let-7a, let-7b, or miR-10b molecule.

Methods of the invention also relate to inhibiting cellular proliferation comprising introducing into or providing to the cell an effective amount of i) an miRNA inhibitor molecule or ii) a synthetic or nonsynthetic miRNA molecule that corresponds to an miRNA sequence. In certain embodiments the methods involves providing to or introducing into cells an effective amount of 1) at least one nucleic acid molecule capable of being processed into a mature miRNA when it is inside the cell, wherein the mature miRNA is let-7a, let-7b, let-7c, let-7d, let-7g, miR-1, miR-7, miR-15a, miR-16, miR-19a, miR-22, miR-28, miR-29a, miR-34a, miR-92, miR-96, miR-98, miR-101, miR-122, miR-124, miR-126, miR-129, miR-133b, miR-137, miR-147, miR-192, miR-193, miR-195, miR-205, miR-206, miR-208, miR-210, mu-miR-292, mu-miR-297, miR-299, miR-337, mu-miR-344, miR-345, or miR-346; or 2) at least one miRNA inhibitor corresponding to miR-25, miR-27a, miR-31, miR-32, miR-92, miR-139, miR-145, miR-198, miR-212, mu-miR-290, mu-miR-294, miR-323, miR-324, miR-325, miR-331, miR-335, mu-miR-351, miR-369, miR-370, or miR-373.

In some embodiments there are methods of increasing cellular proliferation comprising introducing into or providing to the cell an effective amount of i) an miRNA inhibitor molecule or ii) a synthetic or nonsynthetic miRNA molecule that corresponds to an miRNA sequence. In certain embodiments the methods involves providing to or introducing into cells an effective amount of 1) at least one nucleic acid molecule capable of being processed into a mature miRNA when it is inside the cell, wherein the mature miRNA is miR-25, miR-27a, miR-31, miR-32, miR-92, miR-139, miR-145, miR-198, miR-212, mu-miR-290, mu-miR-294, miR-323, miR-324, miR-325, miR-331, miR-335, mu-miR-351, miR-369, miR-370, or miR-373; or 2) at least one miRNA inhibitor corresponding to let-7a, let-7b, let-7c, let-7d, let-7g, miR-1, miR-7, miR-15a, miR-16, miR-19a, miR-22, miR-28, miR-29a, miR-34a, miR-92, miR-96, miR-98, miR-101, miR-122, miR-124, miR-126, miR-129, miR-133b, miR-137, miR-147, miR-192, miR-193, miR-195, miR-205, miR-206, miR-208, miR-210, mu-miR-292, mu-miR-297, miR-299, miR-337, mu-miR-344, miR-345, or miR-346.

The present invention also covers methods of inhibiting ERK activation introducing into or providing to a cell an effective amount of i) an miRNA inhibitor molecule or ii) a synthetic or nonsynthetic miRNA molecule that corresponds to an miRNA sequence. In certain embodiments the methods involves comprising providing to or introducing into cells an effective amount of one or more miRNA inhibitor corresponding to let-7a, mir-294, mir-295, miR-19a, miR-25, miR-96, miR-125a, miR-134, miR-148, miR-152, miR-206, miR-207, miR-210, miR-212, miR-216, miR-217, miR-218, miR-223, mu-miR-294, mu-miR-295, miR-301, miR-328, mu-miR-329, miR-339, miR-370, or miR-372.

In certain embodiments, it also covers methods of activating ERK by introducing into or providing to a cell an effective amount of i) an miRNA inhibitor molecule or ii) a synthetic or nonsynthetic miRNA molecule that corresponds to an miRNA sequence. In certain embodiments the methods involves providing or introducing into cells an effective amount of one or more nucleic acids capable of being processed into a mature miRNA when it is inside the cell, wherein the mature miRNA is miR-19a, miR-25, miR-96, miR-125a, miR-134, miR-148, miR-152, miR-206, miR-207, miR-210, miR-212, miR-216, miR-217, miR-218, miR-223, mu-miR-294, mu-miR-295, miR-301, miR-328, mu-miR-329, miR-339, miR-370, or miR-372. Alternatively or in addition to the mature miRNA is let-7, miR-19a, miR-25, miR-96, miR-125a, miR-134, miR-148, miR-152, miR-206, miR-207, miR-210, miR-212, miR-216, miR-217, miR-218, miR-223, mu-miR-294, mu-miR-295, miR-301, miR-328, mu-miR-329, miR-339, miR-370, or miR-372.

In other embodiments of the invention, there are methods of increasing the percentage of apoptotic cells in a population comprising introducing into or providing to the cells an effective amount of i) an miRNA inhibitor molecule or ii) a synthetic or nonsynthetic miRNA molecule that corresponds to an miRNA sequence. In certain embodiments the methods involves providing to or introducing into cells an effective amount of 1) one or more nucleic acid molecules capable of being processed into a mature miRNA when it is inside the cell, wherein the mature miRNA is let-7d, miR-22, miR-23a, miR-23b, miR-24, miR-27a, miR-31, miR-128, miR-181a, miR-196, miR-198, miR-199, miR-214, miR-217, mu-miR-290, mu-miR-293, miR-324, miR-338, or mu-miR-412; or 2) an miRNA inhibitor corresponding to miR-34a, miR-96, miR-101, miR-105, miR-126, miR-137, or mu-miR-292. It is specifically contemplated that the population of cells may be diseased or related to a disease or condition.

In further embodiments of the invention, there are methods of decreasing the percentage of apoptotic cells in a population comprising introducing into or providing to the cells an effective amount of i) an miRNA inhibitor molecule or ii) a synthetic or nonsynthetic miRNA molecule that corresponds to an miRNA sequence. In certain embodiments the methods involves providing to or introducing into cells an effective amount of 1) at least one nucleic acid molecule capable of being processed into a mature miRNA when it is inside the cell, wherein the mature miRNA is miR-34a, miR-96, miR-101, miR-105, miR-126, miR-137, or mu-miR-292; or 2) at least one miRNA inhibitor corresponding to let-7d, miR-22, miR-23a, miR-23b, miR-24, miR-27a, miR-31, miR-128, miR-181a, miR-196, miR-198, miR-199, miR-214, miR-217, mu-miR-290, mu-miR-293, miR-324, miR-338, or mu-miR-412. It is specifically contemplated that the population of cells may be involved in diseases or conditions involving atrophy or the decrease in the number of healthy cells as a result of apoptosis. One or more of the miRNAs that induce apoptosis may be introduced into abnormal cells like cancer cells to induce cell death, providing a therapeutic response. This could be especially beneficial if the apoptosis-inducing synthetic miRNAs were injected directly into tumor tissues or otherwise delivered with high efficiency to primary or metastatic cancer cells. These same miRNAs may be co-delivered with other therapeutic agents like chemotherapies to supplement their activities and evoke a therapeutic response. Alternatively, the miRNAs that reduce apoptosis may be introduced into normal cells at the same time that a chemotherapeutic reagent that induces apoptosis is introduced, providing some level of protection to the normal cells while the cancer cells are induced to undergo cell death. The miRNAs may also be used as targets for diagnostic assays or to differentiate cells or to create cell lines with interesting research properties.

Methods of the invention include methods for inhibiting or preventing hTert activity in a cell comprising introducing into or providing to the cell an effective amount of i) an miRNA inhibitor molecule or ii) a synthetic or nonsynthetic miRNA molecule that corresponds to an miRNA sequence. In certain embodiments the methods involves providing to or introducing into the cell an effective amount of at least one i) miRNA inhibitor corresponding to miR-15a, miR-16, miR-21, mir-24, miR-26a, miR-92, miR-105, miR-125a, miR-125b, miR-128, mir-147, miR-195, miR-207, miR-224, miR-295, mir-301, miR-337, mir-368, or mir-371 or ii) a nucleic acid molecule capable of being processed into a mature miRNA when it is inside the cell, wherein the mature miRNA is miR-26a, miR-147, mir-195, and mir-368. It is specifically contemplated that it is desirable to inhibit hTert activity in cancer cells or in a patient at risk for or suspected of having cancer. Methods of the invention include methods for inducing hTert activity in a cell comprising providing to or introducing into the cell an effective amount of at least one nucleic acid molecule capable of being processed into a mature miRNA when it is inside the cell, wherein the mature miRNA is miR-15a, miR-16, miR-21, mir-24, miR-26a, miR-92, miR-105, miR-125a, miR-125b, miR-128, mir-147, miR-195, miR-207, miR-224, miR-295, mir-301, miR-337, mir-368, or mir-371. Alternatively or additionally, hTert activity may be induced in a cell comprising providing to or introducing into the cell an miRNA inhibitor corresponding to miR-26a, miR-147, mir-195, or mir-368.

In other embodiments of the invention there are methods for identifying an miRNA that inhibits an hTert activating gene product comprising: a) introducing into a cell a candidate miRNA into a cell; and, b) assaying the level of hTert expression or hTert activity in the cell, wherein a reduction in hTert expression or activity compared to a cell lacking the miRNA identifies the miRNA as a potential inhibitor of an hTert activating gene product. In particular embodiments, the sequence of the candidate miRNA was previously evaluated for an ability to inhibit an hTert activating gene product. Computer programs and algorithms may be employed to assess whether a particular miRNA sequence can target a particular cellular gene. In certain embodiments, thTert activating gene product is selected from the group consisting of ACOX1, AKT1, APAF1, COX-5B, COX6, COX7B, CPDX, DUOX2, GPX1, GPX2, GPX4, LPO, MAPK1, MAPK4, MTCO1, NOX3, NOX5, PAOX, PPDX, PRKCA, PRKCD, and TNFRSF6.

These methods may be used for combating telomerase activity and cancer progression. The invention also includes methods for inhibiting stimulation of Stat3 in a cell comprising introducing into or providing to the cell an effective amount of i) an miRNA inhibitor molecule or ii) a synthetic or nonsynthetic miRNA molecule that corresponds to an miRNA sequence. In certain embodiments the methods involves providing to the cell an effective amount of an miRNA selected from the group consisting of mir-93, mir-100, mir-134, mir-99a, mir-103, mir-128, mir-129, mir-181b, mir-193, mir-197, mir-212, mir-218, mir-219, mir-302, mir-323, mir-324-3p, mir-325, mir-330, mir-331, mir-340, mmu-mir-350, mir-425, mir-491, mir-518f, mir-520a*. Such methods can be used for treating diseases and conditions characterized by inflammation. These include, but are not limited to, tissue destruction, organ failure or inflammatory diseases such as Rheumatoid arthritis, Psoriasis, Asthma, Inflammatory bowel disease (Crohn's disease and related conditions), Multiple Sclerosis, obstructive pulmonary disease (COPD), Allergic rhinitis (hay fever), and Cardiovascular disease. Additionally, such methods may be used for therapeutics, diagnostics, prognostics, creating cell lines with interesting research properties, and inducing differentiation.

The present invention also concerns methods of influencing the cell cycle of a cell or population of cells. It is contemplated that methods can involve relatively increasing the number of cells in a particular phase of the cell cycle, such as S, G1, G2/M, or when the number of chromosomes is greater than 2N. Alternatively, it can involve inducing DNA synthesis in a cell. One or more of the miRNAs involved in the cell cycle can be used to modulate a cell, particularly a cancer cell, to achieve a therapeutic benefit for a patient with such cells. Such methods may be used, for example, to enhance the efficacy of a therapeutic agent or they may be employed in the context of research, for instance, to synchronize cells so as to generate a more homogeneous population of cells. Moreover, these miRNAs may regulate genes that are involved in controlling cell cycle progression. Mis-expression of one or more of these miRNAs may profoundly affect the cells in which they reside, leading potentially toward cancer or other diseases associated with altered cell cycle regulation. In addition to using these miRNAs as diagnostic analytes, they might also provide targets for treating disease. For instance, a cancer cell that has bypassed a critical cell cycle signal by having a cell cycle-specific miRNA might be returned to normalcy by introducing the miRNA.

Methods of promoting cells to be in S phase can be achieved by introducing into or providing to the cells an effective amount of i) an miRNA inhibitor molecule or ii) a synthetic or nonsynthetic miRNA molecule that corresponds to an miRNA sequence. In certain embodiments the methods involves providing to or introducing into cells an effective amount of 1) at least one nucleic acid molecule capable of being processed into a mature miRNA when it is inside the cell, wherein the mature miRNA is let-7a, mir-15a, mir-16, mir-20, mir-26a, mir-191, mir-197, mir-205, mir-220, mir-224, mir-290, mir-291, mir-294, mir-295, mir-302, mir-345, mir-372, or mir-411; or 2) at least one miRNA inhibitor corresponding to mir-108, mir-122, mir-128, mir-129, mir-137, mir-142, mir-146, mir-147, mir-186, mir-187, mir-195, mir-297, mir-324-3p, mir-337, or mir-376b.

The invention also includes methods of inhibiting cells to be in S phase by introducing into or providing to the cells an effective amount of i) an miRNA inhibitor molecule or ii) a synthetic or nonsynthetic miRNA molecule that corresponds to an miRNA sequence. In certain embodiments the methods involves providing to or introducing into cells an effective amount of 1) at least one nucleic acid molecule capable of being processed into a mature miRNA when it is inside the cell, wherein the mature miRNA is mir-108, mir-122, mir-128, mir-129, mir-137, mir-142, mir-146, mir-147, mir-186, mir-187, mir-195, mir-297, mir-324-3p, mir-337, or mir-376b; or 2) at least one miRNA inhibitor corresponding to let-7a, mir-15a, mir-16, mir-20, mir-26a, mir-191, mir-197, mir-205, mir-220, mir-224, mir-290, mir-291, mir-294, mir-295, mir-302, mir-345, mir-372, or mir-411.

Methods of promoting cells to be in G1 phase can be achieved by introducing into or providing to the cells an effective amount of i) an miRNA inhibitor molecule or ii) a synthetic or nonsynthetic miRNA molecule that corresponds to an miRNA sequence. In certain embodiments the methods involves providing to or introducing into cells an effective amount of 1) at least one nucleic acid molecule capable of being processed into a mature miRNA when it is inside the cell, wherein the mature miRNA is mir-108, mir-122, mir-124, mir-125a, mir-126, mir-128, mir-129, mir-137, mir-142, mir-146, mir-147, mir-195, mir-201, mir-297, mir-320, mir-325, mir-324-3p, mir-337, mir-371, mir-376b, or mir-409; or 2) at least one miRNA inhibitor corresponding to Let-7a, mir-1, mir-7d, mir-20, mir-21, mir-26a, mir-192, mir-193, mir-206, mir-220, mir-290, mir-294, mir-329, mir-371, mir-373, or mir-409.

Other methods concern inhibiting cells in G1 phase by introducing into or providing to the cells an effective amount of i) an miRNA inhibitor molecule or ii) a synthetic or nonsynthetic miRNA molecule that corresponds to an miRNA sequence. In certain embodiments the methods involves providing to or introducing into cells an effective amount of 1) at least one nucleic acid molecule capable of being processed into a mature miRNA when it is inside the cell, wherein the mature miRNA is Let-7a, mir-1, mir-7d, mir-20, mir-21, mir-26a, mir-192, mir-193, mir-206, mir-220, mir-290, mir-294, mir-329, mir-371, mir-373, mir-409; or 2) at least one miRNA inhibitor corresponding to mir-108, mir-122, mir-124, mir-125a, mir-126, mir-128, mir-129, mir-137, mir-142, mir-146, mir-147, mir-195, mir-201, mir-297, mir-320, mir-325, mir-324-3p, mir-337, mir-371, mir-376b, or mir-409.

Also, there are methods of promoting cells to be in G2/M phase by introducing into or providing to the cells an effective amount of i) an miRNA inhibitor molecule or ii) a synthetic or nonsynthetic miRNA molecule that corresponds to an miRNA sequence. In certain embodiments the methods involves providing to or introducing into cells an effective amount of 1) at least one nucleic acid molecule capable of being processed into a mature miRNA when it is inside the cell, wherein the mature miRNA is mir-1, mir-7a, mir-7d, mir-7g, mir-20, mir-21, mir-26a, mir-145, mir-187, mir-192, mir-193, mir-206, mir-215, mir-220, mir-223, mir-294, mir-329, mir-371, mir-373, or mir-409; or 2) at least one miRNA inhibitor corresponding to mir-15a, mir-18, mir-122, mir-124, mir-126, mir-128, mir-129, mir-137, mir-146, mir-147, mir-195, mir-219, mir-337, or mir-371.

In other embodiments there are methods relating to inhibiting cells to be in G2/M phase by introducing into or providing to the cells an effective amount of i) an miRNA inhibitor molecule or ii) a synthetic or nonsynthetic miRNA molecule that corresponds to an miRNA sequence. In certain embodiments the methods involves providing to or introducing into cells an effective amount of 1) at least one nucleic acid molecule capable of being processed into a mature miRNA when it is inside the cell, wherein the mature miRNA is mir-15a, mir-18, mir-122, mir-124, mir-126, mir-128, mir-129, mir-137, mir-146, mir-147, mir-195, mir-219, mir-337, or mir-371; or 2) at least one miRNA inhibitor corresponding to mir-1, mir-7a, mir-7d, mir-7g, mir-20, mir-21, mir-26a, mir-145, mir-187, mir-192, mir-193, mir-206, mir-215, mir-220, mir-223, mir-294, mir-329, mir-371, mir-373, or mir-409.

The present invention also includes methods of increasing the number of cells with 2× or more DNA in the cell comprising introducing into or providing to the cells an effective amount of i) an miRNA inhibitor molecule or ii) a synthetic or nonsynthetic miRNA molecule that corresponds to an miRNA sequence. In certain embodiments the methods involves providing to or introducing into cells an effective amount of at least one nucleic acid molecule capable of being processed into a mature miRNA when it is inside the cell, wherein the mature miRNA is miR-1, miR-20, miR-21, miR-337, miR-345, or miR-373. The present invention is also concerned with reducing the number of cells with 2× (also referred to as 2N, where N is the number of sets of chromosomes) comprising providing to or introducing into cells an effective amount of an miRNA inhibitor corresponding to miR-1, miR-20, miR-21, miR-337, miR-345, or miR-373.

In certain embodiments, methods also include targeting an miRNA to modulate in a cell or organism. The term "targeting an miRNA to modulate" means a nucleic acid of the invention will be employed so as to modulate the selected miRNA. In some embodiments the modulation is achieved with a synthetic or non-synthetic miRNA that corresponds to the targeted miRNA, which effectively provides the targeted miRNA to the cell or organism (positive modulation). In other embodiments, the modulation is achieved with an miRNA inhibitor, which effectively inhibits the targeted miRNA in the cell or organism (negative modulation).

In some embodiments, the miRNA targeted to be modulated is an miRNA that affects a disease, condition, or pathway. In certain embodiments, the miRNA is targeted because a treatment can be provided by negative modulation of the targeted miRNA. In other embodiments, the miRNA is targeted because a treatment can be provided by positive modulation of the targeted miRNA.

In further embodiments of the invention, there is a step of obtaining a nucleic molecule of the invention that achieves negative modulation of the targeted miRNA. Alternatively, in some cases there is a step of obtaining a nucleic molecule of the invention that achieves positive modulation of the targeted miRNA. Thus, it is contemplated that methods involve selecting and/or obtaining a synthetic miRNA, non-synthetic miRNA or an miRNA inhibitor (collectively "miRNA modulators") that corresponds to a targeted miRNA, such as one that is involved with, affects or is characteristic of a particular disease, condition, pathway, or factor in the pathway.

In certain methods of the invention, there is a further step of administering the selected miRNA modulator to a cell, tissue, organ, or organism (collectively "biological matter") in need of treatment related to modulation of the targeted miRNA or in need of the physiological or biological results discussed herein (such as with respect to a particular cellular pathway or result like decrease in cell viability). Consequently, in some methods of the invention there is a step of identifying a patient in need of treatment that can be provided by the miRNA modulator(s). It is contemplated that an effective amount of an miRNA modulator can be administered in some embodiments. In particular embodiments, there is a therapeutic benefit conferred on the biological matter, where a "therapeutic benefit" refers to an improvement in the one or more conditions or symptoms associated with a disease or condition or an improvement in the prognosis, duration, or status with respect to the disase. It is contemplated that a therapeutic benefit includes, but is not limited to, a decrease in pain, a decrease in morbidity, a decrease in a symptom. For example, with respect to cancer, it is contemplated that a therapeutic benefit can be inhibition of tumor growth, prevention of metastasis, reduction in number of metastases, inhibition of cancer cell proliferation, inhibition of cancer cell proliferation, induction of cell death in cancer cells, inhibition of angiogenesis near cancer cells, induction of apoptosis of cancer cells, reduction in pain, reduction in risk of recurrence, induction of chemo- or radiosensitivity in cancer cells, prolongation of life, and/or delay of death directly or indirectly related to cancer.

It is specifically contemplated that miRNA profiles for patients, particularly those suspected of having a particular disease or condition, can be generated by evaluating any of the miRNAs discussed in this application. The miRNA profile that is generated from the patient will be one that provides information regarding the particular disease or condition. In many embodiments, the miRNA profile is generated using the miRNA array discussed.

Furthermore, it is contemplated that the miRNA compositions may be provided as part of a therapy to a patient, in conjunction with traditional therapies or preventative agents. Moreover, it is contemplated that any method discussed in the context of therapy may be applied as preventatively, particularly in a patient identified to be potentially in need of the therapy or at risk of the condition or disease for which a therapy is needed.

In other embodiments, the invention concerns a method for inducing transformation in a cell comprising administering to the cell an effective amount of at least one miRNA selected from the group consisting of mir-192, mir-198, and mir-199. Alternatively, methods for preventing cell transformation may be achieved by administering to the cell an effective amount of at least one miRNA inhibitor of mir-192, mir-198, or mir-199.

In addition, methods of the invention concern employing one or more nucleic acids corresponding to an miRNA and a therapeutic drug. The nucleic acid can enhance the effect or efficacy of the drug, reduce any side effects or toxicity, modify its bioavailability, and/or decrease the dosage or frequency needed. In certain embodiments, the therapeutic drug is a cancer therapeutic. Consequently, in some embodiments, there is a method of treating cancer in a patient comprising administering to the patient the cancer therapeutic and an effective amount of at least one miRNA molecule that improves the efficacy of the cancer therapeutic or protects non-cancer cells. Furthermore, in some cases the miRNA molecule enhances the efficacy of the cancer therapeutic and is selected from the group consisting of ambi-miR-7100, mir-28, mir-101, mir-124, mir-125a, mir-126, mir-132, mir-136, mir-147, mir-155, mir-182, mir-186, mir-202, mir-206, mir-216, mir-221, mir-224, mir-291, mir-292-3p, mir-297, mir-302, mir-337, mir-372, mir-373, and mir-376b.

Cancer therapies also include a variety of combination therapies with both chemical and radiation based treatments. Combination chemotherapies include but are not limited to, for example, bevacizumab, cisplatin (CDDP), carboplatin, EGFR inhibitors (gefitinib and cetuximab), procarbazine, mechlorethamine, cyclophosphamide, camptothecin, COX-2 inhibitors (e.g., celecoxib) ifosfamide, melphalan, chlorambucil, busulfan, nitrosurea, dactinomycin, daunorubicin, doxorubicin (adriamycin), bleomycin, plicomycin, mitomycin, etoposide (VP16), tamoxifen, raloxifene, estrogen receptor binding agents, taxol, taxotere, gemcitabien, navelbine, farnesyl-protein transferase inhibitors, transplatinum, 5-fluorouracil, vincristin, vinblastin and methotrexate, or any analog or derivative variant of the foregoing.

Alternatively or additionally, the miRNA molecule in methods of the invention protects non-cancer cells from the cancer therapeutic and is selected from the group consisting of mir-16, mir-24, mir-30a-3p, mir-125b, mir-152, mir-194, mir-197, mir-214, and mir-331.

Generally, inhibitors of miRNAs can be given to achieve the opposite effect as compared to when nucleic acid molecules corresponding to the mature miRNA are given. Similarly, nucleic acid molecules corresponding to the mature miRNA can be given to achieve the opposite effect as compared to when inhibitors of the miRNA are given. For example, miRNA molecules that increase cell proliferation can be provided to cells to increase proliferation or inhibitors of such molecules can be provided to cells to decrease cell proliferation. The present invention contemplates these embodiments in the context of the different physiological effects observed with the different miRNA molecules and miRNA inhibitors disclosed herein. These include, but are not limited to, the following physiological effects: increase and decreasing cell proliferation, increasing or decreasing apoptosis, increasing transformation, increasing or decreasing cell viability, activating ERK, activating/inducing or inhibiting hTert, inhibit stimulation of Stat3, reduce or increase viable cell number, and increase or decrease number of cells at a particular phase of the cell cycle. Methods of the invention are generally contemplated to include providing or introducing one or more different nucleic acid molecules corresponding to one or more different miRNA molecules. It is contemplated that the following, at least the following, or at most the following number of different nucleic acid molecules may be provided or introduced: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or any range derivable therein. This also applies to the number of different miRNA molecules that can be provided or introduced into a cell.

The present invention also concerns kit containing compositions of the invention or compositions to implement methods of the invention. In some embodiments, kits can be used to evaluate one or more miRNA molecules. In certain embodiments, a kit contains, contains at least or contains at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more synthetic miRNA molecules or miRNA inhibitors, or any range and combination derivable therein. In some embodiments, there are kits for evaluating miRNA activity in a cell.

Kits may comprise components, which may be individually packaged or placed in a container, such as a tube, bottle, vial, syringe, or other suitable container means.

Individual components may also be provided in a kit in concentrated amounts; in some embodiments, a component is provided individually in the same concentration as it would be in a solution with other components. Concentrations of components may be provided as 1×, 2×, 5×, 10×, or 20× or more.

Kits for using synthetic miRNAs, nonsynthetic, and/or miRNA inhibitors of the invention for therapeutic, prognostic, or diagnostic applications are included as part of the invention. Specifically contemplated are any such molecules corresponding to any miRNA reported to influence biological activity, such as those discussed herein.

Negative and/or Positive Control synthetic miRNAs and/or miRNA inhibitors are included in some kit embodiments. The Control molecules can be used to verify transfection efficiency and/or control for transfection-induced changes in cells.

It is contemplated that any method or composition described herein can be implemented with respect to any other method or composition described herein and that different embodiments may be combined. It is specifically contemplated that any methods and compositions discussed herein with respect to miRNA molecules or miRNA may be implemented with respect to synthetic miRNAs to the extent the synthetic miRNA is exposed to the proper conditions to allow it to become a mature miRNA under physiological circumstances. The claims originally filed are contemplated to cover claims that are multiply dependent on any filed claim or combination of filed claims.

Any embodiment of the invention involving specific miRNAs by name is contemplated also to cover embodiments involving miRNAs whose sequences are at least 80, 81, 82, 83, 84, 85, 86, 87, 88, 89, 90, 91, 92, 93, 94, 95, 96, 97, 98, 99% identical to the mature sequence of the specified miRNA.

Throughout this application, the term "about" is used to indicate that a value includes the standard deviation of error for the device or method being employed to determine the value.

The use of the word "a" or "an" when used in conjunction with the term "comprising" in the claims and/or the specification may mean "one," but it is also consistent with the meaning of "one or more," "at least one," and "one or more than one."

It is specifically contemplated that any embodiments described in the Examples section are included as an embodiment of the invention.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2. Methods for Introducing miRNAs into Cells. There are three basic methods for introducing miRNAs into cells. In the first, a DNA bearing a promoter upstream of a sequence encoding a miRNAs is introduced into cells where it is transcribed to produce an RNA molecule that includes the mature miRNA. Processing and uptake by the protein complex for miRNA-induced gene regulation results in the activation of the miRNA. This method suffers from inefficient introduction of the DNA construct into cells. In the second method, an siRNA-like dsRNA molecule, one of whose strands is identical to an active miRNA is introduced into cells where it is taken up by the protein complex for miRNA activation. This method provides efficient deliver, but often uptake of the unintended complementary RNA molecule. The third method, described herein, involves modifying the complementary strand so as to favor uptake and activation of the active strand of the synthetic miRNA construct.

FIG. 3. Preferential Uptake of Active Strands in synthetic miRNAs of the invention. Reporter vectors with luciferase under the control of target sites for miR-33 or let-7 or the complementary strands of the afore-mentioned siRNAs. Co-transfection of synthetic miRNAs and reporter vectors followed by luciferase assay 24 hours post-transfection revealed miRNAs that are activated following transfection.

FIG. 5. Synthetic miRNA Activity across Cell Types and Against Natural Targets.

Synthetic miRNAs were tested for proper strand activation and cell-type specificity to ensure that the design is robust. Four different cell types were co-transfected with synthetic miRNA and associated active and complementary strand activation. Panel A shows that different cell types respond similarly to synthetic miRNAs. Four different synthetic miRNAs were then transfected into various cell types and the expression levels of natural targets of the miRNAs were measured (Panel B).

Figure 6:
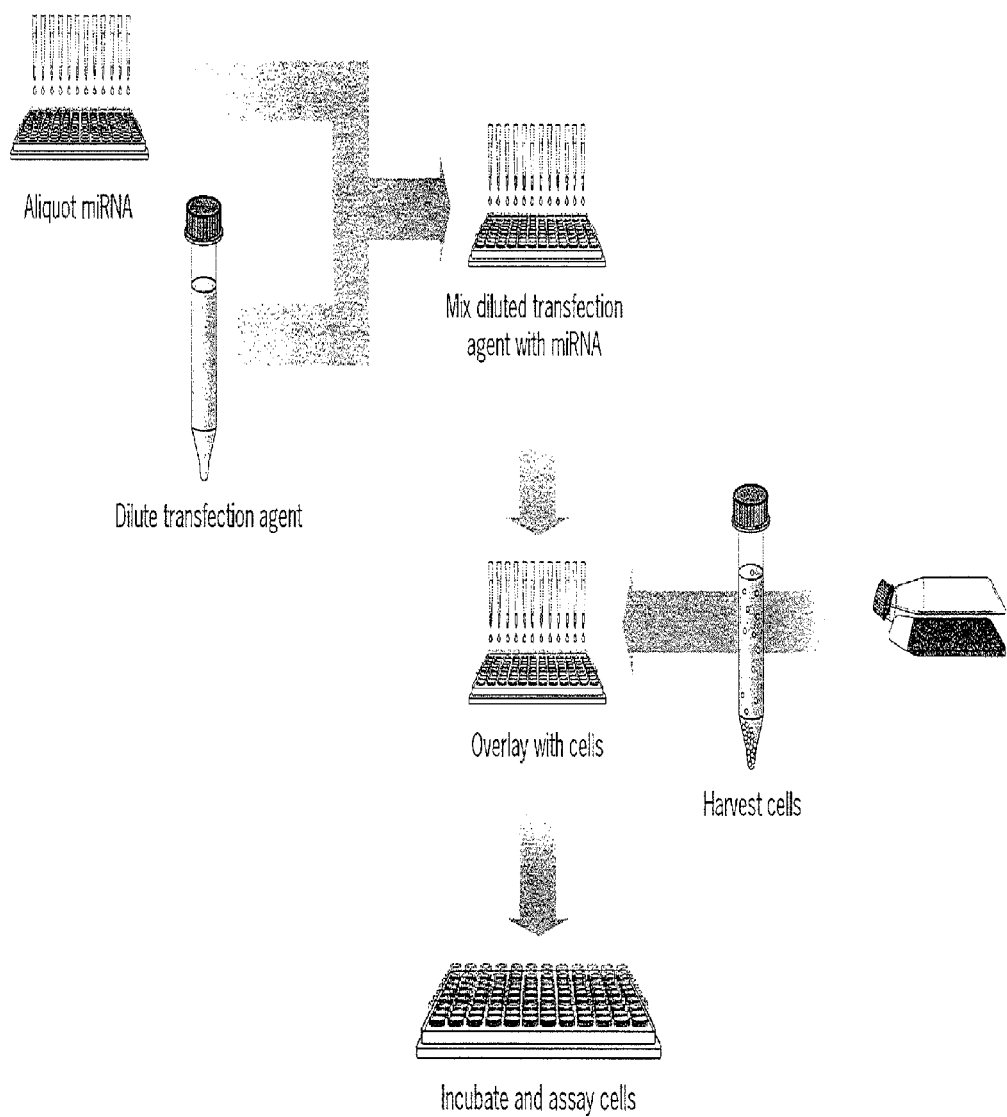

FIG. 6. Schematic for screening with libraries of synthetic miRNAs or miRNA inhibitors. Synthetic miRNAs and/or miRNA inhibitors are distributed to wells of a microtiter plate. Transfection reagent and then cells are added to each well. At some time post-transfection, samples are evaluated for a phenotype. MiRNAs that induce a change that is significant relative to a negative control are selected for further study.

Figure 7:
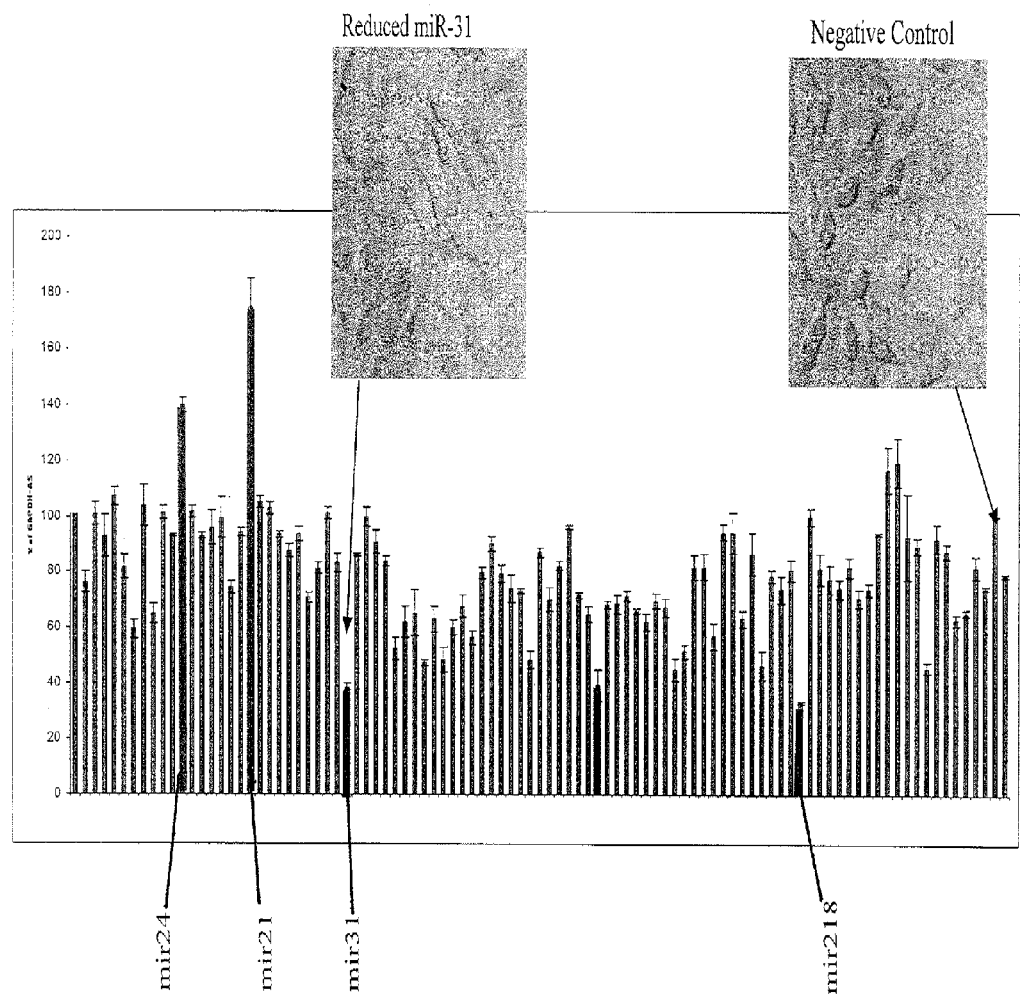

FIG. 7. Screen for miRNAs that affect cell proliferation. In 96-well plates, 8,000 HeLa cells were reverse transfected with miRNA inhibitors (5 pmoles) in triplicates using Ambion siPORT Neo-FX. 72 hours post-transfection, cells were fixed with 4% paraformaldehyde, permiabilized with 0.1% TritonX 100 and stained with propidium iodide to look at total cell number. The plates were scanned using the TTP labtech Acumen Explorer. Morphology changes in cells inhibited for mir 31. HeLa cells were transfected with Anti-mir31 and cells were fixed and stained with anti-beta actin antibody and DAPI to visualize cell morphology changes in response to inhibition to mir-31 micro-RNA function.

Figure 8:
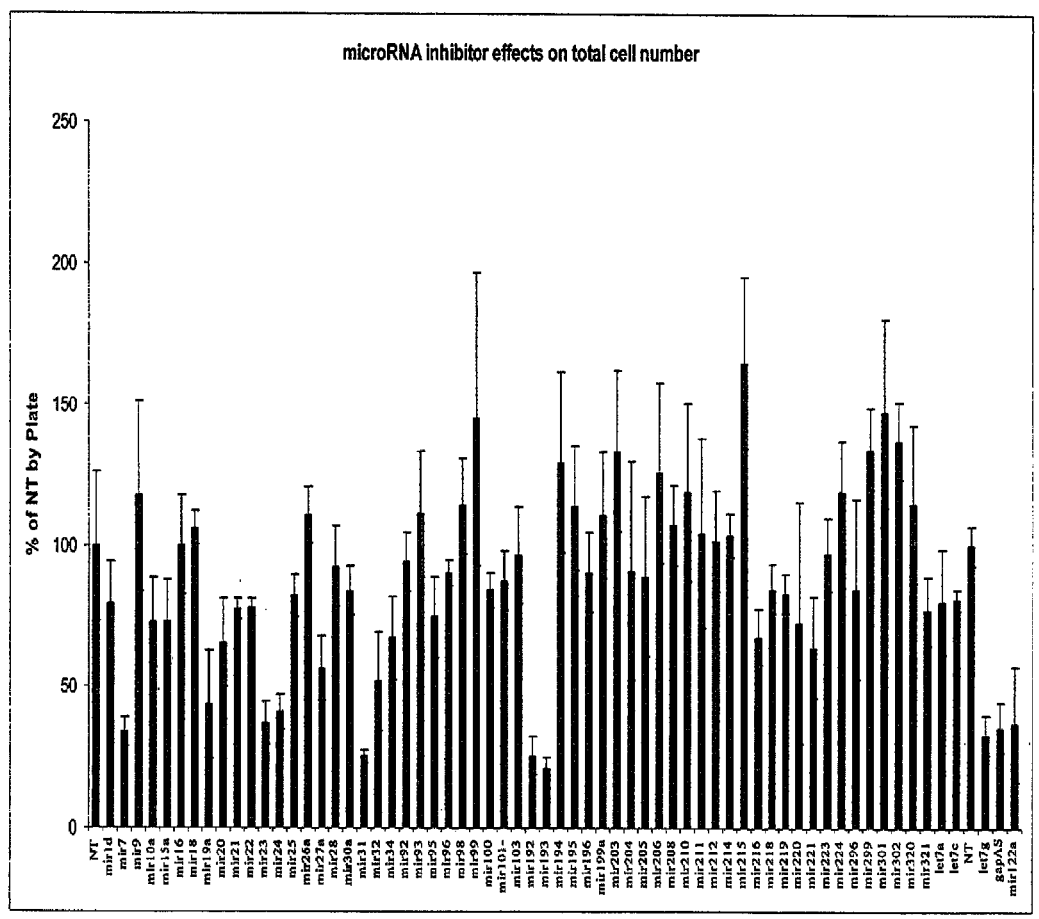

FIG. 8. Screen for miRNAs that affect cell proliferation in A549 cells. Screen for miRNA involved in cell viability in A549 cells. In 96-well plates, 8,000 A549 cells were reverse transfected with miRNA inhibitors (5 pmoles) in triplicates using Ambion siPORT Neo-FX. 72 hours post-transfection cells were trypsinized and counted using the Guava cell counting instrument. Cell number was graphed and normalized to a gap inhibitor. In this figure, "mir1d" refers to mir-1-2.

Figure 9:
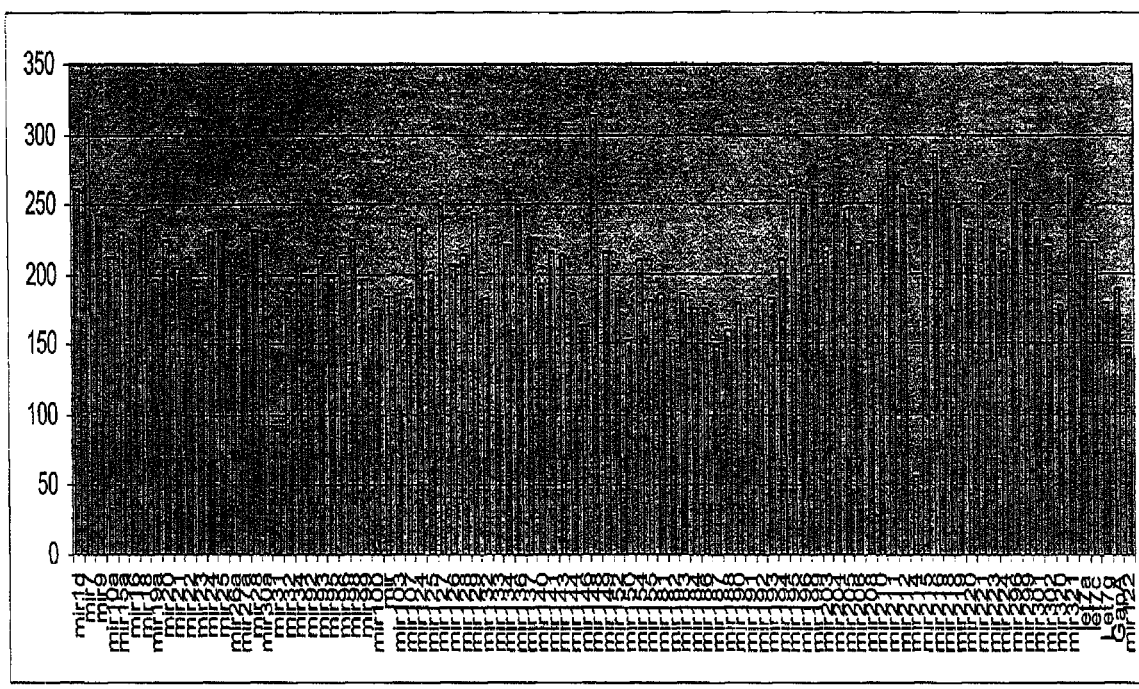

FIG. 9. Screen for miRNAs that affect apoptosis in HeLa cells. Effects of miRNA inhibitors on caspase activity in HeLa. In 96-well plates, 8,000 HeLa cells were reverse transfected with miRNA inhibitors (5 pmoles) in triplicates using Ambion siPORT Neo-FX. 72 hours post-transfection cells were analyzed using caspase activity assay and normalized based on esterase activity assay. In this figure, "mirld" refers to mir-1-2.

Figure 10:
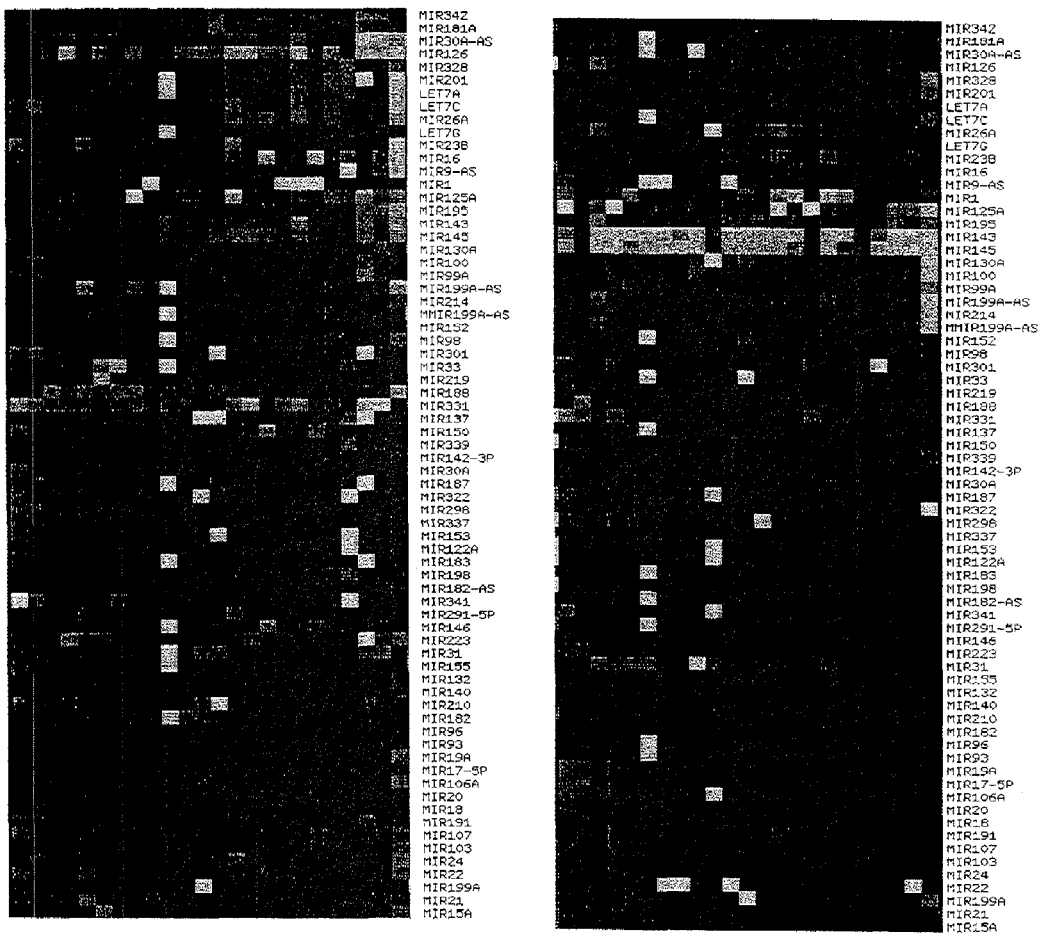

FIG. 10. miRNA Expression in Lung and Colon Cancer Patients. The miRNA expression profiles of tumor vs normal adjacent tissues were compared for lung and colon cancer patients. The miRNAs are provided in rows; the patients are presented in columns. Green in the heat map shows miRNAs that are down-regulated in the tumor sample relative to the normal adjacent tissue sample, and red shows miRNAs that are up-regulated in the tumor sample relative to the normal adjacent tissue sample.

Figure 11:
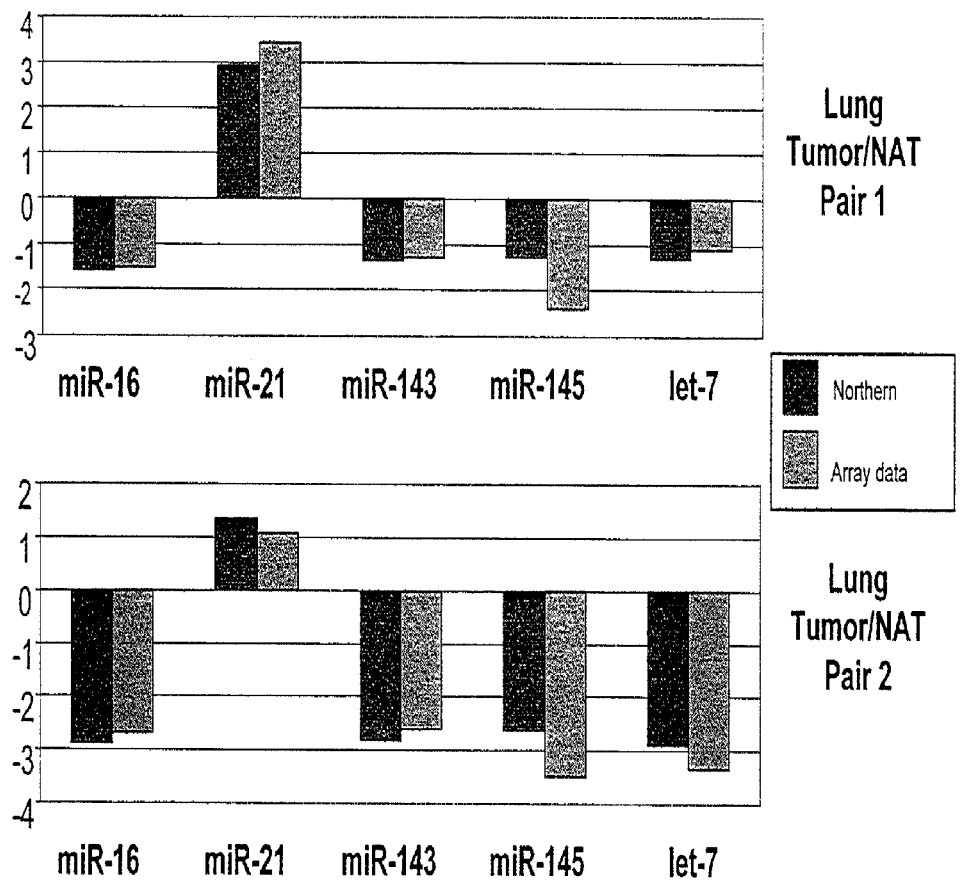

FIG. 11. Validation of miRNA Array Expression Results in Lung Cancer Patients. Total RNA samples from two lung cancer patients were analyzed for expression of miR-16, miR-21, miR-143, miR-145, and let-7 using Northern analysis. The graphs show the relative abundance of each miRNA (ratio of tumor:NAT) from the array analysis and Northern phosphoimager analysis.

Figure 12:
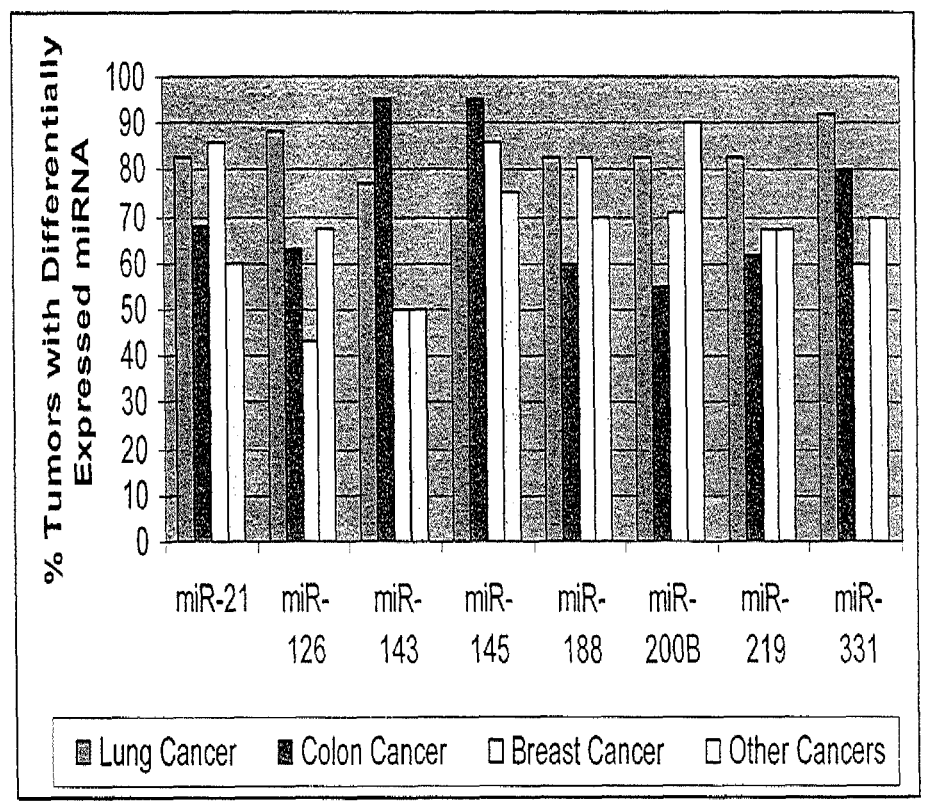

FIG. 12. Some miRNAs are differentially expressed in multiple cancer types. miRNA array analysis comparing tumor and normal adjacent tissues from patients with various types of cancer was used to identify miRNAs that are differentially expressed in cancer. The percentage of patients exhibiting up- or down-regulation of a given miRNA was calculated for each cancer type. The eight that were most often differentially expressed across sample types are presented.

Figure 13:
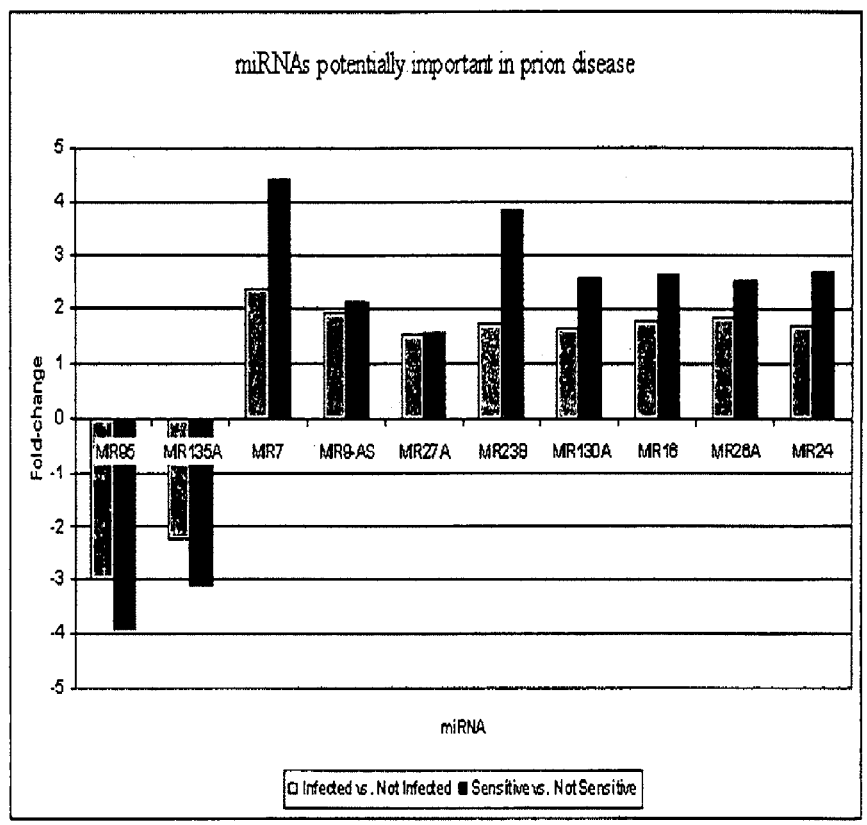

FIG. 13. Shown are miRNAs having greater than 1.5-fold expression changes between both infected vs. uninfected and sensitive vs. insensitive. On the right is a cluster of the results from 2 arrays of each model.

Figure 14:
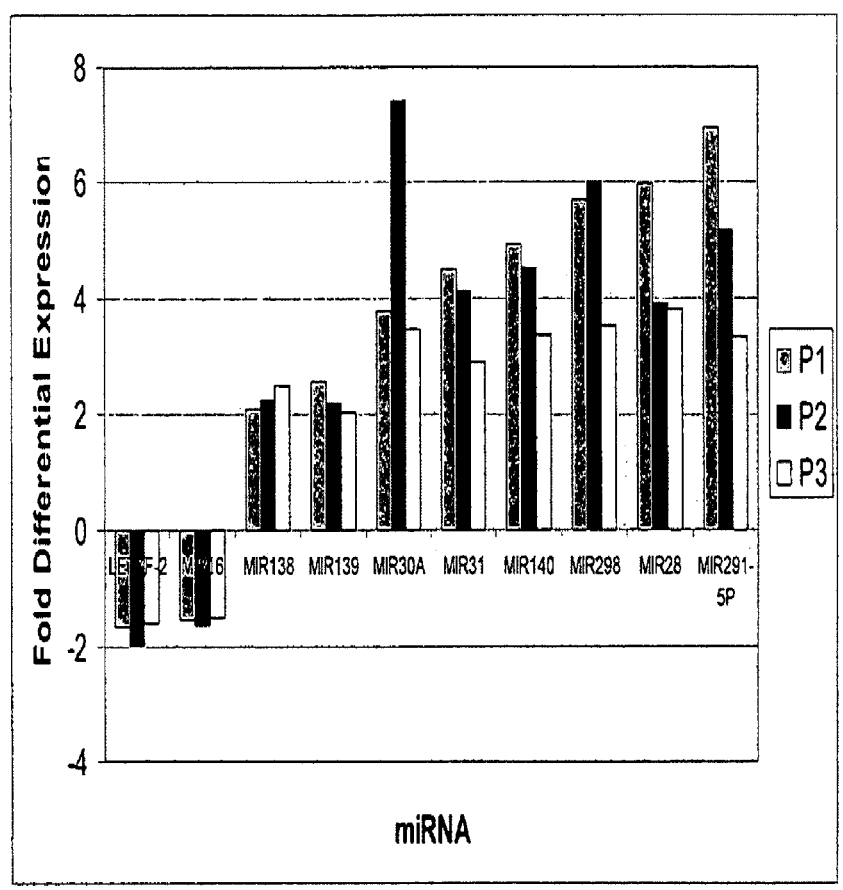

FIG. 14. Differentially expressed miRNAs in 3 preconditioned mice relative to non-treated mice.

FIG. 15A-C. Synthetic miRNAs that decrease cell proliferation. A. BT549 and MCF12A (breast), HeLa (cervical) and 22 Rv1 (prostate) cells were evaluated for cell proliferation. B. TE354T and TE353SK (skin), BJ (skin), and A549 (lung) cells were examined for cell proliferation. C. CRL5826 and HTB-57 (lung), Jurkats (T cell), and primary T cells were evaluated for cell proliferation.

FIG. 16. Synthetic miRNAs that increase cell proliferation. HeLa (cervical), 22 Rv1 (prostate), TE354T and TE353SK (skin), BJ (skin), A549 (lung), Jurkats (T cell), primary T cells, CRL5826 and HTB-57 (lung) cells were evaluated for cell proliferation.

FIG. 17. miRNA inhibitors that reduce cell proliferation. 22 Rv1 (prostate), TE354T (skin), MCF12a (breast), and A549 (lung) cells were evaluated for cell proliferation.

FIG. 18. miRNA inhibitors that increase cell proliferation. 22 Rv1 (prostate), TE354T (skin), MCF12a (breast), and A549 (lung) cells were evaluated for cell proliferation.

FIG. 19. miRNAs that affect cell viability. Jurkats (T cell), primary T cells, HeLa (cervical) and A549 (lung) cells were evaluated for increases and decreases in cell viability.

FIG. 20. miRNAs that affect apoptosis. 22 Rv1 (prostate), TE354T (skin), Jurkats (T cell), and HeLa (cervical) cells were evaluated for increases and decreases in apoptosis.

FIG. 21. miRNAs that affect cell viability in the presence of a therapeutic. A549 (lung) cells were evaluated for increases and decreases in cell viability in the presence and absence of TRAIL or etoposide. HTB-57 and CRL5826 (lung) and HeLa (cervical) cells were evaluated for a reduction in cell viability in the absence and presence of etoposide.

FIG. 22. miRNAs that affect cell cycle. BJ (skin) and HeLa (cervical) cells were evaluated for increases or decreases in the number of cells at certain phases of the cell cycle (G1, S, G2/M, DNA replication).

FIG. 23. Phenotypes of miRNAs with similar sequences. Comparison of related sequences and their effects on A549 and Jurkat cell proliferation. The sequences correspond to positions 6-27 of SEQ ID NO:3. (let-7a-1), 6-27 of SEQ ID NO:6 (let-7b), 11-32 of SEQ ID NO:7 (let-7c), 8-28 of SEQ ID NO:8 (let-7d), and 5-25 of SEQ ID NO:15 (let-7g).

Figure 24:
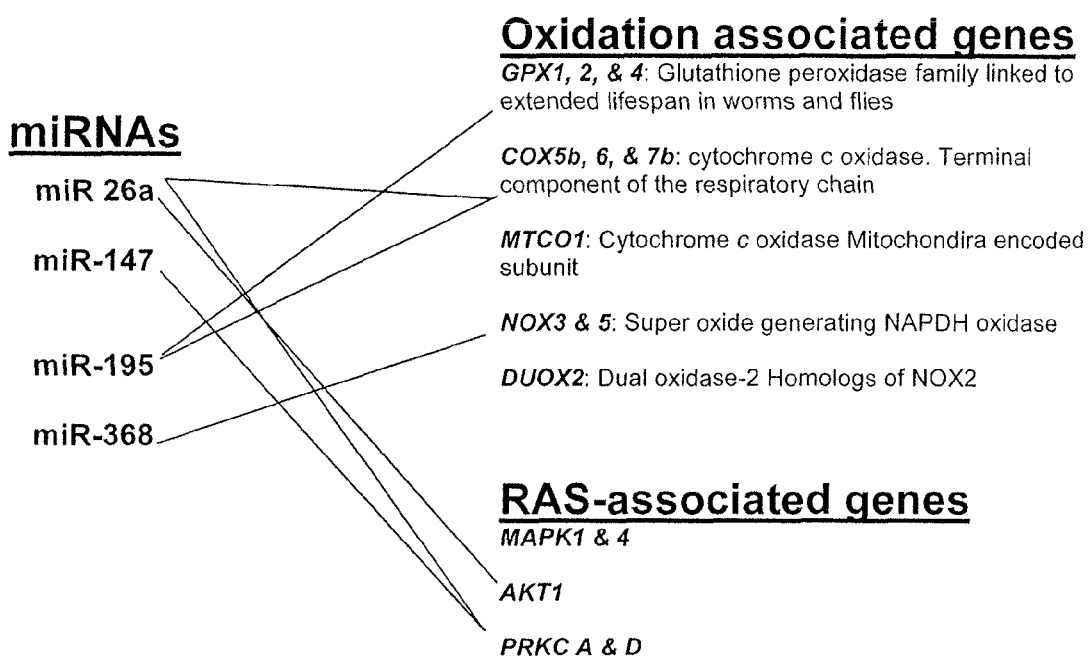

FIG. 24. Genes associated with hTert regulation and miRNA sequences predicted to modulate their expression. FIG. 24 exemplifies 4 miRNAs (miR-26a, miR-147, miR-195, and miR-368) and the thTert activating gene products with which they interact.

DESCRIPTION OF ILLUSTRATIVE EMBODIMENTS

The present invention is directed to compositions and methods relating to preparation and characterization of miRNAs, as well as use of miRNAs for therapeutic, prognostic, and diagnostic applications. To overcome the problem with previous inefficient plasmid-based systems for introducing miRNA into cells, the inventors developed small, partially double-stranded RNAs that can be delivered with high efficiency to both immortalized and primary cells. The small RNAs have the same functional activities as endogenously expressed miRNAs. Because the small RNAs can be delivered to cells with much higher efficiency than can plasmids, they induce a much stronger phenotype that is easier to detect and quantify, making it possible to identify many of the functions of miRNAs in cells.

The inventors have also created a library of the small, double-stranded RNA molecules that can be used to introduce miRNAs into cells, as well as a library of antisense molecules that inhibit the activities of known miRNAs that are present in cells. These libraries have been used to sequentially up- or down-regulate one or more miRNAs in cells to identify those miRNAs that are critical for cellular processes like cell cycle, apoptosis, differentiation, viability, angiogenesis, metabolism, and other processes with therapeutic potential. miRNAs that regulate the expression of important genes like p53, MYC, and RAS are also being identified and characterized to further pinpoint miRNAs that might provide important intervention points for treating disease. For example, let-7 has been shown to be involved with RAS. See Johnson et al., 2005, which is hereby incorporated by reference. These processes of serially modulating miRNA activities and assaying for cellular phenotypes are collectively referred to as miRNA functional screening.

I. miRNA Molecules

MicroRNA molecules ("miRNAs") are generally 21 to 22 nucleotides in length, though lengths of 17 and up to 25 nucleotides have been reported. The miRNAs are each processed from a longer precursor RNA molecule ("precursor miRNA"). Precursor miRNAs are transcribed from non-protein-encoding genes. The precursor miRNAs have two regions of complementarity that enables them to form a stem-loop- or fold-back-like structure, which is cleaved by an enzyme called Dicer in animals. Dicer is ribonuclease III-like nuclease. The processed miRNA is typically a portion of the stem.

The processed miRNA (also referred to as "mature miRNA") become part of a large complex to down-regulate a particular target gene. Examples of animal miRNAs include those that imperfectly basepair with the target, which halts translation (Olsen et al., 1999; Seggerson et al., 2002). SiRNA molecules also are processed by Dicer, but from a long, double-stranded RNA molecule. SiRNAs are not naturally found in animal cells, but they can function in such cells in a RNA-induced silencing complex (RISC) to direct the sequence-specific cleavage of an mRNA target (Denli et al., 2003).

The study of endogenous miRNA molecules is described in U.S. Patent Application 60/575,743, which is hereby incorporated by reference in its entirety.

Synthetic miRNAs miRNAs are apparently active in the cell when the mature, single-stranded RNA is bound by a protein complex that regulates the translation of mRNAs that hybridize to the miRNA. Introducing exogenous RNA molecules that affect cells in the same way as endogenously expressed miRNAs requires that a single-stranded RNA molecule of the same sequence as the endogenous mature miRNA be taken up by the protein complex that facilitates translational control. A variety of RNA molecule designs have been evaluated. Three general designs that maximize uptake of the desired single-stranded miRNA by the miRNA pathway have been identified. An RNA molecule with an miRNA sequence having at least one of the three designs is referred to as a synthetic miRNA.

Synthetic miRNAs of the invention comprise, in some embodiments, two RNA molecules wherein one RNA is identical to a naturally occurring, mature miRNA. The RNA molecule that is identical to a mature miRNA is referred to as the active strand. The second RNA molecule, referred to as the complementary strand, is at least partially complementary to the active strand. The active and complementary strands are hybridized to create a double-stranded RNA, called the synthetic miRNA, that is similar to the naturally occurring miRNA precursor that is bound by the protein complex immediately prior to miRNA activation in the cell. Maximizing activity of the synthetic miRNA requires maximizing uptake of the active strand and minimizing uptake of the complementary strand by the miRNA protein complex that regulates gene expression at the level of translation. The molecular designs that provide optimal miRNA activity involve modifications to the complementary strand.

Two designs incorporate chemical modifications in the complementary strand. The first modification involves creating a complementary RNA with a chemical group other than a phosphate or hydroxyl at its 5' terminus. The presence of the 5' modification apparently eliminates uptake of the complementary strand and subsequently favors uptake of the active strand by the miRNA protein complex. The 5' modification can be any of a variety of molecules including $NH_2$, $NHCOCH_3$, biotin, and others.

The second chemical modification strategy that significantly reduces uptake of the complementary strand by the miRNA pathway is incorporating nucleotides with sugar modifications in the first 2-6 nucleotides of the complementary strand. It should be noted that the sugar modifications consistent with the second design strategy can be coupled with 5' terminal modifications consistent with the first design strategy to further enhance synthetic miRNA activities.

The third synthetic miRNA design involves incorporating nucleotides in the 3' end of the complementary strand that are not complementary to the active strand. Hybrids of the resulting active and complementary RNAs are very stable at the 3' end of the active strand but relatively unstable at the 5' end of the active strand. Studies with siRNAs indicate that 5' hybrid stability is a key indicator of RNA uptake by the protein complex that supports RNA interference, which is at least related to the miRNA pathwy in cells. The inventors have found that the judicious use of mismatches in the complementary RNA strand significantly enhances the activity of the synthetic miRNA.

MiRNA Libraries

A key application for the synthetic miRNAs is the identification of cellular functions for individual or groups of miRNAs. The inventors have created a library of synthetic miRNAs that can be used to sequentially introduce each of the known miRNAs into cultured cells (FIG. 6). Cell populations with each of the different synthetic miRNAs can then be assayed to identify miRNAs whose presence induces a cellular phenotype.

The inventors have created a library of antisense molecules that inhibit miRNA activity. The miRNA inhibitors are used to serially inhibit the activities of miRNAs in cells to identify miRNAs whose absence induces a cellular phenotype.

The number of different synthetic miRNAs or miRNA inhibitors in the libraries is variable. It is contemplated that there may be, be at least, or be at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 31, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 or more, or any range derivable therein, different miRNA-specific molecules in the library. In specific embodiments, libraries have between 5 and 1000 different miRNA-specific molecules, between 20 and 500 different miRNA-specific molecules, between 50 and 250 different miRNA-specific molecules, or between 100 and 225 different miRNA-specific molecules. "Different" miRNA-specific molecules refers to nucleic acids that are specific to miRNAs with different sequences.

Synthetic miRNAs are contemplated to be made primarily of RNA, though in some embodiments, they may be RNA, nucleotide analogs, DNA, or any combination of DNA, RNA, nucleotide analogs, and PNAs.

As suggested above, it is contemplated that libraries of the invention may be specific for one or more miRNAs. In embodiments of the invention, a library has 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 31, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 or more, or any range derivable therein, different miRNAs or miRNA inhibitors. Accordingly, it is understood that the library contains one or more nucleic acids for these different miRNAs. In specific embodiments, the library is specific to human miRNAs, though libraries for multiple organisms are contemplated.

RNA molecules of the invention have miRNA regions or complementary regions. In specific embodiments, a synthetic miRNA or miRNA inhibitor has a sequence or complementary sequence that derives from any of SEQ ID NOs: 1-805, inclusive. It is particularly contemplated that synthetic nucleic acid molecules of the invention may be derived from any of the mature miRNA sequences in SEQ ID NOs:1-805 or their complement.

As discussed above, miRNAs are processed from a precursor molecule. In certain embodiments, the specific length of a mature miRNA is unknown. It is contemplated that versions of the synthetic miRNA and miRNA inhibitor libraries will include sequence that extends at least 1 to 5 nucleotides of coding sequence upstream and/or downstream of the predicted miRNA sequence. In some embodiments, molecules have up to 1, 2, 3, 4, 5, 6, 7, or more contiguous nucleotides, or any range derivable therein, that flank the sequence encoding the predominant processed miRNA on one or both sides (5' and/or 3' end).

The present invention concerns methods for creating functional profile for all of the known miRNAs. The term "functional profile" refers to a set of data regarding the cellular phenotypes that result from introducing and inhibiting miRNAs in cells using synthetic miRNA and miRNA inihibitor libraries. Functional profiles for individual miRNAs will enable identification of miRNAs with therapeutic or diagnostic potential. For instance, a functional profile for a miRNA might reveal that its absence leads to uncontrolled cell proliferation and an inability to induce apoptosis following DNA damage. Furthermore, the expression of p53 correlates with whether the miRNA is being up-regulated with a synthetic miRNA or down-regulated with a miRNA inhibitor. Based on its ties to cell proliferation, apoptosis, and p53 expression, this miRNA might be a target for cancer therapeutics.

In certain embodiments, methods concern identifying miRNAs indicative of a disease or condition by detecting a correlation between the activity of particular miRNAs and cellular phenotypes that coincide with a disease or condition.

Libraries of the invention can contain miRNA sequences from any organism having miRNAs, specifically including but not limited to, mammals such as humans, mice, and rats. Specifically contemplated are libraries having, having at least, or having at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000 or more different synthetic miRNAs and/or miRNA inhibitors (that is, miRNA-specific molecules having different sequences derived from different miRNA genes). Specifically contemplated are such libraries described in the previous sentence with respect to any of SEQ ID NOs:1-805, particularly those corresponding to miRNA sequences (mature sequence) or the complement thereof.

A. Nucleic Acids

The present invention concerns nucleic acid molecules that can introduce or inhibit miRNAs in cultured cells. The nucleic acids may have been produced in cells or in vitro by purified enzymes though they are preferentially produced by chemical synthesis. They may be crude or purified. The term "miRNA," unless otherwise indicated, refers to the processed RNA, after it has been cleaved from its precursor. Table 1 indicates which SEQ ID NO corresponds to the particular precursor sequence of an miRNA and what sequences within the SEQ ID NO correspond to the mature sequence. The name of the miRNA is often abbreviated and referred to without the prefix and will be understood as such, depending on the context. Unless otherwise indicated, miRNAs referred to in the application are human sequences identified as mir-X or let-X, where X is a number and/or letter.

TABLE 1

Human miRNA Sequences

| miRNA name | Precursor | Processed Sequence Relative to Precursor |
|---|---|---|
| hsa-mir-1-2 | SEQ ID NO: 1 | 53-73 |
| hsa-mir-1-1 | SEQ ID NO: 2 | 46-66 |
| hsa-let-7a-1 | SEQ ID NO: 3 | 6-27 |
| hsa-let-7a-2 | SEQ ID NO: 4 | 5-26 |
| hsa-let-7a-3 | SEQ ID NO: 5 | 4-25 |
| hsa-let-7b | SEQ ID NO: 6 | 6-27 |
| hsa-let-7c | SEQ ID NO: 7 | 11-32 |
| hsa-let-7d | SEQ ID NO: 8 | 8-28 |
| hsa-let-7e | SEQ ID NO: 9 | 8-28 |
| hsa-let-7f-1 | SEQ ID NO: 10 | 7-28 |
| hsa-let-7f-2 | SEQ ID NO: 11 | 8-29 |
| hsa-mir-7-1 | SEQ ID NO: 12 | 24-44 |
| hsa-mir-7-2 | SEQ ID NO: 13 | 32-52 |
| hsa-mir-7-3 | SEQ ID NO: 14 | 31-51 |
| hsa-let-7g | SEQ ID NO: 15 | 5-25 |
| hsa-let-7i | SEQ ID NO: 16 | 6-24 |
| hsa-mir-9-1 | SEQ ID NO: 17 | 16-38 and/or 56-76 |
| hsa-mir-9-2 | SEQ ID NO: 18 | 16-38 and/or 54-74 |
| hsa-mir-9-3 | SEQ ID NO: 19 | 16-38 and/or 56-76 |
| hsa-mir-10a | SEQ ID NO: 20 | 22-44 |
| hsa-mir-10b | SEQ ID NO: 21 | 27-48 |
| hsa-mir-15a | SEQ ID NO: 22 | 14-35 |
| hsa-mir-15b | SEQ ID NO: 23 | 20-41 |
| hsa-mir-16-1 | SEQ ID NO: 24 | 14-35 |
| hsa-mir-16-2 | SEQ ID NO: 25 | 10-31 |
| hsa-mir-17 | SEQ ID NO: 26 | 14-37 and/or 51-70 |
| hsa-mir-18 | SEQ ID NO: 27 | 6-27 |
| hsa-mir-19a | SEQ ID NO: 28 | 49-71 |
| hsa-mir-19b-1 | SEQ ID NO: 29 | 54-76 |
| hsa-mir-19b-2 | SEQ ID NO: 30 | 62-84 |
| hsa-mir-20 | SEQ ID NO: 31 | 8-29 |
| hsa-mir-21 | SEQ ID NO: 32 | 8-29 |
| hsa-mir-22 | SEQ ID NO: 33 | 53-74 |
| hsa-mir-23a | SEQ ID NO: 34 | 45-65 |
| hsa-mir-23b | SEQ ID NO: 35 | 58-80 |
| hsa-mir-24-1 | SEQ ID NO: 36 | 6-28 and/or 44-65 |
| hsa-mir-24-2 | SEQ ID NO: 37 | 50-71 |
| hsa-mir-25 | SEQ ID NO: 38 | 52-73 |
| hsa-mir-26a-1 | SEQ ID NO: 39 | 10-31 |
| hsa-mir-26b | SEQ ID NO: 40 | 12-32 |
| hsa-mir-26a-2 | SEQ ID NO: 41 | 14-35 |

TABLE 1-continued

Human miRNA Sequences

| miRNA name | Precursor | Processed Sequence Relative to Precursor |
|---|---|---|
| hsa-mir-27a | SEQ ID NO: 42 | 51-72 |
| hsa-mir-27b | SEQ ID NO: 43 | 61-80 |
| hsa-mir-28 | SEQ ID NO: 44 | 14-35 |
| hsa-mir-29a | SEQ ID NO: 45 | 41-62 |
| hsa-mir-29b-1 | SEQ ID NO: 46 | 51-70 |
| hsa-mir-29b-2 | SEQ ID NO: 47 | 52-71 |
| hsa-mir-29c | SEQ ID NO: 48 | 54-75 |
| hsa-mir-30a | SEQ ID NO: 49 | 47-68 |
| hsa-mir-30c-2 | SEQ ID NO: 50 | 7-29 |
| hsa-mir-30d | SEQ ID NO: 51 | 6-27 |
| hsa-mir-30b | SEQ ID NO: 52 | 17-37 |
| hsa-mir-30c-1 | SEQ ID NO: 53 | 17-39 |
| hsa-mir-30e | SEQ ID NO: 54 | 2-21 |
| hsa-mir-31 | SEQ ID NO: 55 | 9-29 |
| hsa-mir-32 | SEQ ID NO: 56 | 6-26 |
| hsa-mir-33 | SEQ ID NO: 57 | 6-24 |
| hsa-mir-34a | SEQ ID NO: 58 | 22-43 |
| hsa-mir-34b | SEQ ID NO: 59 | 14-35 |
| hsa-mir-34c | SEQ ID NO: 60 | 13-34 |
| hsa-mir-92-1 | SEQ ID NO: 61 | 48-69 |
| hsa-mir-92-2 | SEQ ID NO: 62 | 48-69 |
| hsa-mir-93 | SEQ ID NO: 63 | 12-33 |
| hsa-mir-95 | SEQ ID NO: 64 | 49-70 |
| hsa-mir-96 | SEQ ID NO: 65 | 9-30 |
| hsa-mir-98 | SEQ ID NO: 66 | 2-23 |
| hsa-mir-99a | SEQ ID NO: 67 | 13-34 |
| hsa-mir-99b | SEQ ID NO: 68 | 7-28 |
| hsa-mir-100 | SEQ ID NO: 69 | 13-34 |
| hsa-mir-101-1 | SEQ ID NO: 70 | 47-68 |
| hsa-mir-101-2 | SEQ ID NO: 71 | 49-70 |
| hsa-mir-103-2 | SEQ ID NO: 72 | 48-70 |
| hsa-mir-103-1 | SEQ ID NO: 73 | 48-70 |
| hsa-mir-105-1 | SEQ ID NO: 74 | 13-32 |
| hsa-mir-105-2 | SEQ ID NO: 75 | 13-32 |
| hsa-mir-106a | SEQ ID NO: 76 | 13-36 |
| hsa-mir-106b | SEQ ID NO: 77 | 12-32 |
| hsa-mir-107 | SEQ ID NO: 78 | 50-72 |
| hsa-mir-122a | SEQ ID NO: 79 | 15-37 |
| hsa-mir-124a-1 | SEQ ID NO: 80 | 52-73 |
| hsa-mir-124a-2 | SEQ ID NO: 81 | 61-82 |
| hsa-mir-124a-3 | SEQ ID NO: 82 | 52-73 |
| hsa-mir-125b-1 | SEQ ID NO: 83 | 15-36 |
| hsa-mir-125a | SEQ ID NO: 84 | 15-37 |
| hsa-mir-125b-2 | SEQ ID NO: 85 | 17-38 |
| hsa-mir-126 | SEQ ID NO: 86 | 15-35 and/or 52-72 |
| hsa-mir-127 | SEQ ID NO: 87 | 57-78 |
| hsa-mir-128a | SEQ ID NO: 88 | 50-71 |
| hsa-mir-128b | SEQ ID NO: 89 | 52-73 |
| hsa-mir-129-2 | SEQ ID NO: 90 | 15-35 |
| hsa-mir-130a | SEQ ID NO: 91 | 55-74 |
| hsa-mir-130b | SEQ ID NO: 92 | 51-72 |
| hsa-mir-132 | SEQ ID NO: 93 | 59-80 |
| hsa-mir-133a-1 | SEQ ID NO: 94 | 54-75 |
| hsa-mir-133a-2 | SEQ ID NO: 95 | 60-81 |
| hsa-mir-133b | SEQ ID NO: 96 | 67-87 |
| hsa-mir-134 | SEQ ID NO: 97 | 8-28 |
| hsa-mir-135a-1 | SEQ ID NO: 98 | 17-39 |
| hsa-mir-135a-2 | SEQ ID NO: 99 | 23-45 |
| hsa-mir-135b | SEQ ID NO: 100 | 16-37 |
| hsa-mir-136 | SEQ ID NO: 101 | 15-37 |
| hsa-mir-137 | SEQ ID NO: 102 | 60-81 |
| hsa-mir-138-2 | SEQ ID NO: 103 | 10-26 |
| hsa-mir-138-1 | SEQ ID NO: 104 | 23-39 |
| hsa-mir-139 | SEQ ID NO: 105 | 7-24 |
| hsa-mir-140 | SEQ ID NO: 106 | 24-44 |
| hsa-mir-141 | SEQ ID NO: 107 | 60-80 |
| hsa-mir-142 | SEQ ID NO: 108 | 16-35 and/or 52-74 |
| hsa-mir-143 | SEQ ID NO: 109 | 61-82 |
| hsa-mir-144 | SEQ ID NO: 110 | 52-73 |
| hsa-mir-145 | SEQ ID NO: 111 | 16-39 |
| hsa-mir-146 | SEQ ID NO: 112 | 21-42 |
| hsa-mir-147 | SEQ ID NO: 113 | 47-66 |
| hsa-mir-148a | SEQ ID NO: 114 | 44-65 |
| hsa-mir-148b | SEQ ID NO: 115 | 63-84 |
| hsa-mir-149 | SEQ ID NO: 116 | 15-36 |

TABLE 1-continued

Human miRNA Sequences

| miRNA name | Precursor | Processed Sequence Relative to Precursor |
|---|---|---|
| hsa-mir-150 | SEQ ID NO: 117 | 16-37 |
| hsa-mir-151 | SEQ ID NO: 118 | 46-67 |
| hsa-mir-152 | SEQ ID NO: 119 | 54-74 |
| hsa-mir-153-1 | SEQ ID NO: 120 | 54-73 |
| hsa-mir-153-2 | SEQ ID NO: 121 | 53-72 |
| hsa-mir-154 | SEQ ID NO: 122 | 15-36 |
| hsa-mir-155 | SEQ ID NO: 123 | 4-25 |
| hsa-mir-181a | SEQ ID NO: 124 | 39-61 |
| hsa-mir-181b-1 | SEQ ID NO: 125 | 36-59 |
| hsa-mir-181c | SEQ ID NO: 126 | 27-48 |
| hsa-mir-181b-2 | SEQ ID NO: 127 | 16-39 |
| hsa-mir-182 | SEQ ID NO: 128 | 23-44 and/or 67-87 |
| hsa-mir-183 | SEQ ID NO: 129 | 27-49 |
| hsa-mir-184 | SEQ ID NO: 130 | 53-74 |
| hsa-mir-185 | SEQ ID NO: 131 | 15-32 |
| hsa-mir-186 | SEQ ID NO: 132 | 15-37 |
| hsa-mir-187 | SEQ ID NO: 133 | 71-91 |
| hsa-mir-188 | SEQ ID NO: 134 | 15-36 |
| hsa-mir-190 | SEQ ID NO: 135 | 15-36 |
| hsa-mir-191 | SEQ ID NO: 136 | 16-37 |
| hsa-mir-192 | SEQ ID NO: 137 | 24-44 |
| hsa-mir-193 | SEQ ID NO: 138 | 55-75 |
| hsa-mir-194-1 | SEQ ID NO: 139 | 15-36 |
| hsa-mir-194-2 | SEQ ID NO: 140 | 15-36 |
| hsa-mir-195 | SEQ ID NO: 141 | 15-35 |
| hsa-mir-196-1 | SEQ ID NO: 142 | 7-27 |
| hsa-mir-196-2 | SEQ ID NO: 143 | 25-45 |
| hsa-mir-197 | SEQ ID NO: 144 | 48-69 |
| hsa-mir-198 | SEQ ID NO: 145 | 6-24 |
| hsa-mir-199a-1 | SEQ ID NO: 146 | 6-28 and/or 46-67 |
| hsa-mir-199a-2 | SEQ ID NO: 147 | 31-53 and/or 69-90 |
| hsa-mir-199b | SEQ ID NO: 148 | 26-48 |
| hsa-mir-200b | SEQ ID NO: 149 | 54-77 |
| hsa-mir-200c | SEQ ID NO: 150 | 45-66 |
| hsa-mir-200a | SEQ ID NO: 151 | 54-75 |
| hsa-mir-203 | SEQ ID NO: 152 | 65-86 |
| hsa-mir-204 | SEQ ID NO: 153 | 33-54 |
| hsa-mir-205 | SEQ ID NO: 154 | 34-55 |
| hsa-mir-206 | SEQ ID NO: 155 | 53-74 |
| hsa-mir-208 | SEQ ID NO: 156 | 44-65 |
| hsa-mir-210 | SEQ ID NO: 157 | 66-86 |
| hsa-mir-211 | SEQ ID NO: 158 | 26-47 |
| hsa-mir-212 | SEQ ID NO: 159 | 71-91 |
| hsa-mir-213 | SEQ ID NO: 160 | 24-46 and/or 64-85 |
| hsa-mir-214 | SEQ ID NO: 161 | 71-91 |
| hsa-mir-215 | SEQ ID NO: 162 | 27-47 |
| hsa-mir-216 | SEQ ID NO: 163 | 19-39 |
| hsa-mir-217 | SEQ ID NO: 164 | 35-58 |
| hsa-mir-218-1 | SEQ ID NO: 165 | 25-45 |
| hsa-mir-218-2 | SEQ ID NO: 166 | 25-45 |
| hsa-mir-219-1 | SEQ ID NO: 167 | 21-41 |
| hsa-mir-219-2 | SEQ ID NO: 168 | 19-39 |
| hsa-mir-220 | SEQ ID NO: 169 | 23-43 |
| hsa-mir-221 | SEQ ID NO: 170 | 65-87 |
| hsa-mir-222 | SEQ ID NO: 171 | 69-92 |
| hsa-mir-223 | SEQ ID NO: 172 | 68-88 |
| hsa-mir-224 | SEQ ID NO: 173 | 8-30 |
| hsa-mir-296 | SEQ ID NO: 174 | 14-34 |
| hsa-mir-299 | SEQ ID NO: 175 | 7-28 |
| hsa-mir-301 | SEQ ID NO: 176 | 51-73 |
| hsa-mir-302 | SEQ ID NO: 177 | 44-66 |
| hsa-mir-320 | SEQ ID NO: 178 | 48-70 |
| hsa-mir-321 | SEQ ID NO: 179 | 10-30 |
| hsa-mir-323 | SEQ ID NO: 180 | 50-71 |
| hsa-mir-324 | SEQ ID NO: 181 | 16-38 and/or 51-72 |
| hsa-mir-326 | SEQ ID NO: 182 | 60-79 |
| hsa-mir-328 | SEQ ID NO: 183 | 48-69 |
| hsa-mir-330 | SEQ ID NO: 184 | 57-79 |
| hsa-mir-331 | SEQ ID NO: 185 | 61-81 |
| hsa-mir-335 | SEQ ID NO: 186 | 16-38 |
| hsa-mir-337 | SEQ ID NO: 187 | 56-78 |
| hsa-mir-338 | SEQ ID NO: 188 | 42-64 |
| hsa-mir-339 | SEQ ID NO: 189 | 15-35 |
| hsa-mir-340 | SEQ ID NO: 190 | 58-80 |
| hsa-mir-342 | SEQ ID NO: 191 | 61-84 |
| hsa-mir-345 | SEQ ID NO: 573 | 17-37 |
| hsa-mir-346 | SEQ ID NO: 574 | 4-26 |
| hsa-mir-367 | SEQ ID NO: 575 | 44-65 |
| hsa-mir-368 | SEQ ID NO: 576 | 44-65 |
| hsa-mir-369 | SEQ ID NO: 577 | 44-64 |
| hsa-mir-370 | SEQ ID NO: 578 | 48-68 |
| hsa-mir-371 | SEQ ID NO: 579 | 44-64 |
| hsa-mir-372 | SEQ ID NO: 580 | 42-64 |
| hsa-mir-373 | SEQ ID NO: 581 | 44-66 |
| hsa-mir-374 | SEQ ID NO: 582 | 12-33 |
| hsa-mir-375 | SEQ ID NO: 677 | 40-61 |
| hsa-mir-376a | SEQ ID NO: 678 | 44-64 |
| hsa-mir-377 | SEQ ID NO: 679 | 45-66 |
| hsa-mir-378 | SEQ ID NO: 680 | 5-26 and 44-65 |
| hsa-mir-379 | SEQ ID NO: 681 | 6-24 |
| hsa-mir-380 | SEQ ID NO: 682 | 5-26 and 40-61 |
| hsa-mir-381 | SEQ ID NO: 683 | 49-70 |
| hsa-mir-382 | SEQ ID NO: 684 | 11-32 |
| hsa-mir-383 | SEQ ID NO: 685 | 7-28 |
| hsa-mir-384 | SEQ ID NO: 686 | 57-76 |
| hsa-mir-422a | SEQ ID NO: 687 | 11-32 |
| hsa-mir-423 | SEQ ID NO: 688 | 53-74 |
| hsa-mir-424 | SEQ ID NO: 689 | 11-32 |
| hsa-mir-425 | SEQ ID NO: 690 | 55-75 |
| hsa-mir-448 | SEQ ID NO: 691 | 71-92 |
| hsa-mir-429 | SEQ ID NO: 692 | 51-72 |
| hsa-mir-449 | SEQ ID NO: 693 | 16-37 |
| hsa-mir-450-1 | SEQ ID NO: 694 | 17-38 |
| hsa-mir-450-2 | SEQ ID NO: 704 | 22-43 |
| hsa-mir-451 | SEQ ID NO: 705 | 17-39 |
| hsa-mir-452 | SEQ ID NO: 706 | 17-38 |
| hsa-mir-453 | SEQ ID NO: 707 | 43-64 |
| hsa-mir-455 | SEQ ID NO: 708 | 16-37 |
| hsa-mir-483 | SEQ ID NO: 709 | 48-70 |
| hsa-mir-484 | SEQ ID NO: 710 | 2-23 |
| hsa-mir-485 | SEQ ID NO: 711 | 9-30 |
| hsa-mir-486 | SEQ ID NO: 712 | 4-25 |
| hsa-mir-487 | SEQ ID NO: 713 | 49-70 |
| hsa-mir-488 | SEQ ID NO: 714 | 14-34 |
| hsa-mir-489 | SEQ ID NO: 715 | 51-73 |
| hsa-mir-490 | SEQ ID NO: 716 | 76-97 |
| hsa-mir-491 | SEQ ID NO: 717 | 16-38 |
| hsa-mir-492 | SEQ ID NO: 718 | 30-52 |
| hsa-mir-493 | SEQ ID NO: 719 | 16-37 |
| hsa-mir-494 | SEQ ID NO: 720 | 48-71 |
| hsa-mir-495 | SEQ ID NO: 721 | 50-72 |
| hsa-mir-496 | SEQ ID NO: 722 | 61-77 |
| hsa-mir-497 | SEQ ID NO: 723 | 24-44 |
| hsa-mir-498 | SEQ ID NO: 724 | 34-56 |
| hsa-mir-499 | SEQ ID NO: 725 | 33-55 |
| hsa-mir-500 | SEQ ID NO: 726 | 52-73 |
| hsa-mir-501 | SEQ ID NO: 727 | 14-35 |
| hsa-mir-502 | SEQ ID NO: 728 | 1-21 |
| hsa-mir-503 | SEQ ID NO: 729 | 6-28 |
| hsa-mir-504 | SEQ ID NO: 730 | 13-33 |
| hsa-mir-505 | SEQ ID NO: 731 | 52-73 |
| hsa-mir-506 | SEQ ID NO: 732 | 71-91 |
| hsa-mir-507 | SEQ ID NO: 733 | 56-76 |
| hsa-mir-508 | SEQ ID NO: 734 | 61-83 |
| hsa-mir-509 | SEQ ID NO: 735 | 55-77 |
| hsa-mir-510 | SEQ ID NO: 736 | 10-32 |
| hsa-mir-511-1 | SEQ ID NO: 737 | 16-36 |
| hsa-mir-511-2 | SEQ ID NO: 738 | 16-36 |
| hsa-mir-512-1 | SEQ ID NO: 739 | 14-36 |
| hsa-mir-512-2 | SEQ ID NO: 740 | 20-42 |
| hsa-mir-513-1 | SEQ ID NO: 741 | 37-58 |
| hsa-mir-513-2 | SEQ ID NO: 742 | 36-57 |
| hsa-mir-514-1 | SEQ ID NO: 743 | 39-58 |
| hsa-mir-514-2 | SEQ ID NO: 744 | 39-58 |
| hsa-mir-514-3 | SEQ ID NO: 745 | 39-58 |
| hsa-mir-515-1 | SEQ ID NO: 746 | 14-37 |
| hsa-mir-515-2 | SEQ ID NO: 747 | 14-37 |
| hsa-mir-516-1 | SEQ ID NO: 748 | 61-78 |
| hsa-mir-516-2 | SEQ ID NO: 749 | 61-78 |
| hsa-mir-516-3 | SEQ ID NO: 750 | 15-37 |

TABLE 1-continued

Human miRNA Sequences

| miRNA name | Precursor | Processed Sequence Relative to Precursor |
|---|---|---|
| hsa-mir-516-4 | SEQ ID NO: 751 | 15-37 |
| hsa-mir-517a | SEQ ID NO: 752 | 15-36 |
| hsa-mir-517b | SEQ ID NO: 753 | 6-27 |
| hsa-mir-517c | SEQ ID NO: 754 | 20-41 |
| hsa-mir-518a-1 | SEQ ID NO: 755 | 14-34 |
| hsa-mir-518a-2 | SEQ ID NO: 756 | 15-34 |
| hsa-mir-518b | SEQ ID NO: 757 | 51-72 |
| hsa-mir-518c | SEQ ID NO: 758 | 24-46 |
| hsa-mir-518d | SEQ ID NO: 759 | 16-36 |
| hsa-mir-518e | SEQ ID NO: 760 | 54-75 |
| hsa-mir-518f | SEQ ID NO: 761 | 16-38 |
| hsa-mir-519a-1 | SEQ ID NO: 762 | 15-38 |
| hsa-mir-519a-2 | SEQ ID NO: 763 | 54-78 |
| hsa-mir-519b | SEQ ID NO: 764 | 13-36 |
| hsa-mir-519c | SEQ ID NO: 765 | 16-39 |
| hsa-mir-519d | SEQ ID NO: 766 | 54-76 |
| hsa-mir-519e | SEQ ID NO: 767 | 14-35 |
| hsa-mir-520a | SEQ ID NO: 768 | 15-35 |
| hsa-mir-520b | SEQ ID NO: 769 | 41-61 |
| hsa-mir-520c | SEQ ID NO: 770 | 16-36 |
| hsa-mir-520d | SEQ ID NO: 771 | 15-37 |
| hsa-mir-520e | SEQ ID NO: 772 | 54-74 |
| hsa-mir-520f | SEQ ID NO: 773 | 55-76 |
| hsa-mir-520g | SEQ ID NO: 774 | 55-78 |
| hsa-mir-520h | SEQ ID NO: 775 | 55-76 |
| hsa-mir-521-1 | SEQ ID NO: 776 | 54-75 |
| hsa-mir-521-2 | SEQ ID NO: 777 | 54-75 |
| hsa-mir-522 | SEQ ID NO: 778 | 16-39 |
| hsa-mir-523 | SEQ ID NO: 779 | 16-39 |
| hsa-mir-524 | SEQ ID NO: 780 | 16-37 |
| hsa-mir-525 | SEQ ID NO: 781 | 15-35 |
| hsa-mir-526a-1 | SEQ ID NO: 782 | 15-35 |
| hsa-mir-526a-2 | SEQ ID NO: 783 | 7-27 |
| hsa-mir-526b | SEQ ID NO: 784 | 14-37 |
| hsa-mir-527 | SEQ ID NO: 785 | 14-34 |
| ambi-mir-7100 | SEQ ID NO: 803 | |
| mir-526b* | SEQ ID NO: 804 | |
| mir-520a* | SEQ ID NO: 805 | |

TABLE 2

Mouse miRNA Sequences

| miRNA name | Precursor | Processed Sequence Relative to Precursor |
|---|---|---|
| mmu-mir-1-1 | SEQ ID NO: 192 | 49-69 |
| mmu-mir-1-2 | SEQ ID NO: 193 | 47-67 |
| mmu-let-7g | SEQ ID NO: 194 | 7-27 |
| mmu-let-7i | SEQ ID NO: 195 | 6-24 |
| mmu-let-7d | SEQ ID NO: 196 | 16-36 + 70-91 |
| mmu-let-7a-1 | SEQ ID NO: 197 | 13-34 |
| mmu-let-7a-2 | SEQ ID NO: 198 | 17-38 |
| mmu-let-7b | SEQ ID NO: 199 | 7-28 |
| mmu-let-7c-1 | SEQ ID NO: 200 | 16-37 |
| mmu-let-7c-2 | SEQ ID NO: 201 | 14-35 |
| mmu-let-7e | SEQ ID NO: 202 | 15-35 |
| mmu-let-7f-1 | SEQ ID NO: 203 | 8-29 |
| mmu-let-7f-2 | SEQ ID NO: 204 | 8-29 |
| mmu-mir-7-1 | SEQ ID NO: 205 | 24-44 |
| mmu-mir-7-2 | SEQ ID NO: 206 | 19-39 |
| mmu-mir-7b | SEQ ID NO: 207 | 30-50 |
| mmu-mir-9-2 | SEQ ID NO: 208 | 8-30 and/or 46-66 |
| mmu-mir-9-1 | SEQ ID NO: 209 | 16-38 and/or 56-76 |
| mmu-mir-9-3 | SEQ ID NO: 210 | 16-38 and/or 56-76 |
| mmu-mir-10b | SEQ ID NO: 211 | 7-28 |
| mmu-mir-10a-1 | SEQ ID NO: 212 | 22-44 |
| mmu-mir-10a-2 | SEQ ID NO: 213 | 22-44 |
| mmu-mir-15b | SEQ ID NO: 214 | 4-25 |
| mmu-mir-15a | SEQ ID NO: 215 | 15-36 |
| mmu-mir-16-1 | SEQ ID NO: 216 | 16-37 |
| mmu-mir-16-2 | SEQ ID NO: 217 | 17-38 |

TABLE 2-continued

Mouse miRNA Sequences

| miRNA name | Precursor | Processed Sequence Relative to Precursor |
|---|---|---|
| mmu-mir-17 | SEQ ID NO: 218 | 14-37 and/or 51-70 |
| mmu-mir-18 | SEQ ID NO: 219 | 17-38 |
| mmu-mir-19b-2 | SEQ ID NO: 220 | 54-76 |
| mmu-mir-19a | SEQ ID NO: 221 | 49-71 |
| mmu-mir-19b-1 | SEQ ID NO: 222 | 54-76 |
| mmu-mir-20 | SEQ ID NO: 223 | 27-49 |
| mmu-mir-21 | SEQ ID NO: 224 | 18-39 |
| mmu-mir-22 | SEQ ID NO: 225 | 57-78 |
| mmu-mir-23b | SEQ ID NO: 226 | 46-68 |
| mmu-mir-23a | SEQ ID NO: 227 | 46-66 |
| mmu-mir-24-1 | SEQ ID NO: 228 | 6-28 and/or 44-65 |
| mmu-mir-24-2 | SEQ ID NO: 229 | 61-82 |
| mmu-mir-25 | SEQ ID NO: 230 | 52-73 |
| mmu-mir-26a-1 | SEQ ID NO: 231 | 16-37 |
| mmu-mir-26b | SEQ ID NO: 232 | 15-36 |
| mmu-mir-26a-2 | SEQ ID NO: 233 | 14-35 |
| mmu-mir-27b | SEQ ID NO: 234 | 49-68 |
| mmu-mir-27a | SEQ ID NO: 235 | 56-76 |
| mmu-mir-28 | SEQ ID NO: 236 | 14-35 |
| mmu-mir-29b-1 | SEQ ID NO: 237 | 47-68 |
| mmu-mir-29a | SEQ ID NO: 238 | 53-74 |
| mmu-mir-29c | SEQ ID NO: 239 | 54-75 |
| mmu-mir-29b-2 | SEQ ID NO: 240 | 52-73 |
| mmu-mir-30a | SEQ ID NO: 241 | 47-68 |
| mmu-mir-30b | SEQ ID NO: 242 | 2-22 |
| mmu-mir-30e | SEQ ID NO: 243 | 2-21 |
| mmu-mir-30c-1 | SEQ ID NO: 244 | 17-39 |
| mmu-mir-30c-2 | SEQ ID NO: 245 | 14-36 |
| mmu-mir-30d | SEQ ID NO: 246 | 12-33 |
| mmu-mir-31 | SEQ ID NO: 247 | 28-49 |
| mmu-mir-32 | SEQ ID NO: 248 | 6-26 |
| mmu-mir-33 | SEQ ID NO: 249 | 6-24 |
| mmu-mir-34c | SEQ ID NO: 250 | 13-35 |
| mmu-mir-34b | SEQ ID NO: 251 | 13-35 |
| mmu-mir-34a | SEQ ID NO: 252 | 20-42 |
| mmu-mir-92-2 | SEQ ID NO: 253 | 55-75 |
| mmu-mir-92-1 | SEQ ID NO: 254 | 50-70 |
| mmu-mir-93 | SEQ ID NO: 255 | 15-37 |
| mmu-mir-96 | SEQ ID NO: 256 | 24-46 |
| mmu-mir-98 | SEQ ID NO: 257 | 2-23 |
| mmu-mir-99a | SEQ ID NO: 258 | 6-25 |
| mmu-mir-99b | SEQ ID NO: 259 | 7-28 |
| mmu-mir-100 | SEQ ID NO: 260 | 13-34 |
| mmu-mir-101 | SEQ ID NO: 261 | 38-57 |
| mmu-mir-101b | SEQ ID NO: 262 | 61-82 |
| mmu-mir-103-1 | SEQ ID NO: 263 | 52-74 |
| mmu-mir-103-2 | SEQ ID NO: 264 | 52-74 |
| mmu-mir-106a | SEQ ID NO: 265 | 5-26 |
| mmu-mir-106b | SEQ ID NO: 266 | 12-32 |
| mmu-mir-107 | SEQ ID NO: 267 | 52-74 |
| mmu-mir-122a | SEQ ID NO: 268 | 6-28 |
| mmu-mir-124a-3 | SEQ ID NO: 269 | 43-64 |
| mmu-mir-124a-1 | SEQ ID NO: 270 | 52-73 |
| mmu-mir-124a-2 | SEQ ID NO: 271 | 61-82 |
| mmu-mir-125a | SEQ ID NO: 272 | 6-28 |
| mmu-mir-125b-2 | SEQ ID NO: 273 | 7-28 |
| mmu-mir-125b-1 | SEQ ID NO: 274 | 15-36 |
| mmu-mir-126 | SEQ ID NO: 275 | 9-29 and/or 46-66 |
| mmu-mir-127 | SEQ ID NO: 276 | 43-64 |
| mmu-mir-128a | SEQ ID NO: 277 | 44-65 |
| mmu-mir-128b | SEQ ID NO: 278 | 48-69 |
| mmu-mir-129-1 | SEQ ID NO: 279 | 6-27 |
| mmu-mir-129-2 | SEQ ID NO: 280 | 15-36 |
| mmu-mir-130a | SEQ ID NO: 281 | 42-61 |
| mmu-mir-130b | SEQ ID NO: 282 | 51-72 |
| mmu-mir-132 | SEQ ID NO: 283 | 42-63 |
| mmu-mir-133a-1 | SEQ ID NO: 284 | 44-65 |
| mmu-mir-133a-2 | SEQ ID NO: 285 | 60-81 |
| mmu-mir-133b | SEQ ID NO: 286 | 67-87 |
| mmu-mir-134 | SEQ ID NO: 287 | 7-27 |
| mmu-mir-135a-1 | SEQ ID NO: 288 | 17-39 |
| mmu-mir-135b | SEQ ID NO: 289 | 16-37 |
| mmu-mir-135a-2 | SEQ ID NO: 290 | 23-45 |
| mmu-mir-136 | SEQ ID NO: 291 | 5-27 |
| mmu-mir-137 | SEQ ID NO: 292 | 46-67 |

TABLE 2-continued

Mouse miRNA Sequences

| miRNA name | Precursor | Processed Sequence Relative to Precursor |
|---|---|---|
| mmu-mir-138-2 | SEQ ID NO: 293 | 2-18 |
| mmu-mir-138-1 | SEQ ID NO: 294 | 23-39 |
| mmu-mir-139 | SEQ ID NO: 295 | 7-24 |
| mmu-mir-140 | SEQ ID NO: 296 | 7-27 |
| mmu-mir-141 | SEQ ID NO: 297 | 49-69 |
| mmu-mir-142 | SEQ ID NO: 298 | 4-23 and/or 40-61 |
| mmu-mir-143 | SEQ ID NO: 299 | 40-61 |
| mmu-mir-144 | SEQ ID NO: 300 | 43-64 |
| mmu-mir-145 | SEQ ID NO: 301 | 7-30 |
| mmu-mir-146 | SEQ ID NO: 302 | 6-27 |
| mmu-mir-148a | SEQ ID NO: 303 | 61-82 |
| mmu-mir-149 | SEQ ID NO: 304 | 4-25 |
| mmu-mir-150 | SEQ ID NO: 305 | 6-27 |
| mmu-mir-151 | SEQ ID NO: 306 | 43-63 |
| mmu-mir-152 | SEQ ID NO: 307 | 47-67 |
| mmu-mir-153 | SEQ ID NO: 308 | 44-63 |
| mmu-mir-154 | SEQ ID NO: 309 | 6-27 |
| mmu-mir-155 | SEQ ID NO: 310 | 4-25 |
| mmu-mir-181a | SEQ ID NO: 311 | 7-29 |
| mmu-mir-181b-1 | SEQ ID NO: 312 | 12-35 |
| mmu-mir-181c | SEQ ID NO: 313 | 17-38 |
| mmu-mir-181b-2 | SEQ ID NO: 314 | 16-39 |
| mmu-mir-182 | SEQ ID NO: 315 | 7-28 |
| mmu-mir-183 | SEQ ID NO: 316 | 6-28 |
| mmu-mir-184 | SEQ ID NO: 317 | 45-66 |
| mmu-mir-185 | SEQ ID NO: 318 | 7-24 |
| mmu-mir-186 | SEQ ID NO: 319 | 7-29 |
| mmu-mir-187 | SEQ ID NO: 320 | 40-61 |
| mmu-mir-188 | SEQ ID NO: 321 | 6-27 |
| mmu-mir-190 | SEQ ID NO: 322 | 6-27 |
| mmu-mir-191 | SEQ ID NO: 323 | 7-28 |
| mmu-mir-192 | SEQ ID NO: 324 | 14-31 |
| mmu-mir-193 | SEQ ID NO: 325 | 41-61 |
| mmu-mir-194-1 | SEQ ID NO: 326 | 7-28 |
| mmu-mir-194-2 | SEQ ID NO: 327 | 16-37 |
| mmu-mir-195 | SEQ ID NO: 328 | 1-21 |
| mmu-mir-196-1 | SEQ ID NO: 329 | 24-44 |
| mmu-mir-196-2 | SEQ ID NO: 330 | 16-36 |
| mmu-mir-199a-1 | SEQ ID NO: 331 | 6-28 and/or 45-66 |
| mmu-mir-199a-2 | SEQ ID NO: 332 | 31-53 and/or 69-90 |
| mmu-mir-199b | SEQ ID NO: 333 | 26-48 |
| mmu-mir-200b | SEQ ID NO: 334 | 45-67 |
| mmu-mir-200a | SEQ ID NO: 335 | 54-75 |
| mmu-mir-200c | SEQ ID NO: 336 | 46-67 |
| mmu-mir-201 | SEQ ID NO: 337 | 6-26 |
| mmu-mir-202 | SEQ ID NO: 338 | 45-66 |
| mmu-mir-203 | SEQ ID NO: 339 | 49-69 |
| mmu-mir-204 | SEQ ID NO: 340 | 6-28 |
| mmu-mir-205 | SEQ ID NO: 341 | 7-28 |
| mmu-mir-206 | SEQ ID NO: 342 | 46-67 |
| mmu-mir-207 | SEQ ID NO: 343 | 52-74 |
| mmu-mir-208 | SEQ ID NO: 344 | 50-71 |
| mmu-mir-210 | SEQ ID NO: 345 | 66-86 |
| mmu-mir-211 | SEQ ID NO: 346 | 26-47 |
| mmu-mir-212 | SEQ ID NO: 347 | 56-76 |
| mmu-mir-213 | SEQ ID NO: 348 | 14-36 and/or 54-75 |
| mmu-mir-214 | SEQ ID NO: 349 | 71-91 |
| mmu-mir-215 | SEQ ID NO: 350 | 30-50 |
| mmu-mir-216 | SEQ ID NO: 351 | 7-27 |
| mmu-mir-217 | SEQ ID NO: 352 | 34-57 |
| mmu-mir-218-2 | SEQ ID NO: 353 | 25-45 |
| mmu-mir-219-1 | SEQ ID NO: 354 | 21-41 |
| mmu-mir-219-2 | SEQ ID NO: 355 | 19-39 |
| mmu-mir-221 | SEQ ID NO: 356 | 60-81 |
| mmu-mir-222 | SEQ ID NO: 357 | 49-71 |
| mmu-mir-223 | SEQ ID NO: 358 | 68-88 |
| mmu-mir-224 | SEQ ID NO: 359 | 8-30 |
| mu-miR-290 | SEQ ID NO: 360 | 15-37 |
| mmu-mir-291 | SEQ ID NO: 361 | 14-35 and/or 50-72 |
| mmu-mir-292 | SEQ ID NO: 362 | 12-33 and/or 51-73 |
| mmu-mir-293 | SEQ ID NO: 363 | 48-69 |
| mmu-mir-294 | SEQ ID NO: 364 | 51-72 |
| mmu-mir-295 | SEQ ID NO: 365 | 43-65 |
| mmu-mir-296 | SEQ ID NO: 366 | 13-33 |
| mmu-mir-297-1 | SEQ ID NO: 367 | 15-35 |
| mmu-mir-297-2 | SEQ ID NO: 368 | 36-56 |
| mmu-mir-298 | SEQ ID NO: 369 | 11-32 |
| mmu-mir-299 | SEQ ID NO: 370 | 7-28 |
| mmu-mir-300 | SEQ ID NO: 371 | 51-72 |
| mmu-mir-301 | SEQ ID NO: 372 | 51-73 |
| mmu-mir-302 | SEQ ID NO: 373 | 44-66 |
| mmu-mir-320 | SEQ ID NO: 374 | 48-70 |
| mmu-mir-321 | SEQ ID NO: 375 | 10-30 |
| mmu-mir-323 | SEQ ID NO: 376 | 50-71 |
| mmu-mir-324 | SEQ ID NO: 377 | 18-40 and/or 53-74 |
| mmu-mir-325 | SEQ ID NO: 378 | 16-38 |
| mmu-mir-326 | SEQ ID NO: 379 | 60-80 |
| mmu-mir-328 | SEQ ID NO: 380 | 61-82 |
| mmu-mir-329 | SEQ ID NO: 381 | 61-82 |
| mmu-mir-330 | SEQ ID NO: 382 | 61-83 |
| mmu-mir-331 | SEQ ID NO: 383 | 61-81 |
| mmu-mir-337 | SEQ ID NO: 384 | 61-83 |
| mmu-mir-338 | SEQ ID NO: 385 | 61-83 |
| mmu-mir-339 | SEQ ID NO: 386 | 16-36 |
| mmu-mir-340 | SEQ ID NO: 387 | 61-83 |
| mmu-mir-341 | SEQ ID NO: 388 | 61-81 |
| mmu-mir-342 | SEQ ID NO: 389 | 61-84 |
| mmu-mir-344 | SEQ ID NO: 390 | 61-83 |
| mmu-mir-345 | SEQ ID NO: 391 | 16-36 |
| mmu-mir-346 | SEQ ID NO: 392 | 16-38 |
| mmu-mir-350 | SEQ ID NO: 393 | 61-84 |
| mmu-mir-351 | SEQ ID NO: 583 | 16-39 |
| mmu-mir-370 | SEQ ID NO: 584 | 48-70 |
| mmu-mir-376a | SEQ ID NO: 585 | 44-64 |
| mmu-mir-376b | SEQ ID NO: 586 | 51-72 |
| mmu-mir-380 | SEQ ID NO: 587 | 40-61 |
| mmu-mir-409 | SEQ ID NO: 588 | 47-69 |
| mmu-mir-410 | SEQ ID NO: 589 | 50-71 |
| mmu-mir-411 | SEQ ID NO: 590 | 56-78 |
| mmu-mir-412 | SEQ ID NO: 591 | 50-72 |
| mmu-mir-425 | SEQ ID NO: 695 | 54-74 |
| mmu-mir-429 | SEQ ID NO: 696 | 51-72 |
| mmu-mir-448 | SEQ ID NO: 697 | 72-93 |
| mmu-mir-449 | SEQ ID NO: 698 | 16-37 |
| mmu-mir-450 | SEQ ID NO: 699 | 17-38 |
| mmu-mir-451 | SEQ ID NO: 786 | 17-38 |
| mmu-mir-452 | SEQ ID NO: 787 | 17-38 |
| mmu-mir-463 | SEQ ID NO: 788 | 4-24 |
| mmu-mir-464 | SEQ ID NO: 789 | 47-69 |
| mmu-mir-465 | SEQ ID NO: 790 | 5-27 |
| mmu-mir-466 | SEQ ID NO: 791 | 51-73 |
| mmu-mir-467 | SEQ ID NO: 792 | 50-71 |
| mmu-mir-468 | SEQ ID NO: 793 | 53-75 |
| mmu-mir-469 | SEQ ID NO: 794 | 6-31 |
| mmu-mir-470 | SEQ ID NO: 795 | 9-29 |
| mmu-mir-471 | SEQ ID NO: 796 | 7-29 |
| mmu-mir-483 | SEQ ID NO: 797 | 45-67 |
| mmu-mir-484 | SEQ ID NO: 798 | 2-23 |
| mmu-mir-485 | SEQ ID NO: 799 | 9-30 |
| mmu-mir-486 | SEQ ID NO: 800 | 4-25 |

TABLE 3

Rat miRNA Sequences

| miRNA name | Precursor | Processed Sequence Relative to Precursor |
|---|---|---|
| rno-let-7d | SEQ ID NO: 394 | 14-34 and/or 68-89 |
| rno-mir-7-1 | SEQ ID NO: 395 | 19-39 and/or 61-82 |
| rno-let-7a-1 | SEQ ID NO: 396 | 13-34 |
| rno-let-7a-2 | SEQ ID NO: 397 | 17-38 |
| rno-let-7b | SEQ ID NO: 398 | 7-28 |
| rno-let-7c-1 | SEQ ID NO: 399 | 16-37 |
| rno-let-7c-2 | SEQ ID NO: 400 | 14-35 |
| rno-let-7e | SEQ ID NO: 401 | 15-35 |
| rno-let-7f-1 | SEQ ID NO: 402 | 8-29 |

TABLE 3-continued

Rat miRNA Sequences

| miRNA name | Precursor | Processed Sequence Relative to Precursor |
|---|---|---|
| rno-let-7f-2 | SEQ ID NO: 403 | 8-29 |
| rno-let-7i | SEQ ID NO: 404 | 6-24 |
| rno-mir-7-2 | SEQ ID NO: 405 | 19-39 |
| rno-mir-7b | SEQ ID NO: 406 | 29-49 |
| rno-mir-9-1 | SEQ ID NO: 407 | 16-38 |
| rno-mir-9-3 | SEQ ID NO: 408 | 16-38 |
| rno-mir-9-2 | SEQ ID NO: 409 | 16-38 |
| rno-mir-10a | SEQ ID NO: 410 | 22-44 |
| rno-mir-10b | SEQ ID NO: 411 | 26-47 |
| rno-mir-15b | SEQ ID NO: 412 | 20-41 |
| rno-mir-16 | SEQ ID NO: 413 | 17-38 |
| rno-mir-17 | SEQ ID NO: 414 | 14-37 |
| rno-mir-18 | SEQ ID NO: 415 | 17-38 |
| rno-mir-19b-1 | SEQ ID NO: 416 | 54-76 |
| rno-mir-19b-2 | SEQ ID NO: 417 | 62-84 |
| rno-mir-19a | SEQ ID NO: 418 | 49-71 |
| rno-mir-20 | SEQ ID NO: 419 | 16-38 and/or 52-72 |
| rno-mir-21 | SEQ ID NO: 420 | 18-39 |
| rno-mir-22 | SEQ ID NO: 421 | 57-78 |
| rno-mir-23a | SEQ ID NO: 422 | 46-66 |
| rno-mir-23b | SEQ ID NO: 423 | 58-80 |
| rno-mir-24-1 | SEQ ID NO: 424 | 44-65 |
| rno-mir-24-2 | SEQ ID NO: 425 | 61-82 |
| rno-mir-25 | SEQ ID NO: 426 | 52-73 |
| rno-mir-26a | SEQ ID NO: 427 | 16-37 |
| rno-mir-26b | SEQ ID NO: 428 | 15-36 |
| rno-mir-27b | SEQ ID NO: 429 | 61-80 |
| rno-mir-27a | SEQ ID NO: 430 | 56-76 |
| rno-mir-28 | SEQ ID NO: 431 | 14-35 |
| rno-mir-29b-2 | SEQ ID NO: 432 | 52-73 |
| rno-mir-29a | SEQ ID NO: 433 | 53-74 |
| rno-mir-29b-1 | SEQ ID NO: 434 | 51-72 |
| rno-mir-29c | SEQ ID NO: 435 | 54-75 |
| rno-mir-30c-1 | SEQ ID NO: 436 | 17-39 |
| rno-mir-30e | SEQ ID NO: 437 | 2-21 |
| rno-mir-30b | SEQ ID NO: 438 | 16-36 |
| rno-mir-30d | SEQ ID NO: 439 | 12-33 |
| rno-mir-30a | SEQ ID NO: 440 | 47-68 |
| rno-mir-30c-2 | SEQ ID NO: 441 | 14-36 |
| rno-mir-31 | SEQ ID NO: 442 | 28-49 |
| rno-mir-32 | SEQ ID NO: 443 | 6-26 |
| rno-mir-33 | SEQ ID NO: 444 | 6-24 |
| rno-mir-34b | SEQ ID NO: 445 | 13-35 |
| rno-mir-34c | SEQ ID NO: 446 | 13-35 |
| rno-mir-34a | SEQ ID NO: 447 | 20-42 |
| rno-mir-92-1 | SEQ ID NO: 448 | 48-68 |
| rno-mir-92-2 | SEQ ID NO: 449 | 55-75 |
| rno-mir-93 | SEQ ID NO: 450 | 15-37 |
| rno-mir-96 | SEQ ID NO: 451 | 24-46 |
| rno-mir-98 | SEQ ID NO: 452 | 2-23 |
| rno-mir-99a | SEQ ID NO: 453 | 13-34 |
| rno-mir-99b | SEQ ID NO: 454 | 7-28 |
| rno-mir-100 | SEQ ID NO: 455 | 13-34 |
| rno-mir-101b | SEQ ID NO: 456 | 61-82 |
| rno-mir-101 | SEQ ID NO: 457 | 47-68 |
| rno-mir-103-2 | SEQ ID NO: 458 | 52-74 |
| rno-mir-103-1 | SEQ ID NO: 459 | 52-74 |
| rno-mir-106b | SEQ ID NO: 460 | 12-32 |
| rno-mir-107 | SEQ ID NO: 461 | 52-74 |
| rno-mir-122a | SEQ ID NO: 462 | 15-37 |
| rno-mir-124a-3 | SEQ ID NO: 463 | 52-73 |
| rno-mir-124a-1 | SEQ ID NO: 464 | 52-73 |
| rno-mir-124a-2 | SEQ ID NO: 465 | 61-82 |
| rno-mir-125a | SEQ ID NO: 466 | 15-37 |
| rno-mir-125b-1 | SEQ ID NO: 467 | 15-36 |
| rno-mir-125b-2 | SEQ ID NO: 468 | 17-38 |
| rno-mir-126 | SEQ ID NO: 469 | 9-29 and/or 46-66 |
| rno-mir-127 | SEQ ID NO: 470 | 57-78 |
| rno-mir-128a | SEQ ID NO: 471 | 50-71 |
| rno-mir-128b | SEQ ID NO: 472 | 52-73 |
| rno-mir-129-2 | SEQ ID NO: 473 | 19-40 and/or 61-82 |
| rno-mir-129-1 | SEQ ID NO: 474 | 6-27 |
| rno-mir-130a | SEQ ID NO: 475 | 55-74 |
| rno-mir-130b | SEQ ID NO: 476 | 51-72 |
| rno-mir-132 | SEQ ID NO: 477 | 59-80 |
| rno-mir-133a | SEQ ID NO: 478 | 53-74 |
| rno-mir-134 | SEQ ID NO: 479 | 8-28 |
| rno-mir-135b | SEQ ID NO: 480 | 16-37 |
| rno-mir-135a | SEQ ID NO: 481 | 23-45 |
| rno-mir-136 | SEQ ID NO: 482 | 15-37 |
| rno-mir-137 | SEQ ID NO: 483 | 60-81 |
| rno-mir-138-2 | SEQ ID NO: 484 | 9-25 |
| rno-mir-138-1 | SEQ ID NO: 485 | 23-39 |
| rno-mir-139 | SEQ ID NO: 486 | 7-24 |
| rno-mir-140 | SEQ ID NO: 487 | 23-43 and/or 61-84 |
| rno-mir-141 | SEQ ID NO: 488 | 59-79 |
| rno-mir-142 | SEQ ID NO: 489 | 16-35 and/or 52-74 |
| rno-mir-143 | SEQ ID NO: 490 | 60-81 |
| rno-mir-144 | SEQ ID NO: 491 | 50-71 |
| rno-mir-145 | SEQ ID NO: 492 | 16-39 |
| rno-mir-146 | SEQ ID NO: 493 | 17-38 |
| rno-mir-148b | SEQ ID NO: 494 | 61-82 |
| rno-mir-150 | SEQ ID NO: 495 | 16-37 |
| rno-mir-151 | SEQ ID NO: 496 | 16-37 and/or 50-71 |
| rno-mir-152 | SEQ ID NO: 497 | 53-73 |
| rno-mir-153 | SEQ ID NO: 498 | 53-72 |
| rno-mir-154 | SEQ ID NO: 499 | 15-36 |
| rno-mir-181c | SEQ ID NO: 500 | 24-45 |
| rno-mir-181a | SEQ ID NO: 501 | 39-61 |
| rno-mir-181b-1 | SEQ ID NO: 502 | 36-59 |
| rno-mir-181b-2 | SEQ ID NO: 503 | 15-38 |
| rno-mir-183 | SEQ ID NO: 504 | 27-49 |
| rno-mir-184 | SEQ ID NO: 505 | 47-68 |
| rno-mir-185 | SEQ ID NO: 506 | 14-31 |
| rno-mir-186 | SEQ ID NO: 507 | 15-37 |
| rno-mir-187 | SEQ ID NO: 508 | 66-86 |
| rno-mir-190 | SEQ ID NO: 509 | 15-36 |
| rno-mir-191 | SEQ ID NO: 510 | 15-36 |
| rno-mir-192 | SEQ ID NO: 511 | 24-44 |
| rno-mir-193 | SEQ ID NO: 512 | 54-74 |
| rno-mir-194-1 | SEQ ID NO: 513 | 15-36 |
| rno-mir-194-2 | SEQ ID NO: 514 | 15-36 |
| rno-mir-195 | SEQ ID NO: 515 | 15-35 |
| rno-mir-196 | SEQ ID NO: 516 | 25-45 |
| rno-mir-199a | SEQ ID NO: 517 | 31-53 |
| rno-mir-200c | SEQ ID NO: 518 | 46-67 |
| rno-mir-200a | SEQ ID NO: 519 | 54-75 |
| rno-mir-200b | SEQ ID NO: 520 | 54-77 |
| rno-mir-203 | SEQ ID NO: 521 | 52-73 |
| rno-mir-204 | SEQ ID NO: 522 | 33-54 |
| rno-mir-205 | SEQ ID NO: 523 | 33-54 |
| rno-mir-206 | SEQ ID NO: 524 | 51-72 |
| rno-mir-208 | SEQ ID NO: 525 | 50-71 |
| rno-mir-210 | SEQ ID NO: 526 | 66-86 |
| rno-mir-211 | SEQ ID NO: 527 | 26-47 |
| rno-mir-212 | SEQ ID NO: 528 | 72-92 |
| rno-mir-213 | SEQ ID NO: 529 | 55-76 |
| rno-mir-214 | SEQ ID NO: 530 | 71-91 |
| rno-mir-216 | SEQ ID NO: 531 | 19-39 |
| rno-mir-217 | SEQ ID NO: 532 | 32-55 |
| rno-mir-218-2 | SEQ ID NO: 533 | 25-45 |
| rno-mir-218-1 | SEQ ID NO: 534 | 25-45 |
| rno-mir-219-1 | SEQ ID NO: 535 | 21-41 |
| rno-mir-219-2 | SEQ ID NO: 536 | 19-39 |
| rno-mir-221 | SEQ ID NO: 537 | 65-87 |
| rno-mir-222 | SEQ ID NO: 538 | 62-85 |
| rno-mir-223 | SEQ ID NO: 539 | 68-88 |
| rno-mir-290 | SEQ ID NO: 540 | 14-36 |
| rno-mir-291 | SEQ ID NO: 541 | 14-35 and/or 50-72 |
| rno-mir-292 | SEQ ID NO: 542 | 12-33 and/or 51-73 |
| rno-mir-296 | SEQ ID NO: 543 | 13-33 |
| rno-mir-297 | SEQ ID NO: 544 | 26-48 |
| rno-mir-298 | SEQ ID NO: 545 | 11-32 |
| rno-mir-299 | SEQ ID NO: 546 | 7-28 |
| rno-mir-300 | SEQ ID NO: 547 | 51-72 |
| rno-mir-301 | SEQ ID NO: 548 | 61-85 |
| rno-mir-320 | SEQ ID NO: 549 | 48-70 |
| rno-mir-321 | SEQ ID NO: 550 | 10-30 |
| rno-mir-322 | SEQ ID NO: 551 | 61-80 |
| rno-mir-323 | SEQ ID NO: 552 | 50-71 |

TABLE 3-continued

Rat miRNA Sequences

| miRNA name | Precursor | Processed Sequence Relative to Precursor |
| --- | --- | --- |
| rno-mir-324 | SEQ ID NO: 553 | 16-38 and/or 51-72 |
| rno-mir-325 | SEQ ID NO: 554 | 16-38 |
| rno-mir-326 | SEQ ID NO: 555 | 60-80 |
| rno-mir-328 | SEQ ID NO: 556 | 48-69 |
| rno-mir-329 | SEQ ID NO: 557 | 61-82 |
| rno-mir-330 | SEQ ID NO: 558 | 60-82 |
| rno-mir-331 | SEQ ID NO: 559 | 61-81 |
| rno-mir-333 | SEQ ID NO: 560 | 16-35 |
| rno-mir-336 | SEQ ID NO: 561 | 16-36 |
| rno-mir-337 | SEQ ID NO: 562 | 60-82 |
| rno-mir-338 | SEQ ID NO: 563 | 41-63 |
| rno-mir-339 | SEQ ID NO: 564 | 16-36 |
| rno-mir-341 | SEQ ID NO: 565 | 61-81 |
| rno-mir-342 | SEQ ID NO: 566 | 61-84 |
| rno-mir-344 | SEQ ID NO: 567 | 61-83 |
| rno-mir-345 | SEQ ID NO: 568 | 16-36 |
| rno-mir-346 | SEQ ID NO: 569 | 16-38 |
| rno-mir-349 | SEQ ID NO: 570 | 61-82 |
| rno-mir-350 | SEQ ID NO: 571 | 61-84 |
| rno-mir-351 | SEQ ID NO: 572 | 16-39 |
| rno-mir-352 | SEQ ID NO: 592 | 61-81 |
| rno-mir-421 | SEQ ID NO: 593 | 10-30 |
| rno-mir-429 | SEQ ID NO: 700 | 53-74 |
| rno-mir-448 | SEQ ID NO: 701 | 72-93 |
| rno-mir-449 | SEQ ID NO: 702 | 16-37 |
| rno-mir-450 | SEQ ID NO: 703 | 17-38 |
| rno-mir-451 | SEQ ID NO: 801 | 17-38 |
| rno-mir-483 | SEQ ID NO: 802 | 45-67 |

It is understood that an miRNA is derived from genomic sequences or a gene. In this respect, the term "gene" is used for simplicity to refer to the genomic sequence encoding the precursor miRNA for a given miRNA. However, embodiments of the invention may involve genomic sequences of a miRNA that are involved in its expression, such as a promoter or other regulatory sequences.

The term "recombinant" may be used and this generally refers to a molecule that has been manipulated in vitro or that is the replicated or expressed product of such a molecule.

The term "nucleic acid" is well known in the art. A "nucleic acid" as used herein will generally refer to a molecule (one or more strands) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompass the terms "oligonucleotide" and "polynucleotide," each as a subgenus of the term "nucleic acid."

The term "miRNA" generally refers to a single-stranded molecule, but in specific embodiments, molecules implemented in the invention will also encompass a region or an additional strand that is partially (between 10 and 50% complementary across length of strand), substantially (greater than 50% but less than 100% complementary across length of strand) or fully complementary to another region of the same single-stranded molecule or to another nucleic acid. Thus, nucleic acids may encompass a molecule that comprises one or more complementary or self-complementary strand(s) or "complement(s)" of a particular sequence comprising a molecule. For example, precursor miRNA may have a self-complementary region, which is up to 100% complementary.

As used herein, "hybridization", "hybridizes" or "capable of hybridizing" is understood to mean the forming of a double or triple stranded molecule or a molecule with partial double or triple stranded nature. The term "anneal" as used herein is synonymous with "hybridize." The term "hybridization", "hybridize(s)" or "capable of hybridizing" encompasses the terms "stringent condition(s)" or "high stringency" and the terms "low stringency" or "low stringency condition(s)."

Synthetic nucleic acids of the invention will comprise, in some embodiments the miRNA sequence of any miRNA described in SEQ ID NOs:1-805, and/or any sequence with the complement thereof. It is contemplated that nucleic acids sequences of the invention can have, have at least, or have at most 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150 contiguous nucleotides from SEQ ID NOs: 1-805 (or any ranger derivable therein), or be a complement thereof. In other embodiments, nucleic acids are, are at least, or are at most 80, 81, 82, 83, 84, 85, 86, 87, 88, 89, 90, 91, 92, 93, 94, 95, 96, 97, 98, 99, 100% identical or complementary to the miRNA sequence of SEQ ID NOs:1-805 or to the entire sequence of any of SEQ ID NOs:1-805, or any combination or range derivable therein.

Moreover, sequences are provided in the appendix. The appendix provides a list of 1) miRNAs that were screeened, any one of which can be screened for using any array or method of the present invention; 2) the names of the probe used to screen for that miRNA; and, 3) the sequence of the named probe. It is clear that a particular probe can be used for identifying the level of expression of one or more target miRNAs, or set of target miRNAs (sets of targeted miRNAs may include completely unrelated RNAs, inadditions to sets that are either related or in the same gene family). It is contemplated that any of these sequences in the appendix can be used in embodiments of the invention.

1. Nucleobases

As used herein a "nucleobase" refers to a heterocyclic base, such as for example a naturally occurring nucleobase (i.e., an A, T, G, C or U) found in at least one naturally occurring nucleic acid (i.e., DNA and RNA), and naturally or non-naturally occurring derivative(s) and analogs of such a nucleobase. A nucleobase generally can form one or more hydrogen bonds ("anneal" or "hybridize") with at least one naturally occurring nucleobase in manner that may substitute for naturally occurring nucleobase pairing (e.g., the hydrogen bonding between A and T, G and C, and A and U).

"Purine" and/or "pyrimidine" nucleobase(s) encompass naturally occurring purine and/or pyrimidine nucleobases and also derivative(s) and analog(s) thereof, including but not limited to, those a purine or pyrimidine substituted by one or more of an alkyl, caboxyalkyl, amino, hydroxyl, halogen (i.e., fluoro, chloro, bromo, or iodo), thiol or alkylthiol moeity. Preferred alkyl (e.g., alkyl, caboxyalkyl, etc.) moieties comprise of from about 1, about 2, about 3, about 4, about 5, to about 6 carbon atoms. Other non-limiting examples of a purine or pyrimidine include a deazapurine, a 2,6-diaminopurine, a 5-fluorouracil, a xanthine, a hypoxanthine, a 8-bromoguanine, a 8-chloroguanine, a bromothymine, a 8-aminoguanine, a 8-hydroxyguanine, a 8-methylguanine, a 8-thioguanine, an azaguanine, a 2-aminopurine, a 5-ethylcytosine, a 5-methylcyosine, a 5-bromouracil, a 5-ethyluracil, a 5-iodouracil, a 5-chlorouracil, a 5-propyluracil, a thiouracil, a 2-methyladenine, a methylthioadenine, a N,N-diemethyladenine, an azaadenines, a 8-bromoadenine, a 8-hydroxyadenine, a 6-hydroxyaminopurine, a 6-thiopurine, a 4-(6-aminohexyl/cytosine), and the like. Other examples are well known to those of skill in the art.

A nucleobase may be comprised in a nucleoside or nucleotide, using any chemical or natural synthesis method described herein or known to one of ordinary skill in the art. Such nucleobase may be labeled or it may be part of a molecule that is labeled and contains the nucleobase.

2. Nucleosides

As used herein, a "nucleoside" refers to an individual chemical unit comprising a nucleobase covalently attached to a nucleobase linker moiety. A non-limiting example of a "nucleobase linker moiety" is a sugar comprising 5-carbon atoms (i.e., a "5-carbon sugar"), including but not limited to a deoxyribose, a ribose, an arabinose, or a derivative or an analog of a 5-carbon sugar. Non-limiting examples of a derivative or an analog of a 5-carbon sugar include a 2'-fluoro-2'-deoxyribose or a carbocyclic sugar where a carbon is substituted for an oxygen atom in the sugar ring.

Different types of covalent attachment(s) of a nucleobase to a nucleobase linker moiety are known in the art. By way of non-limiting example, a nucleoside comprising a purine (i.e., A or G) or a 7-deazapurine nucleobase typically covalently attaches the 9 position of a purine or a 7-deazapurine to the 1'-position of a 5-carbon sugar. In another non-limiting example, a nucleoside comprising a pyrimidine nucleobase (i.e., C, T or U) typically covalently attaches a 1 position of a pyrimidine to a 1'-position of a 5-carbon sugar (Kornberg and Baker, 1992).

3. Nucleotides

As used herein, a "nucleotide" refers to a nucleoside further comprising a "backbone moiety". A backbone moiety generally covalently attaches a nucleotide to another molecule comprising a nucleotide, or to another nucleotide to form a nucleic acid. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when a nucleotide comprises derivatives or analogs of a naturally occurring 5-carbon sugar or phosphorus moiety.

4. Nucleic Acid Analogs

A nucleic acid may comprise, or be composed entirely of, a derivative or analog of a nucleobase, a nucleobase linker moiety and/or backbone moiety that may be present in a naturally occurring nucleic acid. RNA with nucleic acid analogs may also be labeled according to methods of the invention. As used herein a "derivative" refers to a chemically modified or altered form of a naturally occurring molecule, while the terms "mimic" or "analog" refer to a molecule that may or may not structurally resemble a naturally occurring molecule or moiety, but possesses similar functions. As used herein, a "moiety" generally refers to a smaller chemical or molecular component of a larger chemical or molecular structure. Nucleobase, nucleoside and nucleotide analogs or derivatives are well known in the art, and have been described (see for example, Scheit, 1980, incorporated herein by reference).

Additional non-limiting examples of nucleosides, nucleotides or nucleic acids comprising 5-carbon sugar and/or backbone moiety derivatives or analogs, include those in: U.S. Pat. No. 5,681,947, which describes oligonucleotides comprising purine derivatives that form triple helixes with and/or prevent expression of dsDNA; U.S. Pat. Nos. 5,652,099 and 5,763,167, which describe nucleic acids incorporating fluorescent analogs of nucleosides found in DNA or RNA, particularly for use as fluorescent nucleic acids probes; U.S. Pat. No. 5,614,617, which describes oligonucleotide analogs with substitutions on pyrimidine rings that possess enhanced nuclease stability; U.S. Pat. Nos. 5,670,663, 5,872,232 and 5,859,221, which describe oligonucleotide analogs with modified 5-carbon sugars (i.e., modified 2'-deoxyfuranosyl moieties) used in nucleic acid detection; U.S. Pat. No. 5,446,137, which describes oligonucleotides comprising at least one 5-carbon sugar moiety substituted at the 4' position with a substituent other than hydrogen that can be used in hybridization assays; U.S. Pat. No. 5,886,165, which describes oligonucleotides with both deoxyribonucleotides with internucleotide linkages and ribonucleotides with internucleotide linkages; U.S. Pat. No. 5,714,606, which describes a modified internucleotide linkage wherein a 3'-position oxygen of the internucleotide linkage is replaced by a carbon to enhance the nuclease resistance of nucleic acids; U.S. Pat. No. 5,672,697, which describes oligonucleotides containing one or more 5' methylene phosphonate internucleotide linkages that enhance nuclease resistance; U.S. Pat. Nos. 5,466,786 and 5,792,847, which describe the linkage of a substituent moiety which may comprise a drug or label to the 2' carbon of an oligonucleotide to provide enhanced nuclease stability and ability to deliver drugs or detection moieties; U.S. Pat. No. 5,223,618, which describes oligonucleotide analogs with a 2 or 3 carbon backbone linkage attaching the 4' position and 3' position of adjacent 5-carbon sugar moiety to enhanced cellular uptake, resistance to nucleases and hybridization to target RNA; U.S. Pat. No. 5,470,967, which describes oligonucleotides comprising at least one sulfamate or sulfamide internucleotide linkage that are useful as nucleic acid hybridization probe; U.S. Pat. Nos. 5,378,825, 5,777,092, 5,623,070, 5,610,289 and 5,602,240, which describe oligonucleotides with three or four atom linker moiety replacing phosphodiester backbone moiety used for improved nuclease resistance, cellular uptake and regulating RNA expression; U.S. Pat. No. 5,858,988, which describes hydrophobic carrier agent attached to the 2'-O position of oligonucleotides to enhanced their membrane permeability and stability; U.S. Pat. No. 5,214,136, which describes oligonucleotides conjugated to anthraquinone at the 5' terminus that possess enhanced hybridization to DNA or RNA; enhanced stability to nucleases; U.S. Pat. No. 5,700,922, which describes PNA-DNA-PNA chimeras wherein the DNA comprises 2'-deoxy-erythro-pentofuranosyl nucleotides for enhanced nuclease resistance, binding affinity, and ability to activate RNase H; and U.S. Pat. No. 5,708,154, which describes RNA linked to a DNA to form a DNA-RNA hybrid; U.S. Pat. No. 5,728,525, which describes the labeling of nucleoside analogs with a universal fluorescent label.

Additional teachings for nucleoside analogs and nucleic acid analogs are U.S. Pat. No. 5,728,525, which describes nucleoside analogs that are end-labeled; U.S. Pat. Nos. 5,637,683, 6,251,666 (L-nucleotide substitutions), and U.S. Pat. No. 5,480,980 (7-deaza-2'deoxyguanosine nucleotides and nucleic acid analogs thereof).

The use of other analogs is specifically contemplated for use in the context of the present invention. Such analogs may be used in synthetic nucleic acid molecules of the invention, both throughout the molecule or at selected nucleotides. They include, but are not limited to, 1) ribose modifications (such as 2'F, 2' $NH_2$, 2'$N_3$, 4'thio, or 2'

O—CH$_3$) and 2) phosphate modifications (such as those found in phosphorothioates, methyl phosphonates, and phosphoroborates). Such analogs have been created to confer stability on RNAs by reducing or eliminating their capacity to be cleaved by ribonucleases. When these nucleotide analogs are present in RNAs, they can have profoundly positive effects on the stability of the RNAs in animals. It is contemplated that the use of nucleotide analogs can be used alone or in conjunction with any of the design modifications of a synthetic miRNA for any nucleic acid of the invention.

5. Modified Nucleotides

Both synthetic miRNAs and miRNA inhibitors of the invention specifically contemplate the use of nucleotides that are modified to enhance their activities. Such nucleotides include those that are at the 5' or 3' terminus of the RNA as well as those that are internal within the molecule. Modified nucleotides used in the complementary strands of synthetic miRNAs either block the 5'OH or phosphate of the RNA or introduce internal sugar modifications that enhance uptake of the active strand of the synthetic miRNA. Modifications for the miRNA inhibitors include internal sugar modifications that enhance hybridization as well as stabilize the molecules in cells and terminal modifications that further stabilize the nucleic acids in cells. Further contemplated are modifications that can be detected by microscopy or other methods to identify cells that contain the synthetic miRNAs or miRNA inhibitors.

B. Preparation of Nucleic Acids

A nucleic acid may be made by any technique known to one of ordinary skill in the art, such as for example, chemical synthesis, enzymatic production or biological production. Though synthetic miRNAs according to the invention could be produced using recombinant methods, it is preferred to produce synthetic miRNAs by chemical synthesis or enzymatic production. Likewise, miRNA inhibitors are preferentially produced by chemical synthesis or enzymatic production. Non-synthetic miRNAs can be produced by a number of methods, including methods involving recombinant DNA technology.

Nucleic acid synthesis is performed according to standard methods. See, for example, Itakura and Riggs (1980). Additionally, U.S. Pat. Nos. 4,704,362, 5,221,619, and 5,583,013 each describe various methods of preparing synthetic nucleic acids. Non-limiting examples of a synthetic nucleic acid (e.g., a synthetic oligonucleotide), include a nucleic acid made by in vitro chemically synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986 and U.S. Pat. Ser. No. 5,705,629, each incorporated herein by reference. In the methods of the present invention, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. Nos. 4,683,202 and 4,682,195, each incorporated herein by reference), or the synthesis of an oligonucleotide described in U.S. Pat. No. 5,645,897, incorporated herein by reference.

Oligonucleotide synthesis is well known to those of skill in the art. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

Basically, chemical synthesis can be achieved by the diester method, the triester method polynucleotides phosphorylase method and by solid-phase chemistry. These methods are discussed in further detail below.

Diester Method. The diester method was the first to be developed to a usable state, primarily by Khorana and co-workers. (Khorana, 1979). The basic step is the joining of two suitably protected deoxynucleotides to form a dideoxynucleotide containing a phosphodiester bond. The diester method is well established and has been used to synthesize DNA molecules (Khorana, 1979).

Triester Method. The main difference between the diester and triester methods is the presence in the latter of an extra protecting group on the phosphate atoms of the reactants and products (Itakura et al., 1975). The phosphate protecting group is usually a chlorophenyl group, which renders the nucleotides and polynucleotide intermediates soluble in organic solvents. Therefore purification's are done in chloroform solutions. Other improvements in the method include (i) the block coupling of trimers and larger oligomers, (ii) the extensive use of high-performance liquid chromatography for the purification of both intermediate and final products, and (iii) solid-phase synthesis.

Polynucleotide Phosphorylase Method. This is an enzymatic method of DNA synthesis that can be used to synthesize many useful oligonucleotides (Gillam et al., 1978; Gillam et al., 1979). Under controlled conditions, polynucleotide phosphorylase adds predominantly a single nucleotide to a short oligonucleotide. Chromatographic purification allows the desired single adduct to be obtained. At least a trimer is required to start the procedure, and this primer must be obtained by some other method. The polynucleotide phosphorylase method works and has the advantage that the procedures involved are familiar to most biochemists.

Solid-Phase Methods. Drawing on the technology developed for the solid-phase synthesis of polypeptides, it has been possible to attach the initial nucleotide to solid support material and proceed with the stepwise addition of nucleotides. All mixing and washing steps are simplified, and the procedure becomes amenable to automation. These syntheses are now routinely carried out using automatic nucleic acid synthesizers.

Phosphoramidite chemistry (Beaucage and Lyer, 1992) has become by far the most widely used coupling chemistry for the synthesis of oligonucleotides. As is well known to those skilled in the art, phosphoramidite synthesis of oligonucleotides involves activation of nucleoside phosphoramidite monomer precursors by reaction with an activating agent to form activated intermediates, followed by sequential addition of the activated intermediates to the growing oligonucleotide chain (generally anchored at one end to a suitable solid support) to form the oligonucleotide product.

Recombinant Methods. Recombinant methods for producing nucleic acids in a cell are well known to those of skill in the art. These include the use of vectors, plasmids, cosmids, and other vehicles for delivery a nucleic acid to a cell, which may be the target cell or simply a host cell (to produce large quantities of the desired RNA molecule). Alternatively, such vehicles can be used in the context of a cell free system so long as the reagents for generating the RNA molecule are present. Such methods include those described in Sambrook, 2003, Sambrook, 2001 and Sambrook, 1989, which are hereby incorporated by reference.

In certain embodiments, the present invention concerns nucleic acid molecules that are not synthetic. In some embodiments, the nucleic acid molecule has a chemical structure of a naturally occuring nucleic acid and a sequence of a naturally occuring nucleic acid, such as the exact and entire sequence of a single stranded primary miRNA (see Lee 2002), a single-stranded precursor miRNA, or a single-stranded mature miRNA. In addition to the use of recombinant technology, such non-synthetic nucleic acids may be generated chemically, such as by employing technology used for creating oligonucleotides.

C. Design of Synthetic miRNAs

Synthetic miRNAs typically comprise two strands, an active strand that is identical in sequence to the mature miRNA that is being studied and a complemenrtary strand that is at least partially complementary to the active strand. The active strand is the biologically relevant molecule and should be preferentially taken up by the complex in cells that modulates translation either through mRNA degradation or translational control. Preferential uptake of the active strand has two profound results: (1) the observed activity of the synthetic miRNA increases dramatically and (2) non-intended effects induced by uptake and activation of the complementary strand are essentially eliminated. According to the invention, several synthetic miRNA designs can be used to ensure the preferential uptake of the active strand.

5' Blocking Agent. The introduction of a stable moiety other than phosphate or hydroxyl at the 5' end of the complementary strand impairs its activity in the miRNA pathway. This ensures that only the active strand of the synthetic miRNA will be used to regulate translation in the cell. 5' modifications include, but are not limited to, $NH_2$, biotin, an amine group, a lower alkylamine group, an acetyl group, 2'O-Me, DMTO, fluoroscein, a thiol, or acridine or any other group with this type of functionality.

Other Sense Strand Modifications. The introduction of nucleotide modifications like 2'-OMe, $NH_2$, biotin, an amine group, a lower alkylamine group, an acetyl group, DMTO, fluoroscein, a thiol, or acridine or any other group with this type of functionality in the complementary strand of the synthetic miRNA can eliminate the activity of the complementary strand and enhance uptake of the active strand of the miRNA.

Base Mismatches in the Sense Strand. As with siRNAs (Schwarz 2003), the relative stability of the 5' and 3' ends of the active strand of the synthetic miRNA apparently determines the uptake and activation of the active by the miRNA pathway. Destabilizing the 5' end of the active strand of the synthetic miRNA by the strategic placement of base mismatches in the 3' end of the complementary strand of the synthetic miRNA enhances the activity of the active strand and essentially eliminates the activity of the complementary strand.

D. Host Cells and Target Cells

The cells used to understand miRNA function may be derived from or contained in any organism (e.g., plant, animal, protozoan, virus, bacterium, or fungus). The plant may be a monocot, dicot or gynmosperm; the animal may be a vertebrate or invertebrate. Preferred microbes are those used in agriculture or by industry, and those that a pathogenic for plants or animals. Fungi include organisms in both the mold and yeast morphologies. Examples of vertebrates include fish and mammals, including cattle, goat, pig, sheep, hamster, mouse, rate and human; invertebrate animals include nematodes, insects, arachnids, and other arthropods. Preferably, the cell is a vertebrate cell. More preferably, the cell is a mammalian cell.

The cells used to understand miRNA function may be from the germ line or somatic, totipotent or pluripotent, dividing or non-dividing, parenchyma or epithelium, immortalized or transformed, or the like. The cell can be a gamete or an embryo; if an embryo, it can be a single cell embryo or a constituent cell or cells from a multicellular embryo. The term "embryo" thus encompasses fetal tissue. The cell used for miRNA functional analysis may be an undifferentiated cell, such as a stem cell, or a differentiated cell, such as from a cell of an organ or tissue, including fetal tissue, or any other cell present in an organism. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells, of the endocrine or exocrine glands. Alternatively, cells may be qualified as germ cells, nurse cells, epithelial cells, endothelial cells, hormone secreting cells, contractile cells, skeletal muscle cells, cardiac muscle cells, blood cells, or cells from the bone, bone marrow, brain, breast, cervix, colon, gastrointestinal tract, heart, kidney, large intestine, liver, lung, lymph nodes, ovary, pancreas, prostate, small intestine, spine or spinal cord, spleen, stomach, testes, *thymus*, or uterus.

As used herein, the terms "cell," "cell line," and "cell culture" may be used interchangeably. All of these terms also include their progeny, which is any and all subsequent generations formed by cell division. It is understood that all progeny may not be identical due to deliberate or inadvertent mutations. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a small, interfering RNA or a template construct encoding a reporter gene has been introduced. Therefore, recombinant cells are distinguishable from naturally occurring cells that do not contain a recombinantly introduced nucleic acid.

A tissue may comprise a host cell or cells to be transformed or contacted with a nucleic acid delivery composition and/or an additional agent. The tissue may be part or separated from an organism. In certain embodiments, a tissue and its constituent cells may comprise, but is not limited to, blood (e.g., hematopoietic cells (such as human hematopoietic progenitor cells, human hematopoietic stem cells, $CD34^+$ cells $CD4^+$ cells), lymphocytes and other blood lineage cells), bone marrow, brain, stem cells, blood vessel, liver, lung, bone, breast, cartilage, cervix, colon, cornea, embryonic, endometrium, endothelial, epithelial, esophagus, facia, fibroblast, follicular, ganglion cells, glial cells, goblet cells, kidney, lymph node, muscle, neuron, ovaries, pancreas, peripheral blood, prostate, skin, skin, small intestine, spleen, stomach, testes.

In certain embodiments, the host cell or tissue may be comprised in at least one organism. In certain embodiments, the organism may be, human, primate or murine. In other embodiments the organism may be any eukaryote or even a prokayrote (e.g., a eubacteria, an archaea), as would be understood by one of ordinary skill in the art (see, for example, webpage http://phylogeny.arizona.edu/tree/phylogeny.html). One of skill in the art would further understand the conditions under which to incubate all of the above described host cells to maintain them and to permit their division to form progeny.

E. Labels and Tags

Synthetic miRNAs and miRNA inhibitors may be labeled with a radioactive, enzymatic, colorimetric, or other label or tag for detection or isolation purposes. Nucleic acids may be labeled with fluorescence in some embodiments of the invention. The fluorescent labels contemplated for use as conjugates include, but are not limited to, Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5, 6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, SYPRO, TAMRA, TET, Tetramethylrhodamine, and/or Texas Red.

It is contemplated that synthetic miRNAs and miRNA inhibitors may be labeled with two different labels. Furthermore, fluorescence resonance energy transfer (FRET) may be employed in methods of the invention (e.g., Klostermeier et al., 2002; Emptage, 2001; Didenko, 2001, each incorporated by reference).

A number of techniques for visualizing or detecting labeled nucleic acids are readily available. The reference by Stanley T. Crooke, 2000 has a discussion of such techniques (Chapter 6) which is incorporated by reference. Such techniques include, microscopy, arrays, Fluorometry, Light cyclers or other real time PCR™ machines, FACS analysis, scintillation counters, Phosphoimagers, Geiger counters, MRI, CAT, antibody-based detection methods (Westerns, immunofluorescence, immunohistochemistry), histochemical techniques, HPLC (Griffey et al., 1997, spectroscopy, capillary gel electrophoresis (Cummins et al., 1996), spectroscopy; mass spectroscopy; radiological techniques; and mass balance techniques. Alternatively, nucleic acids may be labeled or tagged to allow for their efficient isolation. In other embodiments of the invention, nucleic acids are biotinylated.

F. Delivery Methods

The present invention involves in some embodiments delivering a nucleic acid into a cell. This may be done as part of a screening method, or it may be related to a therapeutic or diagnostic application.

RNA molecules may be encoded by a nucleic acid molecule comprised in a vector. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al., 1989 and Ausubel et al., 1996, both incorporated herein by reference. In addition to encoding a modified polypeptide such as modified gelonin, a vector may encode non-modified polypeptide sequences such as a tag or targetting molecule. A targetting molecule is one that directs the desired nucleic acid to a particular organ, tissue, cell, or other location in a subject's body.

The term "expression vector" refers to a vector containing a nucleic acid sequence coding for at least part of a gene product capable of being transcribed. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described There are a number of ways in which expression vectors may be introduced into cells. In certain embodiments of the invention, the expression vector comprises a virus or engineered vector derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubenstein, 1988; Temin, 1986).

The retroviruses are a group of single-stranded RNA viruses characterized by an ability to convert their RNA to double-stranded DNA in infected cells; they can also be used as vectors. Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

Other suitable methods for nucleic acid delivery to effect expression of compositions of the present invention are believed to include virtually any method by which a nucleic acid (e.g., DNA, including viral and nonviral vectors) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783, 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

II. Screening with Synthetic miRNA and miRNA Inhibitor Libraries

As used in the patent application, screening is a process wherein multiple miRNA-specific reagents are delivered separately into individual cell populations or animals. At one or more designated times after delivery, the cell populations or animals are assayed for one or more phenotypes. Those cells or animals that have a significantly different phenotype than cells or animals in the negative control group are classified as positives. The miRNA that was being manipulated in the sample is defined as a hit. Hits represent targets for additional research and potential therapeutic development.

In some embodiments, there is a multi-step process for screening. In certain embodiments, there are four general steps:

(1) Develop Quantitative Assay to Monitor Cellular Process being Studied.

Assays that measure the intensity of a cellular phenotype range from microscopic assays that monitor cell size, cell cycle status, or antibody staining to enzymatic assays that assess the turnover of a specific substrate in a cell lysate to direct measurements of biomolecules or small molecules in lysates, on cells, or in medium.

Critical to the success of a screen is creating an assay that truly measures the cellular phenotype and maximizing the signal-to-noise ratio of the assay. Maximizing signal-to-noise involves testing variables like assay time, assay components, cell type, and length of time between transfection and assay. The greater the difference in the assay results between a positive phenotype and a negative control phenotype, the greater the spread will be in the screening results and the better the opportunity will be to identify interesting genes.

(2) Optimize Transfection Conditions for the Desired Cells.

The first step in this process is identifying a transfection reagent and plating conditions that maximize the uptake of synthetic miRNAs or miRNA inhibitors while maintaining high cell viability. We find it useful to test 2-5 different transfection reagents when using cell lines or 5-10 elelctroporation conditions when using primary or suspension cells. Transfection can be optimized for the reagent or electroporation condition that worked best among the conditions tested. Screening miRNA-specific libraries requires conditions for high-throughput transfection. The inventors have developed and used a rapid process that facilitates the transfection of up to 1,000 wells in less than an hour without the need for robotics (see delivery below).

(3) Screen

Once the assay and transfection process have been developed, a library of synthetic miRNAs or miRNA inhibitors can be introduced sequentially into cells in a 24- or 96-well plate. Triplicate transfections for each reagent provide enough data for reasonable statistical analysis.

(4) Validate Hits

Validating a hit involves showing that the observed phenotype is due to the miRNA being targeted. Hits are typically confirmed by delivering a dilution series of the miRNA inhibitor or synthetic miRNA that registered as a hit into the cell that was originally assayed. It has been the experience of the inventors that true hits show a dose response.

A. Synthetic miRNA and miRNA Inhibitor Library Preparation

The present invention concerns the preparation and use of synthetic miRNA and miRNA inhibitor libraries to induce changes in the activity of specific miRNAs in cells. Preparation of synthetic miRNAs and miRNA inhibitors typically involves the chemical synthesis of the active and complementary strands of the synthetic miRNA and the single-stranded miRNA inhibitor using any of the methods described in this application. If the active and complementary strands of the synthetic miRNAs are two distinct molecules, then the two strands must be hybridized prior to delivery. Hybridization can be achieved by mixing the two nucleic acids together in roughly equimolar amounts and incubating for a time and at a temperature that is appropriate for hybridization. The addition of salt (e.g., NaCl or NaOAC) enhances hybridization as does the inclusion of a heat denaturation step prior to the incubation used for hybridization.

B. Delivery of Synthetic miRNAs and miRNA Inhibitors

Libraries of the invention can be used to sequentially up- or down-regulate one or more miRNAs in samples. This requires methods for introducing the synthetic miRNAs and miRNA inhibitors into cell types with associated cell assays. Lipid-based transfection is typically employed to introduce the nucleic acids inito immortalized cells and electroporation for primary cells.

Suitable methods for nucleic acid delivery according to the present invention are believed to include virtually any method by which a nucleic acid (e.g., DNA, RNA, including viral and nonviral vectors) can be introduced into an organelle, a cell, a tissue or an organism, as described herein or as would be known to one of ordinary skill in the art. Such methods include, but are not limited to, direct delivery of nucleic acids such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783, 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

A variety of compounds have been attached to the ends of oligonucleotides to facilitate their transport across cell membranes. Short signal peptides found in the HIV TAT, HSV VP22, Drosphila antennapedia, and other proteins have been found to enable the rapid transfer of biomolecules across membranes (reviewed by Schwarze 2000). These signal peptides, referred to as Protein Transduction Domains (PTDs), have been attached to oligonucleotides to facilitate their delivery into cultured cells. Cholesterols have been conjugated to oligonucleotides to improve their uptake into cells in animals (MacKellar 1992). The terminal cholesterol groups apparently interact with receptors or lipids on the surfaces of cells and facilitate the internalization of the modified oligonucleotides. Likewise, poly-1-lysine has been conjugated to oligonucleotides to decrease the net negative charge and improve uptake into cells (Leonetti 1990).

A variety of compounds have been developed that complex with nucleic acids, deliver them to surfaces of cells, and facilitate their uptake in and release from endosomes. Among these are: (1) a variety of lipids such as DOTAP (or other cationic lipid), DDAB, DHDEAB, and DOPE and (2) non-lipid-based polymers like polyethylenimine, polyamidoamine, and dendrimers of these and other polymers. In certain of these embodiments a combination of lipids is employed such as DOTAP and cholesterol or a cholesterol derivative (U.S. Pat. No. 6,770,291, which is hereby incorporated by reference). Several of these reagents have been shown to facilitate nucleic acid uptake in animals.

The cellular components involved in the miRNA pathway are becoming known. Proteins that stabilize and/or transport miRNAs within cells might enhance the stability and activity of miRNAs because they should protect and guide the bound miRNAs once they are in cells. Mixtures of miRNA-transporter proteins and miRNAs could enhance the efficacy of miRNA-based therapeutics.

RNAs are hydrophilic molecules by virtue of their anionic phosphate and sugar backbone. Although the nucleobases are hydrophobic, hydrophilicity dominates owing to the extensive hydrogen bonding resulting from the phosphate and sugar residues. The hydrophilic character and anionic backbone reduces cellular permeation. Conjugation of lipophilic groups like cholesterol (Manoharan, 2002) and lauric and lithocholic acid derivatives with C32 functionality (Lorenz et al., 2004), have been shown to improve cellular uptake. Moreover binding of steroid conjugated oligonucleotides to different lipoproteins in the bloodstream, such as LDL, protect their integrity and govern their biodistribution (Rump et al., 2000). Cholesterol attached to anti-sense molecules (Bijsterbosch et al., 2001) and aptamers (Rusconi et al., 2004) has also been shown to stabilize oligonucleotides by allowing binding to lipoproteins. Cholesterol has been demonstrated to enhance uptake and serum stability of siRNAs in vitro (Lorenz et al., 2004) and in vivo (Soutschek et al., 2004). Additionally, a number of small molecules like SB-435495 (Blackie et al., (2002), Isradipine (Oravcova et al., 1994), amlodipine (Oravcova et al., 1994) and 2,2',4,4', 5,5'-hexachlorobiphenyl (Borlakoglu et al., 1990) could enhance cellular uptake, and improve nuclease resistance by promoting lipoprotein association.

The present methods and kits may be employed for high volume screening. A library of synthetic miRNAs and/or miRNA inhibitors can be created using methods of the invention. This library may then be used in high throughput assays, including microarrays. Specifically contemplated by the present inventors are chip-based nucleic acid technologies such as those described by Ziauddin and Sabatini (2001). Briefly, nucleic acids can be immobilized on solid supports. Cells can then be overlaid on the solid support and take up the nucleic acids at the defined locations. The impact on the cells can then be measured to identify cocktails that are having a desirable effect.

C. Labeling and Labeling Techniques

In some embodiments, the present invention concerns miRNA that are labeled, such as for screening assays to evaluate the therapeutic or diagnostic relevance of a particular miRNA species. It is contemplated that miRNA may first be isolated (either from a cell in which the miRNA is endogenous to the cell or from a cell in which miRNA is exogenous to the cell) and/or purified prior to labeling. This may achieve a reaction that more efficiently labels the miRNA, as opposed to other RNA in a sample in which the miRNA is not isolated or purified prior to labeling. In many embodiments of the invention, the label is non-radioactive. Generally, nucleic acids may be labeled by adding labeled nucleotides (one-step process) or adding nucleotides and labeling the added nucleotides (two-step process).

Moreover, miRNA may be labeled as is described in U.S. Patent Application Ser. No. 60/649,584, which is hereby incorporated by reference. Such nucleotides include those that can be labeled with a dye, including a fluorescent dye, or with a molecule such as biotin. Labeled nucleotides are readily available; they can be acquired commercially or they can be synthesized by reactions known to those of skill in the art.

1. Nucleotides for Labeling

Nucleotides for labelling are not naturally occurring nucleotides, but instead, refer to prepared nucleotides that have a reactive moiety on them. Specific reactive functionalities of interest include: amino, sulfhydryl, sulfoxyl, aminosulfhydryl, azido, epoxide, isothiocyanate, isocyanate, anhydride, monochlorotriazine, dichlorotriazine, mono- or dihalogen substituted pyridine, mono- or disubstituted diazine, maleimide, epoxide, aziridine, sulfonyl halide, acid halide, alkyl halide, aryl halide, alkylsulfonate, N-hydroxysuccinimide ester, imido ester, hydrazine, azidonitrophenyl, azide, 3-(2-pyridyl dithio)-propionamide, glyoxal, aldehyde, iodoacetyl, cyanomethyl ester, p-nitrophenyl ester, o-nitrophenyl ester, hydroxypyridine ester, carbonyl imidazole, and the other such chemical groups. In some embodiments, the reactive functionality may be bonded directly to a nucleotide, or it may be bonded to the nucleotide through a linking group. The functional moiety and any linker cannot substantially impair the ability of the nucleotide to be added to the miRNA or to be labeled. Representative linking groups include carbon containing linking groups, typically ranging from about 2 to 18, usually from about 2 to 8 carbon atoms, where the carbon containing linking groups may or may not include one or more heteroatoms, e.g. S, O, N etc., and may or may not include one or more sites of unsaturation. Of particular interest in many embodiments are alkyl linking groups, typically lower alkyl linking groups of 1 to 16, usually 1 to 4 carbon atoms, where the linking groups may include one or more sites of unsaturation. The functionalized nucleotides (or primers) used in the above methods of functionalized target generation may be fabricated using known protocols or purchased from commercial vendors, e.g., Sigma, Roche, Ambion, and NEN. Functional groups may be prepared according to ways known to those of skill in the art, including the representative information found in U.S. Pat. Nos. 4,404,289; 4,405,711; 4,337,063 and 5,268,486, and Br. Pat. No. 1,529,202, which are all incorporated by reference.

Amine-modified nucleotides are used in several embodiments of the invention. The amine-modified nucleotide is a nucleotide that has a reactive amine group for attachment of the label. It is contemplated that any ribonucleotide (G, A, U, or C) or deoxyribonucleotide (G, A, T, or C) can be modified for labeling. Examples include, but are not limited to, the following modified ribo- and deoxyribo-nucleotides: 5-(3-aminoallyl)-UTP; 8-[(4-amino)butyl]-amino-ATP and 8-[(6-amino)butyl]-amino-ATP; $N^6$-(4-amino)butyl-ATP, $N^6$-(6-amino)butyl-ATP, $N^4$-[2,2-oxy-bis-(ethylamine)]-CTP; $N^6$-(6-Amino)hexyl-ATP; 8-[(6-Amino)hexyl]-amino-ATP; 5-propargylamino-CTP, 5-propargylamino-UTP; 5-(3-aminoallyl)-dUTP; 8-[(4-amino)butyl]-amino-dATP and 8-[(6-amino)butyl]-amino-dATP; $N^6$-(4-amino)butyl-dATP, $N^6$-(6-amino)butyl-dATP, $N^4$-[2,2-oxy-bis-(ethylamine)]-dCTP; $N^6$-(6-Amino)hexyl-dATP; 8-[(6-Amino)hexyl]-amino-dATP; 5-propargylamino-dCTP, and 5-propargylamino-dUTP. Such nucleotides can be prepared according to methods known to those of skill in the art. Moreover, a person of ordinary skill in the art could prepare other nucleotide entities with the same amine-modification, such as a 5-(3-aminoallyl)-CTP, GTP, ATP, dCTP, dGTP, dTTP, or dUTP in place of a 5-(3-aminoallyl)-UTP.

2. Labeling Techniques

In some embodiments, nucleic acids are labeled by catalytically adding to the nucleic acid an already labeled nucleotide or nucleotides. One or more labeled nucleotides can be added to miRNA molecules. See U.S. Pat. No. 6,723,509, which is hereby incorporated by reference.

In other embodiments, an unlabeled nucleotide or nucleotides is catalytically added to an miRNA, and the unlabeled nucleotide is modified with a chemical moiety that enables it to be subsequently labeled. In embodiments of the invention, the chemical moiety is a reactive amine such that the nucleotide is an amine-modified nucleotide.

Examples of amine-modified nucleotides are well known to those of skill in the art, many being commercially available such as from Ambion, Sigma, Jena Bioscience, and TriLink.

In contrast to labeling of cDNA during its synthesis, the issue for labeling miRNA is how to label the already existing molecule. The present invention concerns the use of an enzyme capable of using a di- or tri-phosphate ribonucleotide or deoxyribonucleotide as a substrate for its addition to an miRNA, a small RNA molecule. Moreover, in specific embodiments, it involves using a modified di- or tri-phosphate ribonucleotide, which is added to the 3' end of an miRNA. The source of the enzyme is not limiting. Examples of sources for the enzymes include yeast, gram-negative bacteria such as *E. coli, lactococcus lactis*, and sheep pox virus.

Enzymes capable of adding such nucleotides include, but are not limited to, poly(A) polymerase, terminal transferase, and polynucleotide phosphorylase. In specific embodiments of the invention, ligase is contemplated as NOT being the enzyme used to add the label, and instead, a non-ligase enzyme is employed.

Poly(A) polymerase has been cloned from a number of organisms from plants to humans. It has been shown to catalyze the addition of homopolymer tracts to RNA (Martin et al., RNA, 4(2):226-30, 1998).

Terminal transferase catalyzes the addition of nucleotides to the 3' terminus of a nucleic acid.

Polynucleotide phosphorylase can polymerize nucleotide diphosphates without the need for a primer.

3. Labels

Labels on miRNA or miRNA probes may be colorimetric (includes visible and UV spectrum, including fluorescent), luminescent, enzymatic, or positron emitting (including radioactive). The label may be detected directly or indirectly. Radioactive labels include $^{125}$I, $^{32}$P, $^{33}$P, and $^{35}$S. Examples of enzymatic labels include alkaline phosphatase, luciferase, horseradish peroxidase, and β-galactosidase. Labels can also be proteins with luminescent properties, e.g., green fluorescent protein and phicoerythrin.

The colorimetric and fluorescent labels contemplated for use as conjugates include, but are not limited to, Alexa Fluor dyes, BODIPY dyes, such as BODIPY FL; Cascade Blue; Cascade Yellow; coumarin and its derivatives, such as 7-amino-4-methylcoumarin, aminocoumarin and hydroxycoumarin; cyanine dyes, such as Cy3 and Cy5; eosins and erythrosins; fluorescein and its derivatives, such as fluorescein isothiocyanate; macrocyclic chelates of lanthanide ions, such as Quantum Dye™; Marina Blue; Oregon Green; rhodamine dyes, such as rhodamine red, tetramethylrhodamine and rhodamine 6G; Texas Red; fluorescent energy transfer dyes, such as thiazole orange-ethidium heterodimer; and, TOTAB.

Specific examples of dyes include, but are not limited to, those identified above and the following: Alexa Fluor 350, Alexa Fluor 405, Alexa Fluor 430, Alexa Fluor 488, Alexa Fluor 500. Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, and, Alexa Fluor 750; amine-reactive BODIPY dyes, such as BODIPY 493/503, BODIPY 530/550, BODIPY 558/568, BODIPY 564/570, BODIPY 576/589, BODIPY 581/591, BODIPY 630/650, BODIPY 650/655, BODIPY FL, BODIPY R6G, BODIPY TMR, and, BODIPY-TR; Cy3, Cy5, 6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, SYPRO, TAMRA, 2',4',5',7'-Tetrabromosulfonefluorescein, and TET.

Specific examples of fluorescently labeled ribonucleotides are available from Molecular Probes, and these include, Alexa Fluor 488-5-UTP, Fluorescein-12-UTP, BODIPY FL-14-UTP, BODIPY TMR-14-UTP, Tetramethylrhodamine-6-UTP, Alexa Fluor 546-14-UTP, Texas Red-5-UTP, and BODIPY TR-14-UTP. Other fluorescent ribonucleotides are available from Amersham Biosciences, such as Cy3-UTP and Cy5-UTP.

Examples of fluorescently labeled deoxyribonucleotides include Dinitrophenyl (DNP)-11-dUTP, Cascade Blue-7-dUTP, Alexa Fluor 488-5-dUTP, Fluorescein-12-dUTP, Oregon Green 488-5-dUTP, BODIPY FL-14-dUTP, Rhodamine Green-5-dUTP, Alexa Fluor 532-5-dUTP, BODIPY TMR-14-dUTP, Tetramethylrhodamine-6-dUTP, Alexa Fluor 546-14-dUTP, Alexa Fluor 568-5-dUTP, Texas Red-12-dUTP, Texas Red-5-dUTP, BODIPY TR-14-dUTP, Alexa Fluor 594-5-dUTP, BODIPY 630/650-14-dUTP, BODIPY 650/665-14-dUTP; Alexa Fluor 488-7-OBEA-dCTP, Alexa Fluor 546-16-OBEA-dCTP, Alexa Fluor 594-7-OBEA-dCTP, Alexa Fluor 647-12-OBEA-dCTP.

It is contemplated that nucleic acids may be labeled with two different labels. Furthermore, fluorescence resonance energy transfer (FRET) may be employed in methods of the invention (e.g., Klostermeier et al., 2002; Emptage, 2001; Didenko, 2001, each incorporated by reference).

Alternatively, the label may not be detectable per se, but indirectly detectable or allowing for the isolation or separation of the targeted nucleic acid. For example, the label could be biotin, digoxigenin, polyvalent cations, chelator groups and the other ligands, include ligands for an antibody.

4. Visualization Techniques

A number of techniques for visualizing or detecting labeled nucleic acids are readily available. The reference by Stanley T. Crooke, 2000 has a discussion of such techniques (Chapter 6), which is incorporated by reference. Such techniques include, microscopy, arrays, Fluorometry, Light cyclers or other real time PCR machines, FACS analysis, scintillation counters, Phosphoimagers, Geiger counters, MRI, CAT, antibody-based detection methods (Westerns, immunofluorescence, immunohistochemistry), histochemical techniques, HPLC (Griffey et al., 1997, spectroscopy, capillary gel electrophoresis (Cummins et al., 1996), spectroscopy; mass spectroscopy; radiological techniques; and mass balance techniques.

When two or more differentially colored labels are employed, fluorescent resonance energy transfer (FRET) techniques may be employed to characterize the dsRNA. Furthermore, a person of ordinary skill in the art is well aware of ways of visualizing, identifying, and characterizing labeled nucleic acids, and accordingly, such protocols may be used as part of the invention. Examples of tools that may be used also include fluorescent microscopy, a BioAnalyzer, a plate reader, Storm (Molecular Dynamics), Array Scanner, FACS (fluorescent activated cell sorter), or any instrument that has the ability to excite and detect a fluorescent molecule.

C. Array Preparation

The present invention can be employed with miRNA arrays, which are ordered macroarrays or microarrays of nucleic acid molecules (probes) that are fully or nearly complementary or identical to a plurality of miRNA molecules or precursor miRNA molecules and that are positioned on a support material in a spatially separated organization. Macroarrays are typically sheets of nitrocellulose or nylon upon which probes have been spotted. Microarrays position the nucleic acid probes more densely such that up to 10,000 nucleic acid molecules can be fit into a region typically 1 to 4 square centimeters. Microarrays can be fabricated by spotting nucleic acid molecules, e.g., genes, oligonucleotides, etc., onto substrates or fabricating oligonucleotide sequences in situ on a substrate. Spotted or fabricated nucleic acid molecules can be applied in a high density matrix pattern of up to about 30 non-identical nucleic acid molecules per square centimeter or higher, e.g. up to about 100 or even 1000 per square centimeter. Microarrays typically use coated glass as the solid support, in contrast to the nitrocellulose-based material of filter arrays. By having an ordered array of miRNA-complementing nucleic acid samples, the position of each sample can be tracked and linked to the original sample. A variety of different array devices in which a plurality of distinct nucleic acid probes are stably associated with the surface of a solid support are known to those of skill in the art. Useful substrates for arrays include nylon, glass and silicon Such arrays may vary in a number of different ways, including average probe length, sequence or types of probes, nature of bond between the probe and the array surface, e.g. covalent or non-covalent, and the like.

Representative methods and apparatus for preparing a microarray have been described, for example, in U.S. Pat. Nos. 5,143,854; 5,202,231; 5,242,974; 5,288,644; 5,324, 633; 5,384,261; 5,405,783; 5,412,087; 5,424,186; 5,429, 807; 5,432,049; 5,436,327; 5,445,934; 5,468,613; 5,470, 710; 5,472,672; 5,492,806; 5,525,464; 5,503,980; 5,510, 270; 5,525,464; 5,527,681; 5,529,756; 5,532,128; 5,545, 531; 5,547,839; 5,554,501; 5,556,752; 5,561,071; 5,571, 639; 5,580,726; 5,580,732; 5,593,839; 5,599,695; 5,599, 672; 5,610,287; 5,624,711; 5,631,134; 5,639,603; 5,654, 413; 5,658,734; 5,661,028; 5,665,547; 5,667,972; 5,695, 940; 5,700,637; 5,744,305; 5,800,992; 5,807,522; 5,830, 645; 5,837,196; 5,871,928; 5,847,219; 5,876,932; 5,919, 626; 6,004,755; 6,087,102; 6,368,799; 6,383,749; 6,617, 112; 6,638,717; 6,720,138, as well as WO 93/17126; WO 95/11995; WO 95/21265; WO 95/21944; WO 95/35505; WO 96/31622; WO 97/10365; WO 97/27317; WO 99/35505; WO 09923256; WO 09936760; WO0138580; WO 0168255; WO 03020898; WO 03040410; WO 03053586; WO 03087297; WO 03091426; WO03100012; WO 04020085; WO 04027093; EP 373 203; EP 785 280; EP 799 897 and UK 8 803 000; the disclosures of which are all herein incorporated by reference.

It is contemplated that the arrays can be high density arrays, such that they contain 100 or more different probes. It is contemplated that they may contain 1000, 16,000, 65,000, 250,000 or 1,000,000 or more different probes. The probes can be directed to targets in one or more different organisms. The oligonucleotide probes range from 5 to 50, 5 to 45, 10 to 40, or 15 to 40 nucleotides in length in some embodiments. In certain embodiments, the oligonucleotide probes are 20 to 25 nucleotides in length.

The location and sequence of each different probe sequence in the array are generally known. Moreover, the large number of different probes can occupy a relatively small area providing a high density array having a probe density of generally greater than about 60, 100, 600, 1000, 5,000, 10,000, 40,000, 100,000, or 400,000 different oligonucleotide probes per $cm^2$. The surface area of the array can be about or less than about 1, 1.6, 2, 3, 4, 5, 6, 7, 8, 9, or 10 $cm^2$.

Moreover, a person of ordinary skill in the art could readily analyze data generated using an array. Such protocols are disclosed above, and include information found in WO 9743450; WO 03023058; WO 03022421; WO 03029485; WO 03067217; WO 03066906; WO 03076928; WO 03093810; WO 03100448A1, all of which are specifically incorporated by reference.

D. Sample Preparation

It is contemplated that the miRNA of a wide variety of samples can be analyzed using assays described herein. While endogenous miRNA is contemplated for use with some embodiments, recombinant miRNA— including nucleic acids that are complementary or identical to endogenous miRNA or precursor miRNA— can also be handled and analyzed as described herein. Samples may be biological samples, in which case, they can be from blood, tissue, organs, semen, saliva, tears, other bodily fluid, hair follicles, skin, or any sample containing or constituting biological cells. Alternatively, the sample may not be a biological sample, but be a chemical mixture, such as a cell-free reaction mixture (which may contain one or more biological enzymes).

E. Hybridization

After the array is prepared and the miRNA in the sample is labeled, the population of target nucleic acids is contacted with the array under hybridization conditions, where such conditions can be adjusted, as desired, to provide for an optimum level of specificity in view of the particular assay being performed. Suitable hybridization conditions are well known to those of skill in the art and reviewed in Sambrook et al., 1989 and WO 95/21944. Of particular interest in many embodiments is the use of stringent conditions during hybridization. Stringent conditions are known to those of skill in the art.

It is specifically contemplated that a single array may be contacted with multiple samples. The samples may be labeled with different labels to distinguish the samples. For example, a single array can be contacted with a tumor tissue sample labeled with Cy3, and normal tissue sample labeled with Cy5. Differences between the samples for particular miRNAs corresponding to probes on the array can be readily ascertained and quantified.

The small surface area of the array permits uniform hybridization conditions, such as temperature regulation and salt content. Moreover, because of the small area occupied by the high density arrays, hybridization may be carried out in extremely small fluid volumes (e.g., about 250 µl or less, including volumes of about or less than about 5, 10, 25, 50, 60, 70, 80, 90, 100 µl, or any range derivable therein). In small volumes, hybridization may proceed very rapidly.

F. Differential Expression Analyses

Arrays can be used to detect differences between two samples. This can also be used for diagnostic purposes. Specifically contemplated applications include identifying and/or quantifying differences between miRNA from a sample that is normal and from a sample that is not normal or between two differently treated samples. Also, miRNA may be compared between a sample believed to be susceptible to a particular disease or condition and one believed to be not susceptible or resistant to that disease or condition. A sample that is not normal is one exhibiting phenotypic trait(s) of a disease or condition or one believed to be not normal with respect to that disease or condition. It may be compared to a cell that is normal with respect to that disease or condition. Phenotypic traits include symptoms of, or susceptibility to, a disease or condition of which a component is or may or may not be genetic.

G. Cell Assays to Identify miRNAs with Ties to Disease

Specifically contemplated applications include identifying miRNAs that contribute to cellular processes that are themselves parts of a disease or might otherwise be associated with a particular disease state. Also, miRNA functions may be compared between a sample believed to be susceptible to a particular disease or condition and one believed to be not susceptible or resistant to that disease or condition. It is specifically contemplated that RNA molecules of the present invention can be used to treat any of the diseases or conditions discussed in the previous section or modulate any of the cellular pathways discussed in the previous section.

Specifically contemplated applications include identifying miRNAs that contribute to cellular processes that are themselves parts of a disease or might otherwise be associated with a particular disease state. Also, miRNA functions may be compared between a sample believed to be susceptible to a particular disease or condition and one believed to be not susceptible or resistant to that disease or condition.

AIDS, autoimmune diseases (rheumatoid arthritis, multiple sclerosis, diabetes—insulin-dependent and non-independent, systemic lupus erythematosus and Graves disease); cancer (e.g., malignant, benign, metastatic, precancer); cardiovascular diseases (heart disease or coronary artery disease, stroke—ischemic and hemorrhagic, and rheumatic heart disease); diseases of the nervous system; and infection by pathogenic microorganisms (Athlete's Foot, Chickenpox, Common cold, Diarrheal diseases, Flu, Genital herpes, Malaria, Meningitis, Pneumonia, Sinusitis, Skin diseases, Strep throat, Tuberculosis, Urinary tract infections, Vaginal infections, Viral hepatitis); inflammation (allergy, asthma); prion diseases (e.g., CJD, kuru, GSS, FFI).

Moreover, miRNA can be evaluated with respect to the following diseases, conditions, and disorders: Abdominal Adhesions; Anal Abscess; Brain Abscess; Peritonsillar Abscess; Absence Seizures; Achalasia; Acne; Acoustic Neuroma; Acquired Immunodeficiency Syndrome (AIDS); Acrochordon; Actinic Keratosis; Adenocarcinoma of the Lung; ADHD; Adult-Onset Diabetes; Aero-Otitis; Age Spots; Age-Related Hearing Loss; Age-Related Macular Degeneration; Age-Related Vision Change (Presbyopia); Agoraphobia; Alcohol Withdrawal; Alcoholism; Allergen Immunotherapy; Allergic Rhinitis; Allergies; Alopecia (Areata, Hereditary-Patterned, and Traumatic); Altitude Sickness; Alzheimer's Disease; Amaurotic Familial Infantile Idiocy; Amblyopia; Amenorrhea; Amyloidosis; Amyotrophic Lateral Sclerosis (ALS); Anaphylaxis; Androgenetic Alopecia; Anemia (Aplastic, Hemolytic, Pernicious, and Sickle Cell); Angina; Angiomas, Spider; Angioplasty; Ankylosing Spondylitis; Anorexia Nervosa; Anovulatory Bleeding; Antibiotic-Associated Diarrhea; Antiphospholipid Antibody Syndrome; Antisocial Personality Disorder; Anus Fissure, Fistula, Hemorrhoids, Anus Itch, Stricture; Anxiety Disorders (Generalized, Obsessive-Compulsive Disorder, Panic Disorder, Phobia, and Post-Traumatic Stress Disorder); Aortic Aneurysm; Aortic Arch Syndrome; Appendicitis; Arrhythmias, Cardiac; Arteritis, Takayasu's; Arthritic Diseases (Ankylosing Spondylitis, Gout, Infectious, Juvenile, Osteoarthritis, Pseudogout, Psoriatic Arthritis, and Rheumatoid); Asbestosis; Ascending Cholangitis; Asteatotic Eczema; Asthma; Astigmatism; Asymptomatic Bacteriuria; Ataxia, Friedreich's; Atherosclerosis; Athlete's Foot; Atopic Dermatitis; Atrial Fibrillation; Atrophic Vaginitis; Attention-Deficit Hyperactivity Disorder; Autism; Autoimmune Diseases (Celiac Disease, Crohn's Disease, Diabetes Mellitus, Type 1 (Insulin-Dependent; Juvenile-Onset), Diabetes Mellitus, Type 2 (Non-Insulin-Dependent; Adult-Onset), Graves' Disease, Hyperthyroidism, Immune Thrombocytopenic Purpura, Lupus, Myasthenia Gravis, Polyarteritis Nodosa, Rheumatoid Arthritis, Scleroderma, Takayasu's Arteritis, and Ulcerative Colitis); B12 Deficiency; Bacillary Dysentery; Bacterial Gastroenteritis; Bacterial Vaginosis; Balanitis; Baldness, Hereditary-Patterned; Barber's Itch; Barotitis; Barotrauma; Bartholin's Gland Cyst; Basal-Cell Carcinoma; Bed-Wetting; Bedsores; Behcet's Syndrome; Bell's Palsy; Bends; Benign Prostatic Hyperplasia; Bile-Duct Diseases; Biliary Colic; Biopsy; Bipolar Disorder; Bladder conditions (Infection; Interstitial Cystitis; Prolapse; Urethritis; Urinary Incontinence; Urinary Tract Infection); Blepharitis; Blepharoptosis; Blighted Ovum; Friction Blisters; Blood Pressure, High; Boils; Bone diseases and conditions (Osteoporosis; Paget's Disease); Bone Yaws; Borderline Personality Disorder; Bornholm Disease; Botulism; Bowel Obstruction; Bradycardia; Bronchitis; Bulimia Nervosa; Bunion; Bursitis; *C. Difficile* Colitis; Calcaneal Apophysitis; Calcium Pyrophosphate Deposition Disease; Campylobacteriosis; Cancer; Candidiasis; Carbon-Monoxide Poisoning; Carbuncles; Cardiac Arrhythmias (Atrial Fibrillation, Bradycardia); Cardiomyopathy; Carpal Tunnel Syndrome; Cataracts; Cellulitis; Central Serous Retinopathy; Cerebral Palsy; Cerebromacular Degeneration; Cerumen Impaction; Cervicitis, Nabothian Cysts, Cervical Polyps, Cervical Warts; Chalazion; Chickenpox; Chlamydia; Chloasma; Cholangitis; Cholecystitis; Cholesteatoma; Chondromalacia; Chorea; Choroidal Melanoma; Chronic Bronchitis; Chronic Fatigue Syndrome; Chronic Hepatitis;

Chronic Leukemia; Chronic Obstructive Pulmonary Disease; Chronic Otitis Media; Cirrhosis; Cluster Headache; Cogan's Syndrome; Cold, Common; Colic, Biliary; Pseudomembranous Colitis, Ulcerative Colitis, Collapsed Lung; Collarbone Fracture; Coma; Complex Regional Pain Syndrome; Congestive Heart Failure; Conjunctivitis; Constipation; Contact Dermatitis; Conversion Disorder; COPD; Cornea Abrasion, Cornea Keratitis; Corns; Coronary Artery Disease; Creutzfeldt-Jakob Disease; Crossed Eyes; Croup; Cryptorchidism; Cystic Fibrosis; Interstitial Cystitis; Cystocele; Cysts; Cytomegalovirus infection; Dacryocystitis; Dandruff; Decompression Sickness; Decubitus Ulcers; Delirium Tremens; Delusional Disorder; Dementia; Depressive Disorders (Bipolar Disorder, Dysthymia, Major Depression, Manic Depression, Postpartum Depression); Dermatitis; Dermatofibroma; Dermatomyositis; Detached Retina; Developmental Dysplasia of the Hip; Deviated Septum; Devil's Grip; Diabetes (Gestational Diabetes; Type 1 Diabetes (Insulin-Dependent; Juvenile); Type 2 Diabetes (Non-Insulin-Dependent; Adult-Onset); Hypoglycemia, Ketoacidosis, Nephropathy, Neuropathies, Retinopathy) Antibiotic-Associated Diarrhea; Diplopia; Herniated Disk; Dislocated Lens; Hip Dislocation (Developmental); Diverticulitis; Diverticulosis; Dizziness; Doerderland's Vaginitis; Double Vision; Down Syndrome; Drooping Eyelid; Dry Skin; Sun-Damaged Skin; Dry-Eye Syndrome; Duck-Foot; Dysautonomia, Familial; Dysfunctional Uterine Bleeding; Dyslexia; Dyspareunia; Dysthymia; Dysuria; Eating Disorders (Anorexia Nervosa, Bulimia Nervosa); Eclampsia; Eczema; Edema; Emphysema; Encephalitis; Encopresis; End-Stage Renal Disease; Endocarditis; Endometriosis; Endophthalmitis; Endoscopy; Enlarged Prostate; Enuresis; Epidemic Benign Dry Pleurisy; Epididymitis; Epiglottitis; Epilepsy; Epistaxis; Erectile Dysfunction; Erythema Infectiosum; Esophagitis; Esophagus Achalasia; Esophagitis; Essential Hypertension; Essential Tremor; Ewing's Sarcoma; Familial Dysautonomia; Farsightedness; Febrile Seizures; Fecal Incontinence; Fever; Fever-Induced Seizures; Fibroids; Fibromyalgia; Fifth Disease; Filiform Warts; Flat Warts; Flatulence; Flu; Focal Seizures; Food Allergy; Food Poisoning; Forefoot Neuroma; Fragile X Syndrome; Friction Blisters; Friedreich's Ataxia; Frostbite; Fungal Infections (Athlete's Foot, Brain Abscess, Infectious Arthritis, Jock Itch, Onychomycosis, Ringworm, Swimmer's Ear, Tinea Cruris, Tinea Unguium, Tinea Versicolor); Furuncle; Gallstones; Gardnerella Vaginitis; Gastritis; Gastrocnemius Strain; Gastroenteritis; Gastroesophageal Reflux Disease; Gastrointestinal Amebiasis; Generalized Anxiety Disorder; Generalized Barotrauma; Genital Herpes; Genital Warts; GERD; Germ Cell Tumors, Extragonadal; Giant Cell Arteritis; Giardiasis; Glaucoma; Glomerulonephritis; Gluten-Sensitive Enteropathy; GM2 Gangliosidosis; Gonorrhea; Gout; Grand Mal Seizures; Graves' Disease; Graves' Ophthalmopathy; Guillain-Barre Syndrome; Hammertoe; Hay Fever; Headache; Hearing Loss; Heart Attack; Heat Stroke; Heel Spur; Heloma; Spider Hemangiomas; Hematoma; Hematuria; Hemochromatosis; Hemolytic Anemia; Hemophilia; Hemorrhagic Stroke; Subarachnoid Hemorrhagic Stroke; Hemorrhoids; Hepatitis A; Hepatitis B; Hepatitis C; Hereditary-Patterned Baldness; Hernia; Herniated Disk; High Blood Pressure; High Cholesterol; Hirsutism; Histiocytosis X; HIV/AIDS; Hordeolum; Human Papilloma Virus (HPV); Huntington's Disease; Hydatidiform Mole; Hydrocephalus; Hyperactivity; Hypercholesterolemia; Hyperkeratosis; Hyperopia; Hypertension; Ocular Hypertension; Secondary Hypertension; Hypertensive Retinopathy; Hyperthermia; Hyperthyroidism; Hypochondriasis; Hypoglycemia; Hypoparathyroidism; Hypothyroidism; IBS; ICD; Ichthyosis; Immune Thrombocytopenic Purpura; Impetigo; Impotence; Incontinence; Infantile Ganglioside Lipidosis; Infectious Arthritis; Infectious Mononucleosis; Infertility; Inflammatory Bowel Disease; Inguinal Hernia; Insomnia; Intercerebral Hemorrhage; Interdigital Neuroma; Intermetatarsal Neuroma; Intermittent Claudication; Interstitial Cystitis; Intestinal Obstruction; Iron Deficiency; Irritable Bowel Syndrome; Juvenile Arthritis; Kaposi's Sarcoma; Kawasaki Syndrome; Keloids; Keratitis; Actinic Keratosis; Labyrinthitis; Lactose Intolerance; Lacunar Stroke; Langerhans' Cell Histiocytosis; Laryngitis; Laryngotracheitis; Lateral Epicondylitis; Latex Allergy; Lazy Eye; Lead Poisoning; Intermittent Claudication; Restless Legs Syndrome; Shin Splints; Leg Strain; Cataract; Dislocated Lens; Leukemia; Lice; Lichen Simplex Chronicus; Cirrhosis; Hepatitis; Liver Spots; Lockjaw; Lou Gehrig's Disease; Lupus Erythematosus, Systemic; Lyme Disease; Lymphedema; Lymphoma; Macular Degeneration; Malabsorption Syndromes; Malaria; Male Pattern Baldness; Malignant Hyperthermia; Manic Depression; Marfan's Syndrome; Mastoiditis; Measles; Meckel's Diverticulum; Melasma; Meniere's Disease; Meningitis; Menopause; Mental Retardation; Phenylketonuria; Migraine; Miscarriage; Mitral-Valve Prolapse; Mittelschmerz; Molar Pregnancy; Molluscum Contagiosum; Mononucleosis; Morton's Neuroma; Mosaic Warts; Motor Tics; Mucocutaneous Lymph Node Syndrome; Multiple Sclerosis; Mumps; Muscular Dystrophy; Musculoskeletal Disorders (Fibromyalgia, Giant Cell Arteritis, Gout, Infectious Arthritis, Muscular Dystrophy, Myositis, Osteoarthritis, Osteoporosis, Paget's Disease Of Bone, Polymyalgia Rheumatica, Pseudogout, Reflex Sympathetic Dystrophy, Rheumatoid Arthritis, Scleroderma, Systemic Lupus Erythematosus, Tendonitis); Myasthenia Gravis; Myocardial Infarction; Myocarditis; Myopia; Myositis; Nail Felon; Onycholysis; Onychomycosis; Paronychia; Subungual Hematoma; Narcolepsy; Nasal Polyps; Nausea; Nearsightedness; Needle Biopsy; Nephrectomy; Nephroblastoma; Nephrolithiasis; Nephropathy, Diabetic; Neuritis, Retrobulbar; Neuroblastoma; Neuromuscular Disorders; Neuropathies; Guillain-Barre Syndrome; Retrobulbar; Nevi; Nevus Flammeus; Nevus Simplex; Nocturnal Enuresis; Non-Tropical Sprue; Obesity; Obsessive-Compulsive Disorder; Occupational Hearing Loss; Ocular Hypertension; Ocular Rosacea; Onycholysis; Onychomycosis; Glaucoma; Retrobulbar Neuritis; Optic Nerve Swelling; Orbit Fracture; Orchitis; Osgood-Schlatter Disease; Osteoarthritis; Osteoporosis; Osteosarcoma; Otitis Externa; Otitis Media; Chronic Otitis Media; Otosclerosis; Ototoxicity; Pelvic Inflammatory Disease; Polycystic Ovary Syndrome; Painful-Bladder Syndrome; Pancreatitis; Panic Disorder; Papilledema; Paraphimosis; Parkinson's Disease; Paronychia; Partial Seizures; PCL Injuries; Pedunculated Warts; Pelvic Relaxation; Paraphimosis; Peyronie's Disease; Peptic Ulcer; Perforated Eardrum; Pericarditis; Perimenopause; Peripheral Vascular Disease; Peritonsillar Abscess; Persistent Vegetative State; Personality Disorders; Petit Mal Seizures; Peyronie's Disease; Pharyngitis; Pharynx Cancer; Phenylketonuria; Phimosis; Phobia; Photosensitivity; Pigmentation Disorders (Chloasma, Melasma, Vitiligo); Piles; Pinkeye; *Pityriasis Rosea*; PKU; Plague; Plantar Fasciitis; Plantar Warts; Plantaris Strain; Pleurisy; Pleurodynia; PMS; Pneumoconiosis; Pneumonectomy; Pneumonia; Pneumothorax; Lead Poisoning; Polio; Poliomyelitis; Polyarteritis Nodosa; Polychondritis; Polymyalgia Rheumatica; Polymyositis; Colonic Polyps; Nasal Polyps; Vocal Cord Polyps; Port-Wine Stain; Post-Polio Syndrome; Postinfectious Thrombocytopenia;

Postpartum Depression; Preeclampsia; Pregnancy-Induced Hypertension; Premenstrual Syndrome; Pressure Sores; Primary Sclerosing Cholangitis; Prolapse; Enlarged Prostate; Acute Prostatitis; Chronic Prostatitis; Pruritus Ani; Pseudogout; Psoriasis; Psoriatic Arthritis; Ptosis; Pulseless Disease; Pyelonephritis; Quadriceps Strain; Quinsy; Rash; Raynaud's Phenomenon; Rectal Itch; Rectocele; Reflex Sympathetic Dystrophy; Renal Failure; Respiratory Disorders Respiratory Syncytial Virus; Retina Detachment; Retinitis Pigmentosa; Retinopathy; Retrobulbar Neuritis; Reye's Syndrome; Rhabdomyosarcoma; Rheumatoid Arthritis; Allergic Rhinitis; Viral Rhinitis (Common Cold); Riley-Day Syndrome; Ringworm; Rocky Mountain Spotted Fever; Rosacea; Rubeola; Mumps; Salivary Gland Disorders; Salmon Patch; Sarcoidosis; Scabies; Scarlet Fever; Scars; Schizophrenia; Schizotypal Personality Disorder; Sciatica; Scleritis; Scleroderma; Scoliosis; Sebaceous Cysts; Seborrhea; Seborrheic Keratoses; Secondary Hypertension; Seizures; Sexual Dysfunction; Sexually Transmitted Diseases; Shigellosis; Shingles; Sialadenitis; Sialadenosis; Sialolithiasis; Sickle-Cell Anemia; Siderosis; Silicosis; Sinus Cancer; Sjögren's Syndrome; Sleep Disorders; Smallpox; Social Anxiety Disorder; Solar Lentigo; Somatoform Disorders (Hypochondriasis, Somatization Disorder); Somnambulism; Spastic Colon; Spider Veins; Spina *Bifida*; Spinal Cord Trauma; Spontaneous Abortion; Stasis Dermatitis; Strabismus; Strep Throat; Streptococcal Toxic Shock Syndrome; Stroke; Subarachnoid Hemorrhage; Transient Ischemic Attack; Stuttering; Subungual Hematoma; Sun Allergy; Sun-Damaged Skin; Sylvest's Disease; Systemic Lupus Erythematosus; Systemic Sclerosis; Tachycardia; Takayasu's Arteritis; Tay-Sachs Disease; Tear-Duct Infection; Telogen Effluvium; Temporal Arteritis; Tendonitis; Tennis Elbow; Tension Headache; Testicular Torsion; Undescended Testicles; Tetanus; Thrombocytopenia; Thrombophlebitis; Thrombotic Stroke; Tinea; Tinnitus; Tonsillitis; Torsional Deformities; Toxemia Of Pregnancy; Toxic Shock Syndrome, Streptococcal; Toxoplasmosis; Trichomoniasis; Trigeminal Neuralgia (Tic Douloureux); Tuberculosis; Tylosis; Ulcer; Urethritis; Urinary Tract disorders and conditions; Uroliniasis; Urticaria; Uterine disorders; Uterine Prolapse; Uveitis; Vaginitis; Bacterial (*Gardnerella*) Vaginosis; Varicella; Varices, Esophageal; Varicose Veins; Vascular Disorders (Hypertension, Intermittent Claudication, Peripheral Vascular Disease, Polyarteritis Nodosa, Raynaud's Phenomenon, Takayasu's Arteritis, Thrombophlebitis, Vasculitis, Wegener's Granulomatosis); Vein Inflammation; Varicose Veins; Vertigo; Vestibular Schwannoma; Viral Rhinitis; Vitamin B12 Deficiency; Vitiligo; Vocal Tics; Vocal-Cord Disorders; Common Warts; Genital Warts; Plantar Warts; Water On The Brain; Wax Blockage Of Ear Canal; Esophageal Webs; Werlhofs Disease; Wrinkles; *Yersinia Pestis* Infection. It is contemplated that such diseases can be diagnosed or treated using a nucleic acids of the invention that correspond to miRNAs.

Cancers that may be evaluated, diagnosed, and/or treated by methods and compositions of the invention include cancer cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyo sarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. Moreover, miRNA can be evaluated in precancers, such as metaplasia, dysplasia, and hyperplasia.

It is specifically contemplated that the invention can be used to evaluate or diagnose differences between stages of disease, such as between pre-cancer and cancer, or between a primary tumor and a metastasized tumor.

The efficacy of different therapeutic drugs is altered by miRNAs according to the present invention. Such therapeutic drugs include, but are not limited to, chemotherapeutic drugs. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII; dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mito guaz one; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids such as retinoic acid; capecitabine; and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen, raloxifene, droloxifene, 4-hydroxytamoxifen, trioxifene, keoxifene, LY117018, onapristone, and toremifene; aromatase inhibitors that inhibit the enzyme aromatase, which regulates estrogen production in the adrenal glands, such as, for example, 4(5)-imidazoles, aminoglutethimide, megestrol acetate, exemestane, formestanie, fadrozole, vorozole, letrozole, and anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in aberrant cell proliferation, such as, for example, PKC-alpha, Ralf and H-Ras; ribozymes such as a VEGF expression inhibitor and a HER2 expression inhibitor; vaccines such as gene therapy vaccines and pharmaceutically acceptable salts, acids or derivatives of any of the above. A list of U.S. FDA approved oncology drugs with their approved indications can be found on the World Wide Web at accessdata.fda.gov/scripts/cder/onctools/druglist.cfm. Moreover, it is contemplated that samples that have differences in the activity of certain pathways may also be compared. Such cellular pathways include but are not limited to the following: any adhesion or motility pathway including but not limited to those involving cyclic AMP, protein kinase A, G-protein couple receptors, adenylyl cyclase, L-selectin, E-selectin, PECAM, VCAM-1, c-actinin, paxillin, cadherins, AKT, integrin-$\alpha$i, integrin-$\beta$, RAF-1, ERK, PI-3 kinase, vinculin, matrix metalloproteinases, Rho GTPases, p85, trefoil factors, profilin, FAK, MAP kinase, Ras, caveolin, calpain-1, calpain-2, epidermal growth factor receptor, ICAM-1, ICAM-2, cofilin, actin, gelsolin, RhoA, RAC1, myosin light chain kinase, platelet-derived growth factor receptor or ezrin; any apoptosis pathway including but not limited to those involving AKT, Fas ligand, $NF_KB$, caspase-9, PI3 kinase, caspase-3, caspase-7, ICAD, CAD, EndoG, Granzyme B, Bad, Bax, Bid, Bak, APAF-1, cytochrome C, p53, ATM, Bcl-2, PARP, Chk1, Chk2, p21, c-Jun, p73, Rad51, Mdm2, Rad50, c-Abl, BRCA-1, perforin, caspase-4, caspase-8, caspase-6, caspase-1, caspase-2, caspase-10, Rho, Jun kinase, Jun kinase kinase, Rip2, lamin-A, lamin-B1, lamin-B2, Fas receptor, $H_2O_2$, Granzyme A, NADPH oxidase, HMG2, CD4, CD28, CD3, TRADD, IKK, FADD, GADD45, DR3 death receptor, DR4/5 death receptor, FLIPs, APO-3, GRB2, SHC, ERK, MEK, RAF-1, cyclic AMP, protein kinase A, E2F, retinoblastoma protein, Smac/Diablo, ACH receptor, 14-3-3, FAK, SODD, TNF receptor, RIP, cyclin-D1, PCNA, Bcl-XL, PIP2, PIP3, PTEN, ATM, Cdc2, protein kinase C, calcineurin, IKKα, IKKβ, IKKγ, SOS-1, c-FOS, Traf-1, Traf-2, $I_\kappa B\beta$ or the proteasome; any cell activation pathway including but not limited to those involving protein kinase A, nitric oxide, caveolin-1, actin, calcium, protein kinase C, Cdc2, cyclin B, Cdc25, GRB2, SRC protein kinase, ADP-ribosylation factors (ARFs), phospholipase D, AKAP95, p68, Aurora B, CDK1, Eg7, histone H3, PKAc, CD80, PI3 kinase, WASP, Arp2, Arp3, p16, p34, p20, PP2A, angiotensin, angiotensin-converting enzyme, protease-activated receptor-1, protease-activated receptor-4, Ras, RAF-1, PLCβ, PLCγ, COX-1, G-protein-coupled receptors, phospholipase A2, IP3, SUMO1, SUMO 2/3, ubiquitin, Ran, Ran-GAP, Ran-GEF, p53, glucocorticoids, glucocorticoid receptor, components of the SWI/SNF complex, RanBP1, RanBP2, importins, exportins, RCC1, CD40, CD40 ligand, p38, IKKα, $NF_\kappa B$, TRAF2, TRAF3, TRAF5, TRAF6, IL-4, IL-4 receptor, CDK5, AP-1 transcription factor, CD45, CD4, T cell receptors, MAP kinase, nerve growth factor, nerve growth factor receptor, c-Jun, c-Fos, Jun kinase, GRB2, SOS-1, ERK-1, ERK, JAK2, STAT4, IL-12, IL-12 receptor, nitric oxide synthase, TYK2, IFNγ, elastase, IL-8, epithelins, IL-2, IL-2 receptor, CD28, SMAD3, SMAD4, TGFβ or TGFβ receptor; any cell cycle regulation, signaling or differentiation pathway including but not limited to those involving TNFs, SRC protein kinase, Cdc2, cyclin B, Grb2, Sos-1, SHC, p68, Aurora kinases, protein kinase A, protein kinase C, Eg7, p53, cyclins, cyclin-dependent kinases, neural growth factor, epidermal growth factor, retinoblastoma protein, ATF-2, ATM, ATR, AKT, CHK1, CHK2, 14-3-3, WEE1, CDC25 CDC6, Origin Recognition Complex proteins, p15, p16, p27, p21, ABL, c-ABL, SMADs, ubiquitin, SUMO, heat shock proteins, Wnt, GSK-3, angiotensin, p73 any PPAR, TGFα, TGFβ, p300, MDM2, GADD45, Notch, cdc34, BRCA-1, BRCA-2, SKP1, the proteasome, CUL1, E2F, p107, steroid hormones, steroid hormone receptors, $I_\kappa B\alpha$, $I_\kappa B\beta$, Sin3A, heat shock proteins, Ras, Rho, ERKs, IKKs, PI3 kinase, Bcl-2, Bax, PCNA, MAP kinases, dynein, RhoA, PKAc, cyclin AMP, FAK, PIP2, PIP3, integrins, thrombopoietin, Fas, Fas ligand, PLK3, MEKs, JAKs, STATs, acetylcholine, paxillin calcineurin, p38, importins, exportins, Ran, Rad50, Rad51, DNA polymerase, RNA polymerase, Ran-GAP, Ran-GEF, NuMA, Tpx2, RCC1, Sonic Hedgehog, Crml, Patched (Ptc-1), MPF, CaM kinases, tubulin, actin, kinetochore-associated proteins, centromere-binding proteins, telomerase, TERT, PP2A, c-MYC, insulin, T cell receptors, B cell receptors, CBP, IKB, $NF_\kappa B$, RAC1, RAF1, EPO, diacylglycerol, c-Jun, c-Fos, Jun kinase, hypoxia-inducible factors, GATA4, β-catenin, α-catenin, calcium, arrestin, survivin, caspases, procaspases, CREB, CREM, cadherins, PECAMs, corticosteroids, colony-stimulating factors, calpains, adenylyl cyclase, growth factors, nitric oxide, transmembrane receptors, retinoids, G-proteins, ion channels, transcriptional activators, transcriptional coactivators, transcriptional repressors, interleukins, vitamins, interferons, transcriptional corepressors, the nuclear pore, nitrogen, toxins, proteolysis, or phosphorylation; or any metabolic pathway including but not limited to those involving the biosynthesis of amino acids, oxidation of fatty acids, biosynthesis of neurotransmitters and other cell signaling molecules, biosynthesis of polyamines, biosynthesis of lipids and sphingolipids, catabolism of amino acids and nutrients, nucleotide synthesis, eicosanoids, electron transport reactions, ER-associated degradation, glycolysis, fibrinolysis, formation of ketone bodies, formation of phagosomes, cholesterol metabolism, regulation of food intake, energy homeostasis, prothrombin activation, synthesis of lactose and other sugars, multi-drug resistance, biosynthesis of phosphatidylcholine, the proteasome, amyloid precursor protein, Rab GTPases, starch synthesis, glycosylation, synthesis of phosphoglycerides, vitamins, the citric acid cycle, IGF-1 receptor, the urea cycle, vesicular transport, or salvage pathways. It is further contemplated that nucleic acids molecules of the invention can be employed in diagnostic and therapeutic methods with respect to any of the above pathways or factors. Thus, in some embodiments of the invention, a synthetic miRNA, nonsynthetic nucleic acid, or miRNA inhibitor inhibits, eliminate, activates, induces, increases, or otherwise modulates one or more of the above pathways or factors is contemplated as part of methods of the invention. The nucleic acid can be used to diagnosis a disease or condition based on the relation of that miRNA to any of the pathways described above.

Phenotypic traits also include characteristics such as longevity, appearance (e.g., baldness, obesity), strength, speed, endurance, fertility, and susceptibility or receptivity to particular drugs or therapeutic treatments. Synthetic miRNAs or miRNA inhibitors that affect phenotypic traits may provide intervention points for therapeutic development.

H. Other Assays

In addition to the use of arrays and microarrays, it is contemplated that a number of difference assays could be employed to analyze miRNAs, their activities, and their effects. Such assays include, but are not limited to, RT-PCR, in situ hybridization, hybridization protection assay (HPA) (GenProbe), branched DNA (bDNA) assay (Chiron), rolling circle amplification (RCA), single molecule hybridization detection (US Genomics), Invader assay (ThirdWave Technologies), and Bridge Litigation Assay (Genaco). It is contemplated that such methods may be used in the context of arrays, as well as in the context of diagnostic assays.

III. Therapeutic and Diagnostic Applications

Synthetic miRNAs or miRNA inhibitors that affect phenotypic traits provide intervention points for therapeutic applications as well as diagnostic applications (by screening for the presence or absence of a particular miRNA). It is specifically contemplated that RNA molecules of the present invention can be used to treat any of the diseases or conditions discussed in the previous section. Moreover, any of the methods described above can also be employed with respect to therapeutic and diagnostic aspects of the invention. For example, methods with respect to detecting miRNAs or screening for them can also be employed in a diagnostic context.

In therapeutic applications, an effective amount of the synthetic miRNAs or miRNA inhibitors of the present invention is administered to a cell, which may or may not be in an animal. In some embodiments, a therapeutically effective amount of the synthetic miRNAs or miRNA inhibitors of the present invention is administered to an individual for the treatment of disease or condition. The term "effective amount" as used herein is defined as the amount of the molecules of the present invention that are necessary to result in the desired physiological change in the cell or tissue to which it is administered. The term "therapeutically effective amount" as used herein is defined as the amount of the molecules of the present invention that achieves a desired effect with respect to a disease or condition. A skilled artisan readily recognizes that in many cases the molecules may not provide a cure but may provide a partial benefit, such as alleviation or improvement of at least one symptom. In some embodiments, a physiological change having some benefit is also considered therapeutically beneficial. Thus, in some embodiments, an amount of molecules that provides a physiological change is considered an "effective amount" or a "therapeutically effective amount."

In some embodiments the molecule has a sequence that corresponds to the miRNA sequence from that particular animal, as opposed to from another animal. Thus, in some embodiments, a human sequence is utilized in the RNA molecules of the present invention.

A. Modes of Administration and Formulations

The nucleic acid molecules of the invention may be administered to a subject alone or in the form of a pharmaceutical composition for the treatment of a condition or disease. Pharmaceutical compositions may be formulated in conventional manner using one or more physiologically acceptable carriers, diluents, excipients or auxiliaries which facilitate processing of the proteins into preparations which can be used pharmaceutically. Proper formulation is dependent upon the route of administration chosen.

For topical administration the proteins of the invention may be formulated as solutions, gels, ointments, creams, suspensions, etc. as are well-known in the art. Systemic formulations include those designed for administration by injection, e.g. subcutaneous, intravenous, intramuscular, intrathecal or intraperitoneal injection, as well as those designed for transdermal, transmucosal, inhalation, oral or pulmonary administration. For injection, the nucleic acids of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Alternatively, the nucleic acid molecules may be in powder form for constitution with a suitable vehicle, e.g., sterile pyrogen-free water, before use. For transmucosal administration, penetrants appropriate to the barrier to be permeated are used in the formulation. Such penetrants are generally known in the art. For oral administration, the nucleic acids can be readily formulated by combining the molecules with pharmaceutically acceptable carriers well known in the art. Such carriers enable the nucleic acids of the invention to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, e.g. lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate. If desired, solid dosage forms may be sugar-coated or enteric-coated using standard techniques. For oral liquid preparations such as, for example, suspensions, elixirs and solutions, suitable carriers, excipients or diluents include water, glycols, oils, alcohols, etc. Additionally, flavoring agents, preservatives, coloring agents and the like may be added. For buccal administration, the molecules may take the form of tablets, lozenges, etc. formulated in conventional manner. For administration by inhalation, the molecules for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator may be formulated containing a powder mix of the nucleic acids and a suitable powder base such as lactose or starch. The RNA molecules may also be formulated in rectal or vaginal compositions such as suppositories or retention enemas, e.g., containing conventional suppository bases such as cocoa butter or other glycerides.

In addition to the formulations described previously, the molecules may also be formulated as a depot preparation. Such long acting formulations may be administered by implantation (for example subcutaneously or intramuscularly) or by intramuscular injection. Thus, for example, the molecules may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems may be employed. Liposomes and emulsions are well-known examples of delivery vehicles that may be used to deliver nucleic acids of the invention.

A nucleic acid of the invention may be administered in combination with a carrier or lipid to increase cellular uptake. For example, the oligonucleotide may be administered in combination with a cationic lipid. Examples of cationic lipids include, but are not limited to, lipofectin, DOTMA, DOPE, and DOTAP. The publication of WO0071096, which is specifically incorporated by reference, describes different formulations, such as a DOTAP: cholesterol or cholesterol derivative formulation that can effectively be used for gene therapy. Other disclosures also discuss different lipid or liposomal formulations including nanoparticles and methods of administration; these include, but are not limited to, U.S. Patent Publication 20030203865, 20020150626, 20030032615, and 20040048787, which are specifically incorporated by reference to the extent they disclose formulations and other related aspects of administration and delivery of nucleic acids. Methods used for forming particles are also disclosed in U.S. Pat. Nos. 5,844, 107, 5,877,302, 6,008,336, 6,077,835, 5,972,901, 6,200,801, and 5,972,900, which are incorporated by reference for those aspects.

The nucleic acids may also be administered in combination with a cationic amine such as poly(L-lysine). Nucleic acids may also be conjugated to a chemical moiety, such as transferrin and cholesteryls. In addition, oligonucleotides may be targeted to certain organelles by linking specific chemical groups to the oligonucleotide. For example, linking the oligonucleotide to a suitable array of mannose residues will target the oligonucleotide to the liver.

Additionally, the molecules may be delivered using a sustained-release system, such as semipermeable matrices of solid polymers containing the therapeutic agent. Various of sustained-release materials have been established and are well known by those skilled in the art. Sustained-release capsules may, depending on their chemical nature, release the molecules for a few weeks up to over 100 days. Depending on the chemical nature and the biological stability of the chimeric molecules, additional strategies for molecule stabilization may be employed.

Nucleic acids may be included in any of the above-described formulations as the free acids or bases or as pharmaceutically acceptable salts. Pharmaceutically acceptable salts are those salts that substantially retain the biologic activity of the free bases and which are prepared by reaction with inorganic acids. Pharmaceutical salts tend to be more soluble in aqueous and other protic solvents than are the corresponding free base forms.

Pharmaceutical compositions of the present invention comprise an effective amount of one or more synthetic miRNA molecules or miRNA inhibitors dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one chimeric polypeptide or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The chimeric molecules may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g. aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The molecules may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments, the molecules are prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, *acacia*, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

Any embodiment discussed above with respect to delivery or transport to cells can also be employed with respect to implementing delivery of medicinal compounds discussed in this section.

B. Effective Dosages

The molecules of the invention will generally be used in an amount effective to achieve the intended purpose. For use to treat or prevent a disease condition, the molecules of the invention, or pharmaceutical compositions thereof, are administered or applied in a therapeutically effective amount. A therapeutically effective amount is an amount effective to ameliorate or prevent the symptoms, or prolong the survival of, the patient being treated. Determination of a therapeutically effective amount is well within the capabilities of those skilled in the art, especially in light of the detailed disclosure provided herein.

For systemic administration, a therapeutically effective dose can be estimated initially from in vitro assays. For example, a dose can be formulated in animal models to achieve a circulating concentration range that includes the $IC_5$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the molecules which are sufficient to maintain therapeutic effect. Usual patient dosages for administration by injection range from about 0.1 to 5 mg/kg/day, preferably from about 0.5 to 1 mg/kg/day. Therapeutically effective serum levels may be achieved by administering multiple doses each day.

In cases of local administration or selective uptake, the effective local concentration of the proteins may not be related to plasma concentration. One having skill in the art will be able to optimize therapeutically effective local dosages without undue experimentation.

The amount of molecules administered will, of course, be dependent on the subject being treated, on the subject's weight, the severity of the affliction, the manner of administration and the judgment of the prescribing physician.

The therapy may be repeated intermittently while symptoms detectable or even when they are not detectable. The therapy may be provided alone or in combination with other drugs or treatment (including surgery).

C. Toxicity

Preferably, a therapeutically effective dose of the molecules described herein will provide therapeutic benefit without causing substantial toxicity.

Toxicity of the molecules described herein can be determined by standard pharmaceutical procedures in cell cultures or experimental animals, e.g., by determining the LD50 (the dose lethal to 50% of the population) or the $LD_{100}$ (the dose lethal to 100% of the population). The dose ratio between toxic and therapeutic effect is the therapeutic index. Proteins which exhibit high therapeutic indices are preferred. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, In: The Pharmacological Basis of Therapeutics, Ch. 1, p. 1).

D. Pendant Groups

A "pendant group" may be attached or conjugated to the nucleic acid. Pendant groups may increase cellular uptake of the nucleic acid. Pendant groups can be linked to any portion of the nucleic acid but are commonly linked to the end(s) of the oligonucleotide chain. Examples of pendant groups include, but are not limited to: acridine derivatives (i.e.

2-methoxy-6-chloro-9-aminoacridine); cross-linkers such as psoralen derivatives, azidophenacyl, proflavin, and azidoproflavin; artificial endonucleases; metal complexes such as EDTA-Fe(II), o-phenanthroline-Cu(I), and porphyrin-Fe (II); alkylating moieties; nucleases such as amino-1-hexanolstaphylococcal nuclease and alkaline phosphatase; terminal transferases; abzymes; cholesteryl moieties; lipophilic carriers; peptide conjugates; long chain alcohols; phosphate esters; amino; mercapto groups; radioactive markers; nonradioactive markers such as dyes; and polylysine or other polyamines. In one example, the nucleic acid is conjugated to a carbohydrate, sulfated carbohydrate, or glycan.

IV. Kits

Any of the compositions described herein may be comprised in a kit. In a non-limiting example, individual synthetic miRNAs are included in a kit. The kit may further include one or more negative control synthetic miRNAs that can be used to control for the effects of synthetic miRNA delivery. The kit may further include water and hybridization buffer to facilitate hybridization of the two strands of the synthetic miRNAs. The kit may also include one or more transfection reagent(s) to facilitate delivery of the synthetic miRNA to cells.

In another non-limiting example, multiple synthetic miRNAs and/or multiple miRNA inhibitors are included in a kit. The kit may further include one or more negative control synthetic miRNAs and/or miRNA inhibitors that can be used to control for the effects of synthetic miRNA and/or miRNA inhibitor delivery. The kit may also include one or more transfection reagents to facilitate delivery into cells.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit (labeling reagent and label may be packaged together), the kit also will generally contain a second, third or other additional container into which the additional components may be separately placed. However, various combinations of components may be comprised in a vial. The kits of the present invention also will typically include a means for containing the nucleic acids, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred.

However, the components of the kit may be provided as dried powder(s). When reagents and/or components are provided as a dry powder, the powder can be reconstituted by the addition of a suitable solvent. It is envisioned that the solvent may also be provided in another container means.

The container means will generally include at least one vial, test tube, flask, bottle, syringe and/or other container means, into which the nucleic acid formulations are placed, preferably, suitably allocated. The kits may also comprise a second container means for containing a sterile, pharmaceutically acceptable buffer and/or other diluent.

The kits of the present invention will also typically include a means for containing the vials in close confinement for commercial sale, such as, e.g., injection and/or blow-molded plastic containers into which the desired vials are retained.

Such kits may also include components that preserve or maintain the miRNA or that protect against its degradation. Such components may be RNAse-free or protect against RNAses. Such kits generally will comprise, in suitable means, distinct containers for each individual reagent or solution.

A kit will also include instructions for employing the kit components as well the use of any other reagent not included in the kit. Instructions may include variations that can be implemented.

Kits of the invention may also include one or more of the following: synthetic miRNA, nonsynthetic miRNA, library of synthetic miRNAs, library of miRNA inhibitors, library of nonsynthetic miRNA, combination library of synthetic miRNA, miRNA inhibitors, and/or nonsynthetic miRNAs, negative control synthetic miRNA, negative control miRNA inhibitor, negative control nonsynthetic miRNA, nuclease-free water; RNase-free containers, such as 1.5 ml tubes; hybridization buffer; and transfection reagent(s).

It is contemplated that such reagents are embodiments of kits of the invention. Such kits, however, are not limited to the particular items identified above and may include any reagent used for the manipulation or characterization of miRNA.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Unless otherwise designated, catalog numbers refer to products available by that number from Ambion, Inc.®, The RNA Company.

Example 1

Assay for Measuring Activity of Precursor miRNAs (Reporter)

A series of luciferase reporter vectors was created to measure the activities of synthetic miRNAs in cells. The reporter vectors were based on plasmids that had been used to monitor the activity of endogenous miRNAs (Tuschl paper). Briefly, a mammalian expression vector with the luciferase gene under the control of the CMV early promoter was created. Down-stream of the luciferase coding sequence, in the 3' UTR of the gene, sequences complementary to mature miR-1-2, miR-10, miR-124, miR-19a, and miR-130 were added. The reporter vectors were co-transfected into HeLa cells along with synthetic miRNAs designed to introduce one of the five miRNAs listed above. The transfections involved mixing 200 ng of reporter vector with 0.3, 1, and 3 pmoles of each corresponding synthetic miRNA. The reporter/miRNA mixture was mixed with 0.3 µl of Lipofectamine 2000 (Invitrogen) and incubated for 5-15 minutes. Approximately 8,000 cells were added to each miRNA/reporter/transfection reagent complex in individual wells of a 96-well plate. HeLa cells were grown in D-MEM (GIBCO) supplemented with 10% fetal bovine serum (GIBCO) at 37° C. and 5% $CO_2$. 24-48 hrs post transfection, the cells were harvested and assayed using the Luciferase assay as described by the manufacturer (Promega). The level of luciferase expression in the cell populations was compared to cells transfected with the same reporter but a synthetic miRNA with a sequence that does not correspond to the vector. This non-targeting miRNA was referred to as the negative control miRNA.

Final analysis of the synthetic miRNA designs involved measuring the activity of both the active and complementary strands of our synthetic miRNAs. For these studies, reporter vectors with luciferase 3' UTR sequences were created that included regions complementary to both the active and the complementary strands of our synthetic miR-33 and let-7b miRNA designs. When co-transfected with malfunctioning synthetic miRNAs, the reporters with a sequence targeted by the complementary strand exhibit reduced luciferase expression because the complementary strand of the synthetic miRNAs are entering the miRNA pathway in addition to or even instead of the active strand that is desired. For these experiments, the co-transfection and reporter analysis protocols are identical to what is described above.

Example 2

Assay for Measuring Activity of Precursor miRNAs (Endogenous Gene)

While the luciferase reporter constructs were extremely valuable in evaluating the synthetic miRNA designs, it was important to verify the findings of the reporter constructs by measuring the effects of the synthetic miRNAs on endogenous gene targets. For these studies, the expression of RAS and MYC in cells transfected with let-7 miRNAs was chosen for monitoring. Both RAS and MYC are down-regulated by the various members of the let-7 family in humans and C. elegans (publication pending). Using a microarray system specific to miRNAs, the inventors have found that HepG2 cells express undetectable levels of let-7. To test the activities of our various designs of our synthetic miRNAs, synthetic let-7 miRNAs were created and used to transfect HepG2 cells in 24-well plates using siPORT NeoFX (Ambion) according to the manufacturer's suggestions. Three days post-transfection, the cells were fixed with 4% paraformaldehyde, stained with DAPI to localize cell nuclei, and stained with FITC-conjugated antibodies specific to MYC or RAS (US Biological) according to the manufacturer's suggestions. The relative reduction in target protein expression in synthetic let-7 transfected cells was determined by comparing the staining intensity of MYC and RAS to cells transfected with a negative control miRNA using MetaMorph software.

To ensure that the results of our let-7 assays could be verified by additional miRNA interactions that are observed naturally in cells, we created assays for two additional miRNAs with verified targets. In the first, a real-time PCR™ assay was developed to measure the level of the HOXB8 mRNA in cells transfected with synthetic miR-196. It has been shown that miR-196 induces degradation of the HOXB8 mRNA in cells. When transfected into cultured cells using siPORT NeoFX according to the manufacturer's instructions, effective miR-196 synthetic miRNA designs reduce the levels of the HOXB8 mRNA.

To monitor the effectiveness of synthetic miR-1-2 miR-NAs, a reporter vector was created wherein the 3' UTR of the G6PD gene was placed immediately down-stream of the luciferase coding region. An interaction between miR-1-2 and the G6PD 3' UTR has been published (Lewis, 2003). Synthetic miR-1-2 designs were co-transfected with the reporter vector and assayed as described in Example 1.

Example 3

Effectiveness of Partially Complementary miRNAs

Three general sequence designs were compared for miRNA activity. The first, referred to as the "miRNA design," featured an active strand identical to the mature miRNA found in animals and a complementary strand that was identical to the hairpin sequence that is predicted to exist in cells during the processing of the miRNA prior to activation of the miRNA (see below). The second design, referred to as the "mismatch design," was a hybrid of the same active strand as above with a complementary strand with a di-nucleotide, 3' overhang and two mismatches in the final five nucleotides that preceded the 3' overhang (see below). The third design, referred to as the "siRNA design," comprised the same active strand as above hybridized to a second RNA that was fully complementary except that it left 3' di-nucleotide overhangs at either end of the double-stranded molecule (two polynucleotides) (see below). The examples below involve or correspond to human miRNAs.

```
miR-1-2
mature miR-1-2 sequence- UGGAAUGUAAAGAAGUAUGUA (53-73 of SEQ ID NO: 1)

miRNA design = CAUACUUCUUUAUAUGCCCAUA (SEQ ID NO: 594) +
UGGAAUGUAAAGAAGUAUGUA (SEQ ID NO: 595)

mismatch design = CAUACUUCUUUACAUUCUGTT (SEQ ID NO: 596) +
UGGAAUGUAAAGAAGUAUGUA (SEQ ID NO: 597)

siRNA design = CAUACUUCUUUACAUUCCATT (SEQ ID NO: 598) +
UGGAAUGUAAAGAAGUAUGUA (SEQ ID NO: 599)

mir-124a-1
mature miR-124 sequence- UUAAGGCACGCGGUGAAUGCCA (52-73 of SEQ ID NO: 80)

miRNAdesign = GUGUUCACAGCGGACCUUGAUU (SEQ ID NO: 600) +
UUAAGGCACGCGGUGAAUGCCA (SEQ ID NO: 601)
```

-continued mismatch design = GCAUUCACCGCGUGCCUUGGTT (SEQ ID NO: 602) +
UUAAGGCACGCGGUGAAUGCCA (SEQ ID NO: 603)

siRNA design = GCAUUCACCGCGUGCCUUAATT (SEQ ID NO: 604) +
UUAAGGCACGCGGUGAAUGCCA (SEQ ID NO: 605)

miR-130a
mature miR-130 sequence - CAGUGCAAUGUUAAAAGGGC (55-74 of SEQ ID NO: 91)

miRNA design = UCUUUUCACAUUGUGCUAC (SEQ ID NO: 606) +
CAGUGCAAUGUUAAAAGGGC (SEQ ID NO: 607)

mismatch design = UAUUUUAACAUUGCACUGTT (SEQ ID NO: 608) +
CAGUGCAAUGUUAAAAGGGC (SEQ ID NO: 609)

siRNA design = CCUUUUAACAUUGCACUGTT (SEQ ID NO: 610) +
CAGUGCAAUGUUAAAAGGGC (SEQ ID NO: 611)

miR-19a
mature miR-19a sequence - UGUGCAAAUCUAUGCAAAACUGA (49-71 of SEQ ID NO: 28)

miRNA design = AGUUUUGCAUAGUUGCACUA (SEQ ID NO: 612) +
UGUGCAAAUCUAUGCAAAACUGA (SEQ ID NO: 613)

mismatch design = ACAUUUGCAUAGAUUUGCACATT (SEQ ID NO: 614) +
UGUGCAAAUCUAUGCAAAACUGA (SEQ ID NO: 615)

siRNA design = AGUUUUGCAUAGAUUUGCACATT (SEQ ID NO: 616)+
UGUGCAAAUCUAUGCAAAACUGA (SEQ ID NO: 617)

mmu-miR-10a-1 (mouse)
mature miR-10 sequence - UACCCUGUAGAUCCGAAUUUGUG (22-44 of SEQ ID NO: 212)

miRNA design = CAAAUUCGUAUCUAGGGGAAUA (SEQ ID NO: 618) +
UACCCUGUAGAUCCGAAUUUGUG (SEQ ID NO: 619)

mismatch design = AGAAUUCGGAUCUACAGGGUATT (SEQ ID NO: 620) +
UACCCUGUAGAUCCGAAUUUGUG (SEQ ID NO: 621)

siRNA design = CAAAUUCGGAUCUACAGGGUATT (SEQ ID NO: 622) +
UACCCUGUAGAUCCGAAUUUGUG (SEQ ID NO: 623)

miR-33
mature miR-33 sequence - GUGCAUUGUAGUUGCAUUG (6-24 of SEQ ID NO: 57)

miRNA = AUGUUUCCACAGUGCAUCA (SEQ ID NO: 624) +
GUGCAUUGUAGUUGCAUUG (SEQ ID NO: 625)

mismatch design = GUCCAACUACAAUGCACTT (SEQ ID NO: 626) +
GUGCAUUGUAGUUGCAUUG (SEQ ID NO: 627)

siRNA design = AUGCAACUACAAUGCACTT (SEQ ID NO: 628) +
GUGCAUUGUAGUUGCAUUG (SEQ ID NO: 629)

let-7b
mature let-7b sequence - UGAGGUAGUAGGUUGUGUGGUU (6-27 of SEQ ID NO: 6)

miRNA design = CUAUACAACCUACUGCCUUCC (SEQ ID NO: 630) +
UGAGGUAGUAGGUUGUGUGGUU (SEQ ID NO: 631)

mismatch design = CCACACAACCUACUAUCUUATT (SEQ ID NO: 632) +
UGAGGUAGUAGGUUGUGUGGUU (SEQ ID NO: 633)

siRNA design = CCACACAACCUACUACCUCATT (SEQ ID NO: 634) +
UGAGGUAGUAGGUUGUGUGGUU (SEQ ID NO: 635)

miR-196-2
mature miR-196 sequence - UAGGUAGUUUCAUGUUGUUGG (7-27 of SEQ ID NO: 143)

siRNA design = AACAACAUGAAACUACCUATT (SEQ ID NO: 636) +
UAGGUAGUUUCAUGUUGUUGG (SEQ ID NO: 637)

miRNA design = CAAAUUCGUAUCUAGGGGAAUA (SEQ ID NO: 638) +
UAGGUAGUUUCAUGUUGUUGG (SEQ ID NO: 639)

mismatch design = AAUAACAUGAAACUACCUATT (SEQ ID NO: 640) +
UAGGUAGUUUCAUGUUGUUGG (SEQ ID NO: 641)

The assorted mir-1-2, mmu-miR-10a-1, miR-19a, mir-124a-1, and mir-130a synthetic miRNAs were tested for their capacity to reduce the expression of the reporter gene in vectors with appropriate miRNA target sites using the assay described in Example 1. All three designs were similarly capable of down-regulating the appropriate reporter vectors.

To assess whether there were differences between the various miRNA designs ini their ability to affect the expression of endogenous genes, the following cells were transfected: HepG2 cells with three designs of the let-7 synthetic miRNAs, A549 with three designs of the miR-196 synthetic miRNAs, and HeLa with the G6PD reporter vector and three designs of the miR-1-2 synthetic miRNA. As with the reporter vectors, all three synthetic miRNA designs proved capable of reducing the expression of the target genes, though it is notable that the siRNA design performed most poorly.

As a final comparison of the three synthetic miRNA designs, synthetic miRNAs were co-transfected with reporter vectors that included target sites for the complementary strands of the synthetic miRNAs according to the procedure described in Example 1. In this assay, it was apparent that the siRNA design significantly affected the reporter vectors, indicating that the wrong strand of the miRNA was entering the miRNA pathway (FIG. 3). Because the complementary strand might impact the expression of genes that are not natural targets of the miRNA that is being studied, the siRNA design is inappropriate for effective synthetic miRNAs.

Example 4

Effectiveness of Chemically 5' End-Modified Synthetic miRNAs

Although the siRNA design proved problematic in that it exhibited a high rate of complementary strand uptake by the miRNA pathway, it did have the advantage that it was easy to hybridize and easy to deliver to cells. For these reasons, ways to overcome the problems with complementary strand uptake were explored. The siRNA design was used to test the effects of chemical modifications at the 5' ends of the synthetic miRNAs. For these studies, several different complementary strands were synthesized with unique 5' ends. One featured four deoxyribose nucleotides at the 5' end; one was a combination of four deoxyribose nucleotides at the 5' end and a 5' $NH_2$; one had a 5' $NH_2$; one had a 5' $NHCOCH_3$ (see below).

```
miR-33
mature miR-33 sequence - GUGCAUUGUAGUUGCAUUG (6-24 of SEQ ID NO: 57)

siRNA design = AUGCAACUACAAUGCACTT (SEQ ID NO: 642) +
GUGCAUUGUAGUUGCAUUG (SEQ ID NO: 643)

5' amino design = (NH2)AUGCAACUACAAUGCACTT (SEQ ID NO: 644) +
GUGCAUUGUAGUUGCAUUG (SEQ ID NO: 645)

5' acetyl design = (CH3OCNH)AUGCAACUACAAUGCACTT (SEQ ID NO: 646) +
GUGCAUUGUAGUUGCAUUG (SEQ ID NO: 647)

5' DNA design = dAdUdGdCAACUACAAUGCACTT (SEQ ID NO: 648) +
GUGCAUUGUAGUUGCAUUG (SEQ ID NO: 649)

5' amino DNA design = (NH2)dAdUdGdCAACUACAAUGCACTT (SEQ ID NO: 650) +
GUGCAUUGUAGUUGCAUUG (SEQ ID NO: 651)

let-7b
mature let-7b sequence - UGAGGUAGUAGGUUGUGUGGUU (6-27 of SEQ ID NO: 6)

siRNA design = CCACACAACCUACUACCUCATT (SEQ ID NO: 652) +
UGAGGUAGUAGGUUGUGUGGUU (SEQ ID NO: 653)

5' amino design = NH2CCACACAACCUACUACCUCATT (SEQ ID NO: 654) +
UGAGGUAGUAGGUUGUGUGGUU (SEQ ID NO: 655)

5' DNA design = dCdCdAdCACAACCUACUACCUCATT (SEQ ID NO: 656) +
UGAGGUAGUAGGUUGUGUGGUU (SEQ ID NO: 657)

5' amino DNA design = NH2dCdCdAdCACAACCUACUACCUCATT (SEQ ID NO: 658) +
UGAGGUAGUAGGUUGUGUGGUU (SEQ ID NO: 659)

miR-1-2
mature miR-1-2 sequence - UGGAAUGUAAAGAAGUAUGUA (53-73 of SEQ ID NO: 1)

siRNA design = CAUACUUCUUUACAUUCCATT (SEQ ID NO: 660) +
UGGAAUGUAAAGAAGUAUGUA (SEQ ID NO: 661)

5' amino design = NH2CAUACUUCUUUACAUUCCATT (SEQ ID NO: 662) +
UGGAAUGUAAAGAAGUAUGUA (SEQ ID NO: 663)

miR-124a-1
mature miR-124 sequence - UUAAGGCACGCGGUGAAUGCCA (52-73 of SEQ ID NO: 80)

siRNA design = GCAUUCACCGCGUGCCUUAATT (SEQ ID NO: 664) +
UUAAGGCACGCGGUGAAUGCCA (SEQ ID NO: 665)

5' amino design = NH2GCAUUCACCGCGUGCCUUAATT (SEQ ID NO: 666) +
UUAAGGCACGCGGUGAAUGCCA (SEQ ID NO: 667)
```

```
miR-130a
mature miR-130 sequence - CAGUGCAAUGUUAAAAGGGC (55-74 of SEQ ID NO: 91)

siRNA design = CCUUUUAACAUUGCACUGTT (SEQ ID NO: 668) +
CAGUGCAAUGUUAAAAGGGC (SEQ ID NO: 669)

5' amino design = NH2 CCUUUUAACAUUGCACUGTT (SEQ ID NO: 670) +
CAGUGCAAUGUUAAAAGGGC (SEQ ID NO: 671)

miR-10a-1
mature miR-10 sequence - UACCCUGUAGAUCCGAAUUUGUG (22-44 of SEQ ID NO: 212)

siRNA design = CAAAUUCGGAUCUACAGGGUATT (SEQ ID NO: 672) +
UACCCUGUAGAUCCGAAUUUGUG (SEQ ID NO: 673)

5'amino design = NH2CAAAUUCGGAUCUACAGGGUATT (SEQ ID NO: 674) +
UACCCUGUAGAUCCGAAUUUGUG (SEQ ID NO: 675)
```

The miR-33 and let-7b synthetic miRNAs were co-transfected into HeLa and HepG2 cells, respectively, with reporter vectors bearing target sites for the active and complementary strands of miR-33 and let-7b as described in Example 1. Luciferase expression from the active and complementary strand-specific reporter vectors was measured according to the manufacturer's (Promega) protocol. As shown in FIG. 3, the synthetic miRNA designs with the 5' NH$_2$ and 5' NHCOCH$_3$ provided higher active strand activity and significantly reduced complementary strand activity relative to the unmodified, synthetic miRNAs. This is ideal for synthetic miRNAs since the effects seen following transfection will be specific to the activity of the active strand of the synthetic miRNA. Furthermore, the high efficacy of the 5' modified designs will allow lower concentrations to be used for transfections and reduce toxicity that is often observed when transfecting cells with higher amounts of nucleic acid.

Figure 1:
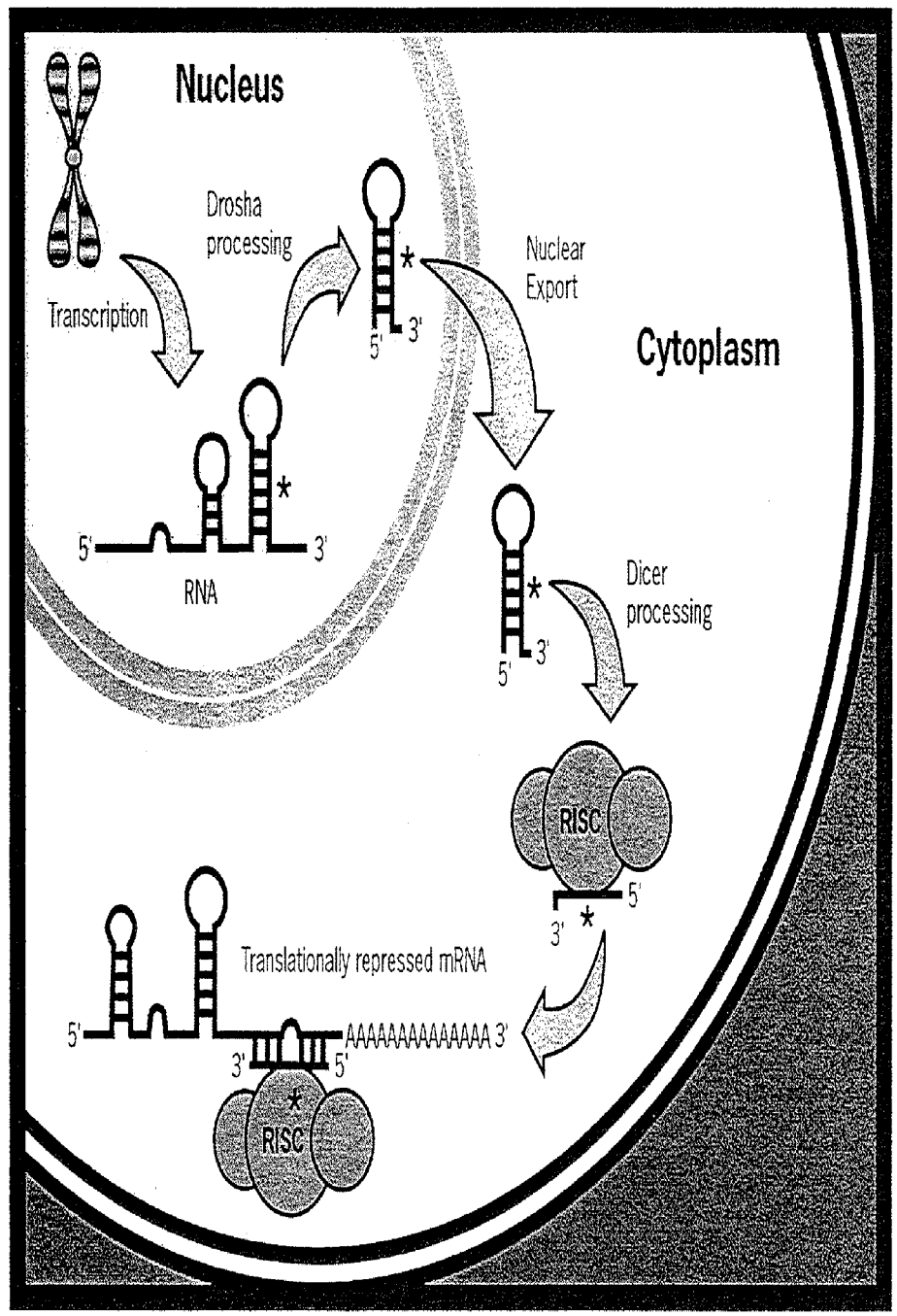
FIG. 1 Overview of miRNA Expression and Activation. MiRNAs are transcribed as part of longer RNA molecules that can be as long as a thousand nucleotides (Lee, 2002). The RNAs are processed in the nucleus into hairpin RNAs of 70-100 nucleotides by the dsRNA-specific ribonuclease Drosha (Lee 2003) (FIG. 1). The hairpin RNAs are transported to the cytoplasm and digested by a second, double-strand specific ribonuclease called Dicer. The resulting 19-23mer miRNA is bound by a complex that is similar to or identical to the RNA-Induced Silencing Complex (RISC) that participates in RNA interference (Hutvagner, 2002). The complex-bound, single-stranded miRNA binds mRNAs with sequences that are significantly, though not completely, complementary to the miRNA. By a mechanism that is not fully understood, but that does not involve mRNA degradation, the bound mRNA is not translated, resulting in reduced expression of the corresponding gene.
Figure 4:
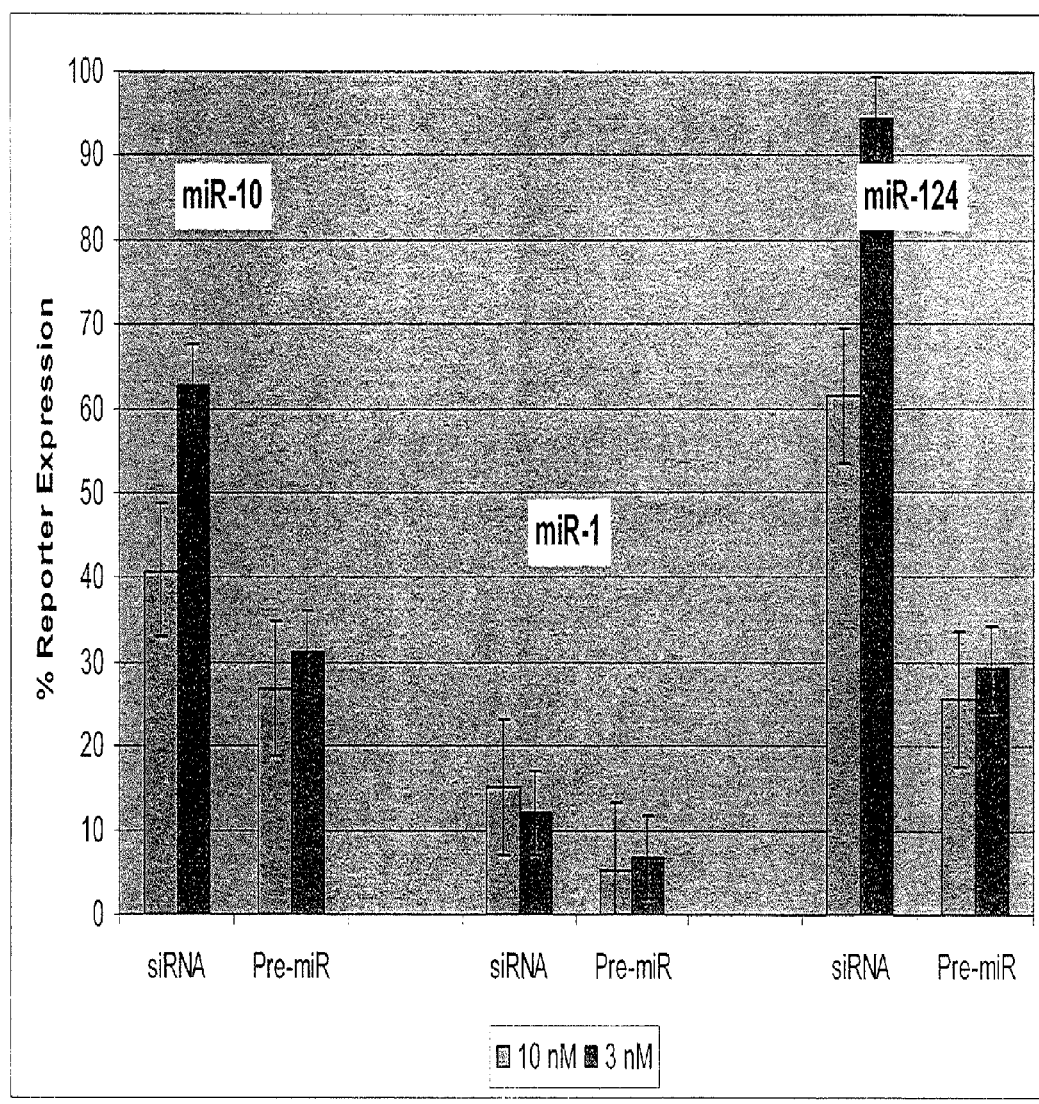
FIG. 4. Synthetic miRNA Activity for various miRNAs. Synthetic miRNAs with siRNA and Pre-miR (5'amine) design were prepared and transfected into HeLa cells at 3 and 10 nM final concentration. The synthetic miRNAs were co-transfected with reporter vectors bearing target sites for the mature miRNAs. The expression of the luciferase reporter in co-transfected cells was measured twenty-four hours post-transfected and expressed in the figure as the reporter expression relative to cells co-transferred with negative control synthetic miRNAs.

To confirm that the 5' amino modification is superior to the standard siRNA design for a broad set of synthetic miRNAs, the effectiveness of both synthetic miRNA designs was measured in cells co-transfected with reporter vectors with miRNA target sites. As seen in FIG. 4, the 5' NH$_2$ is reproducibly superior to the unmodified siRNA design.

Example 5

Effectiveness of Chemically Internally Modified Synthetic miRNAs

The siRNA design was also used to test the effects of chemical modifications at internal domains within the complementary strand. For these studies, 2'O-Me modifications were placed at various locations along the length of the complementary strand. Below is provided an example of a series of synthetic miRNAs with chemically modified complementary strands.

```
                                                   (SEQ ID NO: 676)
miRNA Strand - 5'-UAU ACA AGA GAU GAA AUC CUC-3'

Complementary Strands -
                                                   (SEQ ID NO: 806)
Position 1 - 5'-GGA UUU CAU CUC UUG UAU AUt-3'

(SEQ ID NO: 806)
Position 2 - 5'-GGA UUU CAU CUC UUG UAU AUt-3'

(SEQ ID NO: 806)
Position 3 - 5'-GGA UUU CAU CUC UUG UAU AUt-3'

(SEQ ID NO: 806)
Position 4 - 5'-GGA UUU CAU CUC UUG UAU AUt-3'

(SEQ ID NO: 806)
Position 5 - 5'-GGA UUU CAU CUC UUG UAU AUt-3'

(SEQ ID NO: 806)
Position 6 - 5'-GGA UUU CAU CUC UUG UAU AUt-3'
Note
Positions that are 2'-O-Me are denoted in bold.
```

Synthetic miRNAs with the designs described above were tested for miRNA and complementary strand activity. Interestingly, complementary strand modifications at positions 1 and 5 significantly reduced complementary strand activity without altering the activity of the miRNA strand (FIG. 3).

Example 6

Synthetic miRNA Library Screen for miRNAs that Influence Cell Proliferation A hallmark of cancer is uncontrolled cell proliferation; cell proliferation assays are commonly used by researchers to study the influence of genes in oncogenesis. A cell proliferation assay was used in conjunction with the miRNA inhibitor library to identify miRNAs that influence cell proliferation.

The inventors transfected HeLa cells in triplicate with fifteen different synthetic miRNAs using siPORT NeoFX (Ambion) according to the manufacturer's instructions (FIG. 6). Transfected HeLa cells were analyzed using Alamar Blue (BioSource International, Inc., CA) at 24 hr intervals. Alamar Blue is a compound, that when reduced by cellular metabolism, changes from a non-fluorescent blue color to a fluorescent red form that is easily quantified. The amount of Alamar Blue reduced is directly proportional to the cell number, providing a rapid method for assessing cell proliferation. To perform the assay, the Alamar Blue reagent was added into the tissue culture media at a 10% final concentration. The mixture was incubated for 3-6 hr in growth conditions after which fluorescence was quantified using a Spectra Max™ GeminiXS™ (Molecular Devices, Sunnyvale, Calif.). Cells transfected with synthetic miR-124 and miR-106 exhibited significantly lower proliferation than negative control-transfected samples, as well as smaples transfected with the other synthetic miRNAs.

Example 7

MiRNA Inhibitor Library Screen for miRNAs that Influence Cell Proliferation

A hallmark of cancer is uncontrolled cell proliferation. Cell proliferation assays are commonly used by researchers to study the influence of genes in oncogenesis. A cell proliferation assay was used in conjunction with our miRNA inhibitor library to identify miRNAs that influence cell proliferation.

Cells were transfected with a library of over 90 miRNA inhibitors to identify miRNAs that are involved in cell growth. HeLa cells (8000 cells/well of 96 well plate) were transfected in triplicate with 5 pmoles of miRNA inhibitors using siPORT™ NeoFX™ (Ambion). The media was changed 24 hrs after transfection. 72 hours post-transfection, we fixed cells with 4% paraformaldehyde, permiabilized with 0.1% TritonX 100, and stained with propidium iodide to look at total cell number. The plates were scaned using the TTP labtech Acumen Explorer. Cell number was plotted relative to cells transfected with a negative control miRNA inhibitor (FIG. 7). The red horizontal bars bracket normal variation in cell proliferation (20% variation). Insets: Specific miRNA inhibitors that either increased cell proliferation (left arrow) or did not affect cell proliferation (right arrow) were used in a second round of screening. HeLa cells were transfected with these miRNA inhibitors and cells were fixed and stained with anti b-actin antibody and DAPI to visualize cell morphology changes in response to specific miRNA function. Cells transfected with the miRNA inhibitor that increased cell proliferation show marked alteration in cell morphology (left inset) vs. normal morphology (right inset).

A group of nine miRNA inhibitors were identified that caused significant decreases (miR 31, 150, 187, 125a, 190, 191, 193, 204 and 218) in cell growth and two miRNA inhibitors that caused a significant increase (miR 24 and miR 21) in cell growth following transfection into HeLa cells (Table 4). MiRNA-31 inhibition also caused a distinct cellular morphology. A relative cut off of 20% above and below 100% was chosen as genes that were considered significantly changed. These results demonstrate the ability of individual human miRNAs to regulate important cellular processes. Furthermore, the diversity of the observed effects demonstrates the potential complexity of cellular outcomes of miRNA-mediated regulation of gene expression.

TABLE 4

MiRNAs that affect cell proliferation

| miRNA | Relative Impact on Cell Proliferation |
|---|---|
| miR-31 | Up regulation |
| miR-150 | Up regulation |
| miR-187 | Up regulation |
| miR-125a | Up regulation |
| miR-190 | Up regulation |
| miR-191 | Up regulation |
| miR-193 | Up regulation |
| miR-204 | Up regulation |
| miR218 | Up regulation |
| miR-21 | Down regulation |
| miR-24 | Down regulation |

Example 8

Synthetic miRNA Library Screen for miRNAs that Influence Apoptosis

Many diseases including cancer are characterized by an inability to institute programmed cell death, or apoptosis. A caspase 3/7 activity assay was used in conjunction with a library of synthetic miRNAs to identify miRNAs that are involved in regulating apoptosis.

A library of eighteen synthetic miRNAs was used to transfect A549 cells (8000 cells/well of 96 well plate) in triplicate using siPORT™ NeoFX™ (Ambion). Media was changed after 24 hrs and cells were visually inspected under a microscope to qualitatively inspect cell death 72 hours after transfection. The cells were measured for apoptosis by measuring caspase 3 activity as follows: 1) Cells were washed once with PBS and frozen at −80° C. 2) Cells were lysed by adding 40 μl of cold lysis buffer (50 mM HEPES pH 7.2, 40 mM NaCl, 0.5% NP40, 0.5 mM EDTA) to the wells and incubated for 20 min at 4° C. 3) Add 160 μl ICE buffer (50 mM HEPES pH 7.4, 0.1% CHAPS, 0.1 mM EDTA, 10% sucrose)+5 mM DTT containing 20 μM DEVDafc substrate. 4) Measure fluorescence increase in one hour at 400 ex, 505 em.

Cells transfected with miR-1-2 and miR-33 synthetic miRNAs exhibited reduced caspase 3/7 activity and cells transfected with miR-20 exhibited much higher levels of apoptosis. These three miRNAs likely regulate genes that are involved in controlling apoptosis.

Example 9

Screen for miRNAs that Influence Cell Viability miRNA inhibitors were also used to identify miRNAs that influence cell viability. A library of over 90 miRNA inhibitors was used to transfect A549 cells (8000 cells/well of 96 well plate) in triplicate using siPORT™ NeoFX™ (Ambion). Media was changed after 24 hrs and cells were visually inspected under a microscope to qualitatively inspect cell death 72 hours after transfection. Cells were trypsinized and stained with ViaCount Flex Reagent, which distinguishes between viable and non-viable cells based on permeability of the DNA binding dyes in the reagent. Cells were analyzed using the Guava PCA-96 (Personal Cell Analysis).

Twenty-one miRNA inhibitors induced a significantly different ratio of live to dead cells than did the negative control miRNA inhibitor (FIG. 8). Twelve reduced cell viability and nine increased cell viability (Table 5). Interestingly, there was littleoverlap in the miRNAs that affected cell viability in A549 cells and those that affected cell proliferation in HeLa cells, suggesting that different cells respond differently to have reduced miRNA activities or cell viability and cell proliferation are not affected by the same cellular pathways.

TABLE 5

MiRNAs that affect cell viability

| miRNA | Relative Impact on Cell Viability |
|---|---|
| miR-7 | Down |
| miR-19a | Down |

TABLE 5-continued

MiRNAs that affect cell viability

| miRNA | Relative Impact on Cell Viability |
|---|---|
| miR-23 | Down |
| miR-24 | Down |
| miR-27a | Down |
| miR-31 | Down |
| miR-32 | Down |
| miR-134 | Down |
| miR-140 | Down |
| miR-150 | Down |
| miR-192 | Down |
| miR-193 | Down |
| miR-107 | Up |
| miR-133 | Up |
| miR-137 | Up |
| miR-152 | Up |
| miR-155 | Up |
| miR-181a | Up |
| miR-191 | Up |
| miR-203 | Up |
| miR-215 | Up |

TABLE 6

MiRNAs that affect apoptosis

| miRNA | Relative Impact on Cell Proliferation |
|---|---|
| miR-31 | Down |
| miR-214 | Down |
| miR-7 | Up |
| miR-1-2 | Up |
| miR-148 | Up |
| miR-195 | Up |
| miR-196 | Up |
| miR-199a | Up |
| miR-204 | Up |
| miR-210 | Up |
| miR-211 | Up |
| miR-212 | Up |
| miR-215 | Up |
| miR-216 | Up |
| miR-218 | Up |
| miR-296 | Up |
| miR-321 | Up |

Example 10

Screen for miRNAs that Influence Apoptosis

Apoptosis is a natural cellular process that helps control cancer by inducing death in cells with oncogenic potential. Many oncogenes function by altering induction of apoptosis. To identify miRNAs that participate in apoptosis, an apoptosis assay was used with the miRNA inhibitor library.

Using a library of over 90 miRNA inhibitors, we screened for miRNAs that affect apoptosis. HeLa cells (8000 cells/well of 96 well plate) were transfected in triplicate with miRNA inhibitors (5 pmoles) using Ambion siPORT™ NeoFX™. The media was changed 24 hrs after transfection and processed cells 72 hours after transfection. The cells were measured for apoptosis by measuring caspase 3 activity as follows: 1) Cells were washed once with PBS and frozen at −80° C. 2) Cells were lysed by adding 40 µl of cold lysis buffer (50 mM HEPES pH 7.2, 40 mM NaCl, 0.5% NP40, 0.5 mM EDTA) to the wells and incubated for 20 min at 4° C. 3) Add 160 µl ICE buffer (50 mM HEPES pH 7.4, 0.1% CHAPS, 0.1 mM EDTA, 10% sucrose)+5 mM DTT containing 20 µM DEVDafc substrate. 4) Measure fluorescence increase in one hour at 400 ex, 505 em.

Samples were also analyzed for cell number using a general esterase assay to normalize the caspase 3 results. FDA substrate (0.4 mg/ml fluorescein diacetate (FDA) in acetonitrile) was diluted 1:19 into dilution buffer (40 mM TrisCl pH 7.5, 20 mM NaCl, 0.5% NP-40, 0.02 mg/ml final conc). 40 µl buffer (40 mM TrisCl pH 7.5, 0.5% NP-40) was added to each sample well. Samples were incubated 10 min on ice. 160 µl of diluted FDA substrate was added to each well. Fluorescence was measured for 30 min at 37° C. (ex=488, em=529). The slope of fluorescence increase over time is a function of the cell number in the plate.

Normalized screening data are displayed in FIG. 9. miR-NAs that affect apoptosis are listed in Table 5 and 6.

Example 11

Expression Analyses Using Synthetic RNAs

In addition to using phenotypic assays to identify miR-NAs that influence gross cellular processes or cellular pathways, collections of synthetic miRNAs and/or miRNA inhibitors can be used to identify miRNAs that directly regulate the expression of a gene. A plasmid was created that had a luciferase gene immediately upstream of the 3'UTR of the G6PD gene. A549 cells were co-transfected with the reporter vector and eighteen different synthetic miRNAs. 24 hours post-transfection, luciferase activity in the various cell populations was measured. Interestingly, the miR-1-2 significantly reduced the expression of the luciferase/G6PD gene, indicating that this family of miRNAs regulates the expression of the G6PD gene. Similar experiments can be used to identify miRNAs that regulate the expression of such important genes as p53, BRCA1 and BRCA2, RAS, MYC, BCL-2, and others.

Example 12

Oncogeneic miRNAs—Differential Expression and Cancer Regulation

As noted in previous examples, a number of miRNAs have been identified that are differentially expressed between tumor and normal adjacent tissue samples from the same cancer patients. Interestingly, there is significant overlap in the miRNAs that are differentially expressed between different cancers, suggesting there is a core set of miRNAs that influence cellular processes that when altered, lead to cancer. The following describes experiments aimed at developing a link between miRNA mis-regulation and cancer.

miRNA Expression in Lung Cancer

Twenty-two tumor and normal adjacent tissue (NAT) samples from lung cancer patients were analyzed using the miRNA array system described above. The arrays were analyzed and the relative expression of each miRNA was compared between the tumor and normal adjacent tissues from each patient. The various miRNAs were clustered based on their relative expression in tumors across different patients (FIG. 14). Six miRNAs (miR-126, 30a, 143, 145, 188, and 331) were expressed at significantly lower levels in the tumors of more than 70% of the patients. Two miRNAs (miR-21 and 200b) were expressed at significantly higher levels in the tumors of more than 70% of the patients. The differential expression of a number of these miRNAs was verified by Northern analysis (FIG. 15).

miRNA Expression in Colon Cancer

Twenty-five tumor and NAT samples from colon cancer patients were analyzed using our miRNA array process. Like the lung cancer comparisons, the various miRNAs were clustered based on their relative expression in tumors across the different colon cancer patients (FIG. 14). Five miRNAs (miR-143, 145, 195, 130a, and miR-331) were expressed at significantly lower levels in the tumors of more than 70% of the patients. Five miRNAs (miR-223, 21, 31, 17, and 106) were expressed at significantly higher levels in the tumors of more than 70% of the patients.

miRNAs as Cancer Markers

It is interesting that eight different miRNAs were differentially expressed between the tumor and normal adjacent samples for most of the lung and colon patient samples that we analyzed (FIG. 16). These same miRNAs were also found to be differentially expressed in the breast, thymus, bladder, pancreatic, and prostate cancer patients that we analyzed, suggesting that these miRNAs might control cellular processes that when altered lead to cancer.

miRNAs as Regulators of Oncogene Expression

To address whether specific miRNAs might be participating in cancer through the mis-regulation of oncogenes, we scanned the 3' untranslated regions (UTRs) of 150 well-known oncogenes for sequences with significant homology to the miRNAs identified in our microarray analysis. Potential target sites were selected based on two criteria:

(1) Perfect complementarity between positions 2-9 of the miRNA and the oncogene. This miRNA core sequence has been identified as critical to the activities of miR-NAs and the known miRNA target sites have essentially 100% complementarity at this site (Doench et al. 2004).

(2) Overall $T_m$ of the miRNA/mRNA interaction. In addition to the core sequence, overall binding stability between miRNAs and mRNAs has been shown to be an important indicator of miRNA activity (Doench et al., 2004).

As seen in Table 8, potential target sites in the 3'UTRs of known oncogenes were identified for all of the miRNAs that were observed to be routinely differentially expressed in tumor samples. Interestingly, KRAS2, MYCL1, and CBL have multiple predicted miRNA binding sites which could provide the cooperative miRNA binding that has been implicated as an important factor in miRNA regulation (Doench et al. 2003); Zeng et al., 2003). Many of the genes listed in Table 8 become oncogenic when they are over-expressed, thus it is conceivable that reduced expression of a miRNA could lead to up-regulation of one or more oncogenes and subsequently lead to oncogenesis.

TABLE 7

Cancer-related miRNAs and their putative oncogene targets

| miRNA | Predicted Gene Target |
|---|---|
| let-7 | RAS |
| let-7 | C-MYC |
| miR-21 | mutS homolog 2 (MSH2) |
| miR-21 | v-ski sarcoma viral oncogene homolog (avian) (SKI) |
| miR-143 | breakpoint cluster region (BCR) |
| miR-143 | MCF.2 cell line derived transforming sequence (MCF2) |

TABLE 7-continued

Cancer-related miRNAs and their putative oncogene targets

| miRNA | Predicted Gene Target |
|---|---|
| miR-143 | von Hippel-Lindau tumor suppressor (VHL) |
| miR-143 | v-Ki-ras2 Kirsten rat sarcoma 2 viral oncogene homolog (KRAS2) |
| miR-143 | v-Ki-ras2 Kirsten rat sarcoma 2 viral oncogene homolog (KRAS2) |
| miR-143 | Cas-Br-M (murine) ecotropic retroviral transforming sequence (CBL) |
| miR-143 | Cas-Br-M (murine) ecotropic retroviral transforming sequence (CBL) |
| miR-145 | v-myc myelocytomatosis viral related oncogene (MYCN) |
| miR-145 | fibroblast growth factor receptor 2 (FGFR2) |
| miR-145 | Cas-Br-M (murine) ecotropic retroviral transforming sequence (CBL) |
| miR-188 | v-myc myelocytomatosis viral oncogene homolog 1 (MYCL1) |
| miR-200b | cadherin 13 (CDH13) |
| miR-200b | v-kit Hardy-Zuckerman 4 feline sarcoma viral oncogene homolog (KIT) |
| miR-219 | v-myc myelocytomatosis viral oncogene homolog 1 (MYCL1) |
| miR-219 | B-cell CLL/lymphoma 2 (BCL2) |
| miR-219 | cadherin 1, type 1, E-cadherin (epithelial) (CDH1) |
| miR-331 | vav 1 oncogene (VAV1) |
| miR-331 | fibroblast growth factor receptor 1 (FGFR1) |
| miR-331 | BCL2-antagonist/killer 1 (BAK1) |
| miR-331 | retinoic acid receptor, alpha (RARA) |
| miR-331 | v-src sarcoma (Schmidt-Ruppin A-2) viral oncogene homolog (SRC) |

Example 13

Measuring the Effect of miRNAs on Oncogene Expression

Confirming miRNA target site predictions can be done in a variety of ways. In Drosophila and C. elegans, genetic approaches have been applied wherein mutations in the miRNA and the putative miRNA target site(s) are made and shown to result in similar phenotypes (Ha et al., 1996; Vella et al., 2004). In mammalian cells, where genetic approaches are far more difficult, reporter constructs have been used to show that the 3' UTRs of putative target genes are regulated in cells at levels that are disproportionate to reporter vector controls that contain mutations in the putative miRNA binding sites (Lewis et al. 2003). In addition, vectors and oligonucleotides have been used to introduce or inhibit miRNAs in cells to determine the effects on endogenous levels of putative target genes (Lewis et al., 2003; Kiriakidou et al. 2004). The latter approach has been undertaken to validate the miRNA target site predictions.

Synthetic miRNAs and miRNA inhibitors have been developed that can be transfected into mammalian cells to either introduce miRNAs into cells or inhibit the activity of miRNAs in cells, respectively. See U.S. No. 60/627,171, which is hereby incorporated by reference. A synthetic miRNA and a miRNA inhibitor corresponding to let-7b were used to determine if the target site predictions were correct. In these experiments, cultured cells that express undetectable levels of the miRNA were transfected with the synthetic miRNA using siPORT™ NeoFX Transfection Agent (Ambion). Immunofluorescence assays were used to RAS and C-MYC in the transfected cells. The proteins from both oncogenes were expressed at almost three-fold lower levels in cells transfected with the synthetic miRNA than cells transfected with a Negative Control miRNA (Ambion). In a reciprocal experiment, cells that naturally express high levels of the miRNA were transfected with the let-7 miRNA inhibitor. As expected, the proteins from both oncogenes were higher in cells transfected with the miRNA inhibitor than in cells transfected with the Negative Control inhibitor (Ambion). These results are consistent with the model that the miRNA regulates the expression of the two oncogenes. These data suggest that mis-regulation of a key miRNA could participate in cancer progression by failing to regulate the expression of one or more oncogenes.

Example 14 miRNAs in Lupus

Systemic lupus erythematosus (SLE; Lupus) is a chronic inflammatory auto-immune disease that ultimately leads to immune complex-mediated end-organ failure. It is characterized by an over activation of CD4+ T helper cells and repression of CD8+ T cytotoxic activity, leading to an overproduction of natural antibodies and pathogenic autoantibodies. Recently several histone modifications were reported in peripheral blood mononuclear cells (PBMCs) isolated from lupus patients. Diagnosis of lupus is still frequently incorrect mainly because the symptoms vary so widely and they come and go frequently, and because the disease mimics so many other disorders. Furthermore, diagnosis does not indicate the particular therapy to be used. In the absence of a cure, present-day treatment of lupus is still primarily tailored to symptomatic relief and not to the diagnosis. A diagnostic assay with high specificity and sensitivity would be very important.

Samples were analyzed from 16 individuals, 8 with clinically verified lupus and 8 non-lupus patients that were age- and gender-matched with the lupus patients. Total RNA from these samples was isolated using the glass fiber filter method described above. The total RNA was fractionated by tube electrophoresis to recover the miRNAs. The miRNAs were fluorescently labeled with Cy3 or Cy5 using the two-step fluorescent labeling process described above. The labeled miRNAs were hybridized to miRNA probes arrayed on glass slides as described above. The signal from the hybridized miRNAs was quantified using a GenePix 4000B Scanner (Axon) and the lupus and normal sample signals were compared to identify differentially expressed miRNAs. Each array experiment included duplicate arrays.

Fourteen miRNAs were differentially expressed in all of the lupus samples relative to the matched samples. miR-301, miR-199, miR-95, miR-105, mu-miR-290, miR-215, miR-188, miR-186, miR-211, miR-331, and miR-137 were expressed at 50% or less in the lupus samples than the corresponding normal samples. miR-21, miR-223, and miR-342 were expressed at 50% or greater in the lupus samples than the corresponding normal samples. Several of the miRNAs were differentially expressed by as much as tenfold between the lupus and normal samples. These miRNAs represent targets for diagnostic assay of therapeutic development.

Example 15 miRNAs and Prion Diseases

Novel infectious particles, termed prions, composed largely and perhaps solely of a single protein, are the likely causative agents of a group of transmissible spongiform encephalopathies that produce lethal decline of cognitive and motor function. Evidence indicates that the responsible protein arrives at a pathogenic state by misfolding from a normal form that has ubiquitous tissue distribution.

Using two cell-based prion model systems, the identification of miRNAs that might be associated with the process was pursued. One model system comprises two cell lines, one of which is susceptible to prion formation and one that is not. The second model system involves cells before and after they have been infected with prions. Total RNA from prion-sensitive cells, prion-insensitive cells, and prion-infected cells was isolated using the glass fiber filter method described above. The total RNA was fractionated by tube electrophoresis to recover the miRNAs. The miRNAs were fluorescently labeled with Cy3 or Cy5 using the two-step fluorescent labeling process described above. The labeled miRNAs were hybridized to miRNA probes arrayed on glass slides as described above. The signal from the hybridized miRNAs was quantified using a GenePix 4000B Scanner (Axon) and the signal from each of the samples was compared to identify differentially expressed miRNAs.

As seen in FIG. 13, ten miRNAs were significantly up- or down-regulated in both prion-sensitive and prion-infected cells relative to prion resistant, uninfected cells. Arrays on multiple biological replicates for both model systems have confirmed these results. Based on their expression profiles, miR-95, 135a, 7, 9, 27a, 130a, 16, 26a, and 24 likely are involved directly or indirectly in prion infection and might represent diagnostic or therapeutic targets for prion disease.

Example 16

Stroke-Associated miRNAs

Stroke is a major cause of death and permanent disability in humans. They occur when blood flow to a region of the brain is obstructed and may result in death of brain tissue. There are two main types of stroke: ischemic and hemorrhagic. Ischemic stroke is caused by blockage in an artery that supplies blood to the brain, resulting in a deficiency in blood flow (ischemia). Hemorrhagic stroke is caused by the bleeding of ruptured blood vessels (hemorrhage) in the brain. Understanding miRNAs involved in stroke might enhance detection and/or treatment.

A stroke model system was used wherein mice are "preconditioned" by reducing oxygen flow to the brain (Kitagawa 1991). An equivalent set of six mice were used; three were preconditioned and three were untreated. 24 hours after pre-conditioning, the mice were sacrificed. Total RNA from these samples was isolated using the glass fiber filter method described above. The total RNA was fractionated by tube electrophoresis to recover the miRNAs. The miRNAs were fluorescently labeled with Cy3 or Cy5 using the two-step fluorescent labeling process described above. The labeled miRNAs were hybridized to miRNA probes arrayed on glass slides as described above. The signal from the hybridized miRNAs was quantified using a GenePix 4000B Scanner (Axon) and the preconditioned and normal sample signals were compared to identify differentially expressed miRNAs.

Analysis of the miRNA profiles of the preconditioned animals (labeled P1, P2, and P4) revealed 10 miRNAs that were expressed at significantly different levels in all three pre-conditioned animals relative to the three non-treated animals (FIG. 14). These miRNAs resulted from ischemic pre-conditioning and represent potential targets for stroke diagnosis, prevention, or treatment.

Example 17

Synthetic miRNA Library Screens for miRNAs that Influence Cell Proliferation and Cell Viability in Various Cell Types A hallmark of cancer is uncontrolled cell proliferation; cell proliferation assays are commonly used by researchers to study the influence of genes in oncogenesis. A cell proliferation assay was used in conjunction with the miRNA inhibitor library to identify miRNAs that influence cell proliferation.

HeLa (human ovarian cancer) and A549 (human lung cancer) cells were transfected in triplicate with 150 synthetic miRNAs using siPORT NeoFX (Ambion) according to the manufacturer's instructions. The 150 are as follows: Let-7a, Let-7b, Let-7c, Let-7d, Let-7g, mir-1, mir-7, mir-9, mir-10a, mir-10b, mir-15a, mir-16, mir-18, mir-19a, mir-17-3p, mir-20, mir-21, mir-22, mir-23a, mir-23b, mir-24, mir-25, mir-26a, mir-27a, mir-28, mir-29a, mir-31, mir-32, mir-30a-3p, mir-34a, mir-92, mir-95, mir-96, mir-98, mir-99a, mir-100, mir-101, mir-103, mir-105, mir-107, mir-108, mir-122, mir-124, mir-125a, mir-125b, mir-126, mir-128, mir-129, mir-132, mir-133A, mir-133B, mir-134, mir-135, mir-136, mir-137, mir-139, mir-140, mir-141, mir-142, mir-143, mir-144, mir-145, mir-146, mir-147, mir-148, mir-149, mir-150, mir-151, mir-152, mir-153, mir-155, mir-181a, mir-182, mir-183, mir-184, mir-186, mir-187, mir-188, mir-190, mir-191, mir-192, mir-193, mir-194, mir-195, mir-196, mir-197, mir-198, mir-199, mir-201, mir-203, mir-204, mir-205, mir-206, mir-207, mir-208, mir-210, mir-211, mir-212, mir-214, mir-215, mir-216, mir-217, mir-218, mir-219, mir-220, mir-221, mir-223, mir-224, mir-299, mir-301, mir-302, mir-320, mir-322, mir-323, mir-325, mir-324-3p, mir-328, mir-330, mir-331, mir-335, mir-337, mir-338, mir-339, mir-340, mir-345, mir-346, mir-367, mir-368, mir-369, mir-370, mir-371, mir-372, mir-373, mir-374, mu-mir-290, mu-mir-291, mu-mir-292-3p, mu-mir-293, mu-mir-294, mu-mir-295, mu-mir-297, mu-mir-298, mu-mir-329, mu-mir-341, mu-mir-344, mu-mir-351, mu-mir-376b, mu-mir-380-3p, mu-mir-409, mu-mir-411, mu-mir-412

The synthetic miRNAs were double stranded nucleic acid molecules composed of an active strand and a complementary strand. The active strand contained a sequence that was identical to the corresponding mature miRNA. The complementary strand contained a sequence that was 100% complementary to the relevant region of the mature miRNA sequence, but 1) lacking two nucleotides on its 3' end that were complementary to the mature miRNA sequence (at the 5' end of the active strand) and 2) having a dinucleotide overhang on its 5' end with respect to the active strand. In other words, the two strands were fully complementary to the other's sequence except that each strand has a dinucleotide 5' overhang with respect to the other strand. The same kind of synthetic miRNAs were used for Examples 18-21 as well. Any exceptions are described below. The miRNAs indicated in the tables identify the miRNA that corresponds to the provided synthetic sequence.

Jurkat cells (human leukemia cell) and primary human T-cells in triplicate were electroporated with the same set of synthetic miRNAs using siPorter-96 (Ambion) according to the manufacturer's instruction. All cells were analyzed for viable and non-viable cells 72 hours post-transfection using the PCA-96 (Guava) with the Viacount Assay. Viable cell number is the number of live cells in a well at the point of the assay. The numbers provided in the tables below are equal to the average number of viable cells in wells transfected with a particular miRNA divided by the number of viable cells in wells transfected with negative control synthetic miRNAs multiplied by 100 to yield the % Cell Viability of miRNA-transfected cells relative to negative control transfected cells.

Significance was assigned based on the average values of the negative control transfecetd samples. miRNAs that were significantly different than the negative controls were qualified as "significant" based on being at least two standard deviations above or below the negative control data.

The sequence of miRNA-325 is 5'-ccuaguaggugucca-guaagugu-3'(SEQ ID NO:807).

TABLE 8 miRNAs That Significantly Reduce Cell Viability of HeLa Cells

|  | % Viability | std dev |
|---|---|---|
| mir-345 | 75 | 5.9 |
| mir-346 | 77.8 | 8.2 |
| mir-193 | 79.6 | 14.7 |
| mir-206 | 79.6 | 6.5 |
| mir-337 | 80.8 | 3.1 |
| mmu-mir-293 | 82.6 | 1.7 |
| mir-299 | 84.0 | 4.0 |
| mmu-mir-329 | 84.5 | 4.5 |
| mmu-mir-409 | 86 | 2.8 |
| mmu-mir-292-3p | 86.2 | 2.8 |
| mir-210 | 86.4 | 5.1 |
| mmu-mir-344 | 86.4 | 5.3 |
| mmu-mir-298 | 86.7 | 4.2 |
| mir-208 | 87.4 | 4.5 |
| mir-197 | 87.6 | 7.5 |
| mir-217 | 87.9 | 3.5 |
| mir-1 | 88.2 | 9.0 |
| mir-124 | 88.8 | 4.2 |

TABLE 9 miRNAs That Significantly Reduce Viable Cell Number of HeLa Cells

|  | Total Cell | std dev |
|---|---|---|
| Let-7b | 16.2 | 8.1 |
| Let-7g | 22.7 | 8.2 |
| Let-7c | 24.1 | 7.2 |
| mir-124 | 24.5 | 3.4 |
| Let-7a | 25.4 | 1.2 |
| Let-7d | 37.3 | 2.3 |
| mir-337 | 37.5 | 16.9 |
| mir-1 | 38.7 | 2.2 |
| miR-299 | 38.9 | 4.2 |
| mir-34a | 40.5 | 13.3 |
| mmu-mir-292 | 41.2 | 8.3 |
| mir-122 | 41.2 | 6.5 |
| mir-346 | 41.9 | 4.3 |
| mir-101 | 43.4 | 6.4 |
| mir-210 | 47.1 | 8.4 |
| mir-147 | 47.7 | 8.2 |
| mir-98 | 50.6 | 2.6 |
| mir-345 | 51.8 | 6.8 |
| miR-92 | 52.4 | 6.8 |
| miR-96 | 53.2 | 0.9 |
| mir-7 | 54.0 | 5.3 |
| mir-133b | 55.9 | 3.1 |
| mir-206 | 56.0 | 12.4 |
| mmu-mir-297 | 56.0 | 5.7 |
| mir-19a | 57.2 | 20.6 |
| mmu-mir-344 | 57.5 | 14.1 |
| mir-205 | 58.9 | 18.7 |
| mir-208 | 60.5 | 11.1 |

TABLE 10 miRNAs That Significantly Increase Viable Cell Number of HeLa Cells

| | Total Cell | Std dev |
|---|---|---|
| mir-32 | 142.9 | 25.4 |
| mu-miR-290 | 143.5 | 17.6 |
| mir-212 | 143.5 | 10.4 |
| mir-92 | 144.7 | 16.8 |
| mir-323 | 147.3 | 25.9 |
| mir-145 | 148.1 | 22.2 |
| mir-324 | 148.2 | 9.0 |
| mir-198 | 152.1 | 67.8 |
| mir-27a | 156.2 | 13.4 |
| mir-369 | 158.4 | 27.3 |
| mir-31 | 159.3 | 16.1 |
| mir-335 | 161.7 | 20.8 |
| mmu-mir-351 | 162.3 | 6.9 |
| mir-370 | 164.3 | 4.5 |
| mir-325 | 169.6 | 19.8 |
| mir-331 | 172.5 | 24.0 |
| mir-139 | 181.3 | 11.2 |

TABLE 11 miRNAs That Significantly Reduce Cell Viability of A549 Cells

| | % Viability | St dev |
|---|---|---|
| mir-193 | 92.4 | 2.5 |
| mir-224 | 92.5 | 1.4 |
| mir-96 | 92.6 | 0.1 |
| mir-346 | 93.9 | 1.6 |
| mmu-mir-293 | 94.9 | 0.7 |
| mir-34a | 95 | 0.2 |
| mir-216 | 95.1 | 1.0 |
| mmu-mir-380 | 95.2 | 0.8 |
| mir-182 | 95.6 | 0.8 |
| mir-301 | 95.6 | 1.0 |
| mmu-mir-344 | 95.8 | 0.2 |
| mmu-mir-409 | 95.8 | 0.6 |
| mir-369 | 95.9 | 0.7 |

TABLE 12 miRNAs That Significantly Reduce Viable Cell Number in A549 Cells

| | Cell Number | St Dev |
|---|---|---|
| mir-124 | 44.3 | 2.2 |
| mir-16 | 52.9 | 1.3 |
| mir-337 | 54.7 | 7.0 |
| mir-195 | 59.3 | 6.7 |
| mir-34a | 60.8 | 2.1 |
| mir-15a | 60.9 | 3.7 |
| mir-28 | 61.3 | 0.8 |
| Let-7g | 61.9 | 0.8 |
| mmu-mir-292 | 62.2 | 2.3 |
| mmu-mir-344 | 62.6 | 9.1 |
| mir-7 | 62.9 | 4.6 |
| mir-193 | 63.7 | 3.3 |
| mir-137 | 63.9 | 1.3 |
| mir-147 | 64.8 | 0.5 |
| mir-29a | 67.0 | 3.8 |
| mir-129 | 67.2 | 3.3 |
| mir-22 | 67.5 | 3.4 |
| mir-126 | 68.0 | 2.6 |
| mir-345 | 69.2 | 7.4 |
| mir-192 | 69.5 | 5.9 |
| Let-7b | 70.2 | 2.2 |
| Let-7d | 70.5 | 2.7 |
| mir-346 | 70.9 | 7.1 |

TABLE 13 miRNAs That Significantly Increase Viable Cell Number in A549

| | Total cell | Std dev |
|---|---|---|
| mir-373 | 110.4 | 7.9 |
| mir-25 | 111.8 | 6.0 |
| mmu-mir-294 | 112.1 | 5.9 |
| mir-32 | 120.8 | 4.3 |
| mir-92 | 122.4 | 4.0 |

TABLE 14 miRNAs That Significantly Reduce Cell Viability of Jurkats Cells

| | % Viability | St Dev |
|---|---|---|
| let-7a | 20.54 | 0.70 |
| miR-10b | 35.98 | 2.92 |
| let-7b | 48.79 | 5.08 |
| miR-17-3p | 61.55 | 15.63 |
| miR-30a-3p | 64.36 | 26.60 |
| miR-34a | 65.45 | 20.44 |
| miR-122 | 65.63 | 17.80 |
| miR-29a | 66.44 | 7.14 |
| miR-101 | 67.44 | 29.56 |
| miR-133a | 71.51 | 17.82 |
| miR-19a | 71.77 | 23.79 |
| miR-32 | 75.59 | 11.69 |
| miR-1 | 75.74 | 12.92 |
| miR-132 | 76.32 | 16.22 |
| miR-28 | 77.07 | 16.58 |
| miR-20 | 77.60 | 15.23 |
| miR-134 | 78.96 | 1.75 |

TABLE 15 miRNAs That Significantly Increase Cell Viability in Jurkat Cells

| | Total cell | Std dev |
|---|---|---|
| miR-181-a | 122.77 | 22.40 |
| miR-9 | 124.63 | 9.98 |
| miR-141 | 126.08 | 24.03 |
| miR-98 | 126.24 | 11.90 |
| miR-10a | 126.86 | 8.93 |
| miR-125b | 128.71 | 3.50 |
| miR-126 | 130.69 | 18.20 |
| miR-100 | 130.77 | 14.60 |
| miR-23b | 132.18 | 3.50 |
| miR-140 | 135.73 | 4.08 |
| miR-155 | 142.57 | 22.40 |
| miR-15a | 143.01 | 11.29 |
| miR-129 | 146.94 | 9.92 |
| miR-25 | 150.25 | 17.85 |
| miR-143 | 158.74 | 1.86 |
| miR-26a | 166.09 | 13.65 |

TABLE 16 miRNAs that Significantly Reduce Cell Viability in Primary T-Cells

| | % Viability | St Dev |
|---|---|---|
| miR-184 | 61.04 | 12.16 |
| miR-145 | 68.98 | 11.23 |
| miR-186 | 69.64 | 6.99 |
| miR-139 | 69.85 | 0.29 |
| miR-134 | 71.90 | 22.42 |
| miR-190 | 75.59 | 2.43 |
| miR-144 | 77.13 | 4.18 |
| miR-183 | 77.71 | 2.86 |
| miR-147 | 78.09 | 0.33 |

TABLE 16-continued miRNAs that Significantly Reduce
Cell Viability in Primary T-Cells

|         | % Viability | St Dev |
|---------|-------------|--------|
| miR-140 | 78.70       | 5.81   |
| miR-155 | 79.26       | 10.68  |

TABLE 17 miRNAs that Significantly Increase
Cell Viability of Primary T-Cells

|          | % Viability | St Dev |
|----------|-------------|--------|
| miR-126  | 120.81      | 40.08  |
| miR-10b  | 121.28      | 18.86  |
| miR-17   | 122.46      | 3.71   |
| miR-10a  | 124.11      | 9.46   |
| miR-20   | 124.75      | 13.60  |
| let-7c   | 124.81      | 4.00   |
| miR-125a | 125.66      | 5.13   |
| miR-15a  | 129.07      | 10.96  |
| let-7b   | 130.11      | 13.48  |
| let-7a   | 130.88      | 16.16  |
| miR-18   | 131.73      | 1.75   |

It is interesting to note that the miRNAs that affect one cell type often fail to affect other cell types. This is likely due to the fact that the cellular processes that are active vary between different cell types. This can be vitally important when considering the potential of miRNA-based therapeutics. Abnormal (disease) cells are different from normal cells owing to the fact that different cellular processes are active in the two cell types. Identifying miRNAs that have differential effects on normal and abnormal cells would be ideal since they could be delivered globally and expected to have an effect on only disease cells. When the cell viability data were compared for the leukemia (cancerous T-cell) cells and primary T-cells, it was noted that let-7a, let-7b, and miR-10b all significantly reduce the percentage of viable cells in the leukemia cells while essentially having no effect on the corresponding normal T-cells. These miRNAs are candidates for leukemia drugs.

Example 18

Synthetic miRNA Library Screen for miRNAs that Influence ERK Activation

In order for cancer cells to proliferate they must subvert both the machinery that controls the cell division cycle and the process of programmed cell death (apoptosis). This is frequently achieved by mutation of specific proto-oncogenes such as Ras or tumor suppressors such as p53. The Ras-family of membrane associated GTPases transmit signals into the interior of the cell by the activation of a number of cytosolic signal transduction pathways such as the Raf>MEK>ERK MAP kinase signaling pathway. Disregulation of the Ras/Raf/MEK/ERK pathway plays a major role in cancer pathogenesis (Meijer).

To identify miRNAs that affect ERK activation, HeLa cells were transfected in a 96-well plate format with 150 different synthetic miRNAs. Prior to transfection, the HeLa cells were trypsinized to remove adherent cells and diluted in normal growth medium to $10^5$ cells/mL. 0.5 µl of siPort NeoFX in 9.5 µl of Optimem I medium was added to the cells and incubated for 10 minutes at room temp (10 µL for each sample). miRNAs were rehydrated with 10 µl of diluted siPORT NeoFX. The samples were incubated at 37° C. and then the transfected samples were evaluated 72 hours after transfection.

The controls for ERK activation were performed by depriving the wells of a phosphate source for detection of ERK phosphorylation. 100 µl of serum-free media (DMEM) to 37° C. was added per well and the cells were incubated for 4 hours at 37° C. to attain basal phosphorylation levels. For the positive control wells, serum-free media was aspirated from wells and 100 µL of 100 ng/mL EGF was added before incubating the cells for 7.5 minutes at 37° C.

Media from all wells was removed by aspiration and the cells were immediately fixed in 150 µL of 3.7% Formaldehyde in 1×PBS for 20 minutes at room temp with no shaking. Fixing solution was removed to an appropriate waste container. The fixed cells were washed three times with 1×PBS. The wells were then washed three times with 200 µL of 1×PBS containing 0.1% Triton X-100 for 5 minutes per wash, with shaking at room temp.

Cells were blocked by adding 150 µL of Li-COR Odyssey Blocking Buffer to each well. The solution was moved carefully by pipetting down the sides of the wells to avoid detaching the cells. Blocking was for 90 minutes at room temp with moderate shaking on a rotator and the two primary antibodies were added to a tube containing Odyssey Blocking Buffer. The primary antibody was incubated for 2 hours with gentle shaking at room temp (Phosho-ERK (Rabbit, 1:100 dilution; Cell Signaling Technology 9101). Total ERK2 (Mouse; 1:75 dilution; Santa Cruz Biotechnology SC-1647)). The wells were washed three times with 1×PBS+0.1% Tween-20 for 5 minutes at room temp with gentle shaking, using a generous amount of buffer. The fluorescently labeled secondary antibody was diluted in Odyssey Blocking Buffer (Goat anti-rabbit Alexa Fluor 680 (1:200 dilution; Molecular Probes) Goat anti-mouse IRDye 800CW (1:800 diution; Rockland Immunochemicals)). The antibody solutions were mixed well and 50 µL of the secondary antibody solution was added to each well. The antibody solution was incubated for 60 minutes with gentle shaking at room temp. The plate was washed three times with 1×PBS+0.1% Tween-20 for 5 minutes at room temp with gentle shaking, using a generous amount of buffer. After a final wash, wash solution was completely removed from wells. The plates were scanned with the Odyssey Infrared Imaging System (700 nm detection for Alexa Fluor 680 antibody and 800 nm detection for IRDye 800CW antibody). Negative control transfected cells yield 100% erk activation (meaning background levels of active erk). Transfecting cells with some of our miRNAs alters the level of active erk.

TABLE 18 miRNAs That Activate ERK

| miR         | % Activation | Std Dev |
|-------------|--------------|---------|
| mir-218     | 312.96       | 22.91   |
| mir-210     | 291.74       | 38.23   |
| mir-217     | 273.49       | 26.84   |
| mir-152     | 265.54       | 35.82   |
| mir-148     | 264.38       | 43.55   |
| mir-223     | 264.15       | 39.72   |
| mir-301     | 261.36       | 61.77   |
| mir-328     | 259.48       | 45.87   |
| mir-206     | 255.51       | 55.53   |
| mir-125a    | 252.46       | 27.34   |
| mmu-mir-329 | 243.38       | 5.43    |

TABLE 18-continued miRNAs That Activate ERK

| miR | % Activation | Std Dev |
|---|---|---|
| mir-19a | 241.52 | 31.33 |
| mir-25 | 238.90 | 44.94 |
| mmu-mir-294 | 235.51 | 24.60 |
| mir-212 | 231.36 | 23.61 |
| mmu-mir-295 | 221.47 | 14.05 |
| mir-370 | 220.60 | 22.88 |
| mir-216 | 219.17 | 25.98 |
| mir-96 | 213.93 | 57.07 |
| mir-339 | 213.9 | 42.25 |
| mir-134 | 211.15 | 12.84 |
| mir-372 | 211.13 | 5.67 |
| Positive Control | 245.36 | 10.76 |

Example 19

Screen for miRNAs that Influence Apoptosis

Apoptosis is a natural cellular process that helps control cancer by inducing death in cells with oncogenic potential. Many oncogenes function by altering induction of apoptosis. To identify miRNAs that participate in apoptosis, an apoptosis assay was used with the miRNA inhibitor library.

HeLa cells (8000 cells/well of 96 well plate) were transfected in triplicate with more than 150 synthetic miRNAs (described above) (3 pmoles) using Ambion siPORT™ NeoFX™. The media was changed 24 hrs after transfection and cells were processed 72 hrs after transfection. The cells were measured for apoptosis by measuring caspase 3 activity as follows: 1) Cells were washed once with PBS and frozen at −80° C. 2) Cells were lysed by adding 40 μl of cold lysis buffer (50 mM HEPES pH 7.2, 40 mM NaCl, 0.5% NP40, 0.5 mM EDTA) to the wells and incubated for 20 min at 4° C. 3) Add 160 ul ICE buffer (50 mM HEPES pH 7.4, 0.1% CHAPS, 0.1 mM EDTA, 10% sucrose)+5 mM DTT containing 20 uM DEVDafc substrate. 4) Measure fluorescence increase in one hour at 400 ex, 505 em.

Samples were also analyzed for cell number using a general esterase assay to normalize the caspase 3 results. FDA substrate (0.4 mg/ml fluorescein diacetate (FDA) in acetonitrile) was diluted 1:19 into dilution buffer (40 mM TrisCl pH 7.5, 20 mM NaCl, 0.5% NP-40, 0.02 mg/ml final conc). 40 μl buffer (40 mM TrisCl pH 7.5, 0.5% NP-40) was added to each sample well. Samples were incubated 10 min on ice. 160 ul of diluted FDA substrate was added to each well. Fluorescence was measured for 30 min at 37 deg (ex=488, em=529). The slope of fluorescence increase over time is a function of the cell number in the plate.

miRNAs that affect apoptosis are listed in the table below. These miRNAs apparently regulate pathways that lead to apoptosis. Mis-regulation of these miRNAs could induce cells to undergo apoptosis or might keep the cells from undergoing apoptosis. Introducing or inhibiting these miRNAs in cancer (or other disease) cells that have overcome apoptotic signaling pathways or Parkinson's (or other disease) cells that have prematurely induced apoptosis could be used to treat the diseases.

TABLE 19 miRNAs that Significantly Increase the Percentage of Apoptotic Cells

| | Relative change in apoptotic cells | St Dev |
|---|---|---|
| mir-338 | 773.46 | 69.82 |
| mir-27a | 607.24 | 150.08 |
| mir-128 | 594.42 | 260.06 |
| mir-23a | 473.44 | 208.82 |
| mir-324 | 442.99 | 101.03 |
| mir-22 | 439.13 | 62.59 |
| mir-181a | 409.97 | 65.14 |
| mmu-mir-293 | 403.86 | 53.41 |
| mmu-mir-412 | 402.27 | 42.04 |
| mir-196 | 378.13 | 28.15 |
| mir-31 | 373.90 | 61.39 |
| Let-7d | 369.10 | 88.94 |
| mir-23b | 360.68 | 81.97 |
| mu-miR-290 | 354.90 | 46.63 |
| mir-217 | 347.38 | 56.49 |
| mir-199 | 345.75 | 67.55 |
| mir-24 | 317.43 | 62.85 |
| mir-214 | 312.25 | 7.38 |
| mir-198 | 303.24 | 44.25 |

TABLE 20 miRNAs that Significantly Decrease the Percentage of Apoptotic Cells

| | Relative change in apoptotic cells | St Dev |
|---|---|---|
| mir-105 | 39.97 | 8.91 |
| mir-34a | 37.75 | 8.41 |
| mir-96 | 31.89 | 13.40 |
| mmu-mir-292 | 30.72 | 4.27 |
| mir-126 | 28.71 | 4.24 |
| mir-137 | 12.69 | 11.80 |
| mir-101 | 7.50 | 6.91 |

Example 20

Synthetic miRNA Library Screen for miRNAs that Influence hTert Expression

Telomerase is a complex of proteins and RNA that maintains the ends of chromosomes by appending telomeres. With rare exceptions, terminally differentiated cells lack active telomerase. One of the exceptions is cancer cells. More than 90% of human cancer samples have active telomerase (reviewed in Dong et al. 2005). The hTert gene encodes the catalytic domain of telomerase. The expression of hTert correlates with telomerase activity in cells making it a good surrogate for telomerase activity. An RT-PCR based assay for monitoring hTert mRNA expression in telomerase negative cells has been developed and used to identify miRNAs that participate in the regulation of telomerase. The miRNAs that regulate telomerase activity represent intervention points for cancer therapeutics.

BJ cells are normal human foreskin fibroblasts that lack hTert mRNA and telomerase activity. BJ cells were trypsinized and diluted to 13,000 cells/ml in normal growth media. 0.3 μl of lipofectamine 2000 agent was diluted into 40 μl of OPTI-MEM and incubated for five minutes. The diluted transfection reagent was added to the wells of 96-well plates that contained 150 synthetic miRNAs (as described above) as well as two different negative control synthetic miRNAs. Each well housed a different synthetic miRNA. The synthetic miRNAs and transfection agent were incubated for 15 minutes at room temperature and then 200 µl (2,600 cells) were added on top of the lipid/miRNA complex. Cells were placed in an incubator and RNA was isolated 72 hours later. RNA was isolated from the cells in each well using RNAqueous™-MagMAX96 Total RNA Isolation kit (Cat#1830) standard protocol (lyse cells in wells). Reverse transcription was done using the RETROscript reaction by adding 11 µl of total RNA (20-100 ng/µl) to 1 ul of random decamers and incubated in 70° C. water bath for 3 minutes then place on ice. Next, 8 ul of the cocktail containing Nuc-free water 3.8 µl, 10× Reverse Transcription buffer 2.0 ul, 2.5 mM dNTPs 2.0 ul, RNase Inhibitor Protein (40 U/ul), 0.1 ul MMLV-RT (100 U/µl), and incubated at 42° C. for 1 hour, then 92° C. for 10 minutes.

Real time PCR reactions were assembled to quantify hTert mRNA and 18S rRNA in each of the samples. Nuclease-free water, 10× Complete PCR buffer/SYBR, 25 mM MgCl2, 2.5 mM dNTPs, 50×ROX, 18S- or hTert-specific primers (for & rev mix 3 uM), cDNA from the various samples, and Super taq polymerase into a PCR tube. The reaction was heated to 95° C. for 5 minutes and then subjected to 40 cycles of 95° C. for 15 seconds, 60° C. for 30 seconds, 72° C. for 30 seconds. The amplification products were monitored using the ABI 7600 (Applied Biosystems). BJ cells ordinarily fail to yield amplification products with the hTert primers. Those miRNA-transfected samples that yielded a hTert PCR product were also analyzed for 18S rRNA lavels to ensure that there were not significantlyt more cells in the samples that might have contributed to the amount of hTert in the samples.

The hTert mRNA was detected in duplicate transfections of each of the miRNAs listed below. These miRNAs presumably affect pathways that regulate the expression of the hTert gene. Over-expression of any of these miRNAs might contribute to cancer by activating telomerase. Regulating the activities of these miRNAs in cancer cells could limit their transformation and overcome oncogenesis.

TABLE 21

| hTert Activators |
| --- |
| mmu-mir-295 |
| mir-92 |
| mir-337 |
| mir-26a |
| mir-224 |
| mir-21 |
| mir-195 |
| mir-16 |
| mir-15a |
| mir-128 |
| mir-125b |
| mir-125a |
| mir-105 |

Example 21

Synthetic miRNA Library Screens for miRNAs that Influence Cell Cycle

The adult human body consists of about 50-100 trillion cells. Each day, several billion of these cells divide in two to replace the billions of cells that die and are removed. In the course of an average lifetime, this adds up to an astronomical number of cell divisions, most of which go perfectly well. Errors do occur, however, and if they are not corrected they may lead to cancer. Cell growth and division are normally controlled by an intricate system of checks and balances. But occasionally a cell will start to proliferate wildly, dividing again and again and defying all normal restraints on its growth. That is the beginning of most common forms of cancer.

The inventors transfected 4,000 BJ cells/well in triplicate with 46 synthetic miRNAs using Lipofectamine 2000 (Invitrogen) according to the manufacturer's instructions.

TABLE 22

| 46 Synthetic miRNAs |
| --- |
| let7a |
| let7a |
| mir1 |
| mir1 |
| mir105 |
| mir125a |
| mir128 |
| mir142 |
| mir145 |
| mir146 |
| mir147 |
| mir150 |
| mir15a |
| mir16 |
| mir186 |
| mir187 |
| mir188 |
| mir191 |
| mir195 |
| mir20 |
| mir206 |
| mir21 |
| mir211 |
| mir223 |
| mir224 |
| mir26a |
| mir320 |
| mir324-3p |
| mir325 |
| mir335 |
| mir337 |
| mir338 |
| mir345 |
| mir371 |
| mir373 |
| mir92 |
| mmu201 |
| mmu207 |
| mmu290 |
| mmu291-3p |
| mmu294 |
| mmu295 |
| mmu297 |
| mmu322 |
| mmu376b |
| mmu409 |

The 24 hours post-transfection, half of the BJ cells from each well were removed to fresh medium. 72 hrs post-transfection, the cells were fixed with 4% paraformaldehyde at a final concentration of 2%. The fixed cells were stained with propidium iodide (TTP LabTech protocol) and assessed using the TTP LabTech cell scanner. Propidium iodide stains DNA and the relative DNA content in a cell corresponds with its position in the cell cycle. The cell scanner measured propidium iodide staining in each cell and assigned its position in the cell cycle. The percentage of cells in each stage of cell cycle was calculated and compared to cells transfected with negative control synthetic miRNAs. The relative change in cells in each stage was calculated for each miRNA that was used. Those synthetic miRNAs that induced a significant shift toward or away from a specific stage of cell cycle are listed below. These represent miRNAs that regulate key points in the cell cycle and offer key intervention points for cancer-related therapeutic development.

TABLE 23 miRNAs that significantly reduce the percentage of BJ cells in G1 phase of the cell cycle

| miRNA | % Diff in Cells in G1 | St. Dev. |
|---|---|---|
| mir-21 | 54.4 | 4.2 |
| mir-20 | 63.6 | 9.3 |
| mir-1 | 65.3 | 9.5 |
| mir-206 | 66.8 | 9.0 |
| mir-373 | 72.6 | 5.7 |
| mir-26a | 78.0 | 4.0 |

TABLE 24 miRNAs that significantly increase the percentage of BJ cells in G1 phase of the cell cycle

| miRNA | % Diff in Cells in G1 | St. Dev. |
|---|---|---|
| rno-mir-325 | 121.7 | 5.3 |
| mmu-409 | 123.2 | 13.7 |
| mir-324 | 123.7 | 4.9 |
| mir-195 | 125.1 | 2.5 |
| mmu-376b | 126.5 | 3.1 |
| mir-142 | 127.0 | 13.0 |
| mir-371 | 128.9 | 2.8 |
| let-7a | 131.5 | 4.5 |
| mir-146 | 141.5 | 7.7 |
| mir-128 | 143.0 | 2.4 |

TABLE 25 miRNAs that significantly reduce the percentage of BJ cells in S phase of the cell cycle

| miRNA | % Diff in Cells in S | St. Dev. |
|---|---|---|
| mir-128 | 55.5 | 3.8 |
| let-7a | 57.6 | 8.7 |
| mir-142 | 59.5 | 24.7 |
| mir-146 | 63.5 | 16.8 |
| mmu-297 | 65.0 | 14.1 |
| mir-337 | 65.3 | 11.3 |
| mir-195 | 65.6 | 0.1 |
| mmu-376b | 69.1 | 11.6 |
| mir-324 | 72.2 | 9.4 |
| mir-187 | 72.3 | 10.9 |
| mir-186 | 72.8 | 6.1 |

TABLE 26 miRNAs that significantly increase the percentage of BJ cells in S phase of the cell cycle

| miRNA | % Diff in Cells in S | St. Dev. |
|---|---|---|
| mir-92 | 132.0 | 14.7 |
| mir-15a | 134.8 | 13.9 |
| mir-191 | 135.9 | 29.1 |
| mir-26a | 136.0 | 7.6 |
| mir-20 | 139.7 | 17.6 |
| mmu-290 | 141.0 | 11.7 |
| let-7a | 141.1 | 19.9 |
| mir-345 | 143.3 | 45.8 |
| mir-16 | 150.1 | 24.8 |
| mir-224 | 150.6 | 9.8 |

TABLE 27 miRNAs that significantly reduce the percentage of BJ cells in G2/M phase of the cell cycle

| miRNA | % Diff in Cells in G2/M | St. Dev. |
|---|---|---|
| mir-147 | 51.2 | 6.1 |
| mir-371 | 52.8 | 2.7 |
| mir-146 | 57.2 | 5.3 |
| mir-195 | 58.9 | 4.4 |
| mir-128 | 65.4 | 2.7 |
| mir-15a | 67.4 | 13.7 |
| let-7a | 69.1 | 2.8 |

TABLE 28 miRNAs that significantly increase the percentage of BJ cells in G2/M phase of the cell cycle

| miRNA | % Diff in Cells in G2/M | St. Dev. |
|---|---|---|
| mir-26a | 130.2 | 5.8 |
| mir-187 | 132.0 | 4.3 |
| mir-145 | 136.8 | 13.7 |
| mir-373 | 137.9 | 5.2 |
| mir-20 | 143.0 | 10.6 |
| mir-21 | 160.3 | 7.1 |

TABLE 29 miRNAs that significantly increase the percentage of BJ cells with greater than 2X amount of DNA

| miRNA | % Diff in Cells w/>2X DNA | St. Dev. |
|---|---|---|
| mir-20 | 157.9 | 23.4 |
| mir-1 | 161.9 | 13.6 |
| mir-345 | 176.1 | 17.4 |
| mir-373 | 177.9 | 32.7 |
| mir-337 | 195.0 | 52.1 |
| mir-21 | 209.4 | 45.7 |

Example 22

Synthetic miRNA Library Screen for miRNAs that Influence Cell Proliferation

Cell proliferation assays were used in conjunction with our synthetic miRNA library to identify miRNAs that influence cell proliferation in a broad range of cells, including those from lung, breast, prostate, skin, cervix, T-cell, and foreskin tissues.

Cervical (HeLa), lung (A549, CRL-5826, and HTB-57), breast (MCF12A and BT549), prostate (22Rv1), T-cells (Jurkat and primary normal), and skin (TE354T, TE353SK, and BJ) cells were transfected in triplicate with each of the more than 150 synthetic miRNAs in our library. With the exceptions of Jurkats and Primary T-cells, each cell type was transfected with 5 picomoles of each of the miRNAs in the synthetic miRNA library using siPORT™ NeoFX™ (Ambion) at a plating density of approximately 8000 cells/well of 96 well plate. The Jurkats and primary T-cells were mixed at a rate of approximately 50,000 cells/well with 500 picomoles of each of the synthetic miRNAs. The media was changed 24 hrs after transfection. 72 hours post-transfection, cell number was estimated by one of three methods:

(1) Alamar blue was added to each well and the 96-well plates were analyzed using a plate reader. Alamar blue is a substrate for a metabolic enzyme in cells and the reaction product is fluorescent. The fluorescence in each well correlates with the total number of cells in each well.

(2) ViaCount Flex Reagent (Guava), a dye that fluoresces when it interacts with DNA, was added to each well and fluorescence was quantified using the Guava PCA-96 according to the manufacturer's instructions.

(3) Propidium iodide, a dye that fluoresces when it interacts with DNA, was added to each well and the total number of cells in the well was estimated by counting unique sites of stained DNA using the TTP LabTech Cell Scanner according to the manufacturer's instructions.

The impact of each miRNA on cell proliferation was assessed by dividing the cell number reading of each well by the average cell number reading for wells transfected with a negative control (NC) miRNA.

Presented in FIG. 15A-C are synthetic miRNAs that significantly reduced the proliferation of the various cell types that were analyzed. These miRNAs represent molecules that could be used for therapeutics, diagnostics, creating cell lines with interesting research properties, and inducing differentiation.

Approximately 10% of the miRNAs significantly reduced cell proliferation for at least four different cell types. These miRNAs (presented in ranked order in the table below) are provided below and can be implemented in methods and compositions of the invention.

TABLE 30

| Common Anti-Proliferation miRNAs | |
|---|---|
| miRNA | # Positives |
| miR-124 | 7 |
| miR-16 | 6 |
| miR-101 | 6 |
| miR-126 | 6 |
| miR-147 | 6 |
| miR-15a | 5 |
| miR-96 | 5 |
| miR-105 | 5 |
| miR-142 | 5 |
| miR-215 | 5 |
| miR-346 | 4 |
| miR-206 | 4 |
| miR-192 | 4 |
| miR-194 | 4 |

Among the cells that were used in the synthetic miRNA library screens are matched pairs of cancer and non-cancer cells from breast, skin, and T-cell. Interestingly, many synthetic miRNAs differentially affected proliferation in the cell pairs (see table below).

TABLE 31

| | Breast | | | |
|---|---|---|---|---|
| | Cancer | | Non-Cancer | |
| miRNA | % NC | % Std Dev | % NC | % Std Dev |
| mir-201 | 79 | 14 | 103 | 17 |
| mir-192 | 81 | 3 | 95 | 17 |
| mir-92 | 85 | 11 | 104 | 24 |
| | Skin | | | |
| | Cancer | | Normal | |
| pre-MIR | % of NC | % ST DEV | % of NC | % ST DEV |
| mir-154 | 51 | 5 | 93 | 10 |
| mir-195 | 58 | 3 | 87 | 5 |
| mu-mir-376b | 65 | 3 | 99 | 8 |
| mir-201 | 67 | 8 | 106 | 4 |
| mir-26a | 69 | 12 | 97 | 17 |
| mir-193 | 69 | 4 | 105 | 10 |
| | T-Cell | | | |
| | Leukemia | | Normal | |
| | % NC | % St Dev | % NC | % St Dev |
| let-7a | 21 | 1 | 137 | 15 |
| let-7b | 50 | 5 | 136 | 13 |
| miR-101 | 69 | 30 | 95 | 5 |
| miR-10b | 37 | 3 | 115 | 18 |
| miR-122 | 67 | 18 | 104 | 18 |
| miR-17-3p | 63 | 16 | 116 | 4 |
| miR-29a | 68 | 7 | 111 | 8 |
| miR-30a-3p | 66 | 27 | 97 | 18 |
| miR-34a | 67 | 21 | 100 | 1 |

Presented in FIG. 16 are synthetic miRNAs that significantly increase the proliferation of the various cell types that were analyzed.

Example 23 miRNA Inhibitor Library Screens Identify miRNAs that Influence Cell Proliferation A cell proliferation assay was used in conjunction with our synthetic miRNA library to identify miRNAs that influence cell proliferation in a broad range of cells, including those from lung, breast, prostate, skin, cervix, T-cell, and foreskin tissues.

Breast (MCF12A), prostate (22Rv1), lung (A549), and skin (TE354T) cells were transfected in triplicate with each of the more than 150 miRNA inhibitors in our library. Each cell type was transfected with 10 picomoles of each of the miRNA inhibitors in the library using siPORT™ NeoFX™ (Ambion) at a plating density of approximately 8000 cells/well of 96 well plate. 72 hours post-transfection, cell number was estimated by one of three methods:

(1) Alamar blue was added to each well and the 96-well plates were analyzed using a plate reader. Alamar blue is a substrate for a metabolic enzyme in cells and the reaction product is fluorescent. The fluorescence in each well correlates with the total number of cells in each well.

(2) ViaCount Flex Reagent (Guava), a dye that fluoresces when it interacts with DNA, was added to each well and fluorescence was quantified using the Guava PCA-96 according to the manufacturer's instructions.
(3) Propidium iodide, a dye that fluoresces when it interacts with DNA, was added to each well and the total number of cells in the well was estimated by counting unique sites of stained DNA using the TTP LabTech Cell Scanner according to the manufacturer's instructions.

The impact of each miRNA inhibitor on cell proliferation was assessed by dividing the cell number reading of each well by the average cell number reading for wells transfected with a negative control (NC) miRNA.

Presented in FIG. 17 are miRNAs whose inhibition significantly reduced the proliferation of the various cell types that were analyzed. These miRNAs represent molecules that could be used for therapeutics, diagnostics, creating cell lines with interesting research properties, and inducing differentiation.

Presented in FIG. 18 are miRNA inhibitors that significantly increase the proliferation of the various cell types that were analyzed. These miRNAs represent molecules that could be used for therapeutics, diagnostics, creating cell lines with interesting research properties, and inducing differentiation.

Example 24

Synthetic miRNA Library Screen for miRNAs that Influence Cell Viability

The basis for most human diseases is the subversion of one or more cells to function in ways that are outside what they normally do. For instance, cancer initiates with the immortalization and transformation of a single cell which then divides repeatedly to form a tumor. Compounds that reduce the viability of disease cells are used routinely to treat patients with cancer and other diseases.

Cervical (HeLa), lung (A549), and T-cells (Jurkat and primary normal) were transfected in triplicate with each of the more than 150 synthetic miRNAs in our library. With the exceptions of Jurkats and Primary T-cells, each cell type was transfected with 5 picomoles of each of the miRNAs in the synthetic miRNA library using siPORT™ NeoFX™ (Ambion) at a plating density of approximately 8000 cells/well of 96 well plate. The Jurkats and primary T-cells were mixed at a rate of approximately 50,000 cells/well with 500 picomoles of each of the synthetic miRNAs. For the HeLa and A549 cells, the media was changed 24 hrs after transfection. 72 hours post-transfection, cell viability was estimated by one of two methods:
(1) ViaCount Flex Reagent (Guava), which includes a dye that can only enter dead cells and that fluoresces when it interacts with DNA, was added to each well and fluorescence was quantified using the Guava PCA-96 according to the manufacturer's instructions. The percentage of viable cells was measured by dividing the number of non-dead and non-apoptotic cells in the sample by the total number of cells in the well and multiplying by 100.
(2) Propidium iodide, a dye that fluoresces when it interacts with DNA, was added to each well. Each cell was analyzed using the TTP LabTech Cell Scanner according to the manufacturer's instructions to detect cells with staining patterns consistent with cell death or apoptosis. The percentage of viable cells was measured by dividing the number of non-dead and non-apoptotic cells in the sample by the total number of cells in the well and multiplying by 100.

Presented in FIG. 19 are synthetic miRNAs that significantly decrease or increase viability in the various cell types that were analyzed. A comparison of the viability of jurkat and primary T-cells, which represent the leukemic and normal forms of T-cells, let-7, miR-10, miR-101, miR-17-3p, miR-19, and miR-34a severely reduced the viability of the leukemia cells without adversely affecting the normal T-cells.

Example 25

Synthetic miRNA Library Screen for miRNAs that Influence Apoptosis

To identify miRNAs that participate in apoptosis, an apoptosis assay was used with the miRNA inhibitor library. Approximately 8000 cervical (HeLa), prostate (22Rv1), T-cell (Jurkat), and skin (TE354T) cells per well were transfected in triplicate with each of the more than 150 synthetic miRNAs in our library using siPORT™ NeoFX™ (Ambion). Media was changed after 24 hrs and cells were visually inspected under a microscope to qualitatively inspect cell death 72 hours after transfection. The cells were measured for apoptosis by measuring caspase 3 activity as follows: 1) Cells were washed once with PBS and frozen at −80° C. 2) Cells were lysed by adding 40 µl of cold lysis buffer (50 mM HEPES pH 7.2, 40 mM NaCl, 0.5% NP40, 0.5 mM EDTA) to the wells and incubated for 20 min at 4° C. 3) Add 160 µl ICE buffer (50 mM HEPES pH 7.4, 0.1% CHAPS, 0.1 mM EDTA, 10% sucrose)+5 mM DTT containing 20 µM DEVDafc substrate. 4) Measure fluorescence increase in one hour at 400 ex, 505 em. Samples were also analyzed for cell number using a general esterase assay to normalize the caspase 3 results. FDA substrate (0.4 mg/ml fluorescein diacetate (FDA) in acetonitrile) was diluted 1:19 into dilution buffer (40 mM TrisCl pH 7.5, 20 mM NaCl, 0.5% NP-40, 0.02 mg/ml final conc). 40 µl buffer (40 mM TrisCl pH 7.5, 0.5% NP-40) was added to each sample well. Samples were incubated 10 min on ice. 160 µl of diluted FDA substrate was added to each well. Fluorescence was measured for 30 min at 37 deg (ex=488, em=529). The slope of fluorescence increase over time is a function of the cell number in the plate.

The impact of each miRNA on apoptosis was assessed by dividing the caspase 3 reading of each well by the average caspase 3 reading for wells transfected with a negative control (NC) miRNA.

As seen in FIG. 20, many different miRNAs were able to increase or decrease apoptosis in the four cell types that were analyzed. A few miRNAs (miR-126, miR-26a, miR-1, miR-149, and let-7g) affected apoptosis in multiple cell types suggesting that they regulate apoptosis via genes that are common in multiple cell types.

Example 26

Synthetic miRNA Library Screen for miRNAs that Induce Transformation

Transformation is necessary for tumor formation as it overcomes the cell's natural response to stop dividing when placed in a crowded environment. To identify miRNAs that participate in transformation, a transformation assay featuring NIH3T3 cells was used with the synthetic miRNA library. NIH 3T3 cells are used in transformation assays as they lack the capacity to form colonies when plated in soft agar. Modulation of cell processes that inhibit transformation can be readily detected because they induce NIH3T3 cells to begin forming colonies when plated in soft agar.

Approximately 8000 NIH 3T3 cells were transfected in duplicate with each of the more than 150 synthetic miRNAs in our library using siPORT™ NeoFX™ (Ambion). Media was changed after 24 hrs and the cells were transferred to 24-well dishes containing soft agar. The soft agar limits mobility and ensures that sister cells must remain in contact following cell division. Close contact with other cells typically induces the NIH 3T3 cells to stop dividing. The total number of cells in each well was measured by taking an absorbance reading at 495 nm. The absorbance reading for each well was divided by the average absorbance reading for cells transfected with negative control miRNAs and multiplied by 100 to get the percent change in transformation. An initial screen revealed miR-10, miR-23, miR-24, miR-198, miR-192, and miR-199 as miRNAs that increased transformation relative to cells transfected with negative control. A repeat of the experiment with the initial candidates yielded the following hit as shown below:

TABLE 32

| miRNA | % NC | % SD |
|-------|------|------|
| 198   | 103  | 2.07 |
| 192   | 108  | 5.7  |
| 199   | 113  | 5.59 |

Example 27

MiRNAs that Affect the Efficacy of Therapeutic Compounds

Many compounds have been tested in clinical trials for their capacity to positively affect the outcome of patients. In some cases, these compounds meet the standards set for by the FDA and they become therapeutics. Unfortunately, very few therapeutics are 100% effective. Enhancing the activities of therapeutic compounds provides a significant opportunity within the medical industry. The two most common methods that are used to enhance therapeutics are modifying the chemical structure of the compounds or using multiple therapeutic compounds simultaneously. Whether it would be beneficial to introduce miRNAs in advance of adding compounds that are known to significantly reduce the viability of cancer cells was evaluated. One of the anti-cancer compounds that was introduced was TRAIL, a compound that binds at least two different receptors and activates the apoptosis pathway to induce cell death primarily in cancer cells. The second compound that was tested in combination with synthetic miRNAs was etoposide, a topoisomerase II inhibitor that activates the apoptosis pathway of cancer and normal cells alike by reducing the repair of DNA damage within the cells.

Approximately 8000 cervical (HeLa) and lung (A549, HTB-57, and CRL-5826) cells per well were transfected in triplicate with synthetic miRNAs from our library using siPORT™ NeoFX™ (Ambion). Media was changed after 24 hrs and etoposide and TRAIL were introduced at a final concentration of approximately 25 µM after 48 hours. The cells were visually inspected under a microscope to qualitatively inspect cell death 64 hours after transfection.

The cells treated with etoposide were measured for apoptosis by measuring caspase 3 activity as follows: 1) Cells were washed once with PBS and frozen at −80° C. 2) Cells were lysed by adding 40 µl of cold lysis buffer (50 mM HEPES pH 7.2, 40 mM NaCl, 0.5% NP40, 0.5 mM EDTA) to the wells and incubated for 20 min at 4° C. 3) Add 160 µl ICE buffer (50 mM HEPES pH 7.4, 0.1% CHAPS, 0.1 mM EDTA, 10% sucrose)+5 mM DTT containing 20 µM DEVDafc substrate. 4) Measure fluorescence increase in one hour at 400 ex, 505 em. Samples were also analyzed for cell number using a general esterase assay to normalize the caspase 3 results. FDA substrate (0.4 mg/ml fluorescein diacetate (FDA) in acetonitrile) was diluted 1:19 into dilution buffer (40 mM TrisCl pH 7.5, 20 mM NaCl, 0.5% NP-40, 0.02 mg/ml final conc). 40 µl buffer (40 mM TrisCl pH 7.5, 0.5% NP-40) was added to each sample well. Samples were incubated 10 min on ice. 160 µl of diluted FDA substrate was added to each well. Fluorescence was measured for 30 min at 37 deg (ex=488, em=529). The slope of fluorescence increase over time is a function of the cell number in the plate.

The cells treated with TRAIL were assessed for cell viability by adding alamar blue each well and analyzing fluorescence using a plate reader. Alamar blue is a substrate for a metabolic enzyme in cells and the reaction product is fluorescent. The fluorescence in each well correlates with the total number of cells in each well.

The effect of each miRNA on the treatments was measured by dividing the caspase 3 or alamar blue reading of the cells transfected with miRNAs and treated with TRAIL or etoposide by the same readings for cells that were only transfected with the miRNAs. The change in caspase 3 activity or alamar blue staining for each miRNA was then divided by the differences observed for two negative control miRNAs and multiplied by 100 to calculate the relative effect induced by the combination of each miRNA and the therapeutic compound. These values are listed as % NC in Figure G.

As shown in FIG. 21, a number of miRNAs significantly increased the capacity of the two therapeutic compounds to induce cell death in the cancer cells that were treated. Interestingly, mir-292-3p, mir-132, mir-124, and mir-28 all worked extremely well in combination with both TRAIL and etoposide.

Example 28

Synthetic miRNA Library Screen for miRNAs that Affect Cell Cycle

The adult human body consists of about 50-100 trillion cells. Each day, several billion of these cells divide in two to replace the billions of cells that die and are removed. In the course of an average lifetime, this adds up to an astronomical number of cell divisions, most of which go perfectly well. Errors do occur, however, and if they are not corrected they may lead to cancer. Cell growth and division are normally controlled by an intricate system of checks and balances. But occasionally a cell will start to proliferate wildly, dividing again and again and defying all normal restraints on its growth. That is the beginning of most common forms of cancer.

Approximately 8000 cervical (HeLa) and 4000 skin (BJ) cells per well were transfected in triplicate with each of the more than 150 synthetic miRNAs in our library. HeLa cells were transfected using siPORT™ NeoFX™ (Ambion) and BJ cells were transfected using Lipofectamine 2000 (Invitrogen) according to the manufacturer's instructions. 24 hours post-transfection, half of the cells from each well were removed to fresh medium. 72 hrs post-transfection, the cells were fixed with 4% paraformaldehyde at a final concentration of 2%. The fixed cells were stained with propidium iodide (TTP LabTech protocol) and assessed using the TTP LabTech cell scanner. Propidium iodide stains DNA and the relative DNA content in a cell corresponds with its position in the cell cycle. The cell scanner measured propidium iodide staining in each cell and assigned its position in the cell cycle. The percentage of cells in each stage of cell cycle was calculated and compared to cells transfected with negative control synthetic miRNAs. The relative change in cells in each stage was calculated for each miRNA that was used. Those synthetic miRNAs that induced a significant shift toward or away from a specific stage of cell cycle are listed below. These represent miRNAs that regulate key points in the cell cycle and offer key intervention points for cancer-related therapeutic development.

As seen in FIG. 22, many different miRNAs significantly altered the percentage of cells in the various stages of cell cycle in the two cell types that were analyzed.

Example 29

Synthetic miRNA Library Screen for miRNAs that Influence ERK Activity

In order for cancer cells to proliferate they must subvert both the machinery that controls the cell division cycle and the process of programmed cell death (apoptosis). This is frequently achieved by mutation of specific proto-oncogenes such as Ras or tumor suppressors such as p53. The Ras-family of membrane associated GTPases transmit signals into the interior of the cell by the activation of a number of cytosolic signal transduction pathways such as the Raf>MEK>ERK MAP kinase signaling pathway. Disregulation of the Ras/Raf/MEK/ERK pathway plays a major role in cancer pathogenesis (reviewed in Meijer et al.).

To identify miRNAs that affect ERK activation, HeLa cells were transfected in a 96-well plate format with 160 different synthetic miRNAs. Prior to transfection, the HeLa cells were trypsinized to remove adherent cells and diluted in normal growth medium to $10^5$ cells/mL. 0.5 µl of siPort NeoFX in 9.5 µl of Optimem I medium was added to the cells and incubated for 10 minutes at room temp (10 µL for each sample). miRNAs were rehydrated with 10 µl of diluted siPORT NeoFX. The samples were incubated at 37° C. and then the transfected samples were evaluated 72 hours after transfection.

The controls for ERK activation were performed by depriving the wells of a phosphate source for detection of ERK phosphorylation. 100 µl of serum-free media (DMEM) to 37° C. was added per well and the cells were incubated for 4 hours at 37° C. to attain basal phosphorylation levels. For the positive control wells, serum-free media was aspirated from wells and 100 µL of 100 ng/mL EGF was added before incubating the cells for 7.5 minutes at 37° C.

Media from all wells was removed by aspiration and the cells were immediately fixed in 150 µL of 3.7% Formaldehyde in 1×PBS for 20 minutes at room temp with no shaking. Fixing solution was removed to an appropriate waste container. The fixed cells were washed three times with 1×PBS. The wells were then washed three times with 200 µL of 1×PBS containing 0.1% Triton X-100 for 5 minutes per wash, with shaking at room temp.

Cells were blocked by adding 150 µL of Li-COR Odyssey Blocking Buffer to each well. The solution was moved carefully by pipetting down the sides of the wells to avoid detaching the cells. Blocking was for 90 minutes at room temp with moderate shaking on a rotator and the two primary antibodies were added to a tube containing Odyssey Blocking Buffer. The primary antibody was incubated for 2 hours with gentle shaking at room temp (Phosho-ERK (Rabbit, 1:100 dilution; Cell Signaling Technology 9101). Total ERK2 (Mouse; 1:75 dilution; Santa Cruz Biotechnology SC-1647)). The wells were washed three times with 1×PBS+0.1% Tween-20 for 5 minutes at room temp with gentle shaking, using a generous amount of buffer. The fluorescently labeled secondary antibody was diluted in Odyssey Blocking Buffer (Goat anti-rabbit Alexa Fluor 680 (1:200 dilution; Molecular Probes) Goat anti-mouse IRDye 800CW (1:800 dilution; Rockland Immunochemicals)). The antibody solutions were mixed well and 50 µL of the secondary antibody solution was added to each well. The antibody solution was incubated for 60 minutes with gentle shaking at room temp. The plate was washed three times with 1×PBS+0.1% Tween-20 for 5 minutes at room temp with gentle shaking, using a generous amount of buffer. After a final wash, wash solution was completely removed from wells. The plates were scanned with the Odyssey Infrared Imaging System (700 nm detection for Alexa Fluor 680 antibody and 800 nm detection for IRDye 800CW antibody).

TABLE 33

| miRNAs That Activate ERK | | |
|---|---|---|
| miRNA | % NC | % StDev |
| let-7 | 250 | 25 |
| mir-125a | 252 | 27 |
| mir-134 | 211 | 13 |
| mir-148 | 264 | 44 |
| mir-152 | 266 | 36 |
| mir-19a | 242 | 31 |
| mir-206 | 256 | 56 |
| mir-207 | 224 | 3 |
| mir-210 | 292 | 38 |
| mir-212 | 231 | 24 |
| mir-216 | 219 | 26 |
| mir-217 | 273 | 27 |
| mir-218 | 313 | 23 |
| mir-223 | 264 | 40 |
| mir-25 | 239 | 45 |
| mir-294 | 236 | 25 |
| mir-295 | 221 | 14 |
| mir-301 | 261 | 62 |
| mir-328 | 259 | 46 |
| mir-329 | 243 | 5 |
| mir-339 | 214 | 42 |
| mir-370 | 221 | 23 |
| mir-372 | 211 | 6 |
| mir-96 | 214 | 57 |
| Positive Control | 245 | 11 |

Example 30

Synthetic miRNA Library Screen for miRNAs that Influence hTert Expression

Telomerase is a complex of proteins and RNA that maintains the ends of chromosomes by appending telomeres.

With rare exceptions, terminally differentiated cells lack active telomerase. One of the exceptions is cancer cells. More than 90% of human cancer samples have active telomerase (reviewed in Dong et al., 2005). The hTert gene encodes the catalytic domain of telomerase. The expression of hTert correlates with telomerase activity in cells making it a good surrogate for telomerase activity. We have developed and used an RT-PCR based assay for monitoring hTert mRNA expression in telomerase negative cells to identify miRNAs that participate in the regulation of telomerase. The miRNAs that regulate telomerase activity represent intervention points for cancer therapeutics.

BJ cells are normal foreskin fibroblasts that lack hTert mRNA and telomerase activity. BJ cells were trypsinized and diluted to 13,000 cells/ml in normal growth media. 0.3 μl of lipofectamine 2000 agent was diluted into 40 μl of OPTI-MEM and incubated for five minutes. The diluted transfection reagent was added to the wells of 96-well plates that contained 151 synthetic miRNAs as well as two different negative control synthetic miRNAs. Each well housed a different synthetic miRNA. The synthetic miRNAs and transfection agent were incubated for 15 minutes at room temperature and then 200 μl (2,600 cells) were added on top of the lipid/miRNA complex. Cells were placed in an incubator and RNA was isolated 72 hours later. RNA was isolated from the cells in each well using RNAqueous™-MagMAX96 Total RNA Isolation kit (Cat#1830) standard protocol (lyse cells in wells). Reverse transcription was done using the RETROscript reaction by adding 11 ul of total RNA (20-100 ng/μl) to 1 μl of random decamers and incubated in 70° C. water bath for 3 minutes then place on ice. Next, 8 μl of the cocktail containing Nuc-free water 3.8 μl, 10× Reverse Transcription buffer 2.0 μl, 2.5 mM dNTPs 2.0 μl, RNase Inhibitor Protein (40 U/μl), 0.1 μl MMLV-RT (100 U/μl), and incubated at 42° C. for 1 hour, then 92° C. for 10 minutes.

Real time PCR reactions were assembled to quantify hTert mRNA and 18S rRNA in each of the samples. Nuclease-free water, 10× Complete PCR buffer/SYBR, 25 mM MgCl2, 2.5 mM dNTPs, 50×ROX, 18S- or hTert-specific primers (for & rev mix 3 μM), cDNA from the various samples, and Super taq polymerasewere placed into a PCR tube. The reaction was heated to 95° C. for 5 minutes and then subjected to 40 cycles of 95° C. for 15 seconds, 60° C. for 30 seconds, 72° C. for 30 seconds. The amplification products were monitored using the ABI 7600 (Applied Biosystems). BJ cells ordinarily fail to yield amplification products with the hTert primers. Those miRNA-transfected samples that yielded a hTert PCR product were also analyzed for 18S rRNA lavels to ensure that there were not significantlyt more cells in the samples that might have contributed to the amount of hTert in the samples.

The hTert mRNA was detected in duplicate transfections of each of the miRNAs listed below. These miRNAs presumably affect pathways that regulate the expression of the hTert gene. Over-expression of any of these miRNAs might contribute to cancer by activating telomerase. Regulating the activities of these miRNAs in cancer cells could limit their transformation and overcome oncogenesis.

TABLE 34 hTert miRNA Activators

| miRNA | Log(2) hTert Expression |
|---|---|
| mir-147 | 3.14 |
| mir-195 | 4.25 |
| miR-21 | 1.55 |
| mir-24 | 4.68 |
| mir-26a | 4.35 |
| mir-301 | 4.14 |
| mir-368 | 5.30 |
| mir-371 | 2.43 |

The telomerase activity screen was repeated using a series of siRNAs targeting kinases, phosphatases, GPCRs, transcription factors, and assorted other genes. Targeting the genes below with siRNAs resulted in increased hTert expression. Interestingly, many of these genes are predicted to be targets for the miRNAs that we found to be hTert regulators (see table below).

TABLE 35 hTert Gene Activators

| Gene | Log(2) hTert Expression |
|---|---|
| ACOX1 | 3.44 |
| AKT1 | 1.80 |
| APAF1 | 3.40 |
| COX-5B | 2.78 |
| COX6 | 2.28 |
| COX7B | 3.95 |
| CPOX | 4.66 |
| DUOX2 | 3.80 |
| GPX1 | 1.85 |
| GPX2 | 2.56 |
| GPX4 | 3.17 |
| LPO | 3.37 |
| MAPK1 | 3.07 |
| MAPK4 | 3.61 |
| MTCO1 | 1.58 |
| NOX3 | 2.30 |
| NOX5 | 2.54 |
| PAOX | 1.72 |
| PPOX | 2.09 |
| PRKCA | 2.24 |
| PRKCD | 4.39 |
| TNFRSF6 | 2.25 |

Example 31

Effect of miRNA Primary Sequence on Function

Many miRNAs appear to be very closely related to others based on their primary sequences. For instance, let-7a is a member of the let-7 gene family, which includes 7 unique genes within the human genome. The let-7 genes encode miRNAs that vary by as little as a single nucleotide and as many as four nucleotides. In our synthetic miRNA and miRNA inhibitor libraries, we have five different human let-7 miRNAs. These miRNAs have been used in many different cell types in screens designed to identify miRNAs involved in a variety of different cellular processes. In many of the screens, the various let-7 miRNAs generate similar phenotypes. In some screens, all of the let-7 family members yield similar responses. In contrast, there are some screens wherein the various let-7 family miRNAs yield significantly different results (FIG. 23).

Example 32

Synthetic miRNA Library Screen for miRNAs that Influence Inflammation

Inflammation is the body's natural protective response to an injury or infection. It is designed to hyper-stimulate biological pathways that initiate tissue repair or attack invading pathogens. This response is a delicate balance of both pro- and anti-inflammatory genes and their proteins. If the inflammatory response is maintained too long it can lead to tissue destruction, organ failure or inflammatory diseases such as Rheumatoid arthritis, Psoriasis, Asthma, Inflammatory bowel disease (Crohn's disease and related conditions), Multiple Sclerosis, coronary obstructive pulmonary disease (COPD), Allergic rhinitis (hay fever), and Cardiovascular disease.

Stat3 is the subject of intense scientific investigation, because it's known to be an important transcription factor that turns on genes required for the cell division, induction and suppression of apoptosis, and cell motility. Many STAT3 target genes are known, including those encoding the anti-apoptotic proteins Bcl-xl, Mc1-1, and Bcl-2, the proliferation-associated proteins Cyclin D1 and Myc, and the pro-angiogenic factor VEGF. The inflammatory disease psoriasis is characterized by lesions, which contain epidermal keratinocytes that express high levels of activated Stat3. Stat3 has also recently been discovered to play an important role as an anti-inflammatory regulator. In normal mice, the immune system is initially upregulated in response to bacterial protein challenge creating systemic inflammation followed by down regulation of the initiating factors. Mice with a deletional mutation for Stat3-beta lacked the ability to down regulate the initial inflammatory reaction after bacterial protein challenge which lead to irreversible damage to the animals' own tissues and finally to animal death.

A stat3 response assay was used to identify miRNAs that regulate cellular inflammatory response. The stable Stat3-luciferase reporter cell line from Panomics, which contains a chromosomal integration of a luciferase reporter construct regulated by 3 copies of the Stat1 response element was used for this purpose. The chemical agent Phorbol-12-myristate 13 acetate (PMA) is known to induce an inflammatory response in exposed cells and was used to stimulate inflammation in this experiment. These cells were transfected in triplicate with each of the more than 206 synthetic miRNAs in our library using siPORT™ NeoFX™ (Ambion) at a plating density of approximately 6000 cells/well of 96 well plate. The media was changed 24 h post transfection and exposed to 100 nM PMA for 6 hours starting at 67 hours post transfection. The cells were assayed for changes in total cell number by alamarBlue as previously described and finally harvested at 72 hours post initial transfection. A luciferase assay was performed on all sample lysates to measure Stat3 responsiveness to the procedure. The data was normalized to total cell number using the alamar Blue data and compared to cells transfected with a negative control miRNA that underwent the same procedure.

The following miRNA were able to reduce the ability of PMA to stimulate Stat3.

TABLE 36

The following miRNA were able to reduce the ability of PMA to stimulate Stat3

| | % of NC | % STDEV |
|---|---|---|
| mir-93 | 34 | 74 |
| mir-100 | 13 | 10 |
| mir-134 | 50 | 18 |
| mir-99a | 38 | 96 |
| mir-103 | 38 | 40 |
| mir-128 | 49 | 115 |
| mir-129 | 44 | 112 |
| mir-181b | 11 | 21 |
| mir-193 | 42 | 92 |
| mir-197 | 36 | 78 |
| mir-212 | 42 | 92 |
| mir-218 | 38 | 84 |
| mir-219 | 39 | 86 |
| mir-302 | 40 | 87 |
| mir-323 | 22 | 49 |
| mir-324-3p | 29 | 63 |
| mir-325 | 29 | 63 |
| mir-330 | 21 | 47 |
| mir-331 | 39 | 86 |
| mir-340 | 34 | 75 |
| mmu-mir-350 | 11 | 22 |
| mir-425 | 24 | 49 |
| mir-491 | 25 | 49 |
| mir-518f | 26 | 52 |
| mir-520a* | 28 | 55 |

All of the compositions and methods disclosed and claimed herein can be made and executed without undue experimentation in light of the present disclosure. While the compositions and methods of this invention have been described in terms of embodiments, it will be apparent to those of skill in the art that variations may be applied to the compositions and methods, and in the steps or in the sequence of steps of the methods, described herein without departing from the concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references are specifically incorporated by reference to the extent they relate to topics and subject matter discussed herein.

U.S. Pat. No. 4,337,063
U.S. Pat. No. 4,404,289
U.S. Pat. No. 4,405,711
U.S. Pat. No. 4,659,774
U.S. Pat. No. 4,682,195
U.S. Pat. No. 4,683,202
U.S. Pat. No. 4,684,611
U.S. Pat. No. 4,704,362
U.S. Pat. No. 4,816,571
U.S. Pat. No. 4,828,979
U.S. Pat. No. 4,849,513
U.S. Pat. No. 4,910,300
U.S. Pat. No. 4,952,500
U.S. Pat. No. 4,959,463
U.S. Pat. No. 5,141,813
U.S. Pat. No. 5,143,854
U.S. Pat. No. 5,202,231

U.S. Pat. No. 5,214,136
U.S. Pat. No. 5,221,619
U.S. Pat. No. 5,223,618
U.S. Pat. No. 5,242,974
U.S. Pat. No. 5,264,566
U.S. Pat. No. 5,268,486
U.S. Pat. No. 5,288,644
U.S. Pat. No. 5,302,523
U.S. Pat. No. 5,322,783
U.S. Pat. No. 5,324,633
U.S. Pat. No. 5,378,825
U.S. Pat. No. 5,384,253
U.S. Pat. No. 5,384,261
U.S. Pat. No. 5,405,783
U.S. Pat. No. 5,412,087
U.S. Pat. No. 5,424,186
U.S. Pat. No. 5,428,148
U.S. Pat. No. 5,429,807
U.S. Pat. No. 5,432,049
U.S. Pat. No. 5,436,327
U.S. Pat. No. 5,445,934
U.S. Pat. No. 5,446,137
U.S. Pat. No. 5,464,765
U.S. Pat. No. 5,466,786
U.S. Pat. No. 5,468,613
U.S. Pat. No. 5,470,710
U.S. Pat. No. 5,470,967
U.S. Pat. No. 5,472,672
U.S. Pat. No. 5,480,980
U.S. Pat. No. 5,492,806
U.S. Pat. No. 5,503,980
U.S. Pat. No. 5,510,270
U.S. Pat. No. 5,525,464
U.S. Pat. No. 5,527,681
U.S. Pat. No. 5,529,756
U.S. Pat. No. 5,532,128
U.S. Pat. No. 5,538,877
U.S. Pat. No. 5,538,880
U.S. Pat. No. 5,545,531
U.S. Pat. No. 5,547,839
U.S. Pat. No. 5,550,318
U.S. Pat. No. 5,554,501
U.S. Pat. No. 5,554,744
U.S. Pat. No. 5,556,752
U.S. Pat. No. 5,561,071
U.S. Pat. No. 5,563,055
U.S. Pat. No. 5,571,639
U.S. Pat. No. 5,573,913
U.S. Pat. No. 5,574,146
U.S. Pat. No. 5,580,726
U.S. Pat. No. 5,580,732
U.S. Pat. No. 5,580,859
U.S. Pat. No. 5,583,013
U.S. Pat. No. 5,589,466
U.S. Pat. No. 5,591,616
U.S. Pat. No. 5,593,839
U.S. Pat. No. 5,599,672
U.S. Pat. No. 5,599,695
U.S. Pat. No. 5,602,240
U.S. Pat. No. 5,602,244
U.S. Pat. No. 5,610,042
U.S. Pat. No. 5,610,287
U.S. Pat. No. 5,610,289
U.S. Pat. No. 5,614,617
U.S. Pat. No. 5,623,070
U.S. Pat. No. 5,624,711
U.S. Pat. No. 5,631,134
U.S. Pat. No. 5,637,683
U.S. Pat. No. 5,639,603
U.S. Pat. No. 5,645,897
U.S. Pat. No. 5,652,099
U.S. Pat. No. 5,654,413
U.S. Pat. No. 5,656,610
U.S. Pat. No. 5,658,734
U.S. Pat. No. 5,661,028
U.S. Pat. No. 5,665,547
U.S. Pat. No. 5,667,972
U.S. Pat. No. 5,670,663
U.S. Pat. No. 5,672,697
U.S. Pat. No. 5,681,947
U.S. Pat. No. 5,695,940
U.S. Pat. No. 5,700,637
U.S. Pat. No. 5,700,922
U.S. Pat. No. 5,702,932
U.S. Pat. No. 5,705,629
U.S. Pat. No. 5,708,154
U.S. Pat. No. 5,714,606
U.S. Pat. No. 5,728,525
U.S. Pat. No. 5,736,524
U.S. Pat. No. 5,744,305
U.S. Pat. No. 5,763,167
U.S. Pat. No. 5,777,092
U.S. Pat. No. 5,780,448
U.S. Pat. No. 5,789,215
U.S. Pat. No. 5,792,847
U.S. Pat. No. 5,800,992
U.S. Pat. No. 5,807,522
U.S. Pat. No. 5,830,645
U.S. Pat. No. 5,837,196
U.S. Pat. No. 5,847,219
U.S. Pat. No. 5,858,988
U.S. Pat. No. 5,859,221
U.S. Pat. No. 5,871,928
U.S. Pat. No. 5,872,232
U.S. Pat. No. 5,876,932
U.S. Pat. No. 5,886,165
U.S. Pat. No. 5,919,626
U.S. Pat. No. 5,945,100
U.S. Pat. No. 5,981,274
U.S. Pat. No. 5,994,624
U.S. Pat. No. 6,004,755
U.S. Pat. No. 6,087,102
U.S. Pat. No. 6,251,666
U.S. Pat. No. 6,262,252
U.S. Pat. No. 6,368,799
U.S. Pat. No. 6,376,179
U.S. Pat. No. 6,383,749
U.S. Pat. No. 6,617,112
U.S. Pat. No. 6,638,717
U.S. Pat. No. 6,720,138
U.S. Pat. No. 6,723,509
U.S. Patent Ser. 60/649,584
U.S. Patent Ser. 60/575,743
British Appln. 1,529,202
European Appl. 266,032
European Appl. 373 203
European Appl. 785 280
European Appl. 799 897
PCT Appln. WO 94/09699
PCT Appln. WO 95/06128
PCT Appln. WO 0138580
PCT Appln. WO 0168255
PCT Appln. WO 03020898
PCT Appln. WO 03022421

PCT Appln. WO 03023058
PCT Appln. WO 03029485
PCT Appln. WO 03040410
PCT Appln. WO 03053586
PCT Appln. WO 03066906
PCT Appln. WO 03067217
PCT Appln. WO 03076928
PCT Appln. WO 03087297
PCT Appln. WO 03091426
PCT Appln. WO 03093810
PCT Appln. WO 03100448A1
PCT Appln. WO 04020085
PCT Appln. WO 04027093
PCT Appln. WO 09923256
PCT Appln. WO 09936760
PCT Appln. WO 93/17126
PCT Appln. WO 95/11995
PCT Appln. WO 95/21265
PCT Appln. WO 95/21944
PCT Appln. WO 95/35505
PCT Appln. WO 96/31622
PCT Appln. WO 97/10365
PCT Appln. WO 97/27317
PCT Appln. WO 9743450
PCT Appln. WO 99/35505
PCT Appln. WO03100012
UK 8 803 000;
Agrawal and Zamecnik, *Nucleic Acids Research*, 18(18): 5419-5423, 1990.
Allen et al., *Biochemistry*, 28:4601-4607, 1989.
Ambros, *Cell*, 107(7):823-826, 2001.
Baglioni and Nilson, *Interferon*, 5:23-42, 1983.
Bayer and Wilchek, *Methods of Biochemical Analysis*, 26:1-45, 1980.
Bayer et al, *Analytical Biochemistry*, 149:529-536, 1985.
Beaucage, and Lyer, *Tetrahedron*, 48:2223-2311, 1992.
Bernstein et al., *Nature*, 409: 363-366, 2001.
Bijsterbosch et al., *Biochem. Pharmacol.*, 62(5):627-633, 2001.
Blackie et al., *Bioorg. Med. Chem. Lett.*, 12(18):2603-2606, 2002.
Bobo et al., In: *Diagnosis of Chlamydia trachomatis Cervical Infection by Detection of Amplified DNA with an Enzyme Immunoassay*, 1990.
Borlakoglu et al., *Biochem. Pharmacol.*, 40(2):265-272, 1990.
Bosher and Labouesse, *Nat. Cell Biol.*, 2:E31-E36, 2000.
Brennecke et al., *Cell*, 113:25-36, 2003.
Brumbaugh et al., *Proc Natl Acad Sci USA*, 85(15):5610-5614, 1988.
Brummelkamp et al., *Science*, 296(5567):550-553, 2002
Calin et al., *Proc. Natl. Acad. Sci. USA*, 99:15524-15529, 2002.
Caplen et al., *Proc Natl Acad Sci USA*, 98: 9742-9747, 2001.
Cardullo et al., *Proc Natl Acad Sci USA*, 85(23):8790-8794, 1988
Carrington et al. *Science*, 301(5631):336-338, 2003.
Chang et al., *Nature*, 430(7001):785-789, 2004.
Chen and Okayama, *Mol. Cell Biol.*, 7(8):2745-2752, 1987.
Chen et al., *Science*, 303(5654):83-86, 2004.
Cogoni, C., and Macino, *Science*, 286:342-2344, 1999.
Cogoni. and Macino, *Nature* 399:166-169, 1999.
Conway et al., *Nucleic Acids Res. Symposium Series*, 21:43-44, 1989.
Crooke, In: *Antisense Drug Technology*, Marcel Dekker and Co, Basel, Switzerland, Chapter 6, 2001.
Cummins et al., In: *IRT: Nucleosides and nucleosides*, La Jolla Calif., 72, 1996.
Dalmay et al. *EMBO J*, 20:2069-2078, 2001.
Dalmay et al., *Cell*, 101:543-553, 2000.
Denli et al., *Trends Biochem. Sci.*, 28:196, 2003.
Dewanjee et al., *Biotechniques*, 5: 844-846, 1994.
Didenko, *Biotechniques*, 31(5):1106-16, 1118, 1120-1, 2001.
Doench et al., *Genes & Dev.* 17: 438-442, 2003.
Doench et al., *Genes Dev.* 18(5):504-11, 2004.
Dong et al., *Crit Rev Oncol Hematol.* 54(2):85-93, 2005.
Dostie et al., *RNA*, 9:180-186, 2003.
Draper and Gold, *Biochemistry*, 19:1774-1781, 1980.
Elbashir et al., *Nature*, 411:494-498, 2001.
Emptage et al., *Neuron*, 2001 January; 29(1):197-208, 2001.
Fechheimer et al., *Proc. Natl. Acad. Sci. USA*, 84:8463-8467, 1987.
Fire et al., *Nature*, 391:806-811, 1998.
Forster et al. *Nucleic Acids Res.*, 13(3):745-761, 1985.
Fraley et al., *Proc. Natl. Acad. Sci. USA*, 76:3348-3352, 1979.
Froehler et al., *Nucleic Acids Res.*, 14(13):5399-5407, 1986.
Gillam et al., *J. Biol. Chem.*, 253:2532, 1978.
Gillam et al., *Nucleic Acids Res.*, 6:2973, 1979.
Gopal, *Mol. Cell Biol.*, 5:1188-1190, 1985.
Graham and Van Der Eb, *Virology*, 52:456-467, 1973.
Griffey et al., *J Mass Spectrom*, 32(3):305-13, 1997.
Grishok et al., *Cell*, 106: 23-34, 2001.
Ha et al., *Genes Dev.*, 10, 3041-3050, 1996.
Hamilton and Baulcombe, *Science*, 286:950-952, 1999.
Hammond et al., *Nat. Rev. Genet.*, 2(2):110-9, 2001.
Haralambidis et al., *Nucleic Acids Res.*, 18(3):493-9, 1990.
Harland and Weintraub, *J. Cell Biol.*, 101:1094-1099, 1985.
Holtke and Kessler, *Nucleic Acids Res.*, 18(19):5843-51, 1990.
Hutvagner and Zamore, *Science*, 297(5589):2056-2060, 2002.
Hutvagner et al., *PLoS Biol.* 2(4):E98, 2004.
Hutvagner et al., *Science*, 293:834-838, 2001.
Itakura and Riggs, *Science*, 209:1401-1405, 1980.
Itakura et al., *J. Biol. Chem.*, 250:4592, 1975.
Jablonski et al., *Nucleic Acids Res.*, 14(15):6115-6128, 1986.
Kaeppler et al., *Plant Cell Reports*, 9: 415-418, 1990.
Kaneda et al., *Science*, 243:375-378, 1989.
Kato et al, *J. Biol. Chem.*, 266:3361-3364, 1991.
Keller et al., *Analytical Biochemistry*, 170:441-450, 1988.
Ketting et al., *Cell*, 99:133-141, 1999.
Khorana, *Science*, 203, 614 1979.
Kimura et al., *Cancer Research*, 55:1379-1384, 1995.
Kiriakidou et al. *Genes Dev.* 18(10):1165-78, 2004.
Kitagawa et al., *Brain Res.*, 561:203-11, 1991.
Klostermeier and Millar, *Biopolymers*, 61(3):159-79, 2001-2002
Knight et al., *Science*, 2:2, 2001.
Kornberg and Baker, In: *DNA Replication*, 2d Ed., Freeman, San Francisco, 1992.
Kuhnast et al., *Bioconjug Chem*, 5:627-636, 2000.
Lagos-Quintana et al., *Science*, 294(5543):853-858, 2001.
Langer et al., *Proc. Natl. Acad. Sci. USA*, 78(11):663-6637, 1981.
Lau et al., *Science*, 294(5543):858-862, 2001.
Lee and Ambros, *Science*, 294(5543):862-864, 2001.
Lee et al., *Nature*, 425(6956):415-419 2003.
Lee, *EMBO J.*, 21(17):4663-4670 2002.
Leonetti et al., *Bioconjugate Chem.*, 1:149-153, 1990.
Lewis, *Cell*, 115(7):787-798 2003.

Lin and Avery, *Nature,* 402:128-129, 1999.
Liu et al., *Anal. Biochem.,* 289:239-245, 2001.
Lorenz et al., *Bioorg. Med. Chem. Lett.* 14(19):4975-4977, 2004.
MacKellar et al., *Nucl. Acids Res.,* 20:3411-3417, 1992.
Manoharan, *Antisense Nucleic Acid Drug Dev.,* 12(2):103-128, 2002.
Martin et al., *RNA,* 4(2):226-20, 1998.
Meijer et al., *Progress in Cell cycle research Vol* 5, 219-224. (Meijer, L., Jezequel, A., and Roberge, M. eds), Chapter 22.
Meister et al., *RNA,* 10(3):544-50, 2004.
Montgomery et al., *Proc. Natl. Acad. Sci. USA,* 95:155-215507, 1998.
Mourrain et al., *Cell,* 101:533, 2000.
Nicolau and Sene, *Biochim. Biophys. Acta,* 721:185-190, 1982.
Nicolau et al., *Methods Enzymol.,* 149:157-176, 1987.
Nykanen et al., *Cell,* 107(3):309-321, 2001.
Olsen et al., *Dev. Biol.,* 216:671, 1999.
Omirulleh et al., *Plant Mol. Biol.,* 21(3):415-428, 1993.
Oravcova et al., *Blood Press Suppl.,* 1:61-64, 1994.
Pasquinelli and Ruvkun, *Ann. Rev. Cell Dev. Biol.,* 18:495-513, 2002.
Piutlle et al., *Gene,* 112(1):101-5, 1992.
Plasterk and Ketting, *Curr. Opin. Genet. Dev.,* 10:562-567, 2000.
Potrykus et al., *Mol. Gen. Genet.,* 199(2):169-77, 1985.
Regnier and Preat, *Pharm Res,* 10:1596-602, 1998.
Reinhart et al., *Nature,* 403:901-906, 2000.
Reisfeld et al. *Biochem Biophysic Res Comm,* 142(2):519-526, 1987.
Richardson and Gumport, *Nucleic Acids Res,* 11(18):6167-84, 1983.
Richardson and Macy, *Biochemistry,* 20(5):1133-9, 1981.
Rippe et al., *Mol. Cell Biol.,* 10:689-695, 1990.
Roychoudhury and Kossel, *Eur J Biochem,* 22(3):310-20, 1971.
Rump et al., *Biochem Pharmacol* 59(11): 1407-16, 2000.
Rusckowski et al., *Antisense Nucleic Acid Drug Dev.,* 5:333-345, 2000.
Rusconi et al., *Nat. Biotechnol.,* 22(11):1423-1428, 2004.
Saiki et al. *Science,* 230:1350-1354, 1985
Sambrook et al., *In: DNA microaarays: a molecular cloning manual,* Cold Spring Harbor Laboratory Press, Cold Spring Harbor, N.Y., 2003.
Sambrook et al., *In: Molecular cloning: a laboratory manual,* $2^{nd}$ Ed., Cold Spring Harbor Laboratory Press, Cold Spring Harbor, N.Y., 1989.
Sambrook et al., *In: Molecular cloning: a laboratory manual,* $3^{rd}$ Ed., Cold Spring Harbor Laboratory Press, Cold Spring Harbor, N.Y., 2001.
Scheit, *In: Synthesis and Biological Function,* Wiley-Interscience, New York, 171-172, 1980.
Schwarze et al., *Trends in Cell Biol.,* 10:290-295, 2000.
Sedelnikova et al., *Antisense Nucleic Acid Drug Dev.,* 6:443-452, 2000.
Seggerson et al., *Dev. Biol.,* 243:215, 2002.
Sharp and Zamore, *Science,* 287:2431-2433, 2000.
Smardon et al., *Curr. Biol.,* 10:169-178, 2000.
Sodja et al., *Nucleic Acids Res.,* 5(2):385-401, 1978.
Soutschek et al., *Nature,* 432(7014):173-178, 2004.
Sproat et al., *Nucleic Acids Res.,* 17(9):3373-3386, 1989.
Stalnacke et al., *Eur. J. Nucl. Med.,* 5:166-170, 1985.
Sui et al., *Proc. Natl. Acad. Sci. USA,* 99(8):5515-5520, 2002.
Tabara et al., *Cell,* 99:123-132, 1999.
Takeda and Ikeda, *Nucl. Acids Res.,* 15:101-104, 1984.
Tuschl, *Chembiochem,* 2:239-245, 2001.
Uhlenbeck et al., *Nucleic Acids Res.,* 10(11):3341-52, 1982.
Urdea et al., *Clinical Chemistry,* 35(8):1571-1575, 1989.
Vella et al., *Genes Dev.* 18(2):132-7, 2004.
Viscidi et al., *J. Clinical Microbiology,* 23(2):311-317, 1986.
Vyas et al., *Crit. Rev. Ther. Drug Carrier Syst.,* 18:1-76, 2001.
Waterhouse et al., *Nature,* 411:834-842, 2001.
Weeks et al., *Clin. Chem.,* 29(8):1474-1479, 1983.
Williams et al., *Int. J. Dev. Biol.,* 41(2):359-364, 1997.
Winter and Brownlee, *Nucleic Acids Res.,* 5(9):3129-39, 1978.
Wong et al., *Gene,* 10:87-94, 1980.
Wu et al., *Eur. J. Pharm. Sci.,* 3:179-186, 2000.
Wu-Scharf et al., *Science,* 290:1159-1162, 2000.
Xu et al., *Curr. Biol.,* 13:790-795, 2003.
Yoo et al., *Nucleic Acids Res.,* 21:4225-4231, 2000.
Zamore et al., *Cell,* 101:25-33, 2000.
Zamore, *Nat. Struct. Biol.,* 8:746-750, 2001.
Zeng et al., *Mol Cell.* 9, 1327-33, 2002.
Zeng et al., *Proc. Natl. Acad. Sci.* 100: 9779-9784, 2003.
Zhang et al., *Eur. J. Nucl. Med.,* 11:1700-1707, 2000.
Zhang et al., *J. Mol. Neurosci.,* 1:13-28, 1996.
Zhang et al., *J. Nucl. Med.,* 11:1660-1669, 2001.
Ziauddin and Sabatini, *Nature,* 411(6833):107-110, 2001.

What is claimed is:

1. A method for decreasing cell viability or decreasing cell proliferation of a cancer cell in an individual in need thereof, comprising administering to the individual a therapeutically-effective amount of a pharmaceutical composition comprising:
   a. a synthetic miR-101 molecule comprising:
      i. an active strand comprising a sequence that is at least 90% identical to mature human miR-101; and
      ii. a separate complementary strand that is at least 60% complementary to the active strand and has a 5'-terminal nucleotide that is chemically modified to comprise a lower alkylamine group, and
   b. a pharmaceutically-acceptable excipient.

2. The method of claim 1, wherein the cancer cell is a cervical cancer cell, a lung cancer cell, a cancerous T cell, a prostate cancer cell, or a skin cancer cell.

3. The method of claim 1, wherein the active strand is 22 to 30 nucleotides in length.

4. The method of claim 1, wherein the complementary strand is 100% complementary to the active strand.

5. The method of claim 1, wherein the lower alkylamine group is attached to a 5' phosphate of the 5'-terminal nucleotide of the complementary strand.

6. The method of claim 1, wherein the active strand is 23 nucleotides in length.

7. The method of claim 1, wherein the pharmaceutically-acceptable excipient is a carrier or a lipid.

* * * * *